US010065966B2

(12) United States Patent
D'Agostino et al.

(10) Patent No.: US 10,065,966 B2
(45) Date of Patent: Sep. 4, 2018

(54) SUBSTITUTED PYRIDO[2,3-D]PYRIMIDINES AS INHIBITORS OF PROTEIN KINASES

(71) Applicants: Celgene CAR LLC, Pembroke (BM); Sanofi, Paris (FR)

(72) Inventors: Laura Akullian D'Agostino, Lunenburg, MA (US); Robert Tjin Tham Sjin, Framingham, MA (US); Deqiang Niu, Lexington, MA (US); Joseph John McDonald, Sudbury, MA (US); Zhendong Zhu, Westborough, MA (US); Haibo Liu, Lexington, MA (US); Hormoz Mazdiyasni, Marlborough, MA (US); Russell C. Petter, Stow, MA (US); Juswinder Singh, Southborough, MA (US); Matthieu Barrague, North Brunswick, NJ (US); Alexandre Gross, Jersey City, NJ (US); Mark Munson, Acton, MA (US); Darren Harvey, Acton, MA (US); Andrew Scholte, Somerville, MA (US); Sachin Maniar, Arlington, MA (US)

(73) Assignees: Celgene CAR LLC, Pembroke (BM); Sanofi, Paris (FR)

( * ) Notice: Subject to any disclaimer, the term of this patent is extended or adjusted under 35 U.S.C. 154(b) by 0 days.

(21) Appl. No.: 15/604,786

(22) Filed: May 25, 2017

(65) Prior Publication Data
US 2017/0267685 A1 Sep. 21, 2017

Related U.S. Application Data

(62) Division of application No. 14/776,373, filed as application No. PCT/US2014/029270 on Mar. 14, 2014, now Pat. No. 9,663,524.

(60) Provisional application No. 61/793,113, filed on Mar. 15, 2013.

(30) Foreign Application Priority Data

Mar. 13, 2014 (EP) .................................. 14305361

(51) Int. Cl.
| C07D 471/04 | (2006.01) |
| C07D 487/04 | (2006.01) |
| C07D 239/80 | (2006.01) |
| C07D 519/00 | (2006.01) |

(52) U.S. Cl.
CPC ......... C07D 487/04 (2013.01); C07D 239/80 (2013.01); C07D 471/04 (2013.01); C07D 519/00 (2013.01)

(58) Field of Classification Search
CPC .................................................. C07D 471/04

USPC .......................................................... 544/279
See application file for complete search history.

(56) References Cited

U.S. PATENT DOCUMENTS

| 5,952,333 | A | 9/1999 | Barker |
| 5,952,342 | A | 9/1999 | Blankley et al. |
| 6,150,373 | A | 11/2000 | Harris et al. |
| 6,451,804 | B1 | 9/2002 | Dunn et al. |
| 6,506,749 | B2 | 1/2003 | Chen et al. |
| 6,518,276 | B2 | 2/2003 | Arzeno et al. |
| 6,642,241 | B1 | 11/2003 | Dunn et al. |
| 6,753,427 | B2 | 6/2004 | Arzeno et al. |
| 6,770,742 | B1 | 8/2004 | Ullrich et al. |
| 6,861,423 | B2 | 3/2005 | Chen et al. |
| 7,022,711 | B2 | 4/2006 | Hamby et al. |
| 7,084,270 | B2 | 8/2006 | Chen et al. |
| 7,091,345 | B2 | 8/2006 | Cai et al. |
| 7,112,676 | B2 | 9/2006 | Dermatakis et al. |
| 7,115,740 | B2 | 10/2006 | Chen et al. |
| 7,129,351 | B2 | 10/2006 | Luk et al. |
| 7,196,090 | B2 | 3/2007 | Connolly et al. |
| 7,238,698 | B2 | 7/2007 | Dunn et al. |
| 7,297,774 | B2 | 11/2007 | Ullrich et al. |
| 7,371,750 | B2 | 5/2008 | Sim et al. |
| 7,449,582 | B2 | 11/2008 | Ding et al. |
| 7,456,185 | B2 | 11/2008 | Dunn et al. |

(Continued)

FOREIGN PATENT DOCUMENTS

| CN | 102887895 A | 1/2013 |
| JP | 2004-519422 A | 7/2004 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — Choate, Hall & Stewart LLP; Kristen C. Buteau; Nicholas J. Pace

(57) ABSTRACT

The present invention provides compounds of formula I-h:

useful as inhibitors of protein kinases, pharmaceutically acceptable compositions thereof, and methods of using the same.

27 Claims, 4 Drawing Sheets
Specification includes a Sequence Listing.

(56) References Cited

U.S. PATENT DOCUMENTS

| | | |
|---|---|---|
| 7,494,993 B2 | 2/2009 | Engh et al. |
| 7,501,425 B1 | 3/2009 | Dobrusin et al. |
| 7,618,982 B2 | 11/2009 | Vanotti et al. |
| 7,642,255 B2 | 1/2010 | Sim et al. |
| 7,645,764 B2 | 1/2010 | Gabriel et al. |
| 7,655,651 B2 | 2/2010 | Engh et al. |
| 7,678,372 B2 | 3/2010 | Ullrich et al. |
| 7,737,149 B2 | 6/2010 | Buttar et al. |
| 7,767,687 B2 | 8/2010 | Oslob et al. |
| 8,043,806 B2 | 10/2011 | Ullrich et al. |
| 8,071,614 B2 | 12/2011 | Saxty et al. |
| 8,129,391 B2 | 3/2012 | Foote et al. |
| 8,173,134 B2 | 5/2012 | Bosch et al. |
| 8,293,746 B2 | 10/2012 | Bold et al. |
| 8,436,004 B2 | 5/2013 | Bamba et al. |
| 8,450,335 B2 | 5/2013 | Singh et al. |
| 8,461,179 B1 | 6/2013 | Flynn et al. |
| 8,507,505 B2 | 8/2013 | Bamba et al. |
| 8,518,958 B2 | 8/2013 | Murthi et al. |
| 8,552,002 B2 | 10/2013 | Ding et al. |
| 8,575,179 B2 | 11/2013 | Bamba et al. |
| 8,604,022 B2 | 12/2013 | Foote et al. |
| 8,609,679 B2 | 12/2013 | Singh et al. |
| 8,759,517 B2 | 6/2014 | Bold et al. |
| 8,802,697 B2 | 8/2014 | Bifulco, Jr. et al. |
| 8,859,582 B2 | 10/2014 | Saxty et al. |
| 8,895,745 B2 | 11/2014 | Berdini et al. |
| 8,940,756 B2 | 1/2015 | Flynn et al. |
| 9,067,896 B2 | 6/2015 | Berghausen et al. |
| 9,126,951 B2 | 9/2015 | Bifulco, Jr. et al. |
| 9,321,786 B2 | 4/2016 | D'Agostino et al. |
| 9,663,524 B2 | 5/2017 | D'Agostino et al. |
| 9,695,132 B2 | 7/2017 | D'Agostino et al. |
| 2004/0019210 A1 | 1/2004 | Chivikas Connolly et al. |
| 2004/0038995 A1 | 2/2004 | Chen et al. |
| 2004/0043986 A1 | 3/2004 | Nahra et al. |
| 2004/0087600 A1 | 5/2004 | Cai et al. |
| 2004/0152739 A1 | 8/2004 | Hanau et al. |
| 2004/0192709 A1 | 9/2004 | Arzeno et al. |
| 2004/0204427 A1 | 10/2004 | Chen et al. |
| 2004/0209897 A1 | 10/2004 | Vernier et al. |
| 2004/0209904 A1 | 10/2004 | Dunn et al. |
| 2005/0009849 A1 | 1/2005 | Veach et al. |
| 2005/0222177 A1 | 10/2005 | Sim et al. |
| 2007/0248605 A1 | 10/2007 | Hestir et al. |
| 2008/0113971 A1 | 5/2008 | Hanau et al. |
| 2009/0118261 A1 | 5/2009 | Aquila et al. |
| 2009/0137583 A1 | 5/2009 | Kishikawa et al. |
| 2009/0258369 A1 | 10/2009 | Khan et al. |
| 2009/0298844 A1 | 12/2009 | Pollard |
| 2009/0312321 A1 | 12/2009 | Ren et al. |
| 2010/0048552 A1 | 2/2010 | Ren et al. |
| 2010/0105667 A1 | 4/2010 | Furet et al. |
| 2010/0185419 A1 | 7/2010 | Singh et al. |
| 2010/0234400 A1 | 9/2010 | Chen et al. |
| 2011/0039845 A1 | 2/2011 | Kashima et al. |
| 2011/0059976 A1 | 3/2011 | Oslob et al. |
| 2011/0117073 A1 | 5/2011 | Singh et al. |
| 2011/0135657 A1 | 6/2011 | Hu et al. |
| 2011/0224432 A1 | 9/2011 | Singh et al. |
| 2012/0040961 A1 | 2/2012 | Gray et al. |
| 2012/0258940 A1 | 10/2012 | Caponigro et al. |
| 2012/0258967 A1 | 10/2012 | Qiao et al. |
| 2013/0012476 A1 | 1/2013 | Ding et al. |
| 2013/0012704 A1 | 1/2013 | Ding et al. |
| 2013/0065879 A1 | 3/2013 | Singh et al. |
| 2013/0116263 A1 | 5/2013 | Campbell et al. |
| 2014/0066455 A1 | 3/2014 | Buttar et al. |
| 2014/0163003 A1 | 6/2014 | Murthi et al. |
| 2014/0163004 A1 | 6/2014 | Murthi et al. |
| 2014/0163005 A1 | 6/2014 | Murthi et al. |
| 2014/0163006 A1 | 6/2014 | Murthi et al. |
| 2014/0163007 A1 | 6/2014 | Murthi et al. |
| 2014/0163222 A1 | 6/2014 | Murthi et al. |
| 2014/0163223 A1 | 6/2014 | Murthi et al. |
| 2014/0187559 A1 | 7/2014 | Miduturu |
| 2014/0296206 A1 | 10/2014 | DiPietro et al. |
| 2014/0296233 A1 | 10/2014 | D'Agostino et al. |
| 2014/0378481 A1 | 12/2014 | Bifulco, Jr. et al. |
| 2015/0031693 A1 | 1/2015 | Mckew et al. |
| 2015/0111857 A1 | 4/2015 | Hodous et al. |
| 2015/0111887 A1 | 4/2015 | Hodous et al. |
| 2015/0119405 A1 | 4/2015 | Bifulco, Jr. et al. |
| 2015/0197519 A1 | 7/2015 | Bifulco, Jr. et al. |
| 2015/0210694 A1 | 7/2015 | Bifulco, Jr. et al. |
| 2015/0299134 A1 | 10/2015 | Buttar et al. |
| 2016/0046634 A1 | 2/2016 | D'Agostino et al. |
| 2016/0221966 A1 | 8/2016 | D'Agostino et al. |
| 2018/0022713 A1 | 1/2018 | D'Agostino et al. |

FOREIGN PATENT DOCUMENTS

| | | |
|---|---|---|
| JP | 2006-511563 A | 4/2006 |
| JP | 2015-523383 A | 8/2015 |
| WO | WO-98/33798 A2 | 8/1998 |
| WO | WO-99/37299 A1 | 7/1999 |
| WO | WO-99/61444 A2 | 12/1999 |
| WO | WO-00/24744 A1 | 5/2000 |
| WO | WO-01/29041 A1 | 4/2001 |
| WO | WO-01/29042 A1 | 4/2001 |
| WO | WO-01/64679 A1 | 9/2001 |
| WO | WO-02/12238 A2 | 2/2002 |
| WO | WO-02/18379 A2 | 3/2002 |
| WO | WO-02/18380 A1 | 3/2002 |
| WO | WO-02/076985 A1 | 10/2002 |
| WO | WO-2004/011465 A1 | 2/2004 |
| WO | WO-2004/014869 A2 | 2/2004 |
| WO | WO-2004/018472 A2 | 3/2004 |
| WO | WO-2004/041821 A1 | 5/2004 |
| WO | WO-2004/041822 A1 | 5/2004 |
| WO | WO-2004/041823 A1 | 5/2004 |
| WO | WO-2004/056822 A1 | 7/2004 |
| WO | WO-2004/058176 A2 | 7/2004 |
| WO | WO-2004/063195 A1 | 7/2004 |
| WO | WO-2004/089955 A1 | 10/2004 |
| WO | WO-2004/092144 A2 | 10/2004 |
| WO | WO-2005/011597 A2 | 2/2005 |
| WO | WO-2005/034869 A2 | 4/2005 |
| WO | WO-2005/072826 A2 | 8/2005 |
| WO | WO-2005/105097 A2 | 11/2005 |
| WO | WO-2006/000420 A1 | 1/2006 |
| WO | WO-2006/024486 A2 | 3/2006 |
| WO | WO-2006/024487 A1 | 3/2006 |
| WO | WO-2006/024834 A1 | 3/2006 |
| WO | WO-2006/038112 A1 | 4/2006 |
| WO | WO-2006/065703 A1 | 6/2006 |
| WO | WO-2006/118256 A1 | 11/2006 |
| WO | WO-2006/135824 A1 | 12/2006 |
| WO | WO-2006/137421 A1 | 12/2006 |
| WO | WO-2007/014250 A2 | 2/2007 |
| WO | WO-2007/071621 A1 | 6/2007 |
| WO | WO-2007/071752 A2 | 6/2007 |
| WO | WO-2007/136465 A2 | 11/2007 |
| WO | WO-2008/021369 A2 | 2/2008 |
| WO | WO-2008/047307 A1 | 4/2008 |
| WO | WO-2008/055842 A1 | 5/2008 |
| WO | WO-2008/075068 A2 | 6/2008 |
| WO | WO-2008/078091 A1 | 7/2008 |
| WO | WO-2008/150260 A1 | 12/2008 |
| WO | WO-2008/153207 A1 | 12/2008 |
| WO | WO-2009/047522 A1 | 4/2009 |
| WO | WO-2009/131173 A1 | 10/2009 |
| WO | WO-2009/158571 A1 | 12/2009 |
| WO | WO-2010/067886 A1 | 6/2010 |
| WO | WO-2010/067888 A1 | 6/2010 |
| WO | WO-2010/080712 A2 | 7/2010 |
| WO | WO-2011/071821 A1 | 6/2011 |
| WO | WO-2011/075620 A1 | 6/2011 |
| WO | WO-2011/135376 A1 | 11/2011 |
| WO | WO-2012/138975 A1 | 10/2012 |
| WO | WO-2012/158843 A2 | 11/2012 |
| WO | WO-2013/067423 A1 | 5/2013 |
| WO | WO-2013/067434 A1 | 5/2013 |
| WO | WO-2013/184119 A1 | 12/2013 |

(56) References Cited

FOREIGN PATENT DOCUMENTS

| | | |
|---|---|---|
| WO | WO-2014/011900 A2 | 1/2014 |
| WO | WO-2014/144737 A1 | 9/2014 |
| WO | WO-2014/160521 A1 | 10/2014 |
| WO | WO-2015/006492 A1 | 1/2015 |
| WO | WO-2015/017528 A1 | 2/2015 |
| WO | WO-2015/017533 A1 | 2/2015 |
| WO | WO-2015/057873 A1 | 4/2015 |
| WO | WO-2015/057938 A1 | 4/2015 |
| WO | WO-2015/057963 A1 | 4/2015 |
| WO | WO-2015/058129 A1 | 4/2015 |
| WO | WO-2015/061572 A1 | 4/2015 |
| WO | WO-2015/108992 A1 | 7/2015 |

OTHER PUBLICATIONS

Hackam, et al. JAMA, 296(14), 2006, 1731-1732.*
Apsel, B. et. al., Targeted polypharmacology: discovery of dual inhibitors of tyrosine and phosphoinositide kinases, Nat. Chem. Biol., 4(11): 691-699 (2008).
AstraZeneca, Press Release, 3 pages (Sep. 29, 2014).
Author Unknown, CAS Registry No. 1186655-68-4, N-[4-[[3-(2,6-dichloro-3,5-dimethoxyphenyl)-7-[[4-(diethylamino)butyl]amino]-3,4-dihydro-2-oxopyrimido[4,5-d]pyrimidin-1(2H)-yl]methyl]phenyl]-2-propenamide (Sep. 30, 2009).
Author Unknown, CAS Registry No. 1191930-07-0, 8-(2-Fluoropyridin 5-yl)-7-methoxy-6-[2-methyl-5-[N-(3-trifluoromethylphenyl)carbamoyl]phenyl]-2-[(tetrahydropyran-4-yl)amino]quinazoline (Nov. 9, 2009).
Author Unknown, CAS Registry No. 1191930-08-1, 7-Methoxy-8-(1-methyl-1H-pyrazol-4-yl)-6-[2-methyl-5-[N-(3-trifluoromethylphenyl)carbamoyl]phenyl]-2-[(tetrahydropyran-4-yl)amino]quinazoline (Nov. 9, 2009).
Author Unknown, CAS Registry No. 1191930-09-2, 7-Methoxy-6-[2-methyl-5-[N-(3-trifluoromethylphenyl)carbamoyl]-phenyl]-8-(2-pyridyl)-2-[(tetrahydropyran-4-yl)amino]quinazoline (Nov. 9, 2009).
Author Unknown, CAS Registry No. 1191930-10-5, (7-Hydroxy-6-[2-methyl-5-[N-(3-trifluoromethylphenyl)carbamoyl]-phenyl]-8-(2-pyridyl)-2-[(tetrahydropyran-4-yl)amino]quinazoline (Nov. 9, 2009).
Author Unknown, CAS Registry No. 1191930-11-6, 7-Hydroxy-8-(1-methyl-1H-pyrazol-4-yl)-6-[2-methyl-5-[N-(3-trifluoromethylphenyl)carbamoyl]phenyl]-2-[(tetrahydropyran-4-yl)amino]quinazoline (Nov. 9, 2009).
Author Unknown, CAS Registry No. 1191931-59-5, 8-(4-Fluorophenyl)-7-hydroxy-6-[2-methyl-5-[N-(3-trifluoromethylphenyl)carbamoyl]phenyl]-2-[(tetrahydropyran-4-yl)amino]quinazoline (Nov. 9, 2009).
Author Unknown, CAS Registry No. 1191931-68-6, 8-(2-Fluoropyridin-5-yl)-7-hydroxy-6-[2-methyl-5-[N-(3 trifluoromethylphenyl)carbamoyl]phenyl]-2-[(tetrahydropyran-4-yl)amino]quinazoline (Nov. 9, 2009).
Author Unknown, CAS Registry No. 1191932-36-1, 3-[8-bromo-7-methoxy-2-[(tetrahydro-2H-pyran-4-yl)amino]-6-quinazolinyl]-4-methyl-N-[3-(trifluoromethyl)phenyl]-benzamide (Nov. 9, 2009).
Author Unknown, CAS Registry No. 1222803-87-3, N-[3-[7-[[4-(diethylamino)butyl]amino]-3-(3,5-dimethoxyphenyl)-3,4-dihydro-2-oxopyrimido[4,5-d]pyrimidin-1(2H)-yl]phenyl]-2-propenamide (May 13, 2010).
Author Unknown, CAS Registry No. 1222818-46-3, N-[3-[[7-[[4-(diethylamino)butyl]amino]-3-(3,5-dimethoxyphenyl)-3,4-dihydro-2-oxopyrimido[4,5-d]pyrimidin-1(2H)-yl]methyl]phenyl]-2-propenamide (May 13, 2010).
Author Unknown, CAS Registry No. 1222867-14-2, N-[3-[3-(2,6-dichloro-3,5-dimethoxyphenyl)-7-[[4-(diethylamino)butyl]amino]-3,4-dihydro-2-oxopyrimido[4,5-d]pyrimidin-1(2H)-yl]phenyl]-2-propenamide (May 13, 2010).
Author Unknown, CAS Registry No. 1255650-64-6, N-[3-[[3-(2,6-dichloro-3,5-dimethoxyphenyl)-7-[[4-(diethylamino)butyl]amino]-3,4-dihydro-2-oxopyrimido[4,5-d]pyrimidin-1(2H)-yl]methyl]phenyl]-propanamide (Dec. 7, 2010).
Author Unknown, CAS Registry No. 1256152-35-8, N-[3-[[3-(2,6-Dichloro-3,5-dimethoxyphenyl)-7-[[4-(diethylamino)butyl]amino]-3,4-dihydro-2-oxopyrimido[4,5-d]pyrimidin-1(2H)-yl]methyl]phenyl]-2-propenamide (Dec. 9, 2010).
Author Unknown, CAS Registry No. 1442470-70-3, 3-(5-Amino-2-chloro-4-fluorophenyl)-1-ethyl-7-(tetrahydrofuran-3-ylamino)-1,6-naphthyridin-2(1H)-one (Jun. 28, 2013).
Author Unknown, CAS Registry No. 1442472-85-6, 1-[4-Chloro-5-[1-ethyl-2-oxo-7-(tetrahydrofuran-3-ylamino)-1,2-dihydro-1,6-naphthyridin-3-yl]-2-fluorophenyl]-3-phenylurea (Jun. 28, 2013).
Author Unknown, CAS Registry No. 1442472-93-6, 3-(5-Amino-2-chloro-4-fluorophenyl)-1-ethyl-7-(1-methylpyrrolidin-3-ylamino)-1,6-naphthyridin-2(1H)-one (Jun. 28, 2013).
Author Unknown, CAS Registry No. 1442472-95-8, 1-[4-Chloro-5-[1-ethyl-7-(1-methylpyrrolidin-3-ylamino)-2-oxo-1,2-dihydro-1,6-naphthyridin-3-yl]-2-fluorophenyl]-3-phenylurea (Jun. 28, 2013).
Author Unknown, CAS Registry No. 839706-57-9, N-[3-[7-(cyclopropylamino)-1,4-dihydro-2-oxo-1-[2-(2-pyridinyl)ethyl]pyrimido[4,5-d]pyrimidin-3(2H)-yl]-5-methoxyphenyl]-3-(trifluoromethyl)-benzamide (Mar. 1, 2005).
Author Unknown, CAS Registry No. 914391-54-1, 6-(2-Chlorophenyl)-7-methoxy-2-[(tetrahydropyran-4-yl)amino]quinazoline (Nov. 30, 2006).
Author Unknown, CAS Registry No. 914395-29-2, 6-(3-Acetylaminophenyl)-7-methoxy-2-[(tetrahydropyran-4-yl)amino]quinazoline (Nov. 30, 2006).
Chang, S. et al., Design, Synthesis, and Biological Evaluation of Novel Conformationally Constrained Inhibitors Targeting Epidermal Growth Factor Receptor Threonine$^{790}$--> Methionine$^{790}$ Mutant, J. Med. Chem., 55: 2711-2723 (2012).
Cheng, A.L. et al., Targeting fibroblast growth factor receptor signaling in hepatocellular carcinoma, Oncology, 81(5-6): 372-380 (2011).
Guagnano, V. et al., NVP-BGJ398: A Potent and Selective Inhibitor of the Fibroblast Growth Factor Receptor Family, Novartis, Poster, Abstract #B246 (2011).
Harrington, E.A. et al., VX-680, a potent and selective small-molecule inhibitor of the Aurora kinases, suppresses tumor growth in vivo, Nature Medicine, 10(3): 262-267 (2004).
Ho, H. K. et al., Developing FGFR4 Inhibitors as Potential Anti-Cancer Agents via in Silico Design, Supported by In Vitro and Cell-Based Testing, Current Medicinal Chemistry, 20: 1203-1217 (2013).
International Search Report for PCT/US14/29270, 4 pages (dated Aug. 11, 2014).
Knights, V. and Cook, S.J., De-regulated FGF receptors as therapeutic targets in cancer, Pharmacology & Therapeutics, 125(1): 105-117 (2010).
Miraoui, H. and Marie, P.J., Fibroblast growth factor receptor signaling crosstalk in skeletogenesis, Sci. Signal., 3(146): re9 1-5 (2010).
Mohammadi, M. et al., Crystal structure of an angiogenesis inhibitor bound to the FGF receptor tyrosine kinase domain, EMBO J., 17(20): 5896-5904 (1998).
Pike, et al., Identifying Selective Inhibitors of FGFR4 kinase, Abstract LE098, EFMC International Symposium on Medicinal Chemistry, LE098 (Sep. 7-11, 2014).
Prime et al., Phthalazinone Pyrazoles as Potent, Selective, and Orally Bioavailable Inhibitors of Aurora-A Kinase, J. Med. Chem., 54(1): 312-319 (2011).
Thompson, A.M. et al., Synthesis and structure-activity relationships of soluble 7-substituted 3-(3,5-dimethoxyphenyl)-1,6-naphthyridin-2-amines and related ureas as dual inhibitors of the fibroblast growth factor receptor-1 and vascular endothelial growth factor receptor-2 tyrosine kinases, J. Med. Chem., 48(14): 4628-4653 (2005).
Turner, N. and Grose, R., Fibroblast growth factor signalling: from development to cancer, Nature Reviews Cancer, 10(2): 116-129 (2010).

(56) References Cited

OTHER PUBLICATIONS

Written Opinion for PCT/US14/29270, 7 pages (dated Aug. 11, 2014).
Zhou et al., A Structure-Guided Approach to Creating Covalent FGFR Inhibitors', Chem. Biol., 17: 285-295 (2010).
U.S. Appl. No. 15/635,954, filed Jun. 28, 2017, Heteroaryl Compounds and Uses Thereof, 2018/0022713-A1, pending.

* cited by examiner

THE AMINO ACID SEQUENCE OF FGFR4 (SEQ ID NO. 1)

```
          10         20         30         40         50         60
     MRLLLALLGV LLSVPGPPVL SLEASEEVEL EPCLAPSLEQ QEQELTVALG QPVRLCCGRA
          70         80         90        100        110        120
     ERGGHWYKEG SRLAPAGRVR GWRGRLEIAS FLPEDAGRYL CLARGSMIVL QNLTLITGDS
         130        140        150        160        170        180
     LTSSNDDEDP KSHRDPSNRH SYPQQAPYWT HPQRMEKKLH AVPAGNTVKF RCPAAGNPTP
         190        200        210        220        230        240
     TIRWLKDGQA FHGENRIGGI RLRHQHWSLV MESVVPSDRG TYTCLVENAV GSIRYNYLLD
         250        260        270        280        290        300
     VLERSPHRPI LQAGLPANTT AVVGSDVELL CKVYSDAQPH IQWLKHIVIN GSSFGADGFP
         310        320        330        340        350        360
     YVQVLKTADI NSSEVEVLYL RNVSAEDAGE YTCLAGNSIG LSYQSAWLTV LPEEDPTWTA
         370        380        390        400        410        420
     AAPEARYTDI ILYASGSLAL AVLLLLAGLY RGQALHGRHP RPPATVQKLS RFPLARQFSL
         430        440        450        460        470        480
     ESGSSGKSSS SLVRGVRLSS SGPALLAGLV SLDLPLDPLW EFPRDRLVLG KPLGEGCFGQ
         490        500        510        520        530        540
     VVRAEAFGMD PARPDQASTV AVKMLKDNAS DKDLADLVSE MEVMKLIGRH KNIINLLGVC
         550        560        570        580        590        600
     TQEGPLYVTV ECAKGNLRE FLRARRPPGP DLSPDGPRSS EGPLSFPVLV SCAYQVARGM
         610        620        630        640        650        660
     QYLESRKCIH RDLAARNVLV TEDNVMKIAD FGLARGVHHI DYYKKTSNGR LPVKWMAPEA
         670        680        690        700        710        720
     LFDRVYTHQS DVWSFGILLW EIFTLGGSPY PGIPVEELFS LLREGHRMDR PPHCPPELYG
         730        740        750        760        770        780
     LMRECWHAAP SQRPTFKQLV EALDKVLLAV SEEYLDLRLT FGPYSPSGGD ASSTCSSSDS
         790        800
     VFSHDPLPLG SSSFPFGSGV QT
```

SUBSTITUTED PYRIDO[2,3-D]PYRIMIDINES AS INHIBITORS OF PROTEIN KINASES

CROSS-REFERENCE TO RELATED APPLICATIONS

The present application is a divisional of U.S. Ser. No. 14/776,373, filed Sep. 14, 2015 (now U.S. Pat. No. 9,663,524), which is a national phase application under 35 U.S.C. § 371 of PCT International Application No. PCT/US2014/029270, filed Mar. 14, 2014, which claims priority to U.S. provisional application No. 61/793,113, filed Mar. 15, 2013, and European application number EP14305361, filed Mar. 13, 2014, the entirety of each of which is hereby incorporated by reference.

TECHNICAL FIELD OF THE INVENTION

The present invention relates to compounds useful as inhibitors of protein kinases. The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_7O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases.

Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of one or more protein kinases. Such compounds have general formula I:

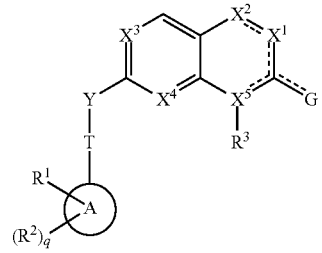

or a pharmaceutically acceptable salt thereof, wherein each of Ring A, $R^1$, $R^2$, $R^3$, $X^1$, $X^2$, $X^3$, $X^4$, $X^5$, G, Y, T, and q, is as defined and described in embodiments herein. In certain embodiments, $R^1$ is a warhead group.

Compounds of the present invention, and pharmaceutically acceptable compositions thereof, are useful for treating a variety of diseases, disorders or conditions, associated with abnormal cellular responses triggered by protein kinase-mediated events. Such diseases, disorders, or conditions include those described herein.

Compounds provided by this invention are also useful for the study of kinases in biological and pathological phenomena; the study of intracellular signal transduction pathways mediated by such kinases; and the comparative evaluation of new kinase inhibitors.

BRIEF DESCRIPTION OF THE DRAWINGS

FIG. 4: The amino acid sequence of FGFR4 (SEQ ID NO. 1).

DETAILED DESCRIPTION OF CERTAIN EMBODIMENTS

Figure 1:
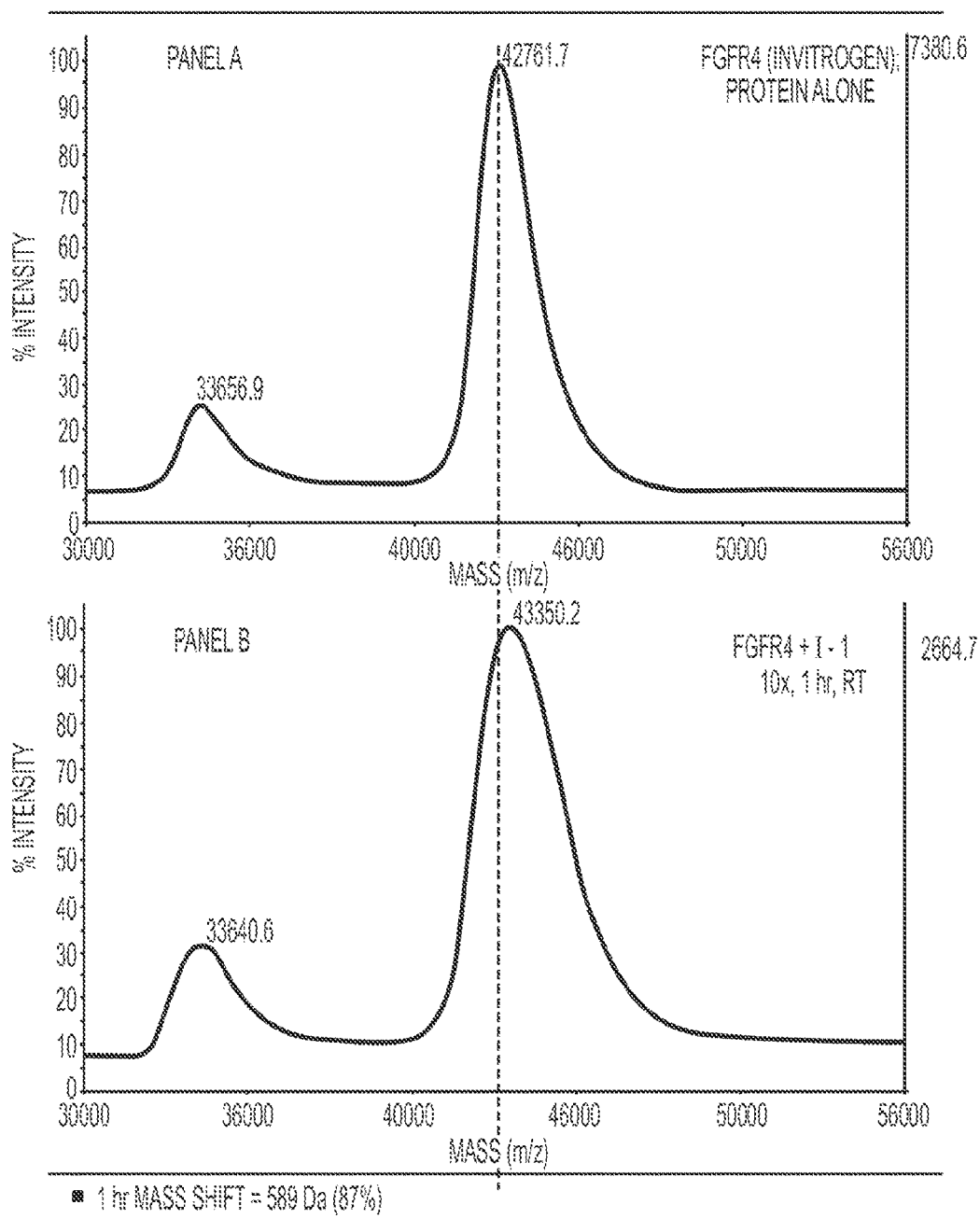
FIG. 1: Mass Modification of FGFR4 by I-1.

1. General Description of Compounds of the Invention

In certain embodiments, the present invention provides irreversible inhibitors of FGFR4. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

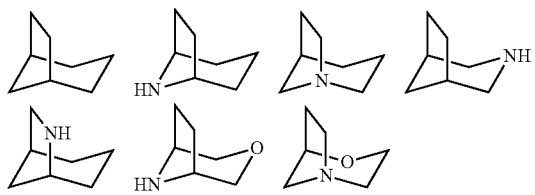

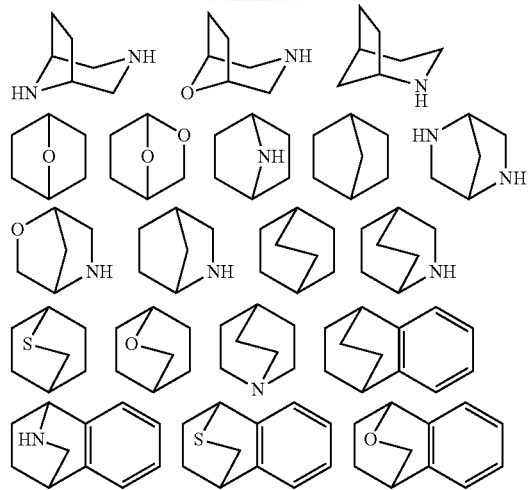

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

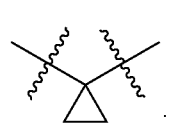 [SMILES: *C1(*)CC1]

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

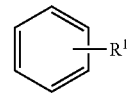

refers to at least

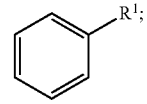

and

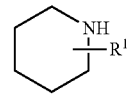

refers to at least

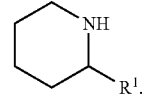

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which are optionally substituted with R°; —(CH$_2$)$_{0-4}$O(CH$_2$)$_{0-1}$Ph which is optionally substituted with R°; —CH=CHPh, which is optionally substituted with R°; —(CH$_2$)$_{0-4}$O(CH$_2$)$_{0-1}$-pyridyl which is optionally substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R; —OC(O)(CH$_2$)$_{0-4}$SR°, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° is optionally substituted as defined below and is independently hydrogen, C$_{1-6}$ aliphatic, —CH$_2$Ph, —O(CH$_2$)$_{0-4}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R° is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR°), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In some embodiments, the $R^1$ group comprises one or more deuterium atoms.

As used herein, the term "irreversible" or "irreversible inhibitor" refers to an inhibitor (i.e. a compound) that is able to be covalently bonded to a target protein kinase in a substantially non-reversible manner. That is, whereas a reversible inhibitor is able to bind to (but is generally unable to form a covalent bond) the target protein kinase, and therefore can become dissociated from the target protein kinase, an irreversible inhibitor will remain substantially bound to the target protein kinase once covalent bond formation has occurred. Irreversible inhibitors usually display time dependency, whereby the degree of inhibition increases with the time with which the inhibitor is in contact with the enzyme. In certain embodiments, an irreversible inhibitor will remain substantially bound to a kinase once covalent bond formation has occurred and will remain bound for a time period that is longer than the life of the protein.

Methods for identifying if a compound is acting as an irreversible inhibitor are known to one of ordinary skill in the art. Such methods include, but are not limited to, enzyme kinetic analysis of the inhibition profile of the compound with the protein kinase target, the use of mass spectrometry of the protein drug target modified in the presence of the inhibitor compound, discontinuous exposure, also known as "washout," experiments, and the use of labeling, such as radiolabelled inhibitor, to show covalent modification of the enzyme, as well as other methods known to one of skill in the art.

One of ordinary skill in the art will recognize that certain reactive functional groups can act as "warheads." As used herein, the term "warhead" or "warhead group" refers to a functional group present on a compound of the present invention wherein that functional group is capable of covalently binding to an amino acid residue (such as cysteine, lysine, histidine, or other residues capable of being covalently modified) present in the binding pocket of the target protein, thereby irreversibly inhibiting the protein. It will be appreciated that the -L-Y group, as defined and described herein, provides such warhead groups for covalently, and irreversibly, inhibiting the protein. In certain instances, a "pro-warhead group" is used in place of a warhead groups. Such pro-warhead groups convert to a warhead group in vivo or in vitro.

As used herein, the term "inhibitor" is defined as a compound that binds to and/or inhibits the target protein kinase with measurable affinity. In certain embodiments, an inhibitor has an $IC_{50}$ and/or binding constant of less about 50 μM, less than about 1 μM, less than about 500 nM, less than about 100 nM, or less than about 10 nM.

The terms "measurable affinity" and "measurably inhibit," as used herein, means a measurable change in FGFR4 activity between a sample comprising a compound of the present invention, or composition thereof, and FGFR4, and an equivalent sample comprising FGFR4, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

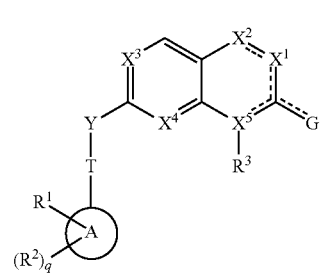

I or a pharmaceutically acceptable salt thereof, wherein:
$X^1$ is —$NR^4$, N, —$CR^4R^{4'}$, or —$CR^4$;
$X^2$ is —$NR^5$, N, —$CR^5R^{5'}$, or —$CR^5$;
$X^3$ is N or $CR^6$;
$X^4$ is N or $CR^7$;
$X^5$ is N, C, or CH; wherein at least one of $X^1$, $X^2$, $X^3$, $X^4$, or $X^5$ is N;
G is H, O, OR, or N(R)(R);
Ring A is an optionally substituted group selected from phenyl, a 3-8 membered saturated or partially unsaturated carbocyclic ring, a 5-6 membered monocyclic heteroaryl ring having 1-4 heteroatoms independently selected from nitrogen, oxygen, or sulfur, a 4-7 membered saturated or partially unsaturated heterocyclic ring having 1-4 heteroatoms independently selected from nitrogen, oxygen, or sulfur, or a 7-10 membered bicyclic saturated, partially unsaturated or aryl ring;
each R is independently hydrogen or an optionally substituted group selected from $C_{1-6}$ aliphatic, phenyl, a 3-8 membered saturated or partially unsaturated carbocyclic ring, a 4-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; or
two R groups on the same nitrogen are taken together with the nitrogen atom to which they are attached to form a 4-7 membered heterocyclic ring having 0-2 additional heteroatoms independently selected from nitrogen, oxygen, or sulfur, or a 4-7 membered heteroaryl ring having 0-4 additional heteroatoms independently selected from nitrogen, oxygen, or sulfur;
$R^1$ is a warhead group; wherein $R^1$ is attached to an atom adjacent to the atom where T is attached;
each $R^2$ is independently —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;
$R^3$ is hydrogen, $C_{2-6}$ alkenyl, —W-Cy, or $C_{1-6}$ alkyl, wherein the $C_{1-6}$ alkyl is optionally substituted with 1-3 groups independently selected from halogen, —CN, oxo, —OR', or —C(O)O($C_{1-6}$ alkyl);
W is absent or is a bivalent $C_{1-3}$ alkylene chain optionally substituted with one or more R" and wherein one methylene unit of W is optionally replaced with —O—, —S—, or —NR'—;
each R' is independently hydrogen or $C_{1-6}$ alkyl;
each R" is independently halogen or $C_{1-6}$ alkyl, wherein the $C_{1-6}$ alkyl is optionally substituted with 1-3 groups independently selected from halogen, —CN, oxo, or —OR';
Cy is phenyl, $C_{3-7}$ cycloalkyl, or a 3-7 membered monocyclic or 5-10 membered bicyclic saturated, partially unsaturated, or heteroaryl ring having 1-3 heteroatoms independently selected from nitrogen, oxygen, or sulfur, wherein Cy is optionally substituted with 1-3 $R^x$;
each $R^x$ is independently H, —CN, oxo, —$NH_2$, $C_{1-6}$ alkyl, halogen, —OR', —N(R')$_2$, —NHC(O)($C_{1-6}$ alkyl), —C(O)N(R')$_2$, —C(O)O($C_{1-6}$ alkyl), —$NHSO_2$($C_{1-6}$ alkyl), or —$SO_2$N(R')$_2$;
or $R^3$ is absent if not allowed by valence;
each of $R^4$ and $R^{4'}$ is independently hydrogen or an optionally substituted group selected from $C_{1-6}$ aliphatic, phenyl, a 3-8 membered saturated or partially unsaturated carbocyclic ring which is optionally bridged, a 4-7 membered heterocyclic ring having 1-4 heteroatoms independently selected from nitrogen, oxygen, or sulfur, a 5-6 membered monocyclic heteroaryl ring having 1-4 heteroatoms independently selected from nitrogen, oxygen, or sulfur, or a 7-10 membered bicyclic saturated, partially unsaturated or aryl ring, which is optionally bridged;
each of $R^5$ and $R^{5'}$ is independently —R, halogen, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;
Y is O or $NR^a$;
$R^a$ is hydrogen or an optionally substituted $C_{1-6}$ aliphatic group;
T is a covalent bond or a bivalent straight or branched, saturated or unsaturated $C_{1-6}$ hydrocarbon chain wherein one or more methylene units are optionally replaced by —O—, —S—, —N(R)—, —C(O)—, —OC(O)—, —C(O)O—, —C(O)N(R)—, —N(R)C(O)—, —N(R)C(O)N(R)—, —S(O)—, —$SO_2$—, —$SO_2$N(R)—, —N(R)$SO_2$—, or —N(R)$SO_2$N(R)—;
q is 0-6; and
each of $R^6$ and $R^7$ is independently —R, halogen, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$.

In certain embodiments, $X^1$ is —$NR^4$. In certain embodiments, $X^1$ is N. In certain embodiments, $X^1$ is —$CR^4R^{4'}$. In certain embodiments, $X^1$ is —$CR^4$.

In certain embodiments, $X^2$ is —$NR^5$. In certain embodiments, $X^2$ is N. In certain embodiments, $X^2$ is —$CR^5R^{5'}$. In certain embodiments, $X^2$ is —$CR^5$.

In certain embodiments, $X^3$ is N. In certain embodiments, $X^3$ is $CR^6$.

In certain embodiments, $X^4$ is N. In certain embodiments, $X^4$ is $CR^7$.

In certain embodiments, $X^5$ is N. In certain embodiments, $X^5$ is C. In certain embodiments, $X^5$ is CH.

In certain embodiments, G is H. In certain embodiments, G is O. In certain embodiments, G is OR. In certain embodiments, G is N(R)(R).

In certain embodiments, G is OMe. In certain embodiments, G is $NH_2$.

In certain embodiments, Y is O. In certain embodiments, Y is $NR^a$.

As defined generally above, Ring A is an optionally substituted group selected from phenyl, a 3-8 membered saturated or partially unsaturated carbocyclic ring, a 5-6 membered monocyclic heteroaryl ring having 1-4 heteroatoms independently selected from nitrogen, oxygen, or sulfur, a 4-7 membered saturated or partially unsaturated heterocyclic ring having 1-4 heteroatoms independently selected from nitrogen, oxygen, or sulfur, or a 7-10 membered bicyclic saturated, partially unsaturated or aryl ring.

In certain embodiments, Ring A is an optionally substituted phenyl group. In some embodiments, Ring A is an optionally substituted a 3-8 membered saturated or partially unsaturated carbocyclic ring. In some embodiments, Ring A is an optionally substituted 5-6 membered monocyclic heteroaryl ring having 1-4 heteroatoms independently selected from nitrogen, oxygen, or sulfur. In some embodiments, Ring A is an optionally substituted 4-7 membered saturated or partially unsaturated heterocyclic ring having 1-4 heteroatoms independently selected from nitrogen, oxygen, or sulfur. In some embodiments, Ring A is an optionally substituted 7-10 membered bicyclic saturated, partially unsaturated or aryl ring.

In various embodiments, Ring A is cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, Ring A is phenyl, cyclohexyl, cyclohexenyl, cyclopentyl, cyclobutyl, cyclopropyl, pyridine, pyrmidine, pyrazine, pyridazine, pyrrole, pyrazole, piperidine, piperidin-one, pyrrolidine, tetrahydropyran, tetrahydrofuran, tetrahydrothiophene dioxide, or cyclobutene dione.

In certain embodiments, Ring A is an optionally substituted group selected from phenyl, cyclohexyl, a 7-8 membered saturated or partially unsaturated carbocyclic ring, or a 4-7 membered saturated or partially unsaturated heterocyclic ring having 1-3 heteroatoms independently selected from nitrogen, oxygen, or sulfur.

In various embodiments, Ring A is an optionally substituted group selected from phenyl or cyclohexyl.

In certain embodiments, Ring A is substituted as defined herein. In some embodiments, Ring A is substituted with one, two, or three $R^2$ groups each of which is independently selected. Exemplary substituents on Ring A include Br, I, Cl, F, Me, —$CF_3$, —OMe, —OR, —$N(R)_2$, pyrazolyl, thiazolyl, piperidinyl, piperazinyl, or morpholinyl.

Exemplary Ring A groups are set forth below:

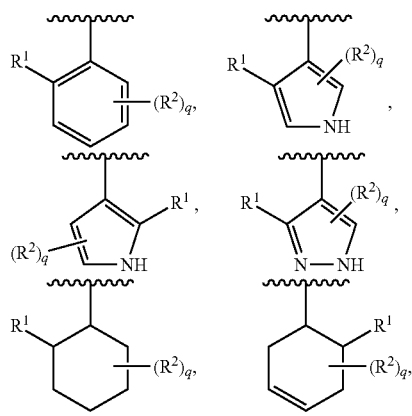

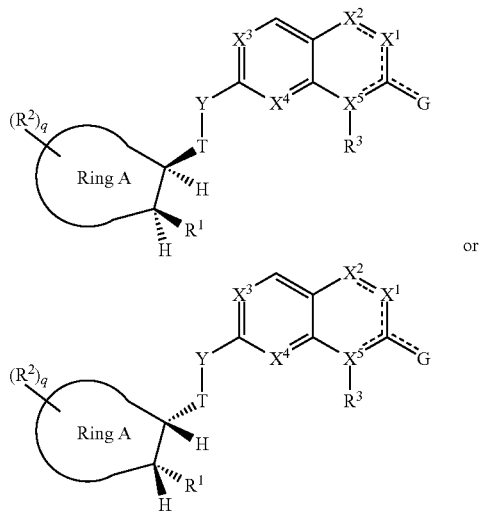

In some embodiments, Ring A comprises one or more chiral centers which are of a particular configuration.

In certain embodiments, Ring A is a 3-8 membered saturated or partially unsaturated carbocyclic ring, a 4-7 membered saturated or partially unsaturated heterocyclic ring having 1-4 heteroatoms independently selected from nitrogen, oxygen, or sulfur, or a 7-10 membered bicyclic saturated or partially unsaturated ring, wherein substituents -T-Y— and $R^1$ of Ring A are in a "cis" configuration.

One of skill in the chemical arts will appreciate that by "cis," in the context substituents -T-Y— and $R^1$ of Ring A, is meant a compound comprising either of the following Ring A configurations:

wherein each of Ring A, $R^1$, $R^2$, $R^3$, $X^1$, $X^2$, $X^3$, $X^4$, $X^5$, G, Y, T, and q, is as defined above and described in embodiments, classes and subclasses above and herein, singly or in combination.

In some embodiments, a compound of the present invention is of formula I-cis(1):

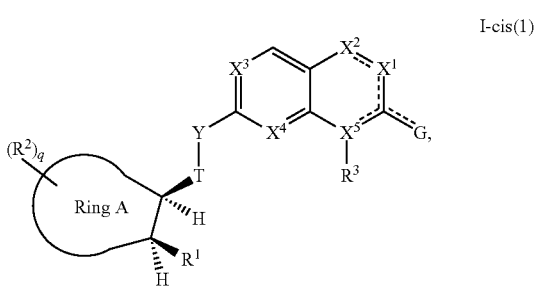

or a pharmaceutically acceptable salt thereof, or a pharmaceutically acceptable salt thereof, wherein each of Ring A, $R^1$, $R^2$, $R^3$, $X^1$, $X^2$, $X^3$, $X^4$, $X^5$, G, Y, T, and q, is as defined above and described in embodiments, classes and subclasses above and herein, singly or in combination.

For instance, in some embodiments, the present invention provides a compound of formula I-cis(1), wherein Ring A is a 3-8 membered saturated or partially unsaturated carbocyclic ring. In some embodiments, the present invention provides a compound of formula I-cis(1), wherein Ring A is a 4-7 membered saturated or partially unsaturated heterocyclic ring having 1-4 heteroatoms independently selected from nitrogen, oxygen, or sulfur. In some embodiments, the present invention provides a compound of formula I-cis(1), wherein Ring A is a 7-10 membered bicyclic saturated or partially unsaturated ring.

In certain embodiments, the present invention provides a compound of formula I-cis(1), wherein Ring A is optionally substituted and is selected from cyclohexyl, cyclohexenyl, cyclopentyl, cyclobutyl, cyclopropyl, piperidine, piperidinone, pyrrolidine, tetrahydropyran, tetrahydrofuran, tetrahydrothiophene dioxide, or cyclobutene dione. In certain embodiments, the present invention provides a compound of formula I-cis(1), wherein Ring A is optionally substituted tetrahydrofuran.

Exemplary compounds of formula I-cis(1) include, for instance, compounds I-82, I-92, I-114, I-241, I-186, and the like.

In some embodiments, the present invention provides a compound of formula I-cis(2), wherein Ring A is any of the structures described above and herein which are capable of having chiral centers at the sites depicted in formula I-cis(1).

In some embodiments, a compound of the present invention is of formula I-cis(2):

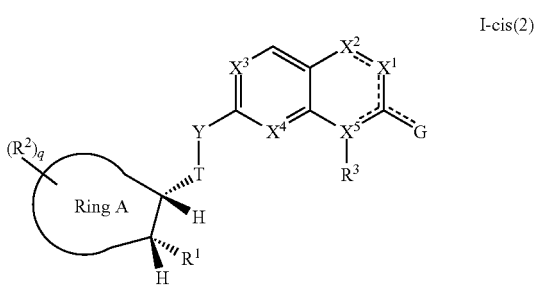

or a pharmaceutically acceptable salt thereof, or a pharmaceutically acceptable salt thereof, wherein each of Ring A, $R^1$, $R^2$, $R^3$, $X^1$, $X^2$, $X^3$, $X^4$, $X^5$, G, Y, T, and q, is as defined above and described in embodiments, classes and subclasses above and herein, singly or in combination.

For instance, in some embodiments, the present invention provides a compound of formula I-cis(2), wherein Ring A is a 3-8 membered saturated or partially unsaturated carbocyclic ring. In some embodiments, the present invention provides a compound of formula I-cis(2), wherein Ring A is a 4-7 membered saturated or partially unsaturated heterocyclic ring having 1-4 heteroatoms independently selected from nitrogen, oxygen, or sulfur. In some embodiments, the present invention provides a compound of formula I-cis(2), wherein Ring A is a 7-10 membered bicyclic saturated or partially unsaturated ring.

In certain embodiments, the present invention provides a compound of formula I-cis(2), wherein Ring A is optionally substituted and is selected from cyclohexyl, cyclohexenyl, cyclopentyl, cyclobutyl, cyclopropyl, piperidine, piperidinone, pyrrolidine, tetrahydropyran, tetrahydrofuran, tetrahydrothiophene dioxide, or cyclobutene dione. In certain embodiments, the present invention provides a compound of formula I-cis(2), wherein Ring A is optionally substituted tetrahydrofuran.

Exemplary compounds of formula I-cis(2) include, for instance, compounds I-66, I-93, I-119, I-240, I-185, and the like.

In some embodiments, the present invention provides a compound of formula I-cis(2), wherein Ring A is any of the structures described above and herein which are capable of having chiral centers at the sites depicted in formula I-cis(2).

In another embodiment, each $R^2$ is independently —R.

In another embodiment, each $R^2$ is hydrogen.

In another embodiment, each $R^2$ is independently halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, each $R^2$ is independently methyl, ethyl, propyl, i-propyl, F, Cl, Br, I, CF$_3$, piperidinyl, piperazinyl, morpholinyl, tetrahydropyridinyl, pyrazolyl, thiazolyl, or tetrazolyl.

In certain embodiments, each $R^2$ is independently —CH$_3$, —Cl, —F, —CF$_3$, or —OMe; or is selected from

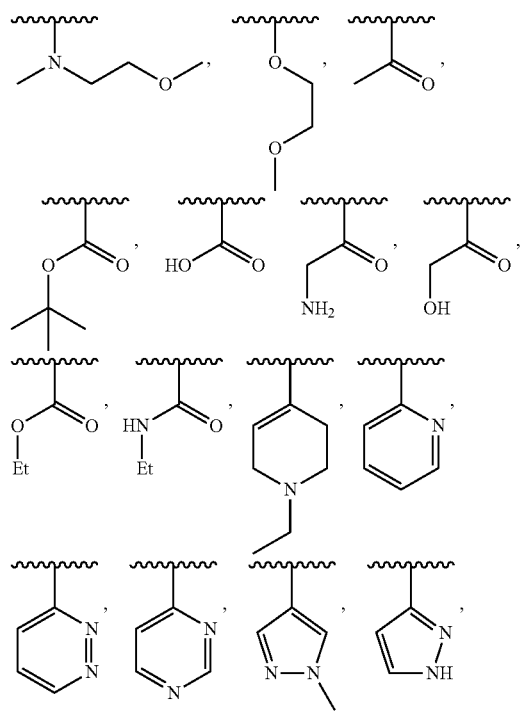

-continued
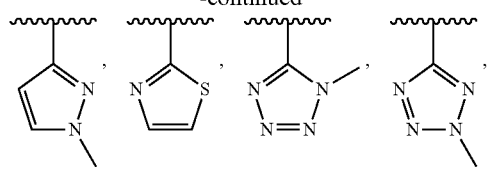
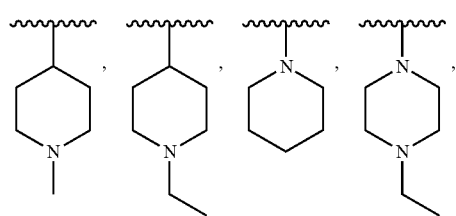
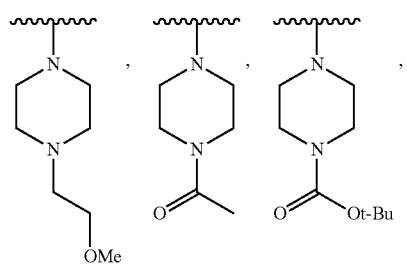
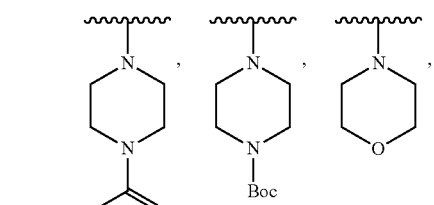
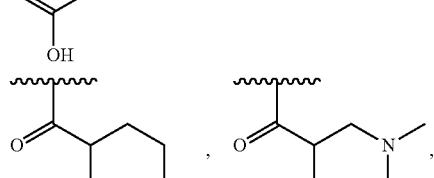
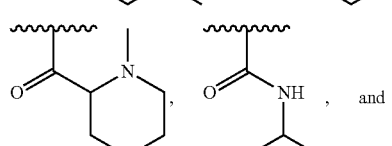, and
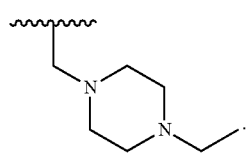.
In certain embodiments, Ring A is selected from
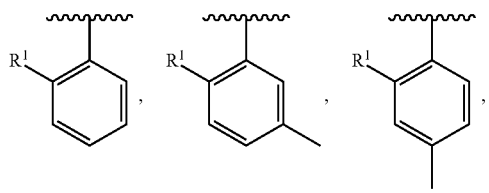
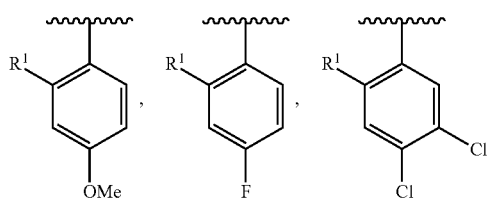
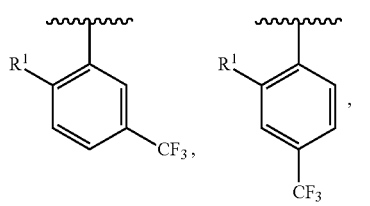
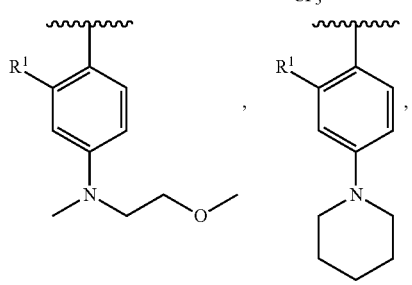
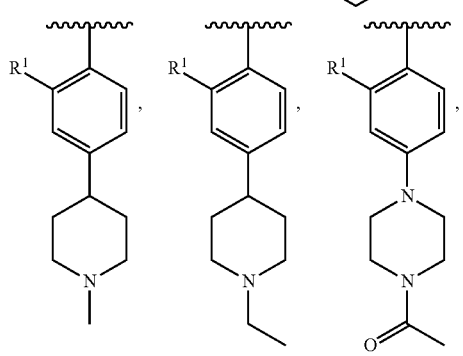
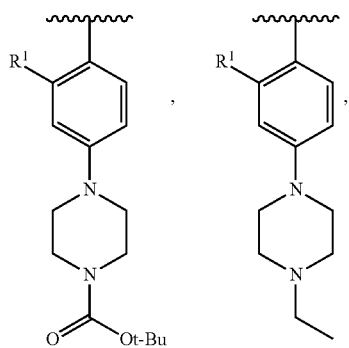

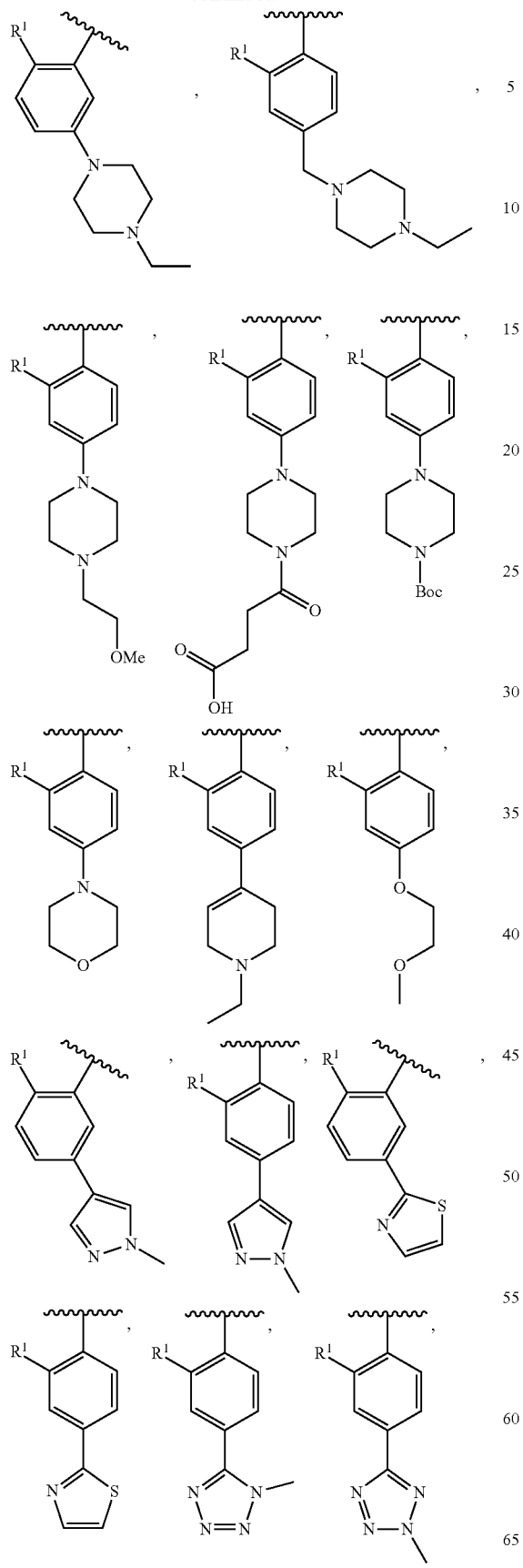
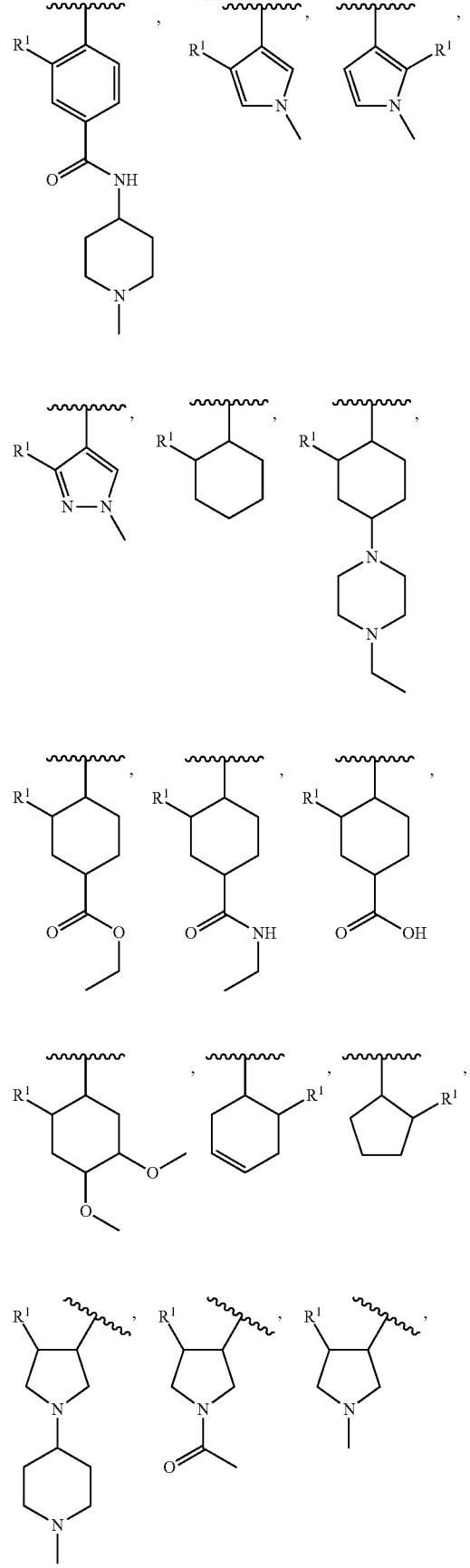

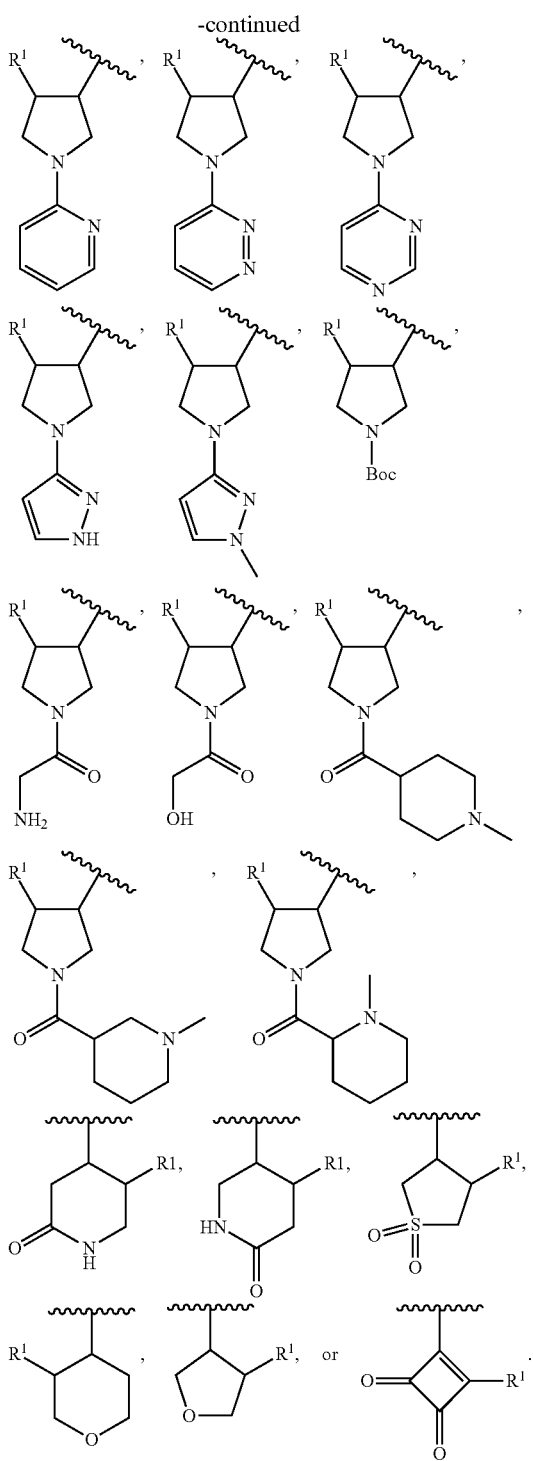

In various embodiments, $R^3$ is hydrogen.

In various embodiments, $R^3$ is $C_{2-6}$ alkenyl, —W-Cy, or $C_{1-6}$ alkyl, wherein the $C_{1-6}$ alkyl is optionally substituted with 1-3 groups independently selected from halogen, —CN, oxo, —OR', or —C(O)O($C_{1-6}$ alkyl).

In certain embodiments, W is absent (i.e., W is a covalent bond). In certain embodiments, W is a bivalent $C_{1-3}$ alkylene chain optionally substituted with one or more R" and wherein one methylene unit of W is optionally replaced with —O—, —S—, or —NR'—. In certain embodiments, Cy is phenyl wherein Cy is optionally substituted with 1-3 $R^x$. In certain embodiments, Cy is $C_{3-7}$ cycloalkyl wherein Cy is optionally substituted with 1-3 $R^x$. In certain embodiments, Cy is a 3-7 membered monocyclic or 5-10 membered bicyclic saturated or partially unsaturated heterocyclic having 1-3 heteroatoms independently selected from nitrogen, oxygen, or sulfur, wherein Cy is optionally substituted with 1-3 $R^x$. In certain embodiments, Cy is a 3-7 membered monocyclic or 5-10 membered bicyclic heteroaryl ring having 1-3 heteroatoms independently selected from nitrogen, oxygen, or sulfur, wherein Cy is optionally substituted with 1-3 $R^x$.

In some embodiments, each $R^x$ is independently H, —CN, oxo, —NH$_2$, $C_{1-6}$ alkyl, halogen, —OR', —N(R')$_2$, —C(O)R', —NHC(O)($C_{1-6}$ alkyl), —C(O)N(R')$_2$, —C(O)O($C_{1-6}$ alkyl), —NHSO$_2$($C_{1-6}$ alkyl), or —SO$_2$N(R')$_2$.

In some embodiments, $R^x$ is —C(O)R'. In some embodiments, $R^x$ is —C(O)Me.

In certain embodiments, $R^3$ is $C_{1-6}$ alkyl.

In certain embodiments, $R^3$ is cyclopropyl, cyclobutyl, cyclopentyl, cyclohexyl, cycloheptyl, oxetanyl, phenyl, piperidinyl, pyridinyl, pyrazolyl, thiazolyl, or pyridin-one-yl.

In certain embodiments, $R^3$ is

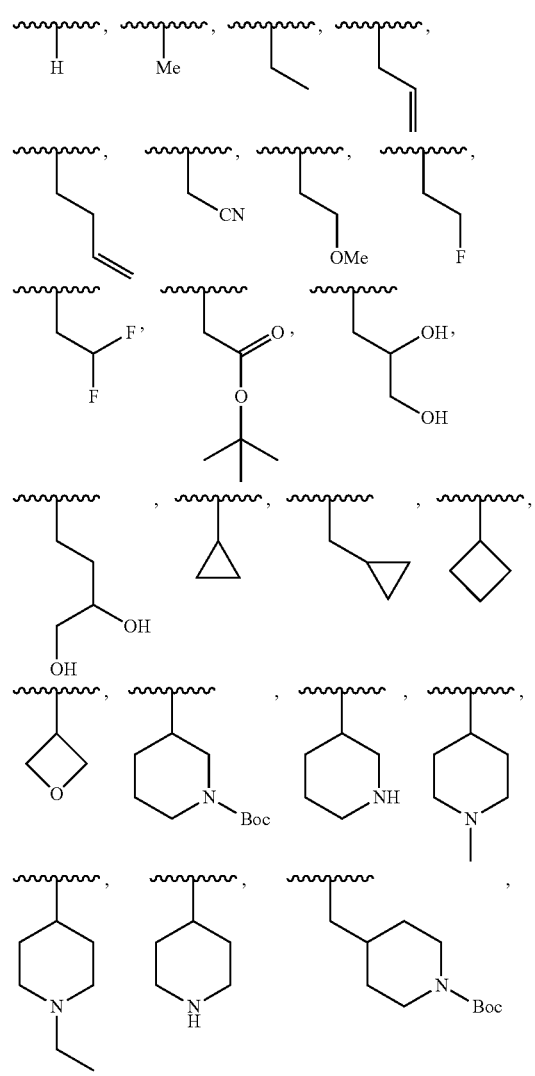

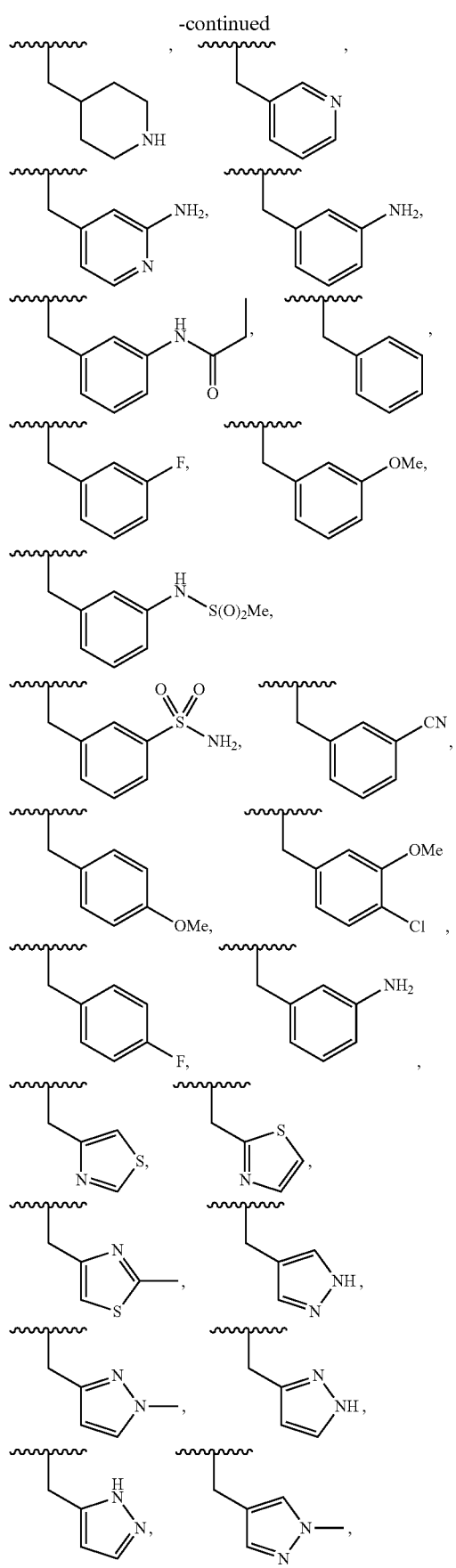

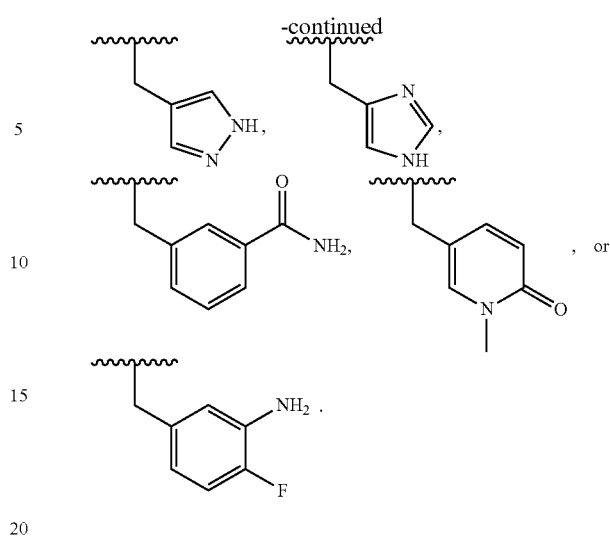

In some embodiments, $R^3$ is

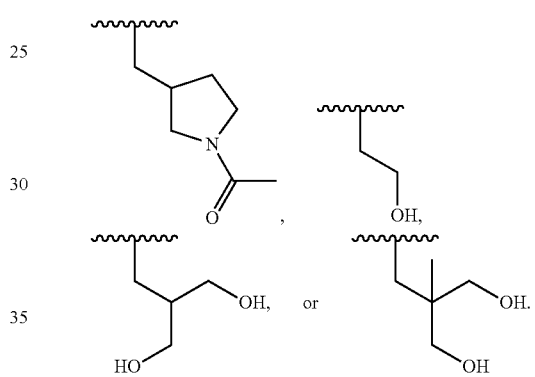

In certain embodiments, $R^3$ is absent.

In certain embodiments, each of $R^4$ and $R^{4'}$ is independently hydrogen.

In certain embodiments, each of $R^4$ and $R^{4'}$ is independently an optionally substituted phenyl. In certain embodiments, each of $R^4$ and $R^{4'}$ is independently an optionally substituted $C_{1-6}$ aliphatic. In certain embodiments, each of $R^4$ and $R^{4'}$ is independently a 3-8 membered saturated or partially unsaturated carbocyclic ring. In other embodiments, each of $R^4$ and $R^{4'}$ is independently an optionally substituted 4-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, each of $R^4$ and $R^{4'}$ is independently an optionally substituted phenyl or a 3-8 membered saturated or partially unsaturated carbocyclic ring. In certain embodiments, each of $R^4$ and $R^{4'}$ is independently an optionally substituted phenyl.

In certain embodiments, each of $R^4$ and $R^{4'}$ is independently an optionally substituted cyclopropyl, cyclobutyl, cyclopentyl, cyclohexyl, cycloheptyl, oxetanyl, phenyl, piperidinyl, pyridinyl, pyrazolyl, thiazolyl, or pyridin-one-yl.

In certain embodiments, each of $R^4$ and $R^{4'}$ is independently is ethyl, phenyl, cyclohexyl,

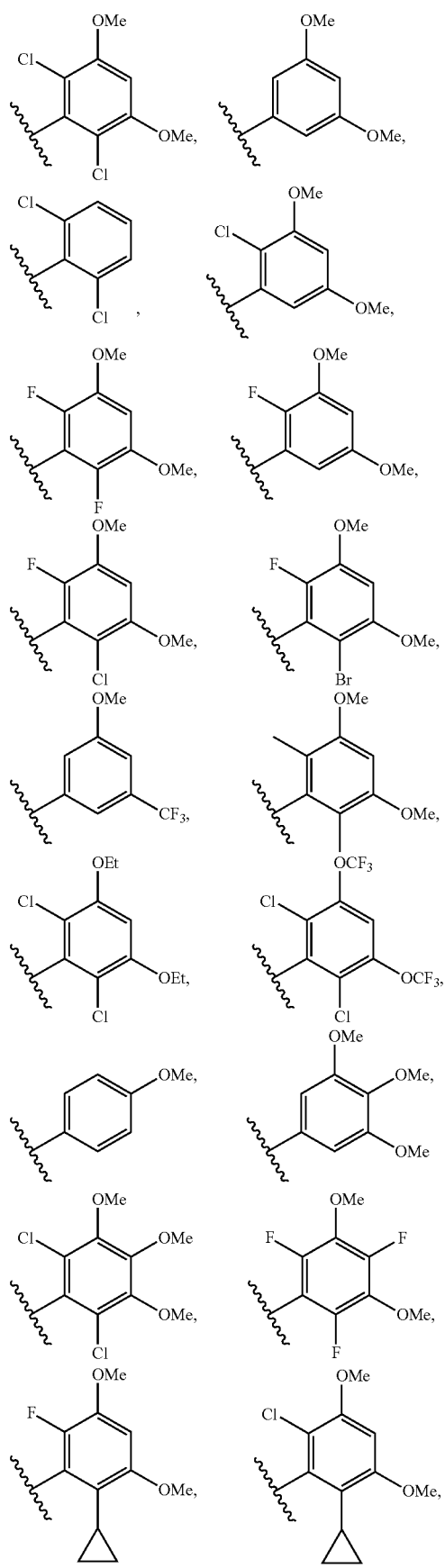
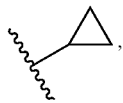
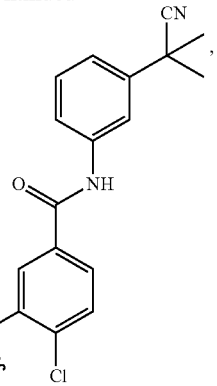
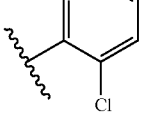
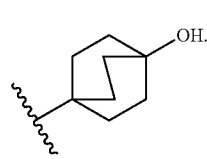
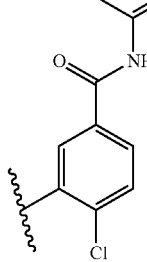
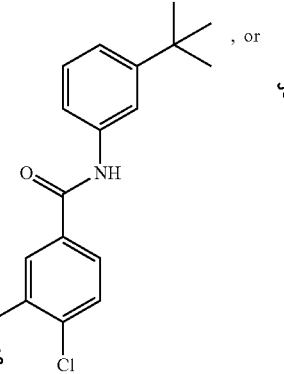

In certain embodiments, each of $R^5$ and $R^{5'}$ is independently —R.

In certain embodiments, each of $R^5$ and $R^{5'}$ is independently H. In certain embodiments, both of $R^5$ and $R^{5'}$ are H. In certain embodiments, one of $R^5$ and $R^{5'}$ is H. In certain embodiments, each of $R^5$ and $R^{5'}$ is independently H, or -Me.

In certain embodiments, each of $R^5$ and $R^{5'}$ is independently halogen, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$.

In some embodiments, $R^a$ is hydrogen. In some embodiments, $R^a$ is optionally substituted $C_{1-6}$ aliphatic group.

In another embodiment, T is a covalent bond. In another embodiment, T is a bivalent straight or branched, saturated or unsaturated $C_{1-6}$ hydrocarbon chain wherein one or more methylene units are optionally replaced by —O—, —S—, —N(R)—, —C(O)—, —OC(O)—, —C(O)O—, —C(O)N(R)—, —N(R)C(O)—, —N(R)C(O)N(R)—, —S(O)—, —$SO_2$—, —$SO_2N(R)$—, —N(R)$SO_2$—, or —N(R)$SO_2$N(R)—.

In another embodiment, T is a bivalent straight or branched, saturated or unsaturated $C_{1-6}$ hydrocarbon chain wherein one or more methylene units are optionally replaced by —O—, —S—, —N(R)—, —C(O)—, —OC(O)—, —C(O)O—, —C(O)N(R)—, —N(R)C(O)—, —N(R)C(O)N(R)—, —N(R)$SO_2$—, or —N(R)$SO_2$N(R)—.

In another embodiment, T is a covalent bond or a bivalent straight or branched, saturated or unsaturated $C_{1-6}$ hydrocarbon chain.

In certain embodiments, q is 0. In other embodiments, q is 1. In other embodiments, q is 2-6.

In certain embodiments, the present invention provides a compound of formula I-a,

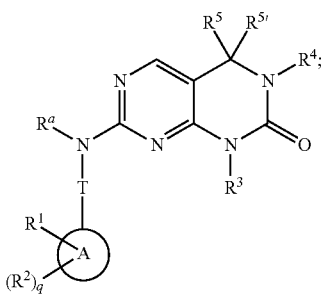

I-a or a pharmaceutically acceptable salt thereof, wherein each of $R^1$, $R^2$, $R^3$, $R^4$, $R^5$, $R^{5'}$, $R^a$, T, and q is as defined above and described in embodiments, classes and subclasses above and herein, singly or in combination.

In certain embodiments, the compound is of formula I-b:

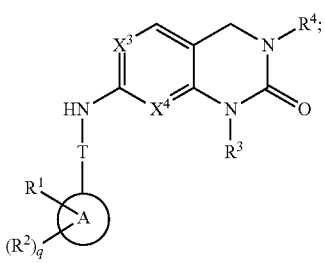

I-b or a pharmaceutically acceptable salt thereof, wherein each of Ring A, $R^1$, $R^2$, $R^3$, $R^4$, T, and q is as defined above and described in embodiments, classes and subclasses above and herein, singly or in combination.

In certain embodiments, the invention provides a compound of formula I-c:

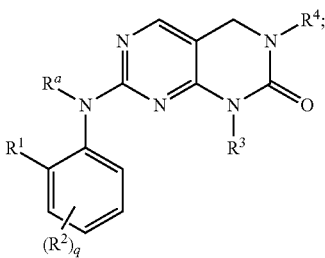

I-c or a pharmaceutically acceptable salt thereof, wherein each of $R^1$, $R^2$, $R^3$, $R^4$, $R^a$, and q is as defined above and described in embodiments, classes and subclasses above and herein, singly or in combination.

In certain embodiments, the invention provides a compound of formula I-d:

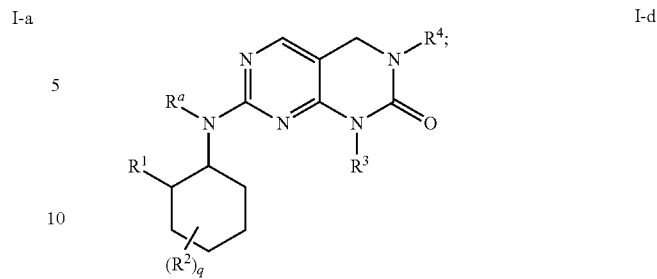

I-d or a pharmaceutically acceptable salt thereof, wherein each of $R^1$, $R^2$, $R^3$, $R^4$, $R^a$, and q is as defined above and described in embodiments, classes and subclasses above and herein, singly or in combination.

In other embodiments, the invention provides a compound of formula I-e:

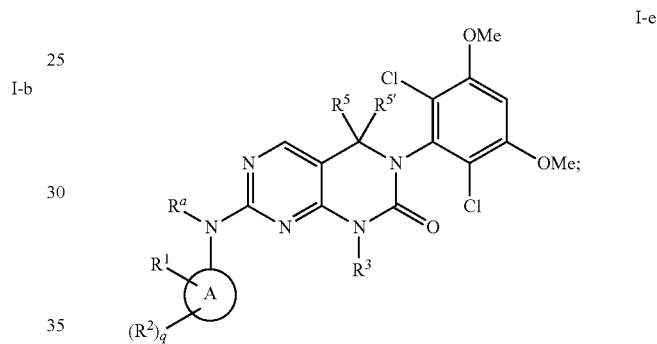

I-e or a pharmaceutically acceptable salt thereof, wherein each of Ring A, $R^1$, $R^2$, $R^3$, $R^5$, $R^{5'}$, $R^a$, and q is as defined above and described in embodiments, classes and subclasses above and herein, singly or in combination.

In other embodiments, the invention provides a compound of formula I-f:

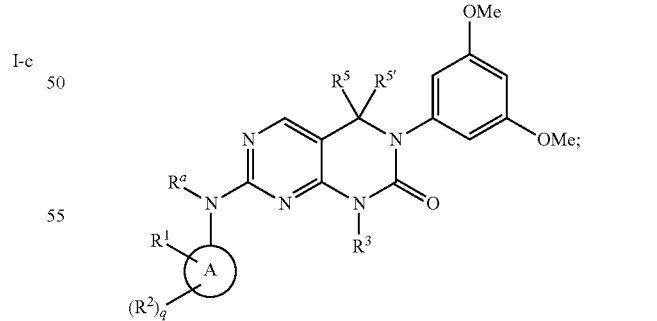

I-f or a pharmaceutically acceptable salt thereof, wherein each of Ring A, $R^1$, $R^2$, $R^3$, $R^5$, $R^{5'}$, $R^a$, and q is as defined above and described in embodiments, classes and subclasses above and herein, singly or in combination.

In certain embodiments, the invention provides a compound of formula I-g:

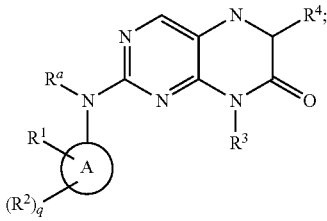

I-g or a pharmaceutically acceptable salt thereof, wherein each of Ring A, $R^1$, $R^2$, $R^3$, $R^4$, $R^a$, and q is as defined above and described in embodiments, classes and subclasses above and herein, singly or in combination.

In certain embodiments, the invention provides a compound of formula I-h:

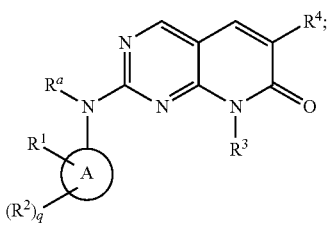

I-h or a pharmaceutically acceptable salt thereof, wherein each of Ring A, $R^1$, $R^2$, $R^3$, $R^4$, $R^a$, and q is as defined above and described in embodiments, classes and subclasses above and herein, singly or in combination.

In certain embodiments, the present invention provides a compound of formula I-h, wherein Ring A is an optionally substituted group selected from phenyl, a 3-8 membered saturated or partially unsaturated carbocyclic ring, a 5-6 membered monocyclic heteroaryl ring having 1-4 heteroatoms independently selected from nitrogen, oxygen, or sulfur, a 4-7 membered saturated or partially unsaturated heterocyclic ring having 1-4 heteroatoms independently selected from nitrogen, oxygen, or sulfur, or a 7-10 membered bicyclic saturated, partially unsaturated or aryl ring.

In some embodiments, a compound is of formula I-h and Ring A is an optionally substituted monocyclic ring. In some embodiments, a compound is of formula I-h and Ring A is an optionally substituted monocyclic carbocycle. In some embodiments, a compound is of formula I-h and Ring A is an optionally substituted monocyclic heterocycle.

In some embodiments, a compound is of formula I-h and Ring A is optionally substituted aryl. In certain embodiments, a compound is of formula I-h and Ring A is optionally substituted phenyl.

In some embodiments, a compound is of formula I-h and Ring A is optionally substituted heteroaryl. In certain embodiments, a compound is of formula I-h and Ring A is optionally substituted pyridinyl.

In some embodiments, a compound is of formula I-h and Ring A is an optionally substituted 4-7 membered saturated or partially unsaturated heterocyclic ring having 1-3 heteroatoms independently selected from nitrogen, oxygen, or sulfur. In certain embodiments, a compound is of formula I-h and Ring A is an optionally substituted 5 membered saturated heterocyclic ring having 1-3 heteroatoms independently selected from nitrogen, oxygen, or sulfur.

In certain embodiments, a compound is of formula I-h and Ring A is phenyl, cyclohexyl, cyclohexenyl, cyclopentyl, cyclobutyl, cyclopropyl, pyridine, pyrmidine, pyrazine, pyridazine, pyrrole, pyrazole, piperidine, piperidin-one, pyrrolidine, tetrahydropyran, tetrahydrofuran, tetrahydrothiophene dioxide, or cyclobutene dione.

In certain embodiments, a compound is of formula I-h and Ring A is an optionally substituted group selected from tetrahydropyran, tetrahydrofuran, or tetrahydrothiophene dioxide. In certain embodiments, a compound is of formula I-h and Ring A is optionally substituted tetrahydropyran. In certain embodiments, a compound is of formula I-h and Ring A is unsubstituted tetrahydropyran. In certain embodiments, a compound is of formula I-h and Ring A is optionally substituted tetrahydrofuran. In certain embodiments, a compound is of formula I-h and Ring A is unsubstituted tetrahydrofuran. In certain embodiments, a compound is of formula I-h and Ring A is optionally substituted tetrahydrothiophene dioxide. In certain embodiments, a compound is of formula I-h and Ring A is unsubstituted tetrahydrothiophene dioxide.

In certain embodiments, a compound is of formula I-h and Ring A is substituted as defined herein.

In some embodiments, a compound is of formula I-h and Ring A is substituted with one, two, or three $R^2$ groups each of which is independently selected. Exemplary substituents on Ring A include Br, I, Cl, F, Me, —$CF_3$, —OMe, —OR, —$N(R)_2$, pyrazolyl, thiazolyl, piperidinyl, piperazinyl, or morpholinyl.

In some embodiments, a compound is of formula I-h and Ring A is substituted with one, two, or three $R^2$ groups each of which is independently selected. Exemplary substituents on Ring A include Br, I, Cl, F, Me, —$CF_3$, —OMe, —OR, —$N(R)_2$, —C(O)R', =O, or an optionally substituted group selected from cycloalkyl, pyrazolyl, thiazolyl, piperidinyl, piperazinyl, pyridizinyl, imidazolyl, or morpholinyl.

In some embodiments, a compound is of formula I-h and Ring A is a 4-7 membered saturated or partially unsaturated heterocyclic ring having 1-3 heteroatoms independently selected from nitrogen, oxygen, or sulfur, wherein Ring A is substituted with one, two, or three $R^2$ groups each of which is independently selected.

In some embodiments, a compound is of formula I-h and Ring A is tetrahydropyran substituted with one, two, or three $R^2$ groups each of which is independently selected.

In some embodiments, a compound is of formula I-h and Ring A is tetrahydrofuran substituted with one, two, or three $R^2$ groups each of which is independently selected.

In some embodiments, a compound is of formula I-h and Ring A is tetrahydrothiophene dioxide substituted with one, two, or three $R^2$ groups each of which is independently selected.

In certain embodiments, a compound is of formula I-h and each $R^2$ is independently methyl, ethyl, propyl, i-propyl, F, Cl, Br, I, $CF_3$, piperidinyl, piperazinyl, morpholinyl, tetrahydropyridinyl, pyrazolyl, thiazolyl, or tetrazolyl.

In some embodiments, a compound is of formula I-h and $R^2$ is optionally substituted pyrazolyl. In some embodiments, a compound is of formula I-h and $R^2$ is n-substituted pyrazolyl. In some embodiments, a compound is of formula I-h and $R^2$ is n-alkyl pyrazolyl. In some embodiments, a compound is of formula I-h and $R^2$ is n-methyl pyrazolyl.

In some embodiments, a compound is of formula I-h and $R^2$ is optionally substituted pyridinyl. In some embodiments, a compound is of formula I-h and $R^2$ is unsubstituted pyridinyl.

In some embodiments, a compound is of formula I-h and $R^2$ is n-substituted tetrazolyl. In some embodiments, a compound is of formula I-h and $R^2$ is n-alkyl tetrazolyl. In some embodiments, a compound is of formula I-h and $R^2$ is n-methyl tetrazolyl.

In some embodiments, a compound is of formula I-h and $R^2$ is optionally substituted piperazinyl. In some embodiments, a compound is of formula I-h and $R^2$ is n-substituted piperazinyl. In some embodiments, a compound is of formula I-h and $R^2$ is n-alkyl piperazinyl. In some embodiments, a compound is of formula I-h and $R^2$ is n-methyl piperazinyl. In some embodiments, a compound is of formula I-h and $R^2$ is n-ethyl piperazinyl.

In some embodiments, a compound is of formula I-h and each $R^2$ is independently halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In some embodiments, a compound is of formula I-h and $R^2$ is —OR. In certain embodiments, a compound is of formula I-h and $R^2$ is —OH.

In some embodiments, a compound is of formula I-h and $R^2$ is —C(O)R. In certain embodiments, a compound is of formula I-h and $R^2$ is —C(O)Me.

In some embodiments, a compound is of formula I-h and each $R^2$ is independently —R.

In some embodiments, a compound is of formula I-h and $R^2$ is optionally substituted cycloalkyl. In some embodiments, a compound is of formula I-h and $R^2$ is optionally substituted cyclopropyl. In some embodiments, a compound is of formula I-h and $R^2$ is unsubstituted cyclopropyl.

In some embodiments, a compound is of formula I-h and $R^3$ is $C_{2-6}$ alkenyl, —W-Cy, or $C_{1-6}$ alkyl, wherein the $C_{1-6}$ alkyl is optionally substituted with 1-3 groups independently selected from halogen, —CN, oxo, —OR', or —C(O)O($C_{1-6}$ alkyl).

For instance, in certain embodiments, a compound is of formula I-h and $R^3$ is $C_{1-6}$ alkyl, wherein the $C_{1-6}$ alkyl is optionally substituted with 1-3-OH groups. In certain embodiments, a compound is of formula I-h and $R^3$ is $C_{1-6}$ alkyl, wherein the $C_{1-6}$ alkyl is optionally substituted with 1-2-OH groups. In certain embodiments, a compound is of formula I-h and $R^3$ is $C_{3-6}$ alkyl optionally substituted with 1-3-OH groups. In certain embodiments, a compound is of formula I-h and $R^3$ is $C_{3-6}$ alkyl optionally substituted with 1-2-OH groups.

In some embodiments, a compound is of formula I-h and $R^3$ is $C_{1-6}$ alkyl. In some embodiments, a compound is of formula I-h and $R^3$ is methyl, ethyl, or propyl. In certain embodiments, a compound is of formula I-h and $R^3$ is methyl. In certain embodiments, a compound is of formula I-h and $R^3$ is ethyl. In certain embodiments, a compound is of formula I-h and $R^3$ is propyl, e.g., isopropyl.

In some embodiments, a compound is of formula I-h and $R^3$ is —W-Cy. In some embodiments, a compound is of formula I-h, $R^3$ is —W-Cy, and W is absent (i.e., W is a covalent bond).

In certain embodiments, a compound is of formula I-h, $R^3$ is —W-Cy, and W is a bivalent $C_{1-3}$ alkylene chain optionally substituted with one or more R" and wherein one methylene unit of W is optionally replaced with —O—, —S—, or —NR'—. In certain embodiments, a compound is of formula I-h, $R^3$ is —W-Cy, and Cy is $C_{3-7}$ cycloalkyl wherein Cy is optionally substituted with 1-3 $R^x$.

In certain embodiments, a compound is of formula I-h, $R^3$ is —W-Cy, and Cy is a 3-7 membered monocyclic saturated ring having 1-3 heteroatoms independently selected from nitrogen, oxygen, or sulfur, wherein Cy is optionally substituted with 1-3 $R^x$. In certain embodiments, a compound is of formula I-h, $R^3$ is —W-Cy, W is a bivalent $C_{1-3}$ alkylene chain optionally substituted with one or more R", and Cy is a 3-7 membered monocyclic saturated ring having 1-3 heteroatoms independently selected from nitrogen, oxygen, or sulfur, wherein Cy is optionally substituted with 1-3 $R^x$. In certain embodiments, a compound is of formula I-h, $R^3$ is —W-Cy, W is a bivalent $C_1$ alkylene chain optionally substituted with one or more R", and Cy is a 3-7 membered monocyclic saturated ring having 1-3 heteroatoms independently selected from nitrogen, oxygen, or sulfur, wherein Cy is optionally substituted with 1-3 $R^x$. In certain embodiments, a compound is of formula I-h, $R^3$ is —W-Cy, W is a bivalent $C_{1-3}$ alkylene chain optionally substituted with one or more R", and Cy is a 3-5 membered monocyclic saturated ring having 1-3 heteroatoms independently selected from nitrogen, oxygen, or sulfur, wherein Cy is optionally substituted with 1-3 $R^x$. In certain embodiments, a compound is of formula I-h, $R^3$ is —W-Cy, W is a bivalent $C_1$ alkylene chain optionally substituted with one or more R", and Cy is a 5 membered monocyclic saturated ring having 1-3 heteroatoms independently selected from nitrogen, oxygen, or sulfur, wherein Cy is optionally substituted with 1-3 $R^x$. In certain embodiments, a compound is of formula I-h, $R^3$ is —W-Cy, W is a bivalent $C_1$ alkylene chain optionally substituted with one or more R", and Cy is a 5 membered monocyclic saturated ring having 1 heteroatom independently selected from nitrogen, oxygen, or sulfur, wherein Cy is optionally substituted with 1-3 $R^x$. In certain embodiments, $R^3$ is as described above and $R^x$ is —C(O)R'. In certain embodiments, $R^3$ is as described above and $R^x$ is —C(O)Me.

In certain embodiments, a compound is of formula I-h and $R^3$ is

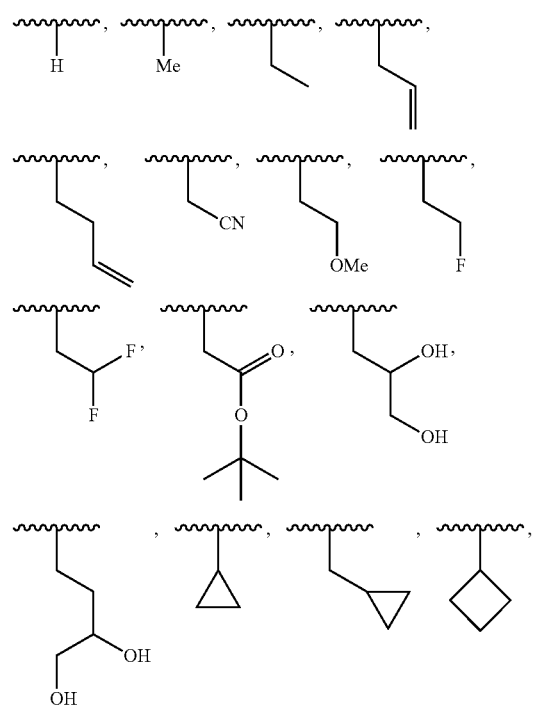

-continued

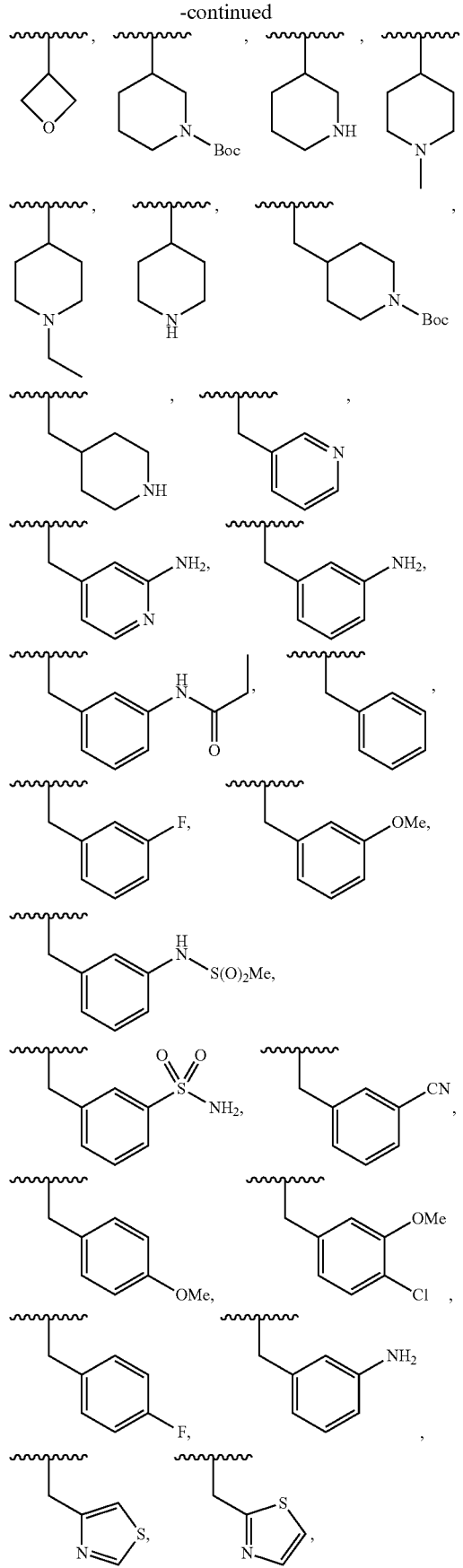

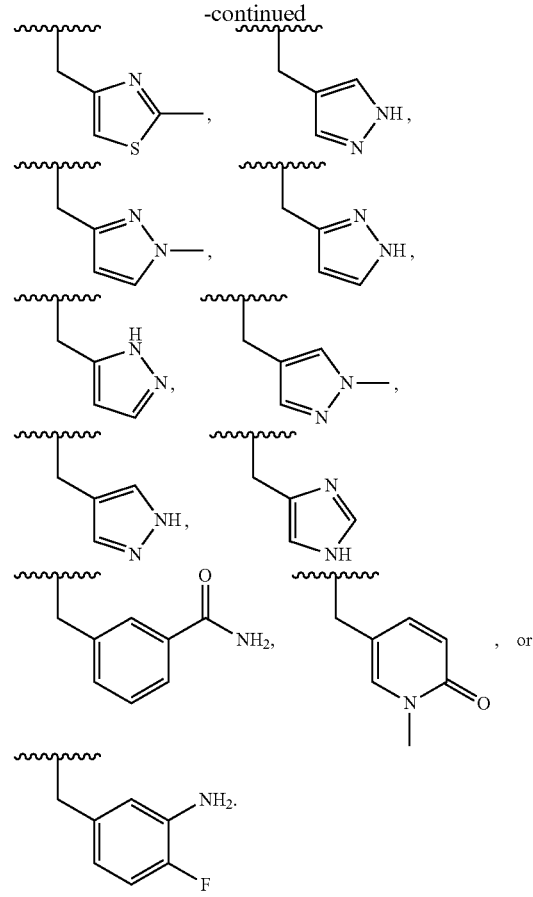

In certain embodiments, a compound is of formula I-h and R³ is:

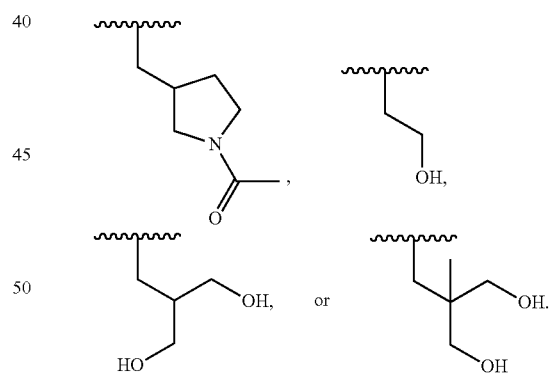

In certain embodiments, a compound is of formula I-h and R⁴ is optionally substituted phenyl. In certain embodiments, a compound is of formula I-h and R⁴ is phenyl optionally substituted with 1-5 halogens. In certain embodiments, a compound is of formula I-h and R⁴ is phenyl optionally substituted with 1-5 alkoxy groups. In certain embodiments, a compound is of formula I-h and R⁴ is phenyl optionally substituted with 1-5 groups independently selected from halogen and alkoxy groups. In certain embodiments, a compound is of formula I-h and R⁴ is phenyl optionally substituted with 1-5 groups independently selected from chloro, fluoro, methoxy, and ethoxy. In certain embodiments, a compound is of formula I-h and R⁴ is optionally substituted phenyl, wherein the optional substitution is any of those described above and herein.
In certain embodiments, a compound is of formula I-h and R⁴ is ethyl, phenyl, cyclohexyl,
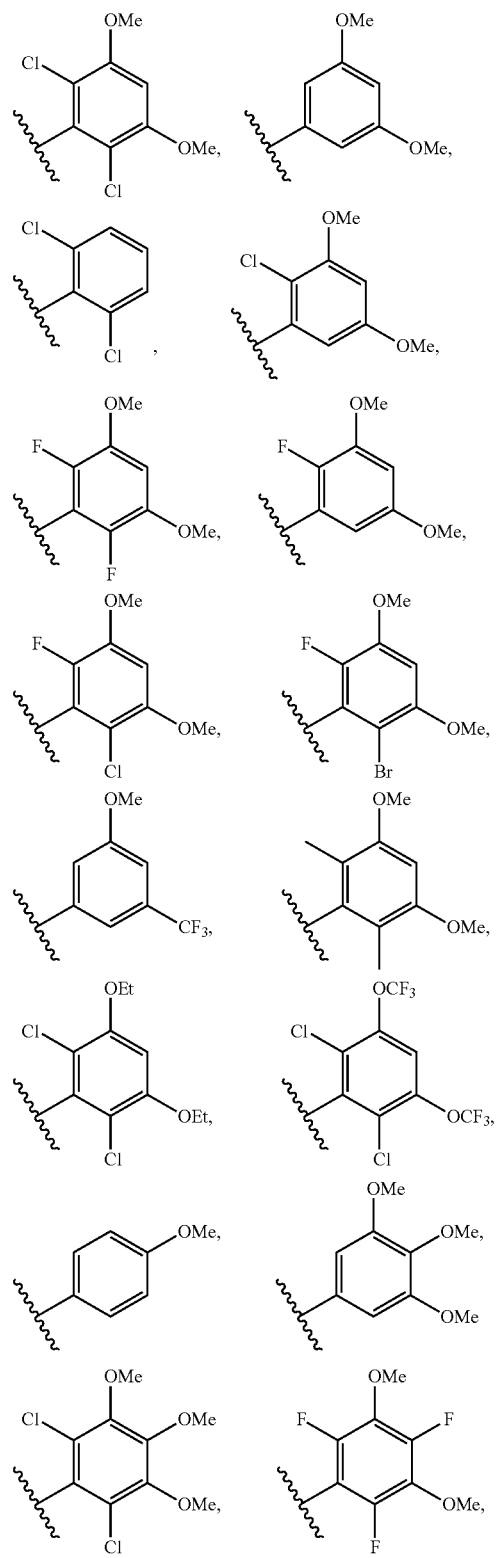
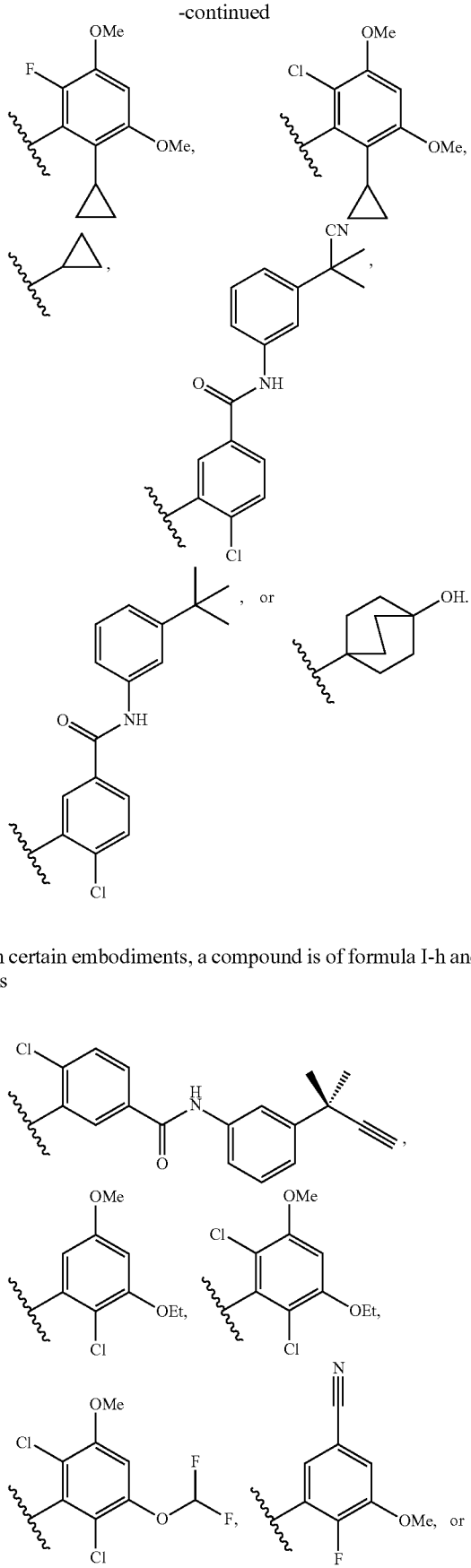
In certain embodiments, a compound is of formula I-h and R⁴ is -continued

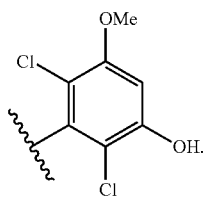

In some embodiments, a compound of formula I-h is of formula I-h(cis)(1) or I-h(cis)(2):

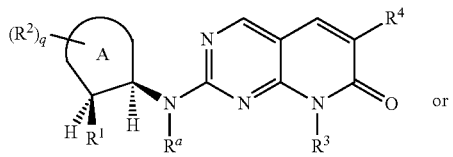

I-h(cis)(1)

or

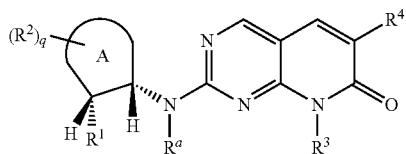

I-h(cis)(2)

or a pharmaceutically acceptable salt thereof, wherein each of Ring A, $R^1$, $R^2$, $R^3$, $R^4$, $R^a$, and q is as defined above and described in embodiments, classes and subclasses above and herein, singly or in combination.

In certain embodiments, a compound of formula I-h is of formula I-h(cis)(1):

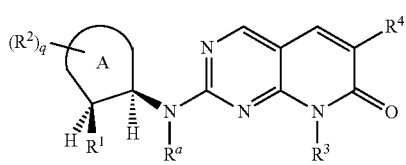

I-h(cis)(1)

or a pharmaceutically acceptable salt thereof, wherein each of Ring A, $R^1$, $R^2$, $R^3$, $R^4$, $R^a$, and q is as defined above and described in embodiments, classes and subclasses above and herein, singly or in combination.

In certain embodiments, a compound of formula I-h is of formula I-H(cis)(2):

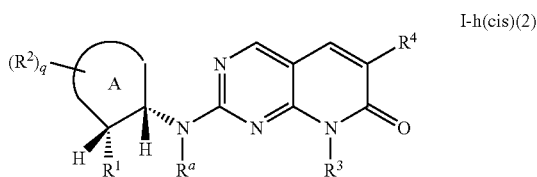

I-h(cis)(2)

or a pharmaceutically acceptable salt thereof, wherein each of Ring A, $R^1$, $R^2$, $R^3$, $R^4$, $R^a$, and q is as defined above and described in embodiments, classes and subclasses above and herein, singly or in combination.

In certain embodiments, the invention provides a compound of formula I-j:

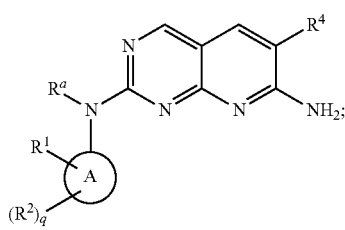

I-j or a pharmaceutically acceptable salt thereof, wherein each of Ring A, $R^1$, $R^2$, $R^4$, $R^a$, and q is as defined above and described in embodiments, classes and subclasses above and herein, singly or in combination.

In certain embodiments, the invention provides a compound of formula I-k:

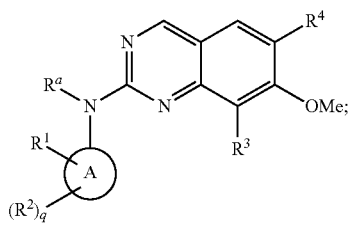

I-k or a pharmaceutically acceptable salt thereof, wherein each of Ring A, $R^1$, $R^2$, $R^3$, $R^4$, $R^a$, and q is as defined above and described in embodiments, classes and subclasses above and herein, singly or in combination.

In certain embodiments, the invention provides a compound of formula I-n:

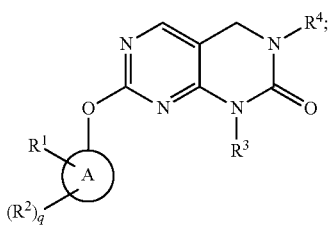

I-n or a pharmaceutically acceptable salt thereof, wherein each of Ring A, $R^1$, $R^2$, $R^3$, $R^4$, and q is as defined above and described in embodiments, classes and subclasses above and herein, singly or in combination.

In certain embodiments, the compound is of formula I-q:

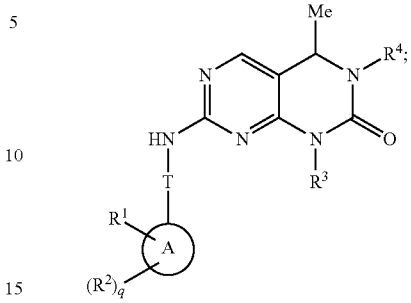

I-q or a pharmaceutically acceptable salt thereof, wherein each of Ring A, $R^1$, $R^2$, $R^3$, $R^4$, T, and q is as defined above and described in embodiments, classes and subclasses above and herein, singly or in combination.

In certain embodiments, the invention provides a compound selected from Table 1 or Table 2:

TABLE 1

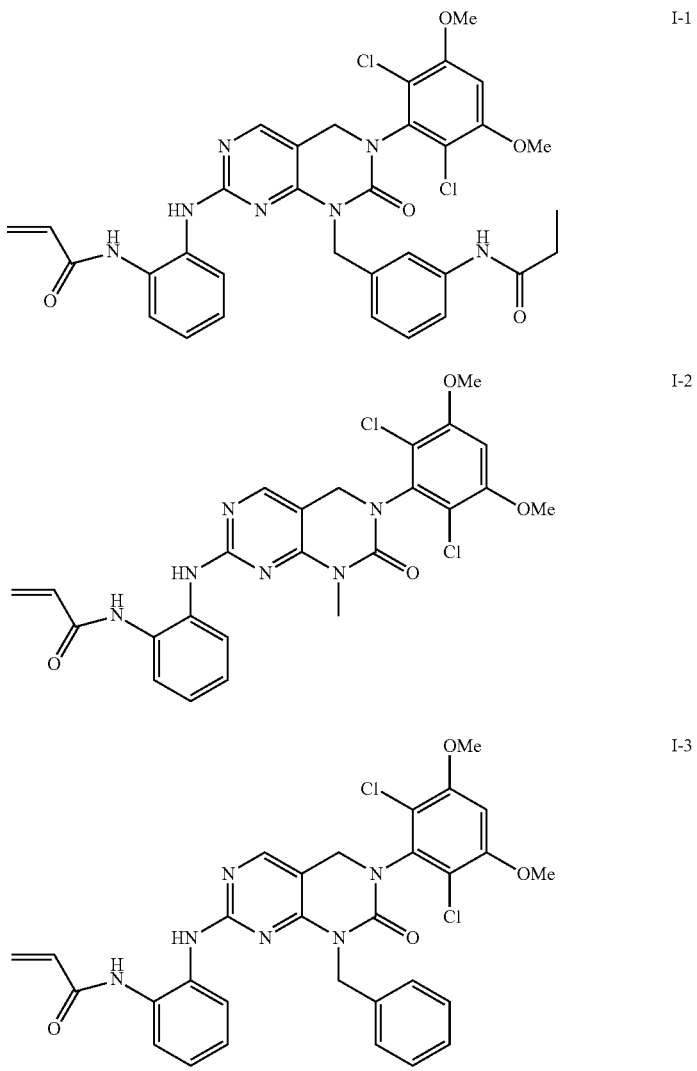

TABLE 1-continued
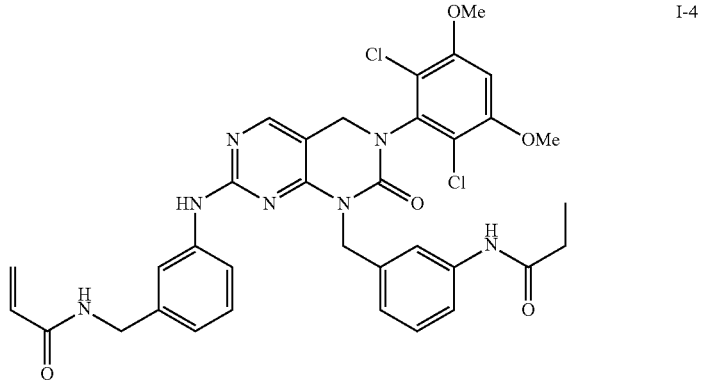 I-4
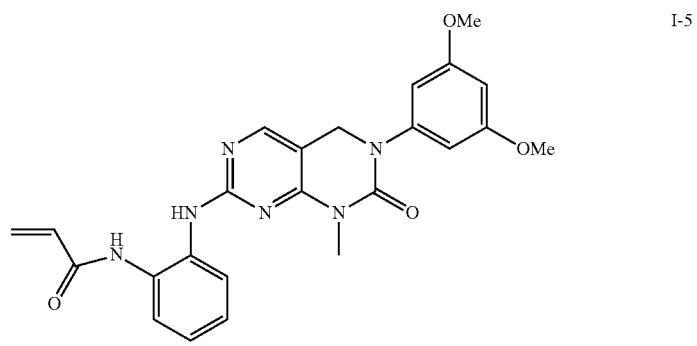 I-5
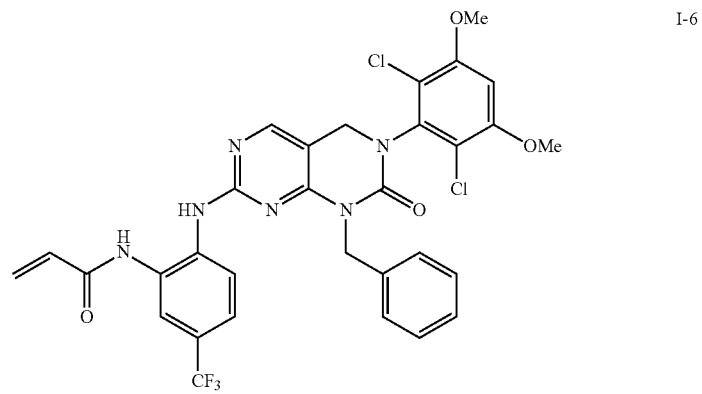 I-6
trans-
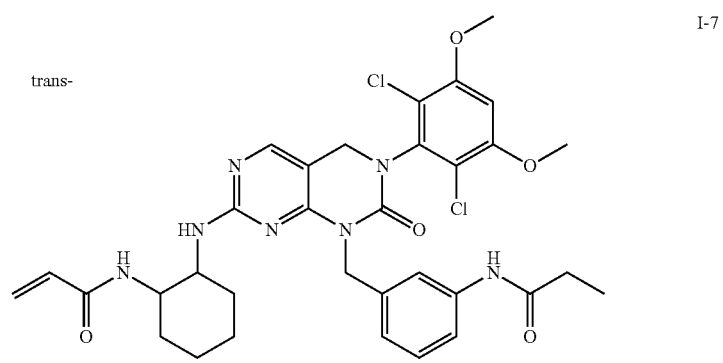 I-7

TABLE 1-continued
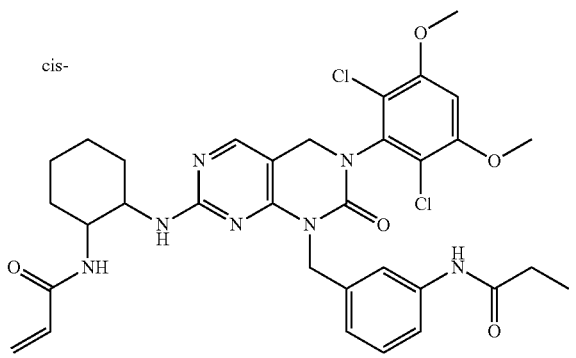 [SMILES: C=CC(=O)NC1CCCCC1Nc1ncc2c(n1)N(Cc1cccc(NC(=O)CC)c1)C(=O)N(c1c(Cl)c(OC)cc(OC)c1Cl)C2]
I-8
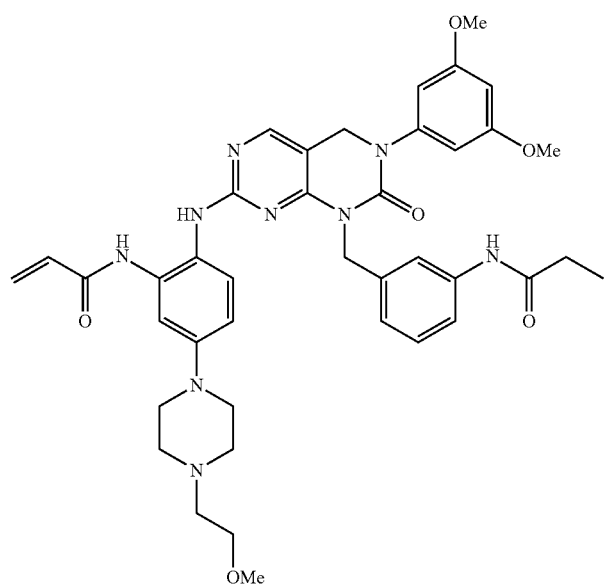 [SMILES: C=CC(=O)Nc1cc(N2CCN(CCOC)CC2)ccc1Nc1ncc2c(n1)N(Cc1cccc(NC(=O)CC)c1)C(=O)N(c1cc(OC)cc(OC)c1)C2]
I-9
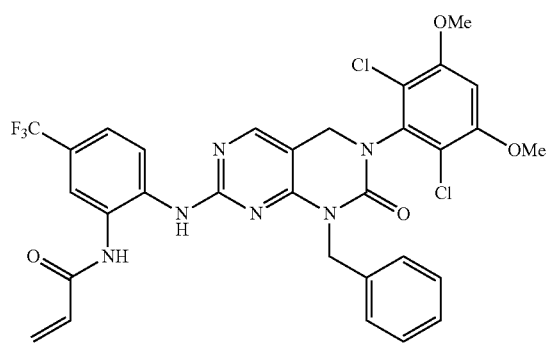 [SMILES: C=CC(=O)Nc1cc(C(F)(F)F)ccc1Nc1ncc2c(n1)N(Cc1ccccc1)C(=O)N(c1c(Cl)c(OC)cc(OC)c1Cl)C2]
I-10
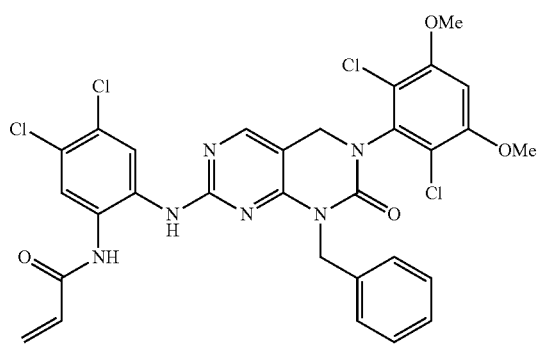 [SMILES: C=CC(=O)Nc1cc(Cl)c(Cl)cc1Nc1ncc2c(n1)N(Cc1ccccc1)C(=O)N(c1c(Cl)c(OC)cc(OC)c1Cl)C2]
I-11

TABLE 1-continued
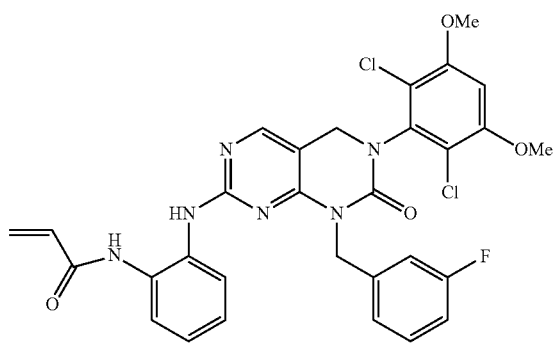 [SMILES: C=CC(=O)Nc1ccccc1Nc1ncc2c(n1)N(Cc1cccc(F)c1)C(=O)N(c1c(Cl)c(OC)cc(OC)c1Cl)C2]
I-12
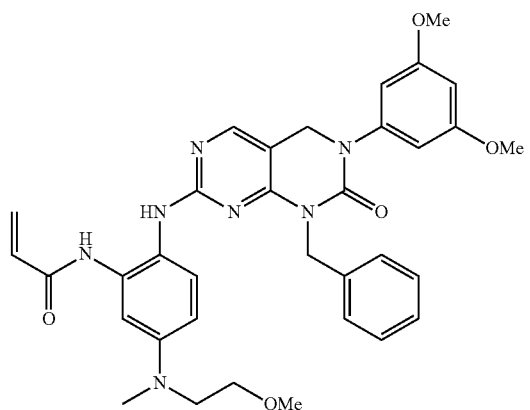 [SMILES: C=CC(=O)Nc1cc(N(C)CCOC)ccc1Nc1ncc2c(n1)N(Cc1ccccc1)C(=O)N(c1cc(OC)cc(OC)c1)C2]
I-13
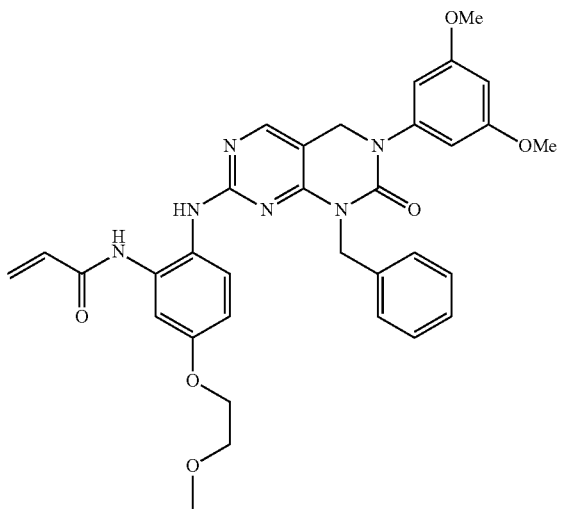 [SMILES: C=CC(=O)Nc1cc(OCCOC)ccc1Nc1ncc2c(n1)N(Cc1ccccc1)C(=O)N(c1cc(OC)cc(OC)c1)C2]
I-14

TABLE 1-continued
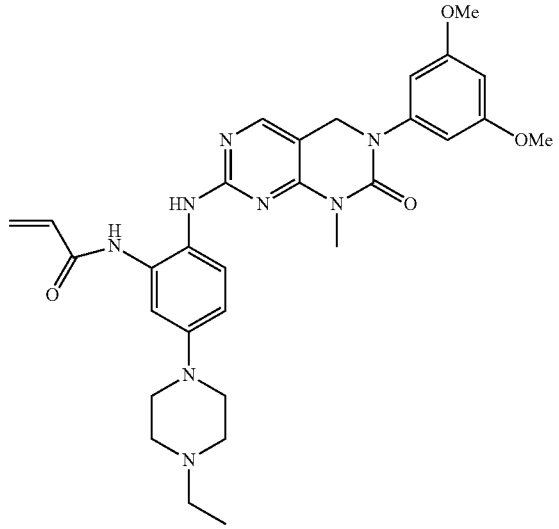 [SMILES: C=CC(=O)Nc1cc(N2CCN(CC)CC2)ccc1Nc1ncc2c(n1)N(C)C(=O)N(c1cc(OC)cc(OC)c1)C2]
I-15
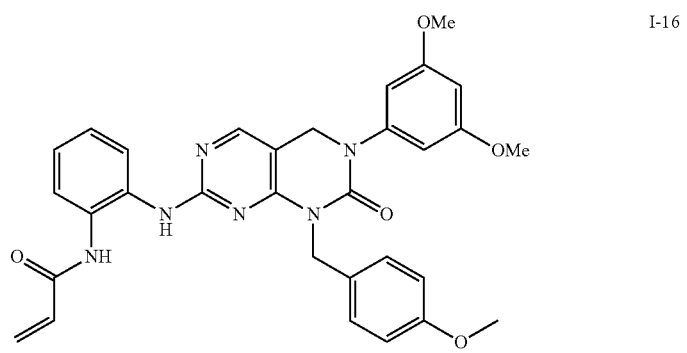
I-16
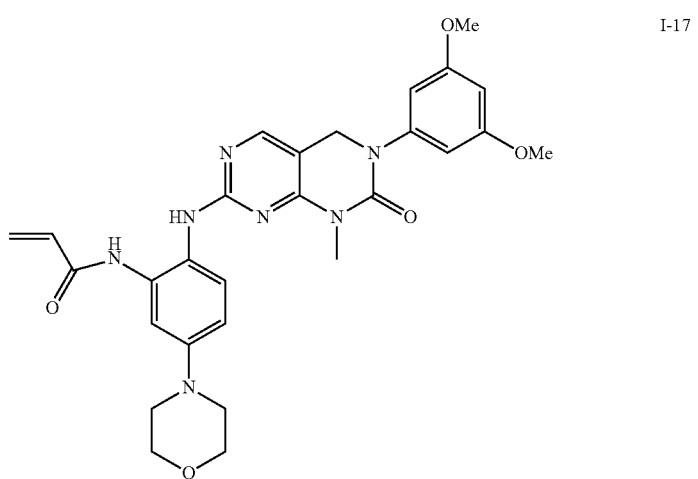
I-17

TABLE 1-continued
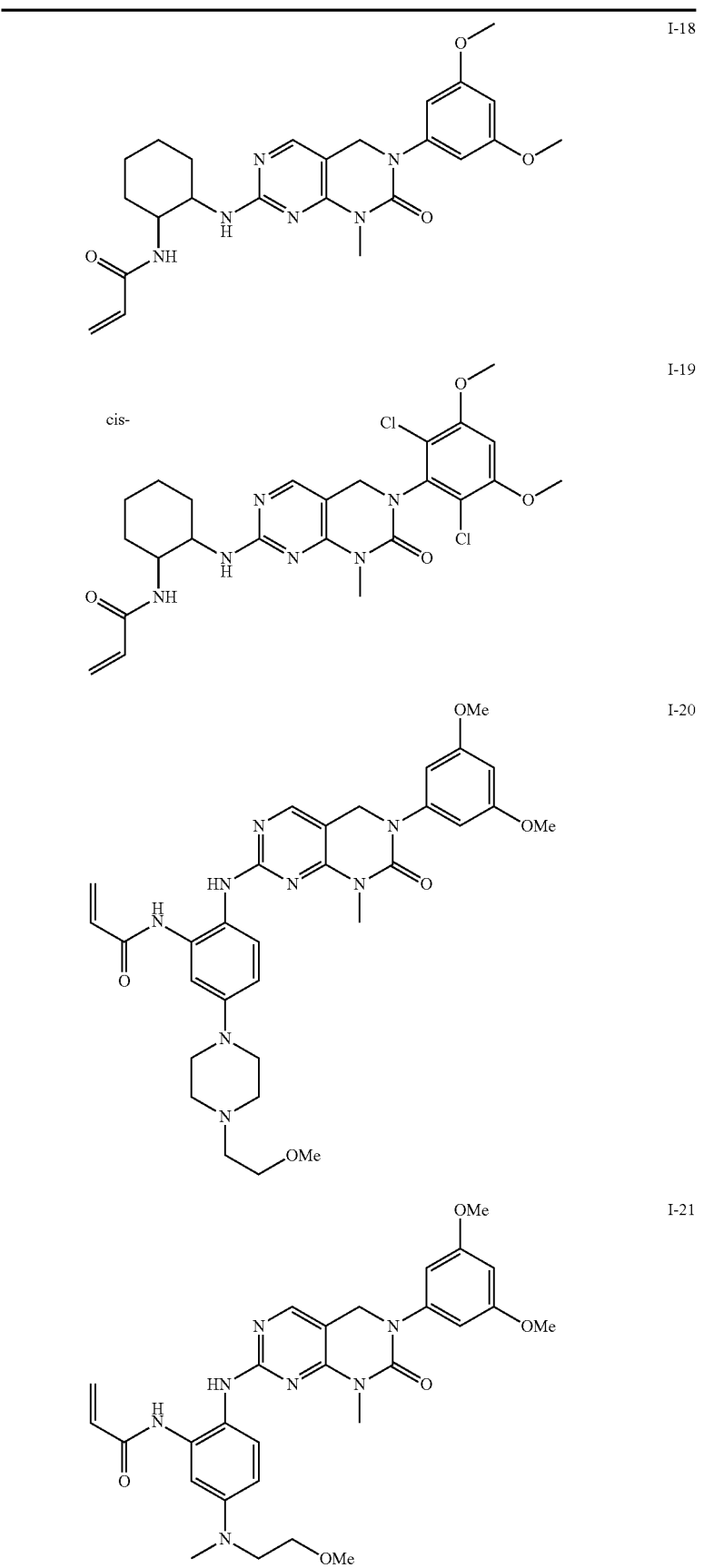

TABLE 1-continued
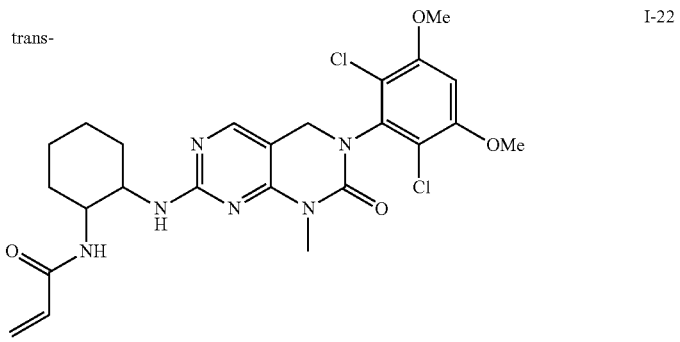
I-22
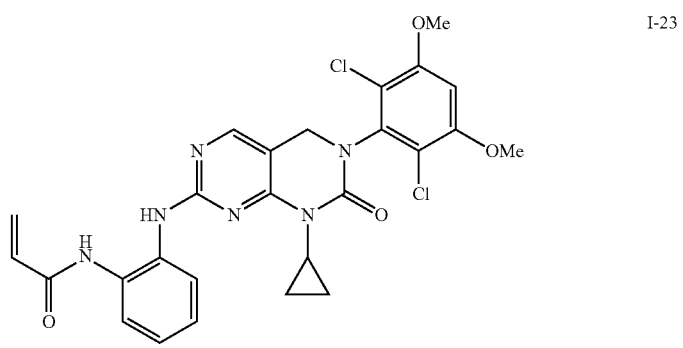
I-23
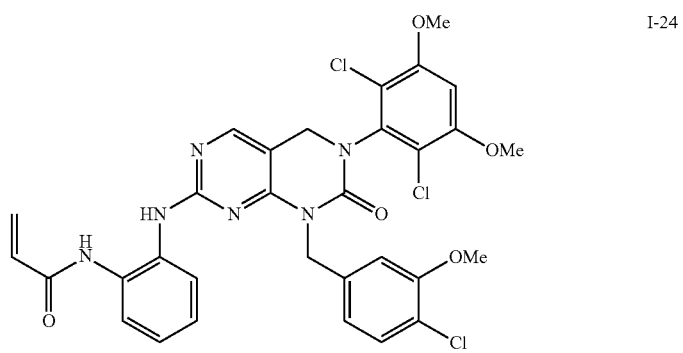
I-24
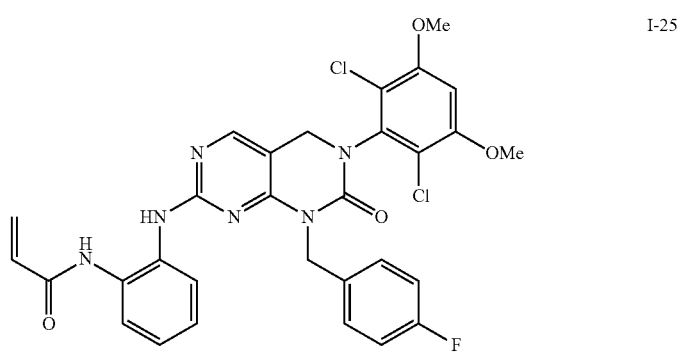
I-25

TABLE 1-continued
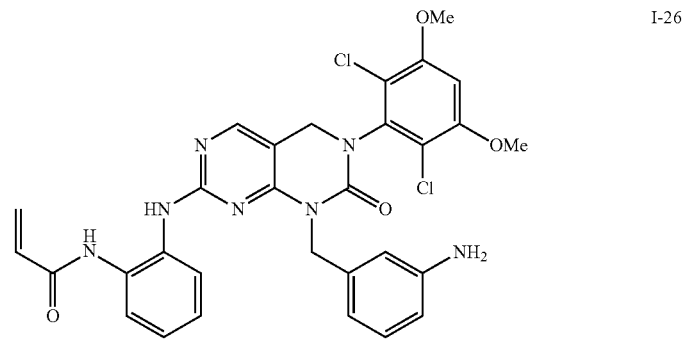
I-26
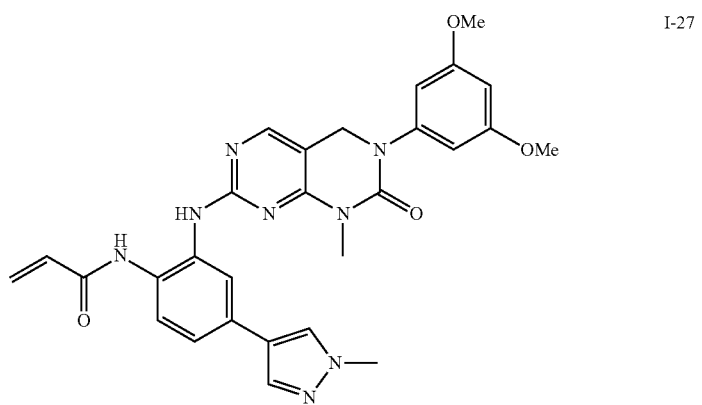
I-27
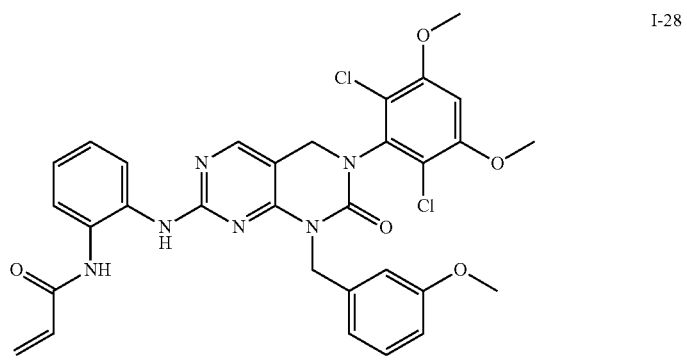
I-28
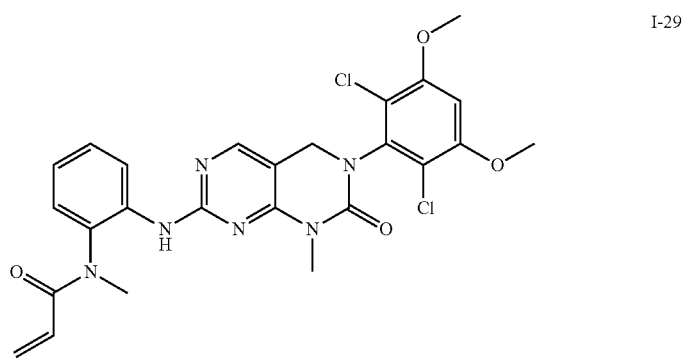
I-29

TABLE 1-continued
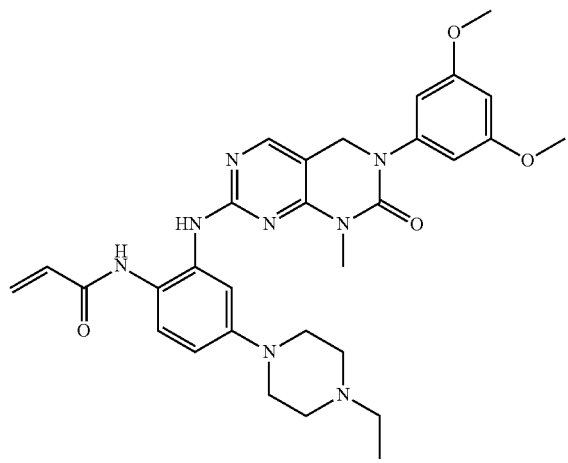 [SMILES: C=CC(=O)Nc1ccc(N2CCN(CC)CC2)cc1Nc1ncc2c(n1)N(C)C(=O)N(c1cc(OC)cc(OC)c1)C2]
I-30
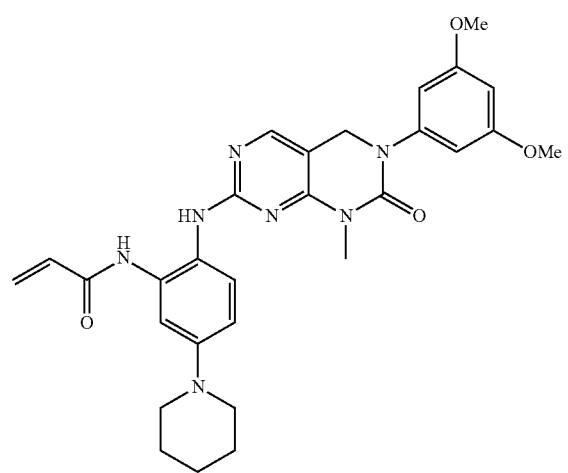 [SMILES: C=CC(=O)Nc1cc(N2CCCCC2)ccc1Nc1ncc2c(n1)N(C)C(=O)N(c1cc(OC)cc(OC)c1)C2]
I-31
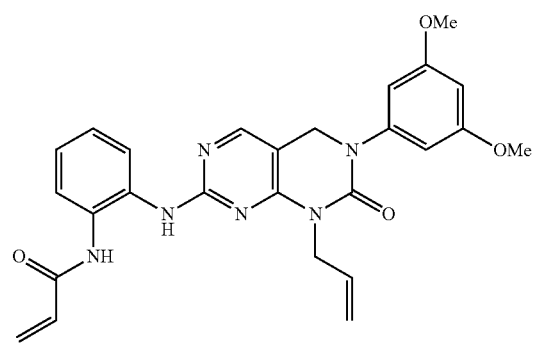 [SMILES: C=CCN1C(=O)N(c2cc(OC)cc(OC)c2)Cc2cnc(Nc3ccccc3NC(=O)C=C)nc21]
I-32
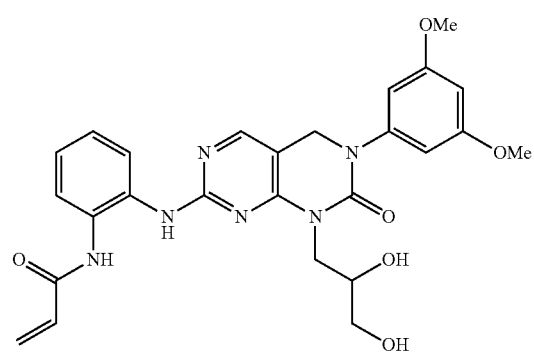 [SMILES: C=CC(=O)Nc1ccccc1Nc1ncc2c(n1)N(CC(O)CO)C(=O)N(c1cc(OC)cc(OC)c1)C2]
I-33

TABLE 1-continued
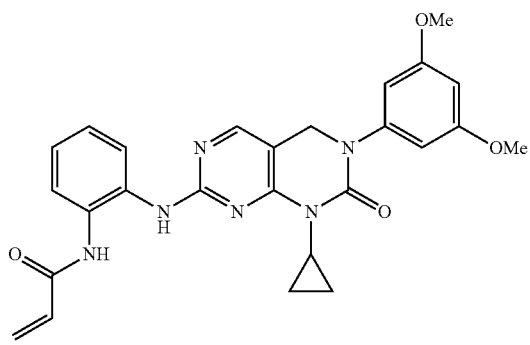 [SMILES: C=CC(=O)Nc1ccccc1Nc1ncc2c(n1)N(C1CC1)C(=O)N(c1cc(OC)cc(OC)c1)C2]
I-34
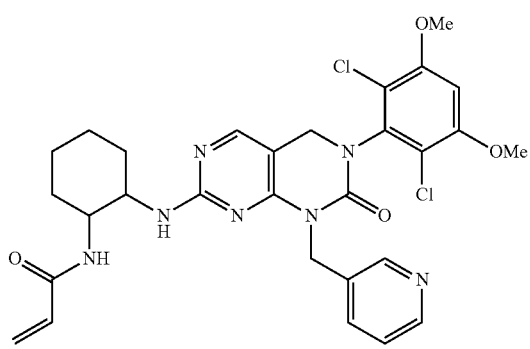 [SMILES: C=CC(=O)NC1CCCCC1Nc1ncc2c(n1)N(Cc1cccnc1)C(=O)N(c1c(Cl)c(OC)cc(OC)c1Cl)C2]
I-35
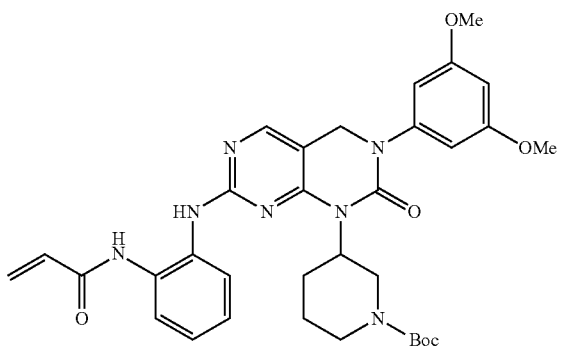 [SMILES: C=CC(=O)Nc1ccccc1Nc1ncc2c(n1)N(C1CCCN(C(=O)OC(C)(C)C)C1)C(=O)N(c1cc(OC)cc(OC)c1)C2]
I-36
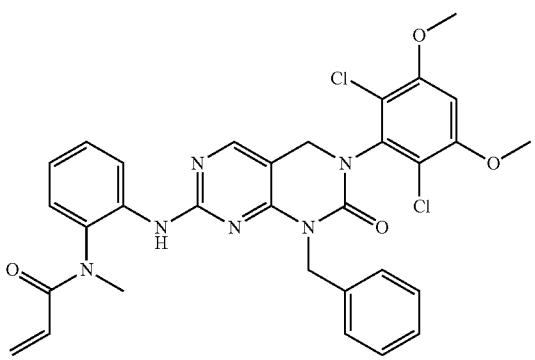 [SMILES: C=CC(=O)N(C)c1ccccc1Nc1ncc2c(n1)N(Cc1ccccc1)C(=O)N(c1c(Cl)c(OC)cc(OC)c1Cl)C2]
I-37

TABLE 1-continued
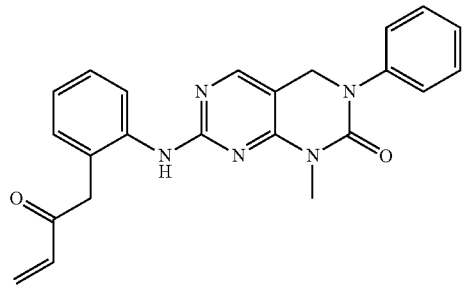 [SMILES: C=CC(=O)Cc1ccccc1Nc1ncc2c(n1)N(C)C(=O)N(c1ccccc1)C2]
I-38
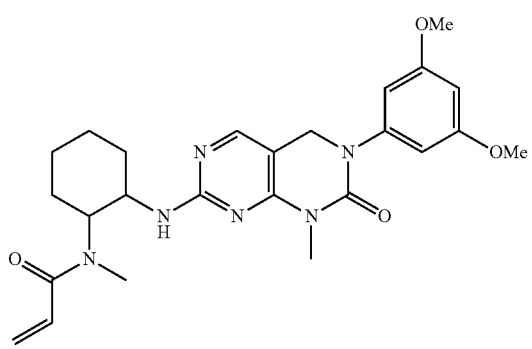 [SMILES: C=CC(=O)N(C)C1CCCCC1Nc1ncc2c(n1)N(C)C(=O)N(c1cc(OC)cc(OC)c1)C2]
I-39
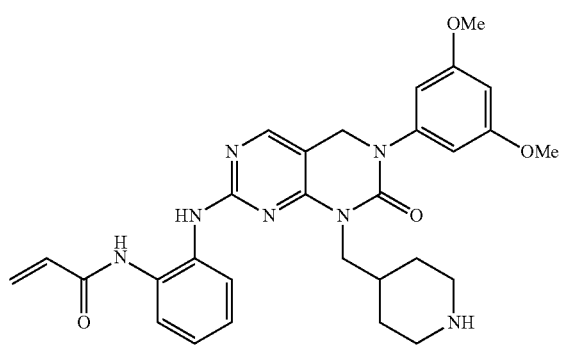 [SMILES: C=CC(=O)Nc1ccccc1Nc1ncc2c(n1)N(CC1CCNCC1)C(=O)N(c1cc(OC)cc(OC)c1)C2]
I-40
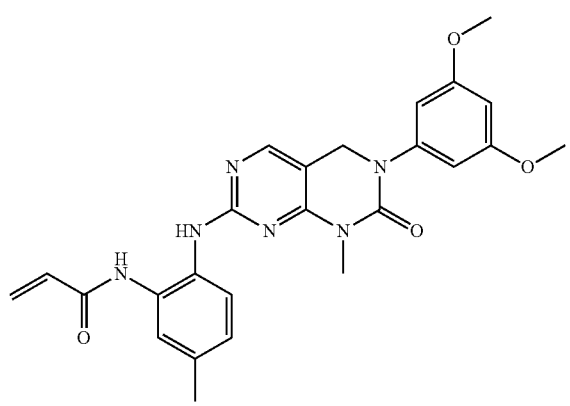 [SMILES: C=CC(=O)Nc1cc(C)ccc1Nc1ncc2c(n1)N(C)C(=O)N(c1cc(OC)cc(OC)c1)C2]
I-41

TABLE 1-continued
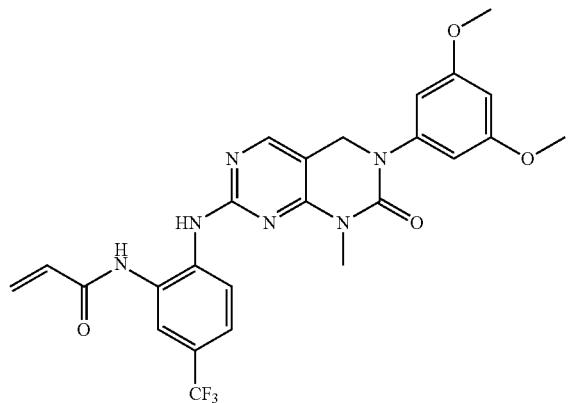 [SMILES: C=CC(=O)Nc1cc(C(F)(F)F)ccc1Nc1ncc2c(n1)N(C)C(=O)N(c1cc(OC)cc(OC)c1)C2]
I-42
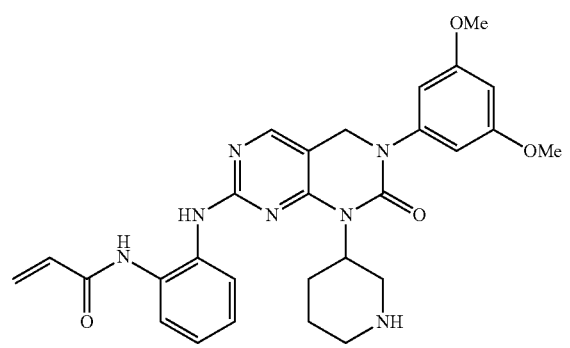 [SMILES: C=CC(=O)Nc1ccccc1Nc1ncc2c(n1)N(C1CCCNC1)C(=O)N(c1cc(OC)cc(OC)c1)C2]
I-43
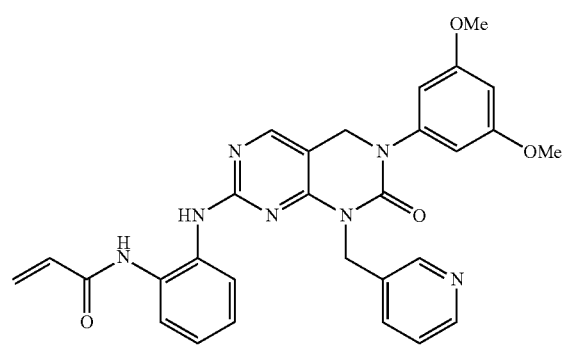 [SMILES: C=CC(=O)Nc1ccccc1Nc1ncc2c(n1)N(Cc1cccnc1)C(=O)N(c1cc(OC)cc(OC)c1)C2]
I-44
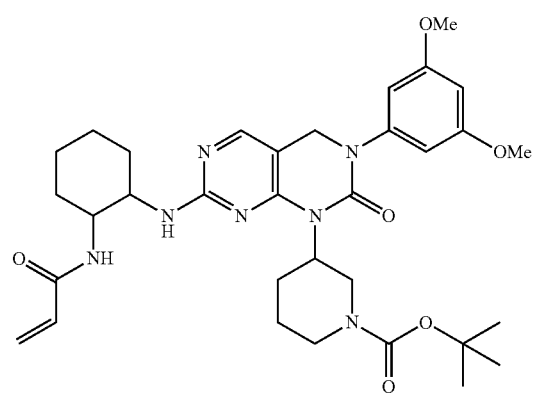 [SMILES: C=CC(=O)NC1CCCCC1Nc1ncc2c(n1)N(C1CCCN(C(=O)OC(C)(C)C)C1)C(=O)N(c1cc(OC)cc(OC)c1)C2]
I-45

TABLE 1-continued
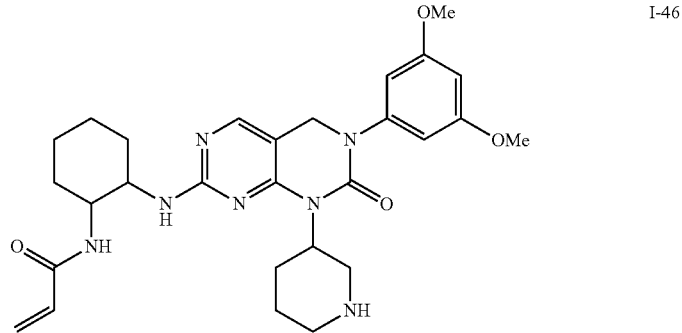
I-46
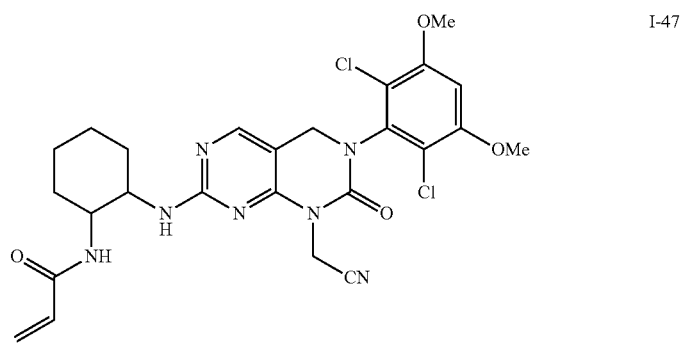
I-47
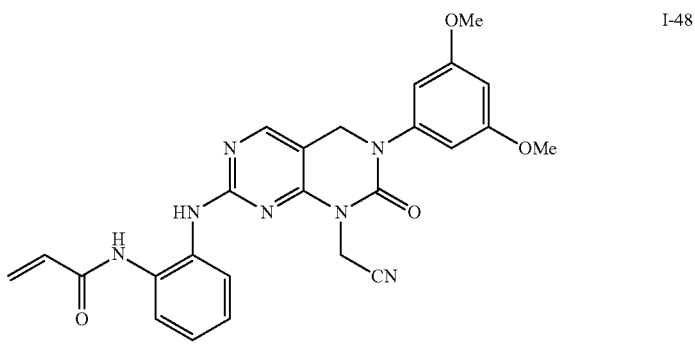
I-48
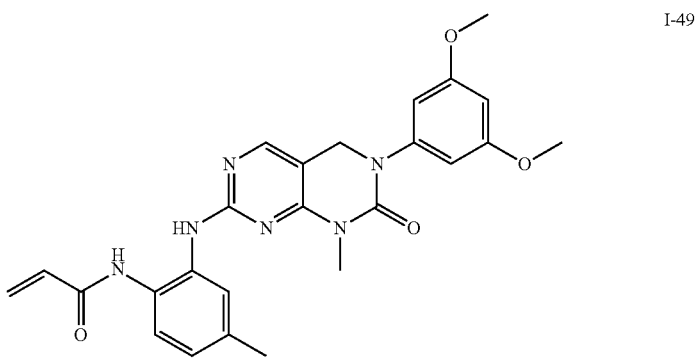
I-49

TABLE 1-continued
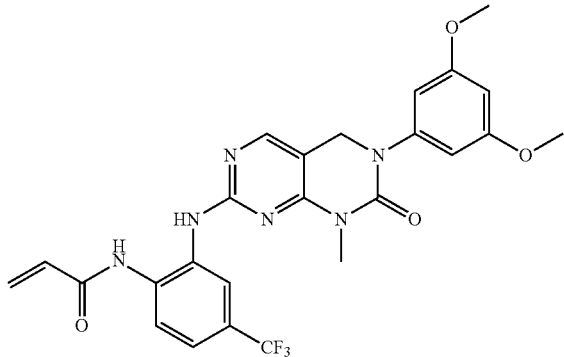 [SMILES: C=CC(=O)Nc1ccc(C(F)(F)F)cc1Nc1ncc2c(n1)N(C)C(=O)N(c1cc(OC)cc(OC)c1)C2]
I-50
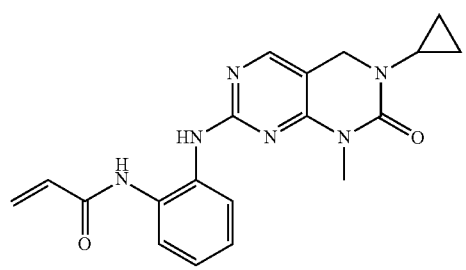 [SMILES: C=CC(=O)Nc1ccccc1Nc1ncc2c(n1)N(C)C(=O)N(C1CC1)C2]
I-51
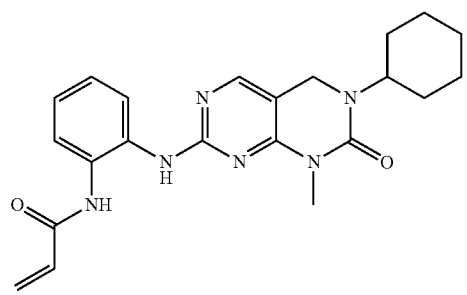 [SMILES: C=CC(=O)Nc1ccccc1Nc1ncc2c(n1)N(C)C(=O)N(C1CCCCC1)C2]
I-52
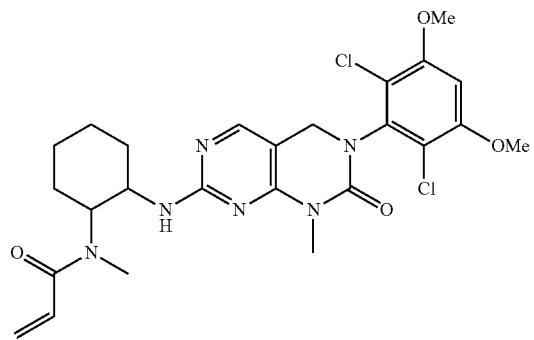 [SMILES: C=CC(=O)N(C)C1CCCCC1Nc1ncc2c(n1)N(C)C(=O)N(c1c(Cl)c(OC)cc(OC)c1Cl)C2]
I-53

TABLE 1-continued
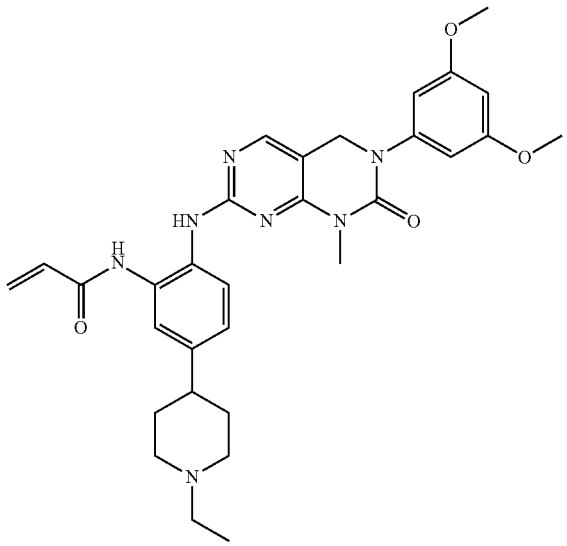 [SMILES: C=CC(=O)Nc1cc(C2CCN(CC)CC2)ccc1Nc1ncc2c(n1)N(C)C(=O)N(c1cc(OC)cc(OC)c1)C2]
I-54
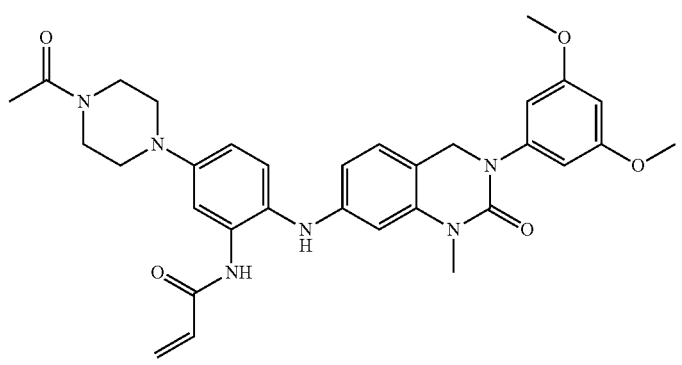 [SMILES: C=CC(=O)Nc1cc(N2CCN(C(C)=O)CC2)ccc1Nc1ccc2c(c1)N(C)C(=O)N(c1cc(OC)cc(OC)c1)C2]
I-55
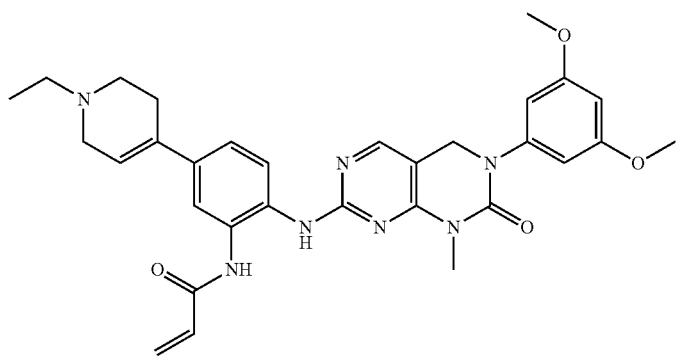 [SMILES: C=CC(=O)Nc1cc(C2=CCN(CC)CC2)ccc1Nc1ncc2c(n1)N(C)C(=O)N(c1cc(OC)cc(OC)c1)C2]
I-56
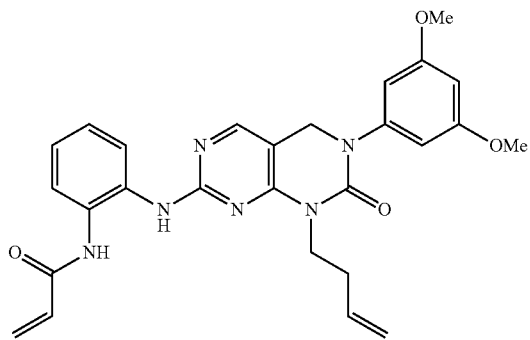 [SMILES: C=CCCN1C(=O)N(c2cc(OC)cc(OC)c2)Cc2cnc(Nc3ccccc3NC(=O)C=C)nc21]
I-57

TABLE 1-continued
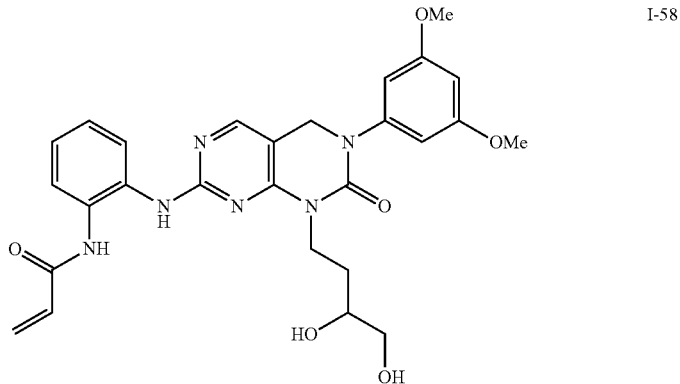
I-58
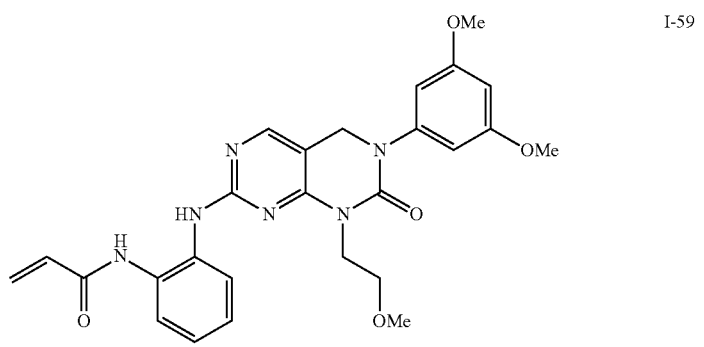
I-59
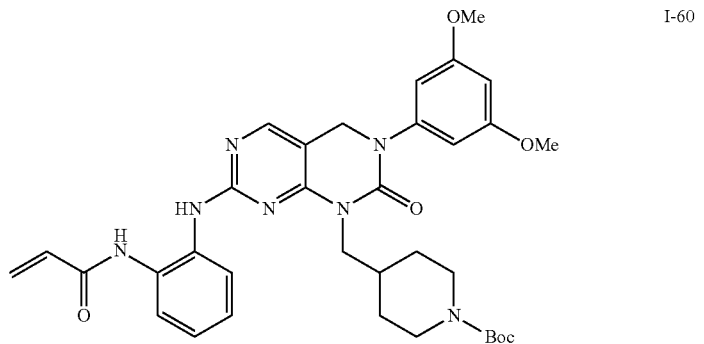
I-60
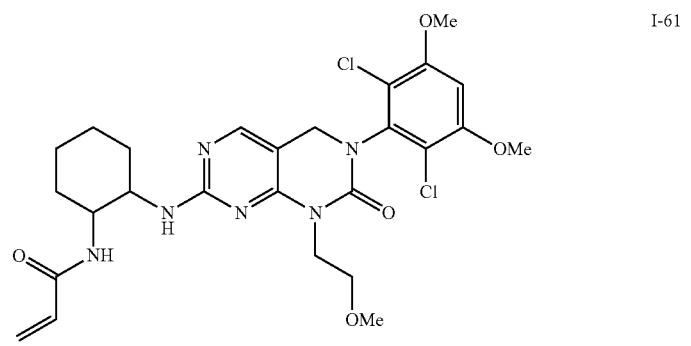
I-61

TABLE 1-continued
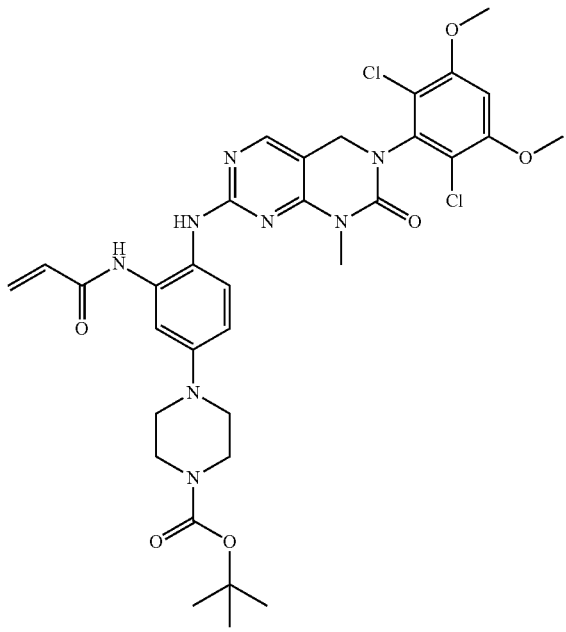 [SMILES: C=CC(=O)Nc1cc(N2CCN(C(=O)OC(C)(C)C)CC2)ccc1Nc1ncc2c(n1)N(C)C(=O)N(c1c(Cl)c(OC)cc(OC)c1Cl)C2]
I-62
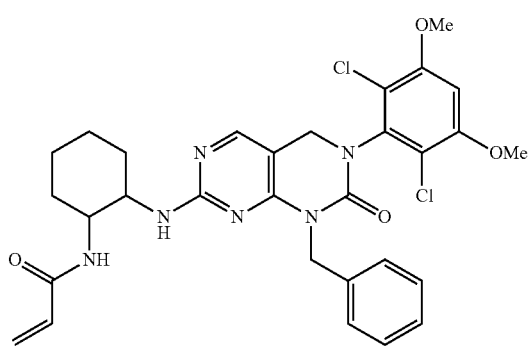 [SMILES: C=CC(=O)NC1CCCCC1Nc1ncc2c(n1)N(Cc1ccccc1)C(=O)N(c1c(Cl)c(OC)cc(OC)c1Cl)C2]
I-63
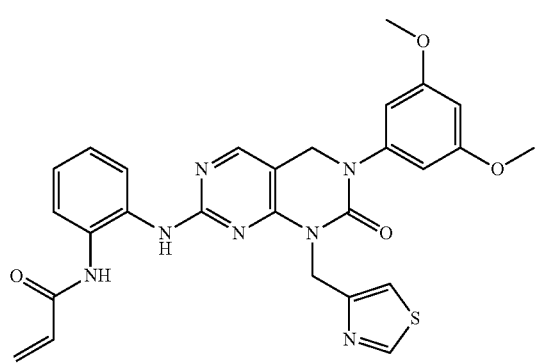 [SMILES: C=CC(=O)Nc1ccccc1Nc1ncc2c(n1)N(Cc1cscn1)C(=O)N(c1cc(OC)cc(OC)c1)C2]
I-64

TABLE 1-continued
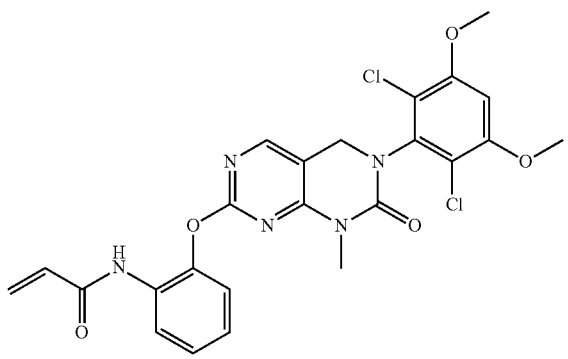 [SMILES: C=CC(=O)Nc1ccccc1Oc1ncc2c(n1)N(C)C(=O)N(c1c(Cl)c(OC)cc(OC)c1Cl)C2]
I-65
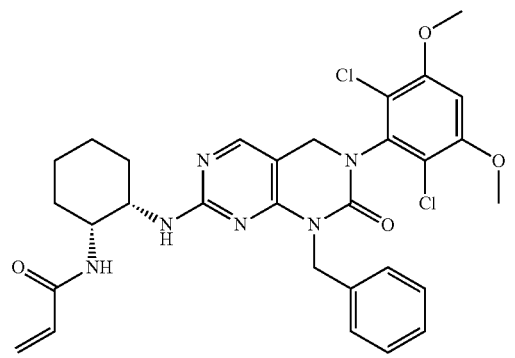 [SMILES: C=CC(=O)N[C@@H]1CCCC[C@@H]1Nc1ncc2c(n1)N(Cc1ccccc1)C(=O)N(c1c(Cl)c(OC)cc(OC)c1Cl)C2]
I-66
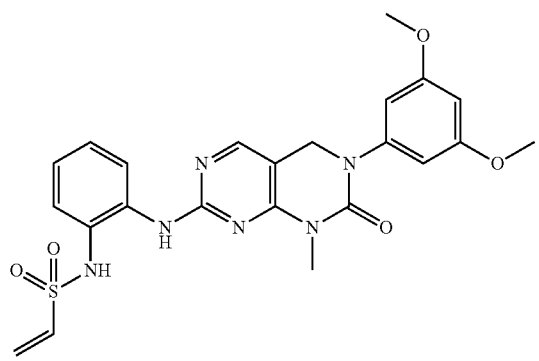 [SMILES: C=CS(=O)(=O)Nc1ccccc1Nc1ncc2c(n1)N(C)C(=O)N(c1cc(OC)cc(OC)c1)C2]
I-67
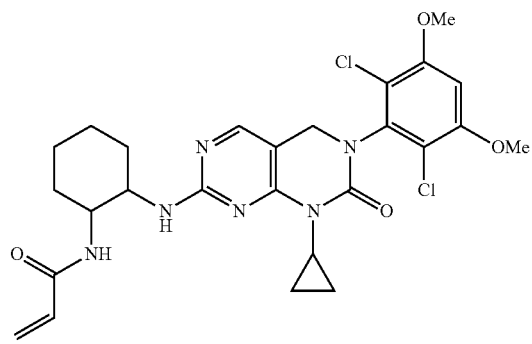 [SMILES: C=CC(=O)NC1CCCCC1Nc1ncc2c(n1)N(C1CC1)C(=O)N(c1c(Cl)c(OC)cc(OC)c1Cl)C2]
I-68

TABLE 1-continued
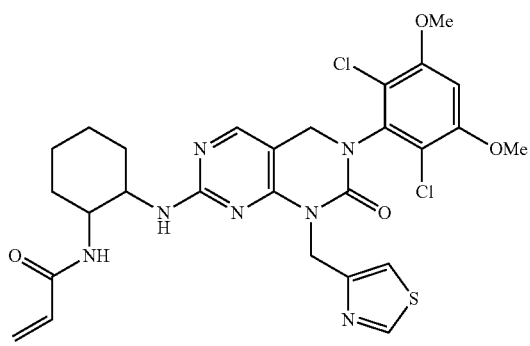 [SMILES: C=CC(=O)NC1CCCCC1Nc1ncc2c(n1)N(Cc1cscn1)C(=O)N(c1c(Cl)c(OC)cc(OC)c1Cl)C2]
I-69
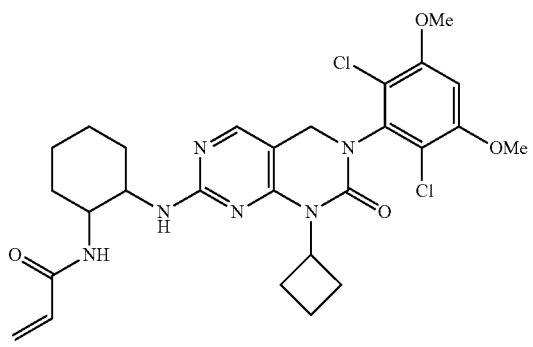 [SMILES: C=CC(=O)NC1CCCCC1Nc1ncc2c(n1)N(C1CCC1)C(=O)N(c1c(Cl)c(OC)cc(OC)c1Cl)C2]
I-70
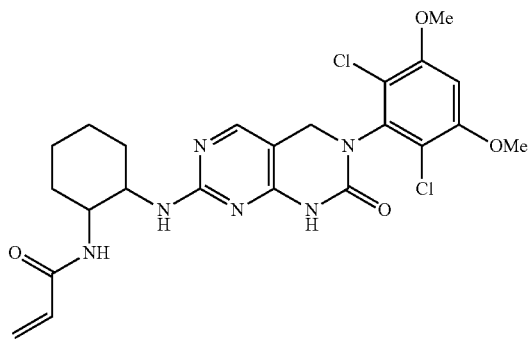 [SMILES: C=CC(=O)NC1CCCCC1Nc1ncc2c(n1)NC(=O)N(c1c(Cl)c(OC)cc(OC)c1Cl)C2]
I-73
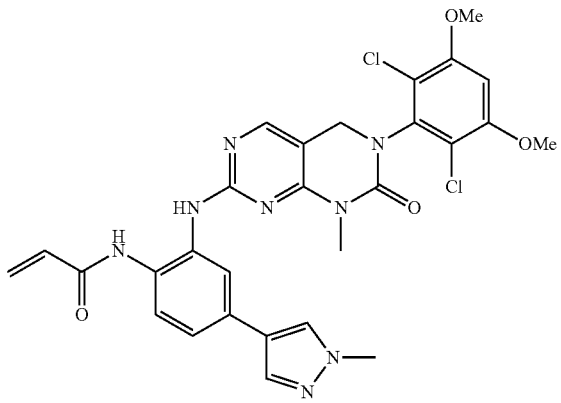 [SMILES: C=CC(=O)Nc1ccc(-c2cnn(C)c2)cc1Nc1ncc2c(n1)N(C)C(=O)N(c1c(Cl)c(OC)cc(OC)c1Cl)C2]
I-74

TABLE 1-continued
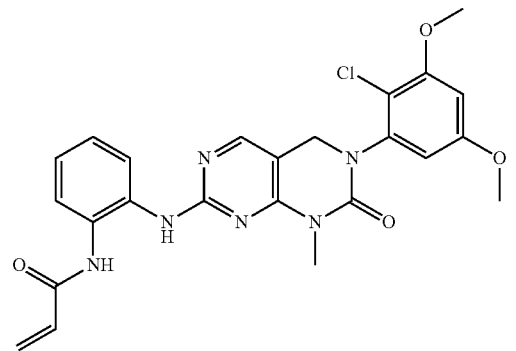 [SMILES: C=CC(=O)Nc1ccccc1Nc1ncc2c(n1)N(C)C(=O)N(c1cc(OC)cc(OC)c1Cl)C2]
I-75
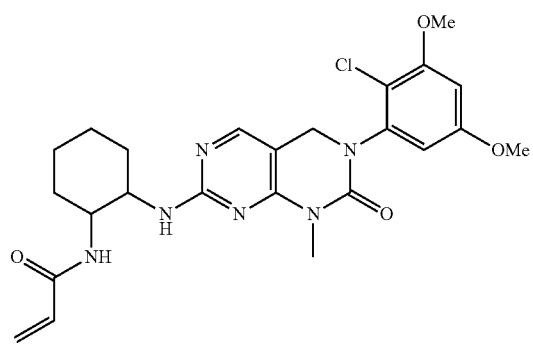 [SMILES: C=CC(=O)NC1CCCCC1Nc1ncc2c(n1)N(C)C(=O)N(c1cc(OC)cc(OC)c1Cl)C2]
I-76
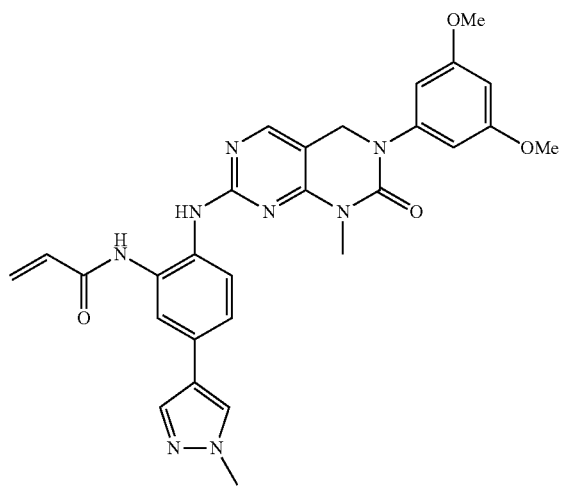 [SMILES: C=CC(=O)Nc1cc(-c2cnn(C)c2)ccc1Nc1ncc2c(n1)N(C)C(=O)N(c1cc(OC)cc(OC)c1)C2]
I-77
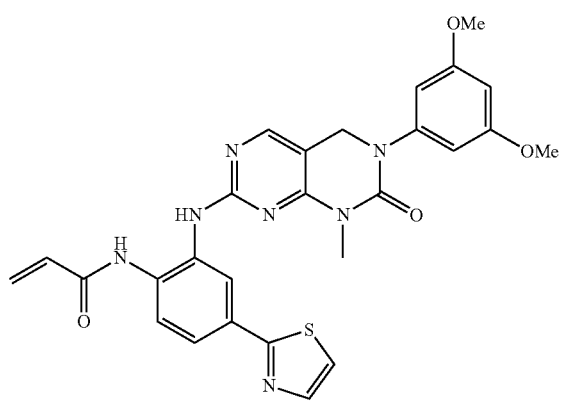 [SMILES: C=CC(=O)Nc1ccc(-c2nccs2)cc1Nc1ncc2c(n1)N(C)C(=O)N(c1cc(OC)cc(OC)c1)C2]
I-78

TABLE 1-continued
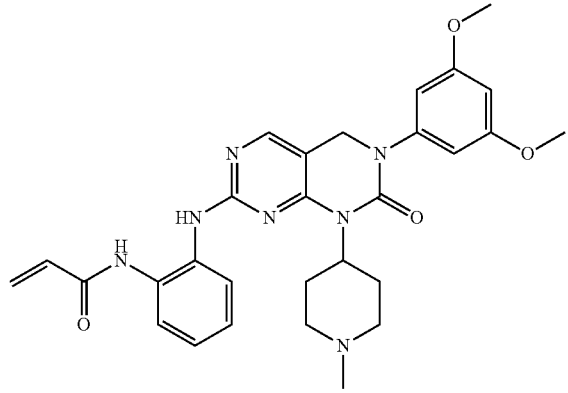 [SMILES: C=CC(=O)Nc1ccccc1Nc1ncc2c(n1)N(C1CCN(C)CC1)C(=O)N(c1cc(OC)cc(OC)c1)C2]
I-79
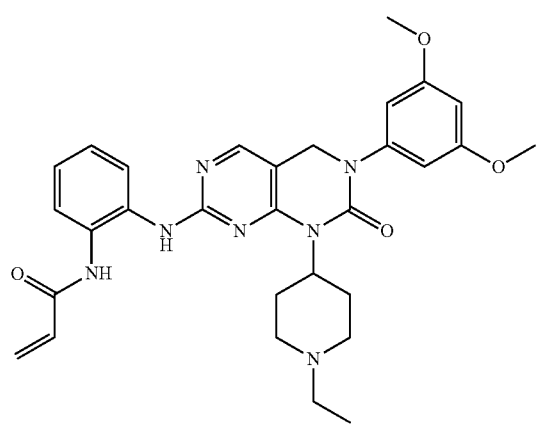 [SMILES: C=CC(=O)Nc1ccccc1Nc1ncc2c(n1)N(C1CCN(CC)CC1)C(=O)N(c1cc(OC)cc(OC)c1)C2]
I-80
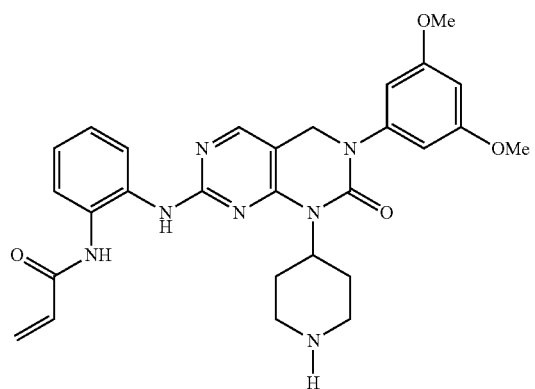 [SMILES: C=CC(=O)Nc1ccccc1Nc1ncc2c(n1)N(C1CCNCC1)C(=O)N(c1cc(OC)cc(OC)c1)C2]
I-81
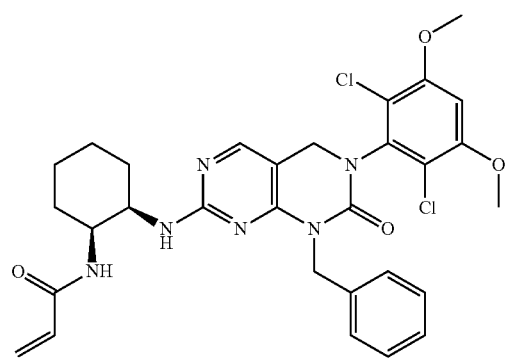 [SMILES: C=CC(=O)N[C@H]1CCCC[C@H]1Nc1ncc2c(n1)N(Cc1ccccc1)C(=O)N(c1c(Cl)c(OC)cc(OC)c1Cl)C2]
I-82

TABLE 1-continued
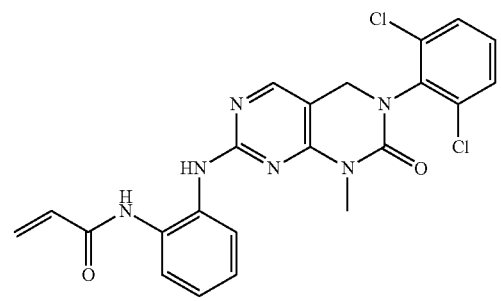 [SMILES: C=CC(=O)Nc1ccccc1Nc1ncc2c(n1)N(C)C(=O)N(c1c(Cl)cccc1Cl)C2]
I-83
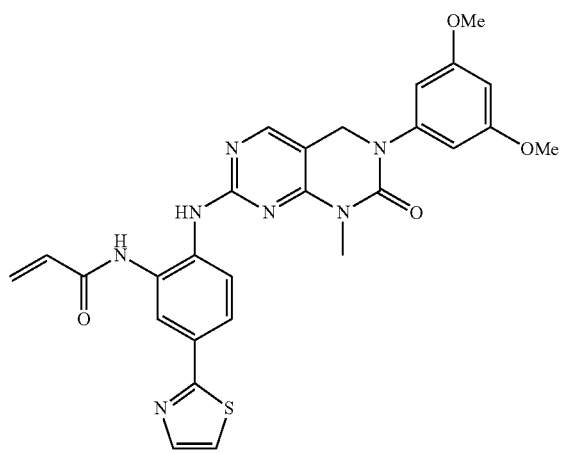 [SMILES: C=CC(=O)Nc1cc(-c2nccs2)ccc1Nc1ncc2c(n1)N(C)C(=O)N(c1cc(OC)cc(OC)c1)C2]
I-84
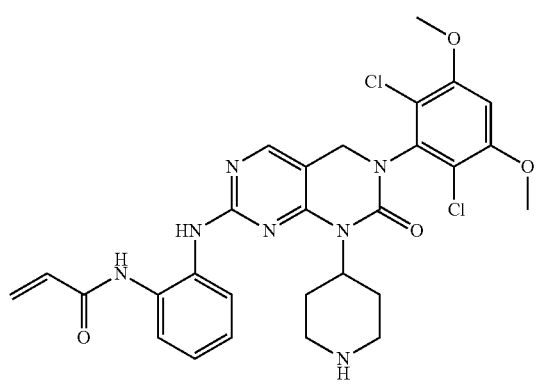 [SMILES: C=CC(=O)Nc1ccccc1Nc1ncc2c(n1)N(C1CCNCC1)C(=O)N(c1c(Cl)c(OC)cc(OC)c1Cl)C2]
I-85
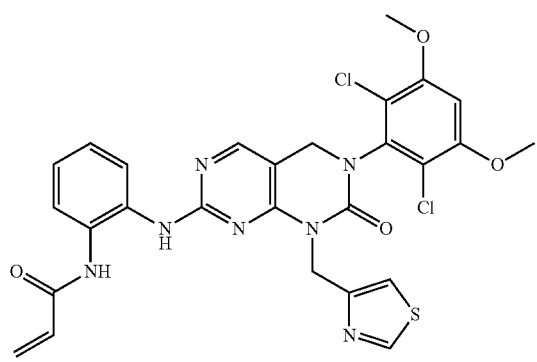 [SMILES: C=CC(=O)Nc1ccccc1Nc1ncc2c(n1)N(Cc1cscn1)C(=O)N(c1c(Cl)c(OC)cc(OC)c1Cl)C2]
I-86

TABLE 1-continued
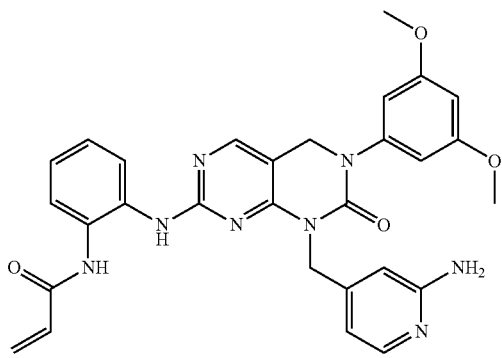 [SMILES: C=CC(=O)Nc1ccccc1Nc1ncc2c(n1)N(Cc1ccnc(N)c1)C(=O)N(c1cc(OC)cc(OC)c1)C2]
I-87
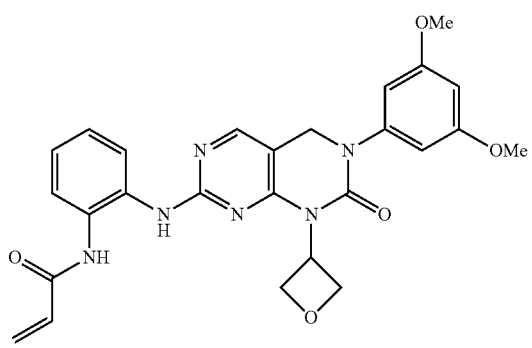 [SMILES: C=CC(=O)Nc1ccccc1Nc1ncc2c(n1)N(C1COC1)C(=O)N(c1cc(OC)cc(OC)c1)C2]
I-88
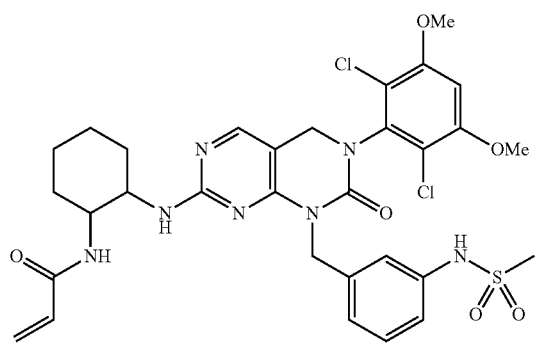 [SMILES: C=CC(=O)NC1CCCCC1Nc1ncc2c(n1)N(Cc1cccc(NS(C)(=O)=O)c1)C(=O)N(c1c(Cl)c(OC)cc(OC)c1Cl)C2]
I-89
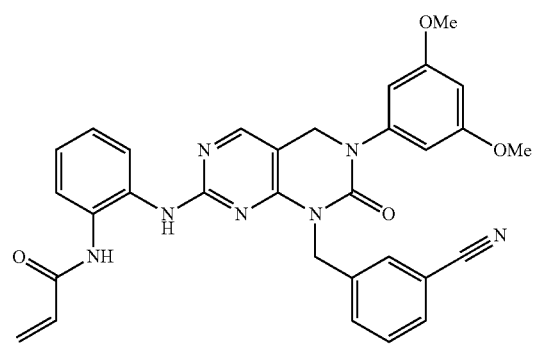 [SMILES: C=CC(=O)Nc1ccccc1Nc1ncc2c(n1)N(Cc1cccc(C#N)c1)C(=O)N(c1cc(OC)cc(OC)c1)C2]
I-90

TABLE 1-continued
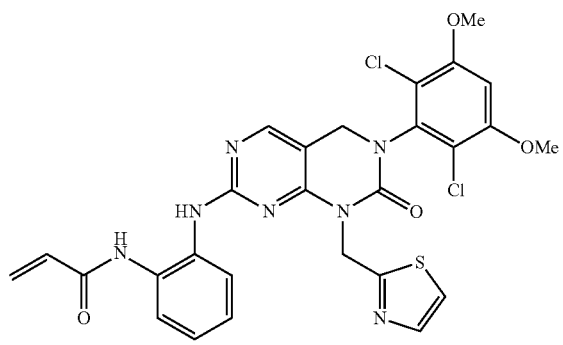 [SMILES: C=CC(=O)Nc1ccccc1Nc1ncc2c(n1)N(Cc1nccs1)C(=O)N(c1c(Cl)c(OC)cc(OC)c1Cl)C2]
I-91
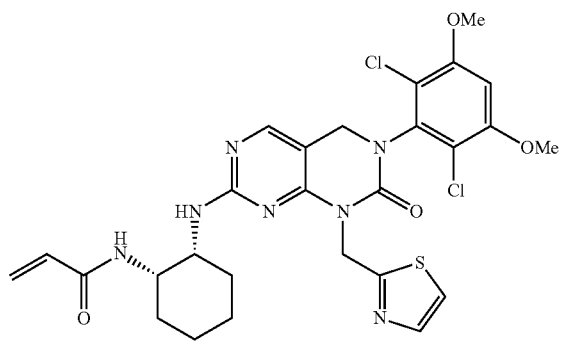 [SMILES: C=CC(=O)N[C@H]1CCCC[C@H]1Nc1ncc2c(n1)N(Cc1nccs1)C(=O)N(c1c(Cl)c(OC)cc(OC)c1Cl)C2]
I-92
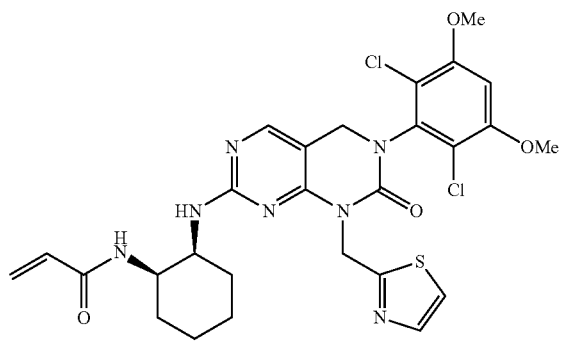 [SMILES: C=CC(=O)N[C@@H]1CCCC[C@@H]1Nc1ncc2c(n1)N(Cc1nccs1)C(=O)N(c1c(Cl)c(OC)cc(OC)c1Cl)C2]
I-93
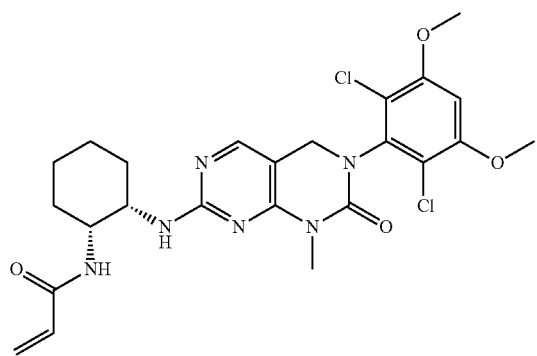 [SMILES: C=CC(=O)N[C@@H]1CCCC[C@@H]1Nc1ncc2c(n1)N(C)C(=O)N(c1c(Cl)c(OC)cc(OC)c1Cl)C2]
I-94

TABLE 1-continued
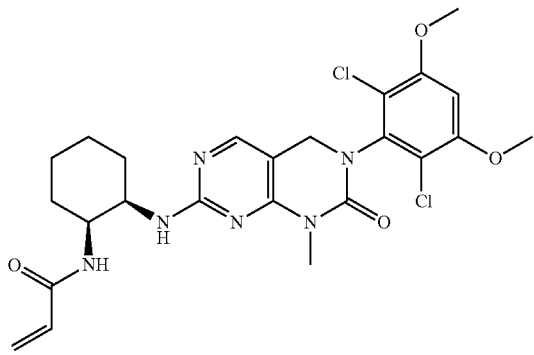 [SMILES: C=CC(=O)N[C@H]1CCCC[C@H]1Nc1ncc2c(n1)N(C)C(=O)N(c1c(Cl)c(OC)cc(OC)c1Cl)C2]
I-95
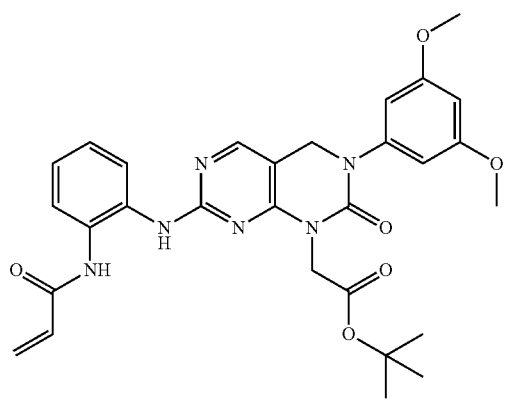 [SMILES: C=CC(=O)Nc1ccccc1Nc1ncc2c(n1)N(CC(=O)OC(C)(C)C)C(=O)N(c1cc(OC)cc(OC)c1)C2]
I-96
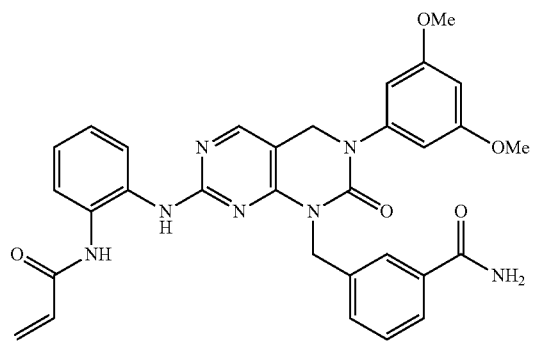 [SMILES: C=CC(=O)Nc1ccccc1Nc1ncc2c(n1)N(Cc1cccc(C(N)=O)c1)C(=O)N(c1cc(OC)cc(OC)c1)C2]
I-97
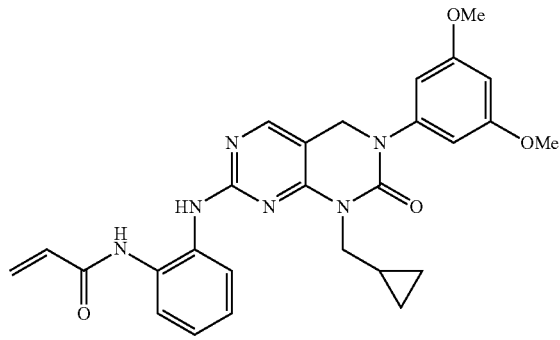 [SMILES: C=CC(=O)Nc1ccccc1Nc1ncc2c(n1)N(CC1CC1)C(=O)N(c1cc(OC)cc(OC)c1)C2]
I-98

TABLE 1-continued
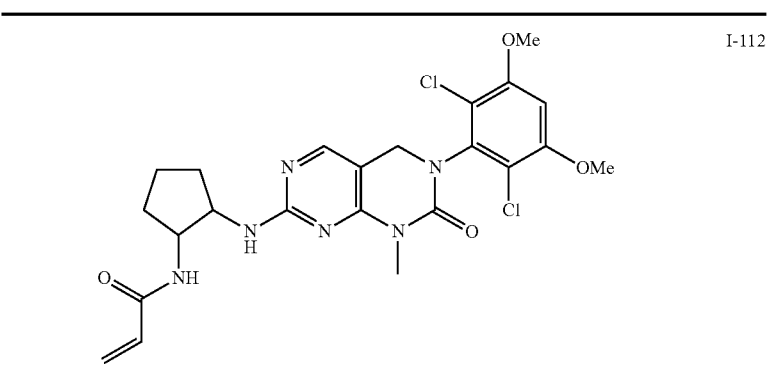
I-112
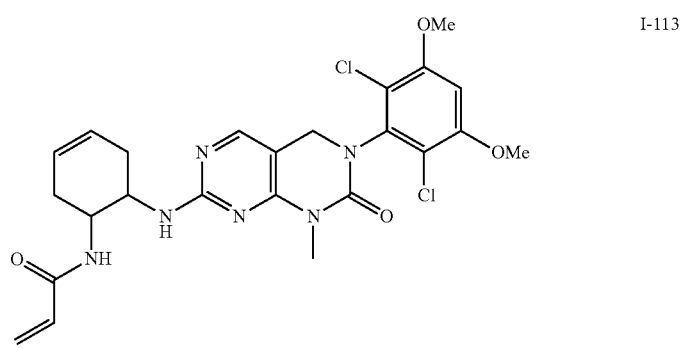
I-113
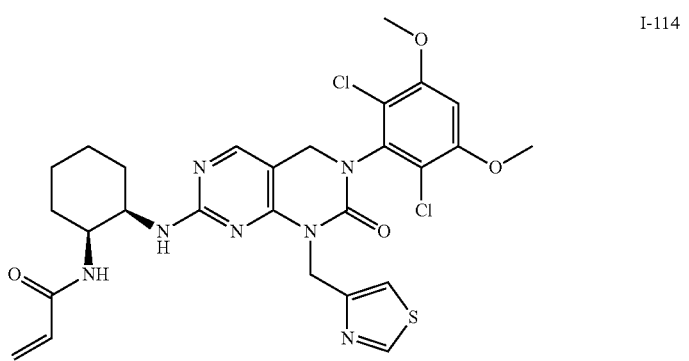
I-114
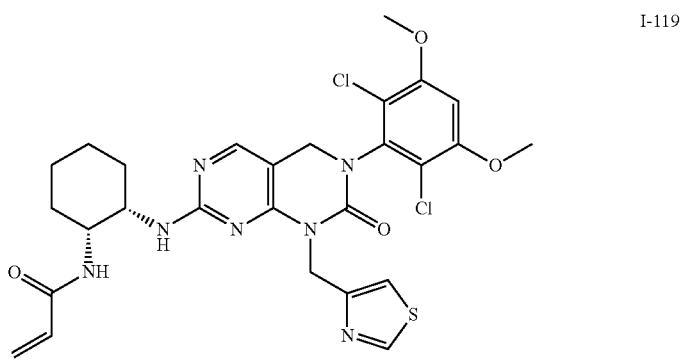
I-119

TABLE 1-continued
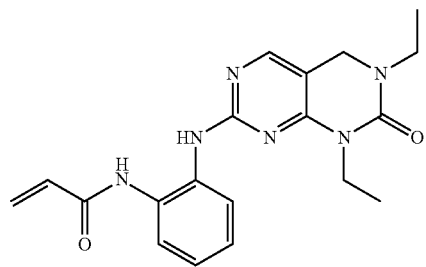 [SMILES: C=CC(=O)Nc1ccccc1Nc1ncc2c(n1)N(CC)C(=O)N(CC)C2]
I-120
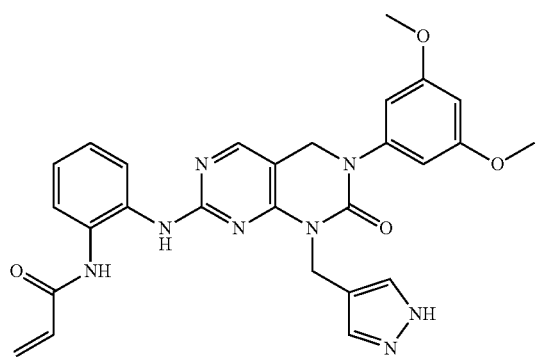 [SMILES: C=CC(=O)Nc1ccccc1Nc1ncc2c(n1)N(Cc1cn[nH]c1)C(=O)N(c1cc(OC)cc(OC)c1)C2]
I-121
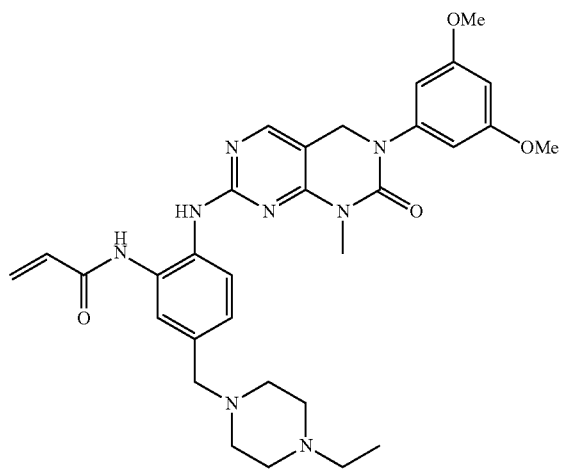 [SMILES: C=CC(=O)Nc1cc(CN2CCN(CC)CC2)ccc1Nc1ncc2c(n1)N(C)C(=O)N(c1cc(OC)cc(OC)c1)C2]
I-122

TABLE 1-continued
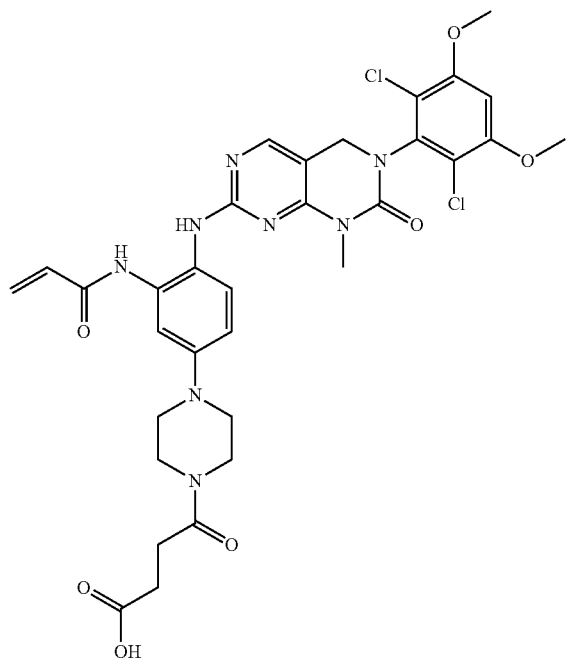 [SMILES: C=CC(=O)Nc1cc(N2CCN(C(=O)CCC(=O)O)CC2)ccc1Nc1ncc2c(n1)N(C)C(=O)N(c1c(Cl)c(OC)cc(OC)c1Cl)C2]
I-123
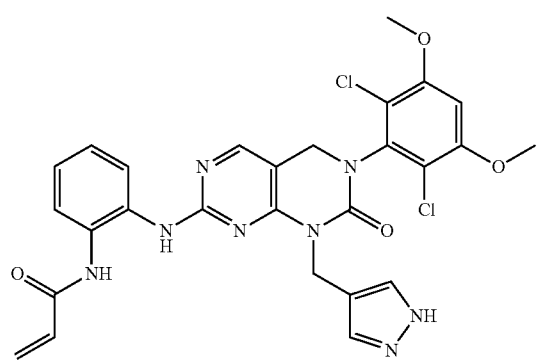
I-124
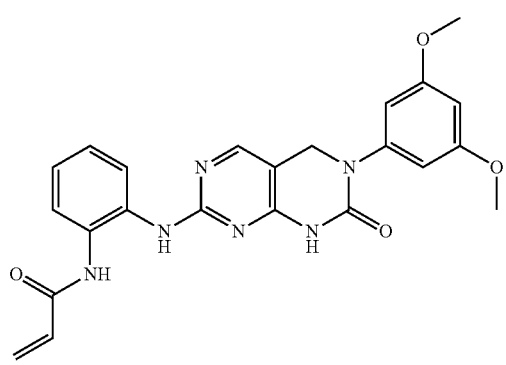 [SMILES: C=CC(=O)Nc1ccccc1Nc1ncc2c(n1)NC(=O)N(c1cc(OC)cc(OC)c1)C2]
I-125

TABLE 1-continued
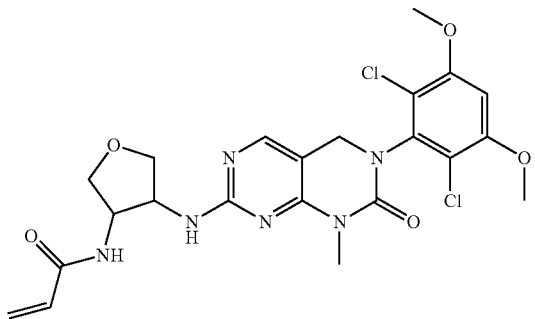 [SMILES: C=CC(=O)NC1COCC1Nc1ncc2c(n1)N(C)C(=O)N(c1c(Cl)c(OC)cc(OC)c1Cl)C2]
I-126
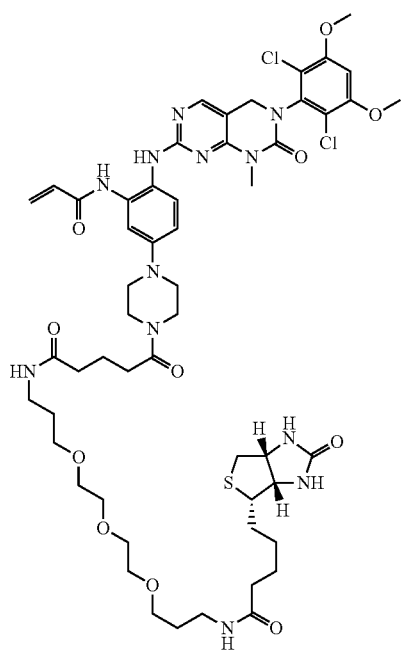 [SMILES: C=CC(=O)Nc1cc(N2CCN(C(=O)CCCC(=O)NCCCOCCOCCOCCCNC(=O)CCCC[C@@H]3SC[C@@H]4NC(=O)N[C@@H]43)CC2)ccc1Nc1ncc2c(n1)N(C)C(=O)N(c1c(Cl)c(OC)cc(OC)c1Cl)C2]
I-127
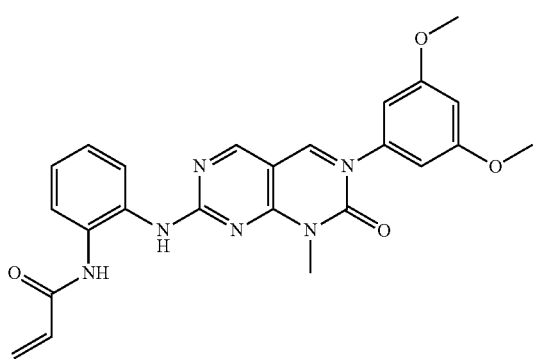
I-128

TABLE 1-continued
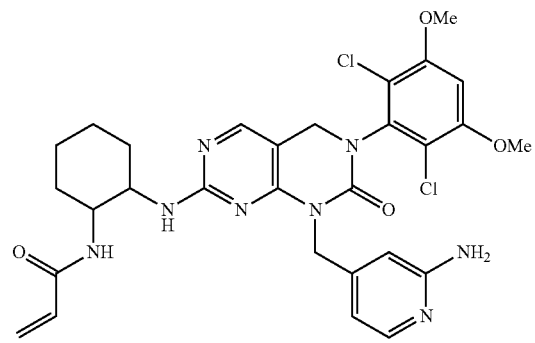 [SMILES: C=CC(=O)NC1CCCCC1Nc1ncc2c(n1)N(Cc1ccnc(N)c1)C(=O)N(c1c(Cl)c(OC)cc(OC)c1Cl)C2]
I-133
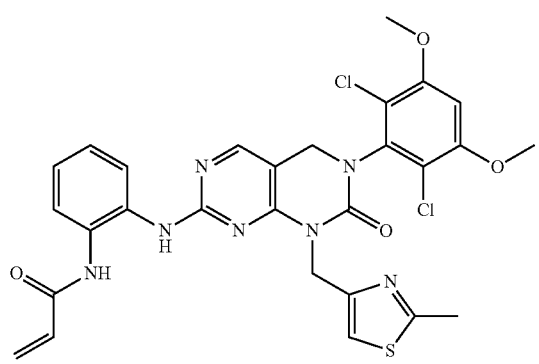 [SMILES: C=CC(=O)Nc1ccccc1Nc1ncc2c(n1)N(Cc1csc(C)n1)C(=O)N(c1c(Cl)c(OC)cc(OC)c1Cl)C2]
I-134
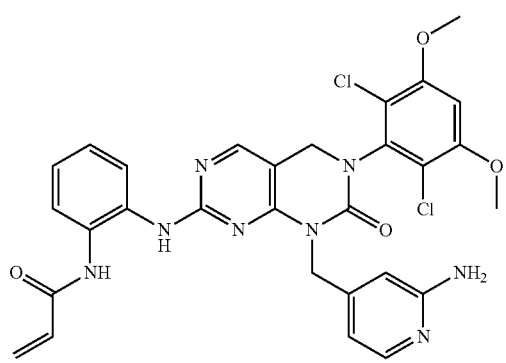 [SMILES: C=CC(=O)Nc1ccccc1Nc1ncc2c(n1)N(Cc1ccnc(N)c1)C(=O)N(c1c(Cl)c(OC)cc(OC)c1Cl)C2]
I-135
I-136

TABLE 1-continued
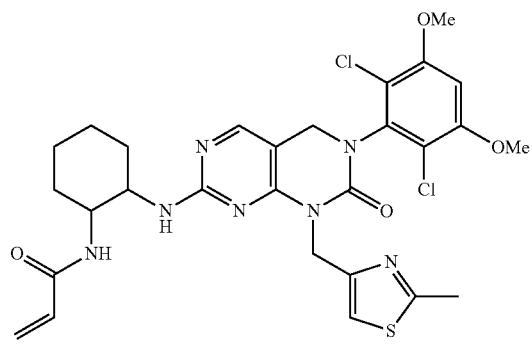 [SMILES: C=CC(=O)NC1CCCCC1Nc1ncc2c(n1)N(Cc1csc(C)n1)C(=O)N(c1c(Cl)c(OC)cc(OC)c1Cl)C2]
I-137
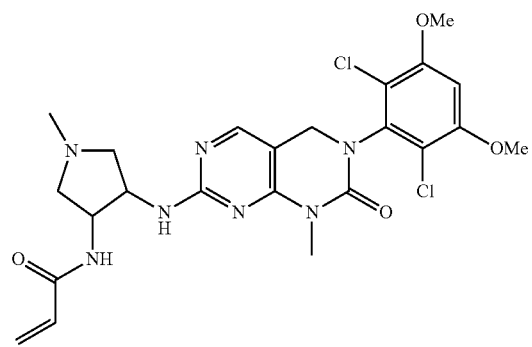 [SMILES: C=CC(=O)NC1CN(C)CC1Nc1ncc2c(n1)N(C)C(=O)N(c1c(Cl)c(OC)cc(OC)c1Cl)C2]
I-138
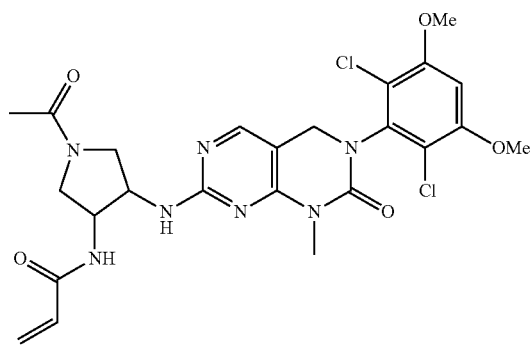 [SMILES: C=CC(=O)NC1CN(C(C)=O)CC1Nc1ncc2c(n1)N(C)C(=O)N(c1c(Cl)c(OC)cc(OC)c1Cl)C2]
I-139
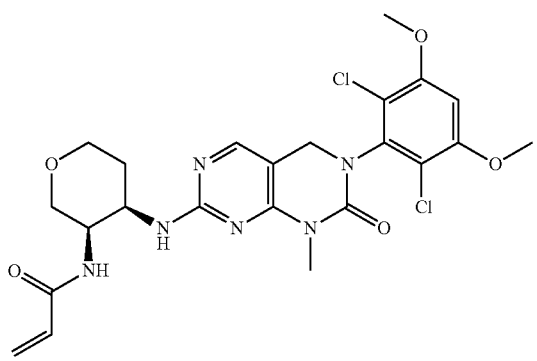 [SMILES: C=CC(=O)N[C@H]1COCC[C@H]1Nc1ncc2c(n1)N(C)C(=O)N(c1c(Cl)c(OC)cc(OC)c1Cl)C2]
I-140

TABLE 1-continued
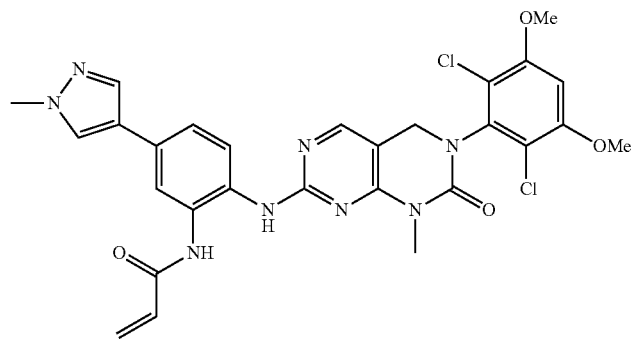 [SMILES: C=CC(=O)Nc1cc(-c2cnn(C)c2)ccc1Nc1ncc2c(n1)N(C)C(=O)N(c1c(Cl)c(OC)cc(OC)c1Cl)C2]
I-141
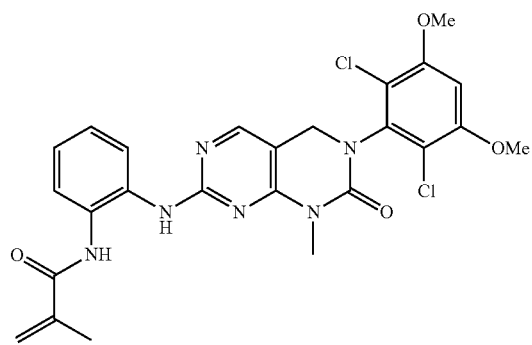 [SMILES: C=C(C)C(=O)Nc1ccccc1Nc1ncc2c(n1)N(C)C(=O)N(c1c(Cl)c(OC)cc(OC)c1Cl)C2]
I-142
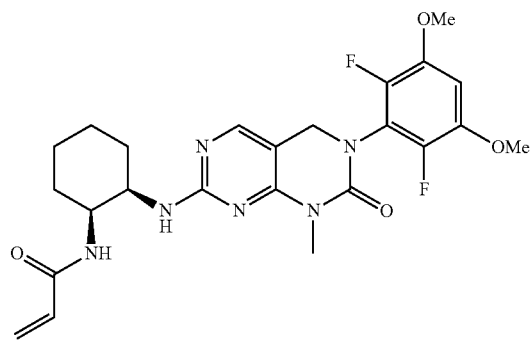 [SMILES: C=CC(=O)N[C@H]1CCCC[C@H]1Nc1ncc2c(n1)N(C)C(=O)N(c1c(F)c(OC)cc(OC)c1F)C2]
I-143
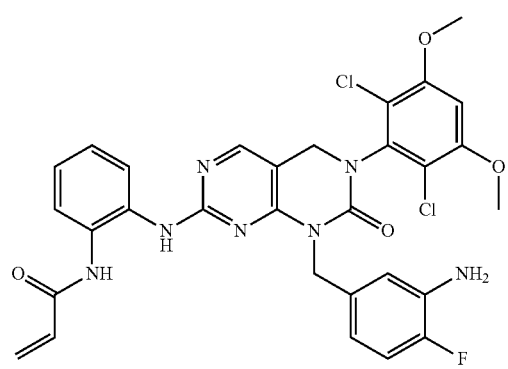 [SMILES: C=CC(=O)Nc1ccccc1Nc1ncc2c(n1)N(Cc1ccc(F)c(N)c1)C(=O)N(c1c(Cl)c(OC)cc(OC)c1Cl)C2]
I-144

TABLE 1-continued
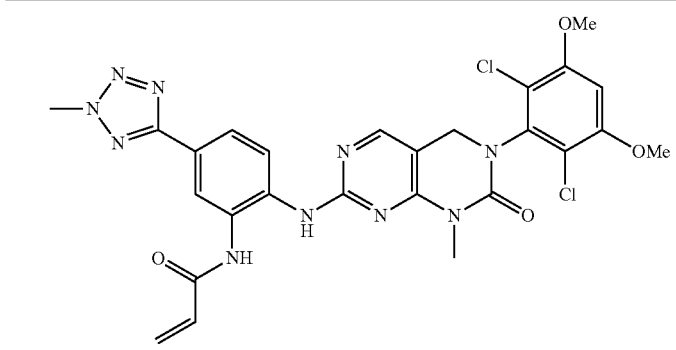 [SMILES: C=CC(=O)Nc1cc(-c2nnn(C)n2)ccc1Nc1ncc2c(n1)N(C)C(=O)N(c1c(Cl)c(OC)cc(OC)c1Cl)C2] I-145
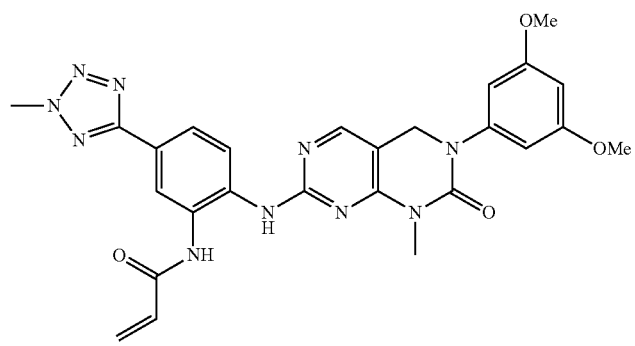 [SMILES: C=CC(=O)Nc1cc(-c2nnn(C)n2)ccc1Nc1ncc2c(n1)N(C)C(=O)N(c1cc(OC)cc(OC)c1)C2] I-146
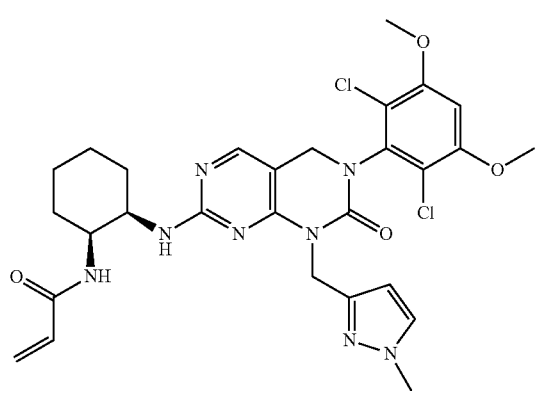 [SMILES: C=CC(=O)N[C@H]1CCCC[C@H]1Nc1ncc2c(n1)N(Cc1ccn(C)n1)C(=O)N(c1c(Cl)c(OC)cc(OC)c1Cl)C2] I-147
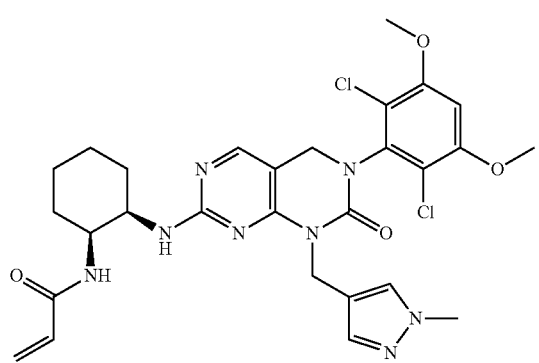 [SMILES: C=CC(=O)N[C@H]1CCCC[C@H]1Nc1ncc2c(n1)N(Cc1cnn(C)c1)C(=O)N(c1c(Cl)c(OC)cc(OC)c1Cl)C2] I-148

TABLE 1-continued
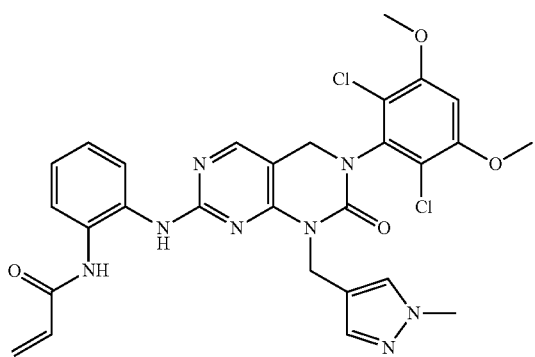 [SMILES: C=CC(=O)Nc1ccccc1Nc1ncc2c(n1)N(Cc1cnn(C)c1)C(=O)N(c1c(Cl)c(OC)cc(OC)c1Cl)C2]
I-149
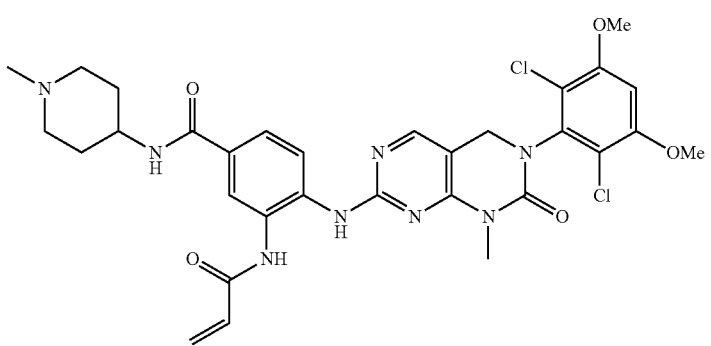 [SMILES: C=CC(=O)Nc1cc(C(=O)NC2CCN(C)CC2)ccc1Nc1ncc2c(n1)N(C)C(=O)N(c1c(Cl)c(OC)cc(OC)c1Cl)C2]
I-150
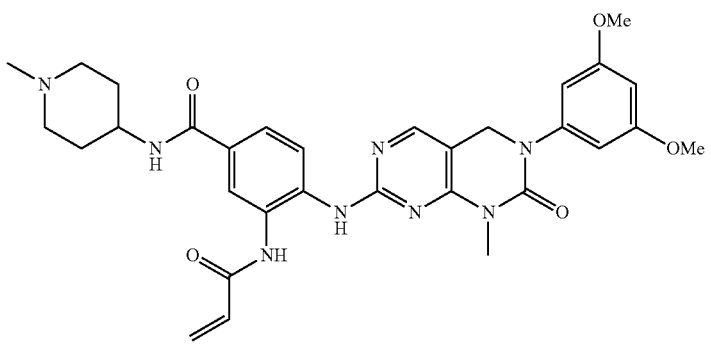 [SMILES: C=CC(=O)Nc1cc(C(=O)NC2CCN(C)CC2)ccc1Nc1ncc2c(n1)N(C)C(=O)N(c1cc(OC)cc(OC)c1)C2]
I-151
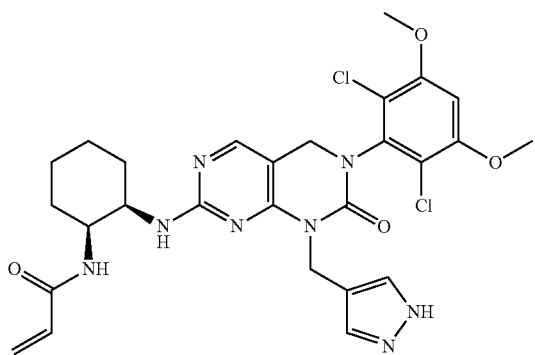 [SMILES: C=CC(=O)N[C@H]1CCCC[C@H]1Nc1ncc2c(n1)N(Cc1cn[nH]c1)C(=O)N(c1c(Cl)c(OC)cc(OC)c1Cl)C2]
I-152

TABLE 1-continued
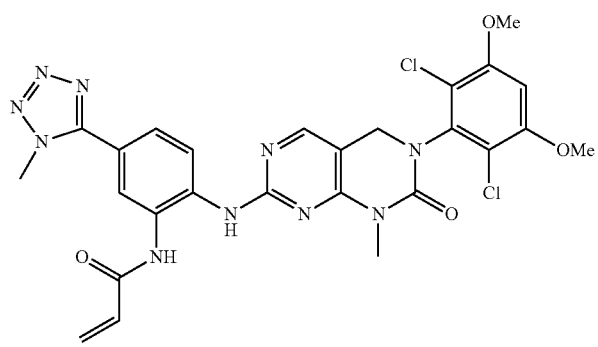 [SMILES: C=CC(=O)Nc1cc(-c2nnnn2C)ccc1Nc1ncc2c(n1)N(C)C(=O)N(c1c(Cl)c(OC)cc(OC)c1Cl)C2] I-153
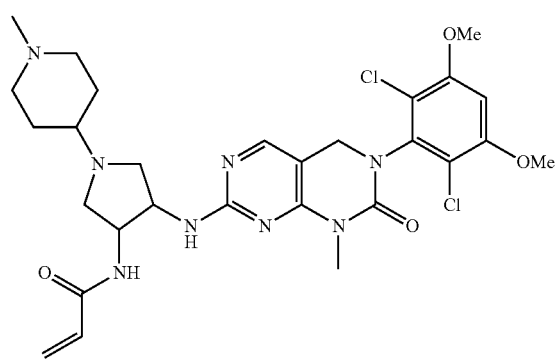 [SMILES: C=CC(=O)NC1CN(C2CCN(C)CC2)CC1Nc1ncc2c(n1)N(C)C(=O)N(c1c(Cl)c(OC)cc(OC)c1Cl)C2] I-154
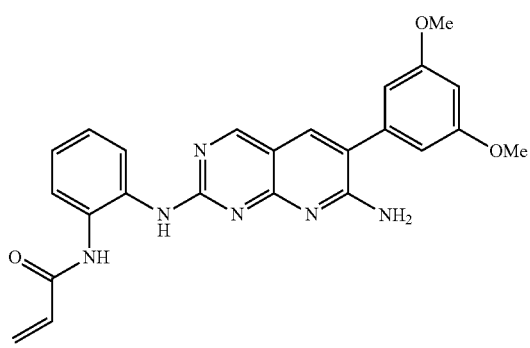 [SMILES: C=CC(=O)Nc1ccccc1Nc1ncc2cc(-c3cc(OC)cc(OC)c3)c(N)nc2n1] I-155
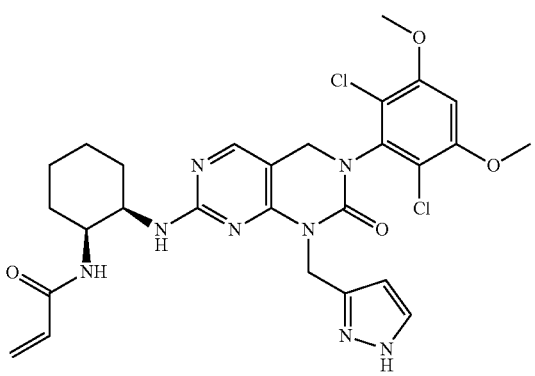 [SMILES: C=CC(=O)N[C@H]1CCCC[C@H]1Nc1ncc2c(n1)N(Cc1cc[nH]n1)C(=O)N(c1c(Cl)c(OC)cc(OC)c1Cl)C2] I-156

TABLE 1-continued
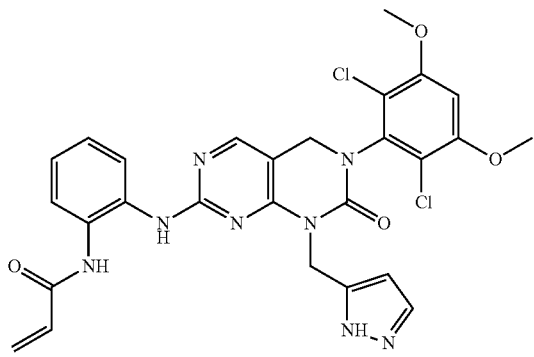 [SMILES: C=CC(=O)Nc1ccccc1Nc1ncc2c(n1)N(Cc1ccn[nH]1)C(=O)N(c1c(Cl)c(OC)cc(OC)c1Cl)C2]
I-157
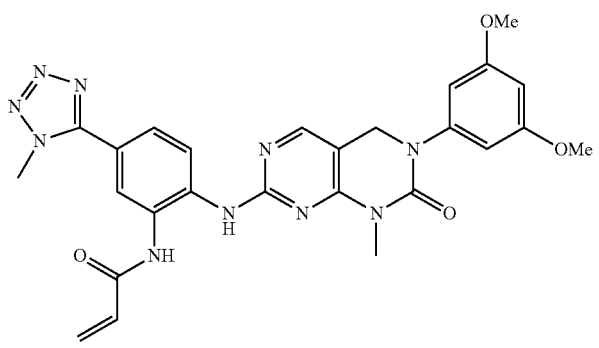 [SMILES: C=CC(=O)Nc1cc(-c2nnnn2C)ccc1Nc1ncc2c(n1)N(C)C(=O)N(c1cc(OC)cc(OC)c1)C2]
I-158
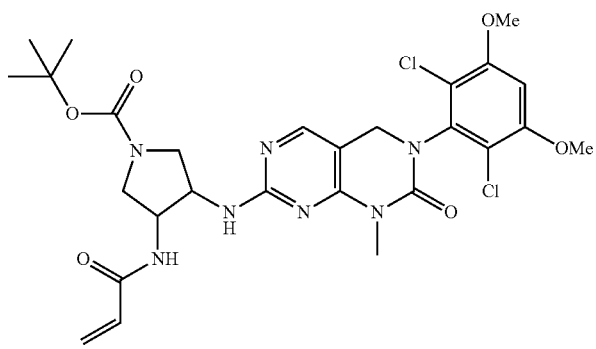 [SMILES: C=CC(=O)NC1CN(C(=O)OC(C)(C)C)CC1Nc1ncc2c(n1)N(C)C(=O)N(c1c(Cl)c(OC)cc(OC)c1Cl)C2]
I-159
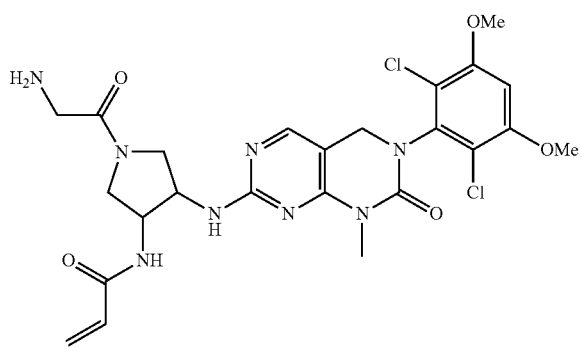 [SMILES: C=CC(=O)NC1CN(C(=O)CN)CC1Nc1ncc2c(n1)N(C)C(=O)N(c1c(Cl)c(OC)cc(OC)c1Cl)C2]
I-160

TABLE 1-continued
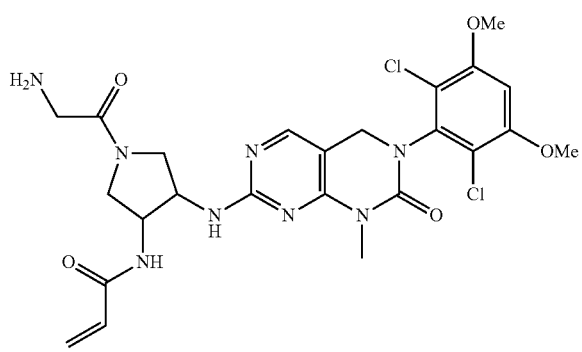 [SMILES: C=CC(=O)NC1CN(C(=O)CN)CC1Nc1ncc2c(n1)N(C)C(=O)N(c1c(Cl)c(OC)cc(OC)c1Cl)C2]
I-161
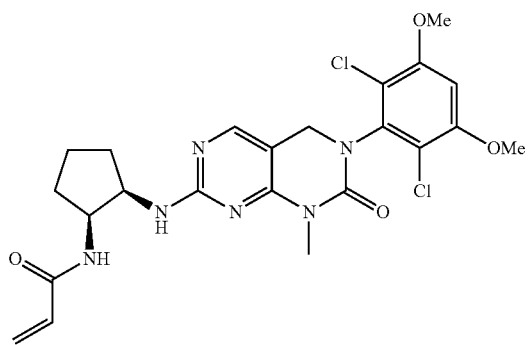 [SMILES: C=CC(=O)N[C@H]1CCC[C@H]1Nc1ncc2c(n1)N(C)C(=O)N(c1c(Cl)c(OC)cc(OC)c1Cl)C2]
I-162
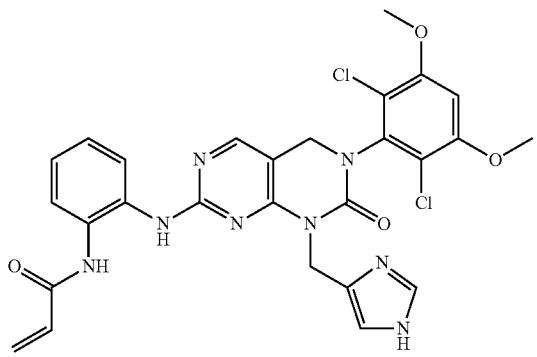 [SMILES: C=CC(=O)Nc1ccccc1Nc1ncc2c(n1)N(Cc1c[nH]cn1)C(=O)N(c1c(Cl)c(OC)cc(OC)c1Cl)C2]
I-163
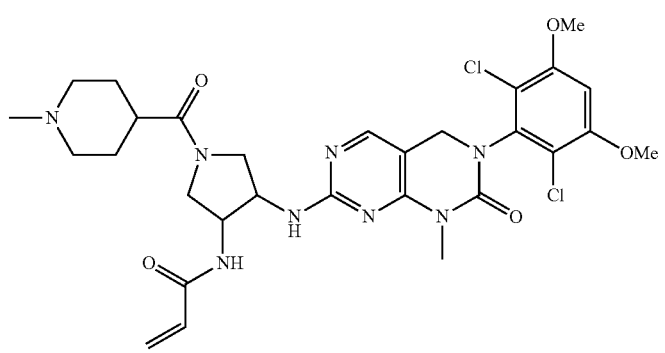 [SMILES: C=CC(=O)NC1CN(C(=O)C2CCN(C)CC2)CC1Nc1ncc2c(n1)N(C)C(=O)N(c1c(Cl)c(OC)cc(OC)c1Cl)C2]
I-164

TABLE 1-continued
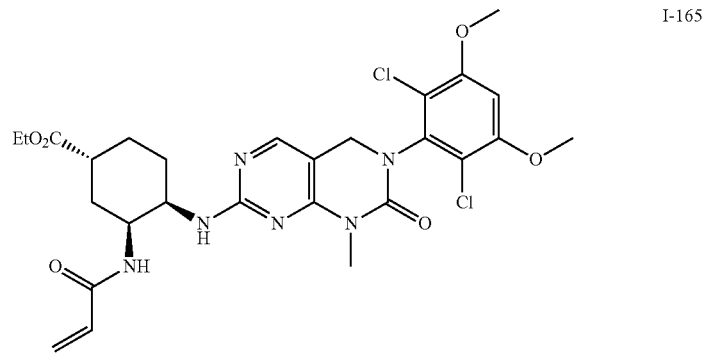
I-165
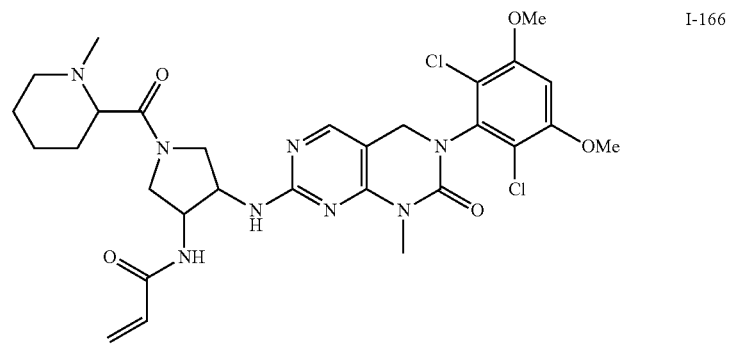
I-166
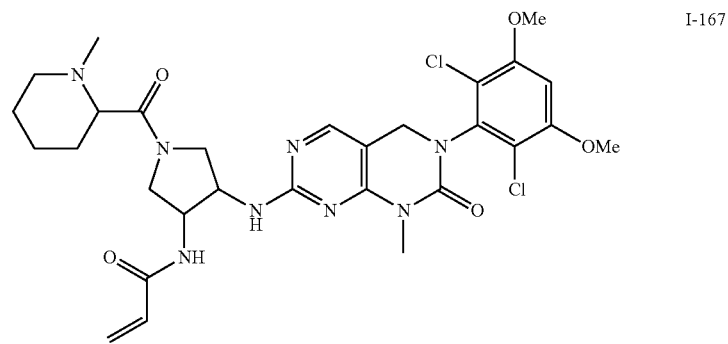
I-167
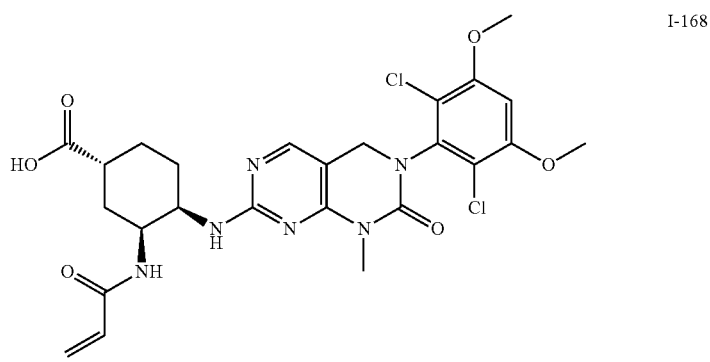
I-168

TABLE 1-continued
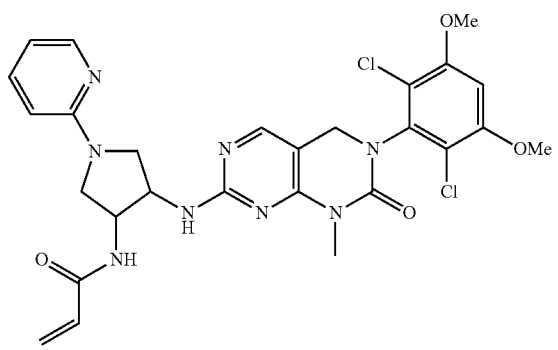
I-170
I-171
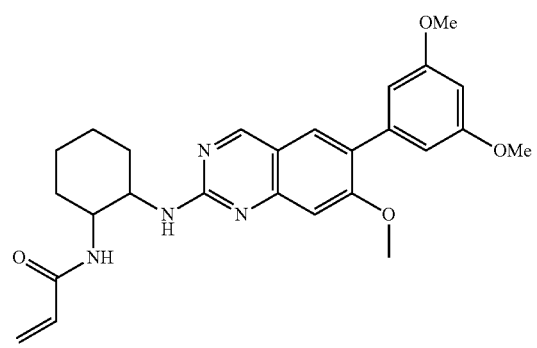 [SMILES: C=CC(=O)NC1CCCCC1Nc1ncc2cc(-c3cc(OC)cc(OC)c3)c(OC)cc2n1]
I-172
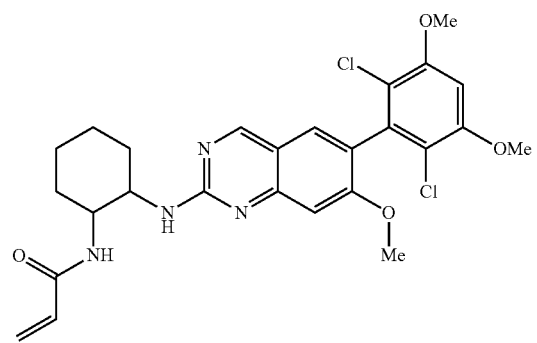 [SMILES: C=CC(=O)NC1CCCCC1Nc1ncc2cc(-c3c(Cl)c(OC)cc(OC)c3Cl)c(OC)cc2n1]
I-173

TABLE 1-continued
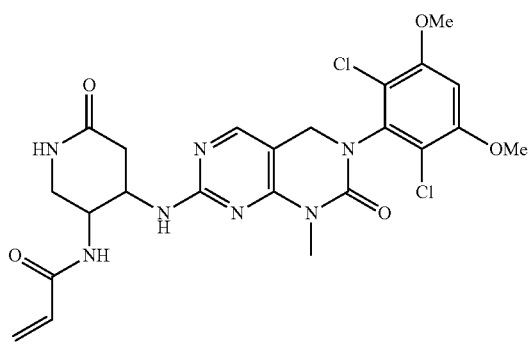 [SMILES: C=CC(=O)NC1CNC(=O)CC1Nc1ncc2c(n1)N(C)C(=O)N(c1c(Cl)c(OC)cc(OC)c1Cl)C2] I-174
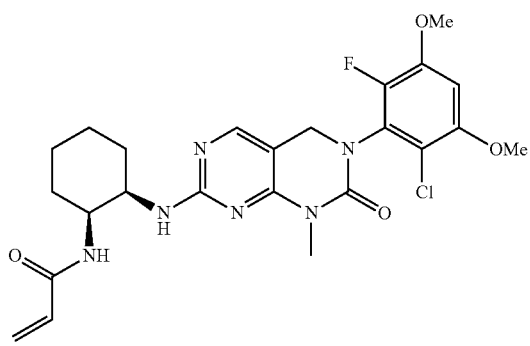 [SMILES: C=CC(=O)N[C@H]1CCCC[C@H]1Nc1ncc2c(n1)N(C)C(=O)N(c1c(F)c(OC)cc(OC)c1Cl)C2] I-175
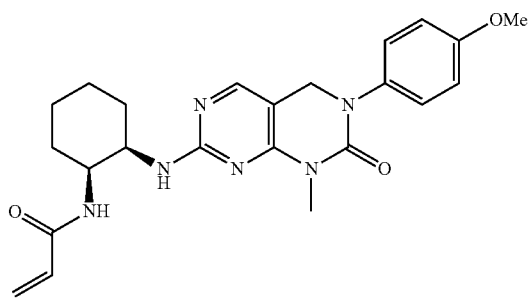 [SMILES: C=CC(=O)N[C@H]1CCCC[C@H]1Nc1ncc2c(n1)N(C)C(=O)N(c1ccc(OC)cc1)C2] I-176
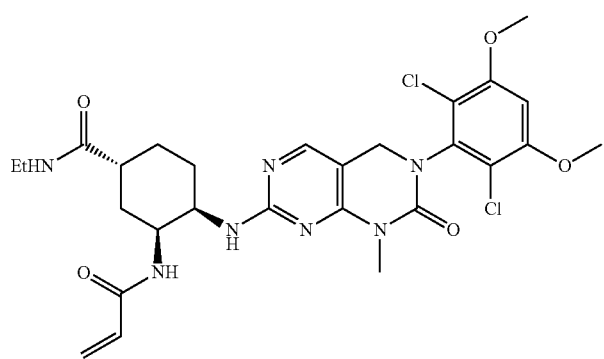 I-177

TABLE 1-continued
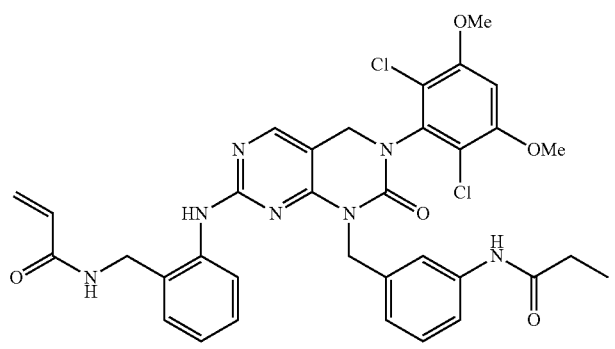 [SMILES: C=CC(=O)NCc1ccccc1Nc1ncc2c(n1)N(Cc1cccc(NC(=O)CC)c1)C(=O)N(c1c(Cl)c(OC)cc(OC)c1Cl)C2]
I-179
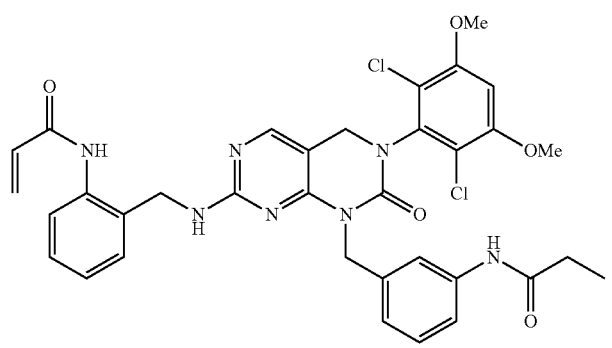 [SMILES: C=CC(=O)Nc1ccccc1CNc1ncc2c(n1)N(Cc1cccc(NC(=O)CC)c1)C(=O)N(c1c(Cl)c(OC)cc(OC)c1Cl)C2]
I-180
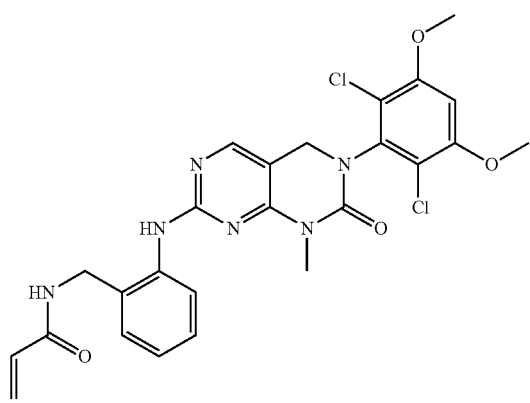 [SMILES: C=CC(=O)NCc1ccccc1Nc1ncc2c(n1)N(C)C(=O)N(c1c(Cl)c(OC)cc(OC)c1Cl)C2]
I-181
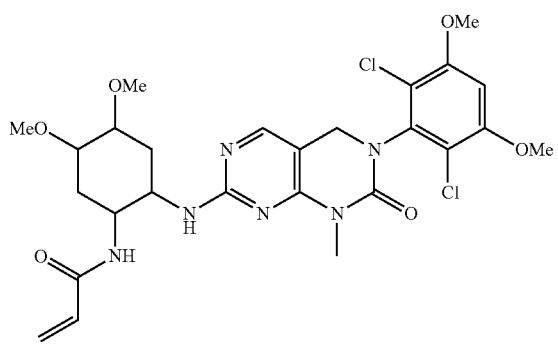 [SMILES: C=CC(=O)NC1CC(OC)C(OC)CC1Nc1ncc2c(n1)N(C)C(=O)N(c1c(Cl)c(OC)cc(OC)c1Cl)C2]
I-182

TABLE 1-continued
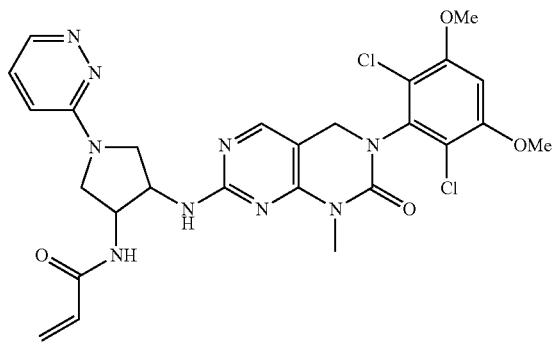 [SMILES: C=CC(=O)NC1CN(c2cccnn2)CC1Nc1ncc2c(n1)N(C)C(=O)N(c1c(Cl)c(OC)cc(OC)c1Cl)C2]
I-183
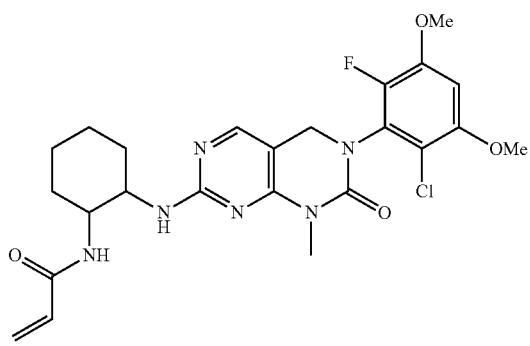 [SMILES: C=CC(=O)NC1CCCCC1Nc1ncc2c(n1)N(C)C(=O)N(c1c(F)c(OC)cc(OC)c1Cl)C2]
I-184
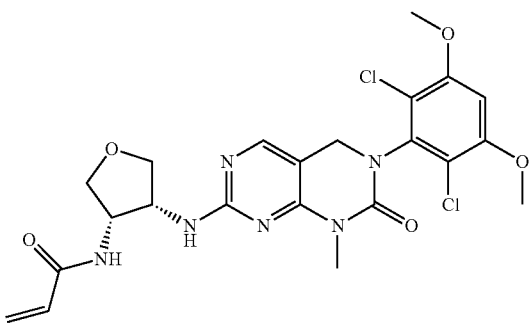
I-185
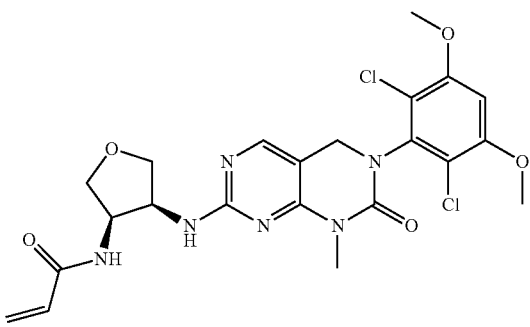 [SMILES: C=CC(=O)N[C@H]1COC[C@H]1Nc1ncc2c(n1)N(C)C(=O)N(c1c(Cl)c(OC)cc(OC)c1Cl)C2]
I-186
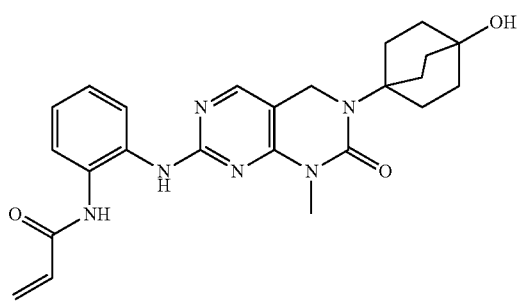 [SMILES: C=CC(=O)Nc1ccccc1Nc1ncc2c(n1)N(C)C(=O)N(C13CCC(O)(CC1)CC3)C2]
I-187

TABLE 1-continued
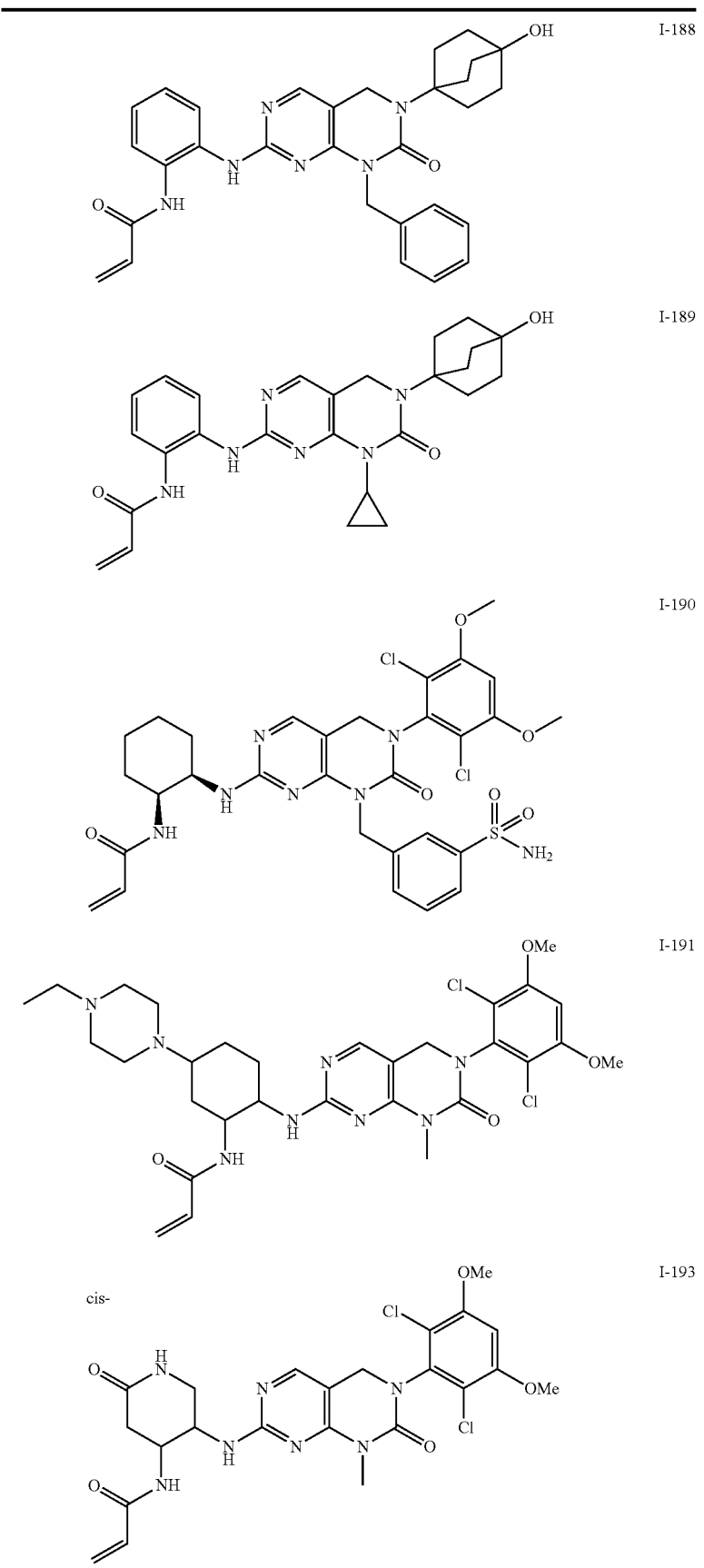

TABLE 1-continued
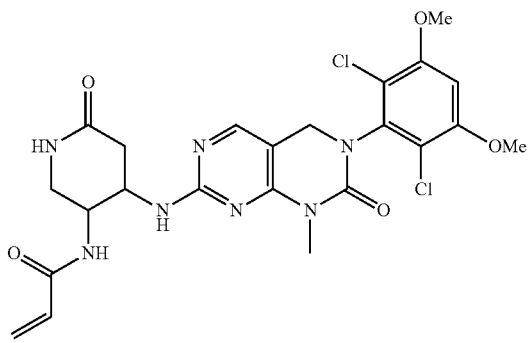 [SMILES: C=CC(=O)NC1CNC(=O)CC1Nc1ncc2c(n1)N(C)C(=O)N(c1c(Cl)c(OC)cc(OC)c1Cl)C2]
I-194
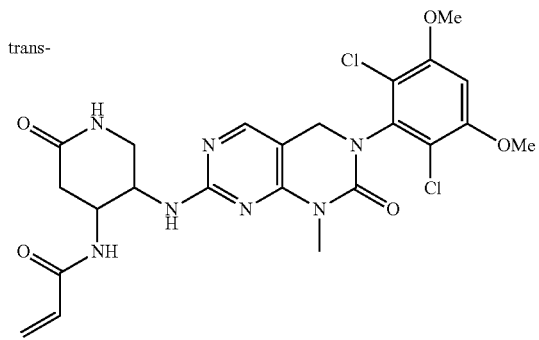 [SMILES: C=CC(=O)NC1CC(=O)NCC1Nc1ncc2c(n1)N(C)C(=O)N(c1c(Cl)c(OC)cc(OC)c1Cl)C2]
trans-
I-195
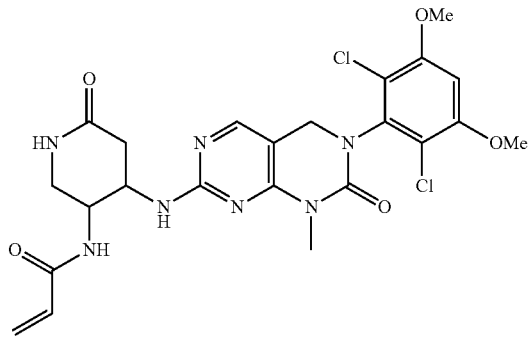 [SMILES: C=CC(=O)NC1CNC(=O)CC1Nc1ncc2c(n1)N(C)C(=O)N(c1c(Cl)c(OC)cc(OC)c1Cl)C2]
I-196
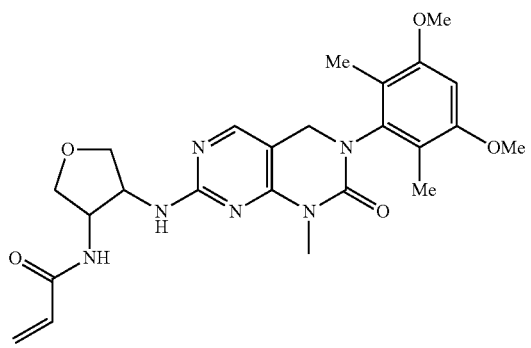 [SMILES: C=CC(=O)NC1COCC1Nc1ncc2c(n1)N(C)C(=O)N(c1c(C)c(OC)cc(OC)c1C)C2]
I-197

TABLE 1-continued
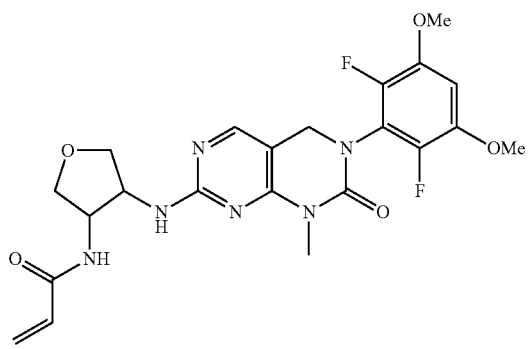 [SMILES: C=CC(=O)NC1COCC1Nc1ncc2c(n1)N(C)C(=O)N(c1c(F)c(OC)cc(OC)c1F)C2]
I-198
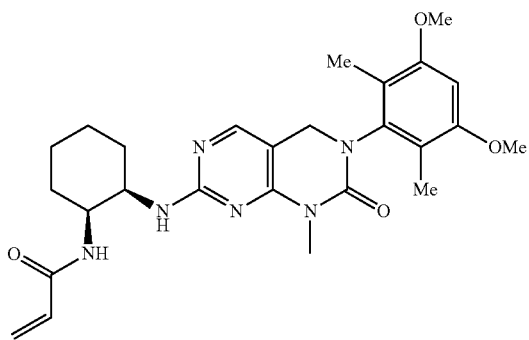 [SMILES: C=CC(=O)N[C@H]1CCCC[C@H]1Nc1ncc2c(n1)N(C)C(=O)N(c1c(C)c(OC)cc(OC)c1C)C2]
I-199
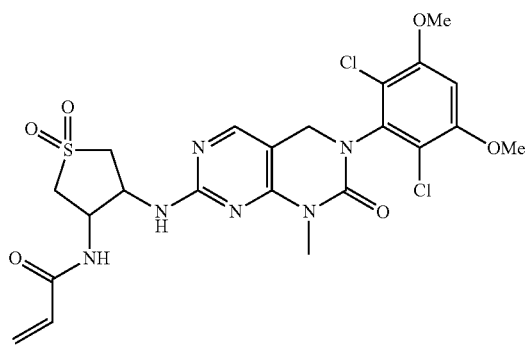 [SMILES: C=CC(=O)NC1CS(=O)(=O)CC1Nc1ncc2c(n1)N(C)C(=O)N(c1c(Cl)c(OC)cc(OC)c1Cl)C2]
I-200
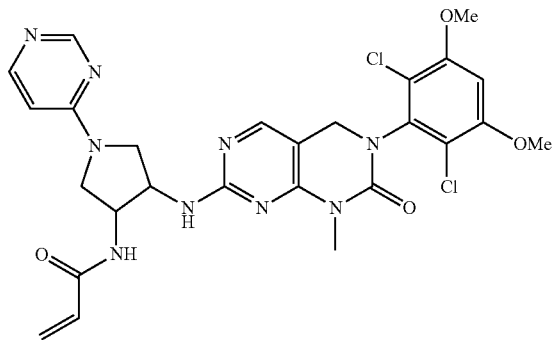 [SMILES: C=CC(=O)NC1CN(c2ccncn2)CC1Nc1ncc2c(n1)N(C)C(=O)N(c1c(Cl)c(OC)cc(OC)c1Cl)C2]
I-201

TABLE 1-continued
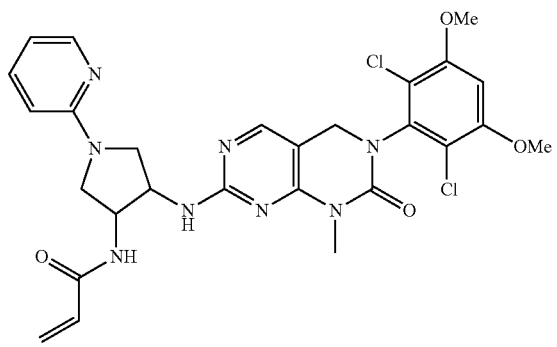 [SMILES: C=CC(=O)NC1CN(c2ccccn2)CC1Nc1ncc2c(n1)N(C)C(=O)N(c1c(Cl)c(OC)cc(OC)c1Cl)C2]
I-202
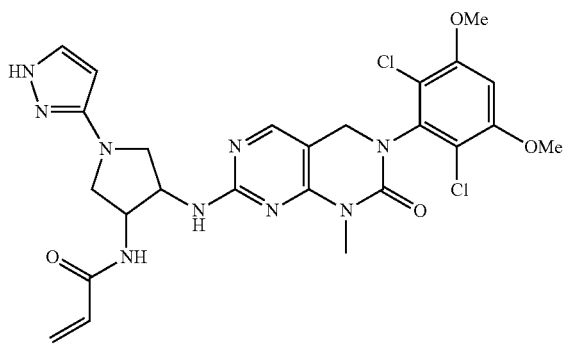 [SMILES: C=CC(=O)NC1CN(c2cc[nH]n2)CC1Nc1ncc2c(n1)N(C)C(=O)N(c1c(Cl)c(OC)cc(OC)c1Cl)C2]
I-203
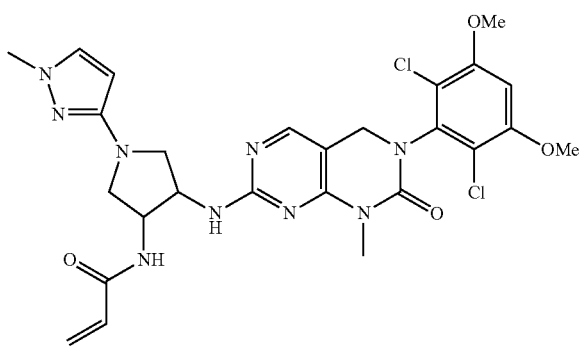 [SMILES: C=CC(=O)NC1CN(c2ccn(C)n2)CC1Nc1ncc2c(n1)N(C)C(=O)N(c1c(Cl)c(OC)cc(OC)c1Cl)C2]
I-204
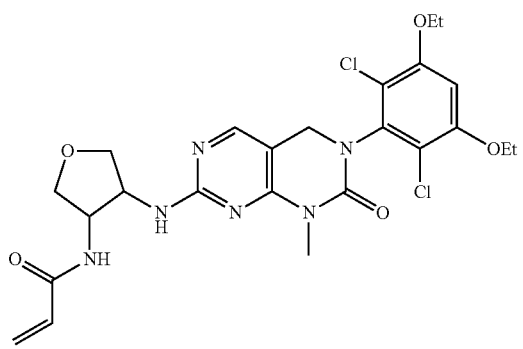 [SMILES: C=CC(=O)NC1COCC1Nc1ncc2c(n1)N(C)C(=O)N(c1c(Cl)c(OCC)cc(OCC)c1Cl)C2]
I-205

TABLE 1-continued
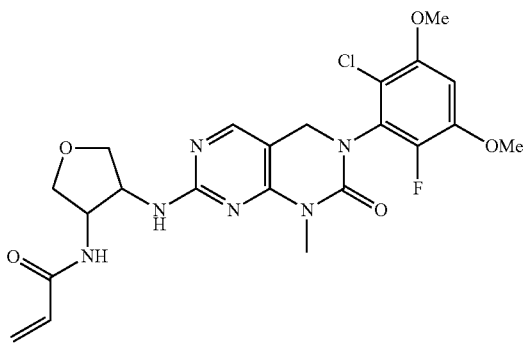
I-206
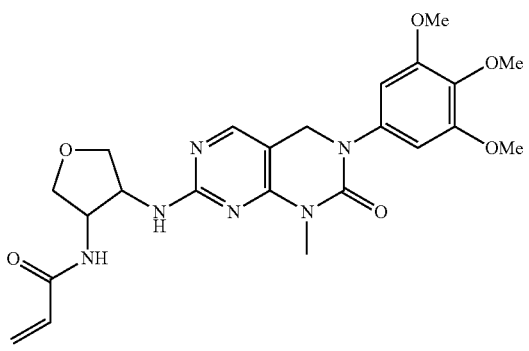 [SMILES: C=CC(=O)NC1COCC1Nc1ncc2c(n1)N(C)C(=O)N(c1cc(OC)c(OC)c(OC)c1)C2]
I-207
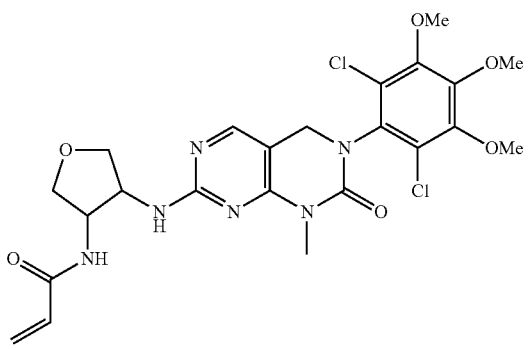 [SMILES: C=CC(=O)NC1COCC1Nc1ncc2c(n1)N(C)C(=O)N(c1c(Cl)c(OC)c(OC)c(OC)c1Cl)C2]
I-208
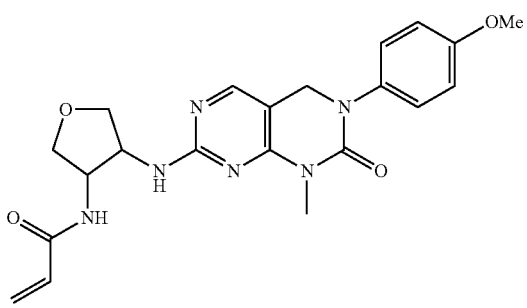 [SMILES: C=CC(=O)NC1COCC1Nc1ncc2c(n1)N(C)C(=O)N(c1ccc(OC)cc1)C2]
I-209

TABLE 1-continued
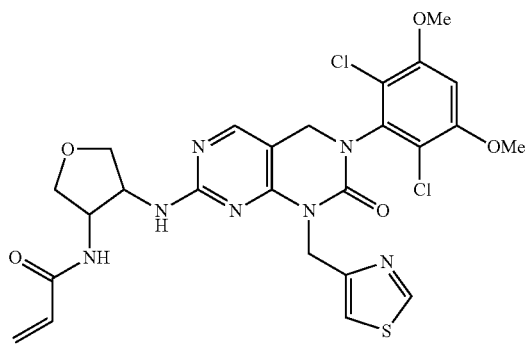 [SMILES: C=CC(=O)NC1COCC1Nc1ncc2c(n1)N(Cc1cscn1)C(=O)N(c1c(Cl)c(OC)cc(OC)c1Cl)C2]
I-210
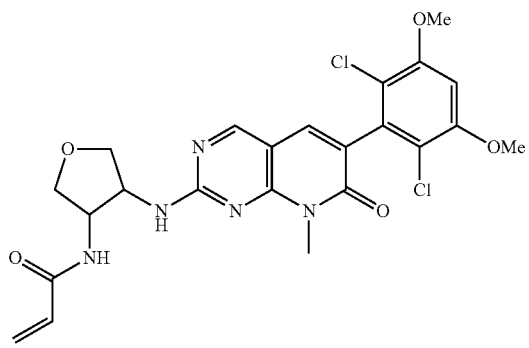 [SMILES: C=CC(=O)NC1COCC1Nc1ncc2cc(-c3c(Cl)c(OC)cc(OC)c3Cl)c(=O)n(C)c2n1]
I-211
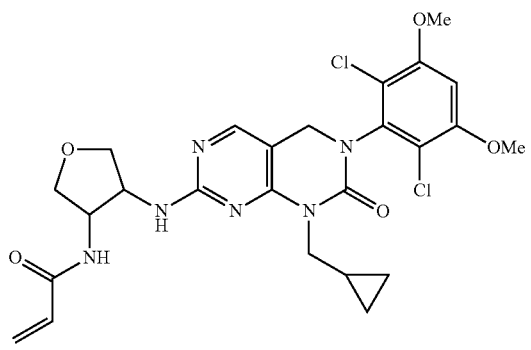 [SMILES: C=CC(=O)NC1COCC1Nc1ncc2c(n1)N(CC1CC1)C(=O)N(c1c(Cl)c(OC)cc(OC)c1Cl)C2]
I-212
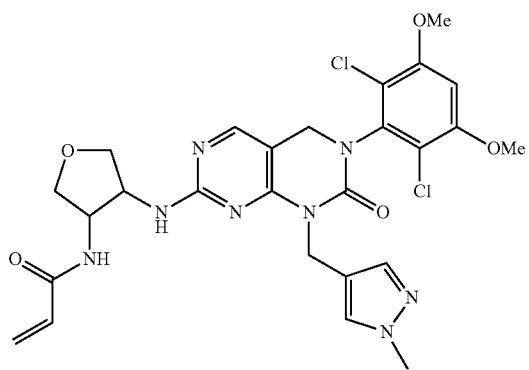 [SMILES: C=CC(=O)NC1COCC1Nc1ncc2c(n1)N(Cc1cnn(C)c1)C(=O)N(c1c(Cl)c(OC)cc(OC)c1Cl)C2]
I-213

TABLE 1-continued
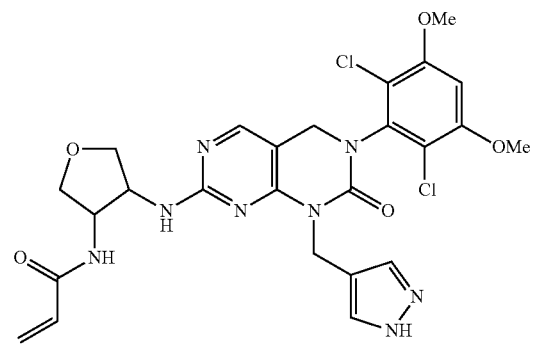 [SMILES: C=CC(=O)NC1COCC1Nc1ncc2c(n1)N(Cc1cn[nH]c1)C(=O)N(c1c(Cl)c(OC)cc(OC)c1Cl)C2]
I-214
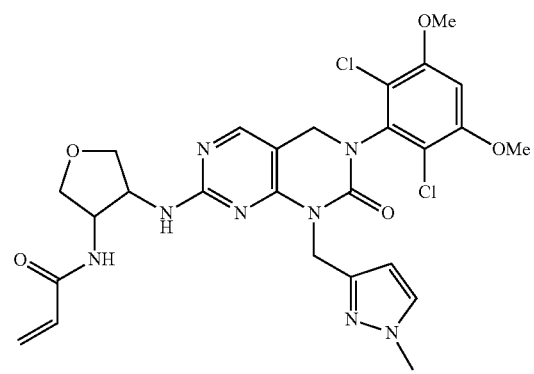 [SMILES: C=CC(=O)NC1COCC1Nc1ncc2c(n1)N(Cc1ccn(C)n1)C(=O)N(c1c(Cl)c(OC)cc(OC)c1Cl)C2]
I-215
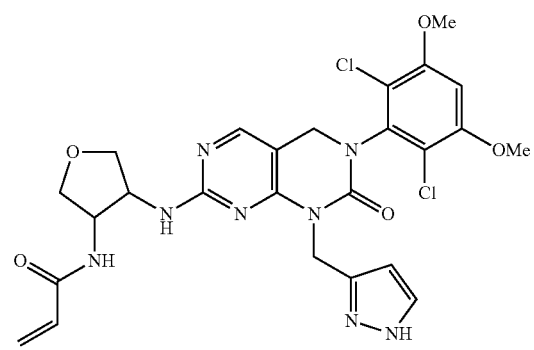 [SMILES: C=CC(=O)NC1COCC1Nc1ncc2c(n1)N(Cc1cc[nH]n1)C(=O)N(c1c(Cl)c(OC)cc(OC)c1Cl)C2]
I-216
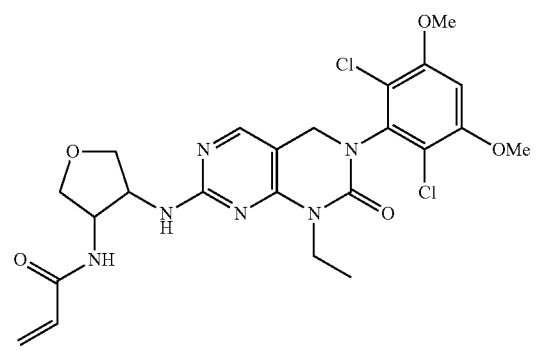 [SMILES: C=CC(=O)NC1COCC1Nc1ncc2c(n1)N(CC)C(=O)N(c1c(Cl)c(OC)cc(OC)c1Cl)C2]
I-217

TABLE 1-continued
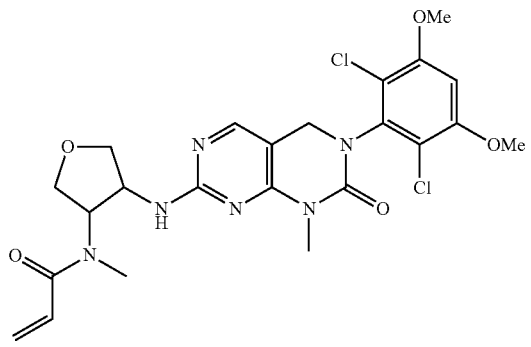 [SMILES: C=CC(=O)N(C)C1COCC1Nc1ncc2c(n1)N(C)C(=O)N(c1c(Cl)c(OC)cc(OC)c1Cl)C2]
I-218
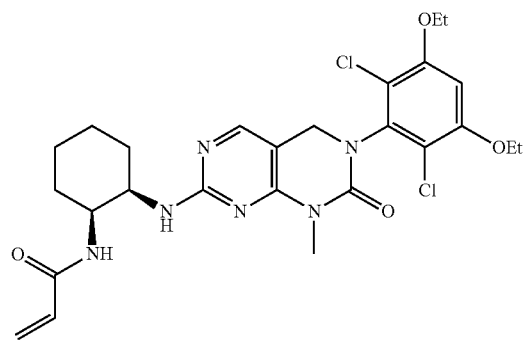 [SMILES: C=CC(=O)N[C@H]1CCCC[C@H]1Nc1ncc2c(n1)N(C)C(=O)N(c1c(Cl)c(OCC)cc(OCC)c1Cl)C2]
I-219
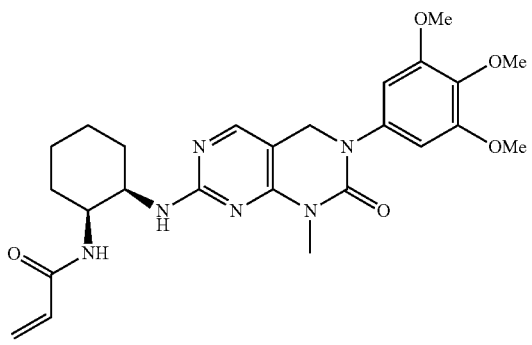 [SMILES: C=CC(=O)N[C@H]1CCCC[C@H]1Nc1ncc2c(n1)N(C)C(=O)N(c1cc(OC)c(OC)c(OC)c1)C2]
I-220
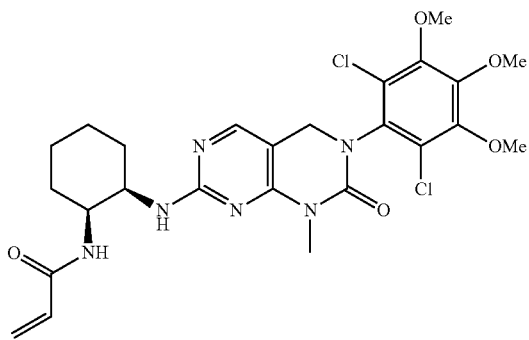 [SMILES: C=CC(=O)N[C@H]1CCCC[C@H]1Nc1ncc2c(n1)N(C)C(=O)N(c1c(Cl)c(OC)c(OC)c(OC)c1Cl)C2]
I-221

TABLE 1-continued
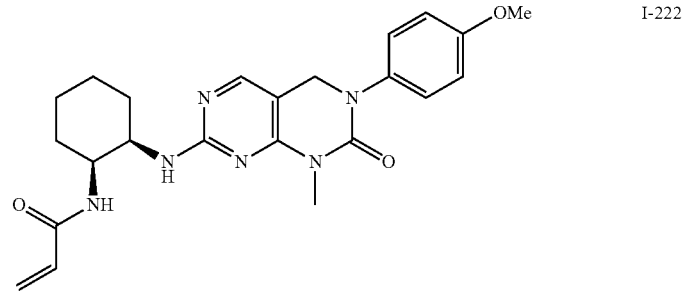 I-222
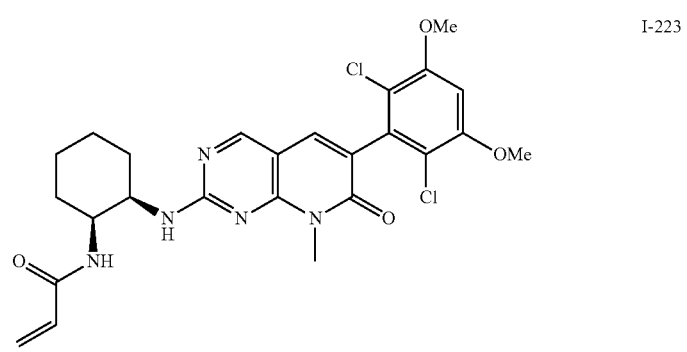 I-223
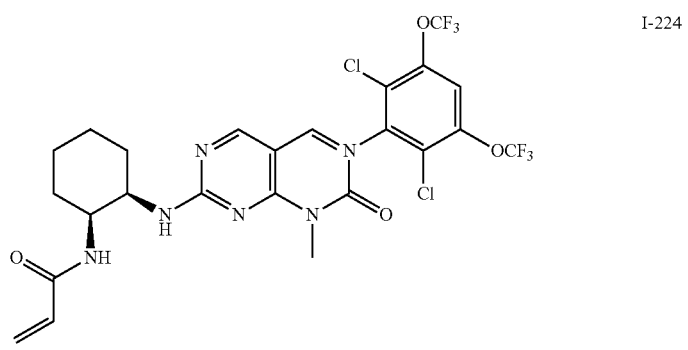 I-224
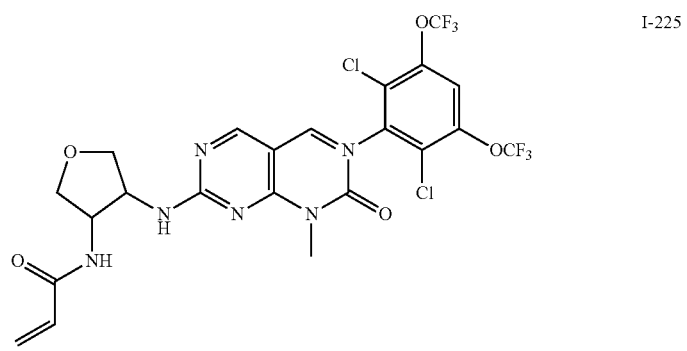 I-225

TABLE 1-continued
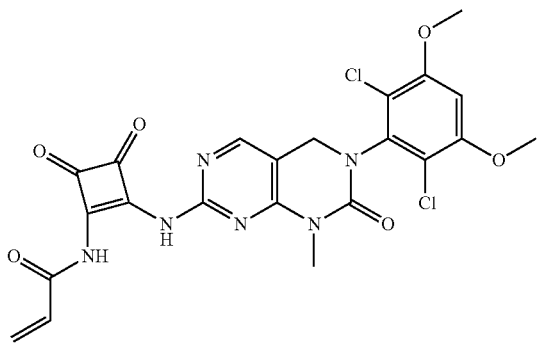 [SMILES: C=CC(=O)Nc1c(Nc2ncc3c(n2)N(C)C(=O)N(c2c(Cl)c(OC)cc(OC)c2Cl)C3)c(=O)c1=O]
I-226
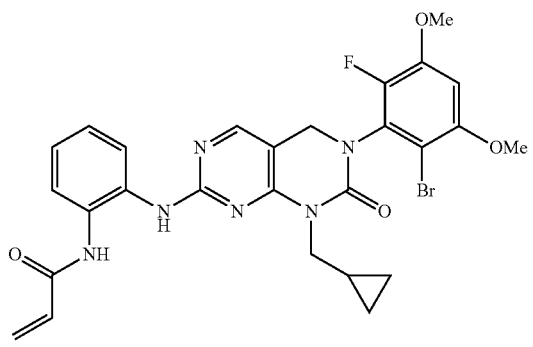
I-227
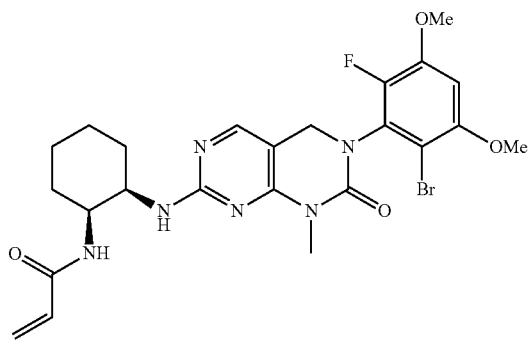 [SMILES: C=CC(=O)N[C@H]1CCCC[C@H]1Nc1ncc2c(n1)N(C)C(=O)N(c1c(F)c(OC)cc(OC)c1Br)C2]
I-228
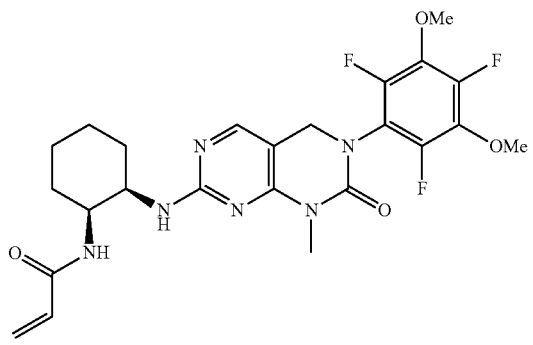 [SMILES: C=CC(=O)N[C@H]1CCCC[C@H]1Nc1ncc2c(n1)N(C)C(=O)N(c1c(F)c(OC)c(F)c(OC)c1F)C2]
I-229

TABLE 1-continued
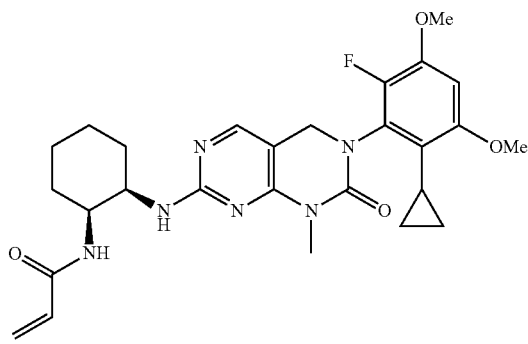 [SMILES: C=CC(=O)N[C@H]1CCCC[C@H]1Nc1ncc2c(n1)N(C)C(=O)N(c1c(F)c(OC)cc(OC)c1C1CC1)C2]
I-230
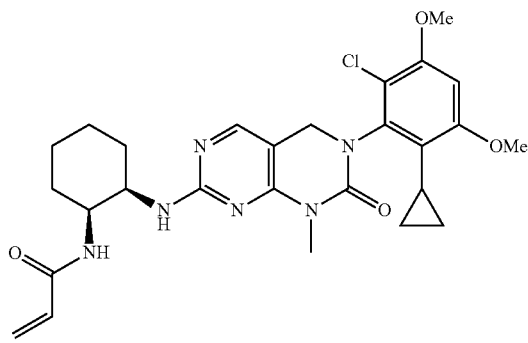 [SMILES: C=CC(=O)N[C@H]1CCCC[C@H]1Nc1ncc2c(n1)N(C)C(=O)N(c1c(Cl)c(OC)cc(OC)c1C1CC1)C2]
I-231
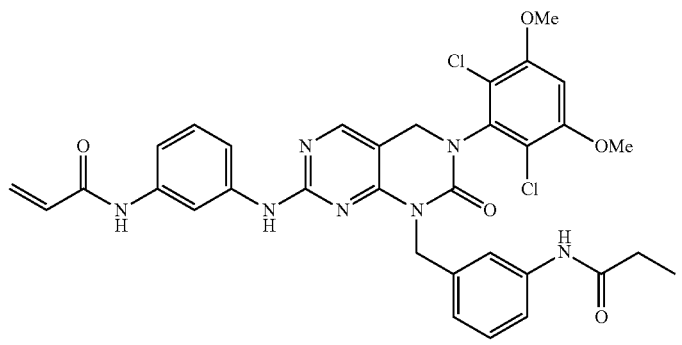 [SMILES: C=CC(=O)Nc1cccc(Nc2ncc3c(n2)N(Cc2cccc(NC(=O)CC)c2)C(=O)N(c2c(Cl)c(OC)cc(OC)c2Cl)C3)c1]
I-232
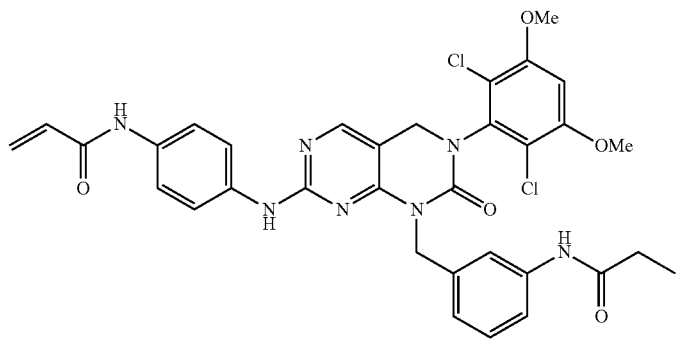 [SMILES: C=CC(=O)Nc1ccc(Nc2ncc3c(n2)N(Cc2cccc(NC(=O)CC)c2)C(=O)N(c2c(Cl)c(OC)cc(OC)c2Cl)C3)cc1]
I-233

TABLE 1-continued
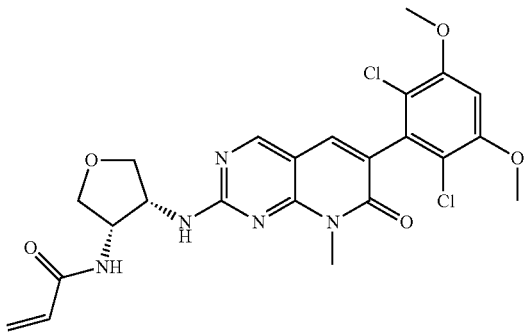 [SMILES: C=CC(=O)N[C@@H]1COC[C@@H]1Nc1ncc2cc(-c3c(Cl)c(OC)cc(OC)c3Cl)c(=O)n(C)c2n1]
I-240
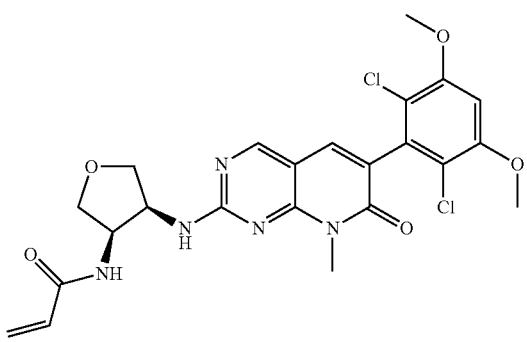 [SMILES: C=CC(=O)N[C@H]1COC[C@H]1Nc1ncc2cc(-c3c(Cl)c(OC)cc(OC)c3Cl)c(=O)n(C)c2n1]
I-241
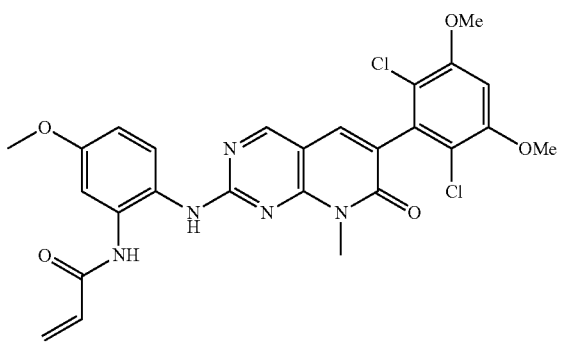 [SMILES: C=CC(=O)Nc1cc(OC)ccc1Nc1ncc2cc(-c3c(Cl)c(OC)cc(OC)c3Cl)c(=O)n(C)c2n1]
I-242
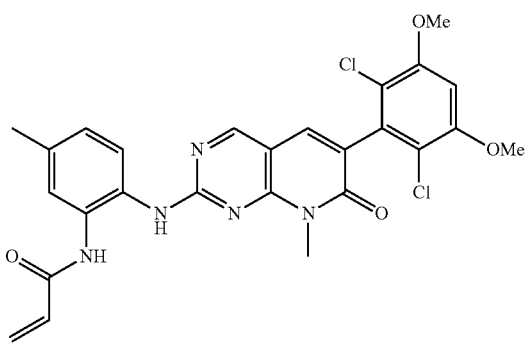 [SMILES: C=CC(=O)Nc1cc(C)ccc1Nc1ncc2cc(-c3c(Cl)c(OC)cc(OC)c3Cl)c(=O)n(C)c2n1]
I-243

TABLE 1-continued
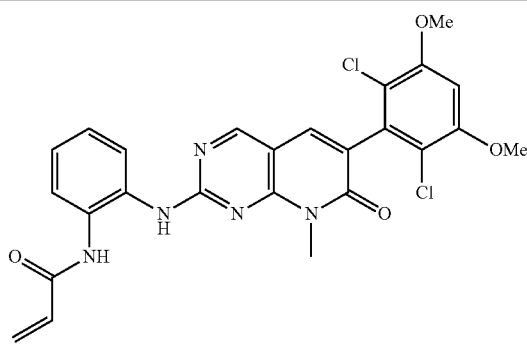 [SMILES: C=CC(=O)Nc1ccccc1Nc1ncc2cc(-c3c(Cl)c(OC)cc(OC)c3Cl)c(=O)n(C)c2n1]
I-244
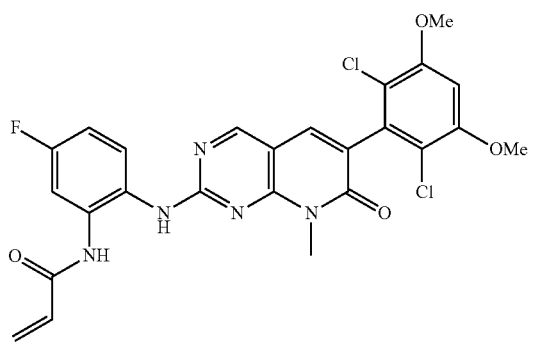
I-245
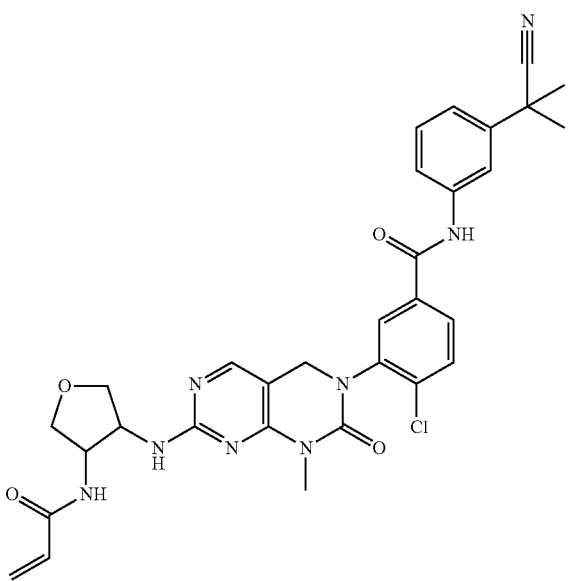 [SMILES: C=CC(=O)NC1COCC1Nc1ncc2c(n1)N(C)C(=O)N(c1cc(C(=O)Nc3cccc(C(C)(C)C#N)c3)ccc1Cl)C2]
I-246

TABLE 1-continued
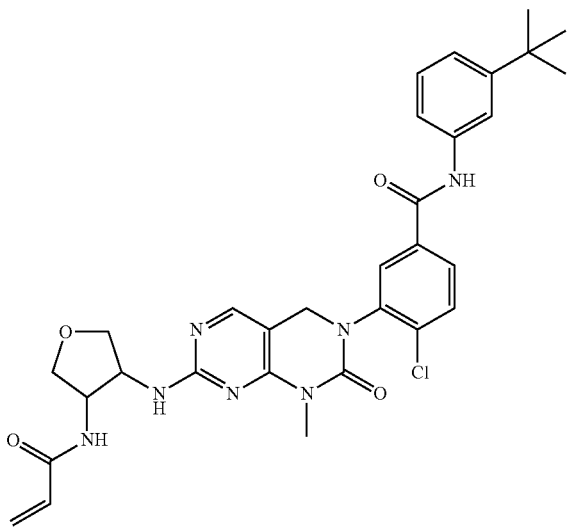 [SMILES: C=CC(=O)NC1COCC1Nc1ncc2c(n1)N(C)C(=O)N(c1cc(C(=O)Nc3cccc(C(C)(C)C)c3)ccc1Cl)C2]
I-247
In certain embodiments, the invention provides a compound selected from Table 2:
TABLE 2
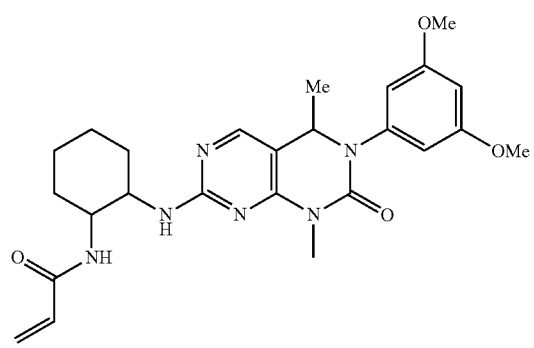 [SMILES: C=CC(=O)NC1CCCCC1Nc1ncc2c(n1)N(C)C(=O)N(c1cc(OC)cc(OC)c1)C2C]
I-71
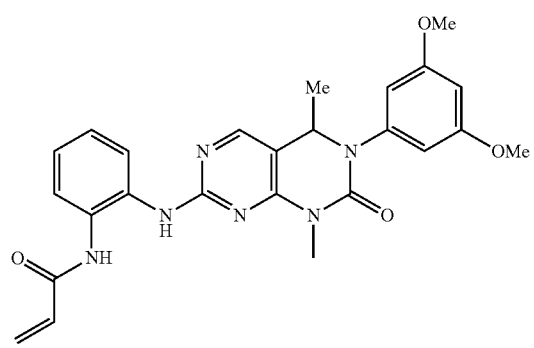 [SMILES: C=CC(=O)Nc1ccccc1Nc1ncc2c(n1)N(C)C(=O)N(c1cc(OC)cc(OC)c1)C2C]
I-72

TABLE 2-continued
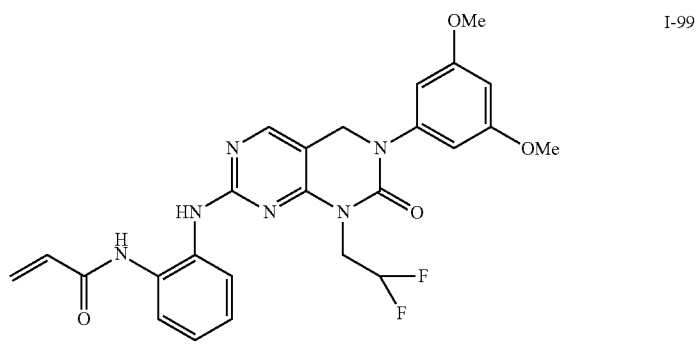
I-99
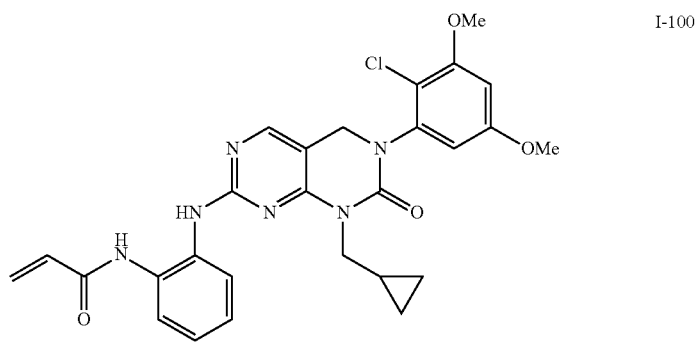
I-100
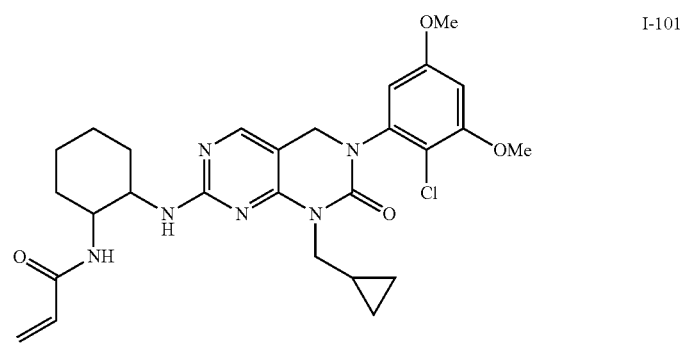
I-101
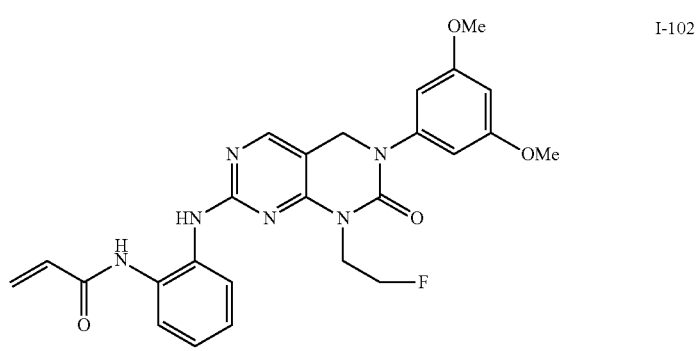
I-102

TABLE 2-continued
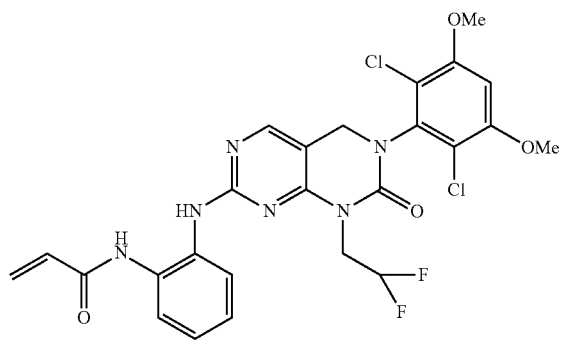 [SMILES: C=CC(=O)Nc1ccccc1Nc1ncc2c(n1)N(CC(F)F)C(=O)N(c1c(Cl)c(OC)cc(OC)c1Cl)C2]
I-103
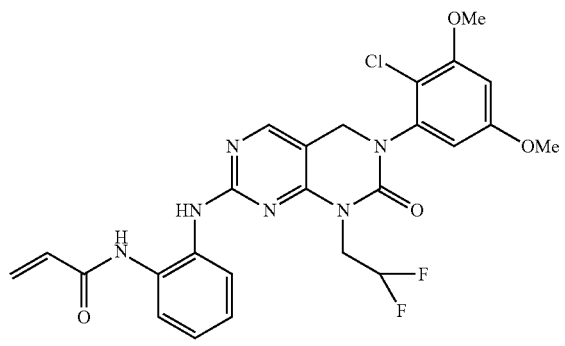 [SMILES: C=CC(=O)Nc1ccccc1Nc1ncc2c(n1)N(CC(F)F)C(=O)N(c1cc(OC)cc(OC)c1Cl)C2]
I-104
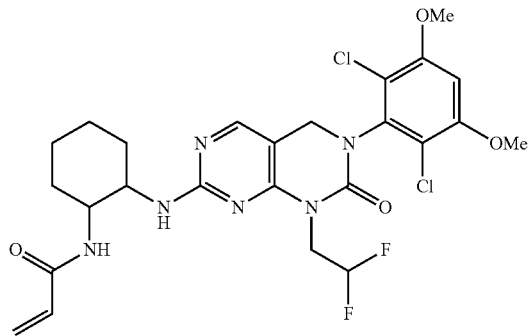 [SMILES: C=CC(=O)NC1CCCCC1Nc1ncc2c(n1)N(CC(F)F)C(=O)N(c1c(Cl)c(OC)cc(OC)c1Cl)C2]
I-105
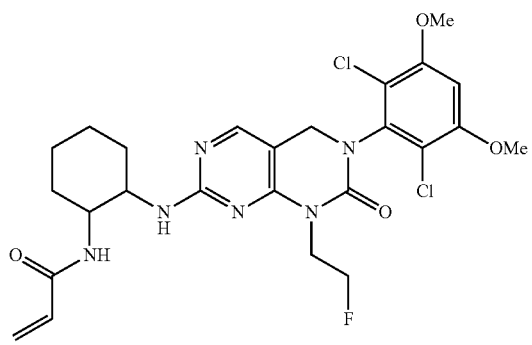 [SMILES: C=CC(=O)NC1CCCCC1Nc1ncc2c(n1)N(CCF)C(=O)N(c1c(Cl)c(OC)cc(OC)c1Cl)C2]
I-106

TABLE 2-continued
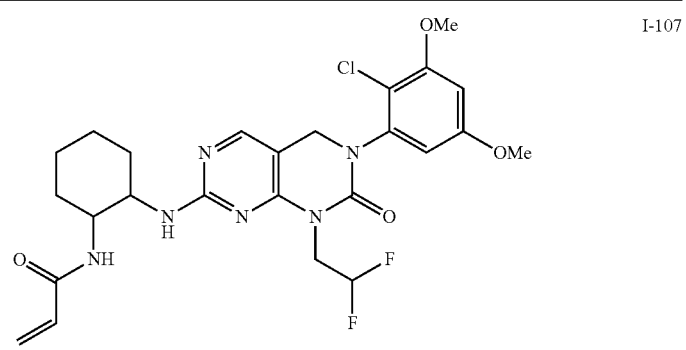
I-107
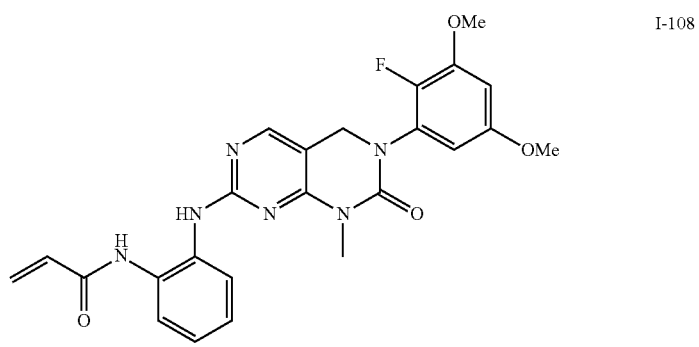
I-108
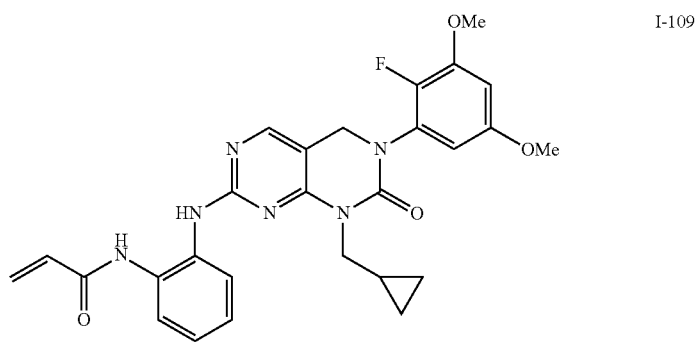
I-109
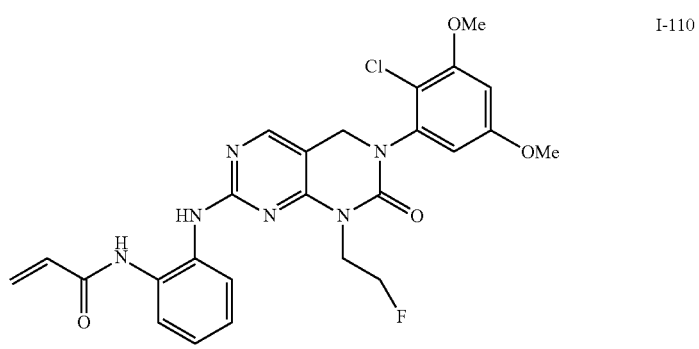
I-110

TABLE 2-continued
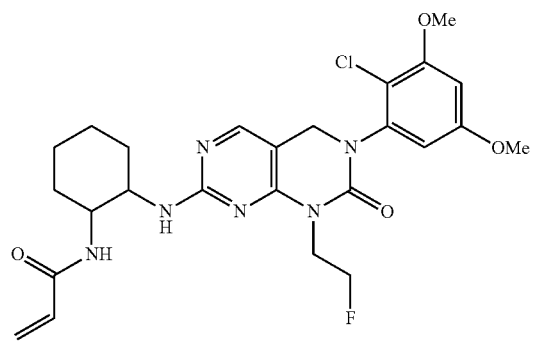 [SMILES: C=CC(=O)NC1CCCCC1Nc1ncc2c(n1)N(CCF)C(=O)N(c1cc(OC)cc(OC)c1Cl)C2]
I-111
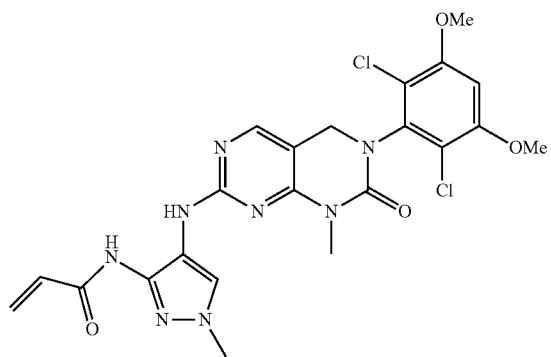 [SMILES: C=CC(=O)Nc1nn(C)cc1Nc1ncc2c(n1)N(C)C(=O)N(c1c(Cl)c(OC)cc(OC)c1Cl)C2]
I-117
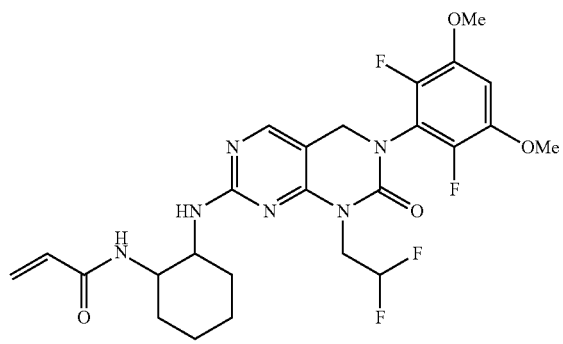 [SMILES: C=CC(=O)NC1CCCCC1Nc1ncc2c(n1)N(CC(F)F)C(=O)N(c1c(F)c(OC)cc(OC)c1F)C2]
I-115
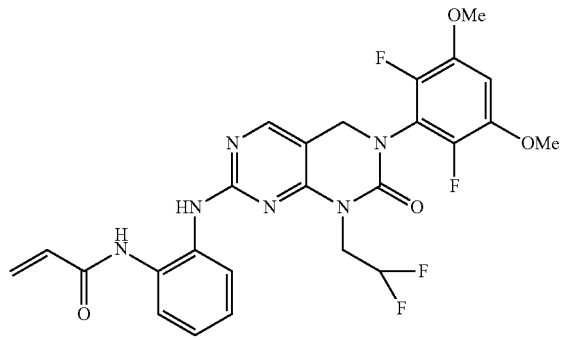
I-116

TABLE 2-continued
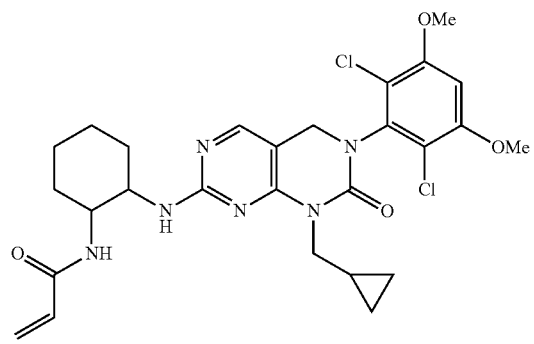 [SMILES: C=CC(=O)NC1CCCCC1Nc1ncc2c(n1)N(CC1CC1)C(=O)N(c1c(Cl)c(OC)cc(OC)c1Cl)C2]
I-129
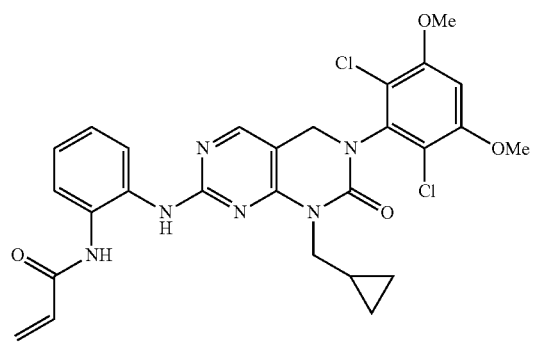 [SMILES: C=CC(=O)Nc1ccccc1Nc1ncc2c(n1)N(CC1CC1)C(=O)N(c1c(Cl)c(OC)cc(OC)c1Cl)C2]
I-130
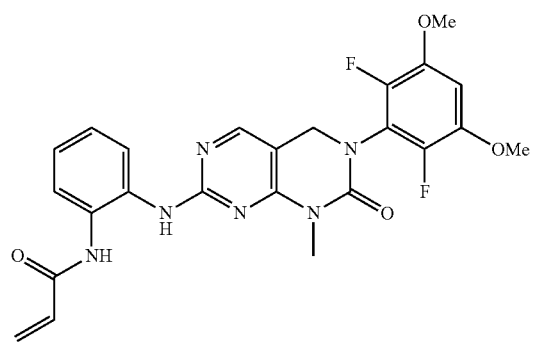 [SMILES: C=CC(=O)Nc1ccccc1Nc1ncc2c(n1)N(C)C(=O)N(c1c(F)c(OC)cc(OC)c1F)C2]
I-131

TABLE 2-continued
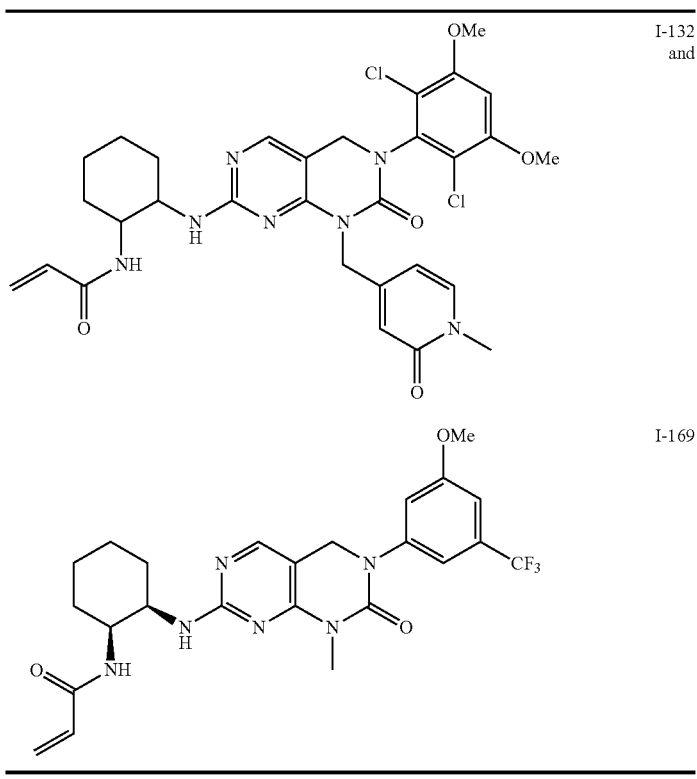
In certain embodiments, the invention provides a compound selected from:
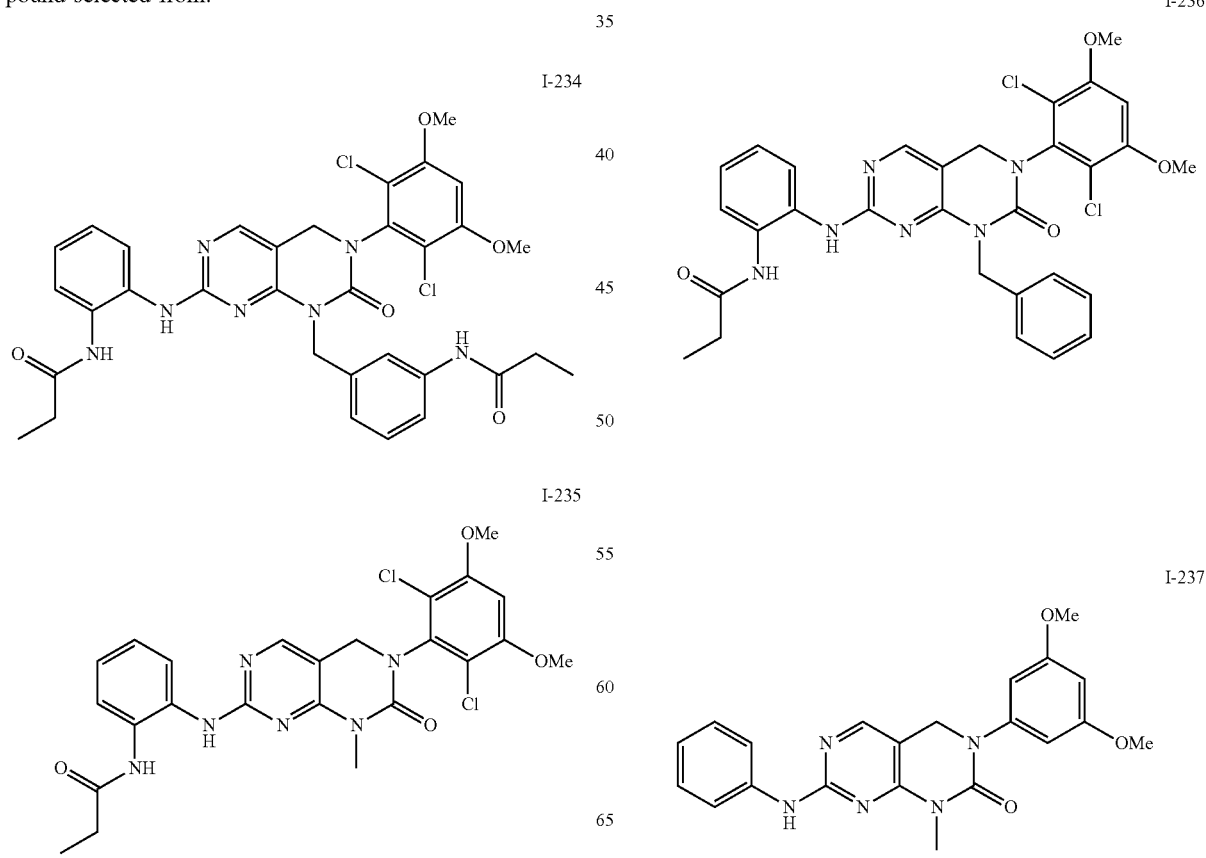

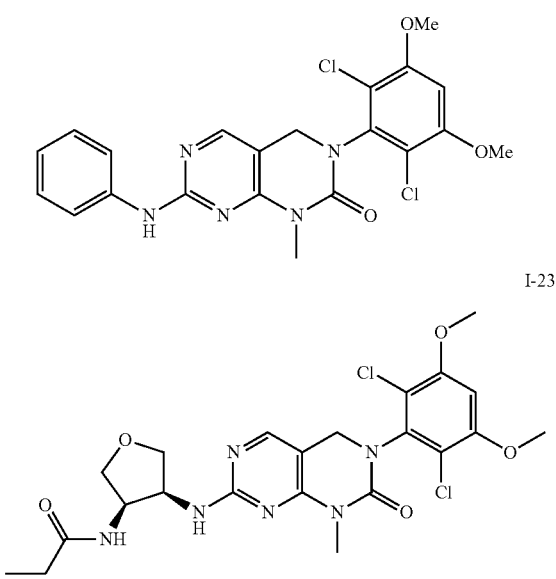
I-238
I-239
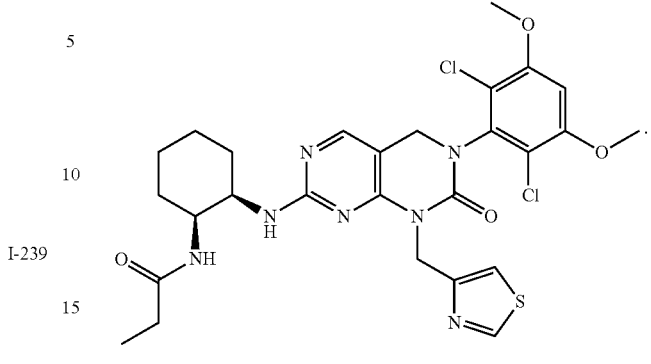
I-118
In some embodiments, the present invention provides a compound selected from Table 3
TABLE 3
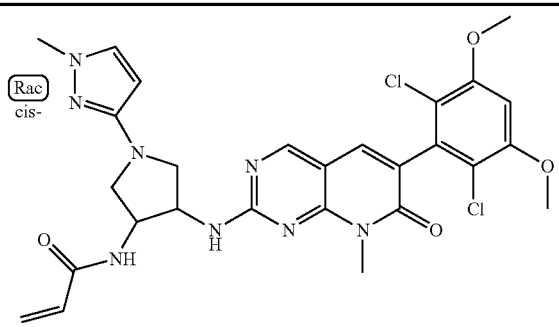
I-248
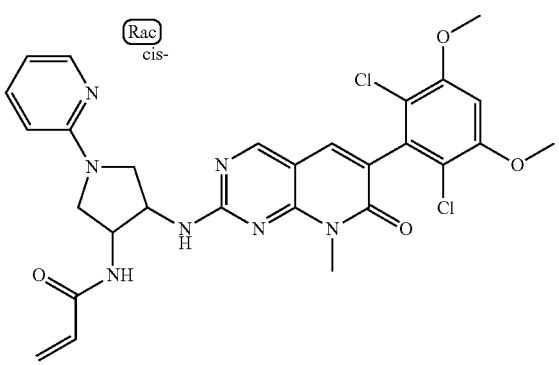 [SMILES: C=CC(=O)NC1CN(c2ccccn2)CC1Nc1ncc2cc(-c3c(Cl)c(OC)cc(OC)c3Cl)c(=O)n(C)c2n1]
I-252
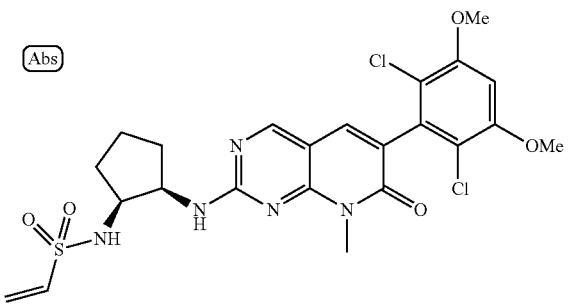 [SMILES: C=CS(=O)(=O)N[C@H]1CCC[C@H]1Nc1ncc2cc(-c3c(Cl)c(OC)cc(OC)c3Cl)c(=O)n(C)c2n1]
I-253

TABLE 3-continued
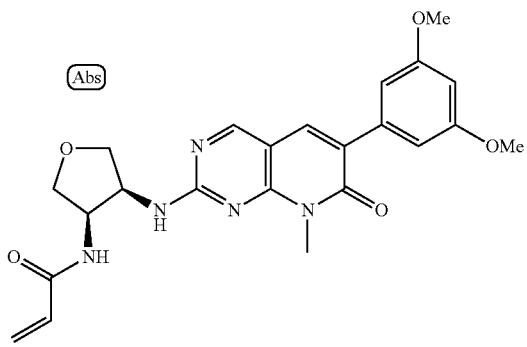 [SMILES: C=CC(=O)N[C@H]1COC[C@H]1Nc1ncc2cc(-c3cc(OC)cc(OC)c3)c(=O)n(C)c2n1]
I-255
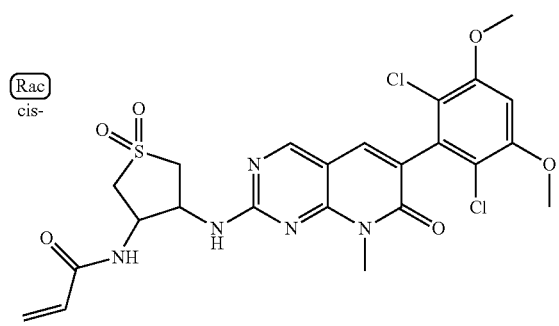 [SMILES: C=CC(=O)NC1CS(=O)(=O)CC1Nc1ncc2cc(-c3c(Cl)c(OC)cc(OC)c3Cl)c(=O)n(C)c2n1]
I-256
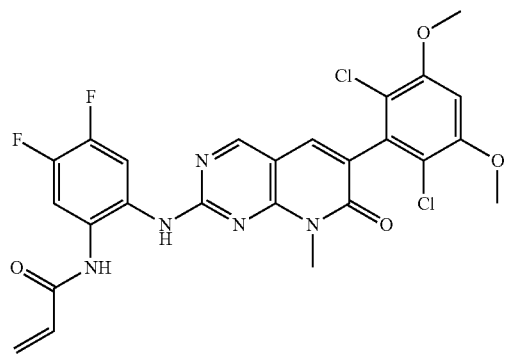 [SMILES: C=CC(=O)Nc1cc(F)c(F)cc1Nc1ncc2cc(-c3c(Cl)c(OC)cc(OC)c3Cl)c(=O)n(C)c2n1]
I-257
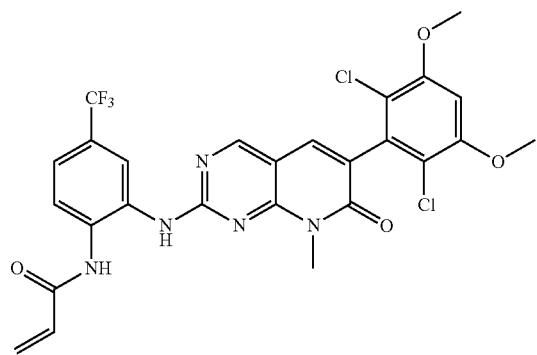 [SMILES: C=CC(=O)Nc1ccc(C(F)(F)F)cc1Nc1ncc2cc(-c3c(Cl)c(OC)cc(OC)c3Cl)c(=O)n(C)c2n1]
I-258

TABLE 3-continued
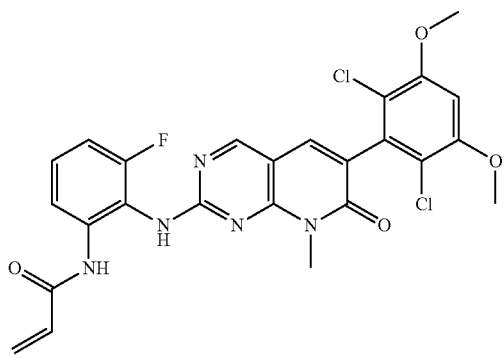 [SMILES: C=CC(=O)Nc1cccc(F)c1Nc1ncc2cc(-c3c(Cl)c(OC)cc(OC)c3Cl)c(=O)n(C)c2n1]
I-259
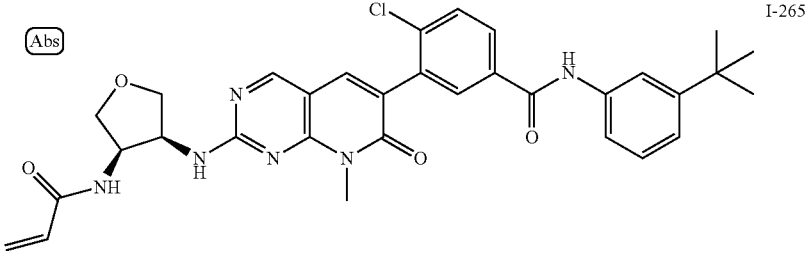
I-265
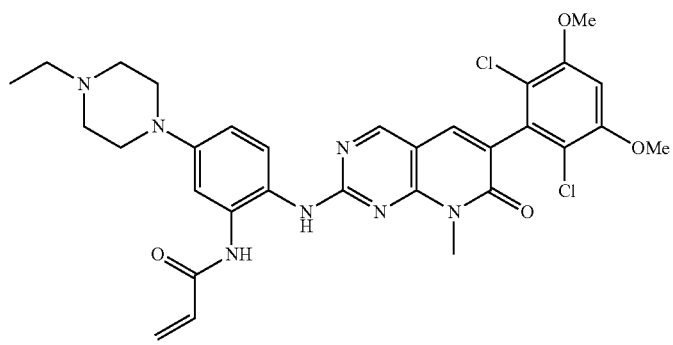 [SMILES: C=CC(=O)Nc1cc(N2CCN(CC)CC2)ccc1Nc1ncc2cc(-c3c(Cl)c(OC)cc(OC)c3Cl)c(=O)n(C)c2n1]
I-269
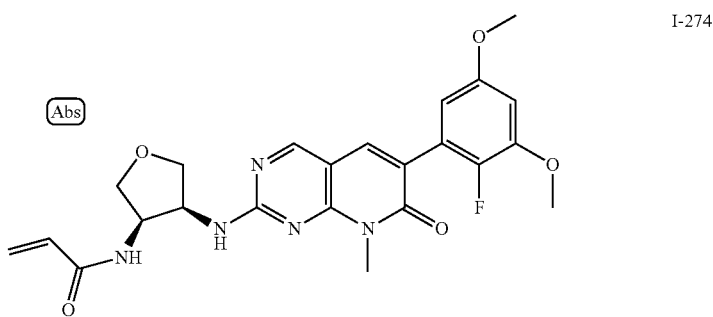
I-274
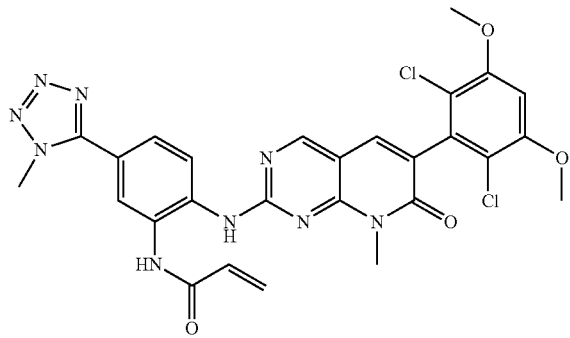 [SMILES: C=CC(=O)Nc1cc(-c2nnnn2C)ccc1Nc1ncc2cc(-c3c(Cl)c(OC)cc(OC)c3Cl)c(=O)n(C)c2n1]
I-276

TABLE 3-continued
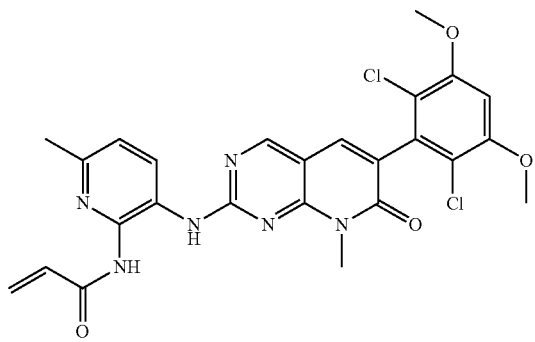 [SMILES: C=CC(=O)Nc1nc(C)ccc1Nc1ncc2cc(-c3c(Cl)c(OC)cc(OC)c3Cl)c(=O)n(C)c2n1]
I-278
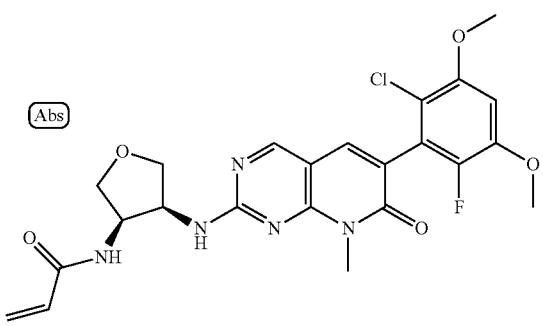 [SMILES: C=CC(=O)N[C@H]1COC[C@H]1Nc1ncc2cc(-c3c(F)c(OC)cc(OC)c3Cl)c(=O)n(C)c2n1]
I-279
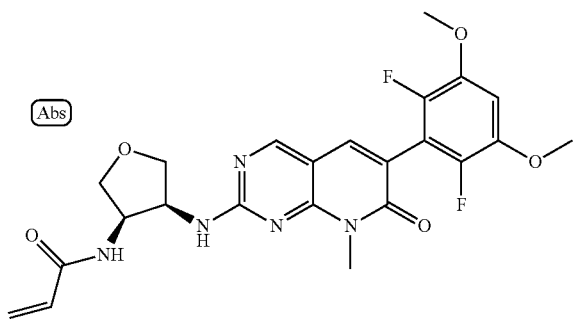 [SMILES: C=CC(=O)N[C@H]1COC[C@H]1Nc1ncc2cc(-c3c(F)c(OC)cc(OC)c3F)c(=O)n(C)c2n1]
I-281
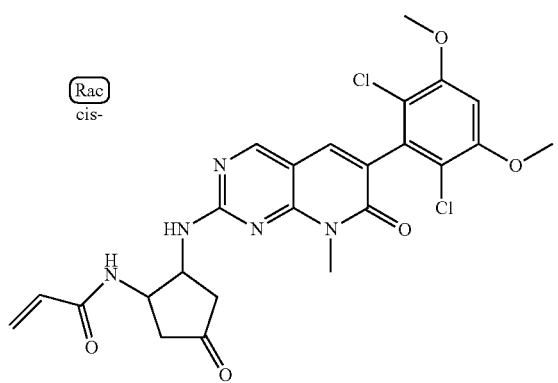 [SMILES: C=CC(=O)NC1CC(=O)CC1Nc1ncc2cc(-c3c(Cl)c(OC)cc(OC)c3Cl)c(=O)n(C)c2n1]
I-286

TABLE 3-continued
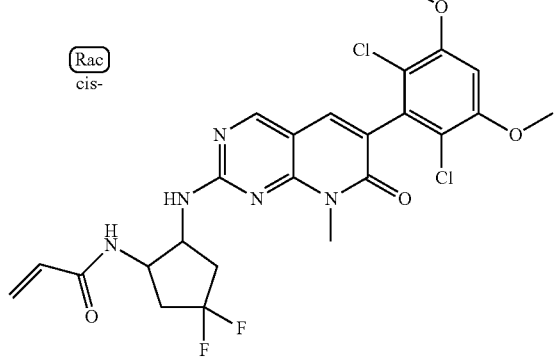
I-288
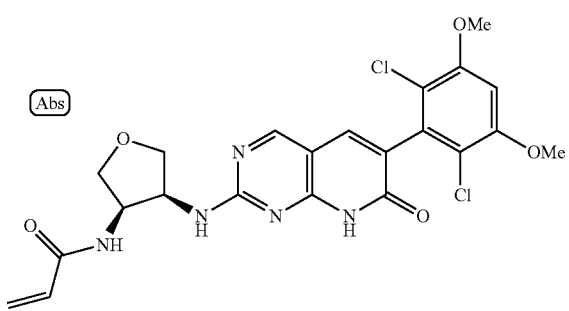 [SMILES: C=CC(=O)N[C@H]1COC[C@H]1Nc1ncc2cc(-c3c(Cl)c(OC)cc(OC)c3Cl)c(=O)[nH]c2n1]
I-290
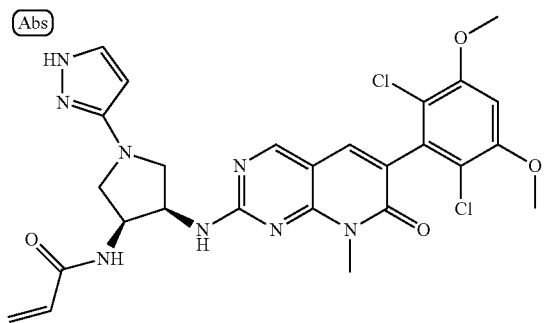 [SMILES: C=CC(=O)N[C@H]1CN(c2cc[nH]n2)C[C@H]1Nc1ncc2cc(-c3c(Cl)c(OC)cc(OC)c3Cl)c(=O)n(C)c2n1]
I-292
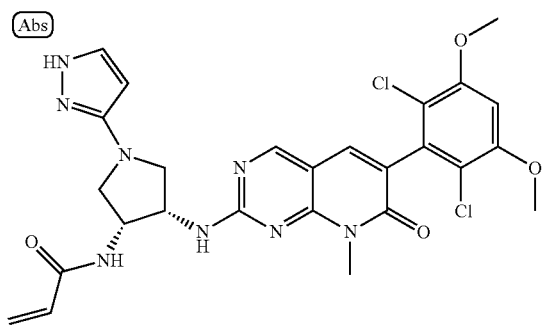 [SMILES: C=CC(=O)N[C@@H]1CN(c2cc[nH]n2)C[C@@H]1Nc1ncc2cc(-c3c(Cl)c(OC)cc(OC)c3Cl)c(=O)n(C)c2n1]
I-293

TABLE 3-continued

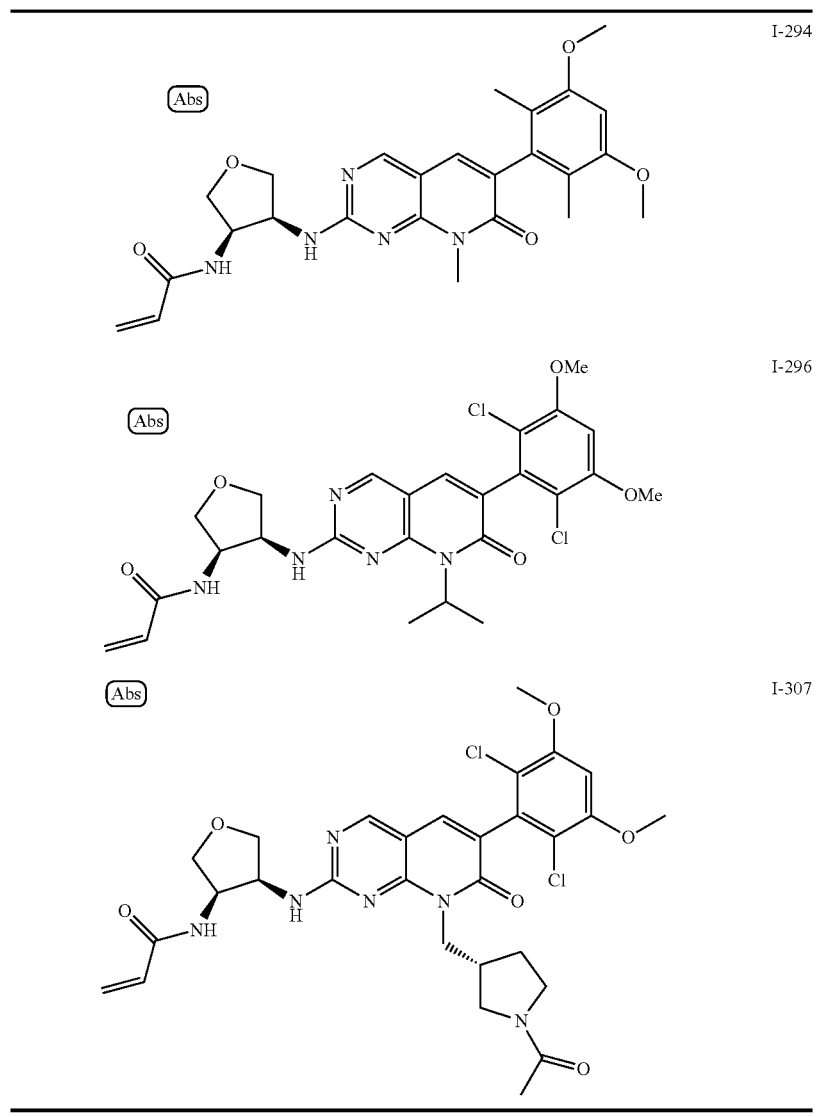

In some embodiments, the present invention provides a compound selected from those depicted above, or a pharmaceutically acceptable salt thereof.

As defined generally above, the $R^1$ group of any of the formulae herein is -L-Y, wherein:

L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—;

Y is hydrogen, $C_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 $R^e$ groups; and each $R^e$ is independently selected from -Q-Z, oxo, NO$_2$, halogen, CN, a suitable leaving group, or a $C_{1-6}$ aliphatic optionally substituted with oxo, halogen, NO$_2$, or CN, wherein:

Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and Z is hydrogen or $C_{1-6}$ aliphatic optionally substituted with oxo, halogen, NO$_2$, or CN.

In certain embodiments, L is a covalent bond.

In certain embodiments, L is a bivalent $C_{1-8}$ saturated or unsaturated, straight or branched, hydrocarbon chain. In certain embodiments, L is —CH$_2$—.

In certain embodiments, L is a covalent bond, —CH$_2$—, —NH—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, —NHC(O)CH$_2$OC(O)—, or —SO$_2$NH—.

In some embodiments, L is a bivalent $C_{2-8}$ straight or branched, hydrocarbon chain wherein L has at least one double bond and one or two additional methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O)—.

In certain embodiments, L is a bivalent C$_{2-8}$ straight or branched, hydrocarbon chain wherein L has at least one double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—.

In some embodiments, L is a bivalent C$_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—.

As described above, in certain embodiments, L is a bivalent C$_{2-8}$ straight or branched, hydrocarbon chain wherein L has at least one double bond. One of ordinary skill in the art will recognize that such a double bond may exist within the hydrocarbon chain backbone or is "exo" to the backbone chain and thus forming an alkylidene group. By way of example, such an L group having an alkylidene branched chain includes —CH$_2$C(=CH$_2$)CH$_2$—. Thus, in some embodiments, L is a bivalent C$_{2-8}$ straight or branched, hydrocarbon chain wherein L has at least one alkylidenyl double bond. Exemplary L groups include —NHC(O)C(=CH$_2$)CH$_2$—.

In certain embodiments, L is a bivalent C$_{2-8}$ straight or branched, hydrocarbon chain wherein L has at least one double bond and at least one methylene unit of L is replaced by —C(O)—. In certain embodiments, L is —C(O)CH=CH(CH$_3$)—, —C(O)CH=CHCH$_2$NH(CH$_3$)—, —C(O)CH=CH(CH$_3$)—, —C(O)CH=CH—, —CH$_2$C(O)CH=CH—, —CH$_2$C(O)CH=CH(CH$_3$)—, —CH$_2$CH$_2$C(O)CH=CH—, —CH$_2$CH$_2$C(O)CH=CHCH$_2$—, —CH$_2$CH$_2$C(O)CH=CHCH$_2$NH(CH$_3$)—, or —CH$_2$CH$_2$C(O)CH=CH(CH$_3$)—, or —CH(CH$_3$)OC(O)CH=CH—.

In certain embodiments, L is a bivalent C$_{2-8}$ straight or branched, hydrocarbon chain wherein L has at least one double bond and at least one methylene unit of L is replaced by —OC(O)—.

In some embodiments, L is a bivalent C$_{2-8}$ straight or branched, hydrocarbon chain wherein L has at least one double bond and at least one methylene unit of L is replaced by —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—. In some embodiments, L is —CH$_2$OC(O)CH=CHCH$_2$—, —CH$_2$—OC(O)CH=CH—, or —CH(CH=CH$_2$)OC(O)CH=CH—.

In certain embodiments, L is —NRC(O)CH=CH—, —NRC(O)CH=CHCH$_2$N(CH$_3$)—, —NRC(O)CH=CHCH$_2$O—, —CH$_2$NRC(O)CH=CH—, —NRSO$_2$CH=CH—, —NRSO$_2$CH=CHCH$_2$—, —NRC(O)(C=N$_2$)—, —NRC(O)(C=N$_2$)C(O)—, —NRC(O)CH=CHCH$_2$N(CH$_3$)—, —NRC(O)C(=CH$_2$)CH$_2$—, —CH$_2$NRC(O)—, —CH$_2$CH$_2$NRC(O)—, or —CH$_2$NRC(O)cyclopropylene-; wherein R is H or optionally substituted C$_{1-6}$ aliphatic; and Y is hydrogen or C$_{1-6}$ aliphatic optionally substituted with oxo, halogen, NO$_2$, or CN.

In certain embodiments, L is —NHC(O)CH=CH—, —NHC(O)CH=CHCH$_2$N(CH$_3$)—, —NHC(O)CH=CHCH$_2$O—, —CH$_2$NHC(O)CH=CH—, —NHSO$_2$CH=CH—, —NHSO$_2$CH=CHCH$_2$—, —NHC(O)(C=N$_2$)—, —NHC(O)(C=N$_2$)C(O)—, —NHC(O)C(=CH$_2$)CH$_2$—, —CH$_2$NHC(O)—, —CH$_2$CH$_2$NHC(O)—, or —CH$_2$NHC(O)cyclopropylene-.

In some embodiments, L is a bivalent C$_{2-8}$ straight or branched, hydrocarbon chain wherein L has at least one triple bond. In certain embodiments, L is a bivalent C$_{2-8}$ straight or branched, hydrocarbon chain wherein L has at least one triple bond and one or two additional methylene units of L are optionally and independently replaced by —NRC(O)—, —C(O)NR—, —S—, —S(O)—, —SO$_2$—, —C(=S)—, —C(=NR)—, —O—, —N(R)—, or —C(O)—. In some embodiments, L has at least one triple bond and at least one methylene unit of L is replaced by —N(R)—, —N(R)C(O)—, —C(O)—, —C(O)O—, or —OC(O)—, or —O—.

Exemplary L groups include —C≡C—, —C≡CCH$_2$N(isopropyl)-, —NHC(O)C≡CCH$_2$CH$_2$—, —CH$_2$—C≡C—CH$_2$—, —C≡CCH$_2$O—, —CH$_2$C(O)C≡C—, —C(O)C≡C—, or —CH$_2$OC(=O)C≡C—.

In certain embodiments, L is a bivalent C$_{2-8}$ straight or branched, hydrocarbon chain wherein one methylene unit of L is replaced by cyclopropylene and one or two additional methylene units of L are independently replaced by —C(O)—, —NRC(O)—, —C(O)NR—, —N(R)SO$_2$—, or —SO$_2$N(R)—. Exemplary L groups include —NHC(O)-cyclopropylene-SO$_2$— and —NHC(O)— cyclopropylene-.

As defined generally above, Y is hydrogen, C$_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with at 1-4 R$^e$ groups, each R$^e$ is independently selected from -Q-Z, oxo, NO$_2$, halogen, CN, a suitable leaving group, or C$_{1-6}$ aliphatic, wherein Q is a covalent bond or a bivalent C$_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and, Z is hydrogen or C$_{1-6}$ aliphatic optionally substituted with oxo, halogen, NO$_2$, or CN.

In certain embodiments, Y is hydrogen.

In certain embodiments, Y is C$_{1-6}$ aliphatic optionally substituted with oxo, halogen, NO$_2$, or CN. In some embodiments, Y is C$_{2-6}$ alkenyl optionally substituted with oxo, halogen, NO$_2$, or CN. In other embodiments, Y is C$_{2-6}$ alkynyl optionally substituted with oxo, halogen, NO$_2$, or CN. In some embodiments, Y is C$_{2-6}$ alkenyl. In other embodiments, Y is C$_{2-4}$ alkynyl.

In other embodiments, Y is C$_{1-6}$ alkyl substituted with oxo, halogen, NO$_2$, or CN. Such Y groups include —CH$_2$F, —CH$_2$Cl, —CH$_2$CN, and —CH$_2$NO$_2$.

In certain embodiments, Y is a saturated 3-6 membered monocyclic ring having 0-3 heteroatoms independently selected from nitrogen, oxygen, or sulfur, wherein Y is substituted with 1-4 R$^e$ groups, wherein each R$^e$ is as defined above and described herein.

In some embodiments, Y is a saturated 3-4 membered heterocyclic ring having 1 heteroatom selected from oxygen or nitrogen wherein said ring is substituted with 1-2 R$^e$ groups, wherein each R$^e$ is as defined above and described herein. Exemplary such rings are epoxide and oxetane rings, wherein each ring is substituted with 1-2 R$^e$ groups, wherein each R$^e$ is as defined above and described herein.

In other embodiments, Y is a saturated 5-6 membered heterocyclic ring having 1-2 heteroatom selected from oxygen or nitrogen wherein said ring is substituted with 1-4 $R^e$ groups, wherein each $R^e$ is as defined above and described herein. Such rings include piperidine and pyrrolidine, wherein each ring is substituted with 1-4 $R^e$ groups, wherein each $R^e$ is as defined above and described herein. In certain embodiments, Y is

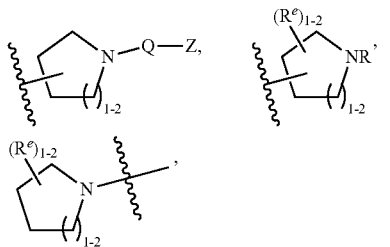

wherein each R, Q, Z, and $R^e$ is as defined above and described herein.

In some embodiments, Y is a saturated 3-6 membered carbocyclic ring, wherein said ring is substituted with 1-4 $R^e$ groups, wherein each $R^e$ is as defined above and described herein. In certain embodiments, Y is cyclopropyl, cyclobutyl, cyclopentyl, or cyclohexyl, wherein each ring is substituted with 1-4 $R^e$ groups, wherein each $R^e$ is as defined above and described herein. In certain embodiments, Y is

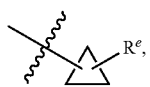

wherein $R^e$ is as defined above and described herein. In certain embodiments, Y is cyclopropyl optionally substituted with halogen, CN or $NO_2$.

In certain embodiments, Y is a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein.

In some embodiments, Y is a partially unsaturated 3-6 membered carbocyclic ring, wherein said ring is substituted with 1-4 $R^e$ groups, wherein each $R^e$ is as defined above and described herein. In some embodiments, Y is cyclopropenyl, cyclobutenyl, cyclopentenyl, or cyclohexenyl wherein each ring is substituted with 1-4 $R^e$ groups, wherein each $R^e$ is as defined above and described herein. In certain embodiments, Y is

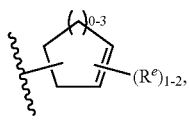

wherein each $R^e$ is as defined above and described herein.

In certain embodiments, Y is a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein. In certain embodiments, Y is selected from:

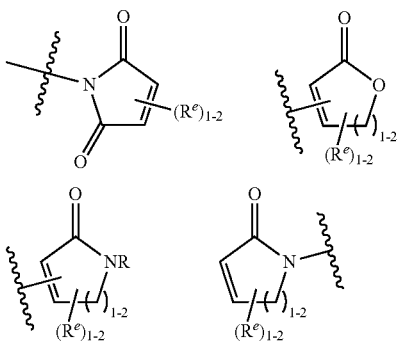

wherein each R and $R^e$ is as defined above and described herein.

In certain embodiments, Y is a 6-membered aromatic ring having 0-2 nitrogens wherein said ring is substituted with 1-4 $R^e$ groups, wherein each $R^e$ group is as defined above and described herein. In certain embodiments, Y is phenyl, pyridyl, or pyrimidinyl, wherein each ring is substituted with 1-4 $R^e$ groups, wherein each $R^e$ is as defined above and described herein.

In some embodiments, Y is selected from:

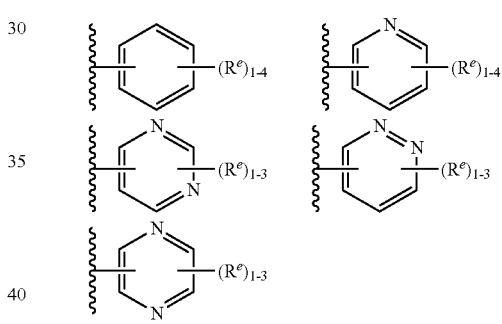

wherein each $R^e$ is as defined above and described herein.

In other embodiments, Y is a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein. In some embodiments, Y is a 5 membered partially unsaturated or aryl ring having 1-3 heteroatoms independently selected from nitrogen, oxygen, and sulfur, wherein said ring is substituted with 1-4 $R^e$ groups, wherein each $R^e$ group is as defined above and described herein. Exemplary such rings are isoxazolyl, oxazolyl, thiazolyl, imidazolyl, pyrazolyl, pyrrolyl, furanyl, thienyl, triazole, thiadiazole, and oxadiazole, wherein each ring is substituted with 1-3 $R^e$ groups, wherein each $R^e$ group is as defined above and described herein. In certain embodiments, Y is selected from:

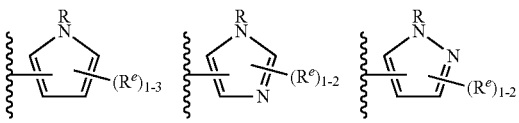

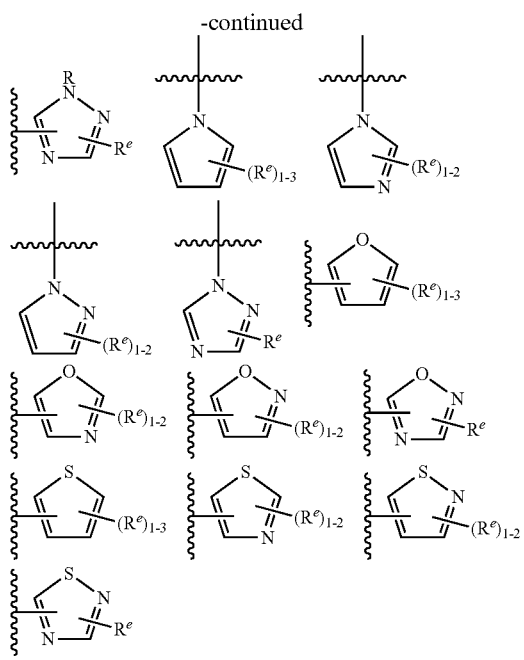

wherein each R and $R^e$ is as defined above and described herein.

In certain embodiments, Y is an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein. According to another aspect, Y is a 9-10 membered bicyclic, partially unsaturated, or aryl ring having 1-3 heteroatoms independently selected from nitrogen, oxygen, or sulfur, wherein said ring is substituted with 1-4 $R^e$ groups, wherein $R^e$ is as defined above and described herein. Exemplary such bicyclic rings include 2,3-dihydrobenzo[d]isothiazole, wherein said ring is substituted with 1-4 $R^e$ groups, wherein $R^e$ is as defined above and described herein.

As defined generally above, each $R^e$ group is independently selected from -Q-Z, oxo, $NO_2$, halogen, CN, a suitable leaving group, or $C_{1-6}$ aliphatic optionally substituted with oxo, halogen, $NO_2$, or CN, wherein Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and Z is hydrogen or $C_{1-6}$ aliphatic optionally substituted with oxo, halogen, $NO_2$, or CN.

In certain embodiments, $R^e$ is $C_{1-6}$ aliphatic optionally substituted with oxo, halogen, $NO_2$, or CN. In other embodiments, $R^e$ is oxo, $NO_2$, halogen, or CN.

In some embodiments, $R^e$ is -Q-Z, wherein Q is a covalent bond and Z is hydrogen (i.e., $R^e$ is hydrogen). In other embodiments, $R^e$ is -Q-Z, wherein Q is a bivalent $C_{1-6}$ saturated or unsaturated, straight or branched, hydrocarbon chain, wherein one or two methylene units of Q are optionally and independently replaced by —NR—, —NRC(O)—, —C(O)NR—, —S—, —O—, —C(O)—, —SO—, or —SO$_2$—. In other embodiments, Q is a bivalent $C_{2-6}$ straight or branched, hydrocarbon chain having at least one double bond, wherein one or two methylene units of Q are optionally and independently replaced by —NR—, —NRC(O)—, —C(O)NR—, —S—, —O—, —C(O)—, —SO—, or —SO$_2$—. In certain embodiments, the Z moiety of the $R^e$ group is hydrogen. In some embodiments, -Q-Z is —NHC(O)CH=CH$_2$ or —C(O)CH=CH$_2$.

In certain embodiments, each $R^e$ is independently selected from oxo, $NO_2$, CN, fluoro, chloro, —NHC(O)CH=CH$_2$, —C(O)CH=CH$_2$, —CH$_2$CH=CH$_2$, —C≡CH, —C(O)OCH$_2$Cl, —C(O)OCH$_2$F, —C(O)OCH$_2$CN, —C(O)CH$_2$Cl, —C(O)CH$_2$F, —C(O)CH$_2$CN, or —CH$_2$C(O)CH$_3$.

In certain embodiments, $R^e$ is a suitable leaving group, ie a group that is subject to nucleophilic displacement. A "suitable leaving" is a chemical group that is readily displaced by a desired incoming chemical moiety such as the thiol moiety of a cysteine of interest. Suitable leaving groups are well known in the art, e.g., see, "Advanced Organic Chemistry," Jerry March, $5^{th}$ Ed., pp. 351-357, John Wiley and Sons, N.Y. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, acyl, and diazonium moieties. Examples of suitable leaving groups include chloro, iodo, bromo, fluoro, acetoxy, methanesulfonyloxy (mesyloxy), tosyloxy, triflyloxy, nitro-phenylsulfonyloxy (nosyloxy), and bromo-phenylsulfonyloxy (brosyloxy).

In certain embodiments, the following embodiments and combinations of -L-Y apply:

(a) L is a bivalent $C_{2-8}$ straight or branched, hydrocarbon chain wherein L has at least one double bond and one or two additional methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O)—; and Y is hydrogen or $C_{1-6}$ aliphatic optionally substituted with oxo, halogen, $NO_2$, or CN; or (b) L is a bivalent $C_{2-8}$ straight or branched, hydrocarbon chain wherein L has at least one double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, $NO_2$, or CN; or (c) L is a bivalent $C_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, $NO_2$, or CN; or (d) L is a bivalent $C_{2-8}$ straight or branched, hydrocarbon chain wherein L has at least one double bond and at least one methylene unit of L is replaced by —C(O)—; and Y is hydrogen or $C_{1-6}$ aliphatic optionally substituted with oxo, halogen, $NO_2$, or CN; or (e) L is a bivalent $C_{2-8}$ straight or branched, hydrocarbon chain wherein L has at least one double bond and at least one methylene unit of L is replaced by —OC(O)—; and Y is hydrogen or $C_{1-6}$ aliphatic optionally substituted with oxo, halogen, $NO_2$, or CN; or (f) L is —NRC(O)CH=CH—, —NRC(O)CH=CHCH$_2$N(CH$_3$)—, —NRC(O)

CH=CHCH₂O—, —CH₂NRC(O)CH=CH—, —NRSO₂CH=CH—, —NRSO₂CH=CHCH₂—, —NRC(O)(C=N₂)—, —NRC(O)(C=N₂)C(O)—, —NRC(O)CH=CHCH₂O—, —NRC(O)C(=CH₂) CH₂—, —CH₂NRC(O)—, —CH₂CH₂NRC(O)—, or —CH₂NRC(O)cyclopropylene-; wherein R is H or optionally substituted C₁₋₆ aliphatic; and Y is hydrogen or C₁₋₆ aliphatic optionally substituted with oxo, halogen, NO₂, or CN; or (g) L is —NHC(O)CH=CH—, —NHC(O) CH=CHCH₂N(CH₃)—, —NHC(O) CH=CHCH₂O—, —CH₂NHC(O)CH=CH—, —NHSO₂CH=CH—, —NHSO₂CH=CHCH₂—, —NHC(O)(C=N₂)—, —NHC(O)(C=N₂)C(O)—, —NHC(O)C(=CH₂)CH₂—, —CH₂NHC(O)—, —CH₂CH₂NHC(O)—, or —CH₂NHC(O)cyclopropylene-; and Y is hydrogen or C₁₋₆ aliphatic optionally substituted with oxo, halogen, NO₂, or CN; or (h) L is a bivalent C₂₋₈ straight or branched, hydrocarbon chain wherein L has at least one alkylidenyl double bond and at least one methylene unit of L is replaced by —C(O)—, —NRC(O)—, —C(O)NR—, —N(R) SO₂—, —SO₂N(R)—, —S—, —S(O)—, —SO₂—, —OC(O)—, or —C(O)O—, and one or two methylene units of L are optionally and independently replaced by cyclopropylene, —O—, —N(R)—, or —C(O)—; and Y is hydrogen or C₁₋₆ aliphatic optionally substituted with oxo, halogen, NO₂, or CN; or (i) L is a bivalent C₂₋₈ straight or branched, hydrocarbon chain wherein L has at least one triple bond and one or two additional methylene units of L are optionally and independently replaced by —NRC(O)—, —C(O) NR—, —N(R)SO₂—, —SO₂N(R)—, —S—, —S(O)—, —SO₂—, —OC(O)—, or —C(O)O—, and Y is hydrogen or C₁₋₆ aliphatic optionally substituted with oxo, halogen, NO₂, or CN; or (j) L is —C≡C—, —C≡CCH₂N(isopropyl)-, —NHC(O) C≡CCH₂CH₂—, —CH₂—C≡C—CH₂—, —C≡CCH₂O—, —CH₂C(O)C≡C—, —C(O)C≡C—, or —CH₂OC(=O)C≡C—; and Y is hydrogen or C₁₋₆ aliphatic optionally substituted with oxo, halogen, NO₂, or CN; or (k) L is a bivalent C₂₋₈ straight or branched, hydrocarbon chain wherein one methylene unit of L is replaced by cyclopropylene and one or two additional methylene units of L are independently replaced by —NRC(O)—, —C(O)NR—, —N(R)SO₂—, —SO₂N(R)—, —S—, —S(O)—, —SO₂—, —OC(O)—, or —C(O)O—; and Y is hydrogen or C₁₋₆ aliphatic optionally substituted with oxo, halogen, NO₂, or CN; or (l) L is a covalent bond and Y is selected from:
  (i) C₁₋₆ alkyl substituted with oxo, halogen, NO₂, or CN;
  (ii) C₂₋₆ alkenyl optionally substituted with oxo, halogen, NO₂, or CN; or
  (iii) C₂₋₆ alkynyl optionally substituted with oxo, halogen, NO₂, or CN; or
  (iv) a saturated 3-4 membered heterocyclic ring having 1 heteroatom selected from oxygen or nitrogen wherein said ring is substituted with 1-2 Rᵉ groups, wherein each Rᵉ is as defined above and described herein; or
  (v) a saturated 5-6 membered heterocyclic ring having 1-2 heteroatom selected from oxygen or nitrogen wherein said ring is substituted with 1-4 Rᵉ groups, wherein each Rᵉ is as defined above and described herein; or

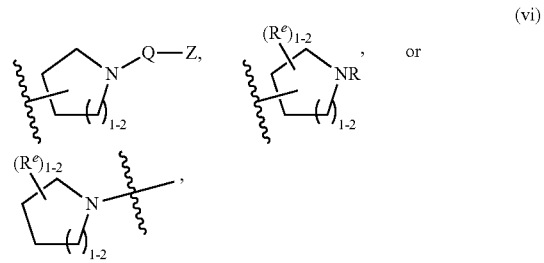

wherein each R, Q, Z, and Rᵉ is as defined above and described herein; or
  (vii) a saturated 3-6 membered carbocyclic ring, wherein said ring is substituted with 1-4 Rᵉ groups, wherein each Rᵉ is as defined above and described herein; or
  (viii) a partially unsaturated 3-6 membered monocyclic ring having 0-3 heteroatoms independently selected from nitrogen, oxygen, or sulfur, wherein said ring is substituted with 1-4 Rᵉ groups, wherein each Rᵉ is as defined above and described herein; or
  (ix) a partially unsaturated 3-6 membered carbocyclic ring, wherein said ring is substituted with 1-4 Rᵉ groups, wherein each Rᵉ is as defined above and described herein; or

wherein each Rᵉ is as defined above and described herein; or
  (xi) a partially unsaturated 4-6 membered heterocyclic ring having 1-2 heteroatoms independently selected from nitrogen, oxygen, or sulfur, wherein said ring is substituted with 1-4 Rᵉ groups, wherein each Rᵉ is as defined above and described herein; or

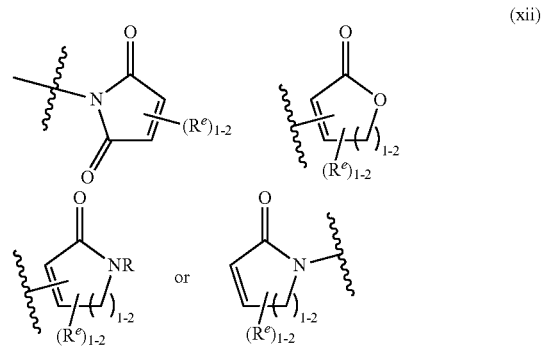

wherein each R and Rᵉ is as defined above and described herein; or
  (xiii) a 6-membered aromatic ring having 0-2 nitrogens wherein said ring is substituted with 1-4 Rᵉ groups, wherein each Rᵉ group is as defined above and described herein; or

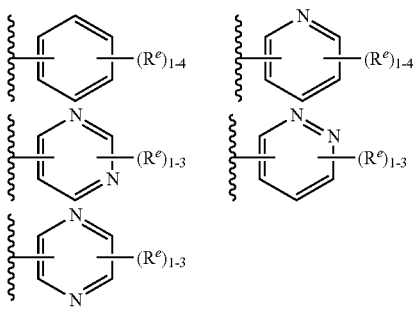

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or

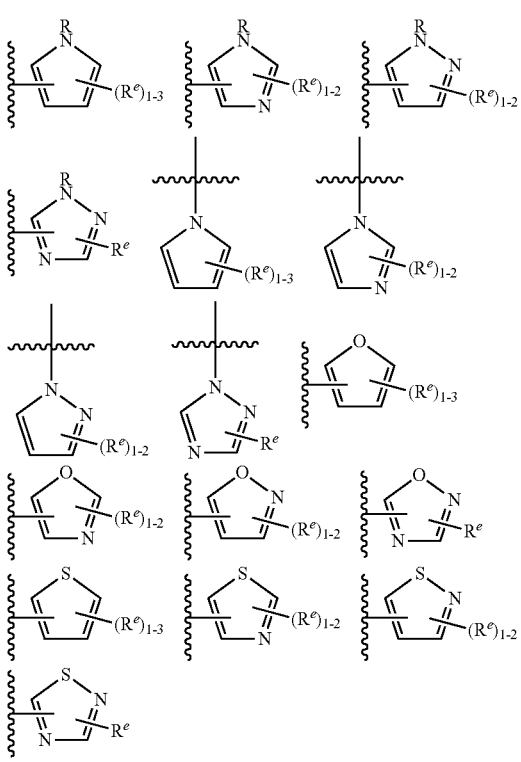

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(m) L is —C(O)— and Y is selected from:
(i) $C_{1-6}$ alkyl substituted with oxo, halogen, $NO_2$, or CN; or
(ii) $C_{2-6}$ alkenyl optionally substituted with oxo, halogen, $NO_2$, or CN; or
(iii) $C_{2-6}$ alkynyl optionally substituted with oxo, halogen, $NO_2$, or CN; or
(iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or
(v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or

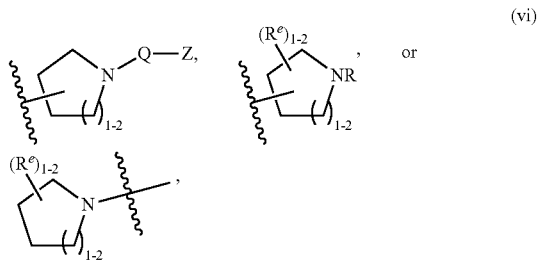

wherein each R, Q, Z, and $R^e$ is as defined above and described herein; or
(vii) a saturated 3-6 membered carbocyclic ring, wherein said ring is substituted with 1-4 $R^e$ groups, wherein each $R^e$ is as defined above and described herein; or
(viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or
(ix) a partially unsaturated 3-6 membered carbocyclic ring, wherein said ring is substituted with 1-4 $R^e$ groups, wherein each $R^e$ is as defined above and described herein; or

wherein each $R^e$ is as defined above and described herein; or
(xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or

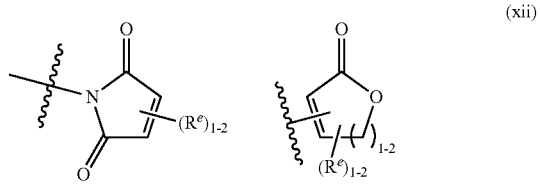

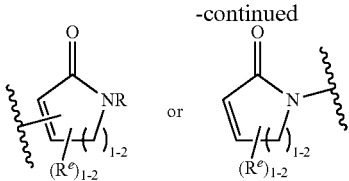

wherein each R and R$^e$ is as defined above and described herein; or (xiii) a 6-membered aromatic ring having 0-2 nitrogens wherein said ring is substituted with 1-4 R$^e$ groups, wherein each R$^e$ group is as defined above and described herein; or

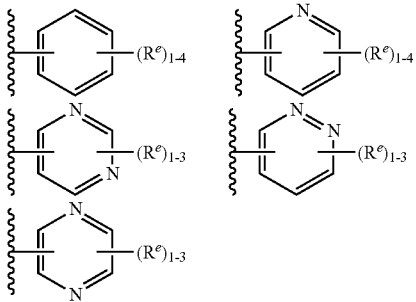

wherein each R$^e$ is as defined above and described herein; or (xv) a 5-membered heteroaryl ring having 1-3 heteroatoms independently selected from nitrogen, oxygen, or sulfur, wherein said ring is substituted with 1-3 R$^e$ groups, wherein each R$^e$ group is as defined above and described herein; or

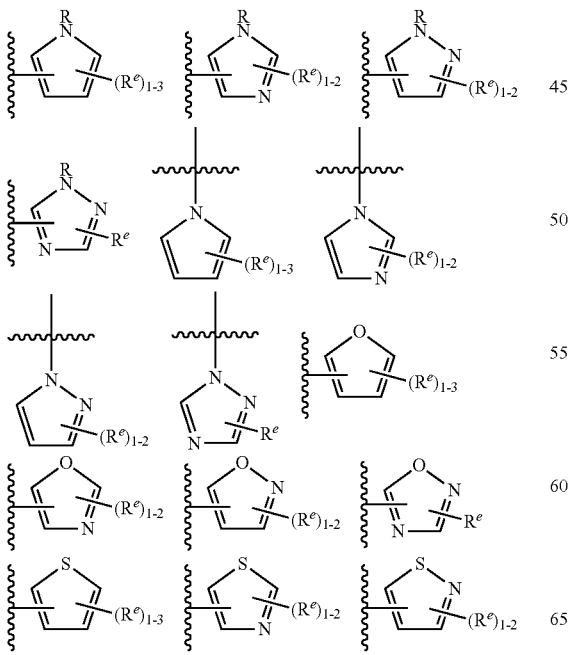

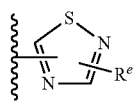

wherein each R and R$^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 R$^e$ groups, wherein R$^e$ is as defined above and described herein;

(n) L is —N(R)C(O)— and Y is selected from:
  (i) $C_{1-6}$ alkyl substituted with oxo, halogen, $NO_2$, or CN; or
  (ii) $C_{2-6}$ alkenyl optionally substituted with oxo, halogen, $NO_2$, or CN; or
  (iii) $C_{2-6}$ alkynyl optionally substituted with oxo, halogen, $NO_2$, or CN; or
  (iv) a saturated 3-4 membered heterocyclic ring having 1 heteroatom selected from oxygen or nitrogen wherein said ring is substituted with 1-2 R$^e$ groups, wherein each R$^e$ is as defined above and described herein; or
  (v) a saturated 5-6 membered heterocyclic ring having 1-2 heteroatom selected from oxygen or nitrogen wherein said ring is substituted with 1-4 R$^e$ groups, wherein each R$^e$ is as defined above and described herein; or

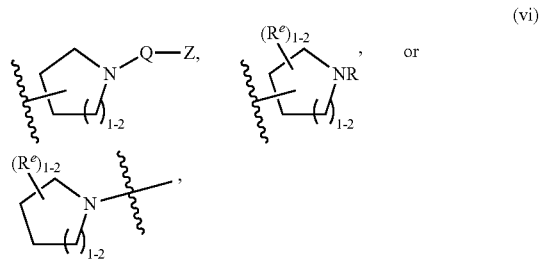

wherein each R, Q, Z, and R$^e$ is as defined above and described herein; or (vii) a saturated 3-6 membered carbocyclic ring, wherein said ring is substituted with 1-4 R$^e$ groups, wherein each R$^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 R$^e$ groups, wherein each R$^e$ is as defined above and described herein; or (ix) a partially unsaturated 3-6 membered carbocyclic ring, wherein said ring is substituted with 1-4 R$^e$ groups, wherein each R$^e$ is as defined above and described herein; or

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or

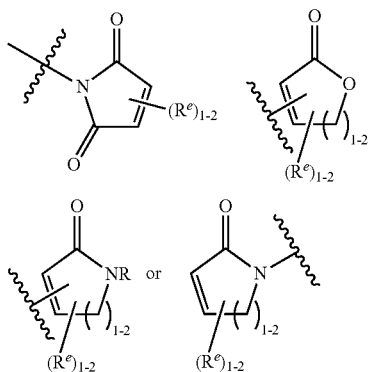

(xii)

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein;

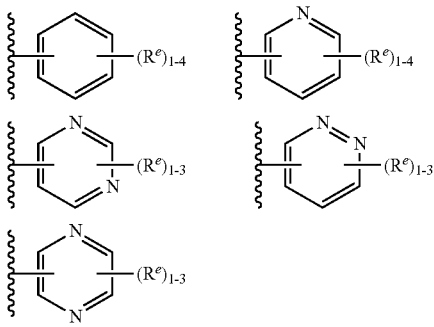

(xiv)

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or

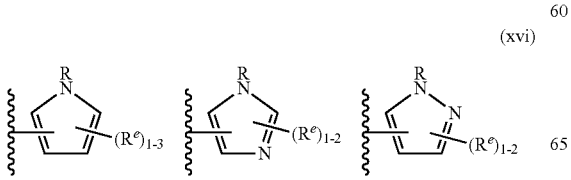

(xvi)

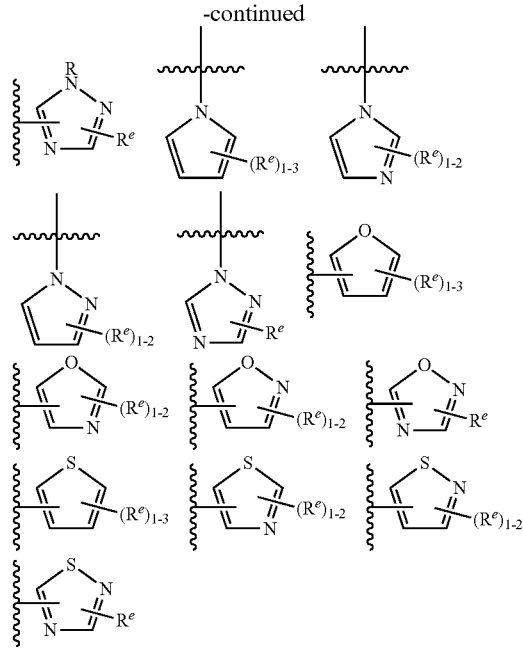

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(o) L is a bivalent $C_{1-8}$ saturated or unsaturated, straight or branched, hydrocarbon chain; and Y is selected from:

(i) $C_{1-6}$ alkyl substituted with oxo, halogen, $NO_2$, or CN;

(ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or

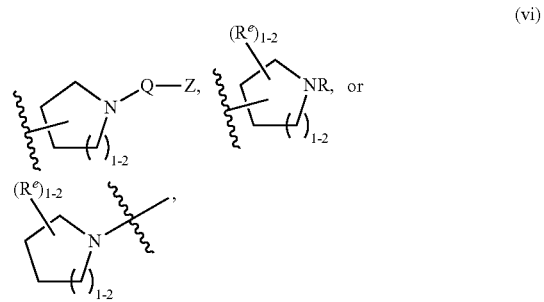

(vi)

wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or

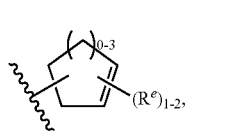

(x)

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or

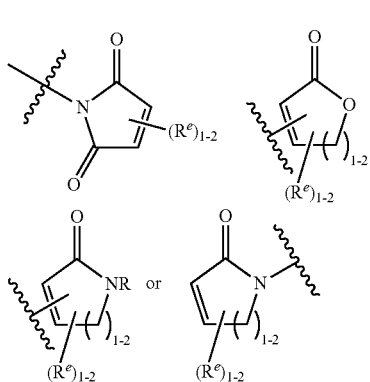

(xii)

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or

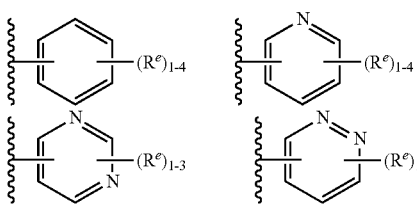

(xiv)

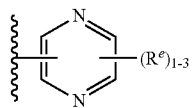

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or

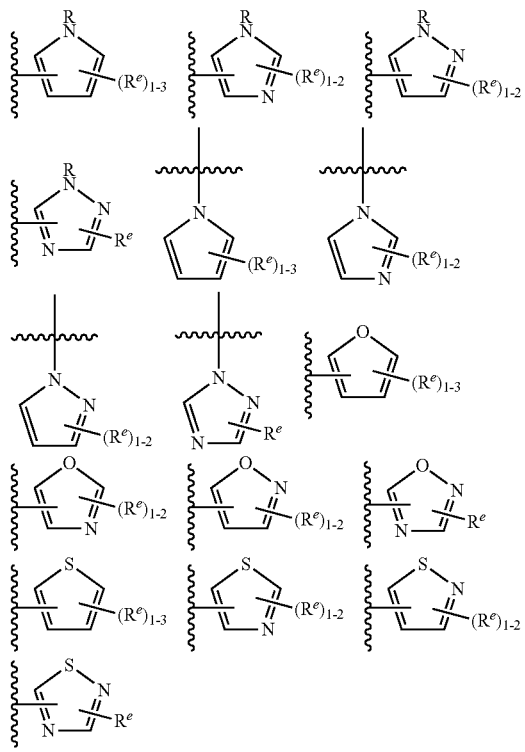

(xvi)

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(p) L is a covalent bond, —$CH_2$—, —NH—, —C(O)—, —$CH_2$NH—, —NH$CH_2$—, —NHC(O)—, —NHC(O)$CH_2$OC(O)—, —$CH_2$NHC(O)—, —NH$SO_2$—, —NH$SO_2CH_2$—, —NHC(O)$CH_2$OC(O)—, or —$SO_2$NH—; and Y is selected from:

(i) $C_{1-6}$ alkyl substituted with oxo, halogen, $NO_2$, or CN; or (ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 R$^e$ groups, wherein each R$^e$ is as defined above and described herein; or (v) a saturated 5-6 membered heterocyclic ring having 1-2 heteroatom selected from oxygen or nitrogen wherein said ring is substituted with 1-4 R$^e$ groups, wherein each R$^e$ is as defined above and described herein; or (vi)

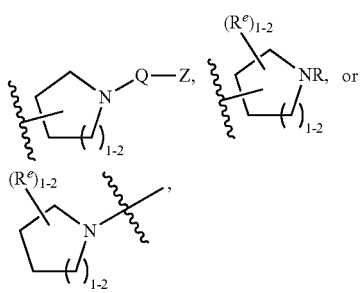

wherein each R, Q, Z, and R$^e$ is as defined above and described herein; or (vii) a saturated 3-6 membered carbocyclic ring, wherein said ring is substituted with 1-4 R$^e$ groups, wherein each R$^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 R$^e$ groups, wherein each R$^e$ is as defined above and described herein; or (ix) a partially unsaturated 3-6 membered carbocyclic ring, wherein said ring is substituted with 1-4 R$^e$ groups, wherein each R$^e$ is as defined above and described herein; or (x)

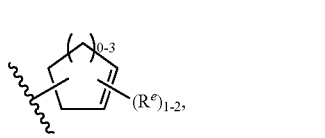

wherein each R$^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 R$^e$ groups, wherein each R$^e$ is as defined above and described herein; or (xii)

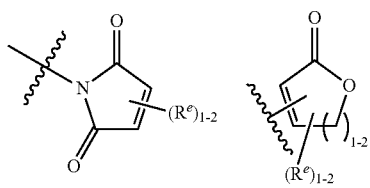

-continued

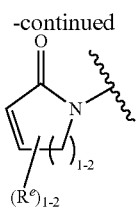

wherein each R and R$^e$ is as defined above and described herein; or (xiii) a 6-membered aromatic ring having 0-2 nitrogens wherein said ring is substituted with 1-4 R$^e$ groups, wherein each R$^e$ group is as defined above and described herein; or (xiv)

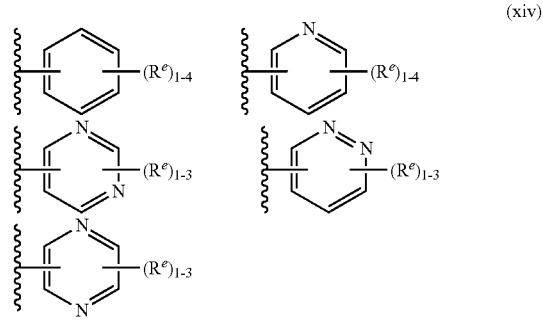

wherein each R$^e$ is as defined above and described herein; or (xv) a 5-membered heteroaryl ring having 1-3 heteroatoms independently selected from nitrogen, oxygen, or sulfur, wherein said ring is substituted with 1-3 R$^e$ groups, wherein each R$^e$ group is as defined above and described herein; or (xvi)

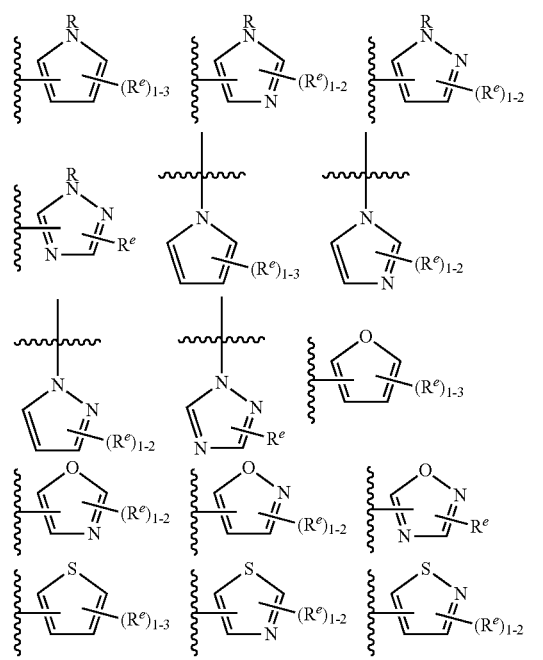

-continued

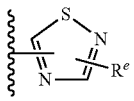

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein.

(q) L is a bivalent $C_{2-8}$ straight or branched, hydrocarbon chain wherein two or three methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O)—; and Y is hydrogen or $C_{1-6}$ aliphatic optionally substituted with oxo, halogen, NO$_2$, or CN.

(r) L-Y is "pro-warhead" that is converted in vitro or in vivo to an irreversible warhead. In certain embodiments, L-Y is

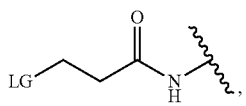

wherein LG is a leaving group. In certain embodiments, L-Y is

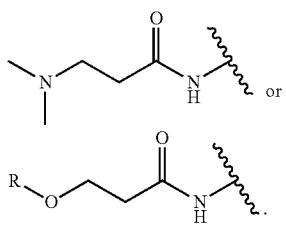

In certain embodiments, the "pro-warhead" is converted to an irreversible warhead according to the following:

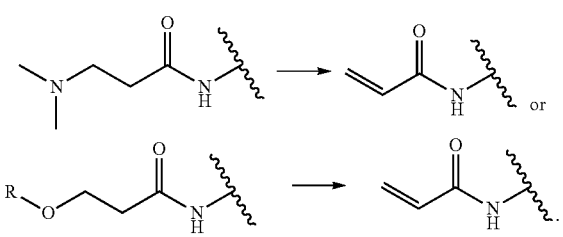

In certain embodiments, the Y group of any of the formulae herein is selected from those set forth in Table 1, Table 2, Table 3, Table 7, or Table 8, wherein each wavy line indicates the point of attachment to the rest of the molecule.

In certain embodiments, $R^1$ is -L-Y, wherein:
L is a covalent bond or a bivalent $C_{1-8}$ saturated or unsaturated, straight or branched, hydrocarbon chain, wherein one, two, or three methylene units of L are optionally and independently replaced by —N(R)—, —N(R)C(O)—, —N(R)SO$_2$—, —O—, —C(O)—, or —SO$_2$—; and Y is hydrogen, or $C_{1-6}$ aliphatic optionally substituted with oxo, halogen, N(R)$_2$, NO$_2$, or CN.

In certain embodiments, the Y group of $R^1$ group, -L-Y, is selected from those set forth in Table 4, below, wherein each wavy line indicates the point of attachment to the rest of the molecule.

TABLE 4

Exemplary Y groups:

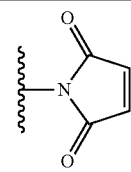 a

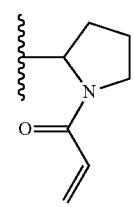 [SMILES: *C1CCCN1C(=O)C=C] b

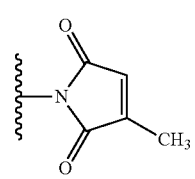 [SMILES: *N1C(=O)C=C(C)C1=O] c

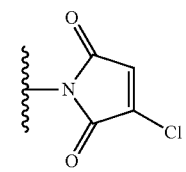 [SMILES: *N1C(=O)C=C(Cl)C1=O] d

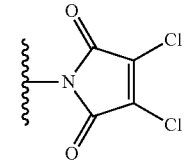 [SMILES: *N1C(=O)C(Cl)=C(Cl)C1=O] e

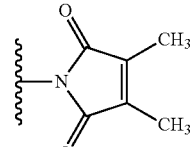 f

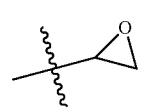 [SMILES: *C1CO1] g

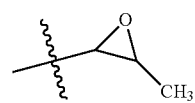 h

TABLE 4-continued
Exemplary Y groups:
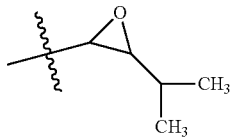 [SMILES: *C1OC1C(C)C] i
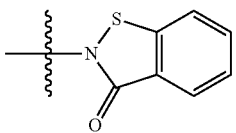 [SMILES: *n1sc2ccccc2c1=O] j
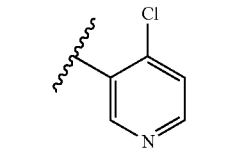 [SMILES: *c1cnccc1Cl] k
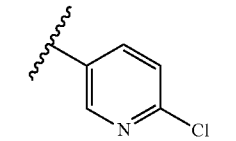 [SMILES: *c1ccc(Cl)nc1] l
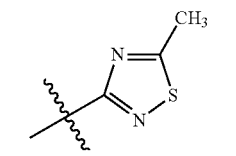 [SMILES: *c1nsc(C)n1] m
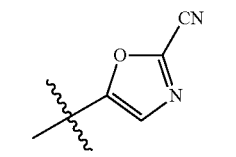 [SMILES: *c1cnc(C#N)o1] n
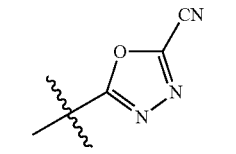 [SMILES: *c1nnc(C#N)o1] o
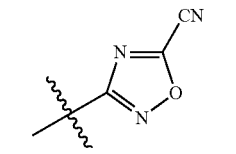 [SMILES: *c1noc(C#N)n1] p
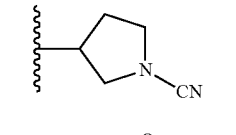 q
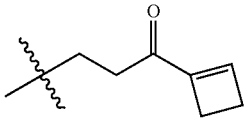 [SMILES: *CCC(=O)C1=CCC1] r
TABLE 4-continued
Exemplary Y groups:
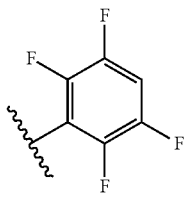 [SMILES: *c1c(F)c(F)cc(F)c1F] s
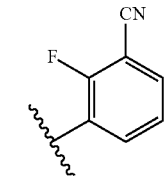 [SMILES: *c1cccc(C#N)c1F] t
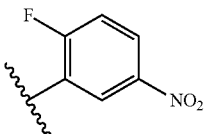 [SMILES: *c1cc([N+](=O)[O-])ccc1F] u
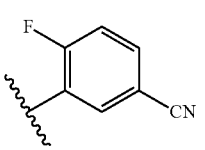 [SMILES: *c1cc(C#N)ccc1F] v
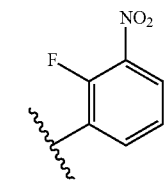 [SMILES: *c1cccc([N+](=O)[O-])c1F] w
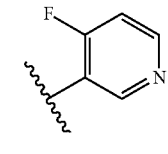 [SMILES: *c1cnccc1F] x
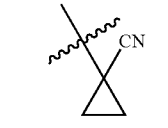 y
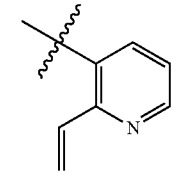 [SMILES: *c1cccnc1C=C] z
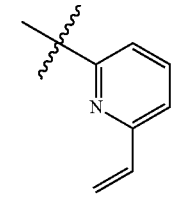 [SMILES: *c1cccc(C=C)n1] aa TABLE 4-continued
Exemplary Y groups:
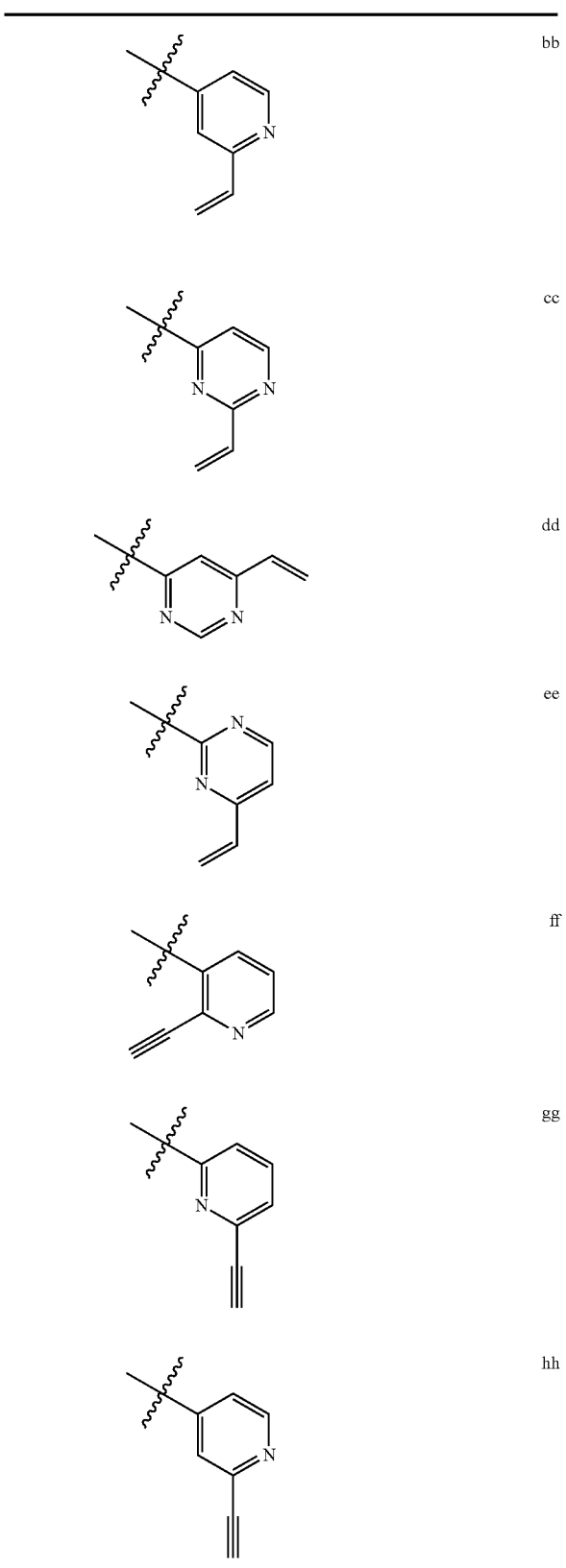
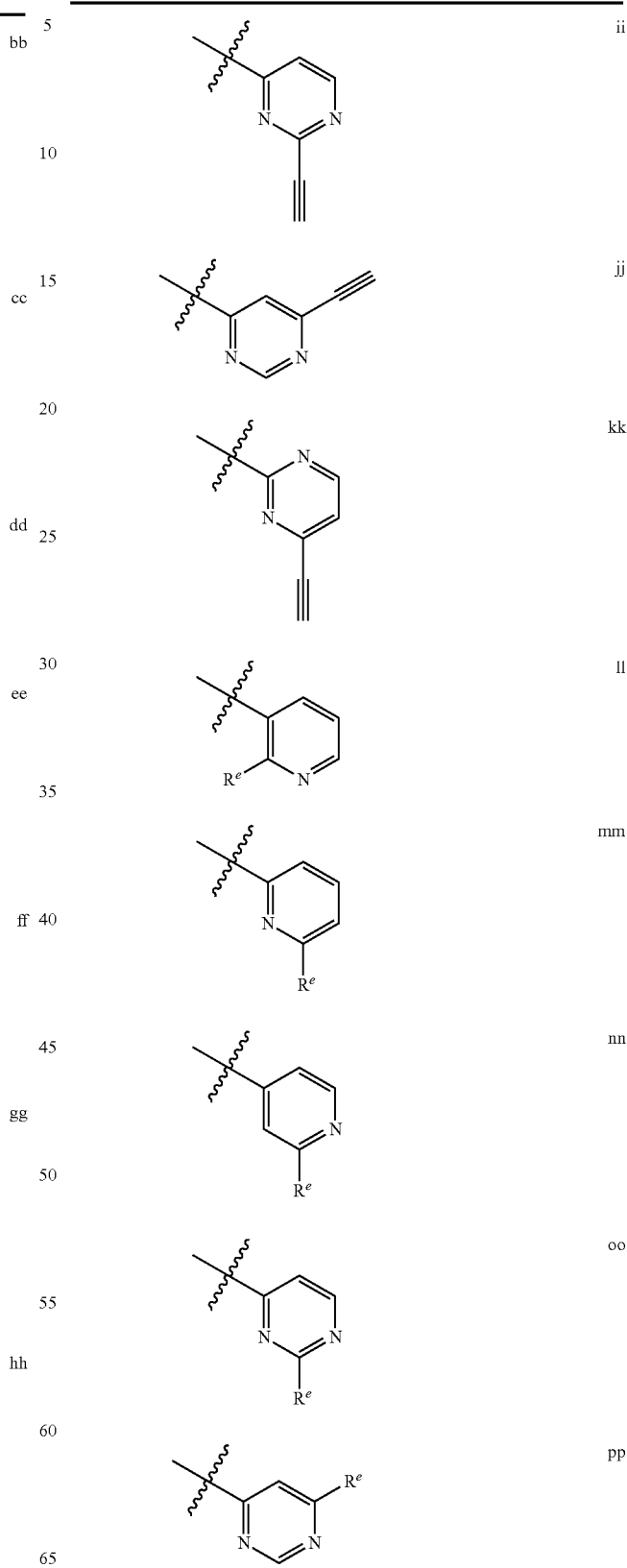

TABLE 4-continued
Exemplary Y groups:
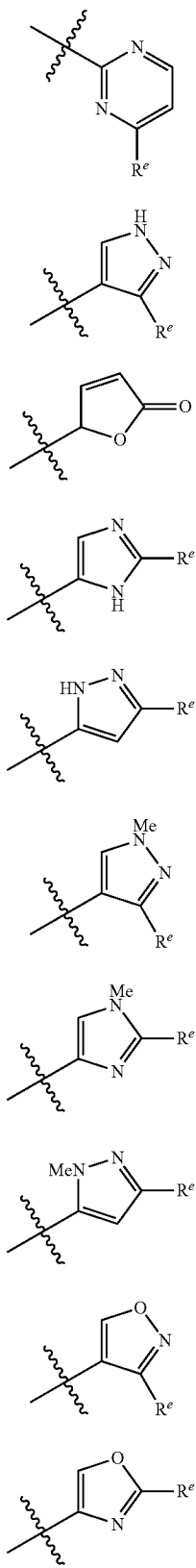
qq
rr
ss
tt
uu
vv
ww
xx
yy
zz
TABLE 4-continued
Exemplary Y groups:
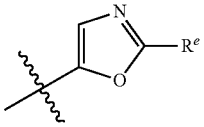 aaa
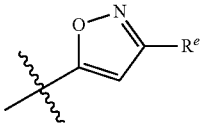 bbb
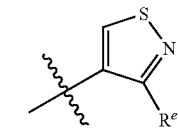 ccc
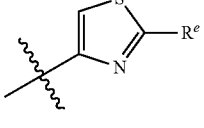 ddd
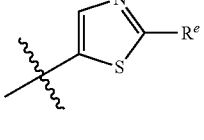 eee
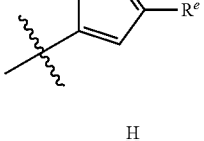 fff
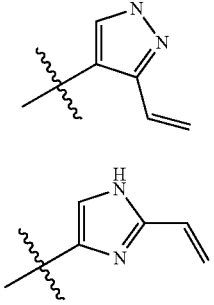 ggg
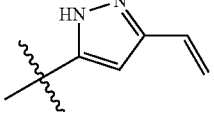 hhh
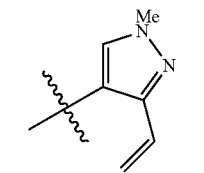 [SMILES: *c1cn(C)nc1C=C] iii
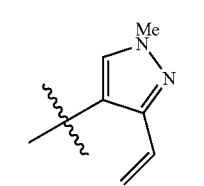 jjj TABLE 4-continued
Exemplary Y groups:
| | |
|---|---|
| 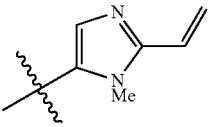 [SMILES: *c1cnc(C=C)n1C] | kkk |
| 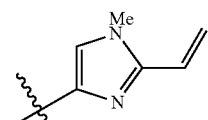 | lll |
| 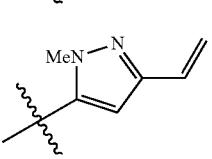 | mmm |
| 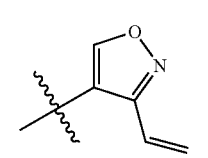 | nnn |
| 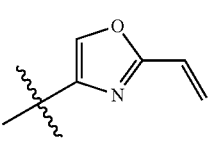 | ooo |
| 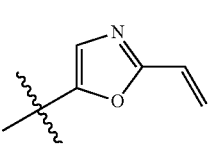 [SMILES: *c1cnc(C=C)o1] | ppp |
| 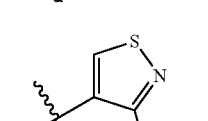 | qqq |
| 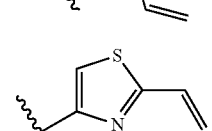 | rrr |
| 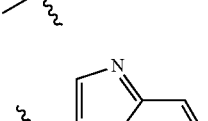 | sss |
| 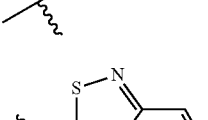 | ttt |
| 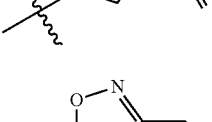 | uuu |
TABLE 4-continued
Exemplary Y groups:
| | |
|---|---|
| 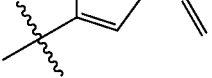 | vvv |
| 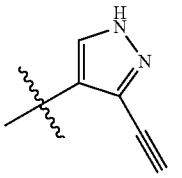 [SMILES: *c1c[nH]nc1C#C] | qqq |
| 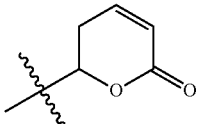 [SMILES: *C1CC=CC(=O)O1] | www |
| 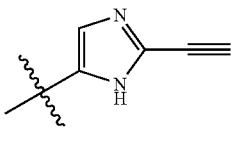 [SMILES: *c1cnc(C#C)[nH]1] | xxx |
| 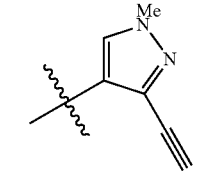 [SMILES: *c1cn(C)nc1C#C] | yyy |
| 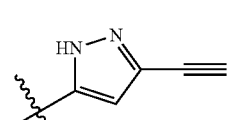 | zzz |
| 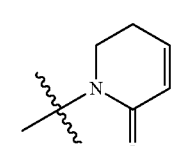 | aaaa |
| 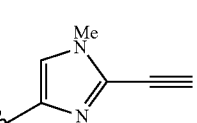 | bbbb |
| 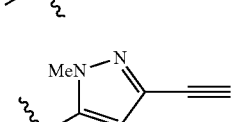 | cccc |
| 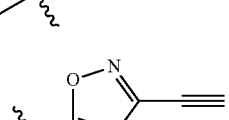 | dddd |

TABLE 4-continued
| Exemplary Y groups: | | Exemplary Y groups: | |
|---|---|---|---|
| 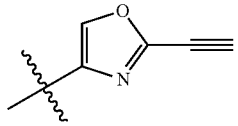 [SMILES: *c1coc(C#C)n1] | eeee | 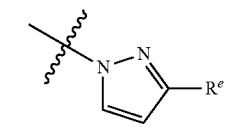 | oooo |
| 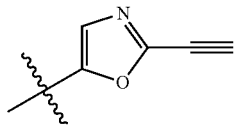 | ffff | 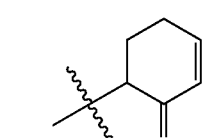 | pppp |
| 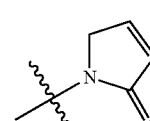 | gggg | 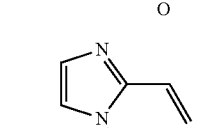 | qqqq |
| 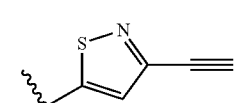 | hhhh | 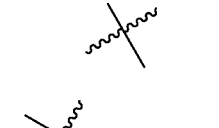 | rrrr |
| 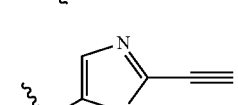 | iiii | 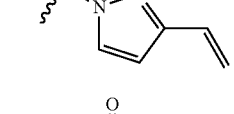 | ssss |
| 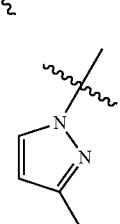 | jjjj | 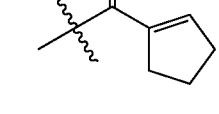 | tttt |
| 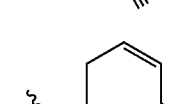 | kkkk | 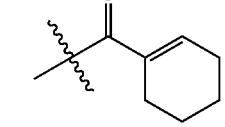 | uuuu |
| 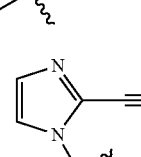 | llll | 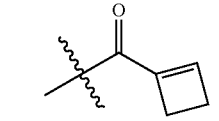 [SMILES: *C(=O)C1=CCC1] | vvvv |
| 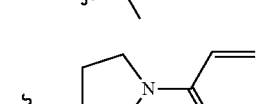 | mmmm | 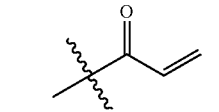 | wwww |
| 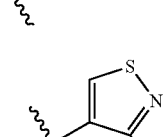 | nnnn | 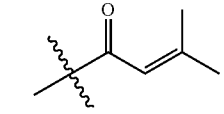 | xxxx |
| | | 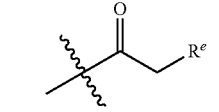 | yyyy |

TABLE 4-continued

Exemplary Y groups:

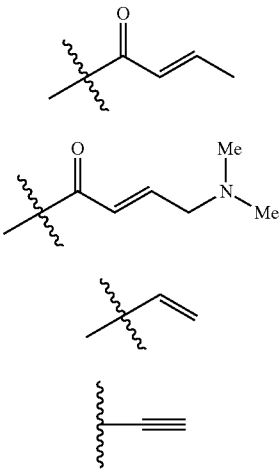

| | |
|---|---|
| zzzz | 5 |
| aaaaa | 10 |
| bbbbb | 15 |
| ccccc | 20 | wherein each $R^e$ is independently a suitable leaving group, $NO_2$, CN, or oxo.

In certain embodiments, $R^1$ is —C(O)CH$_2$CH$_2$C(O)CH=C(CH$_3$)$_2$, —C(O)CH$_2$CH$_2$C(O)CH=CH(cyclopropyl), —C(O)CH$_2$CH$_2$C(O)CH=CHCH$_3$, —C(O)CH$_2$CH$_2$C(O)CH=CHCH$_2$CH$_3$, or —C(O)CH$_2$CH$_2$C(O)C(=CH$_2$)CH$_3$. In certain embodiments, $R^1$ is —C(O)CH$_2$NHC(O)CH=CH$_2$, —C(O)CH$_2$NHC(O)CH$_2$CH$_2$C(O)CH=CHCH$_3$, or —C(O)CH$_2$NHC(O)CH$_2$CH$_2$C(O)C(=CH$_2$)CH$_3$. In certain embodiments, $R^1$ is —S(O)$_2$CH$_2$CH$_2$NHC(O)CH$_2$CH$_2$C(O)CH=C(CH$_3$)$_2$, —S(O)$_2$CH$_2$CH$_2$NHC(O)CH$_2$CH$_2$C(O)CH=CHCH$_3$, or —S(O)$_2$CH$_2$CH$_2$NHC(O)CH$_2$CH$_2$C(O)CH=CH$_2$. In certain embodiments, $R^1$ is —C(O)(CH$_2$)$_3$NHC(O)CH$_2$CH$_2$C(O)CH=CHCH$_3$ or —C(O)(CH$_2$)$_3$NHC(O)CH$_2$CH$_2$C(O)CH=CH$_2$.

In certain embodiments, $R^1$ is —C≡CH, —C≡CCH$_2$NH (isopropyl), —NHC(O)C≡CCH$_2$CH$_3$, —CH$_2$—C≡C—CH$_3$, —C≡CCH$_2$OH, —CH$_2$C(O)C≡CH, —C(O)C≡CH, or —CH$_2$OC(=O)C≡CH. In some embodiments, $R^1$ is selected from —NHC(O)CH=CH$_2$, —NHC(O)CH=CHCH$_2$N(CH$_3$)$_2$, or —CH$_2$NHC(O)CH=CH$_2$.

In certain embodiments, $R^1$ is selected from those set forth in Table 5, below, wherein each wavy line indicates the point of attachment to the rest of the molecule.

TABLE 5

Exemplary $R^1$ Groups

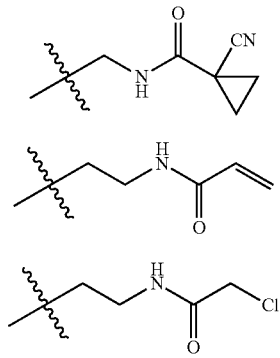

| | |
|---|---|
| a | |
| b | 60 |
| c | 65 |

TABLE 5-continued

Exemplary $R^1$ Groups

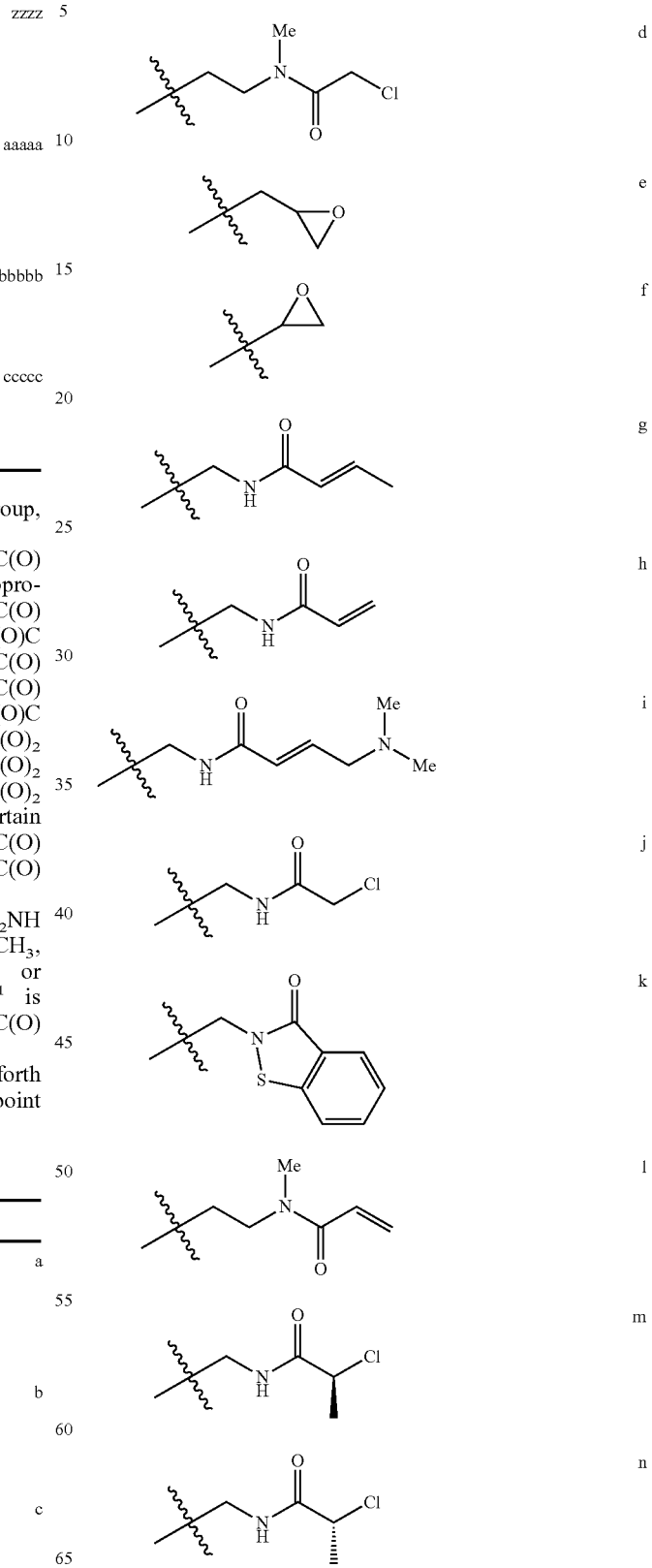

| | |
|---|---|
| d | |
| e | |
| f | |
| g | |
| h | |
| i | |
| j | |
| k | |
| l | |
| m | |
| n | |

TABLE 5-continued

Exemplary R¹ Groups

| Structure | Label |
|---|---|
| -CH₂-NH-C(=O)-CHCl- | o |
| -CH₂-N(Me)-C(=O)-CH=CH₂ | p |
| -CH₂-NH-C(=O)-C(=CH₂)-CH₃ | q |
| -CH₂-NH-C(=O)-C(=CH₂)-CF₃ | r |
| -CH₂CH₂-C(=O)-CH=CH₂ | s |
| -CH₂CH₂-C(=O)-CH=CH-CH₃ | t |
| -CH₂CH₂-C(=O)-CH=CH-CH₂-N(Me)₂ | u |
| -CH₂CH₂-C(=O)-CH=C(Me)₂ | v |
| -CH₂-C(=O)-CH=C(Me)₂ | w |
| -CH₂-O-C(=O)-CH=CH₂ | x |
| -CH(-)-O-C(=O)-CH=CH₂ | y |
| -CH₂-O-C(=O)-CH=CH-CH₃ | z |

TABLE 5-continued

Exemplary R¹ Groups

| Structure | Label |
|---|---|
| -CH(-)-O-C(=O)-CH=CH-CH₃ | aa |
| -CH₂CH₂-N(Et)-C(=O)-CH=CH₂ | bb |
| -CH₂CH₂-N(allyl)-C(=O)-CH=CH₂ | cc |
| -CH₂-N(Et)-C(=O)-CH=CH₂ | dd |
| -CH₂-N(allyl)-C(=O)-CH=CH₂ | ee |
| 3-(2-vinylpyridyl) | ff |
| 2-(6-vinylpyridyl) | gg |
| 4-(2-vinylpyridyl) | hh |
| 4-(2-vinylpyrimidinyl) | ii |

TABLE 5-continued
Exemplary R¹ Groups
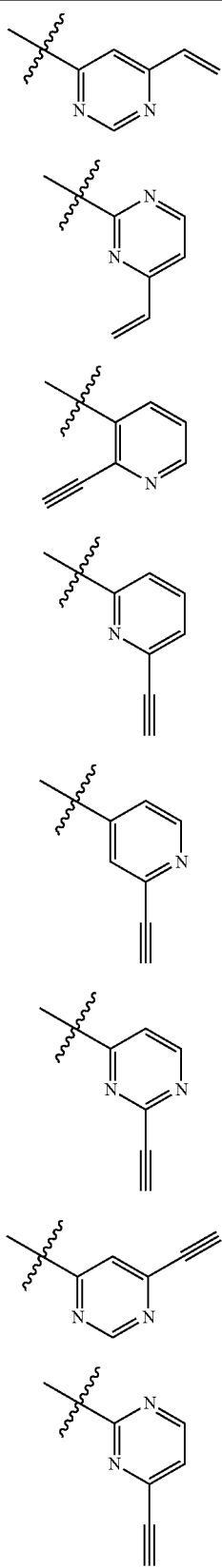
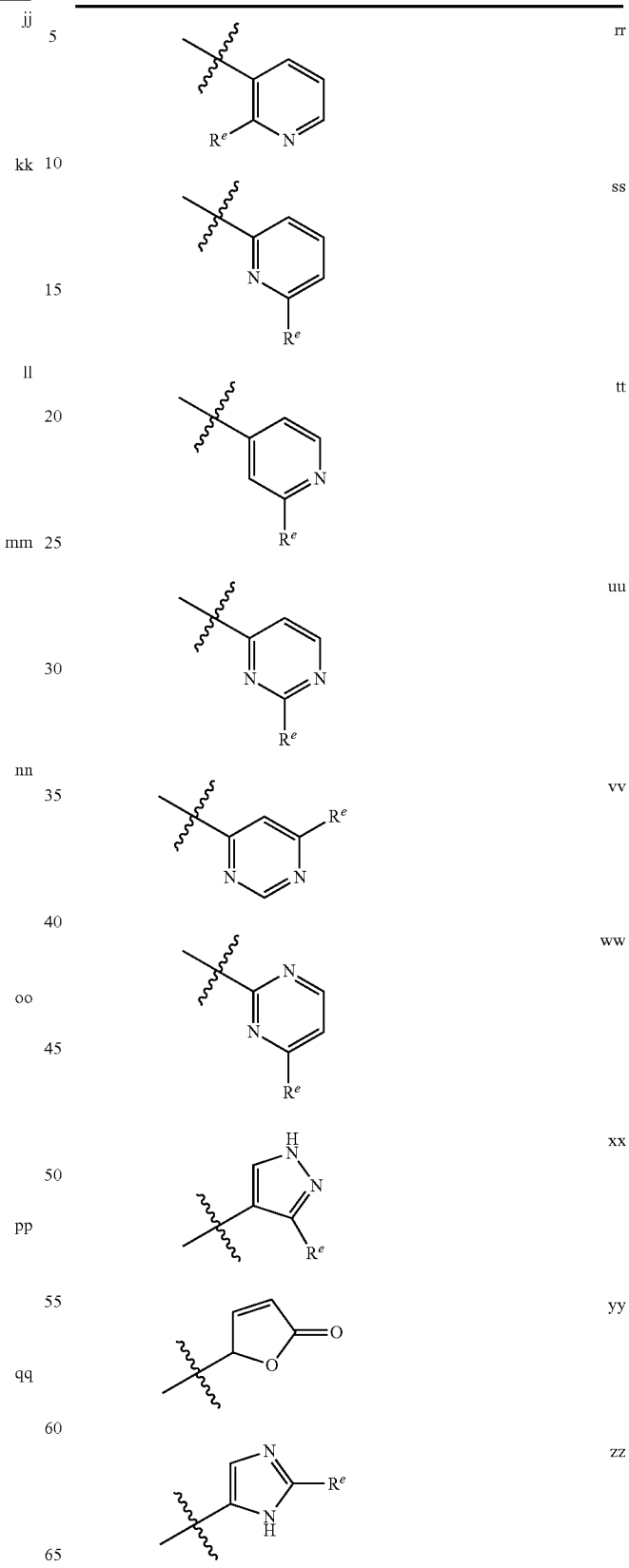

TABLE 5-continued

Exemplary R¹ Groups

| | |
|---|---|
| (aaa) pyrazole-NH with Rᵉ | (kkk) thiazole with Rᵉ |
| (bbb) N-Me pyrazole with Rᵉ | (lll) thiazole with Rᵉ |
| (ccc) N-Me imidazole with Rᵉ | (mmm) isothiazole with Rᵉ |
| (ddd) N-Me imidazole with Rᵉ | (nnn) pyrazole-NH with vinyl |
| (eee) N-Me pyrazole with Rᵉ | (ooo) imidazole-NH with vinyl |
| (fff) isoxazole with Rᵉ | (ppp) pyrazole-NH with vinyl |
| (ggg) oxazole with Rᵉ | (qqq) N-Me pyrazole with vinyl |
| (hhh) oxazole with Rᵉ | |
| (iii) isoxazole with Rᵉ | (rrr) isoxazole with vinyl |
| (jjj) isothiazole with Rᵉ | (sss) oxazole with vinyl |

213
TABLE 5-continued
Exemplary R¹ Groups
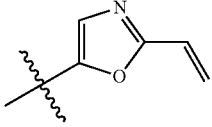 [SMILES: *c1cnc(C=C)o1] ttt
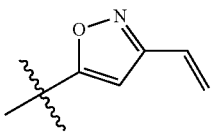 [SMILES: *c1cc(C=C)no1] uuu
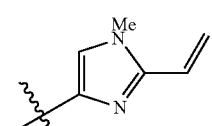 vvv
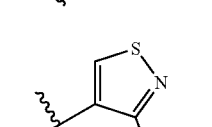 www
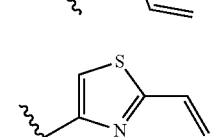 xxx
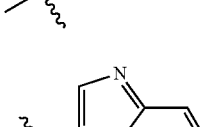 yyy
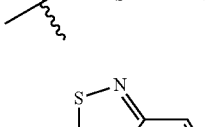 zzz
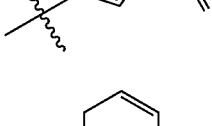 aaaa
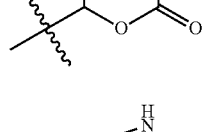 bbbb
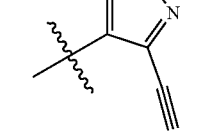 cccc
214
TABLE 5-continued
Exemplary R¹ Groups
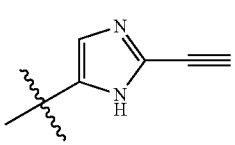 dddd
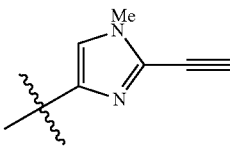 [SMILES: *c1cn(C)c(C#C)n1] eeee
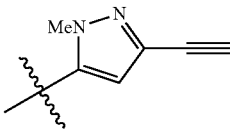 [SMILES: *c1cc(C#C)nn1C] ffff
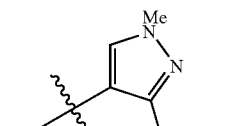 gggg
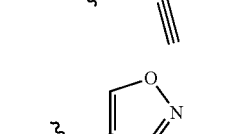 hhhh
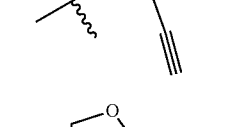 iiii
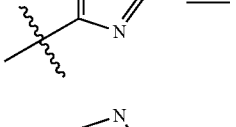 jjjj
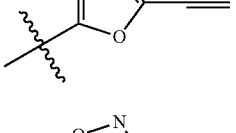 kkkk
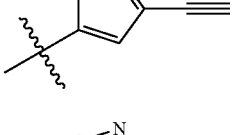 llll
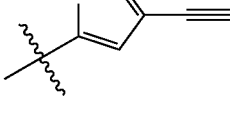 mmmm TABLE 5-continued
Exemplary R¹ Groups
| | | |
|---|---|---|
| 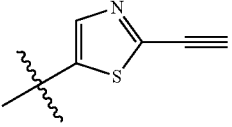 [SMILES: *c1cnc(C#C)s1] | nnnn | |
| 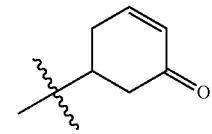 [SMILES: *C1CC=CC(=O)C1] | oooo | |
| 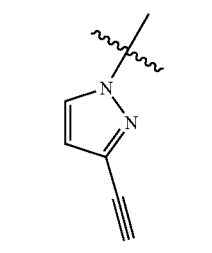 [SMILES: *n1ccc(C#C)n1] | pppp | |
| 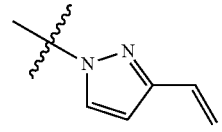 [SMILES: *n1ccc(C=C)n1] | qqqq | |
| 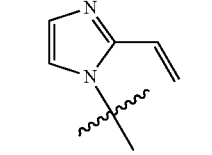 [SMILES: *n1ccnc1C=C] | rrrr | |
| 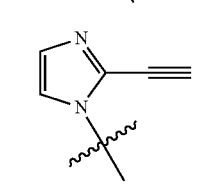 | ssss | |
| 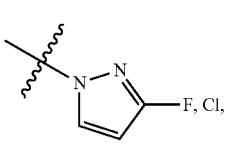 | tttt | |
| 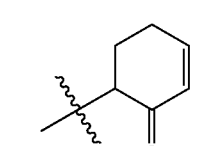 | uuuu | |
| 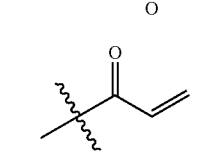 | vvvv | |
| 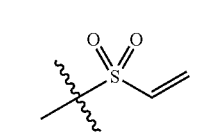 | wwww | |
TABLE 5-continued
Exemplary R¹ Groups
| | | |
|---|---|---|
| 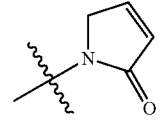 | xxxx | |
| 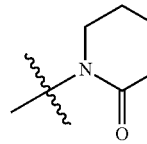 | yyyy | |
| 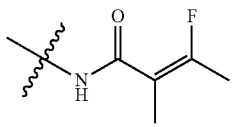 [SMILES: *NC(=O)/C(C)=C(/C)F] | zzzz | |
| 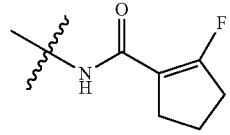 [SMILES: *NC(=O)C1=C(F)CCC1] | aaaaa | |
| 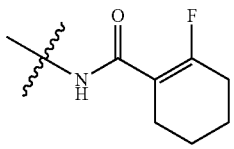 [SMILES: *NC(=O)C1=C(F)CCCC1] | bbbbb | |
| 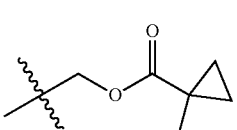 | ccccc | |
| 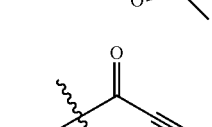 | ddddd | |
| 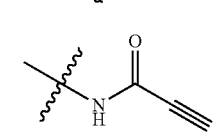 | eeeee | |
| 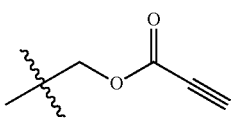 [SMILES: *COC(=O)C#C] | fffff | |
| 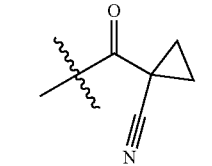 [SMILES: *C(=O)C1(C#N)CC1] | ggggg | |
|  | hhhhh | |

TABLE 5-continued

Exemplary R¹ Groups

| Structure | Label |
|---|---|
| pyrrolidine-N-acryloyl | iiiii |
| -CH₂-N(CH₃)-C(O)-CH=CH-CH₂-N(CH₃)₂ | jjjjj |
| -CH₂-N(CH₂CH₃)-C(O)-CH=CH-CH₂-N(CH₃)₂ | kkkkk |
| -CH₂-N(CH₂CH=CH₂)-C(O)-CH=CH-CH₂-N(CH₃)₂ | lllll |
| -(CH₂)₂-C(O)-cyclobutenyl | mmmmm |
| -(CH₂)₂-C(O)-cyclopentenyl | nnnnn |
| -(CH₂)₂-C(O)-cyclohexenyl | ooooo |
| -C(CH₃)₂-O-C(O)-CH=CH₂ | ppppp |
| -C(CH₃)₂-O-C(O)-CH=CH-CH₃ | qqqqq |
| -C(O)-CH=CH-CH₂-N(CH₃)₂ | rrrrr |
| -C(CH₃)₂-O-C(O)-CH=CH-CH₂-N(CH₃)₂ | sssss |
| -NH-C(O)-CH=CH₂ | ttttt |
| -NH-C(O)-CH=CH-CH₂-N(CH₃)₂ | uuuuu |
| -C(O)-CH=CH₂ | vvvvv |
| -S(O)₂-CH=CH₂ | wwwww |
| -C(O)-CH₂-Cl | xxxxx |
| -C(CH₃)₂-C≡CH | yyyyy |
| -CH₂-CH=CH₂ | zzzzz |
| -C(O)-CH₂-CN | aaaaaa |
| -C(O)-CH₂-F | bbbbbb |
| -C(CH₃)₂-NH-S(O)₂-CH=CH₂ | cccccc |
| -C(O)-CH=C(CH₃)₂ | dddddd |
| -C(O)-CH₂-Ac | eeeeee |
| -C(O)-CH=CH₂ | ffffff |

TABLE 5-continued
Exemplary R[1] Groups
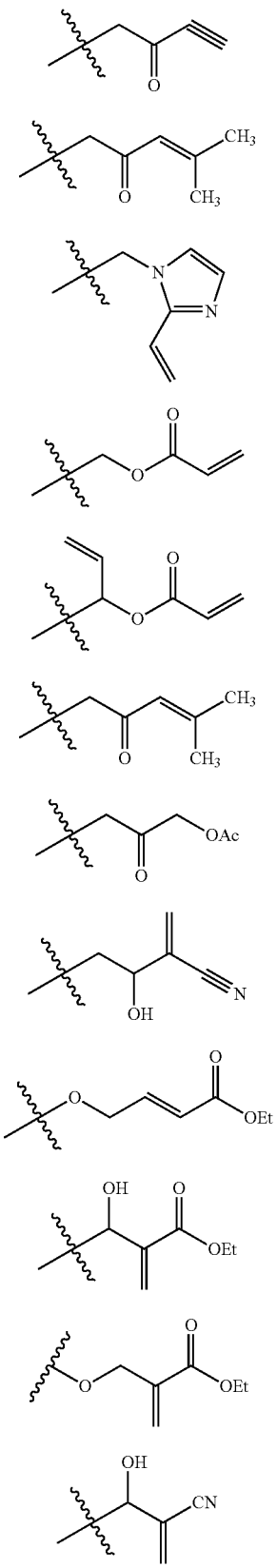
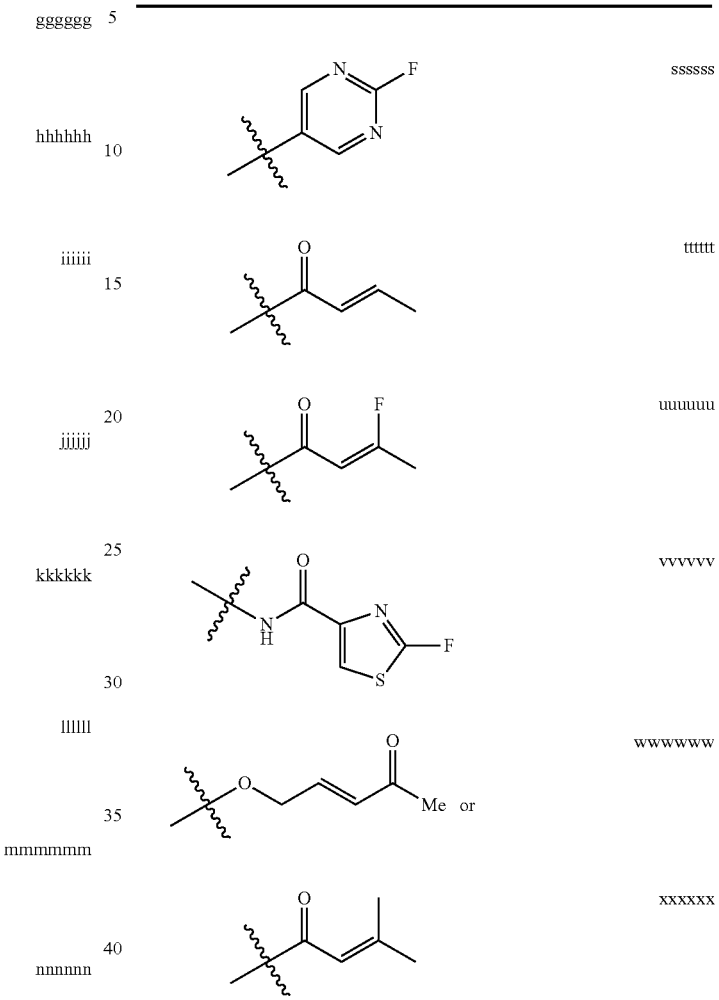
wherein each $R^e$ is independently a suitable leaving group, $NO_2$, CN, or oxo.
In certain embodiments, $R^1$ is selected from
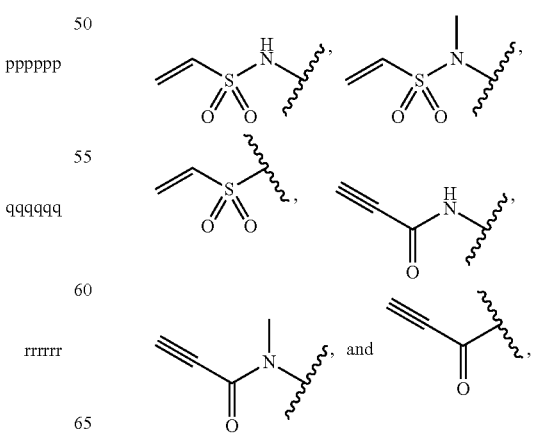

In certain embodiments, R¹ is selected from

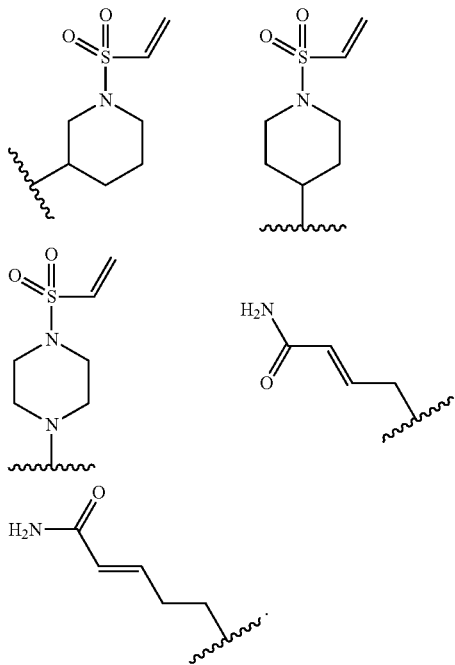

In certain embodiments, R¹ is selected from:

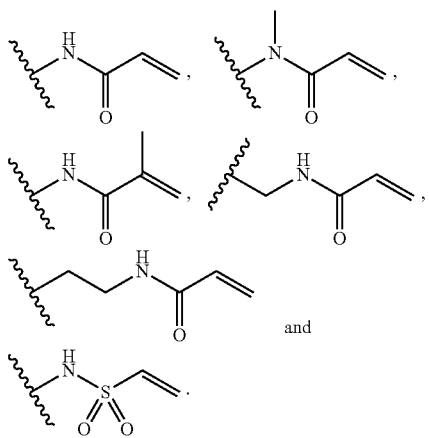

In some embodiments, R¹ is selected from those depicted in Table 1, Table 2, Table 3, Table 7, or Table 8.

As defined generally above, R¹ is a warhead group. Without wishing to be bound by any particular theory, it is believed that such R¹ groups, i.e. warhead groups, are particularly suitable for covalently binding to a key cysteine residue in the binding domain of certain protein kinases. Protein kinases having a cysteine residue in the binding domain are known to one of ordinary skill in the art and include FGFR4, or a mutant thereof. FIG. 4 provides SEQ ID NO. 1, which is the amino acid sequence of FGFR4. In certain embodiments, compounds of the present invention have a warhead group characterized in that inventive compounds target the cysteine 552 residue (which is highlighted by a box in FIG. 4 and in bold with underlining below):

```
FGFR4 subsequence containing C552:
LGVCTQEGPLYVIVECAAKGNLREFLRARRP
```

Thus, in some embodiments, R¹ is characterized in that the -L-Y moiety is capable of covalently binding to the cysteine 552 residue thereby irreversibly inhibiting the enzyme. The cysteine residue is Cys552 of FGFR4, or a mutant thereof, where the provided residue numbering is in accordance with Uniprot P22455).

One of ordinary skill in the art will recognize that a variety of warhead groups, as defined herein, are suitable for such covalent binding.

In certain embodiments, R¹ is characterized in that the -L-Y moiety is capable of covalently binding to a cysteine residue of FGFR4, thereby irreversibly inhibiting the enzyme. In some embodiments, the cysteine residue is Cys 552.

One of ordinary skill in the art will recognize that a variety of warhead groups, as defined herein, are suitable for such covalent bonding. Such R¹ groups include, but are not limited to, those described herein and depicted above.

In certain embodiments, the present invention provides any compound depicted in any table above, or a pharmaceutically acceptable salt thereof.

As described herein, compounds of the present invention are irreversible inhibitors of FGFR4, or a mutant thereof.

In certain embodiments, the present invention provides a conjugate of the formula A:

$$\text{Cys552-modifier-inhibitor moiety} \qquad A$$

wherein:

the Cys552 is Cys552 of FGFR4;

the modifier is a bivalent group resulting from covalent bonding of a warhead group with the Cys552 of FGFR4 kinase;

the warhead group is a functional group capable of covalently binding to Cys552; and the inhibitor moiety is a moiety that binds in the binding site of the FGFR4 kinase.

In certain embodiments, the inhibitor moiety of conjugate A is of formula I-i:

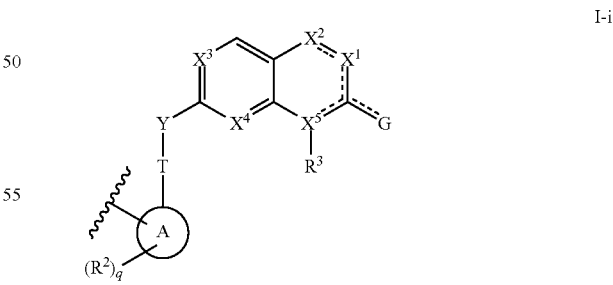

I-i wherein the wavy bond indicates the point of attachment to Cys552 of conjugate A via the modifier; and wherein each of Ring A, R², R³, X¹, X², X³, X⁴, X⁵, Y, G, T, and q, of formula I-i is as defined for formula I above and as defined and described in embodiments herein.

In certain embodiments, the inhibitor moiety of conjugate A is of formula I-a-i:

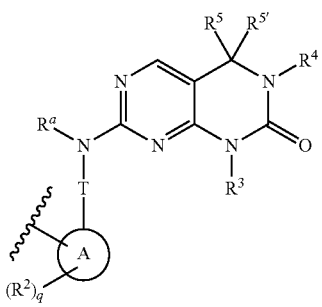

I-a-i wherein the wavy bond indicates the point of attachment to Cys552 of conjugate A via the modifier; and wherein each of Ring A, $R^2$, $R^3$, $R^4$, $R^5$, $R^{5'}$, $R^a$, T, and q, of formula I-a-i is as defined for formula I-a above and as defined and described in embodiments herein.

In certain embodiments, the inhibitor moiety of conjugate A is of formula I-b-i:

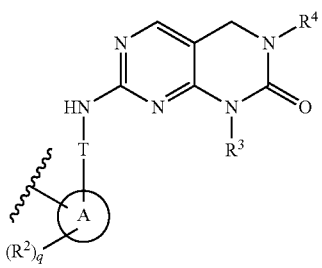

I-b-i wherein the wavy bond indicates the point of attachment to Cys552 of conjugate A via the modifier; and wherein each of Ring A, $R^2$, $R^3$, $R^4$, T, and q, of formula I-b-i is as defined for formula I-b above and as defined and described in embodiments herein.

In certain embodiments, the inhibitor moiety of conjugate A is of formula I-c-i:

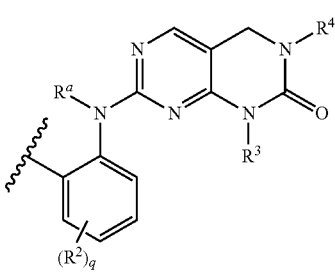

I-c-i wherein the wavy bond indicates the point of attachment to Cys552 of conjugate A via the modifier; and wherein each of $R^2$, $R^3$, $R^4$, $R^a$, and q, of formula I-c-i is as defined for formula I-c above and as defined and described in embodiments herein.

In certain embodiments, the inhibitor moiety of conjugate A is of formula I-d-i:

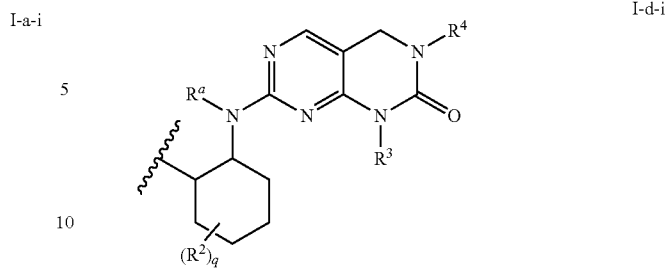

I-d-i wherein the wavy bond indicates the point of attachment to Cys552 of conjugate A via the modifier; and wherein each of $R^2$, $R^3$, $R^4$, $R^a$, and q, of formula I-d-i is as defined for formula I-d above and as defined and described in embodiments herein.

In certain embodiments, the inhibitor moiety of conjugate A is of formula I-e-i:

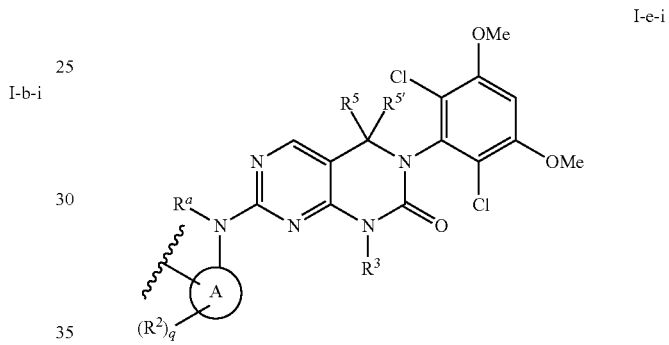

I-e-i wherein the wavy bond indicates the point of attachment to Cys552 of conjugate A via the modifier; and wherein each of Ring A, $R^2$, $R^3$, $R^5$, $R^{5'}$, $R^a$, and q, of formula I-e-i is as defined for formula I-e above and as defined and described in embodiments herein.

In certain embodiments, the inhibitor moiety of conjugate A is of formula I-f-i:

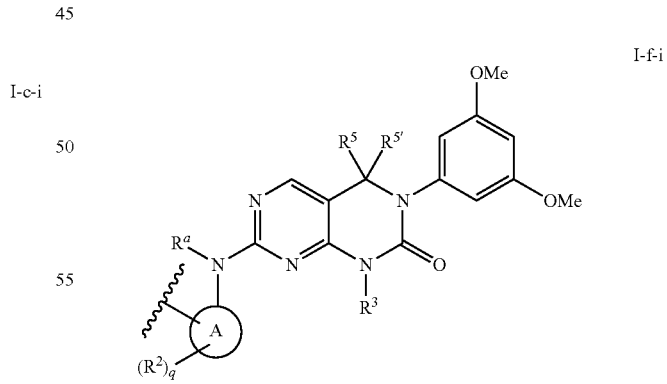

I-f-i wherein the wavy bond indicates the point of attachment to Cys552 of conjugate A via the modifier; and wherein each of Ring A, $R^2$, $R^3$, $R^5$, $R^{5'}$, $R^a$, and q, of formula I-f-i is as defined for formula I-f above and as defined and described in embodiments herein.

In certain embodiments, the inhibitor moiety of conjugate A is of formula I-g-i:

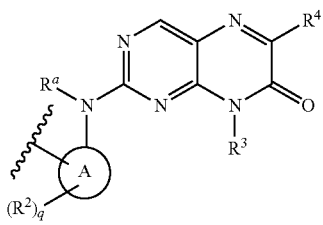

I-g-i wherein the wavy bond indicates the point of attachment to Cys552 of conjugate A via the modifier; and wherein each of Ring A, $R^2$, $R^3$, $R^4$, $R^a$, and q, of formula I-g-i is as defined for formula I-g above and as defined and described in embodiments herein.

In certain embodiments, the inhibitor moiety of conjugate A is of formula I-h-i:

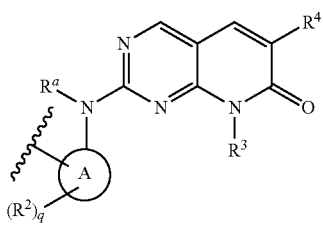

I-h-i wherein the wavy bond indicates the point of attachment to Cys552 of conjugate A via the modifier; and wherein each of Ring A, $R^2$, $R^3$, $R^4$, $R^a$, and q, of formula I-h-i is as defined for formula I-h above and as defined and described in embodiments herein.

In certain embodiments, the inhibitor moiety of conjugate A is of formula I-j-i:

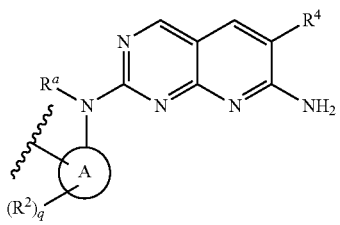

I-j-i wherein the wavy bond indicates the point of attachment to Cys552 of conjugate A via the modifier; and wherein each of Ring A, $R^2$, $R^4$, $R^a$, and q, of formula I-j-i is as defined for formula I-j above and as defined and described in embodiments herein.

In certain embodiments, the inhibitor moiety of conjugate A is of formula I-k-i:

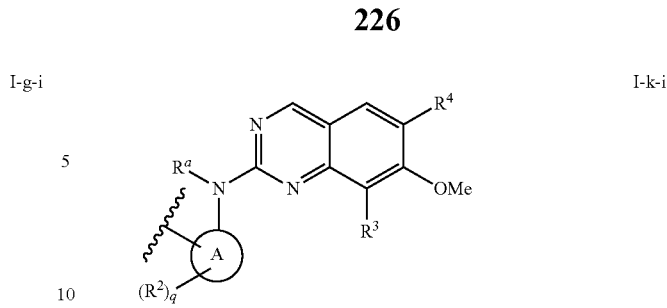

I-k-i wherein the wavy bond indicates the point of attachment to Cys552 of conjugate A via the modifier; and wherein each of Ring A, $R^2$, $R^3$, $R^4$, $R^a$, and q, of formula I-k-i is as defined for formula I-k above and as defined and described in embodiments herein.

In certain embodiments, the inhibitor moiety of conjugate A is of formula I-n-i:

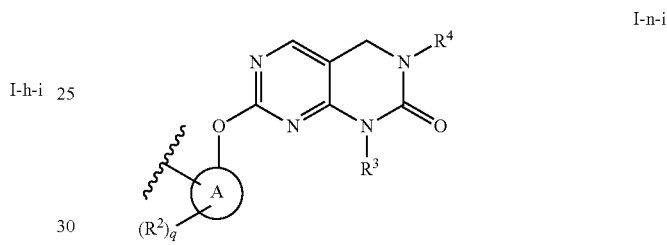

I-n-i wherein the wavy bond indicates the point of attachment to Cys552 of conjugate A via the modifier; and wherein each of Ring A, $R^2$, $R^3$, $R^4$, and q, of formula I-n-i is as defined for formula I-n above and as defined and described in embodiments herein.

In certain embodiments, the inhibitor moiety of conjugate A is of formula I-q-i:

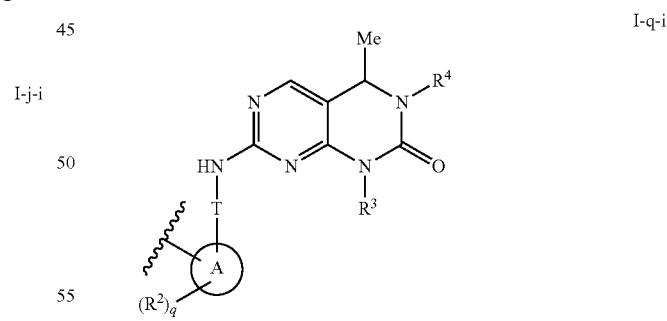

I-q-i wherein the wavy bond indicates the point of attachment to Cys552 of conjugate A via the modifier; and wherein each of Ring A, $R^2$, $R^3$, $R^4$, $R^a$, T, and q, of formula I-q-i is as defined for formula I-q above and as defined and described in embodiments herein.

In certain embodiments, the present invention provides a conjugate of any of the formulae below:

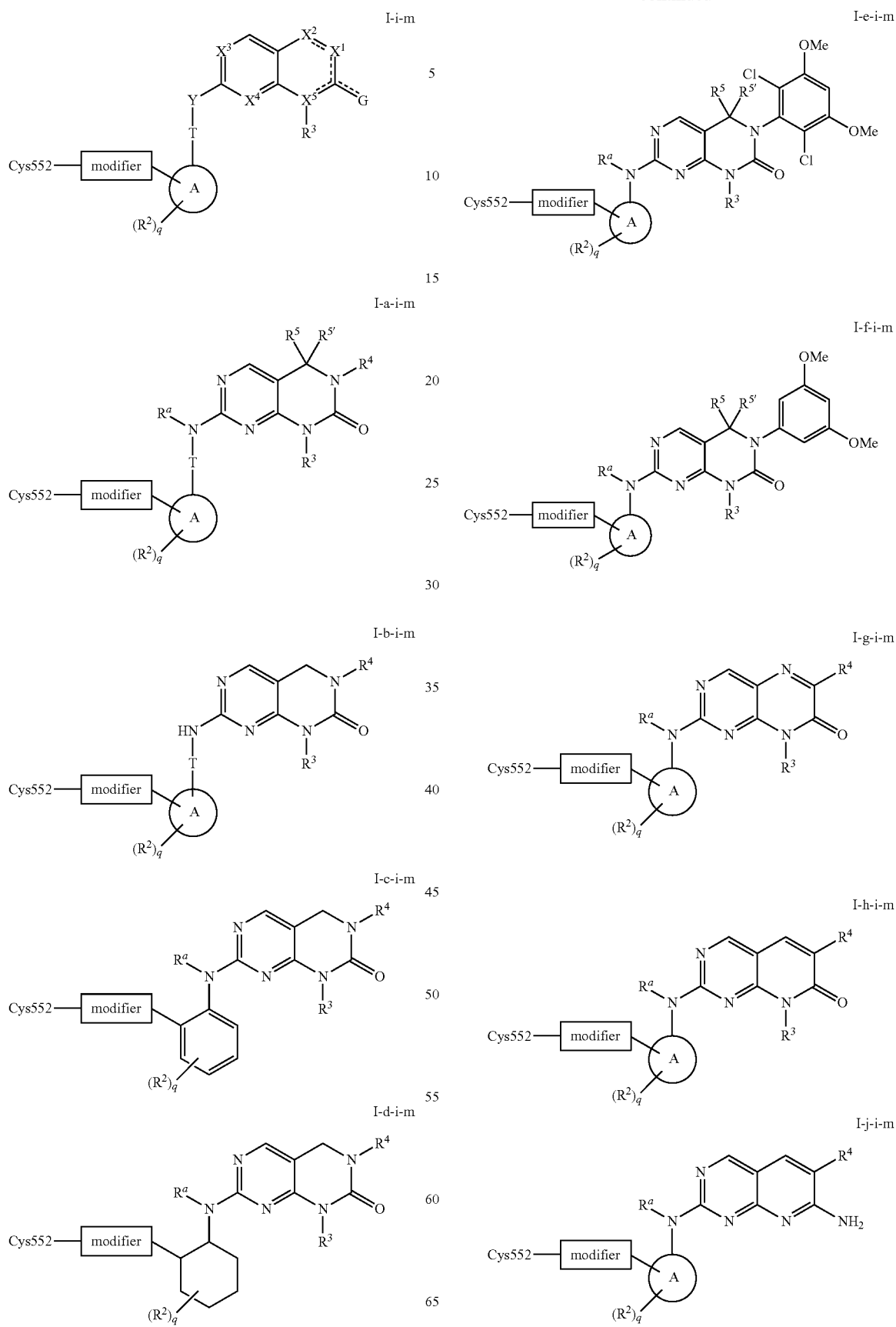

-continued

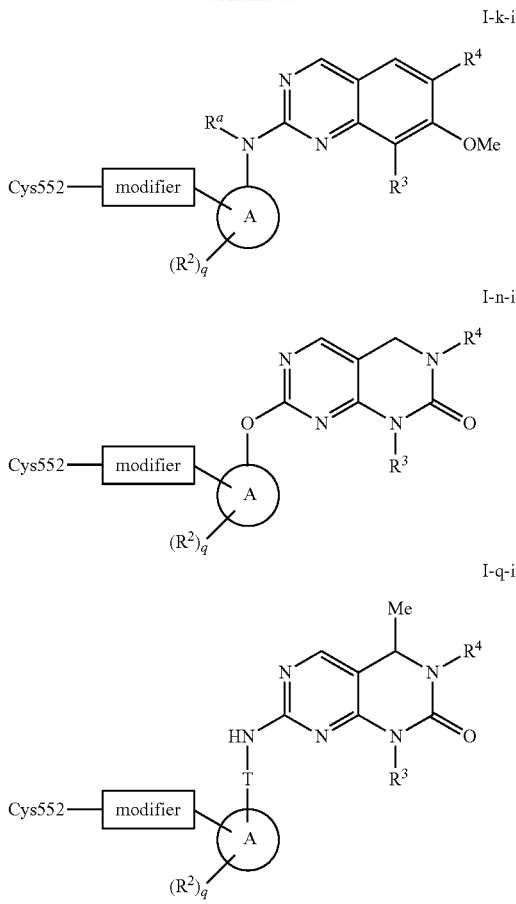

wherein each of Cys552, Modifier, Ring A, $R^2$, $R^3$, $R^4$, $R^5$, $R^{5'}$, $R^a$, $X^1$, $X^2$, $X^3$, $X^4$, $X^5$, T, Y, G and q, with respect to the above formulae is as defined and described in embodiments herein for formulae I, I-a, I-b, I-c, I-d, I-e, I-f, I-g, I-h, I-j, I-k, I-n, and I-q.

In other embodiments, the modifier moiety of any of conjugate described above is selected from those set forth in Table 6, below. Exemplary modifiers further include any bivalent group resulting from covalent bonding of a warhead moiety found in Table 1, Table 2, Table 3, Table 5, Table 7, or Table 8 with cysteine 552 of FGFR4. It will be understood that the exemplary modifiers below are shown as conjugated to the sulfhydryl of Cys552.

TABLE 6

Exemplary Modifiers Conjugated to Cys552:

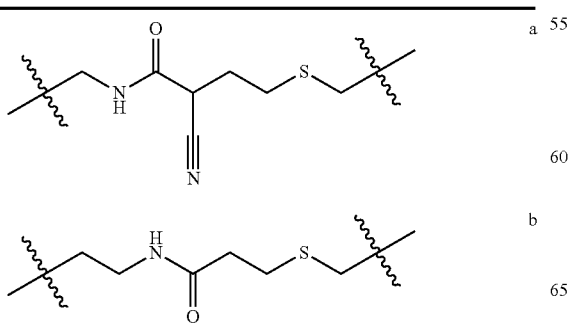

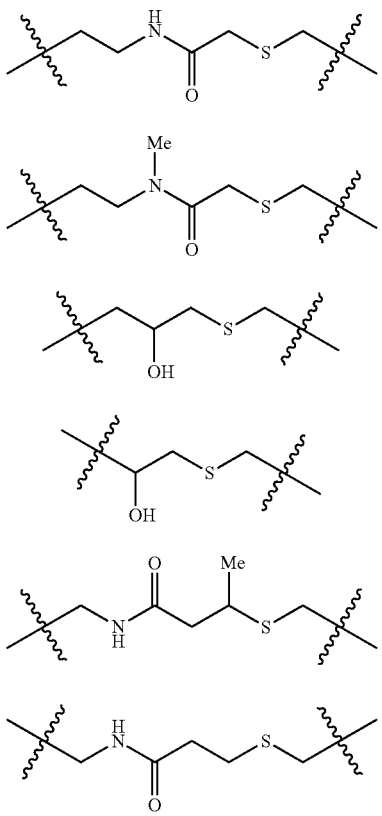

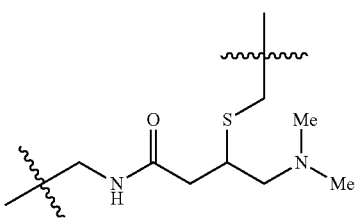

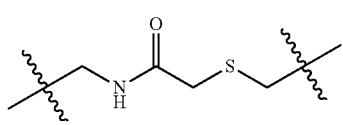 [SMILES: *CNC(=O)CSC*]

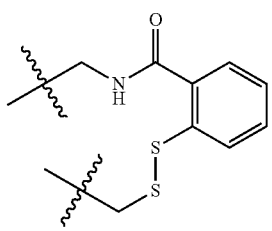 [SMILES: *CNC(=O)c1ccccc1SSC*]

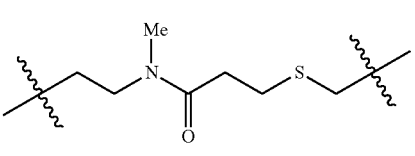 [SMILES: *CCN(C)C(=O)CCSC*]

TABLE 6-continued
Exemplary Modifiers Conjugated to Cys552:
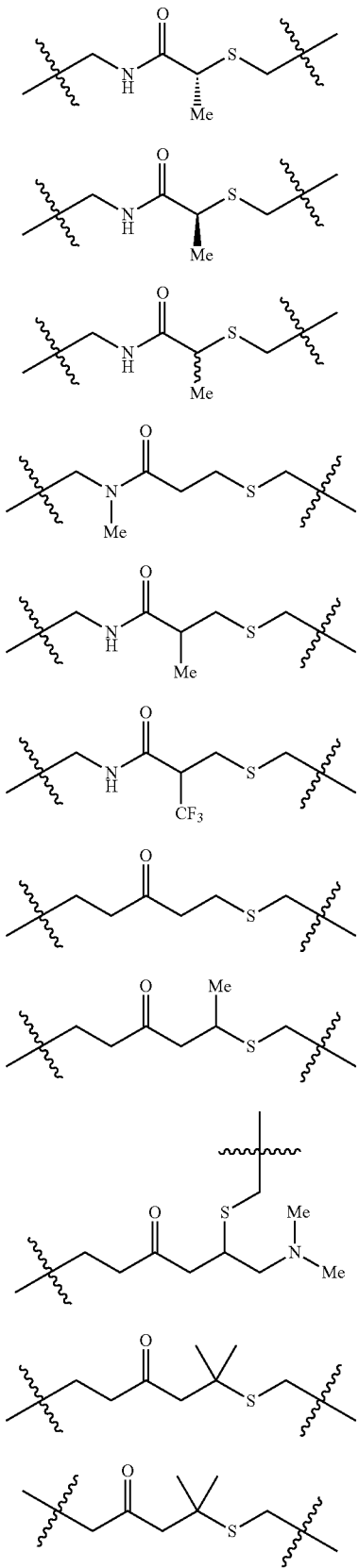
m
n
o
p
q
r
s
t
u
v
w
TABLE 6-continued
Exemplary Modifiers Conjugated to Cys552:
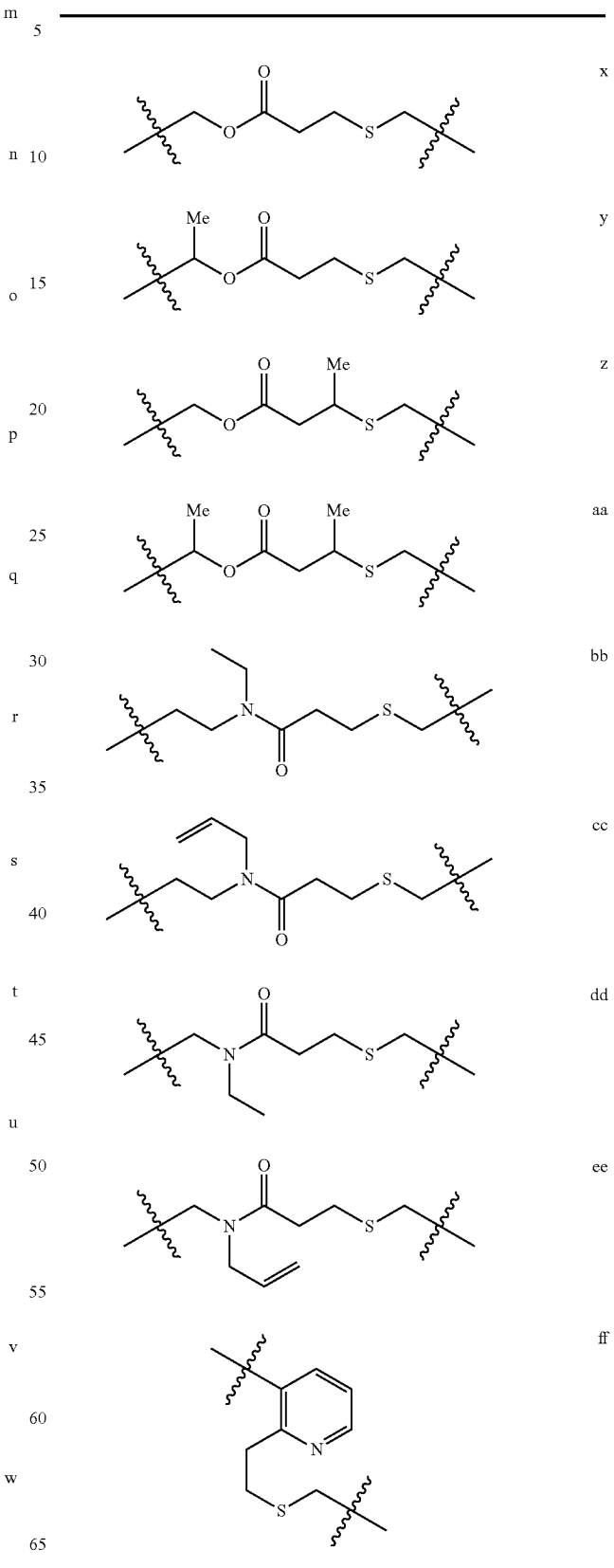
x
y
z
aa
bb
cc
dd
ee
ff TABLE 6-continued
Exemplary Modifiers Conjugated to Cys552:
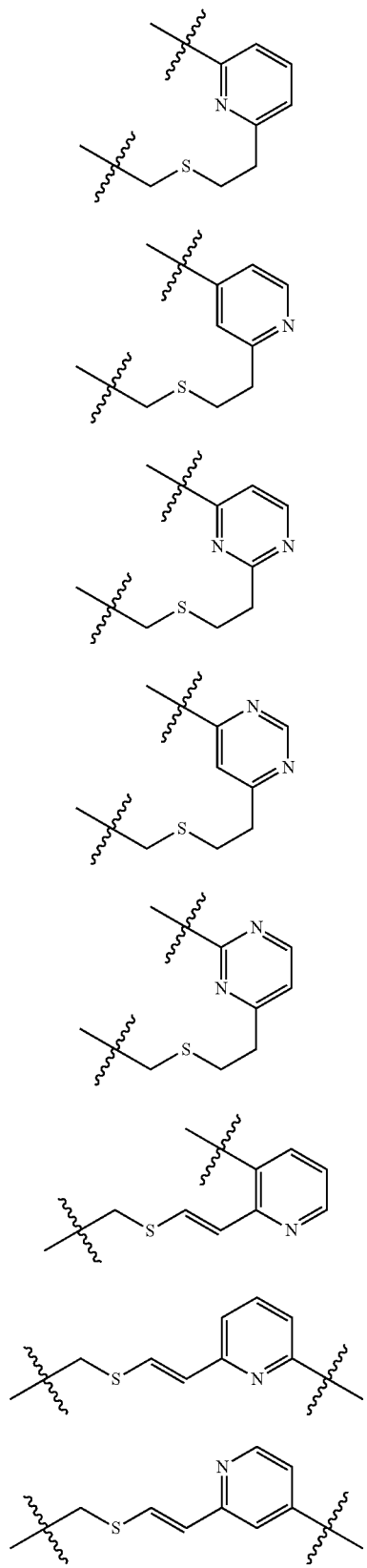
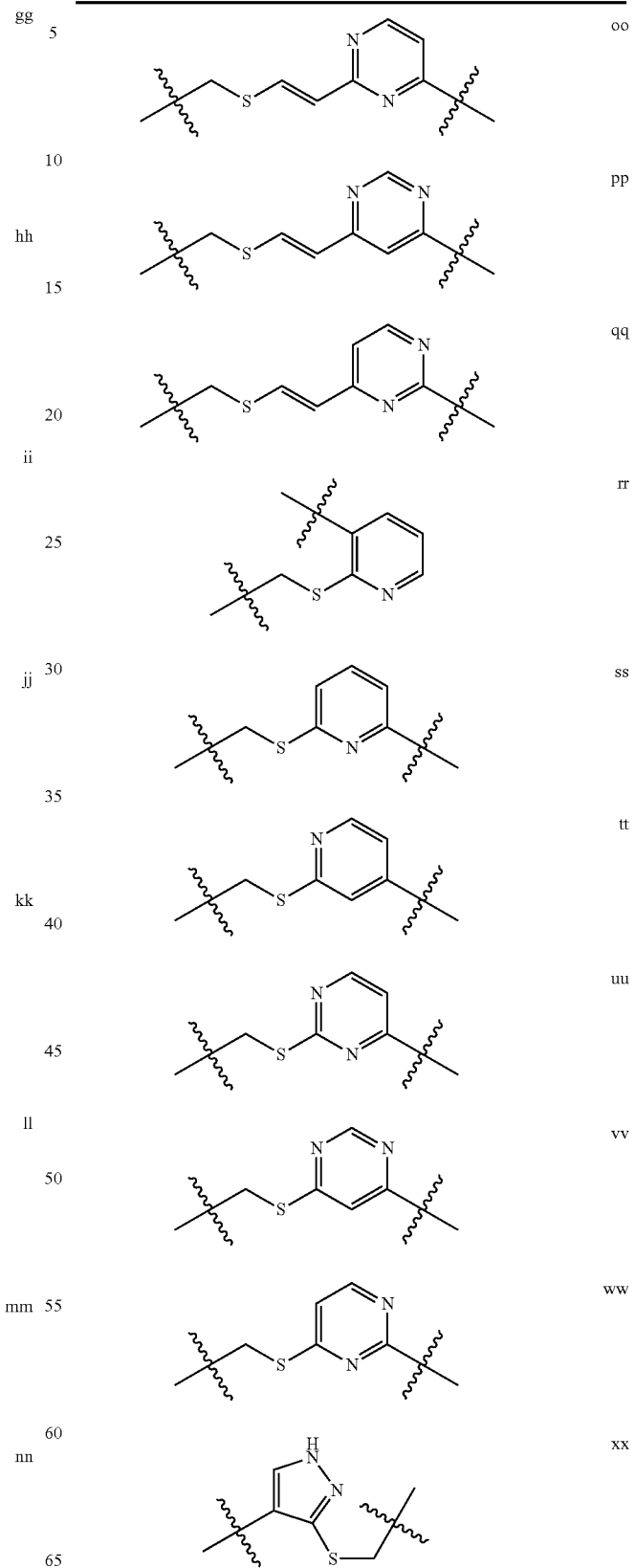

TABLE 6-continued
Exemplary Modifiers Conjugated to Cys552:
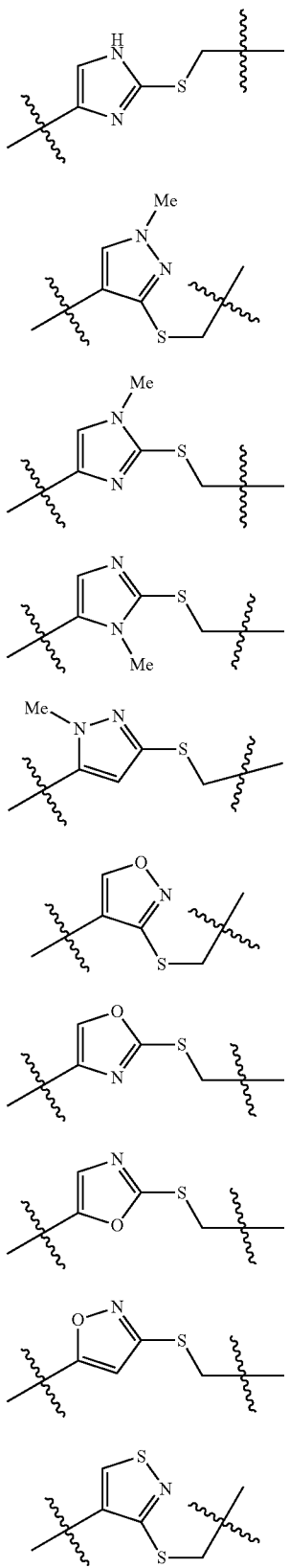
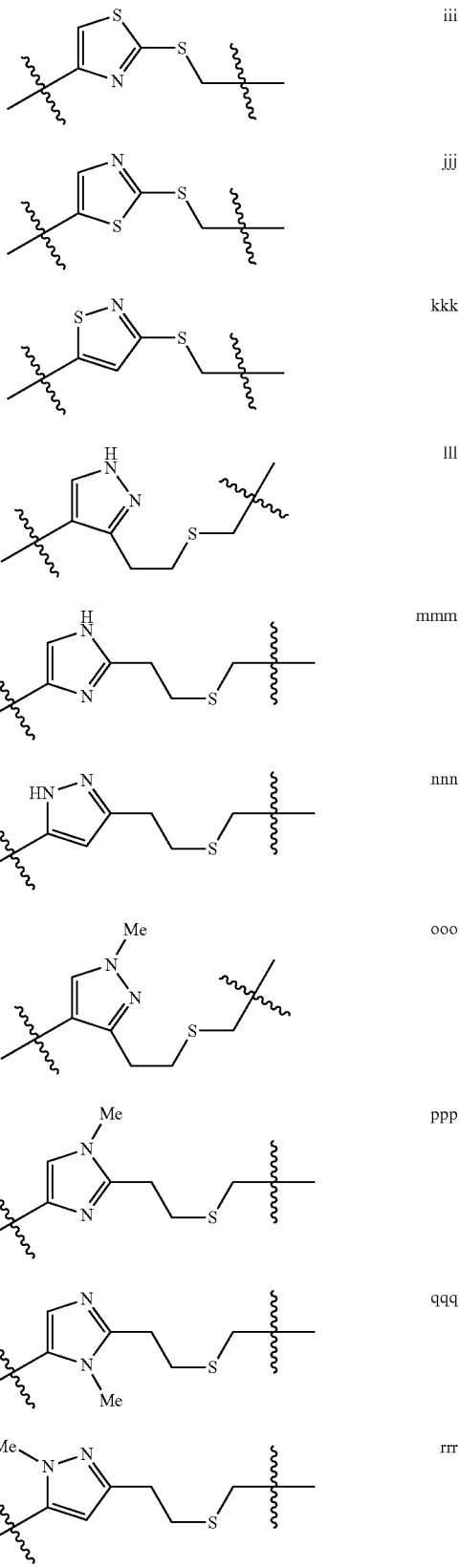

TABLE 6-continued
Exemplary Modifiers Conjugated to Cys552:
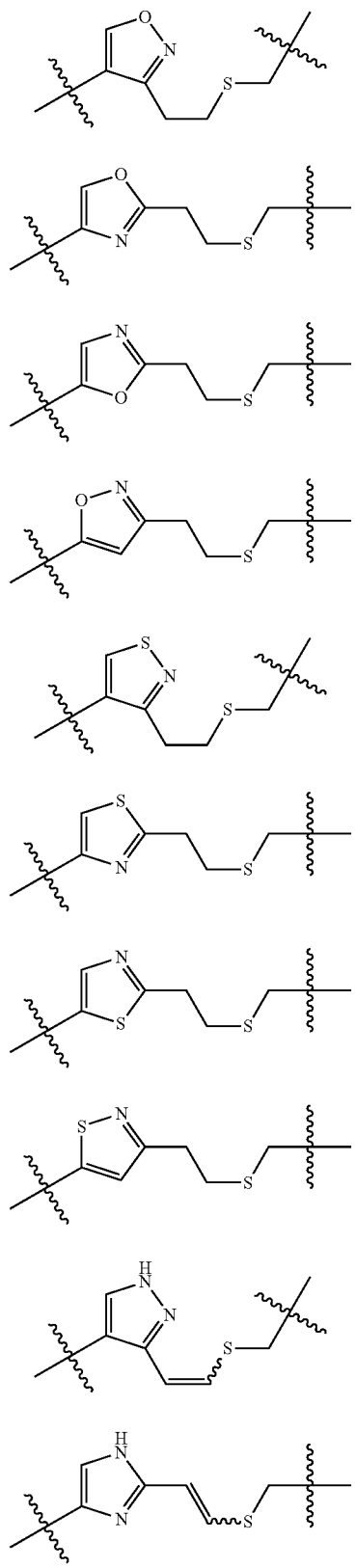
sss
ttt
uuu
vvv
www
xxx
yyy
zzz
aaaa
bbbb
TABLE 6-continued
Exemplary Modifiers Conjugated to Cys552:
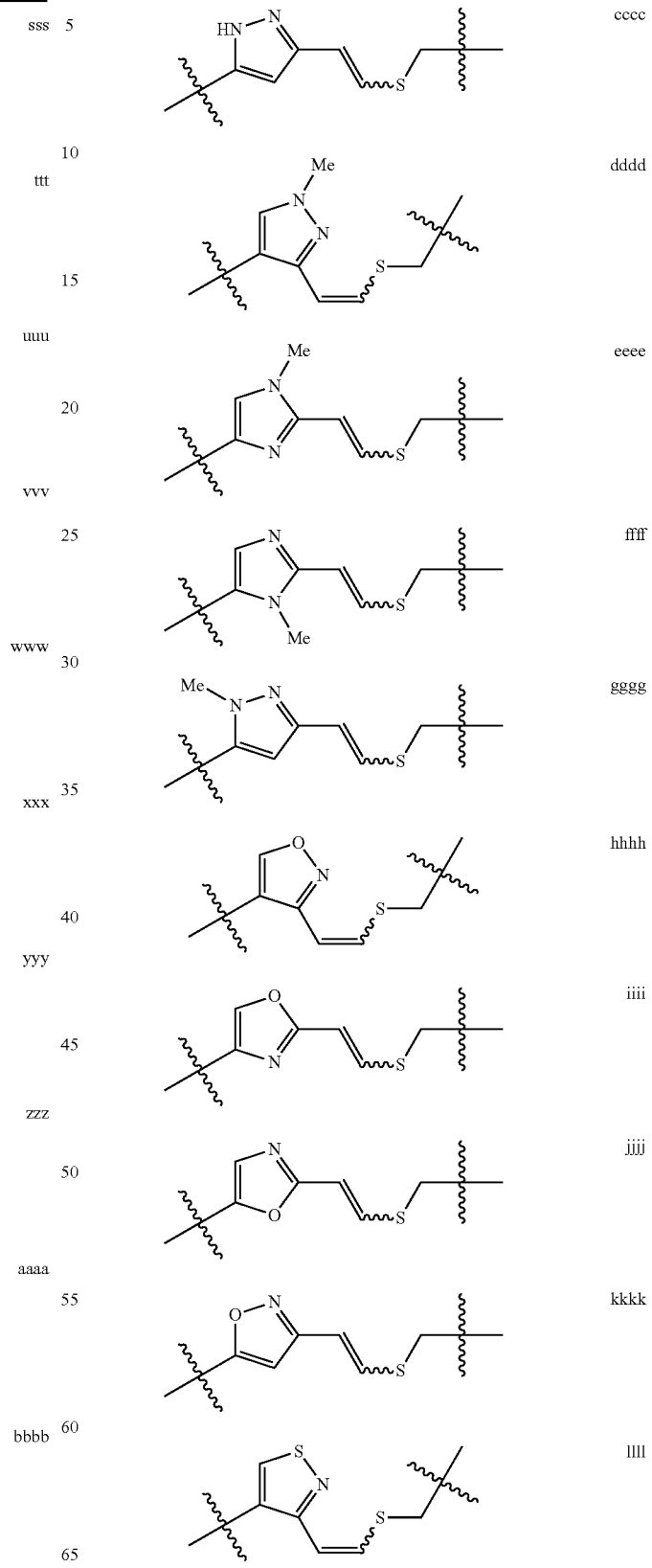
cccc
dddd
eeee
ffff
gggg
hhhh
iiii
jjjj
kkkk
llll TABLE 6-continued
Exemplary Modifiers Conjugated to Cys552:
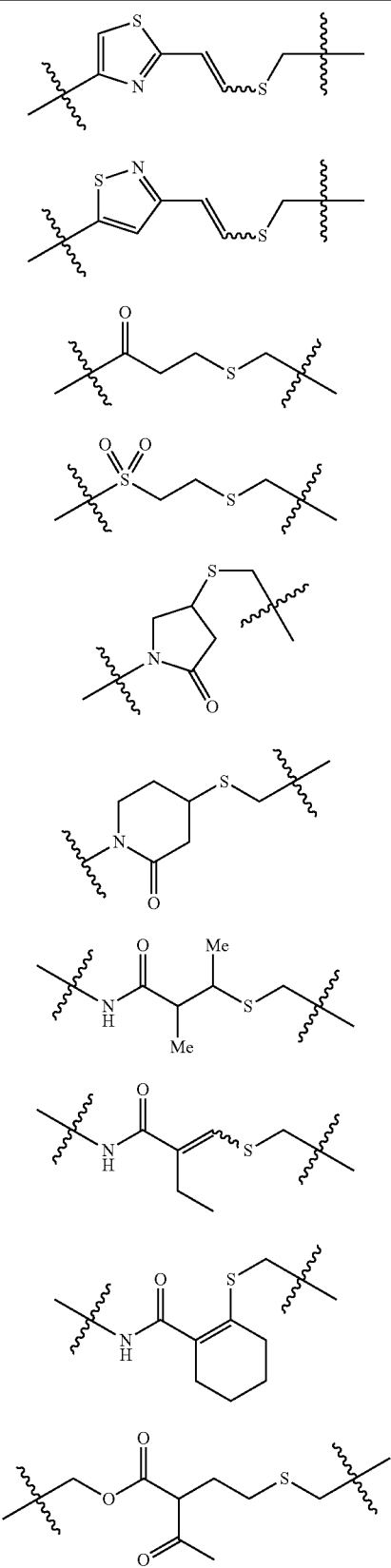
mmmm
nnnn
oooo
pppp
qqqq
rrrr
ssss
tttt
uuuu
vvvv
TABLE 6-continued
Exemplary Modifiers Conjugated to Cys552:
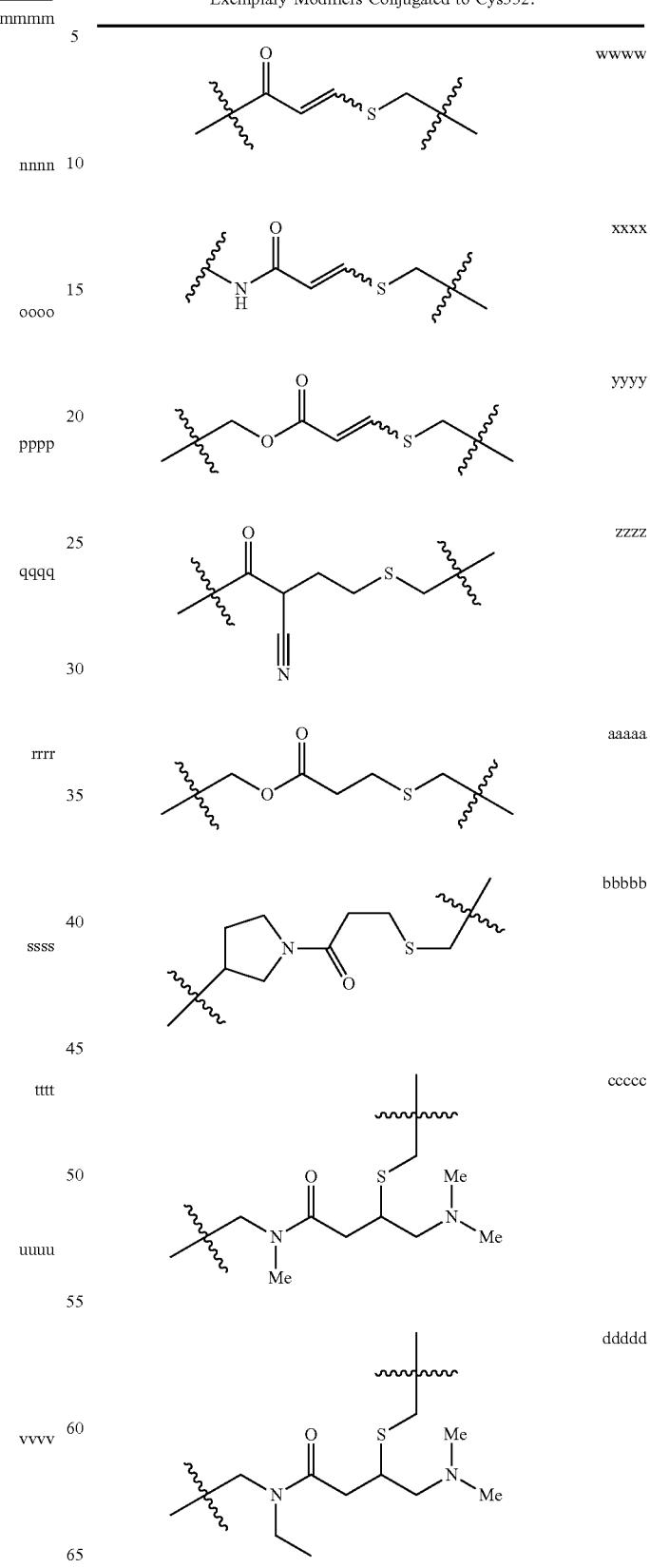
wwww
xxxx
yyyy
zzzz
aaaaa
bbbbb
ccccc
ddddd

TABLE 6-continued

Exemplary Modifiers Conjugated to Cys552:

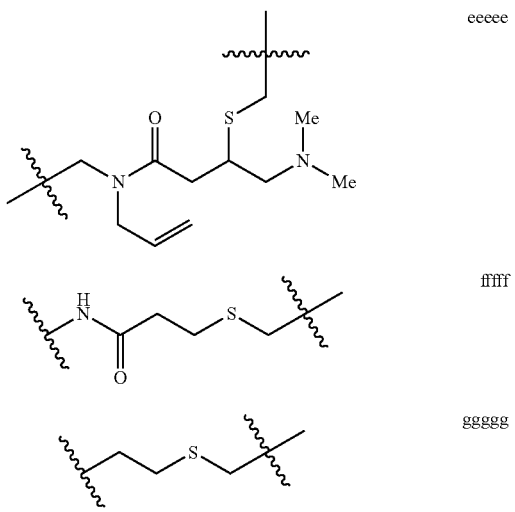

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit a protein kinase, particularly FGFR4, or a mutant thereof, in a biological sample or in a patient. In certain embodiments, the amount of compound in compositions of this invention is such that is effective to measurably inhibit FGFR4, or a mutant thereof, in a biological sample or in a patient. In certain embodiments, a composition of this invention is formulated for administration to a patient in need of such composition. In some embodiments, a composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of FGFR4, or a mutant thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation is also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions are optionally formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions are formulated in an ointment such as petrolatum.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of protein kinase activity of one or more enzymes.

Drug resistance is emerging as a significant challenge to targeted therapies. For example, drug resistance has been reported for Gleevec® and Iressa®, as well as several other kinase inhibitors in development. In addition, drug resistance has been reported for the cKit and PDGFR receptors. It has been reported that irreversible inhibitors may be effective against drug resistant forms of protein kinases (Kwak, E. L., R. Sordella, et al. (2005). "Irreversible inhibitors of the EGF receptor may circumvent acquired resistance to gefitinib." PNAS 102(21): 7665-7670.) Without wishing to be bound by any particular theory, the compounds of the present invention are effective inhibitors of drug resistant forms of protein kinases.

Examples of kinases that are inhibited by the compounds and compositions described herein and against which the methods described herein are useful include FGFR4, or a mutant thereof. In some embodiments, a provided compound inhibits FGFR4 selectively as compared to other FGFR kinases.

The activity of a compound utilized in this invention as a test compound of FGFR4, or a mutant thereof, may be assayed in vitro, in vivo or in a cell line. In vitro assays include assays that determine inhibition of either the phosphorylation activity and/or the subsequent functional consequences, or ATPase activity of activated FGFR4, or a mutant thereof. Alternate in vitro assays quantitate the ability of the test compound to bind to FGFR4. Inhibitor binding may be measured by radiolabeling the inhibitor prior to binding, isolating the test compound/FGFR4 complex and determining the amount of radiolabel bound. Alternatively, test compound binding may be determined by running a competition experiment where new test compounds are incubated with FGFR4 bound to known radioligands. Detailed conditions for assaying a compound utilized in this invention as a test compound of FGFR4, or a mutant thereof, are set forth in the Examples below.

Protein tyrosine kinases are a class of enzymes that catalyze the transfer of a phosphate group from ATP or GTP to a tyrosine residue located on a protein substrate. Receptor tyrosine kinases act to transmit signals from the outside of a cell to the inside by activating secondary messaging effectors via a phosphorylation event. A variety of cellular processes are promoted by these signals, including proliferation, carbohydrate utilization, protein synthesis, angiogenesis, cell growth, and cell survival.

(a) FGFR Family

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signalling molecules which act as autocrine as well as paracrine factors. Autocrine FGF signalling may be particularly important in the progression of steroid hormone-dependent cancers to a hormone independent state (Powers, et al. (2000) Endocr. Relat. Cancer, 7, 165-197).

FGFs and their receptors are expressed at increased levels in several tissues and cell lines and overexpression is believed to contribute to the malignant phenotype.

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4). Upon ligand binding, the receptors dimerize and auto- or trans-phosphorylate specific cytoplasmic tyrosine residues to transmit an intracellular signal that ultimately regulates nuclear transcription factor effectors.

Compounds which inhibit FGFR will be useful in providing a means of preventing the growth or inducing apoptosis in tumors, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors.

Various studies described targeting of either FGFR4 kinase activity or its ligand FGF 19 with an antibody antagonist inhibited proliferation and induced apoptosis in cell line models. Ho et al (2009) Journal of Hepatology, 50 showed that one third of patients with a common polymorphism in the FGFR4 gene expressed high levels of mRNA and these tumours were associated with high secreted levels of the hepatocellular carcinoma marker alpha-fetoprotein.

In certain embodiments, the invention provides a method for inhibiting FGFR4, or a mutant thereof, activity in a patient or in a biological sample comprising the step of administering to said patient or contacting said biological sample with a compound according to the invention.

In certain embodiments, the FGFR4, or a mutant thereof, activity is inhibited irreversibly. In certain embodiments, FGFR4, or a mutant thereof, activity is inhibited irreversibly by covalently modifying Cys 552 of FGFR4.

In certain embodiments, the invention provides a method for treating a FGFR4-mediated disorder in a patient in need thereof, comprising the step of administering to said patient a compound according to the invention, or a pharmaceutically acceptable composition thereof.

In some embodiments, the present invention provides a method for treating hepatocellular carcinoma in a patient in need thereof, comprising the step of administering to said patient a compound according to the invention, or a pharmaceutically acceptable composition thereof.

In some embodiments, the present invention provides a method for treating Rhabdomyosarcoma, esophageal cancer, breast cancer, or cancer of a head or neck, in a patient in need thereof, comprising the step of administering to said patient a compound according to the invention, or a pharmaceutically acceptable composition thereof.

As used herein, the term "clinical drug resistance" refers to the loss of susceptibility of a drug target to drug treatment as a consequence of mutations in the drug target.

As used herein, the term "resistance" refers to changes in the wild-type nucleic acid sequence coding a target protein, and/or the protein sequence of the target, which changes decrease or abolish the inhibitory effect of the inhibitor on the target protein.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprise buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting FGFR4, or a mutant thereof, activity in a biological sample comprising the step of contacting said biological sample with a compound of this invention, or a composition comprising said compound. In certain embodiments, the invention relates to a method of irreversibly inhibiting FGFR4, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of FGFR4, or a mutant thereof, activity in a biological sample is useful for a variety of purposes that are known to one of skill in the art. Examples of such purposes include, but are not limited to, blood transfusion, organ transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting FGFR4, or a mutant thereof, activity in a patient comprising the step of administering to said patient a compound of the present invention, or a composition comprising said compound. According to certain embodiments, the invention relates to a method of irreversibly inhibiting FGFR4, or a mutant thereof, activity in a patient comprising the step of administering to said patient a compound of the present invention, or a composition comprising said compound. In other embodiments, the present invention provides a method for treating a disorder mediated by FGFR4, or a mutant thereof, in a patient in need thereof, comprising the step of administering to said patient a compound according to the present invention or pharmaceutically acceptable composition thereof. Such disorders are described in detail herein.

The compounds of this invention, or pharmaceutical compositions thereof, are optionally incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects are prevented or mitigated by pre-coating the device with a pharmaceutically acceptable composition comprising a kinase inhibitor. Implantable devices coated with a compound of this invention are another embodiment of the present invention.

5. Probe Compounds

In certain aspects, a compound of the present invention is tethered to a detectable moiety to form a probe compound. In one aspect, a probe compound of the invention comprises an irreversible protein kinase inhibitor of any formulae as described herein, a detectable moiety, and a tethering moiety that attaches the inhibitor to the detectable moiety.

In some embodiments, such probe compounds of the present invention comprise a provided compound of any formulae as described herein, tethered to a detectable moiety, $R^t$, by a bivalent tethering moiety, -$T^1$-. The tethering moiety is attached to a compound of the invention via Ring A, Ring B, or $R^1$. One of ordinary skill in the art will appreciate that when a tethering moiety is attached to $R^1$, $R^1$ is a bivalent warhead group denoted as $R^{1'}$. In certain embodiments, a provided probe compound is selected from any of formula I-t:

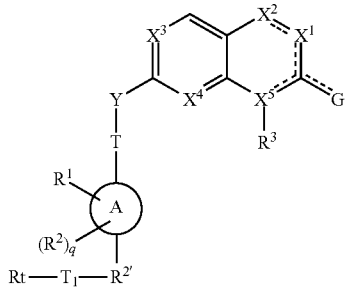

I-t wherein each of Ring A, $R^1$, $R^2$, $R^3$, $X^1$, $X^2$, $X^3$, $X^4$, $X^5$, G, Y, T, and q, is as defined above, and described in classes and subclasses herein, $R^{2'}$ is a bivalent $R^2$; $T^1$ is a bivalent tethering moiety; and $R^t$ is a detectable moiety.

In some embodiments, $R^t$ is a detectable moiety selected from a primary label or a secondary label. In certain embodiments, $R^t$ is a detectable moiety selected from a fluorescent label (e.g., a fluorescent dye or a fluorophore), a mass-tag, a chemiluminescent group, a chromophore, an electron dense group, or an energy transfer agent. In some embodiments, $R^t$ is biotin, biotin sulfoxide, a radioisotope, or a fluorescent label.

As used herein, the term "detectable moiety" is used interchangeably with the term "label" and "reporter" and relates to any moiety capable of being detected, e.g., primary labels and secondary labels. A presence of a detectable moiety can be measured using methods for quantifying (in absolute, approximate or relative terms) the detectable moiety in a system under study. In some embodiments, such methods are well known to one of ordinary skill in the art and include any methods that quantify a reporter moiety (e.g., a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, quantum dot(s), a novel functional group, a group that covalently or noncovalently interacts with other molecules, a photocaged moiety, an actinic radiation excitable moiety, a ligand, a photoisomerizable moiety, biotin, a biotin analog (e.g., biotin sulfoxide), a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, and any combination of the above).

Primary labels, such as radioisotopes (e.g., tritium, $^{32}P$, $^{33}P$, $^{35}S$, $^{14}C$, $^{123}I$, $^{124}I$, $^{125}I$, or $^{131}I$), mass-tags are stable isotopes (e.g., $^{13}C$, $^{2}H$, $^{17}O$, $^{18}O$, $^{15}N$, $^{19}F$, and $^{127}I$), positron emitting isotopes (e.g., $^{11}C$, $^{18}F$, $^{13}N$, $^{124}I$, and $^{15}O$), and fluorescent labels, which are signal generating reporter groups which can be detected without further modifications. Detectable moities are analyzed by methods. Exemplary methods are fluorescence, positron emission tomography, SPECT medical imaging, chemiluminescence, electron-spin resonance, ultraviolet/visible absorbance spectroscopy, mass spectrometry, nuclear magnetic resonance, magnetic resonance, flow cytometry, autoradiography, scintillation counting, phosphoimaging, and electrochemical methods.

The term "secondary label" as used herein refers to moieties such as biotin and various protein antigens that require the presence of a second intermediate for production of a detectable signal. For biotin, the secondary intermediate includes streptavidin-enzyme conjugates. For antigen labels, secondary intermediates include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxyfluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis(2,4,6-trimethylphenyl)-3,4:9,10-perylenebis(dicarboximide, HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), FlASH-CCXXCC, Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, and SuperGlo GFP.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) are also used as mass-tags. Stable isotopes (e.g., $^{13}C$, $^{2}H$, $^{17}O$, $^{18}O$, and $^{15}N$) are also used as mass-tags.

The term "chemiluminescent group," as used herein, refers to a group which emits light as a result of a chemical reaction without the addition of heat. By way of example, luminol (5-amino-2,3-dihydro-1,4-phthalazinedione) reacts with oxidants like hydrogen peroxide ($H_2O_2$) in the presence of a base and a metal catalyst to produce an excited state product (3-aminophthalate, 3-APA).

The term "chromophore," as used herein, refers to a molecule which absorbs light of visible wavelengths, UV wavelengths or IR wavelengths.

The term "dye," as used herein, refers to a soluble, coloring substance which contains a chromophore.

The term "electron dense group," as used herein, refers to a group which scatters electrons when irradiated with an electron beam. Such groups include, but are not limited to, ammonium molybdate, bismuth subnitrate, cadmium iodide, carbohydrazide, ferric chloride hexahydrate, hexamethylene tetramine, indium trichloride anhydrous, lanthanum nitrate, lead acetate trihydrate, lead citrate trihydrate, lead nitrate, periodic acid, phosphomolybdic acid, phosphotungstic acid, potassium ferricyanide, potassium ferrocyanide, ruthenium red, silver nitrate, silver proteinate (Ag Assay: 8.0-8.5%) "Strong", silver tetraphenylporphin (S-TPPS), sodium chloroaurate, sodium tungstate, thallium nitrate, thiosemicarbazide (TSC), uranyl acetate, uranyl nitrate, and vanadyl sulfate.

The term "energy transfer agent," as used herein, refers to a molecule which either donates or accepts energy from another molecule. By way of example only, fluorescence resonance energy transfer (FRET) is a dipole-dipole coupling process by which the excited-state energy of a fluorescence donor molecule is non-radiatively transferred to an unexcited acceptor molecule which then fluorescently emits the donated energy at a longer wavelength.

The term "moiety incorporating a heavy atom," as used herein, refers to a group which incorporates an ion of atom which is usually heavier than carbon. In some embodiments, such ions or atoms include, but are not limited to, silicon, tungsten, gold, lead, and uranium.

The term "photoaffinity label," as used herein, refers to a label with a group, which, upon exposure to light, forms a linkage with a molecule for which the label has an affinity.

The term "photocaged moiety," as used herein, refers to a group which, upon illumination at certain wavelengths, covalently or non-covalently binds other ions or molecules.

The term "photoisomerizable moiety," as used herein, refers to a group wherein upon illumination with light changes from one isomeric form to another.

The term "radioactive moiety," as used herein, refers to a group whose nuclei spontaneously give off nuclear radiation, such as alpha, beta, or gamma particles; wherein, alpha particles are helium nuclei, beta particles are electrons, and gamma particles are high energy photons.

The term "spin label," as used herein, refers to molecules which contain an atom or a group of atoms exhibiting an unpaired electron spin (i.e. a stable paramagnetic group) that in some embodiments are detected by electron spin resonance spectroscopy and in other embodiments are attached to another molecule. Such spin-label molecules include, but are not limited to, nitryl radicals and nitroxides, and in some embodiments are single spin-labels or double spin-labels.

The term "quantum dots," as used herein, refers to colloidal semiconductor nanocrystals that in some embodiments are detected in the near-infrared and have extremely high quantum yields (i.e., very bright upon modest illumination).

One of ordinary skill in the art will recognize that a detectable moiety is attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties are directly attached to a provided compound or via a tethering moiety, such as a bivalent saturated or unsaturated hydrocarbon chain.

In some embodiments, detectable moieties are attached to a provided compound via click chemistry. In some embodiments, such moieties are attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57. In some embodiments, a click ready inhibitor moiety is provided and reacted with a click ready -T-$R^t$ moiety. As used herein, "click ready" refers to a moiety containing an azide or alkyne for use in a click chemistry reaction. In some embodiments, the click ready inhibitor moiety comprises an azide. In certain embodiments, the click ready -T-$R^t$ moiety comprises a strained cyclooctyne for use in a copper-free click chemistry reaction (for example, using methods described in Baskin et al., Proc. Natl. Acad. Sci. USA 2007, 104, 16793-16797).

In some embodiments, the detectable moiety, $R^t$, is selected from a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, quantum dot(s), a novel functional group, a group that covalently or noncovalently interacts with other molecules, a photocaged moiety, an actinic radiation excitable moiety, a ligand, a photoisomerizable moiety, biotin, a biotin analog (e.g., biotin sulfoxide), a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, or a combination thereof.

In some embodiments, $R^t$ is biotin or an analog thereof. In certain embodiments, $R^t$ is biotin. In certain other embodiments, $R^t$ is biotin sulfoxide.

In another embodiment, $R^t$ is a fluorophore. In a further embodiment, the fluorophore is selected from Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis(2,4,6-trimethylphenyl)-3,4:9,10-perylenebis(dicarboximide, HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), FlASH-CCXXCC, Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, or SuperGlo GFP.

As described generally above, a provided probe compound comprises a tethering moiety, -T-, that attaches the irreversible inhibitor to the detectable moiety. As used herein, the term "tether" or "tethering moiety" refers to any bivalent chemical spacer. Exemplary tethers are a covalent bond, a polymer, a water soluble polymer, optionally substituted alkyl, optionally substituted heteroalkyl, optionally substituted heterocycloalkyl, optionally substituted cycloalkyl, optionally substituted heterocyclyl, optionally substituted heterocycloalkylalkyl, optionally substituted heterocycloalkylalkenyl, optionally substituted aryl, optionally substituted heteroaryl, optionally substituted heterocycloalkylalkenylalkyl, an optionally substituted amide moiety, an ether moiety, an ketone moiety, an ester moiety, an optionally substituted carbamate moiety, an optionally substituted hydrazone moiety, an optionally substituted hydrazine moiety, an optionally substituted oxime moiety, a disulfide moiety, an optionally substituted imine moiety, an optionally substituted sulfonamide moiety, a sulfone moiety, a sulfoxide moiety, a thioether moiety, or any combination thereof.

In some embodiments, the tethering moiety, -$T^1$-, is selected from a covalent bond, a polymer, a water soluble polymer, optionally substituted alkyl, optionally substituted heteroalkyl, optionally substituted heterocycloalkyl, optionally substituted cycloalkyl, optionally substituted heterocycloalkylalkyl, optionally substituted heterocycloalkylalkenyl, optionally substituted aryl, optionally substituted heteroaryl, and optionally substituted heterocycloalkylalkenylalkyl. In some embodiments, the tethering moiety is an optionally substituted heterocycle. In other embodiments, the heterocycle is selected from aziridine, oxirane, episulfide, azetidine, oxetane, pyrroline, tetrahydrofuran, tetrahydrothiophene, pyrrolidine, pyrazole, pyrrole, imidazole, triazole, tetrazole, oxazole, isoxazole, oxirene, thiazole, isothiazole, dithiolane, furan, thiophene, piperidine, tetrahydropyran, thiane, pyridine, pyran, thiapyrane, pyridazine, pyrimidine, pyrazine, piperazine, oxazine, thiazine, dithiane, and dioxane. In some embodiments, the heterocycle is piperazine. In further embodiments, the tethering moiety is optionally substituted with halogen, —CN, —OH, —$NO_2$, alkyl, S(O), and S(O)$_2$. In other embodiments, the water soluble polymer is a PEG group.

In other embodiments, the tethering moiety provides sufficient spatial separation between the detectable moiety and the protein kinase inhibitor moiety. In further embodiments, the tethering moiety is stable. In yet a further embodiment, the tethering moiety does not substantially affect the response of the detectable moiety. In other embodiments, the tethering moiety provides chemical stability to the probe compound. In further embodiments, the tethering moiety provides sufficient solubility to the probe compound.

In some embodiments, a tethering moiety, -$T^1$-, such as a water soluble polymer is coupled at one end to a provided irreversible inhibitor and to a detectable moiety, $R^t$, at the other end. In other embodiments, a water soluble polymer is coupled via a functional group or substituent of the provided irreversible inhibitor. In further embodiments, a water soluble polymer is coupled via a functional group or substituent of the reporter moiety.

In some embodiments, examples of hydrophilic polymers, for use in tethering moiety -$T^1$-, include, but are not limited to: polyalkyl ethers and alkoxy-capped analogs thereof (e.g., polyoxyethylene glycol, polyoxyethylene/propylene glycol, and methoxy or ethoxy-capped analogs thereof, polyoxyethylene glycol, the latter is also known as polyethylene glycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof, hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof, terpolymers thereof, mixtures thereof, and derivatives of the foregoing. In other embodiments, a water soluble polymer is any structural form. Exemplary forms are linear, forked or branched. In further embodiments, multifunctional polymer derivatives include, but are not limited to, linear polymers having two termini, each terminus being bonded to a functional group which is the same or different.

In some embodiments, a water polymer comprises a poly(ethylene glycol) moiety. In further embodiments, the molecular weight of the polymer is of a wide range. Exemplary ranges are between about 100 Da and about 100,000 Da or more. In yet further embodiments, the molecular weight of the polymer is between about 100 Da and about 100,000 Da, about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, about 1,000 Da, about 900 Da, about 800 Da, about 700 Da, about 600 Da, about 500 Da, about 400 Da, about 300 Da, about 200 Da, and about 100 Da. In some embodiments, the molecular weight of the polymer is between about 100 Da and 50,000 Da. In some embodiments, the molecular weight of the polymer is between about 100 Da and 40,000 Da. In some embodiments, the molecular weight of the polymer is between about 1,000 Da and 40,000 Da. In some embodiments, the molecular weight of the polymer is between about 5,000 Da and 40,000 Da. In some embodiments, the molecular weight of the polymer is between about 10,000 Da and 40,000 Da. In some embodiments, the poly(ethylene glycol) molecule is a branched polymer. In further embodiments, the molecular weight of the branched chain PEG is between about 1,000 Da and about 100,000 Da. Exemplary ranges are about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, about 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, and about 1,000 Da. In some embodiments, the molecular weight of a branched chain PEG is between about 1,000 Da and about 50,000 Da. In some embodiments, the molecular weight of a branched chain PEG is between about 1,000 Da and about 40,000 Da. In some embodiments, the molecular weight of a branched chain PEG is between about 5,000 Da and about 40,000 Da. In some embodiments, the molecular weight of a branched chain PEG is between about 5,000 Da and about 20,000 Da. The foregoing list for substantially water soluble backbones is by no means exhaustive and is merely illustrative, and in some embodiments, polymeric materials having the qualities described above are suitable for use in methods and compositions described herein.

One of ordinary skill in the art will appreciate that when -$T^1$-$R^t$ is attached to a compound of the formulae herein via the $R^2$ group, then the resulting tethering moiety comprises the $R^2$ group.

In certain embodiments, the tethering moiety, -$T^1$-, has one of the following structures:

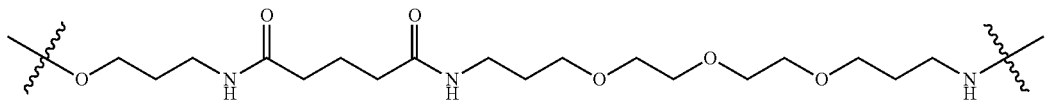 [SMILES: *NCCCOCCOCCOCCCNC(=O)CCCC(=O)NCCCO*]

In some embodiments, the tethering moiety, -$T^1$-, has the following structure:

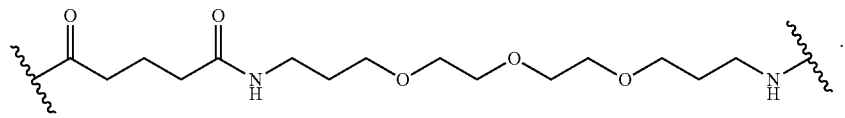 [SMILES: *NCCCOCCOCCOCCCNC(=O)CCCC(*)=O]

In some embodiments, the tethering moiety, -$T^1$-, has the following structure:

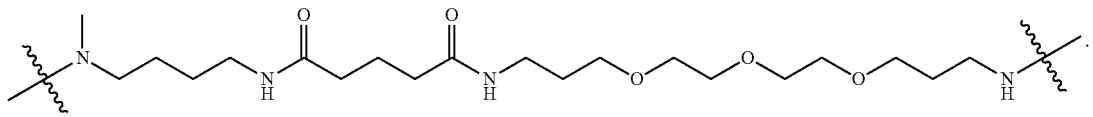 [SMILES: *NCCCOCCOCCOCCCNC(=O)CCCC(=O)NCCCCN(*)C]
In other embodiments, the tethering moiety, -T$^1$-, has the following structure:
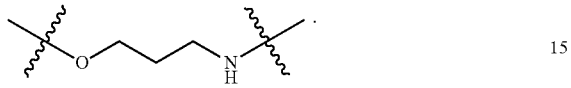
In certain other embodiments, the tethering moiety, -T$^1$-, has the following structure:
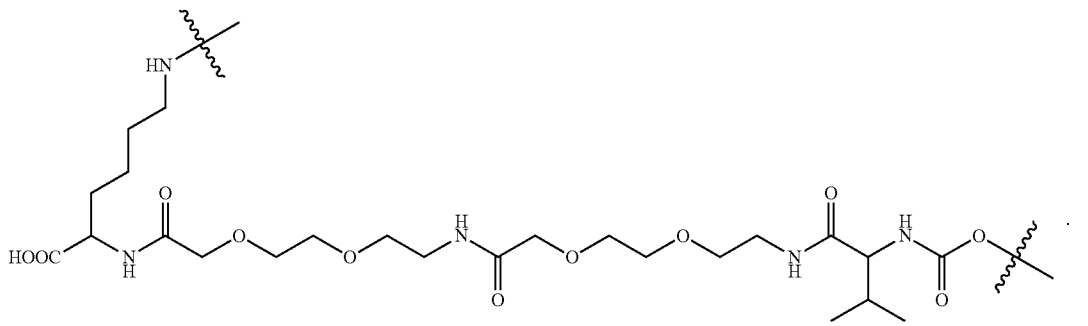 [SMILES: *NCCCCC(NC(=O)COCCOCCNC(=O)COCCOCCNC(=O)C(NC(=O)O*)C(C)C)C(=O)O]
In yet other embodiments, the tethering moiety, -T$^1$-, has the following structure:
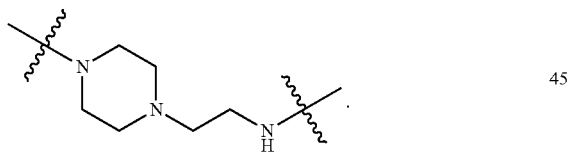
In some embodiments, the tethering moiety, -T$^1$-, has the following structure:
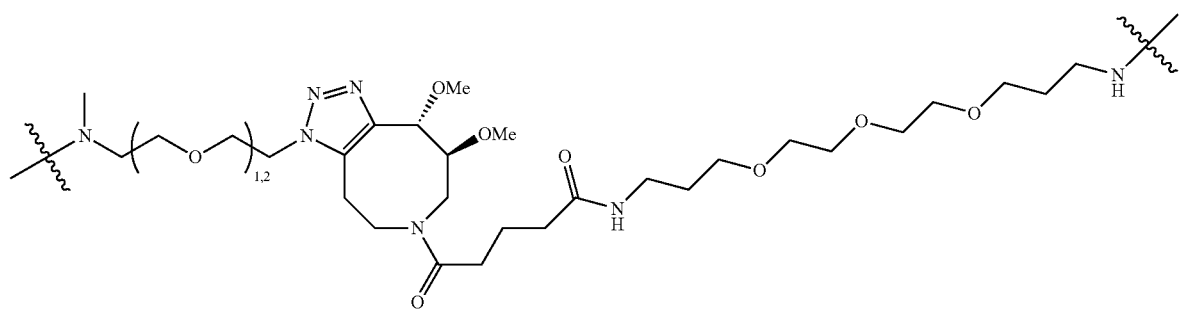

In some embodiments, -T-R' is of the following structure:
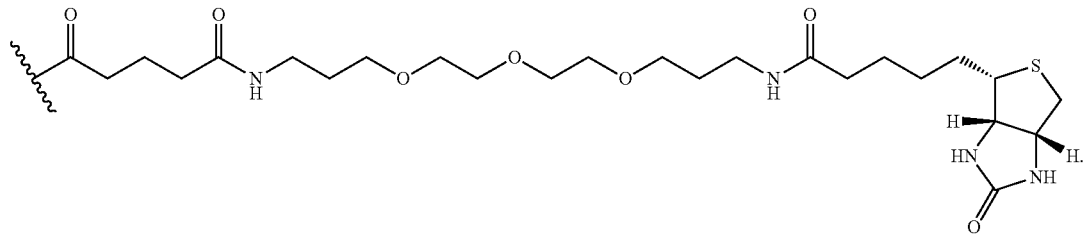
In some embodiments, -T¹-R' is of the following structure:
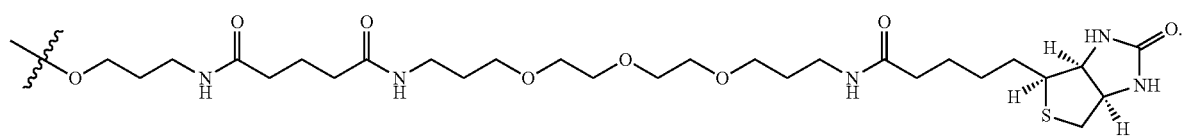 [SMILES: *OCCCNC(=O)CCCC(=O)NCCCOCCOCCOCCCNC(=O)CCCC[C@@H]1SC[C@@H]2NC(=O)N[C@@H]21]
In other embodiments, -T¹-R' is of the following structure:
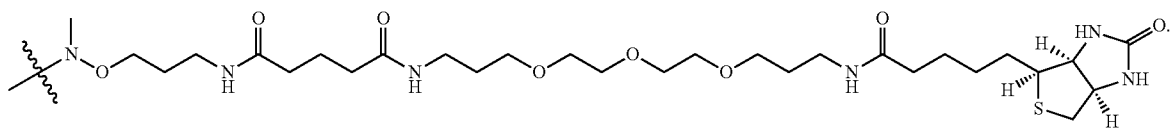 [SMILES: *N(C)OCCCNC(=O)CCCC(=O)NCCCOCCOCCOCCCNC(=O)CCCC[C@@H]1SC[C@@H]2NC(=O)N[C@@H]21]
In certain embodiments, -T¹-R' is of the following structure:
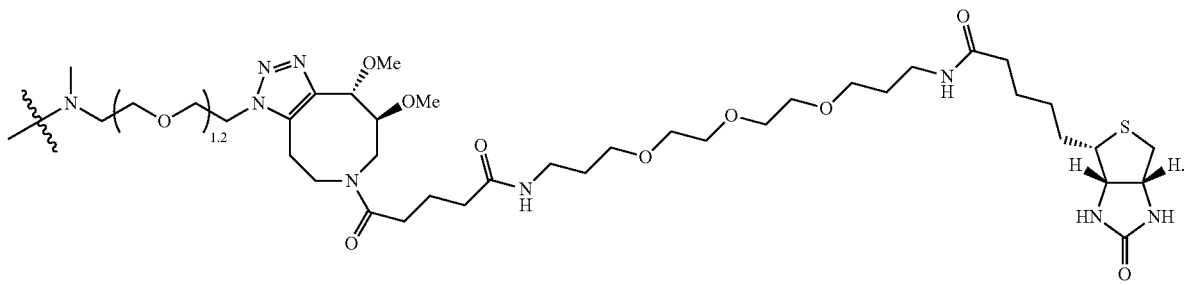

In some embodiments, a probe compound of formula I-t is derived from any compound described herein.

In certain embodiments, the probe compound is one of the following structures:

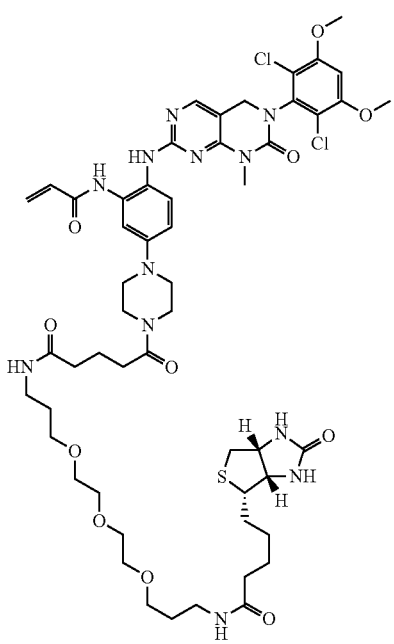

I-127

It will be appreciated that many -T$^1$-R$^t$ reagents are commercially available. For example, numerous biotinylating reagents are available from, e.g., Thermo Scientific having varying tether lengths. Such reagents include NHS-PEG$_4$-Biotin and NHS-PEG$_{12}$-Biotin.

In some embodiments, analogous probe structures to the ones exemplified above are prepared using click-ready inhibitor moieties and click-ready -T-R$^t$ moieties, as described herein.

In some embodiments, a provided probe compound covalently modifies a phosphorylated conformation of a protein kinase. In one aspect, the phosphorylated conformation of the protein kinase is either an active or inactive form of the protein kinase. In certain embodiments, the phosphorylated conformation of the protein kinase is an active form of said kinase. In certain embodiments, the probe compound is cell permeable.

In some embodiments, the present invention provides a method for determining occupancy of a protein kinase by a provided irreversible inhibitor (i.e., a compound of any of the formulae presented herein) in a patient, comprising providing one or more tissues, cell types, or a lysate thereof, obtained from a patient administered at least one dose of a compound of said irreversible inhibitor, contacting said tissue, cell type or lysate thereof with a probe compound (i.e., a compound of formula I-t) to covalent modify at least one protein kinase present in said lysate, and measuring the amount of said protein kinase covalently modified by the probe compound to determine occupancy of said protein kinase by said compound as compared to occupancy of said protein kinase by said probe compound. In certain embodiments, the method further comprises the step of adjusting the dose of the compound of formulae presented herein to increase occupancy of the protein kinase. In certain other embodiments, the method further comprises the step of adjusting the dose of the compound of formulae presented herein to decrease occupancy of the protein kinase.

As used herein, the terms "occupancy" or "occupy" refer to the extent to which a protein kinase is modified by a provided covalent inhibitor compound. One of ordinary skill in the art would appreciate that it is desirable to administer the lowest dose possible to achieve the desired efficacious occupancy of the protein kinase.

In some embodiments, the protein kinase to be modified is FGFR4.

In some embodiments, the probe compound comprises the irreversible inhibitor for which occupancy is being determined.

In some embodiments, the present invention provides a method for assessing the efficacy of a provided irreversible inhibitor in a mammal, comprising administering a provided irreversible inhibitor to the mammal, administering a provided probe compound to tissues or cells isolated from the mammal, or a lysate thereof, measuring the activity of the detectable moiety of the probe compound, and comparing the activity of the detectable moiety to a standard.

In other embodiments, the present invention provides a method for assessing the pharmacodynamics of a provided irreversible inhibitor in a mammal, comprising administering a provided irreversible inhibitor to the mammal, administering a probe compound presented herein to one or more cell types, or a lysate thereof, isolated from the mammal, and measuring the activity of the detectable moiety of the probe compound at different time points following the administration of the inhibitor.

In yet other embodiments, the present invention provides a method for in vitro labeling of a protein kinase comprising contacting said protein kinase with a probe compound described herein. In one embodiment, the contacting step comprises incubating the protein kinase with a probe compound presented herein.

In certain embodiments, the present invention provides a method for in vitro labeling of a protein kinase comprising contacting one or more cells or tissues, or a lysate thereof, expressing the protein kinase with a probe compound described herein.

In certain other embodiments, the present invention provides a method for detecting a labeled protein kinase comprising separating proteins, the proteins comprising a protein kinase labeled by probe compound described herein, by electrophoresis and detecting the probe compound by fluorescence.

In some embodiments, the present invention provides a method for assessing the pharmacodynamics of a provided irreversible inhibitor in vitro, comprising incubating the provided irreversible inhibitor with the target protein kinase, adding the probe compound presented herein to the target protein kinase, and determining the amount of target modified by the probe compound.

In certain embodiments, the probe compound is detected by binding to avidin, streptavidin, neutravidin, or captavidin.

In some embodiments, the probe is detected by Western blot. In other embodiments, the probe is detected by ELISA. In certain embodiments, the probe is detected by flow cytometry.

In other embodiments, the present invention provides a method for probing the kinome with irreversible inhibitors comprising incubating one or more cell types, or a lysate thereof, with a biotinylated probe compound to generate proteins modified with a biotin moiety, digesting the proteins, capturing with avidin or an analog thereof, and performing multi-dimensional LC-MS-MS to identify protein kinases modified by the probe compound and the adduction sites of said kinases.

In certain embodiments, the present invention provides a method for measuring protein synthesis in cells comprising incubating cells with an irreversible inhibitor of the target protein, forming lysates of the cells at specific time points, and incubating said cell lysates with an inventive probe compound to measure the appearance of free protein over an extended period of time.

In other embodiments, the present invention provides a method for determining a dosing schedule in a mammal for maximizing occupancy of a target protein kinase comprising assaying a one or more cell types, or a lysate thereof, isolated from the mammal, (derived from, e.g., splenocytes, peripheral B cells, whole blood, lymph nodes, intestinal tissue, or other tissues) from a mammal administered a provided irreversible inhibitor of any of the formulae presented herein, wherein the assaying step comprises contacting said one or more tissues, cell types, or a lysate thereof, with a provided probe compound and measuring the amount of protein kinase covalently modified by the probe compound.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Compound numbers utilized in the Examples below correspond to compound numbers set forth supra.

In the below illustrative examples, reactions were carried out at room or ambient temperature, in the range of 18-25° C. unless otherwise stated. Organic solutions were dried over anhydrous magnesium sulfate or sodium sulate and evaporation of solvent was carried out using a rotary evaporator under reduced pressure. In general, the courses of reactions were followed by TLC or LCMS and reaction times are representative. Yields are given for illustration only and are not necessarily those which can be obtained by diligent process development. $^1$HNMR data is in delta values for major diagnostic protons, given in parts per million (ppm) relative to tetramethylsilane (TMS) or residual solvent. $^1$HNMR spectra were determined at 400 MHz. Solvent ratios are given in volume:volume (v/v) terms. Mass spectra (MS) data was generated on an LCMS system where the HPLC component comprised generally either an Agilent or Shimadzu LCMS-2020 Instrument and was run on a Sepax BR-C18 (4.6×50 mm, 3 um) column or similar, eluting with acidic eluent (for example, using a gradient between 0-95% water/acetonitrile with 0.1% formic acid or trifluoroacetic acid). Chromatograms were in electrospray (ESI) positive, negative and/or UV. LCMS values for m/z are provided throughout and generally, only ions which indicate the parent mass are reported. Unless otherwise stated the value quoted is the (M+H)+ or (M+1)$^+$ for positive ion mode. Preparative HPLC was performed on C18 reversed-phase silica using decreasingly polar mixtures as eluent, for example decreasingly polar mixtures of water and acetonitrile containing 1% trifluoroacetic acid. Enantioenriched intermediates and final compounds are designated by 'abs' and racemic analogs are designated by 'rac'. Enantioenriched products and intermediates were characterized by chiral HPLC using a CHIRALPAK AD-H (6×150 mm, 5 um) column or similar and generally had enantiomeric ratios≥95:5. Unless otherwise specified, starting materials were commercially available or synthesized according to known methods.

TFA; trifluoroacetic acid
THF; tetrahydrofuran;
DMF; N,N-dimethylformamide
EtOAc; ethyl acetate
DCM; dichloromethane
DMSO; dimethylsulfoxide
DIPEA; N,N-diisopropylethylamine
TBAF; tetra-n-butylammonium fluoride
DMAP; 4-dimethylaminopyridine
NMO; N-methylmorpholine N-oxide
TBDPSCl; tert-butyl(chloro)diphenylsilane
NMP; N-methyl-2-pyrrolidone
Ms; mesyl, methanesulfonyl
SFC; supercritical fluid chromatography
er; enantiomeric ratio
h: hour
min: minute
aq: aqueous
sat: saturated
PBS; phosphate buffered saline
DTT; dithiothreitol
ATP; adenosine triphosphate Example 1: Synthesis of Common Intermediate 6

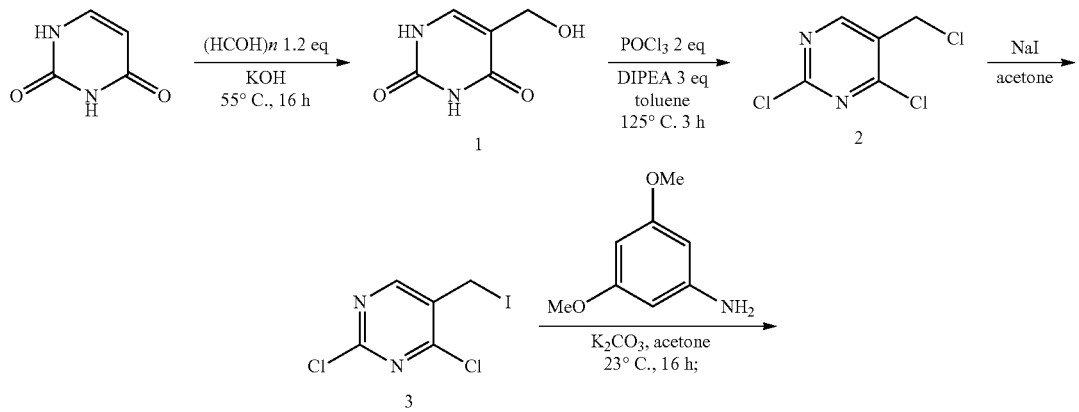

-continued

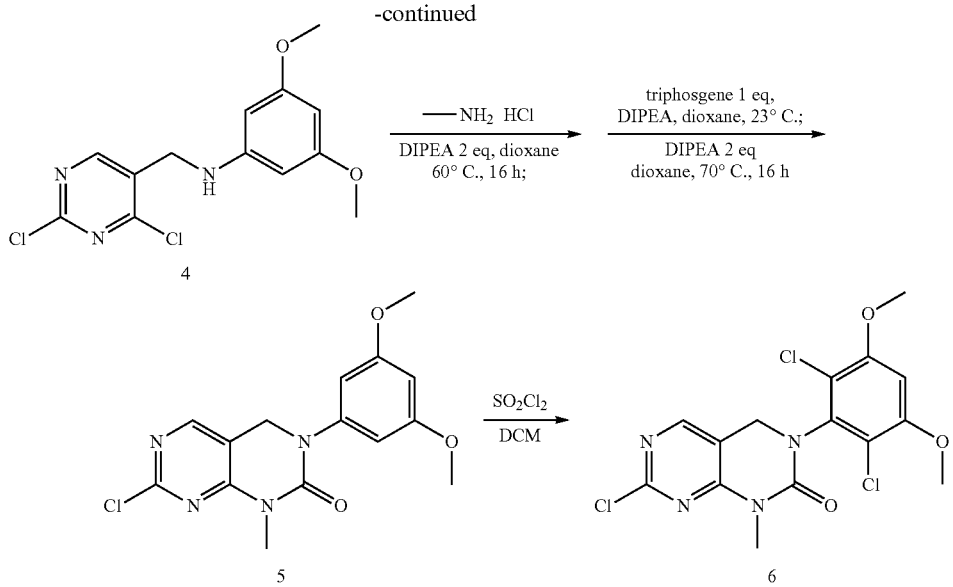

Step 1: Intermediate 1

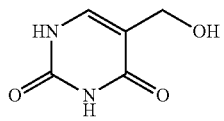

A 1-L, three-necked flask equipped with a mechanical stirrer, was charged with uracil (45.0 g, 401 mmol) and paraformaldehyde (14.5 g, 483 mmol). A solution of potassium hydroxide (0.5 M, 600 mL, 0.30 mol) was added in one portion. The resulting mixture was stirred at 55° C. overnight. The mixture was cooled in an ice-water bath and the pH was adjusted to 6 with 12 N HCl. The resulting precipitate was collected by filtration and dried to afford the title compound (46.0 g) as a white solid which was used in the next step without further purification. $^1$H NMR (400 MHz, DMSO-d6): δ 4.12 (d, 2H), 4.78 (t, 1H), 7.24 (s, 1H), 10.64 (s, 1H), 10.98 (s, 1H).

Step 2: Intermediate 2

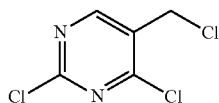

A 500-mL, three-necked flask equipped with a mechanical stirrer was charged with Intermediate 1 (25.0 g, 176 mmol), toluene (30 mL), and phosphorous oxychloride (125 mL). DIPEA (130 mL) was added dropwise over 10 min. The resulting mixture was heated at reflux overnight. The solution was concentrated and the resulting residue was slowly poured onto cooled (0° C.) 1.5 M HCl and extracted with EtOAc. The organic phase was washed with water, saturated aqueous NaHCO$_3$, brine, dried over anhydrous Na$_2$SO$_4$ and concentrated to afford the title compound (32.0 g) which was used in the next step without further purification. $^1$H NMR (400 MHz, CDCl$_3$): δ 4.64 (s, 2H), 8.66 (s, 1H).

Step 3: Intermediate 3

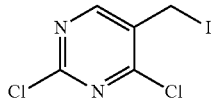

A 500-mL, three-necked flask equipped with a mechanical stirrer was charged with Intermediate 2 (32.0 g, 111 mmol), acetone (150 mL), NaI (26.5 g, 177 mmol). The mixture was allowed to stir at ambient temperature for 15 min then was heated at reflux for 30 min. The mixture was cooled to ambient temperature and filtered to remove the resultant solid. The filtrate was concentrated to afford 46.0 g of the title compound which was used in the next step without further purification. $^1$H NMR (400 MHz, CDCl$_3$): δ 4.39 (s, 2H), 8.60 (s, 1H).

Step 4: Intermediate 4

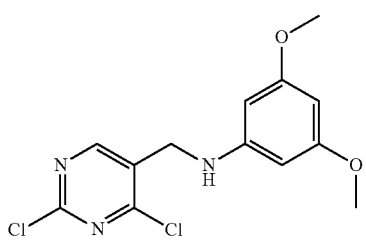 [SMILES: COc1cc(NCc2cnc(Cl)nc2Cl)cc(OC)c1]

A mixture of Intermediate 3 (15.0 g, 47.9 mmol), 3,5-dimethoxyaniline (8.80 g, 57.4 mmol), and K$_2$CO$_3$ (14.4 g, 104 mmol) in acetone (150 mL) was stirred at ambient temperature overnight. The solution was cooled in an ice-water bath and filtered to remove the resultant solid. The filtrate was concentrated and the residue was triturated with EtOH (100 mL) then stirred at 0° C. for 30 min. The precipitate was collected by filtration and dried to afford 9.40 g of the title compound. MS m/z: 314.2 (M+H+). 1H NMR (400 MHz, CDCl3): δ 3.73 (s, 6H), 4.22 (br s, 1H), 4.40 (s, 2H), 5.74 (d, 2H), 5.94 (t, 1H), 8.53 (s, 1H).

Step 5: Intermediate 5

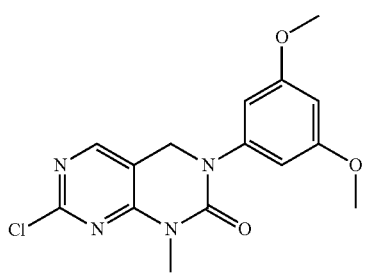 [SMILES: COc1cc(OC)cc(N2Cc3cnc(Cl)nc3N(C)C2=O)c1]

A solution of Intermediate 4 (9.40 g, 29.9 mmol), DIPEA (9.60 g, 74.3 mmol), and MeNH2HCl (2.40 g, 35.8 mmol) in dioxane (150 mL) was stirred in sealed tube at 60° C. overnight. The solution was cooled to ambient temperature. DIPEA (9.60 g, 74.3 mmol) was added followed by slow addition of triphosgene (9.30 g, 31.3 mmol) in dioxane (60 mL). The solution was allowed to stir at ambient temperature for 1 h after which it was heated to 70° C. for 3 h. The solution was concentrated, water was added, and the mixture was allowed to stir for 30 min at ambient temperature. The resultant solid was collected by filtration then was dissolved in MeOH/H2O (135 mL/15 mL) and heated at reflux for 10 min after which, the solution was cooled in ice-water bath and the resultant solid was collected by filtration, washed with cold MeOH/H2O (v/v: 18/2) and dried to afford the title compound (5.80 g) which was used in the next step without further purification. MS m/z: 335.3 (M+H+). 1H NMR (400 MHz, CDCl3): δ 3.46 (s, 3H), 3.79 (s, 6H), 4.74 (s, 2H), 6.41 (t, 1H), 6.46 (d, 2H), 8.12 (s, 1H).

Step 6: Common Intermediate 6

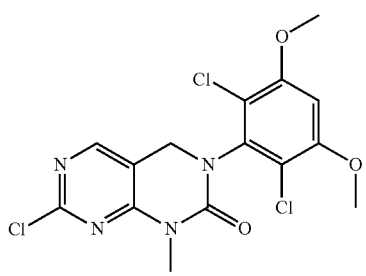 [SMILES: COc1cc(OC)c(Cl)c(N2Cc3cnc(Cl)nc3N(C)C2=O)c1Cl]

A solution of Intermediate 5 (5.50 g, 16.4 mmol) in DCM (150 mL) was cooled to 0° C. and SO2Cl2 (4.70 g, 34.8 mmol) in DCM (20 mL) was added dropwise. The resulting mixture was allowed to stir at 0° C. for 1 h after which it was poured into saturated aqueous NaHCO3 and the organic phase was separated, washed with water, brine, dried over Na2SO4 and concentrated to afford 6.00 g of the title compound. MS m/z: 403.3 (M+H+). 1H NMR (400 MHz, CDCl3): δ 3.47 (s, 3H), 3.95 (s, 6H), 4.65 (s, 2H), 6.62 (s, 1H), 8.12 (s, 1H).

Example 2: Synthesis of Common Intermediate 8

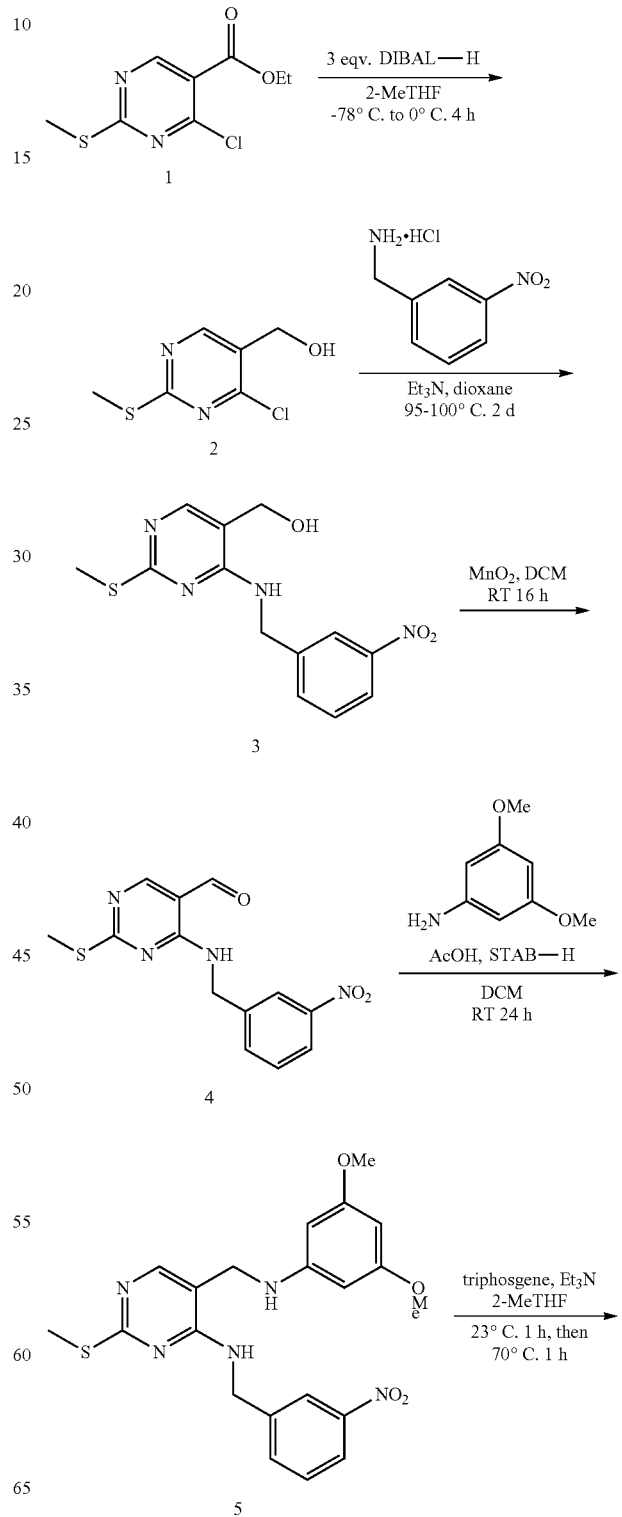

Step 2: Intermediate 3

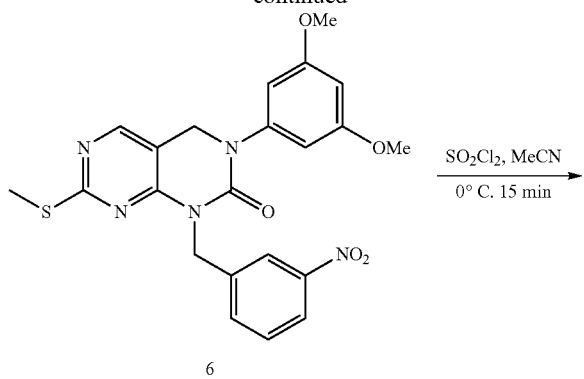

To a suspension of Intermediate 2 (2.10 g, 11.0 mmol) in 140 mL of 1,4-dioxane was added 3-nitrobenzylamine hydrochloride (2.49 g, 13.2 mmol) and triethylamine (5.22 mL, 37.5 mmol). The mixture was allowed to stir at 95° C. for 24 h. Additional 3-nitrobenzylamine hydrochloride (208 mg, 1.10 mmol) and triethylamine (3.08 mL, 22.1 mmol) were added and the reaction was stirred at 100° C. for 17 h. The reaction mixture was concentrated and the crude product was subjected to flash chromatography on silica gel (eluting with a gradient of 50-100% EtOAc in heptane). The resulting residue was then triturated with EtOAc to provide 2.05 g of the title compound. MS m/z: 307.0 (M+H)$^+$. $^1$H NMR (400 MHz, DMSO-d6): δ: 8.18 (1H, s), 7.85 (1H, s), 7.74 (1H, d), 7.59 (2H, m), 5.11 (1H, t), 4.66 (2H, d), 4.35 (2H, d), 2.28 (3H, s).

Step 3: Intermediate 4

To a solution of Intermediate 3 (2.10 g, 6.69 mmol) in 140 mL of DCM was added manganese oxide (8.02 g, 53.5 mmol) and the mixture was stirred at ambient temperature for 17 h. The reaction mixture was filtered through Celite, washed with DCM and the filtrate concentrated under reduced pressure to give 1.85 g of the title compound, which was used directly without purification. MS m/z: 305.1 (M+H$^+$). $^1$H NMR (400 MHz, CDCl$_3$): δ: 9.75 (1H, s), 9.08 (1H, br s), 8.38 (1H, s), 8.20 (1H, s), 8.15 (1H, d), 7.66 (1H, d), 7.52 (1H, t), 4.87 (2H, d), 2.48 (3H, s).

Step 4: Intermediate 5

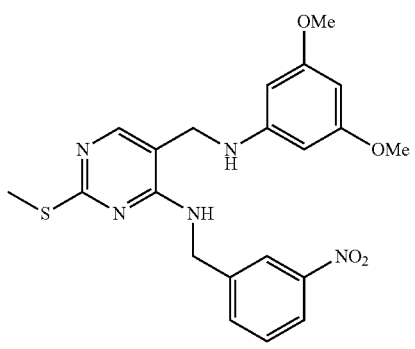 [SMILES: COc1cc(NCc2cnc(SC)nc2NCc2cccc([N+](=O)[O-])c2)cc(OC)c1]

To a solution of Intermediate 4 (500 mg, 1.64 mmol) in 9 mL of DCM was added 3,5-dimethoxyaniline (229 mg, 1.49 mmol) and acetic acid (94.1 μL, 1.64 mmol) under argon. The mixture was allowed to stir at ambient temperature for 15 min prior to the addition of sodium triacetoxyborohydride (2×238 mg, 2.24 mmol) in 2 portions with a 15 min interval in between. The reaction was stirred at ambient temperature for 17 h, extra sodium triacetoxyborohydride (476 mg, 2.24 mmol) was added and the mixture was stirred for an additional 6 h. The reaction was quenched with 10 mL of 1 M NaOH which caused vigorous evolution of gas after which the mixture was stirred for 15 min. The aqueous layer was extracted with DCM (×3) and the combined organic layers were washed with brine, dried (Na$_2$SO$_4$), filtered and concentrated. The crude product was subjected to flash chromatography on silica gel (eluting with 50% EtOAc in heptane), which gave 591 mg of title compound. MS m/z: 442.1 (M+H)$^+$.

Step 5: Intermediate 6

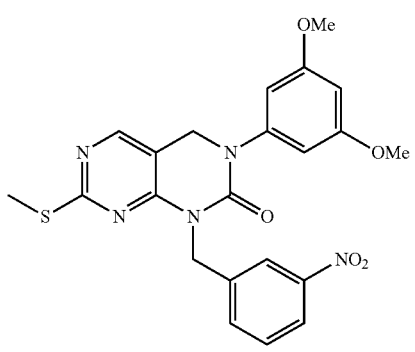 [SMILES: COc1cc(OC)cc(N2Cc3cnc(SC)nc3N(Cc3cccc([N+](=O)[O-])c3)C2=O)c1]

To a solution of Intermediate 5 (591 mg, 1.34 mmol) in 6 mL of 2-MeTHF was added triphosgene (437 mg, 1.47 mmol) followed by slow addition of triethylamine (578 μL, 4.15 mmol) under argon. The mixture was stirred at ambient temperature for 1 h, then at 70° C. for 1.5 h. The reaction was quenched with a 1:1 mixture of saturated aqueous NaHCO$_3$/H$_2$O (12 mL) and the resultant solids were removed by filtration and washed with EtOAc. The filtrate layers were separated and the aqueous was extracted with EtOAc followed by DCM. The combined organic layers were washed with brine, dried (Na$_2$SO$_4$), filtered and concentrated in vacuo. The crude product was subjected to dry-flash chromatography on silica gel (eluting with a gradient of 50-70% EtOAc in heptane). The resultant residue was then triturated with Et$_2$O to provide 398 mg of the title compound. MS m/z: 468.0 (ES+, M+H$^+$). $^1$H NMR (400 MHz, CDCl$_3$): δ: 8.34 (1H, s), 8.11 (2H, m), 7.80 (1H, d), 7.47 (1H, t), 6.47 (2H, d), 6.40 (1H, t), 5.38 (2H, s), 4.73 (2H, s), 3.77 (6H, s), 2.52 (3H, s).

Step 6: Intermediate 7

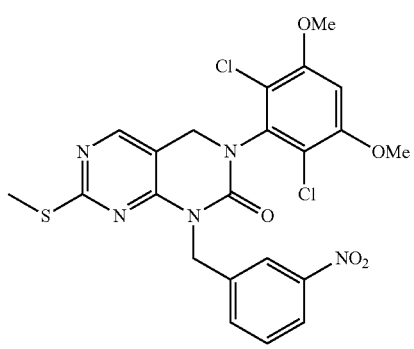 [SMILES: COc1cc(OC)c(Cl)c(N2Cc3cnc(SC)nc3N(Cc3cccc([N+](=O)[O-])c3)C2=O)c1Cl]

To a cooled (0° C.) solution of Intermediate 6 (396 mg, 0.847 mmol) in 7 mL of MeCN and 15 mL of DCM was added sulfuryl chloride (137 μL, 1.69 mmol). The reaction was stirred at 0° C. for 15 min. The reaction was quenched with saturated aqueous NaHCO$_3$ and the aqueous was extracted with DCM (×2). The combined organic layers were dried (Na$_2$SO$_4$), filtered and concentrated in vacuo to give 452 mg of the title product which was used directly without purification. MS m/z: 536.0 (H$^+$). $^1$H NMR (400 MHz, CDCl$_3$): δ: 8.32 (1H, s), 8.09 (2H, m), 7.78 (1H, d), 7.46 (1H, t), 6.61 (1H, s), 5.38 (2H, s), 4.65 (2H, s), 3.94 (6H, s), 2.49 (3H, s).

Step 7: Intermediate 8

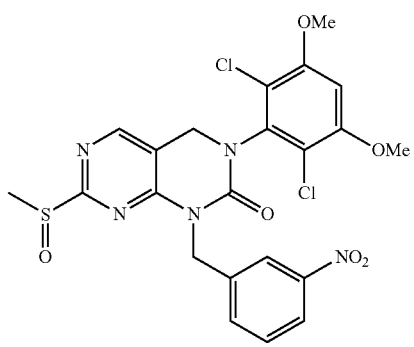 [SMILES: COc1cc(OC)c(Cl)c(N2Cc3cnc(S(C)=O)nc3N(Cc3cccc([N+](=O)[O-])c3)C2=O)c1Cl]

To a solution of Intermediate 7 (451 mg, 0.841 mmol) in 10 mL of DCM was added mCPBA (228 mg, 0.925 mmol). The reaction was stirred at ambient temperature for 1 hour and then quenched with 6 mL of saturated aqueous NaHCO$_3$ and 4 mL of 2 M sodium thiosulfate. The mixture was stirred for 15 min, then diluted with H$_2$O and the aqueous was extracted with DCM (×3). The combined organic layers were dried (Na$_2$SO$_4$), filtered and concentrated to give 468 mg of the title product which was used directly without purification. MS m/z: 552.0 M+H$^+$).

Example 3: Synthesis of I-1
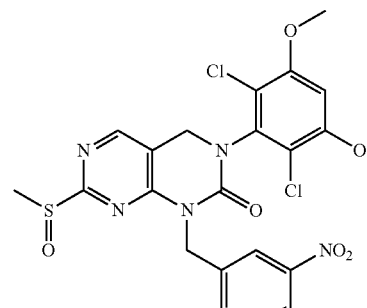
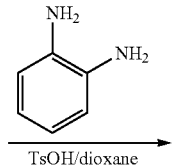
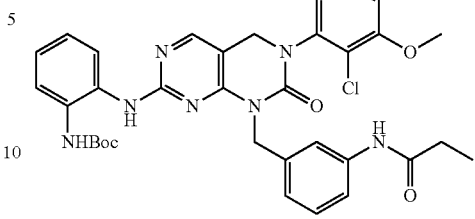
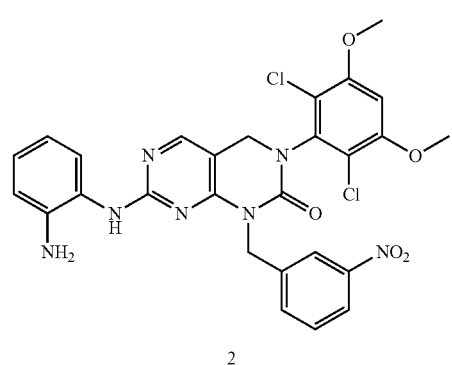
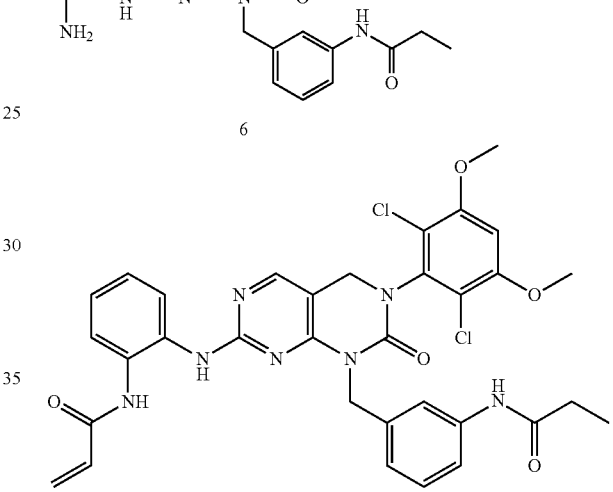
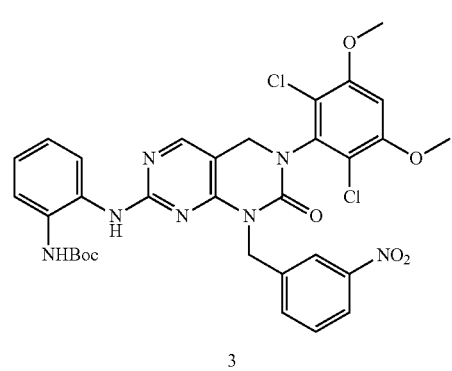
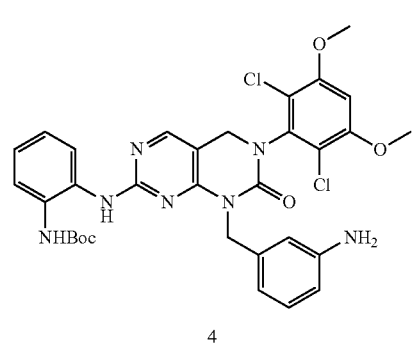
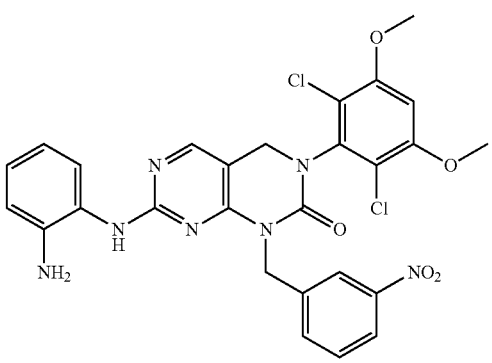 [SMILES: COc1cc(OC)c(Cl)c(N2Cc3cnc(Nc4ccccc4N)nc3N(Cc3cccc([N+](=O)[O-])c3)C2=O)c1Cl]
Step 1: Intermediate 2
To a solution of Intermediate 8 from Example 2 (150 mg, 0.27 mmol), in 1,4-dioxane (8 mL) was added benzene-1,2-diamine (88.1 mg, 0.82 mmol) and p-toluene sulfonic acid (23.4 mg, 0.14 mmol). The mixture was heated at 100° C. overnight under nitrogen. The mixture was cooled to ambient temperature, water was added and the resultant suspension was filtered to afford 145 mg of the title compound. MS m/z: 596.3 (M+H)+.

Step 2: Intermediate 3

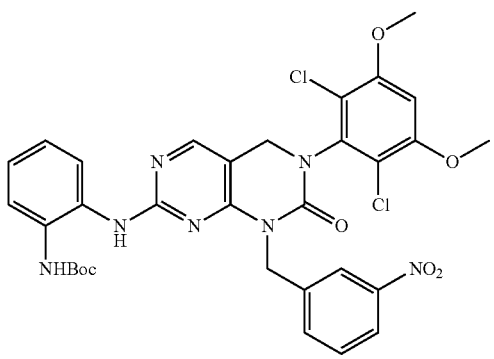 [SMILES: COc1cc(OC)c(Cl)c(N2Cc3cnc(Nc4ccccc4NC(=O)OC(C)(C)C)nc3N(Cc3cccc([N+](=O)[O-])c3)C2=O)c1Cl]

To a solution of Intermediate 2 (145 mg, 0.24 mmol) in THF (15 mL) was added triethylamine (98.0 mg, 0.97 mmol) and (Boc)$_2$O (106 mg, 0.48 mmol). The reaction mixture was heated at reflux overnight. The mixture was cooled to ambient temperature, water was added, and the aqueous layer extracted with EtOAc (30 mL×3). The combined organic layers were dried (Na$_2$SO$_4$), filtered, and concentrated. The crude product was subjected to flash chromatography on silica gel (65% EtOAc/hexanes) to afford 121 mg of the title compound. $^1$H NMR (400 MHz, DMSO-d6): δ 1.44 (s, 9H), 3.97 (s, 6H), 4.62 (s, 2H), 5.16 (s, 2H), 6.96-7.11 (m, 3H), 7.39 (d, 1H), 7.47-7.57 (m, 3H), 8.04-8.07 (m, 2H), 8.16 (s, 1H), 8.48 (s, 1H), 8.58 (s, 1H).

Step 3: Intermediate 4

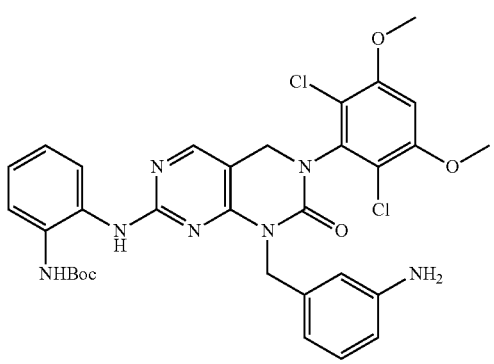 [SMILES: COc1cc(OC)c(Cl)c(N2Cc3cnc(Nc4ccccc4NC(=O)OC(C)(C)C)nc3N(Cc3cccc(N)c3)C2=O)c1Cl]

To a solution of Intermediate 3 (112 mg, 0.16 mmol) in ethanol (8 mL) and water (4 mL) was added iron power (54.0 mg, 0.96 mmol) and NH$_4$Cl (52 mg, 0.96 mmol). The mixture was heated at reflux for 1.5 h. The reaction mixture was cooled to ambient temperature, filtered, and the filtrate was concentrated. Water was added to the resultant residue and the aqueous layer was and extracted with EtOAc (30 mL×3). The combined organic layers were washed with saturated NaHCO$_3$, dried (Na$_2$SO$_4$), filtered and concentrated to afford 104.4 mg of the title compound which was used directly in the next step without purification. MS m/z: 666.4 [M+H]+

Step 4: Intermediate 5

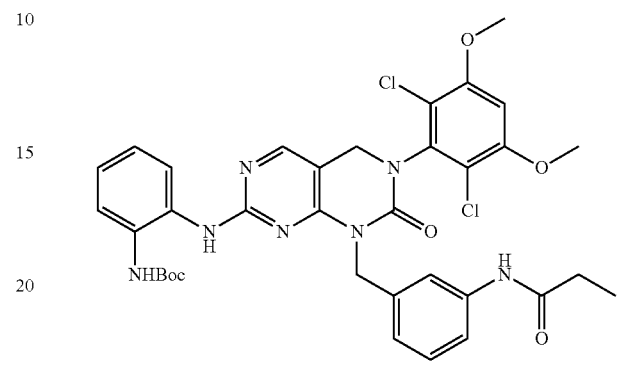

A mixture of Intermediate 4 (98.6 mg, 0.15 mmol), propionic acid (16.4 mg, 0.22 mmol) and HATU (113 mg, 0.30 mmol) in DMF (6 mL) was cooled to 0° C. DIPEA (57.3 mg, 0.44 mmol) was added and the reaction mixture was allowed to stir at ambient temperature overnight. Water was added and the resultant mixture was extracted with EtOAc (60 mL×3). The combined organic layers were dried (Na$_2$SO$_4$), filtered, and concentrated. The crude product was subjected to flash chromatography on silica gel (3% MeOH/DCM) to afford 74 mg of the title compound. MS m/z: 722.4 [M+H]+

Step 5: Intermediate 6

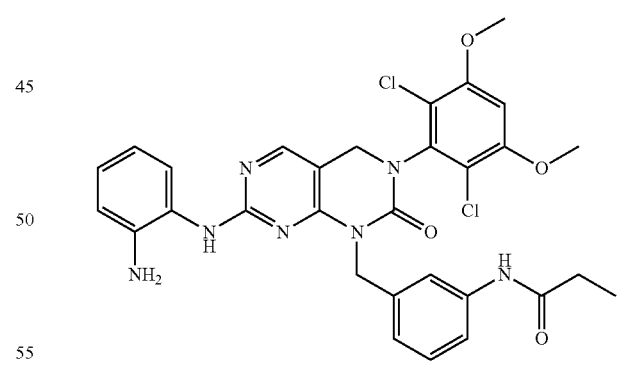

To a solution of Intermediate 5 (74.0 mg, 0.10 mmol) in DCM (2 mL) was added TFA (2 mL) and the solution was allowed to stir at ambient temperature for 30 min. The solvent was removed and water was added to the residue which was extracted with EtOAc (30 mL×3). The combined organic layers were washed with saturated NaHCO$_3$, dried (Na$_2$SO$_4$), filtered and concentrated to afford 79 mg of the title compound which was used without purification. MS m/z: 622.4 [M+H]+

Step 6: I-1

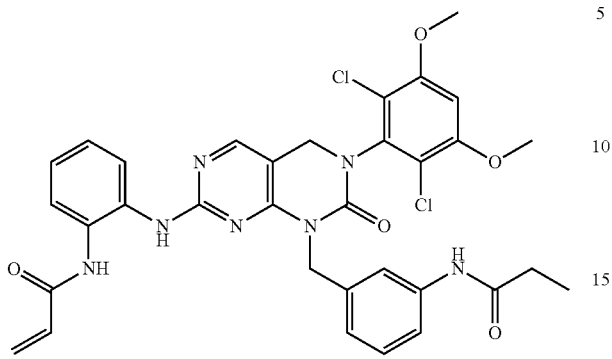

To a cooled (0° C.) solution of Intermediate 6 (79.0 mg, 0.13 mmol) and DIPEA (33.0 mg, 0.25 mmol) in THF (3 mL) was added acryloyl chloride (13.8 mg, 0.15 mmol). The reaction was stirred at 0° C. for 10 min. The reaction was quenched with saturated aqueous NaHCO$_3$ and extracted with EtOAc (30 mL×3). The combined organic layers were washed with saturated aqueous NaHCO$_3$, dried (Na$_2$SO$_4$), filtered and concentrated. The crude product was subjected to flash chromatography on silica gel (5% MeOH/DCM) to 34.3 mg of the title compound. MS m/z: 676.4 [M+H]$^+$. $^1$H NMR (400 MHz, DMSO-d6): δ 1.08 (t, 3H), 2.29 (q, 2H), 3.96 (s, 6H), 4.60 (s, 2H), 5.06 (s, 2H), 5.68-5.83 (m, 1H), 6.26 (dd, 1H), 6.40-6.56 (m, 1H), 6.83 (d, 1H), 6.95-7.09 (m, 3H), 7.16 (t, 1H), 7.37-7.48 (m, 1H), 7.50-7.53 (m, 3H), 8.14 (s, 1H), 8.53 (s, 1H), 9.70 (s, 1H), 9.74 (s, 1H).

Example 4: Synthesis of I-2

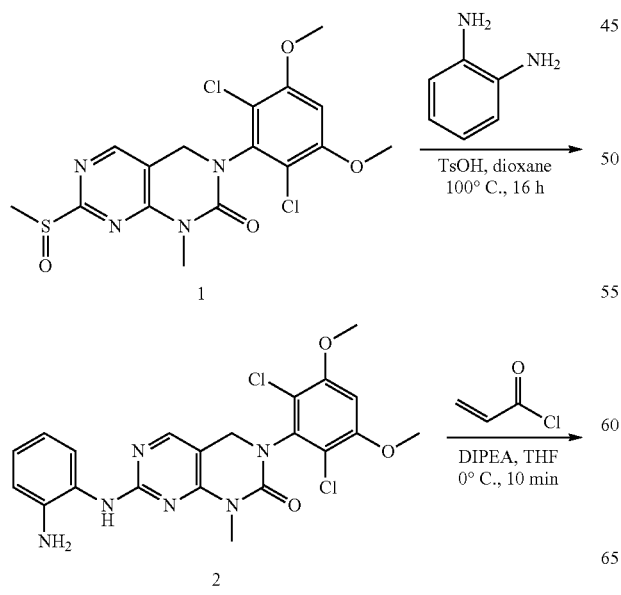

-continued

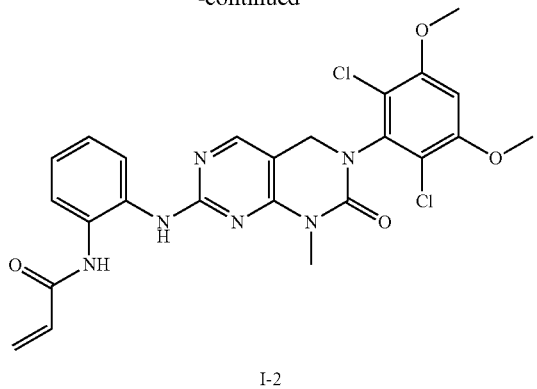

I-2

Step 1: Intermediate 2

A mixture of Intermediate 1 (prepared as described in Example 2 using methylamine in place of 3-nitrobenzylamine in Step 2 (106 mg, 0.25 mmol)), benzene-1,2-diamine (80 mg, 0.74 mmol), and p-TsOH (21.2 mg, 0.12 mmol) in 1,4-dioxane (8 mL) was heated at reflux for 16 h under nitrogen. The reaction mixture was cooled to ambient temperature and partitioned between EtOAc and water. The organic phase was washed with saturated aqueous NaHCO$_3$, brine, dried (Na$_2$SO$_4$) and concentrated in vacuo. The crude product was purified with column chromatography on silica gel (5% MeOH/DCM) to afford the title compound (69.3 mg). MS m/z: 475.3 (M+H)$^+$. $^1$H NMR (400 MHz, DMSO-d6): δ 3.23 (s, 3H), 3.97 (s, 6H), 4.50 (s, 2H), 4.81 (s, 2H), 6.57 (t, 1H), 6.70-6.79 (m, 1H), 6.83-6.94 (m, 1H), 6.99 (s, 1H), 7.35 (d, 1H), 8.04 (s, 1H), 8.45 (s, 1H).

Step 2: I-2

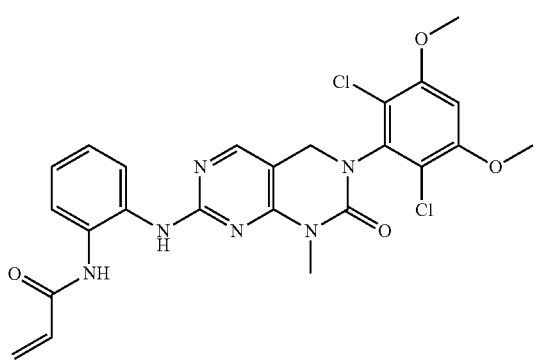 [SMILES: C=CC(=O)Nc1ccccc1Nc1ncc2c(n1)N(C)C(=O)N(c1c(Cl)c(OC)cc(OC)c1Cl)C2]

To a cooled (0° C.) solution of Intermediate 2 (69.1 mg, 0.15 mmol) and DIPEA (37.4 mg, 0.29 mmol) in THF (10 mL) was added acryloyl chloride (15.8 mg, 0.17 mmol). The reaction was allowed to stir at 0° C. for 10 min. The reaction was quenched with saturated aqueous NaHCO$_3$ and extracted with EtOAc (40 mL×3). The combined organic layers were washed with saturated aqueous NaHCO$_3$, dried (Na$_2$SO$_4$), filtered and concentrated in vacuo. The crude product was purified by column chromatography on silica gel (3% MeOH/DCM) to afford I-2 (23.3 mg). MS m/z: 529.3 (M+H)$^+$. $^1$H NMR (400 MHz, DMSO-d6): δ 3.22 (s, 3H), 3.96 (s, 6H), 4.52 (s, 2H), 5.77 (dd, 2.0 Hz, 1H), 6.27 (dd, 2.0 Hz, 1H), 6.47-6.54 (m, 1H), 6.99 (s, 1H), 7.108-7.13 (m, 1H), 7.17-7.22 (m, 1H), 7.56 (d, 1H), 7.80 (d, 1H), 8.09 (s, 1H), 8.59 (s, 1H), 9.76 (s, 1H).

Example 5: Synthesis of I-3

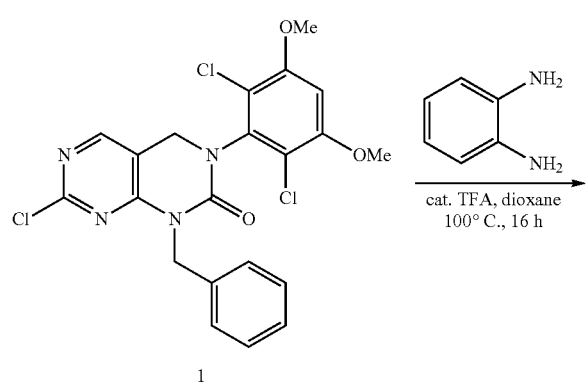

1

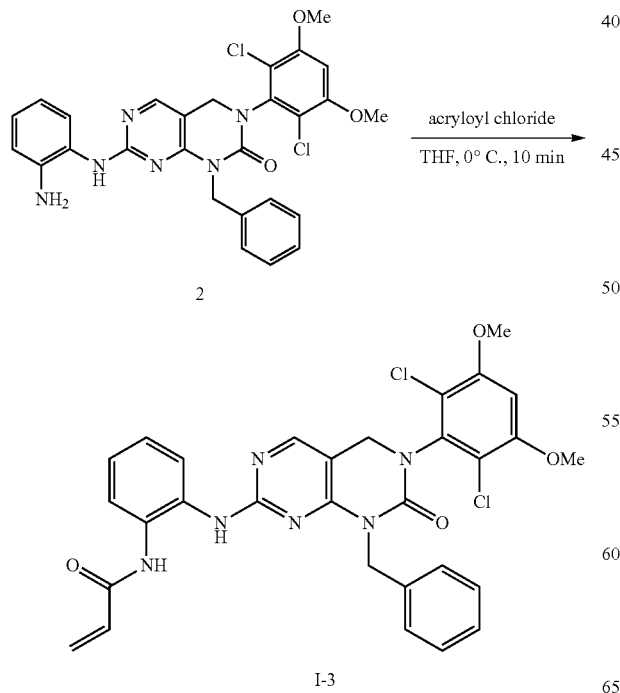

2

I-3

Step 1: Intermediate 2

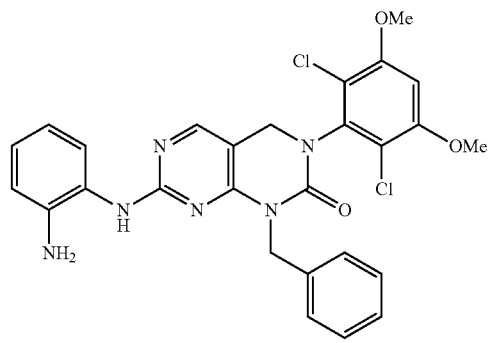 [SMILES: COc1cc(OC)c(Cl)c(N2Cc3cnc(Nc4ccccc4N)nc3N(Cc3ccccc3)C2=O)c1Cl]

To a mixture of Intermediate 1 (prepared as described in Example 1 using benzylamine in place of methylamine in Step 4 (54.0 mg, 0.11 mmol)), was added benzene-1,2-diamine (24.0 mg, 0.22 mmol) in 1,4-dioxane (2 mL) and one drop of TFA. The reaction mixture was heated at reflux in a sealed tube for 16 h after which it was cooled to ambient temperature and partitioned between EtOAc and water. The organic phase was washed with saturated aqueous NaHCO$_3$, brine, dried (Na$_2$SO$_4$) and concentrated in vacuo. The crude product was purified with column chromatography on silica gel (eluting with 100% EtOAc) to afford the title compound (34.5 mg). MS m/z: 551.0 (M+H)$^+$.

Step 2: I-3

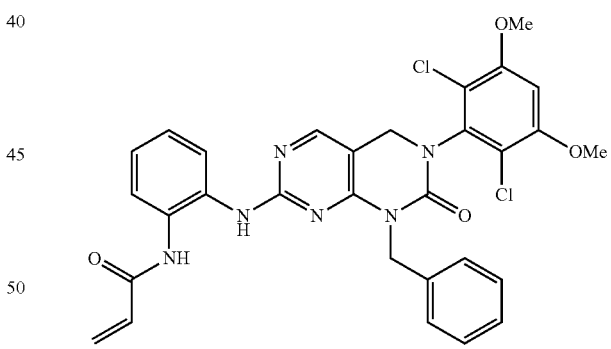

To a cooled (0° C.) solution of Intermediate 2 (14.0 mg, 0.025 mmol) in THF (1 mL) was added acryloyl chloride (1.9 uL, 0.023 mmol). The reaction was stirred at 0° C. for 10 min. after which it was purified by reverse phase HPLC (eluting with a gradient of 0-90% MeCN in water). Combined fractions were stirred with saturated aqueous NaHCO$_3$, extracted with DCM, and the organic layers concentrated to afford 10.6 mg of the title compound. MS m/z: 605.2 (M+H)$^+$.

Example 6: Synthesis of I-4

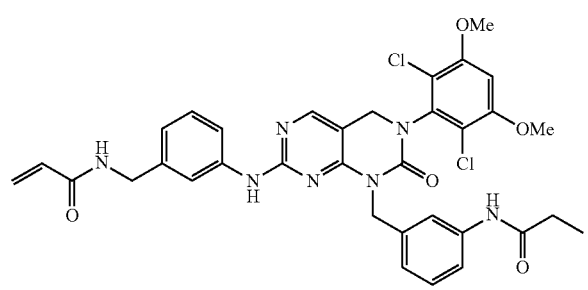 [SMILES: C=CC(=O)NCc1cccc(Nc2ncc3c(n2)N(Cc2cccc(NC(=O)CC)c2)C(=O)N(c2c(Cl)c(OC)cc(OC)c2Cl)C3)c1]

The title compound was prepared as outlined in Example 3 using tert-butyl 3-aminobenzylcarbamate in place of benzene-1,2-diamine in Step 1. MS m/z: 690.2 (M+H$^+$). $^1$H NMR (400 MHz, CD$_3$OD): δ: 8.07 (1H, s), 7.63 (1H, s), 7.45 (1H, s), 7.32 (2H, m), 7.23 (2H, m), 7.00 (2H, m), 6.90 (1H, s), 6.26 (2H, m), 5.66 (1H, m), 5.28 (2H, s), 4.68 (2H, s), 4.33 (2H, s), 3.96 (6H, s), 2.34 (2H, q), 1.89 (3H, t).

Example 7: Synthesis of I-5

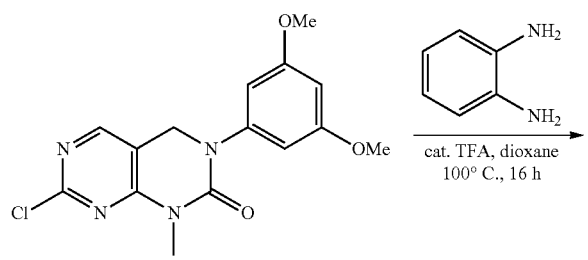

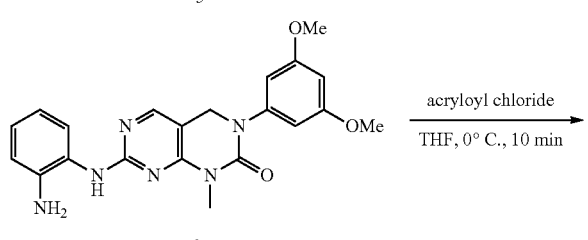

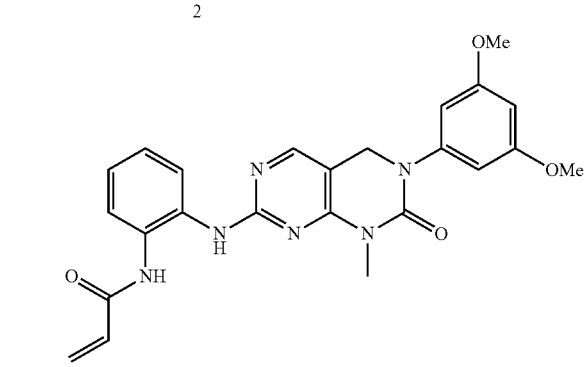

I-5

Step 1: Intermediate 2

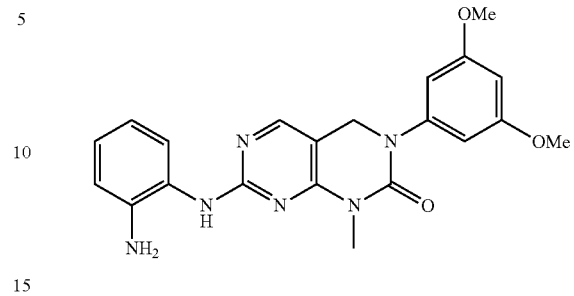

To a mixture of Intermediate 5 (30.1 mg, 0.09 mmol) from Example 1 and benzene-1,2-diamine (19.5 mg, 0.18 mmol) in 1,4-dioxane (1 mL) was added one drop of TFA. The reaction mixture was heated at reflux in a sealed tube for 16 h after which it was cooled to ambient temperature and partitioned between EtOAc and water. The organic phase was washed with saturated aqueous NaHCO$_3$, brine, dried (Na$_2$SO$_4$) and concentrated in vacuo. The crude product was purified through column chromatography on silica gel (eluting with 100% EtOAc) to afford the title compound (16.7 mg). MS m/z: 551.0 (M+H)$^+$.

Step 2: I-5

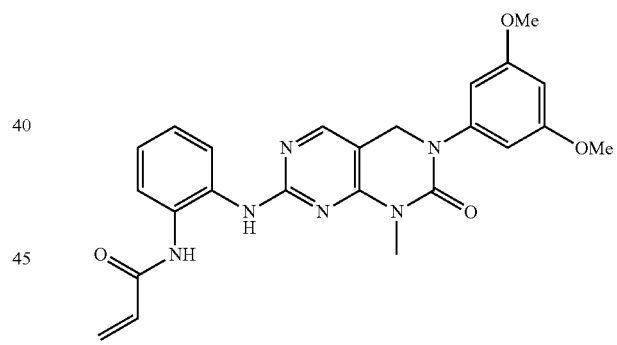

To a cooled (0° C.) solution of Intermediate 2 (14.0 mg, 0.034 mmol) in THF (1 mL) was added acryloyl chloride (2.8 uL, 0.034 mmol). The reaction was stirred at 0° C. for 10 min. after which it was purified by reverse phase HPLC (eluting with a gradient of 0-90% MeCN in water with 0.1% TFA). Combined fractions were concentrated, stirred with saturated aqueous NaHCO$_3$, extracted with DCM, and the organic layers concentrated to afford 14.6 mg of the title compound. MS m/z: 407.2 (M+H)$^+$. $^1$H NMR (400 MHz, DMSO-d6): δ 3.23 (s, 3H), 3.75 (s, 6H), 4.72 (s, 2H), 5.79 (dd, 1H), 6.28 (dd, 1H), 6.56-6.45 (m, 2H), 6.60 (s, 2H), 7.25-7.27 (m, 2H), 7.59 (d, 1H), 7.72 (d, 1H), 8.09 (s, 1H), 9.41 (br s, 1H), 9.88 (s, 1H).

Example 8: Synthesis of I-6
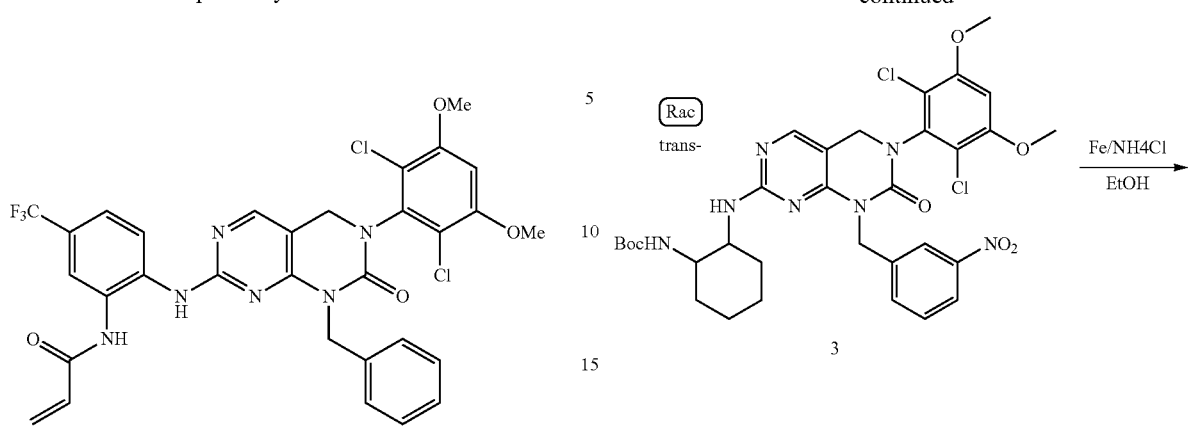
Compound I-6 was prepared as described in Example 5 using tert-butyl (2-amino-4-(trifluoromethyl)phenyl)carbamate instead of benzene-1,2-diamine in Step 1. MS m/z: 673.1 (M+H)+
Example 9: Synthesis of I-7, (Racemic)
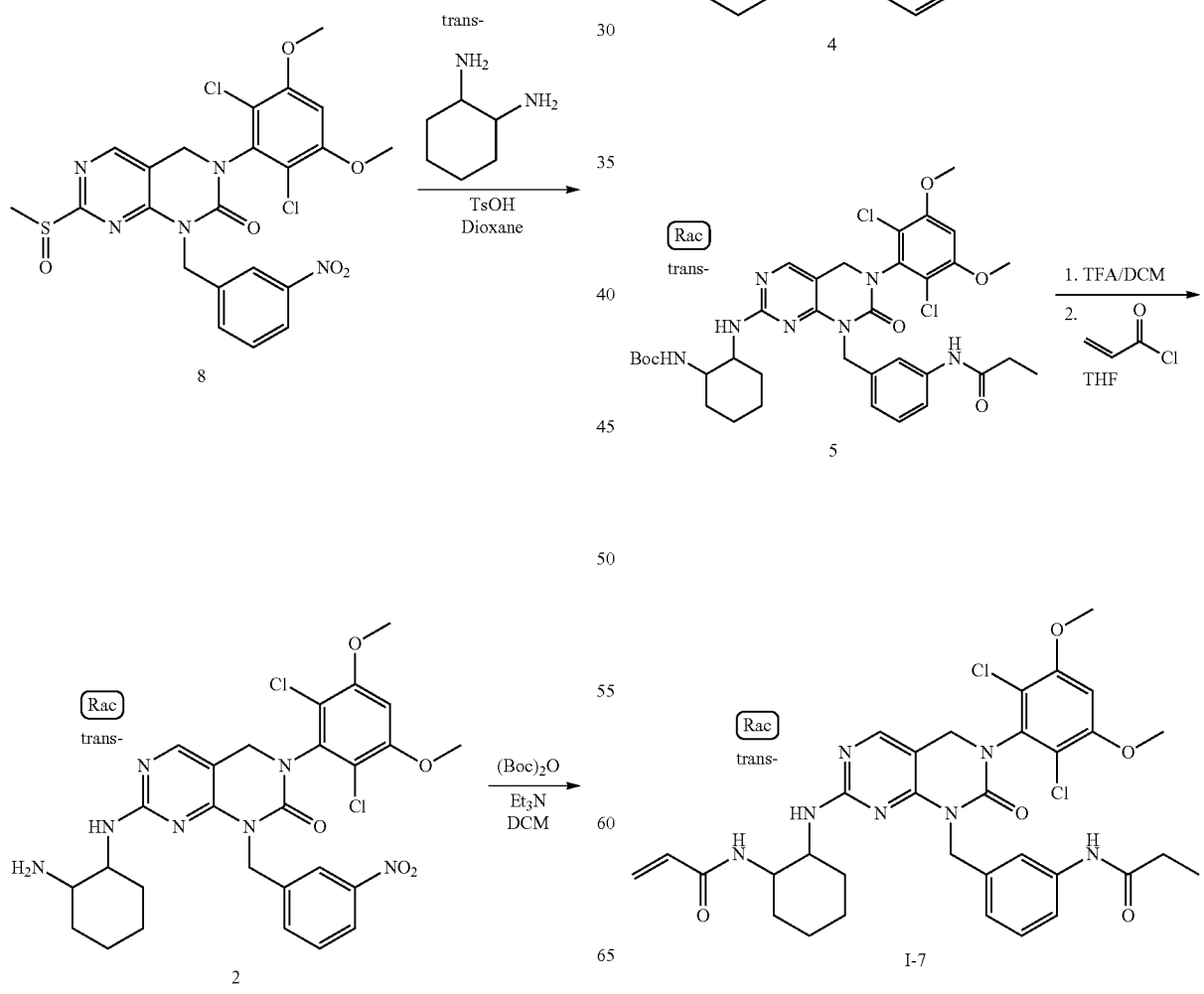

Step 1: Intermediate 2

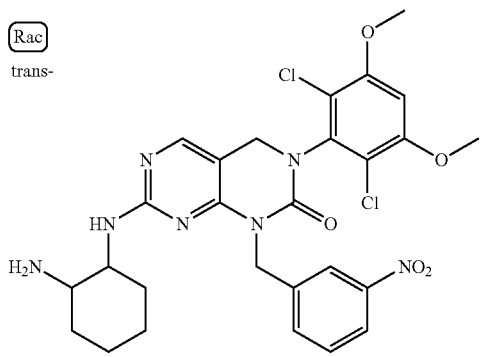 [SMILES: COc1cc(OC)c(Cl)c(N2Cc3cnc(NC4CCCCC4N)nc3N(Cc3cccc([N+](=O)[O-])c3)C2=O)c1Cl]

To a solution of Intermediate 8 from Example 2 (150 mg, 0.27 mmol) in dioxane (15 mL) was added trans-cyclohexane-1,2-diamine (62 mg, 0.54 mmol) and catalytic p-toluene sulfonic acid. The resultant mixture was heated at reflux for 16 h. The reaction mixture was partitioned between EtOAc and saturated aqueous NaHCO$_3$. The organic layer was separated, dried (Na$_2$SO$_4$) and evaporated to dryness. The crude was purified by prep-TLC (6.6% methanol in dichloromethane) to afford the title compound (150 mg). MS m/z: 602.3 (M+H)$^+$.

Step 2: Intermediate 3

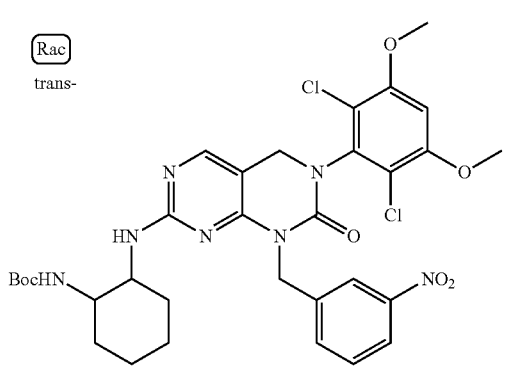 [SMILES: COc1cc(OC)c(Cl)c(N2Cc3cnc(NC4CCCCC4NC(=O)OC(C)(C)C)nc3N(Cc3cccc([N+](=O)[O-])c3)C2=O)c1Cl]

To a solution of Intermediate 2 (150 mg, 0.25 mmol) in DCM (15 mL) was added triethylamine (50 mg, 0.49 mmol) and di-tert-butyl dicarbonate (65 mg, 0.29 mmol). The resultant mixture was allowed to stir at ambient temperature for 2 h. The reaction mixture was partitioned between EtOAc and water. The organic phase was separated, washed with 1 N HCl, saturated aqueous NaHCO$_3$, dried over anhydrous sodium sulfate and evaporated to dryness to afford the title compound (130 mg). MS m/z: 702.3 (M+H)$^+$.

Step 3: Intermediate 4

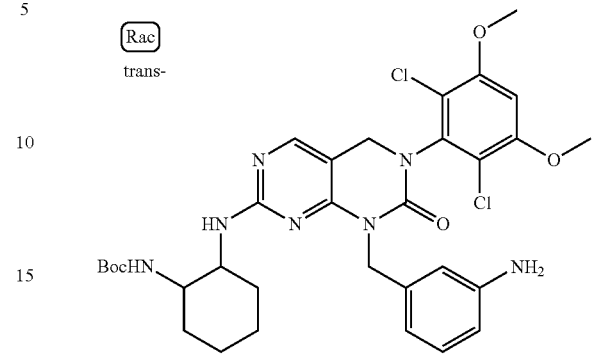

To a suspension of Intermediate 3 (130 mg, 0.180 mmol) in ethanol (15 mL) and saturated aqueous NH$_4$Cl (2 mL) was added Fe powder (83.0 mg, 1.48 mmol) and the resultant mixture was heated at reflux for 2 h after which it was diluted with DCM (60 mL) the organic phase was separated, dried over anhydrous sodium sulfate, and evaporated to dryness to afford the titled product (120 mg).

Step 4: Intermediate 5

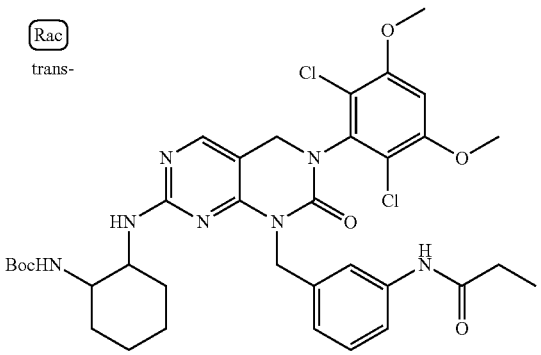 [SMILES: CCC(=O)Nc1cccc(CN2C(=O)N(c3c(Cl)c(OC)cc(OC)c3Cl)Cc3cnc(NC4CCCCC4NC(=O)OC(C)(C)C)nc32)c1]

Intermediate 4 (110 mg, 0.16 mmol), propionic acid (18.0 mg, 0.24 mmol) and HATU (124 mg, 0.33 mmol) were dissolved in DMF (10 mL). The reaction mixture was cooled to 0° C. under N$_2$ and DIPEA (63 mg, 0.49 mmol) was added slowly and the mixture was allowed to stir at ambient temperature for 16 h. The reaction mixture was partitioned between EtOAc and water. The organic phase was separated, washed with water, dried over anhydrous sodium sulfate and evaporated to dryness. The residue was purified by column chromatography with silica gel (4% MeOH in DCM) to afford the title product (80 mg). MS m/z: 728.4 (M+H)$^+$

Step 5: I-7

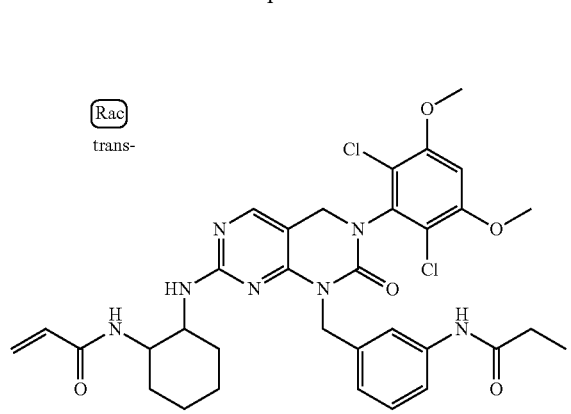

Intermediate 5 (80.0 mg, 0.11 mmol) was dissolved in DCM (2 mL) followed by addition of TFA (5 mL). The resultant mixture was allowed to stir at ambient temperature for 1 h after which it was concentrated. The residue was taken up in DCM, and DIPEA was added until a pH=7 was achieved. The solution was cooled to 0° C., acryloyl chloride (15.0 mg, 0.17 mmol) was added and the mixture was allowed to stir at 0° C. for 10 min. The reaction was quenched by addition of saturated aqueous NaHCO$_3$, extracted with EtOAc, and the organic layer was dried over anhydrous Na$_2$SO$_4$ and concentrated. The residue was purified by prep-TLC (4% MeOH in DCM) to afford the title compound (20 mg, 26%, two steps). MS m/z: 682.4 (M+H)$^+$. $^1$H NMR (400 MHz, DMSO-d$_6$): δ: 1.02-1.11 (t, 3H), 1.16-1.30 (m, 3H), 1.49-1.70 (m, 3H), 1.76-1.94 (m, 2H), 2.28 (q, 2H), 3.66-3.75 (m, 1H), 3.96 (s, 6H), 4.50 (s, 2H), 5.11 (s, 2H), 5.46-5.54 (m, 1H), 6.01 (d, 1H), 6.03-6.15 (m, 1H), 6.61-6.70 (m, 1H), 6.99 (s, 1H), 6.94 (d, 1H), 7.18 (s, 1H), 7.34-7.43 (m, 1H), 7.57-7.65 (m, 1H), 7.96 (s, 1H), 9.76 (s, 1H).

Example 10: Synthesis of I-8, (Racemic)

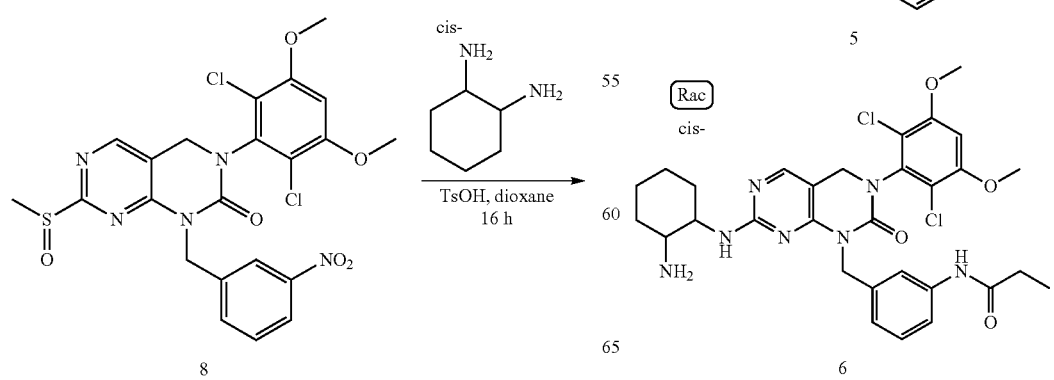

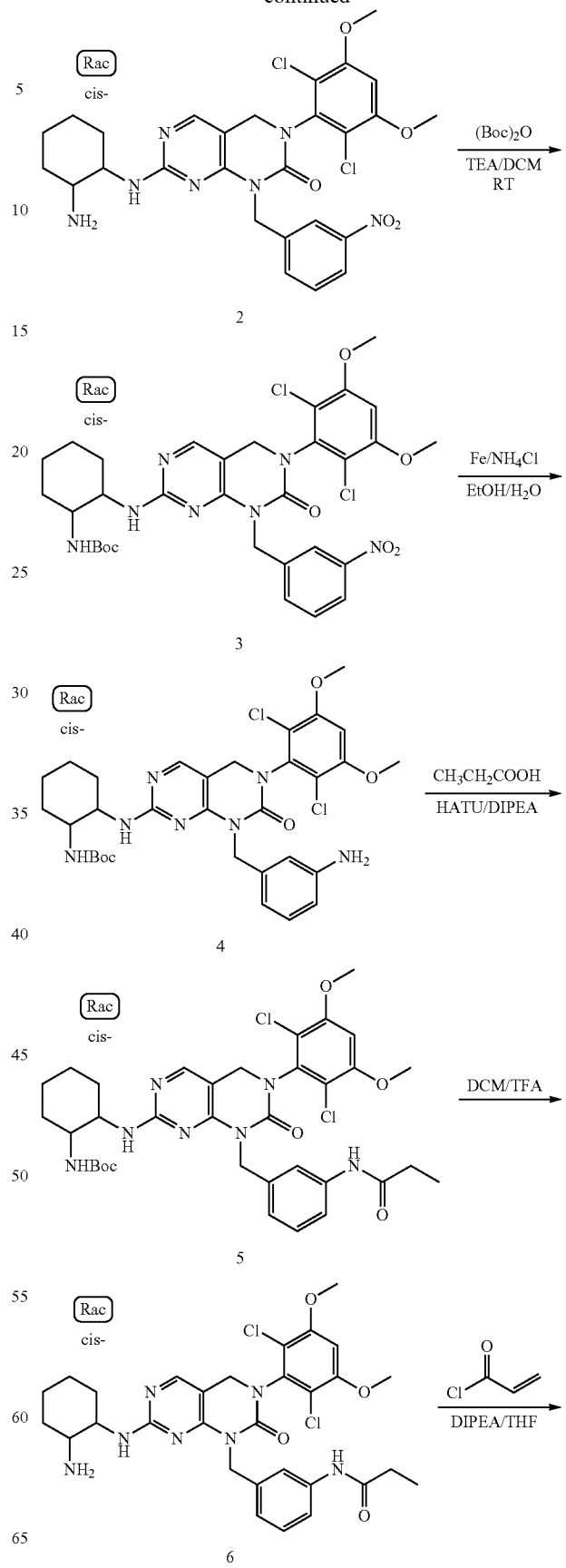

289

-continued

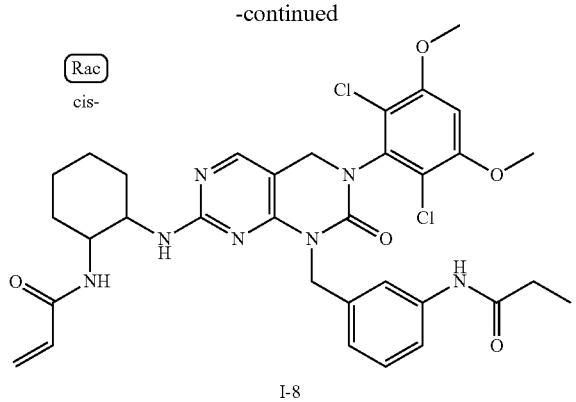

I-8

Step 1: Intermediate 2

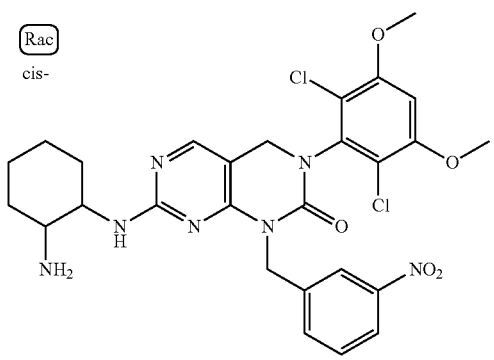 [SMILES: COc1cc(OC)c(Cl)c(N2Cc3cnc(NC4CCCCC4N)nc3N(Cc3cccc([N+](=O)[O-])c3)C2=O)c1Cl]

To a solution of Intermediate 8 from Example 2 (150 mg, 0.27 mmol) in 1,4-dioxane (8 mL) was added cis-cyclohexane-1,2-diamine (93.0 mg, 0.82 mmol) and p-TSA (23.4 mg, 0.14 mmol). The reaction mixture was heated at 100° C. for 16 h. Water was added and the resultant mixture was extracted with EtOAc (50 mL×3). The combined organic layers were dried over $Na_2SO_4$, filtered and concentrated in vacuo to afford the title compound (164 mg) which was used without further purification. MS m/z: 602.3 $[M+1]^+$.

Step 2: Intermediate 3

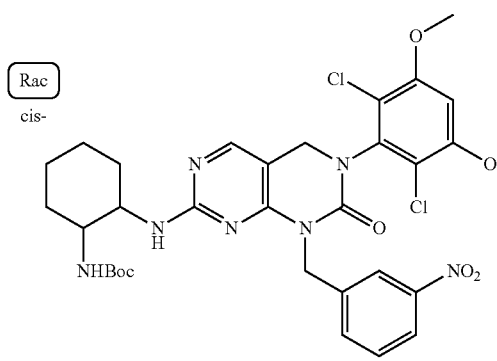

To a solution of Intermediate 2 (164 mg, 0.27 mmol) in DCM (6 mL) was added triethylamine (82.6 mg, 0.82 mmol)

290 and di-tert-butyl dicarbonate (89.0 mg, 0.41 mmol). The reaction mixture was allowed to stir at ambient temperature for 2 h. The reaction mixture was concentrated and the crude product was subjected to column chromatography on silica gel (2% MeOH/DCM) to afford the titled compound (159 mg). $^1$H NMR (400 MHz, DMSO-d6): δ 1.34 (s, 9H), 1.42-1.52 (m, 2H), 1.56-1.77 (m, 2H), 3.25 (d, 2H), 3.48-3.64 (m, 1H), 3.75-3.91 (m, 1H), 3.97 (s, 6H), 4.55 (s, 2H), 5.25 (s, 2H), 6.31-6.47 (m, 1H), 6.54-6.64 (m, 1H), 7.01 (s, 1H), 7.62 (t, 1H), 7.76 (d, 1H), 8.02 (s, 1H), 8.07-8.18 (m, 2H).

Step 3: Intermediate 4

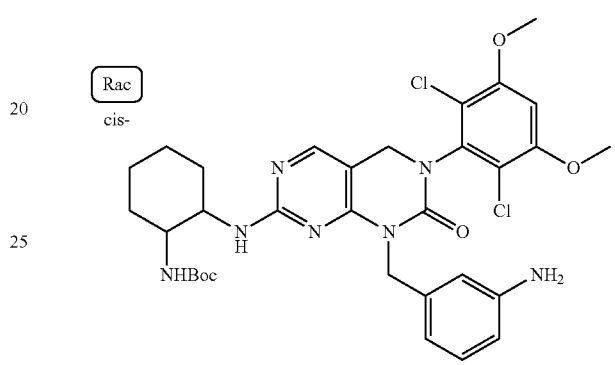

To a solution of Intermediate 3 (153 mg, 0.22 mmol) in EtOH (10 mL) and water (5 mL) was added Fe power (72.0 mg, 1.31 mmol) and $NH_4Cl$ (70.0 mg, 1.31 mmol). The mixture was heated at reflux for 2 h. The reaction mixture was filtered and the filtrate was concentrated in vacuo. To the residue was added water and the aqueous solution extracted with EtOAc (50 mL×3). The combined organic layers were washed with saturated $NaHCO_3$, dried over $Na_2SO_4$, filtered and concentrated in vacuo to afford the titled compound (96.7 mg) which was used without purification. MS m/z: 672.4 $(M+H)^+$ Step 4: Intermediate 5

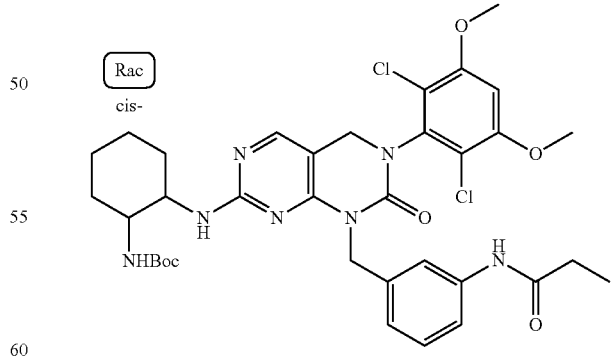

To a solution of Intermediate 4 (96.7 mg, 0.14 mmol) in DMF (6 mL) was added propionic acid (16.0 mg, 0.22 mmol) and HATU (109.5 mg, 0.29 mmol). The mixture was cooled to 0° C. and DIPEA (55.7 mg, 0.43 mmol) was added. The reaction mixture was allowed to stir at ambient temperature for 16 h. Water was added and the mixture was extracted with EtOAc (50 mL×3). The combined organic layers were washed with water, dried (Na₂SO₄), and concentrated in vacuo. The crude product was subjected to column chromatography on silica gel (3% MeOH/DCM) to afford the titled compound (98.0 mg). MS m/z: 728.5 (M+H)⁺

Step 5: Intermediate 6

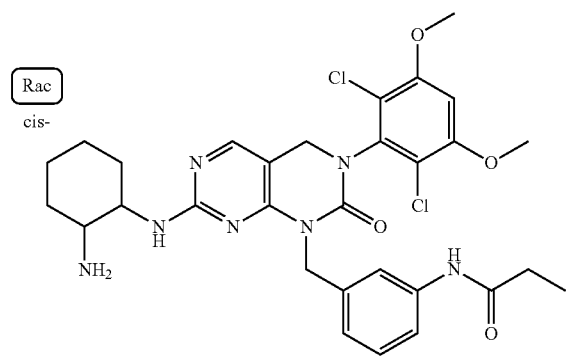 [SMILES: CCC(=O)Nc1cccc(CN2C(=O)N(c3c(Cl)c(OC)cc(OC)c3Cl)Cc3cnc(NC4CCCCC4N)nc32)c1]

To a solution of Intermediate 5 (98.0 mg, 0.13 mmol) in DCM (2 mL) was added TFA (2 mL) and the reaction mixture was allowed to stir at ambient temperature for 30 min. The reaction mixture was concentrated in vacuo, water was added and the resultant mixture was extracted with EtOAc (50 mL×3). The combined organic layers were washed with saturated aqueous NaHCO₃, dried (Na₂SO₄), and concentrated in vacuo to afford the title compound (88.3 mg) which was used without further purification. MS m/z: 628.4 (M+H)⁺

Step 6: I-8

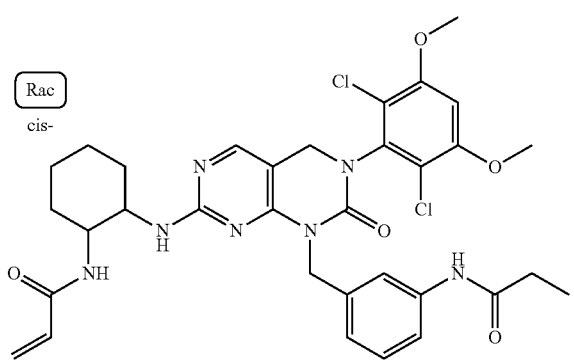 [SMILES: C=CC(=O)NC1CCCCC1Nc1ncc2c(n1)N(Cc1cccc(NC(=O)CC)c1)C(=O)N(c1c(Cl)c(OC)cc(OC)c1Cl)C2]

To a cooled (0° C.) solution of Intermediate 6 (88.3 mg, 0.14 mmol) and DIPEA (36.1 mg, 0.28 mmol) in 4 mL of THF was added acryloyl chloride (15.3 mg, 0.17 mmol). The reaction was allowed to stir at 0° C. for 10 min. The mixture was quenched with saturated aqueous NaHCO₃ and extracted with EtOAc (40 mL×3). The combined organic layers were washed with saturated aqueous NaHCO₃, dried (Na₂SO₄), and concentrated in vacuo. The resultant residue was subjected to column chromatography on silica gel (5% MeOH/DCM) to afford the title compound (55.9 mg) MS m/z: 682.3 (M+H)⁺. ¹H NMR (400 MHz, DMSO-d6): δ 1.07 (t, 3H), 1.22-1.83 (m, 8H), 2.28 (q, 2H), 3.96 (s, 6H), 4.13 (br, 1H), 4.51 (s, 2H), 5.04-5.14 (m, 2H), 5.55 (dd, 2.4 Hz, 1H), 5.74 (s, 1H), 6.05 (dd, 1H), 6.22-6.41 (m, 1H), 6.60 (br s, 1H), 6.91-7.05 (m, 2H), 7.18 (t, 1H), 7.41 (d, 1H), 7.58 (s, 1H), 7.67 (d, 1H), 7.98 (s, 1H), 9.73 (s, 1H).

Example 11: Synthesis of I-9

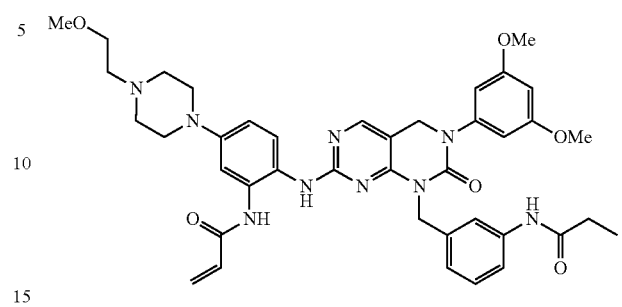

The title compound was prepared as described in Example 17 (below) using 1-(2-methoxyethyl)piperazine in place of N-ethylpiperidine in Step 2 and using an intermediate prepared in a manner as described for Intermediate 6 in Example 2, which was oxidized using mCPBA as described in Example 2. MS m/z: 750.3 (M+H⁺). ¹H NMR (400 MHz, CD₃OD): δ: 7.97 (1H, s), 7.63 (1H, s), 7.40 (2H, d), 7.33 (2H, m), 7.16 (1H, t), 6.87 (2H, m), 6.57 (2H, s), 6.45 (1H, dd), 6.39 (1H, m), 5.75 (1H, dd), 5.13 (2H, s), 4.75 (2H, s), 3.77 (6H, s), 3.76 (1H, m), 3.43 (3H, s), 2.36 (2H, q), 1.62 (3H, t)

Example 12: Synthesis of I-10

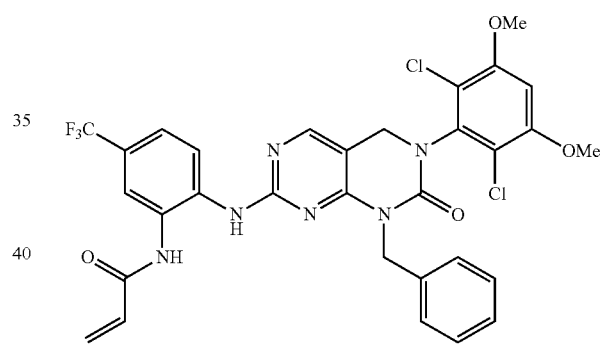

Compound I-10 was prepared as described in Example 5 using tert-butyl (2-amino-5-(trifluoromethyl)phenyl)carbamate instead of benzene-1,2-diamine in Step 1. MS m/z: 673.1 (M+H⁺).

Example 13: Synthesis of I-11

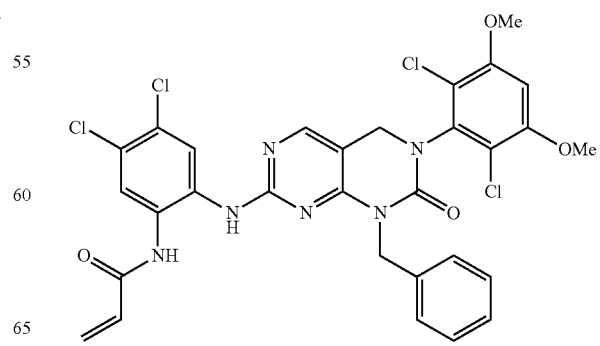

Compound I-11 was prepared as described in Example 5 using 4,5-dichlorobenzene-1,2-diamine instead of benzene-1,2-diamine in Step 1. MS m/z: 673.1 (M+H⁺).

Example 14: Synthesis of I-12

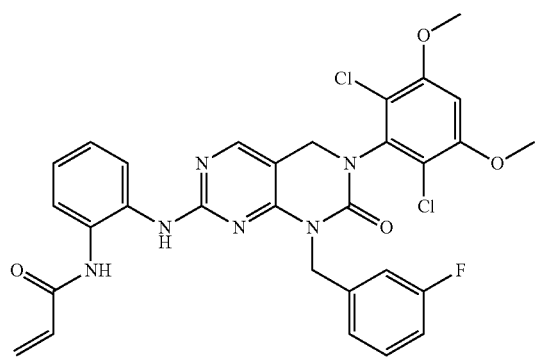

Compound I-12 was prepared as described in Example 5 using (3-fluorophenyl)methanamine in place of methylamine in Step 1. MS m/z: 623.3 (M+H⁺).

Example 15: Synthesis of I-13

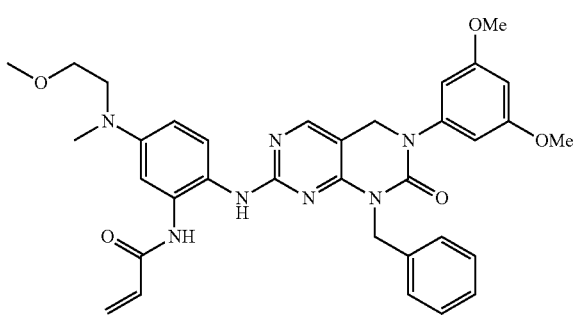 [SMILES: C=CC(=O)Nc1cc(N(C)CCOC)ccc1Nc1ncc2c(n1)N(Cc1ccccc1)C(=O)N(c1cc(OC)cc(OC)c1)C2]

The title compound was prepared as outlined in Example 17 (below) using 2-methoxy-N-methylethanamine in place of N-ethylpiperidine in Step 2 and using a derivative of Intermediate 5 from Example 1 (prepared using benzylamine in place of methylamine in Step 5) in place of Intermediate 4 in Step 4. MS m/z: 624.3 (M+H⁺). $^1$H NMR (400 MHz, CDCl$_3$): δ: 7.92 (1H, s), 7.29 (1H, d), 7.21 (6H, m), 6.78 (1H, dd), 6.55 (2H, s), 6.46 (1H, s), 6.41 (2H, m), 5.77 (1H, dd), 5.15 (2H, s), 4.51 (2H, s), 3.78 (6H, s), 3.60 (2H, t), 3.54 (2H, t), 3.06 (3H, t).

Example 16: Synthesis of I-14

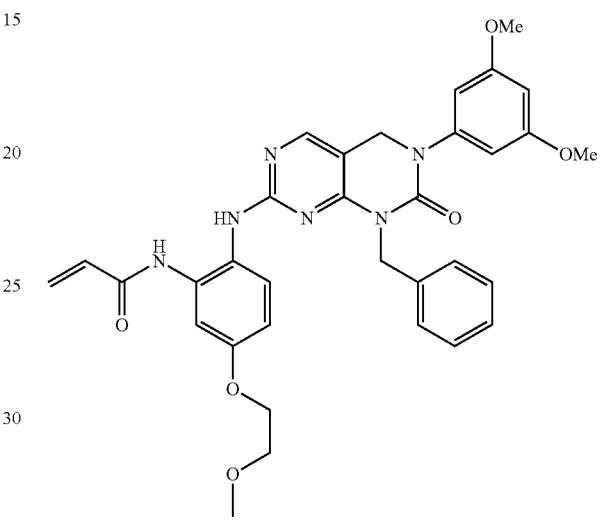

Compound I-14 was prepared as described in Example 17 using 2-methoxy-1-ethanol in place of N-ethylpiperidine in Step 2 and using a derivative of Intermediate 5 from Example 1 (prepared using benzylamine in place of methylamine in Step 5) in place of Intermediate 4 in Step 4. MS m/z: 611.3 (M+H⁺).

Example 17: Synthesis of I-15

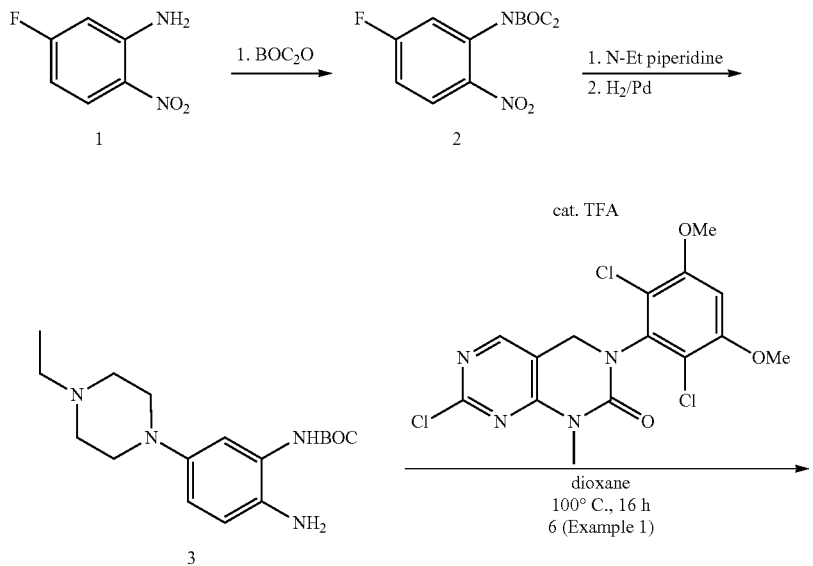

-continued

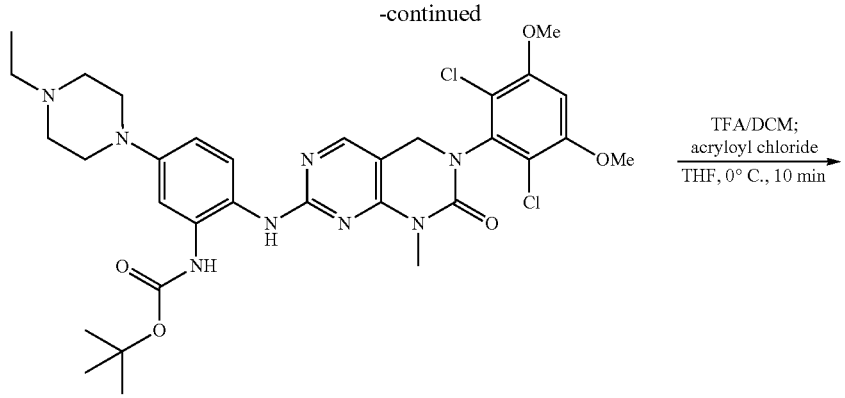

5

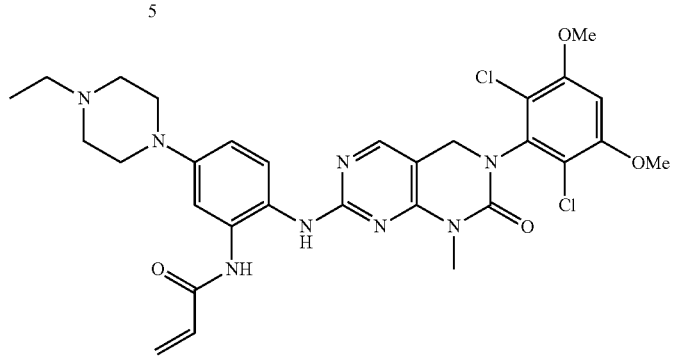

I-15

Step 1: Intermediate 2

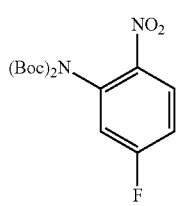

To a solution of Intermediate 1 (2.34 g, 15.0 mmol) in DMF (50 mL) was added (Boc)$_2$O (6.60 g, 30.3 mmol) and DMAP (600 mg, 4.9 mmol). The reaction was stirred at RT overnight. After removing DMF under reduced pressure, the product was isolated by silica gel chromatography. MS m/z: 357.2 (M+H$^+$).

Step 2

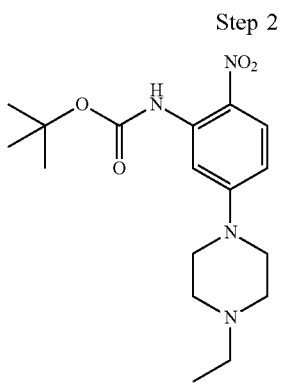

Intermediate 2 (300 mg, 084 mmol) and N-ethylpiperidine (0.30 mL, 2.19 mmol) were mixed in DMF (3.0 mL). The mixture was heated at 110° C. for 3.0 h. Then, the reaction was concentrated in vacuo and purified by flash chromatography on silica gel to afford 330 mg of the title compound. MS m/z: 351.3 (M+H$^+$).

Step 3: Intermediate 3

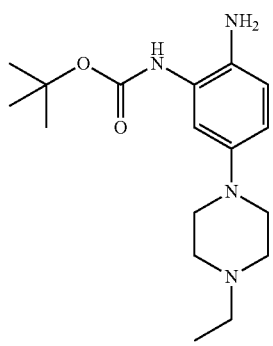 [SMILES: CCN1CCN(c2ccc([N+](=O)[O-])c(NC(=O)OC(C)(C)C)c2)CC1]

The product from Step 2 was dissolved in MeOH (10 mL), and 10 wt % Pd/C (100 mg) was added. The reaction mixture was allowed to stir at ambient temperature under an H$_2$ balloon for 4.5 hr. The reaction mixture was filtered through a short plug of celite and concentrated in vacuo to afford 275 mg of the title compound which was used without purification. MS m/z: 292.1 (M+H$^+$).

Step 4: Intermediate 5

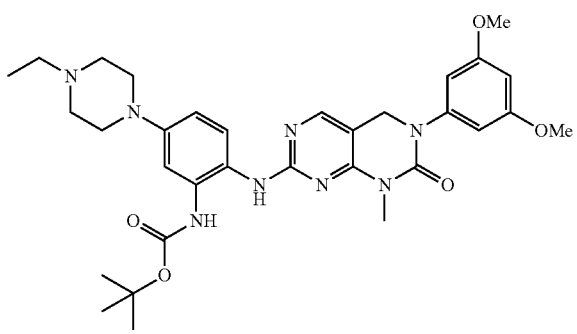 [SMILES: CCN1CCN(c2ccc(Nc3ncc4c(n3)N(C)C(=O)N(c3cc(OC)cc(OC)c3)C4)c(NC(=O)OC(C)(C)C)c2)CC1]

Intermediate 3 (200 mg, 0.68 mmol), Intermediate 6 (from Example 1) (150 mg, 0.37 mmol), and TFA (5.0 μL) were taken up in 1,4-dioxane (2.0 mL) and the reaction mixture was heated at 110° C. for 16 h. The reaction mixture was allowed to cool to ambient temperature, concentrated and purified by silica gel chromatography to afford 110 mg of the title compound. MS m/z: 619.8 (M+H)$^+$.

Step 4: I-15

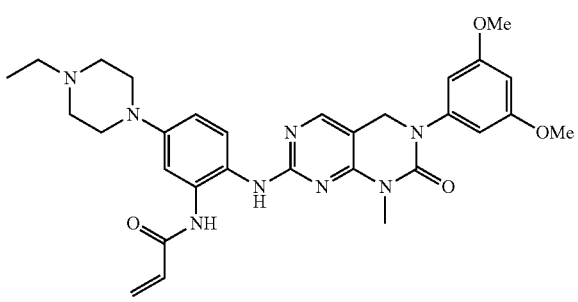 [SMILES: C=CC(=O)Nc1cc(N2CCN(CC)CC2)ccc1Nc1ncc2c(n1)N(C)C(=O)N(c1cc(OC)cc(OC)c1)C2]

Intermediate 5 was dissolved in 20% TFA/DCM at ambient temperature and allowed to stir for 3.5 h. The reaction mixture was concentrated, the resultant residue was taken up in DCM and treated with silica supported carbonate and the mixture filtered. The filtrate was concentrated then dissolved in THF (2.0 mL) and cooled to −10° C., followed by addition of acryloyl chloride (7.0 μL, 0.086 mmol). After 10 min, the reaction was concentrated and purified by prep-HPLC. MS m/z: 573.2 (M+H)$^+$. $^1$H NMR (400 MHz, CDCl$_3$): δ: 8.67 (1H, s), 7.78 (1H, s), 7.67 (1H, s), 7.48 (1H, d), 6.67 (1H, dd), 6.40 (5H, m), 5.74 (1H, dd), 4.63 (2H, s), 3.77 (6H, s), 3.66 (4H, m), 3.41 (2H, m), 3.33 (3H, s), 3.14 (2H, m), 2.89 (2H, m), 1.39 (3H, t).

Example 18: Synthesis of I-16

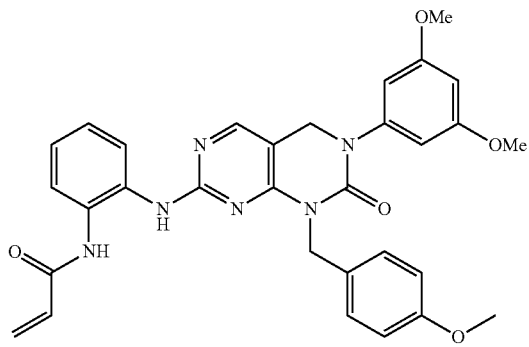 [SMILES: C=CC(=O)Nc1ccccc1Nc1ncc2c(n1)N(Cc1ccc(OC)cc1)C(=O)N(c1cc(OC)cc(OC)c1)C2]

Compound I-16 was prepared as described in Example 5, using (4-methoxyphenyl)methanamine in place of methylamine to prepare the starting material. MS m/z: 635.4 (M+H)$^+$.

Example 19: Synthesis of I-17

The title compound was prepared as described in Example 17 using morpoholine in place of N-ethylpiperidine in Step 2 and Intermediate 5 from Example 1 in place of Intermediate 6 in Step 4. MS m/z: 546.2 (M+H)$^+$. $^1$H NMR (400 MHz, CD$_3$OD): δ: 7.87 (1H, s), 7.40 (1H, d), 7.25 (1H, s), 6.98 (1H, dd), 6.54 (2H, s), 6.46 (1H, m), 6.35 (1H, dd), 5.80 (1H, dd), 4.71 (2H, s), 3.84 (4H, t), 3.77 (6H, s), 3.38 (3H, s), 3.21 (4H, t).

Example 20: Synthesis of I-18 (Racemic)

I-18

Compound I-18 was prepared as described in Example 21 using mCPBA instead of SO$_2$Cl$_2$ in Step 1 (mCPBA oxidation is described in Example 2, Step 7). MS m/z: 476.4 (M+H)$^+$.

Example 21: Synthesis of I-19, (Racemic)

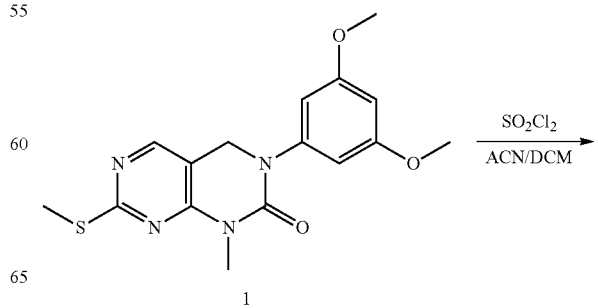

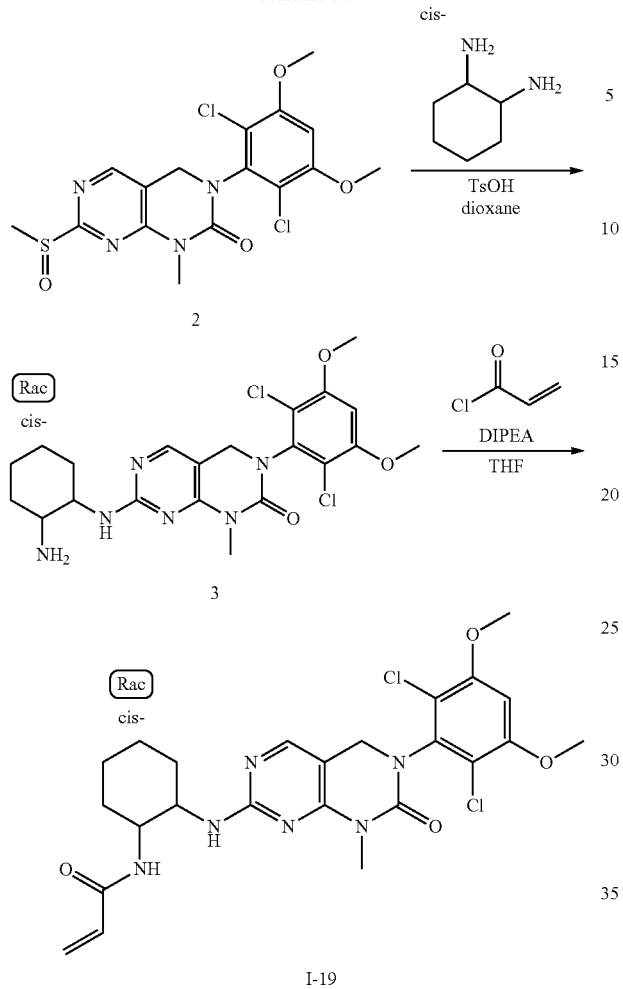

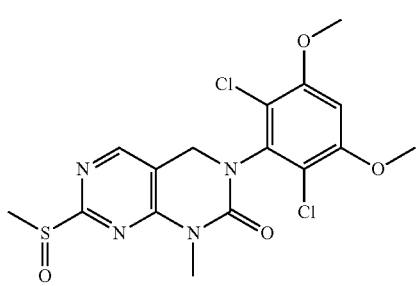

Step 1: Intermediate 2

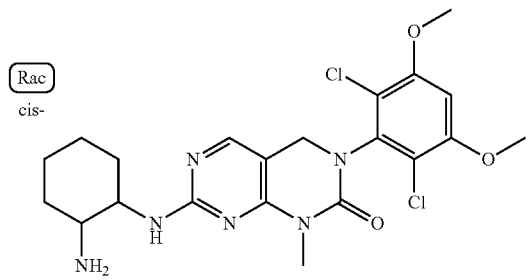 [SMILES: COc1cc(OC)c(Cl)c(N2Cc3cnc(NC4CCCCC4N)nc3N(C)C2=O)c1Cl]

To an ice-cooled solution of Intermediate 1, prepared as described in Example 2 using methylamine in place of 3-nitrobenzylamine in Step 2 and skipping Step 6 (250 mg, 0.72 mmol), in MeCN (2 mL) and DCM (4 mL) was added sulfuryl chloride (0.12 mL, 1.44 mmol). The reaction was stirred at 0° C. for 15 min. The reaction was quenched with saturated aqueous NaHCO₃ and the aqueous layer was extracted with DCM (30 mL×3). The combined organic layers were dried (Na₂SO₄), filtered and concentrated in vacuo. The crude product was purified by column chromatography on silica gel (2% MeOH/DCM) to afford 192 mg, of the title compound. $^1$H NMR (400 MHz, DMSO-d6): δ 2.96 (s, 3H), 3.41 (s, 3H), 4.03 (s, 6H), 4.81 (s, 2H), 7.08 (s, 1H), 8.64 (s, 1H).

Step 2: Intermediate 3

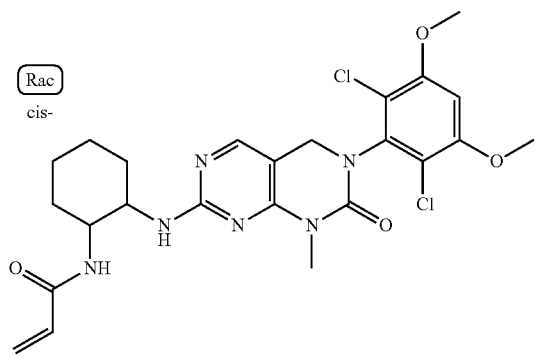 [SMILES: C=CC(=O)NC1CCCCC1Nc1ncc2c(n1)N(C)C(=O)N(c1c(Cl)c(OC)cc(OC)c1Cl)C2]

To a solution of Intermediate 2 (60.0 mg, 0.14 mmol) in 1,4-dioxane (5 mL) was added cis-cyclohexane-1,2-diamine (47.7 mg, 0.42 mmol) and p-TSA (12.0 mg, 0.07 mmol). The reaction was heated at 105° C. overnight. The mixture was cooled to ambient temperature, water was added, and the resultant mixture was extracted with EtOAc (50 mL×3). The combined organic layers were washed with saturated aqueous NaHCO₃, dried (Na₂SO₄), filtered and concentrated in vacuo. The crude product was purified by column chromatography on silica gel (10% MeOH/DCM) to afford 73.9 mg, of the title compound. MS m/z: 481.3 (M+1)⁺

Step 3: I-19

To an ice-cooled solution of Intermediate 3 (73.9 mg, 0.15 mmol) and DIPEA (39.7 mg, 0.31 mmol) in THF (3 mL) was added acryloyl chloride (16.7 mg, 0.18 mmol). The reaction was allowed to stir at 0° C. for 10 min. The reaction was quenched with saturated aqueous NaHCO₃ and extracted with EtOAc (30 mL×3). The combined organic layers were washed with saturated aqueous NaHCO₃, dried (Na₂SO₄), filtered and concentrated in vacuo. The crude product was purified by column chromatography on silica gel (5% MeOH/DCM) to afford 40.7 mg of the title compound. MS m/z: 535.3 (M+1)⁺. $^1$H NMR (400 MHz, DMSO-d6): δ1.35-1.84 (m, 8H), 3.96 (s, 6H), 4.11-4.29 (m, 2H), 4.44 (s, 2H), 5.50-5.75 (m, 1H), 5.99-6.25 (m, 1H), 6.23-6.47 (m, 1H), 6.52-6.86 (m, 1H), 6.97-7.18 (m, 1H), 7.66-7.90 (m, 1H), 7.96-8.14 (m, 1H).

Example 22: Synthesis of I-20

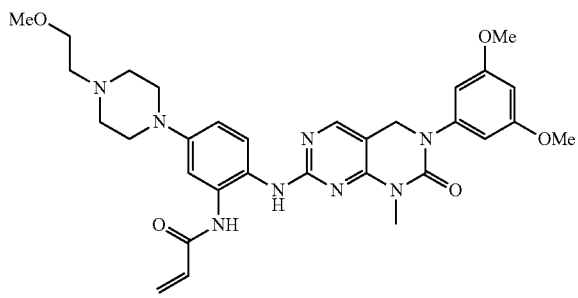 [SMILES: C=CC(=O)Nc1cc(N2CCN(CCOC)CC2)ccc1Nc1ncc2c(n1)N(C)C(=O)N(c1cc(OC)cc(OC)c1)C2]

The title compound was prepared as described in Example 17 using 1-(2-methoxyethyl)piperazine in place of N-ethyl-piperidine in Step 2 and Intermediate 5 (from Example 1) in place of Intermediate 6 in Step 4. MS m/z: 603.3 (M+H$^+$). $^1$H NMR (400 MHz, CD$_3$OD): δ: 7.94 (1H, s), 7.50 (1H, d), 7.40 (1H, d), 7.00 (1H, dd), 6.54 (2H, s), 6.44 (2H, m), 6.39 (1H, m), 5.80 (1H, dd), 4.71 (2H, s), 3.79 (6H, s), 3.44 (5H, m), 3.31 (3H, s).

Example 23: Synthesis of I-21

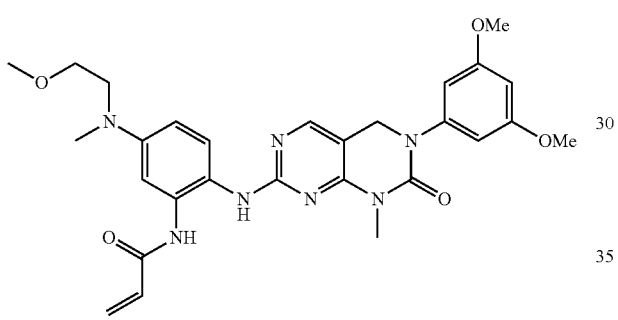

The title compound was prepared as described in Example 17 using 2-methoxy-N-methylethanamine in place of N-ethylpiperidine in Step 2 and Intermediate 5 (from Example 1) in place of Intermediate 6 in Step 4. MS m/z: 548.3 (M+H$^+$). $^1$H NMR (400 MHz, CD$_3$OD): δ: 7.86 (1H, s), 7.39 (1H, d), 7.15 (1H, s), 6.85 (1H, dd), 6.53 (2H, m), 6.46 (1H, m), 6.35 (1H, m), 5.79 (1H, dd), 4.70 (2H, s), 3.77 (6H, s), 3.59 (2H, s), 3.38 (3H, s), 3.06 (3H, s).

Example 24: Synthesis of I-22 (Racemic)

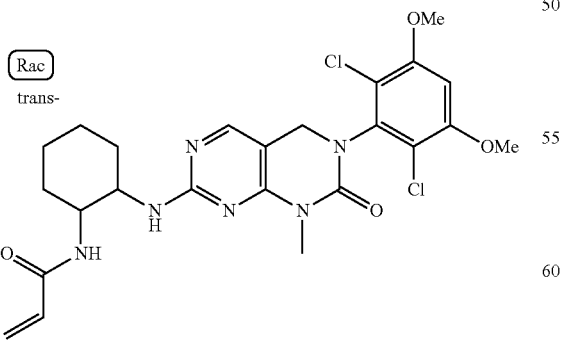

Compound I-22 was prepared as described in Example 21 using trans-cyclohexane-1,2-diamine in place of cis-cyclohexane-1,2-diamine in Step 2. MS m/z: 535.3 (M+H$^+$).

Example 25: Synthesis of I-23

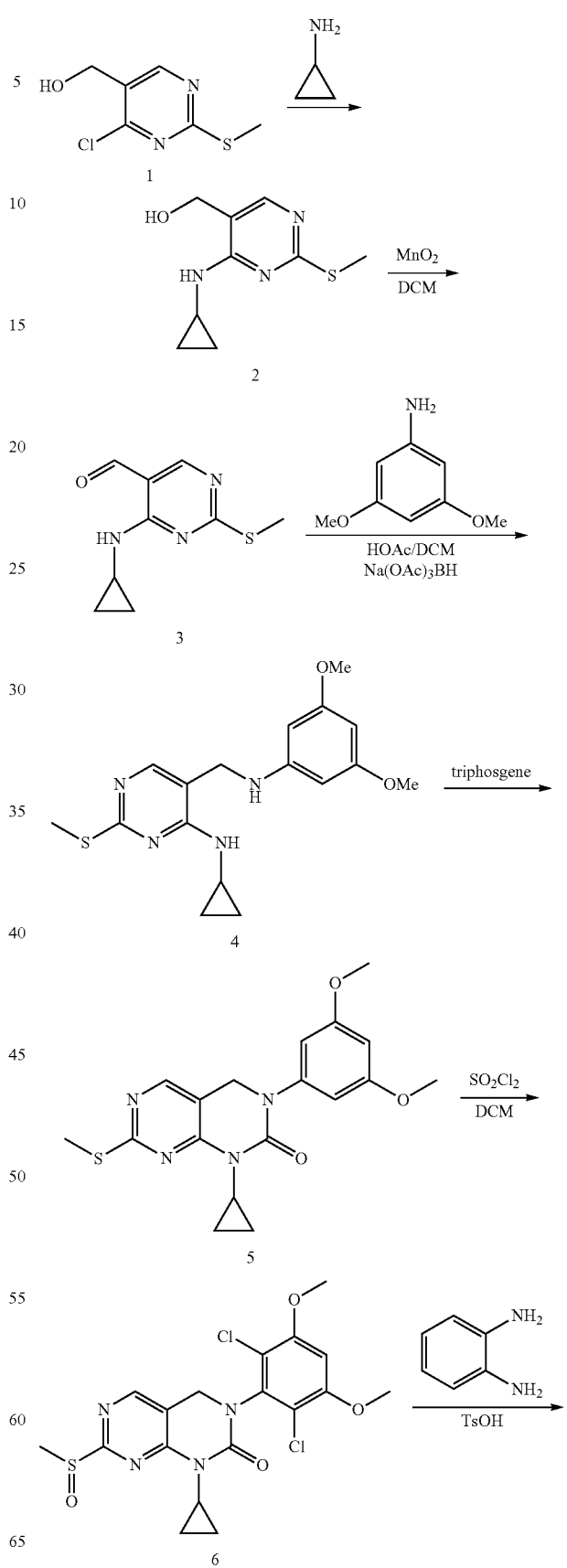

-continued

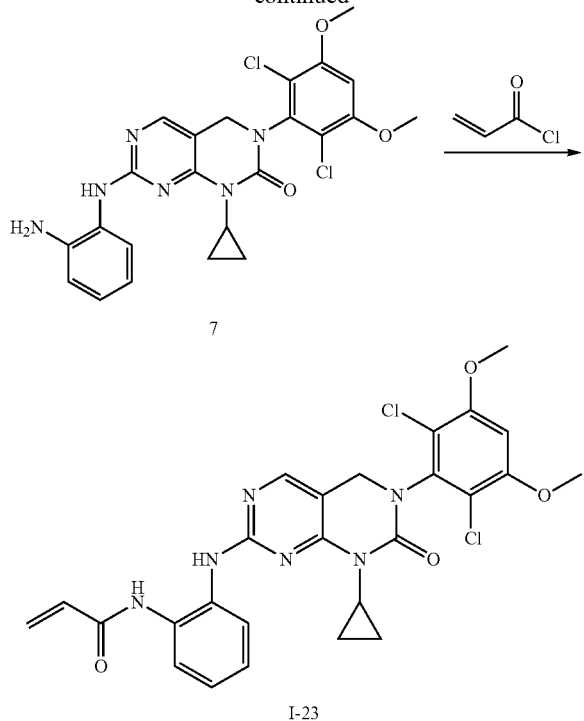

Step 1: Intermediate 2

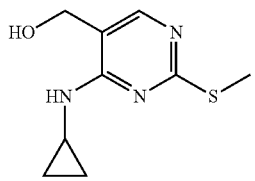

A solution of Intermediate 1 (750 mg, 3.93 mmol) in cyclopropanamine (5 mL) was stirred at ambient temperature overnight after which the solution was concentrated, triturated with EtOAc and filtered to afford 700 mg of the title compound. MS m/z: 212.1 (M+H)+

Step 2: Intermediate 3

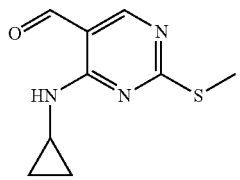

To a solution of Intermediate 2 (700 mg, 3.32 mmol) in DCM (30 mL) was added manganese oxide (2.30 g, 26.4 mmol) and the mixture was allowed to stir at ambient temperature for 3 h. The reaction mixture was filtered through Celite and washed with DCM and the filtrate was concentrated to afford 550 mg of the title compound. MS m/z: 210.2 (M+H)+

Step 3: Intermediate 4

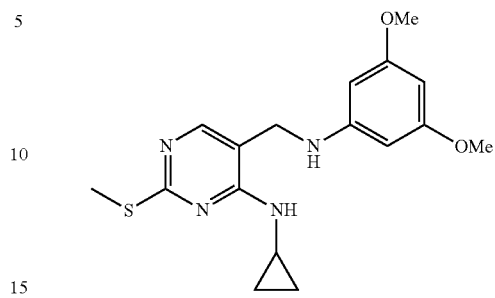

To a solution of Intermediate 3 (550 mg, 2.63 mmol) in DCM (20 mL) was added 3, 5-dimethoxyaniline (480 mg, 3.14 mmol) and acetic acid (0.13 g, 2.17 mmol) under nitrogen. The mixture was stirred at ambient temperature for 15 min followed by the addition of NaBH(OAc)₃ in two portions (0.55 g×2, 5.19 mmol) at a 15 min interval. The reaction was allowed to stir at ambient temperature for 17 h after which it was quenched with 1M NaOH and allowed to stir for 15 min. The aqueous layer was extracted with DCM (50 mL×3) and the combined organic layers were washed with brine, dried (Na₂SO₄), filtered and concentrated. The crude product was subjected to flash chromatography on silica gel (10% EtOAc in DCM) to afford 0.83 g of the title compound. MS m/z: 347.2 (M+H)+

Step 4: Intermediate 5

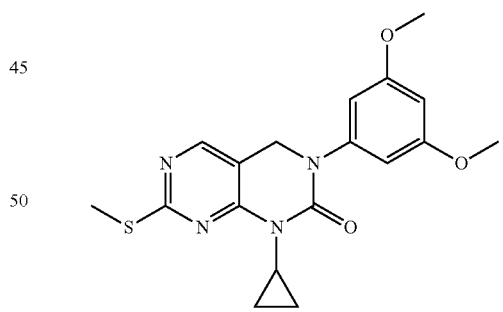

To a solution of Intermediate 4 (830 mg, 2.41 mmol) in THF (20 mL) was added triphosgene (890 mg, 3.57 mmol) followed by addition of triethylamine (1.20 g, 11.9 mmol) under nitrogen. The mixture was allowed to stir at ambient temperature for 1 h, then at reflux for 3 h. The reaction was quenched with a 1:1 mixture of saturated aqueous NaHCO₃/H₂O (20 mL) and extracted with EtOAc (60 mL×3). The combined organic layers were washed with brine, dried (Na₂SO₄), filtered and concentrated. The crude product was washed with hexanes to afford 500 mg of the title compound. MS m/z: 373.3 (M+H)+

Step 5: Intermediate 6

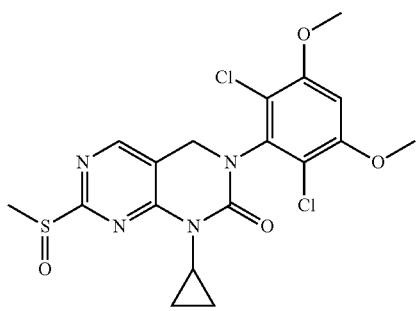

To an ice-cooled solution of Intermediate 5 (150 mg, 0.40 mmol) in MeCN (6 mL) and DCM (12 mL) was added sulfuryl chloride (108 mg, 0.80 mmol). The reaction was allowed to stir at 0° C. for 10 min. The reaction was quenched with saturated aqueous NaHCO$_3$ and the aqueous was extracted with DCM (50 mL×3). The combined organic layers were dried (Na$_2$SO$_4$), filtered and concentrated. The crude was purified by prep-TLC (5% MeOH in DCM) to afford 60 mg of the title compound. MS m/z: 457.2 (M+H)$^+$. $^1$H NMR (400 MHz, DMSO-d6): δ 0.62-0.70 (m, 2H), 1.09-1.00 (m, 2H), 2.73-2.83 (m, 1H), 2.91 (s, 3H), 3.97 (s, 6H), 4.60-4.69 (m, 2H), 7.01 (s, 1H), 8.62 (s, 1H)

Step 6: Intermediate 7

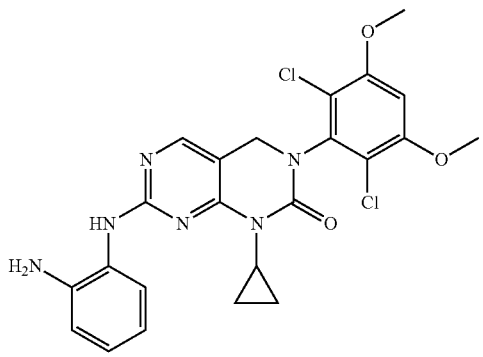 [SMILES: COc1cc(OC)c(Cl)c(N2Cc3cnc(Nc4ccccc4N)nc3N(C3CC3)C2=O)c1Cl]

To a solution of Intermediate 6 (60 mg, 0.13 mmol) in dioxane (10 mL) was added benzene-1,2-diamine (43 mg, 0.39 mmol) and catalytic p-TSA (2 mg). The resultant mixture was heated to reflux overnight. The reaction mixture was cooled to ambient temperature, diluted with EtOAc, washed with saturated aqueous NaHCO$_3$, dried over Na$_2$SO$_4$ and concentrated. The crude product was purified by prep-TLC (2% MeOH in DCM) to afford 30 mg of the title compound. MS m/z: 501.3 (M+H)$^+$. $^1$H NMR (400 MHz, DMSO-d6): δ 0.62 (d, 2H), 0.95 (d, 2H), 2.60 (dd, 1H), 3.95 (s, 6H), 4.39 (s, 2H), 4.83 (s, 2H), 6.47-6.63 (m, 1H), 6.73 (dd, 1H), 6.82-6.86 (m, 1H), 6.98 (s, 1H), 8.06 (s, 1H), 7.51 (d, 1H), 8.39 (s, 1H), Step 7: I-23

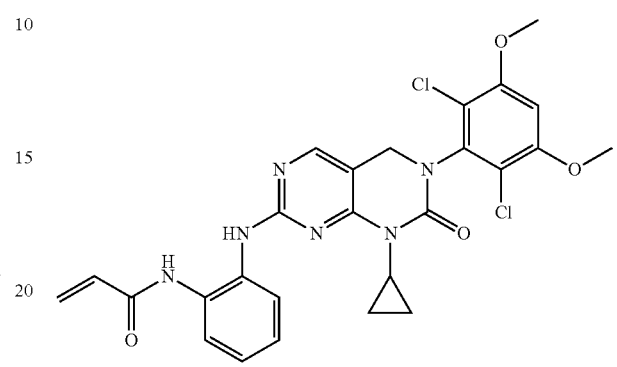

A solution of Intermediate 7 (30 mg, 0.06 mmol) in THF (10 mL) was added DIPEA (15 mg, 0.12 mmol) and cooled to −78° C. To the reaction mixture was added acryloyl chloride (6.5 mg, 0.07 mmol). The reaction mixture was stirred at −78° C. for 10 min. after which it was quenched with a saturated aqueous NaHCO$_3$ solution, extracted with EtOAc, and concentrated. The crude was purified by prep-TLC (3~4% MeOH in DCM) to afford 20 mg of the title compound. MS m/z: 555.3 (M+H)$^+$. $^1$H NMR (400 MHz, DMSO-d$_6$): δ 0.55-0.67 (m, 2H), 0.96 (q, 2H), 2.61-2.64 (m, 1H), 3.95 (s, 6H), 4.41 (s, 2H), 5.78 (dd, 1H), 6.28 (dd, 1H), 6.52 (dd, 1H), 6.98 (s, 1H), 7.06-7.12 (m, 1H), 7.17-7.24 (m, 1H), 7.51 (d, 1H), 7.98 (d, 1H), 8.11 (s, 1H), 8.53 (s, 1H), 9.83 (s, 1H).

Example 26: Synthesis of I-24

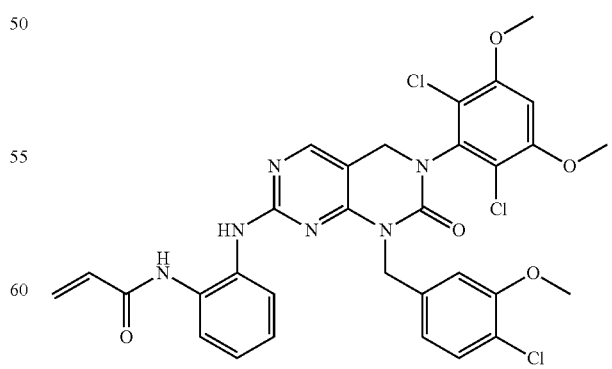

Compound I-24 was prepared as described in Example 25 using (4-chloro-3-methoxyphenyl)methanamine in place of cyclopropanamine in Step 2. MS m/z: 669.4 (M+H$^+$).

Example 27: Synthesis of I-25
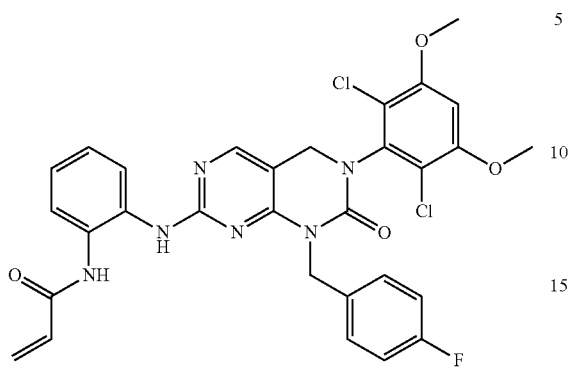
Compound I-25 was prepared as described in Example 25 using (4-fluorophenyl)methanamine in place of cyclopropanamine in Step 2. MS m/z: 623.3 (M+H⁺).
Example 28: Synthesis of I-26
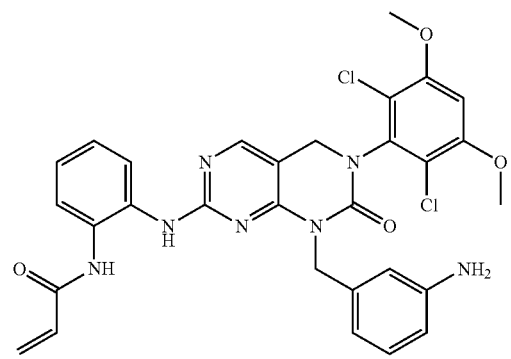 [SMILES: C=CC(=O)Nc1ccccc1Nc1ncc2c(n1)N(Cc1cccc(N)c1)C(=O)N(c1c(Cl)c(OC)cc(OC)c1Cl)C2]
Compound I-26 was prepared as described in various steps from Example 3 but in the following order: Step 1, Step 6, Step 3. MS m/z: 620.4 (M+H⁺).
Example 29: Synthesis of I-27
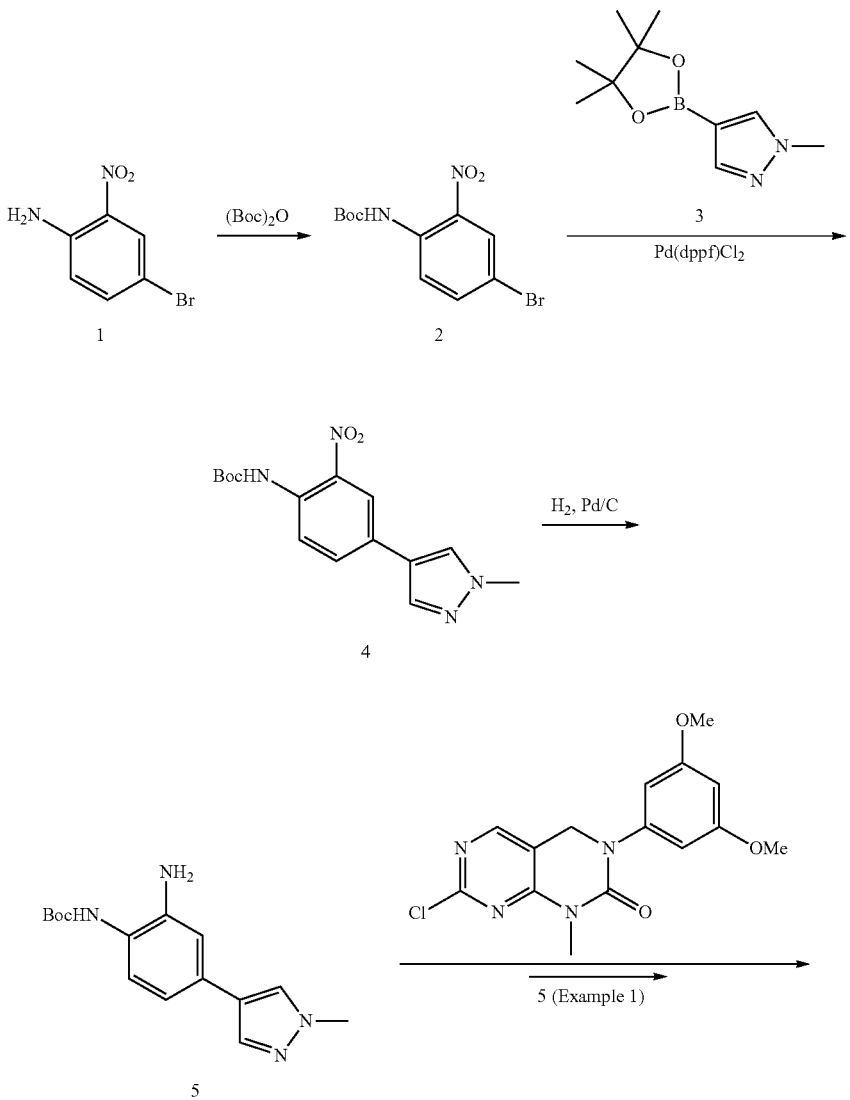

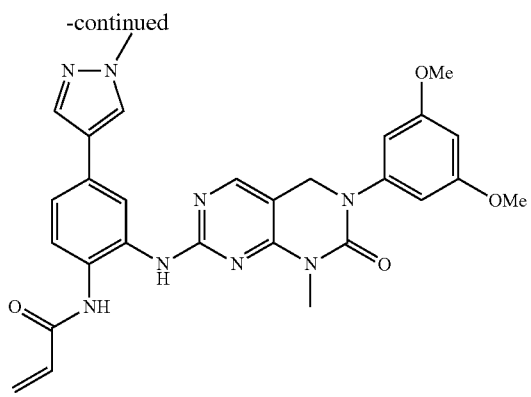

I-27

Step: Intermediate 2

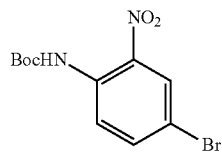 [SMILES: CC(C)(C)OC(=O)Nc1ccc(Br)cc1[N+](=O)[O-]]

To a solution of Intermediate 1 (466 mg, 2.15 mmol) in DMF (6.0 mL) was added (Boc)₂O (515 mg, 2.36 mmol) and DMAP (20 mg). The reaction was stirred at ambient temperature for 16 h. DMF was removed under reduced pressure and purified by silica gel chromatography to afford 480 mg of the title compound. MS m/z: 317.1 (M+H⁺).

Step 2 Intermediate 4

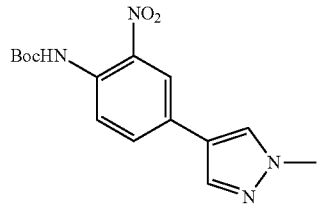 [SMILES: Cn1cc(-c2ccc(NC(=O)OC(C)(C)C)c([N+](=O)[O-])c2)cn1]

Intermediate 2 (90 mg, 0.28 mmol), Intermediate 3 (120 mg, 0.58 mmol), and Pd(dppf)Cl₂ (22.0 mg, 0.03 mmol) were combined in 1,4-dioxane (5 mL) and 2 M aqueous Na₂CO₃ (1.2 mL). The mixture was heated at 110° C. for 30 min. The reaction mixture was diluted with EtOAc, washed with saturated aqueous NaHCO₃ and brine, dried (Na₂SO₄), filtered and concentrated in vacuo. The residue was subjected to flash chromatography on silica gel to afford 47 mg of the title compound. MS m/z: 319.2 (M+H⁺).

Step 3 Intermediate 4

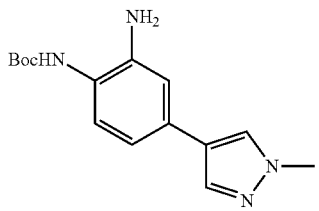

Intermediate 4 (47.0 mg, 0.15 mmol) was dissolved in MeOH (5 mL), to which was added 10 wt % Pd/C (20 mg). The reaction mixture was allowed to stir at ambient temperature under a H₂ balloon for 3.5 hr. The reaction was filtered through a short plug of celite and concentrated in vacuo to afford the title compound (quantitative) which was used directly. MS m/z: 288.1 (M+H⁺).

I-27

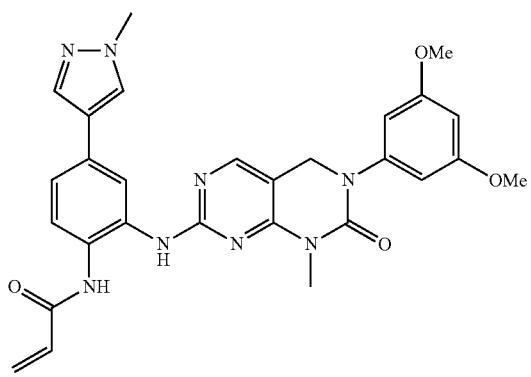 [SMILES: C=CC(=O)Nc1ccc(-c2cnn(C)c2)cc1Nc1ncc2c(n1)N(C)C(=O)N(c1cc(OC)cc(OC)c1)C2]

The title compound was prepared as outlined in Example 5 using common Intermediate 5 from Example 1. MS m/z: 541.2 (M+H⁺). ¹H NMR (400 MHz, CD₃OD): δ: 7.92 (1H, s), 7.31 (2H, m), 7.18 (2H, m), 6.92 (1H, m), 6.86 (1H, s), 6.53 (2H, m), 6.46 (1H, dd), 5.44 (1H, dd), 5.01 (2H, s), 4.89 (6H, s), 4.64 (1H, m), 4.57 (1H, s), 3.93 (3H, s), 3.87 (2H, m), 3.29 (1H, m).

Example 30: Synthesis of I-28

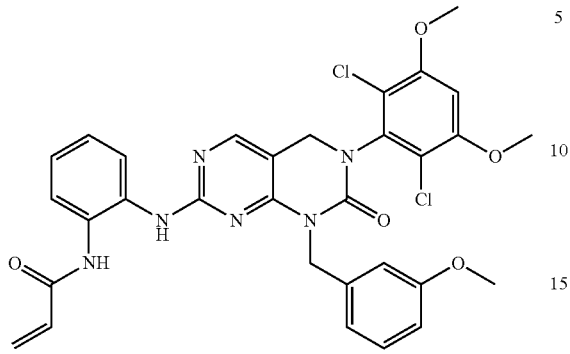

Compound I-28 was prepared as described in Example 5. The starting material was prepared using (3-methoxyphenyl)methanamine in place of methylamine. MS m/z: 654.5 (M+H⁺).

Example 31: Synthesis of I-29

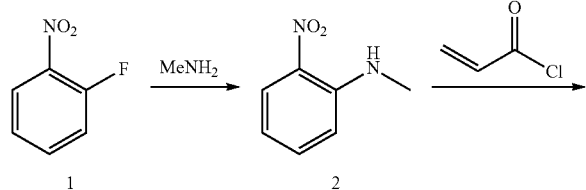

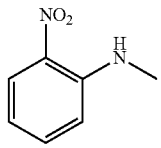

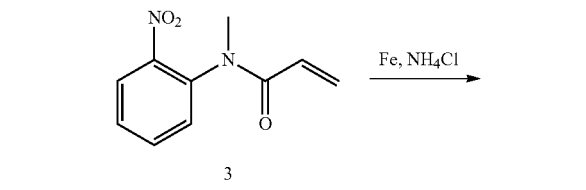

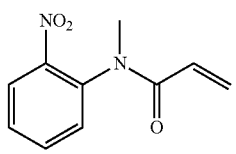

Step 1: Intermediate 2

A solution of Intermediate 1 (3.0 g, 21.3 mmol) in methanamine (ethanol solution, 30 mL) was allowed to stir at ambient temperature for 2 h after which the volatiles were evaporated under reduced pressure. To the residue was added aqueous solution of NaHCO₃ (50 mL) and the mixture was extracted with EtOAc (30 mL×3). The combined organic layers were dried over Na₂SO₄ and concentrated to give 3.53 g of the title compound. ¹H NMR (400 MHz, CDCl₃): δ 3.03 (d, 3H), 6.63-6.67 (m, 1H), 6.84 (d, 1H), 7.43-7.48 (m, 1H), 7.99 (br s, 1H), 8.17 (dd, 1H).

Step 2: Intermediate 3

To a solution of Intermediate 3 (500 mg, 3.29 mmol) and DIPEA (900 mg, 7.0 mmol) in DMF (5 mL), was added acrylol chloride (1.92 g, 21.4 mmol). The reaction was stirred at ambient temperature for 2.5 h. The mixture was partitioned between EtOAc and water. The organic layer was separated and washed with water, brine, dried over Na₂SO₄ and the crude product was subjected to flash chromatography on silica gel (eluting with 6% MeOH in DCM) to afford 583 mg of the title compound. MS m/z: 207.2 (M+1)⁺. ¹H NMR (400 MHz, CDCl₃): δ 3.32 (s, 3H), 5.53 (d, 1H), 5.82-5.89 (m, 1H), 6.37 (d, 1H), 7.37 (d, 1H), 7.56 (t, 1H), 7.67-7.71 (m, 1H), 8.01 (d, 1H).

Step 3: Intermediate 4

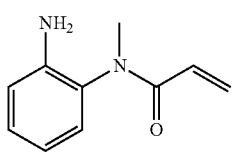

A mixture of Intermediate 3 (200 mg, 0.97 mmol) and Fe (272 mg, 4.85 mmol) in aqueous NH$_4$Cl (3 mL) and EtOH (6 mL) were stirred at 80° C. for 1 h. Solids were removed by filtration and the filtrate was concentrated. The residue was diluted with water and extracted with EtOAc (20 mL×3), the organic layer was washed with brine, dried (Na$_2$SO$_4$) and concentrated in vacuo. The crude product was purified by flash chromatography on silica gel (eluting with 5% MeOH in DCM) to afford 105 mg of the title compound. MS m/z: 177.2 (M+1)$^+$. $^1$H NMR (400 MHz, CDCl$_3$): δ 3.26 (s, 3H), 3.76 (br, 2H), 5.52 (dd, 1H), 6.07 (dd, 1H), 6.39 (dd, 1H), 6.74-6.80 (m, 1H), 6.99 (dd, 1H), 7.14-7.18 (m, 1H), 7.26 (s, 1H)

Step 4: I-29

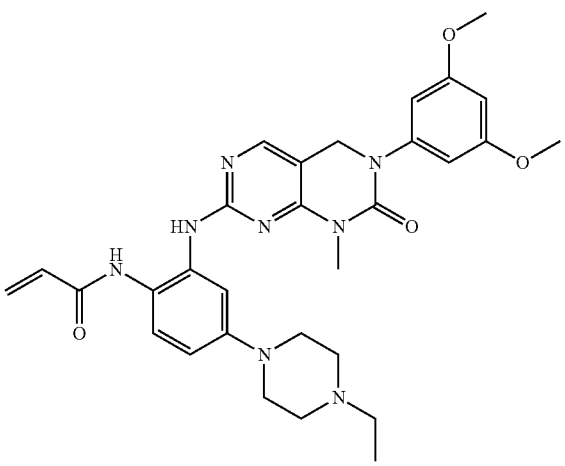 [SMILES: C=CC(=O)Nc1ccc(N2CCN(CC)CC2)cc1Nc1ncc2c(n1)N(C)C(=O)N(c1cc(OC)cc(OC)c1)C2]

A mixture of Intermediate 6 from Example 1 (100 mg, 0.24 mmol), Intermediate 4 (44 mg, 0.24 mmol), Cs$_2$CO$_3$ (162 mg, 0.48 mmol), Pd$_2$(dba)$_3$ (21.4 mg, 0.038 mmol), and Xantphos (43.0 mg, 0.076 mmol) in 1,4-dioxane (2 mL) were allowed to stir at 95° C. under N$_2$ for 5 h. The volatiles were evaporated under reduced pressure. The residue was partitioned between EtOAc and water and the organic layer was washed with brine, dried (Na$_2$SO$_4$), filtered and concentrated in vacuo. The crude product was subjected to flash chromatography on silica gel (eluting with 50% EtOAc in hexanes) to afford 29.8 mg of the title compound. MS m/z: 543.3 (M+1)$^+$. $^1$H NMR (400 MHz, DMSO-d6): δ 3.15 (s, 3H), 3.25 (s, 3H), 4.00 (s, 6H), 4.52 (s, 2H), 5.34-5.57 (m, 1H), 5.88-6.16 (m, 2H), 7.00 (s, 1H), 7.17-7.23 (m, 2H), 7.34-7.43 (m, 1H), 7.87 (d, 1H), 8.05 (s, 1H), 8.76 (s, 1H).

Example 32: Synthesis of I-30

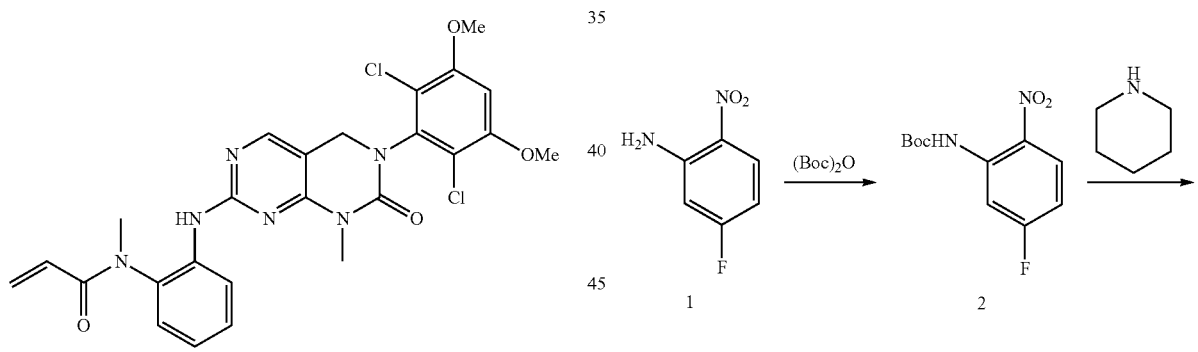

Compound I-30 was prepared as described in Example 17 using Intermediate 5 (from Example 1), in place of Intermediate 6. MS m/z: 573.5 (M+H$^+$).

Example 33: Synthesis of I-31

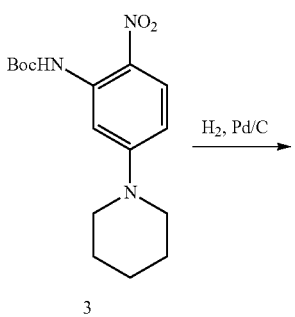

-continued

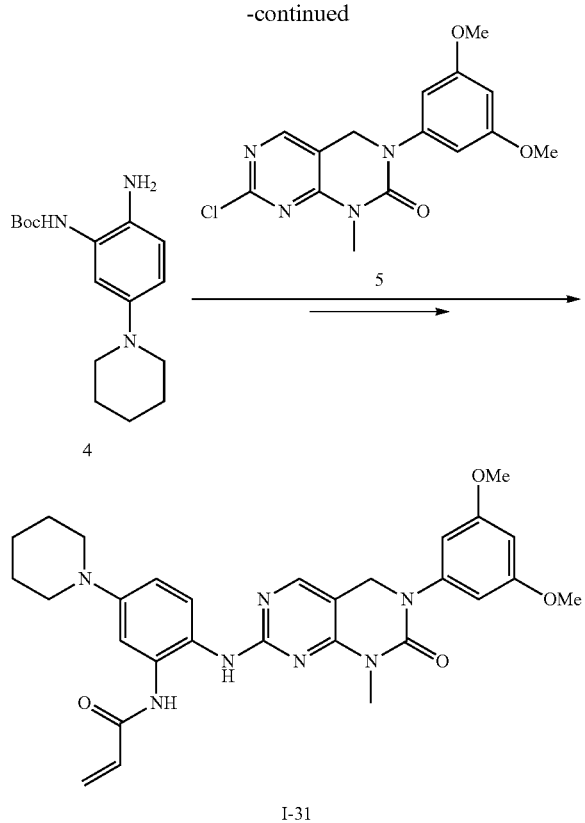

Steps 1: Intermediate 2

To a solution of Intermediate 1 (2.34 g, 15.0 mmol) in DMF (50 mL) was added (Boc)$_2$O (6.60 g, 30.3 mmol) and DMAP (600 mg, 4.9 mmol). The reaction was allowed to stir at ambient temperature overnight. DMF was removed under reduced pressure and the title compound was isolated by silica gel chromatography. MS m/z: 257.2 (M+H$^+$).

Step 2: Intermediate 3

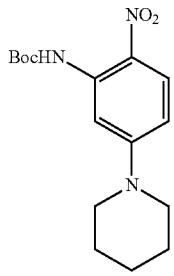 [SMILES: CC(C)(C)OC(=O)Nc1cc(N2CCCCC2)ccc1[N+](=O)[O-]]

Intermediate 2 (660 mg, 2.57 mmol) and piperidine (0.65 mL, 6.60 mmol) were combined in DMF (6.0 mL). The reaction mixture was heated at 110° C. for 3 h. The reaction was concentrated in vacuo and purified by flash chromatography on silica gel to afford 660 mg of the title compound. MS m/z: 322.3 (M+H$^+$).

Step 3: Intermediate 4

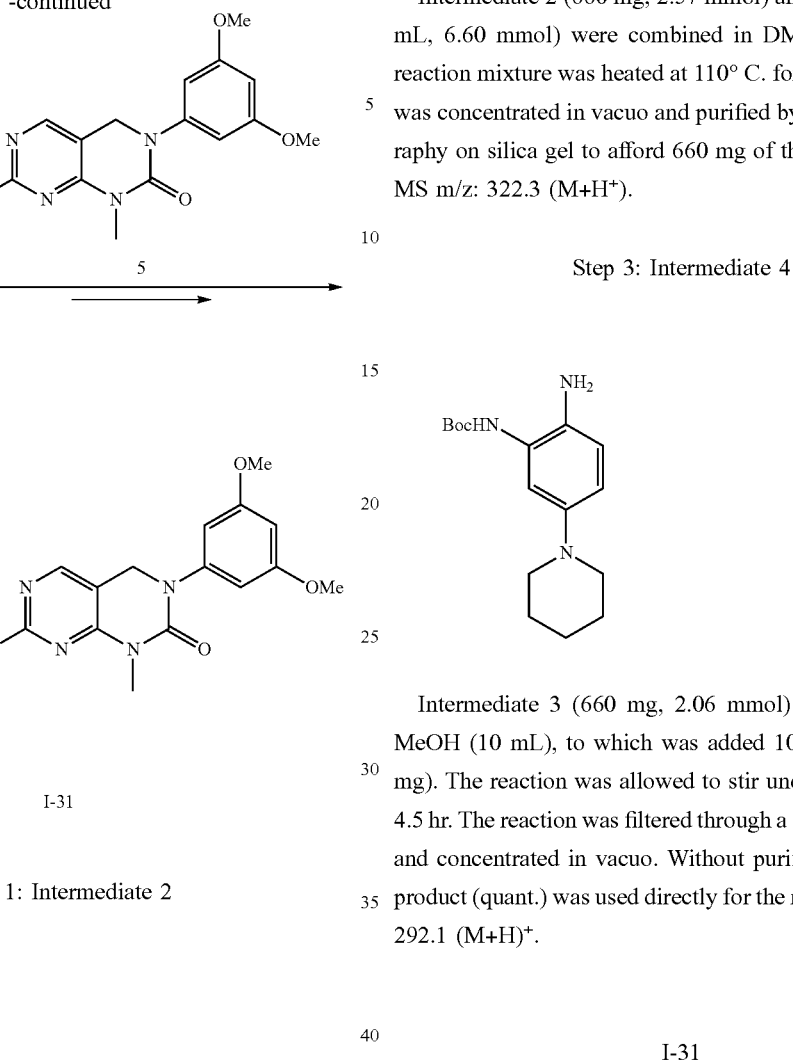

Intermediate 3 (660 mg, 2.06 mmol) was dissolved in MeOH (10 mL), to which was added 10 wt % Pd/C (100 mg). The reaction was allowed to stir under H$_2$ balloon for 4.5 hr. The reaction was filtered through a short plug of celite and concentrated in vacuo. Without purification, the crude product (quant.) was used directly for the next step. MS m/z: 292.1 (M+H)$^+$.

I-31

The title compound was prepared from Intermediate 4 and Intermediate 5 (from Example 1) using the procedure as described in Example 5. MS m/z: 544.3 (M+H$^+$). $^1$H NMR (400 MHz, CDCl$_3$): δ: 8.65 (1H, s), 8.24 (1H, s), 7.71 (1H, m), 7.44 (1H, m), 6.41 (5H, m), 5.79 (1H, dd), 4.65 (2H, s), 3.77 (6H, s), 3.39 (4H, m), 3.34 (3H, s), 2.00 (4H, m), 1.67 (2H, m).

Example 34: Synthesis of I-32

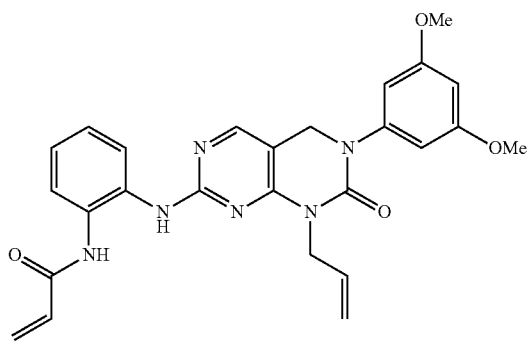 [SMILES: C=CCN1C(=O)N(c2cc(OC)cc(OC)c2)Cc2cnc(Nc3ccccc3NC(=O)C=C)nc21]

Compound I-32 was prepared as described in Example 25 using allylamine in place of cyclopropanamine in Step 1 and mCPBA instead of SO$_2$Cl$_2$ in Step 5 (mCPBA oxidation is described in Example 2, step 7). MS m/z: 487.1 (M+H$^+$).

Example 35: Synthesis of I-33

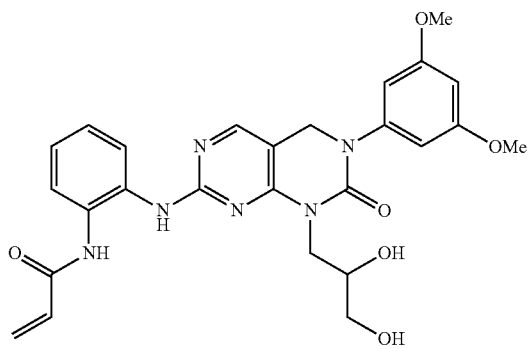 [SMILES: C=CC(=O)Nc1ccccc1Nc1ncc2c(n1)N(CC(O)CO)C(=O)N(c1cc(OC)cc(OC)c1)C2]

Compound I-33 was prepared as described in Example 25 using 3-aminopropane-1,2-diol in place of cyclopropanamine in Step 1 and mCPBA instead of SO$_2$Cl$_2$ in Step 5 (mCPBA oxidation is described in Example 2, step 7). MS m/z: 521.2 (M+H$^+$).

Example 36: Synthesis of I-34

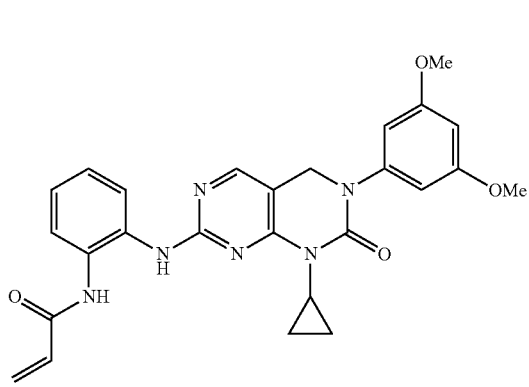 [SMILES: C=CC(=O)Nc1ccccc1Nc1ncc2c(n1)N(C1CC1)C(=O)N(c1cc(OC)cc(OC)c1)C2]

Compound I-34 was prepared as described in Example 7. The starting material was prepared as described in Example 1 using cyclopropanamine in place of methylamine in Step 5. MS m/z: 487.3 (M+H$^+$).

Example 37: Synthesis of I-35 (Racemic)

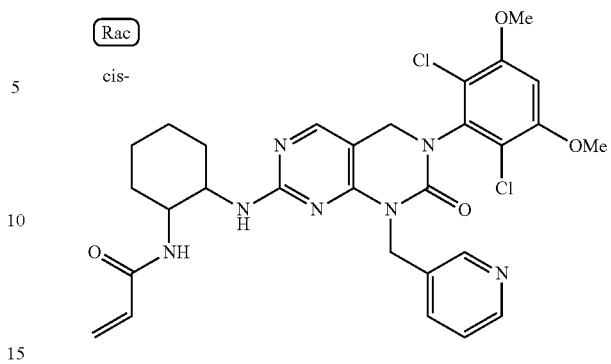

Compound I-35 was prepared as described in Example 21. The starting material was prepared as described in Example 2 using pyridin-3-ylmethanamine in place of 3-nitrobenzylamine in Step 2. MS m/z: 612.3 (M+H$^+$).

Example 38: Synthesis of I-36

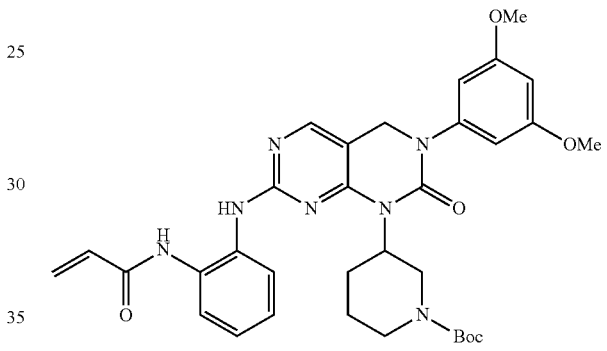

Compound I-36 was prepared as described in Example 7. The starting material was prepared as described in Example 2 using tert-butyl 3-aminopiperidine-1-carboxylate in place of 3-nitrobenzyl amine in Step 2 and skipping Step 6. MS m/z: 630.3 (M+H$^+$).

Example 39: Synthesis of I-37

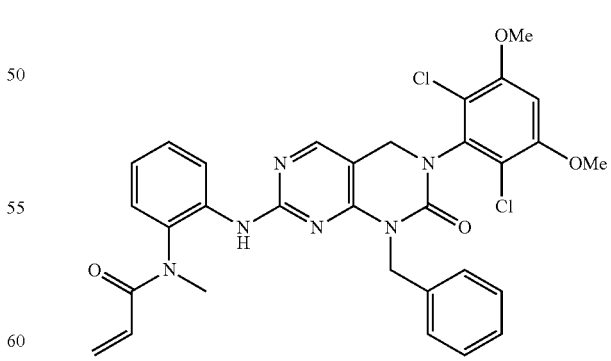

Compound I-37 was prepared as described in Example 5 using tert-butyl (2-aminophenyl)(methyl)carbamate in place of 1,2-benzenediamine in Step 1. A BOC deprotection step was performed prior to Step 2 (as described in Example 3, Step 5). MS m/z: 619.4 (M+H$^+$).

Example 40: Synthesis of I-38

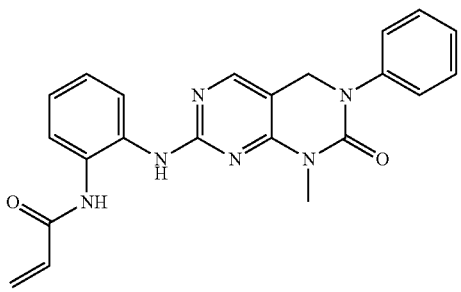 [SMILES: C=CC(=O)Nc1ccccc1Nc1ncc2c(n1)N(C)C(=O)N(c1ccccc1)C2]

Compound I-38 was prepared as described in Example 53 using aniline in place of cyclopropanamine in Step 1. MS m/z: 401.3 (M+H⁺).

Example 41: Synthesis of I-39 (Racemic)

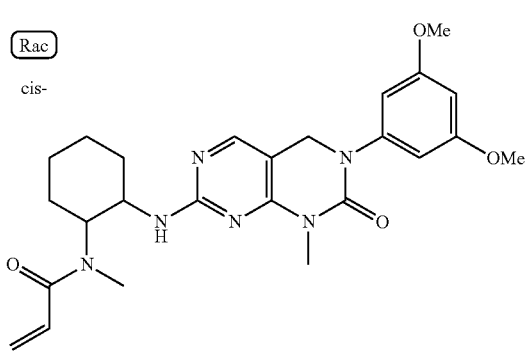 [SMILES: C=CC(=O)N(C)C1CCCCC1Nc1ncc2c(n1)N(C)C(=O)N(c1cc(OC)cc(OC)c1)C2]

Compound I-39 was prepared as described in Example 21 using mCPBA instead of SO$_2$Cl$_2$ in Step 1 (mCPBA oxidation is described in Example 2, Step 7) and tert-butyl (cis-2-aminocyclohexyl)(methyl)carbamate in place of cis-cyclohexane-1,2-diamine in Step 2. A BOC deprotection step was performed prior to Step 3 (as described in Example 3, Step 5). MS m/z: 481.5 (M+H⁺).

Example 42: Synthesis of I-40

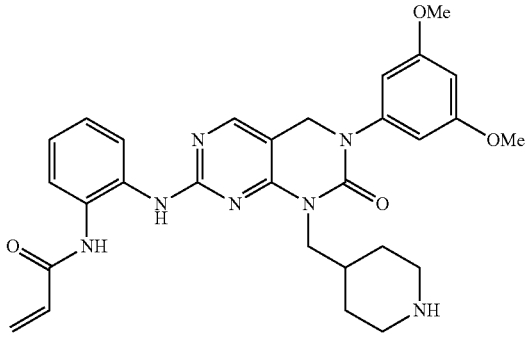 [SMILES: C=CC(=O)Nc1ccccc1Nc1ncc2c(n1)N(CC1CCNCC1)C(=O)N(c1cc(OC)cc(OC)c1)C2]

The title compound was prepared as described in Example 7. The starting material was prepared as described in Example 2 using tert-butyl 4-aminopiperidine-1-carboxylate in place of 3-nitrobenzyl amine in Step 2 and skipping Step 6. A final BOC deprotection step was performed as described in Example 3, Step 5. MS m/z: 544.3 (M+H⁺). ¹H NMR (400 MHz, CD$_3$OD): δ: 8.02 (1H, s), 7.76 (1H, d), 7.55 (1H, d), 7.36 (2H, m), 6.53 (2H, s), 6.46 (1H, m), 6.36 (1H, dd), 5.80 (1H, dd), 4.73 (2H, s), 3.82 (2H, d), 3.77 (6H, s), 3.30 (2H, s), 2.81 (2H, t), 1.92 (1H, m), 1.68 (2H, m), 1.30 (2H, q).

Example 43: Synthesis of I-41

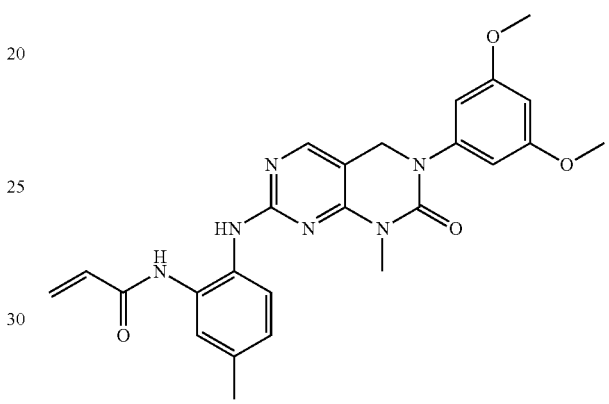

Compound I-41 was prepared as described in Example 7 using tert-butyl (2-amino-5-methylphenyl)carbamate in place of 1,2-benzenediamine in Step 1. A BOC deprotection step was performed prior to Step 2 (as described in Example 3, Step 5). MS m/z: 475.4 (M+H⁺).

Example 44: Synthesis of I-42

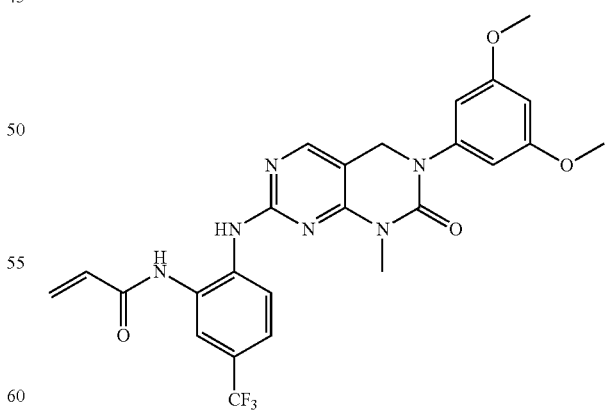

Compound I-42 was prepared as described in Example 7 using tert-butyl (2-amino-5-trifluoromethylphenyl)carbamate in place of 1,2-benzenediamine in Step 1. A BOC deprotection step was performed prior to Step 2 (as described in Example 3, Step 5). MS m/z: 529.4 (M+H⁺).

Example 45: Synthesis of I-43

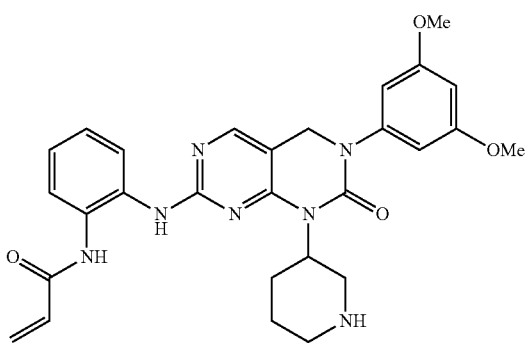 [SMILES: C=CC(=O)Nc1ccccc1Nc1ncc2c(n1)N(C1CCCNC1)C(=O)N(c1cc(OC)cc(OC)c1)C2]

The title compound was prepared as described in Example 7. The starting material was prepared as described in Example 2 using tert-butyl 3-aminopiperidine-1-carboxylate in place of 3-nitrobenzyl amine in Step 2, and skipping Step 6. A final BOC deprotection step was performed as described in Example 3, Step 5. MS m/z: 530.2 (M+H$^+$). $^1$H NMR (400 MHz, CDCl$_3$): δ: 7.87 (1H, s), 7.68 (1H, m), 7.43 (1H, m), 7.24 (1H, m), 7.18 (2H, m), 6.32 (4H, m), 5.68 (1H, dd), 4.85 (1H, m), 4.52 (2H, s), 4.13 (1H, m), 3.70 (6H, s), 3.30 (3H, m), 2.39 (2H, m), 1.72 (2H, m), 1.88 (2H, m).

Example 46: Synthesis of I-44

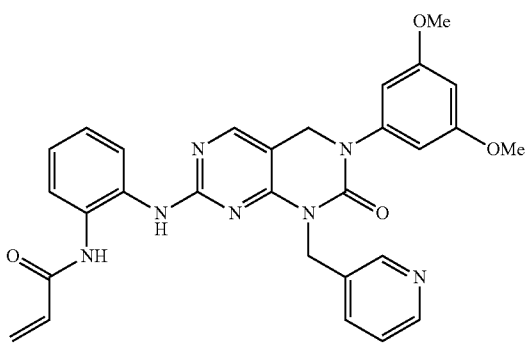 [SMILES: C=CC(=O)Nc1ccccc1Nc1ncc2c(n1)N(Cc1cccnc1)C(=O)N(c1cc(OC)cc(OC)c1)C2]

The title compound was prepared as outlined in Example 5. Intermediate 1 was prepared as described in Example 1 using pyridin-3-ylmethanamine in place of methylamine in Step 5. MS m/z: 538.3 (M+H$^+$). $^1$H NMR (400 MHz, CD$_3$OD): δ: 8.62 (2H, m), 8.23 (1H, d), 8.05 (1H, s), 7.78 (1H, m), 7.65 (1H, dd), 7.48 (1H, dd), 7.31 (2H, m), 6.55 (2H, s), 6.46 (1H, s), 6.36 (2H, m), 5.77 (1H, dd), 5.22 (2H, dd), 4.75 (2H, s), 3.77 (6H, s).

Example 47: Synthesis of I-45 (Racemic)

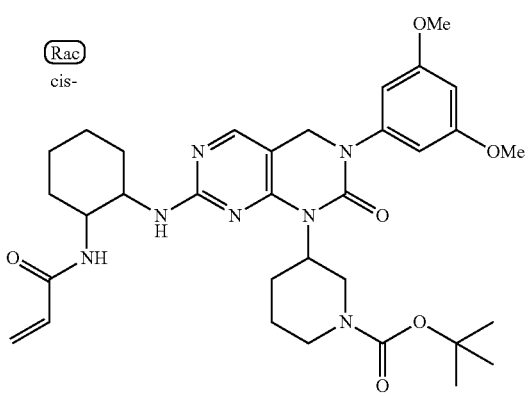 [SMILES: C=CC(=O)NC1CCCCC1Nc1ncc2c(n1)N(C1CCCN(C(=O)OC(C)(C)C)C1)C(=O)N(c1cc(OC)cc(OC)c1)C2]

Compound I-45 was prepared as described in Example 10. The starting material was prepared as described in Example 2 using tert-butyl 3-aminopiperidine-1-carboxylate in place of 3-nitrobenzyl amine in Step 2 and skipping Step 6. MS m/z: 636.3 (M+H$^+$).

Example 48: I-46 (Racemic)

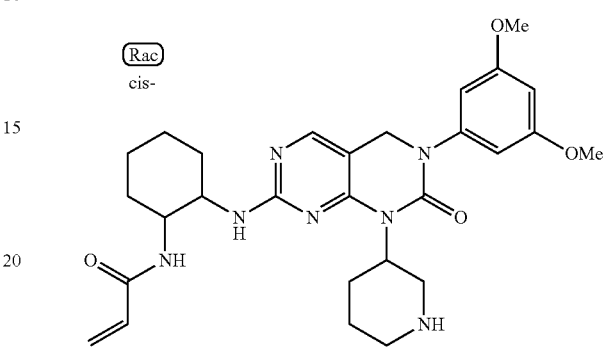

The title compound was prepared as described in Example 21 using mCPBA instead of SO$_2$Cl$_2$ in Step 1 (mCPBA oxidation is described in Example 2, Step 7). The starting material was prepared as described in Example 2 using tert-butyl 3-aminopiperidine-1-carboxylate in place of 3-nitrobenzyl amine in Step 2 and skipping Step 6. A final BOC deprotection step was performed as described in Example 3, Step 5. MS m/z: 536.3 (M+H$^+$). $^1$H NMR (400 MHz, CD$_3$OD): δ: 7.98 (1H, s), 6.51 (2H, s), 6.46 (1H, s), 6.17 (2H, m), 5.62 (1H, dd), 5.03 (1H, m), 4.62 (2H, m), 4.28 (1H, m), 3.93 (1H, m), 3.77 (6H, s), 3.40 (2H, m), 2.94 (1H, m), 2.59 (1H, m), 2.10 (2H, m), 1.96 (2H, m), 1.77 (6H, m), 1.54 (2H, m).

Example 49: I-47, (Racemic)

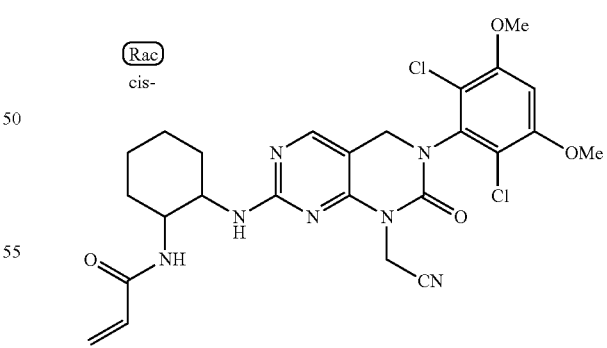

The title compound was prepared as described in Example 21. The starting material was prepared as described in Example 2 using 2-aminoacetonitrile in place of 3-nitrobenzylamine in Step 2. MS m/z: 560.2 (M+H$^+$). $^1$H NMR (400 MHz, CD$_3$OD): δ: 8.07 (1H, s), 6.92 (1H, s), 6.33 (1H, m), 6.18 (1H, dd), 5.63 (1H, dd), 5.01 (2H, s), 4.61 (2H, s), 4.48 (2H, m), 3.97 (6H, s), 1.79 (6H, m), 1.55 (2H, m).

Example 50: I-48

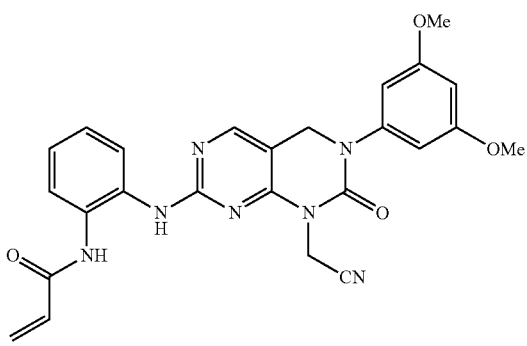 [SMILES: C=CC(=O)Nc1ccccc1Nc1ncc2c(n1)N(CC#N)C(=O)N(c1cc(OC)cc(OC)c1)C2]

The title compound was prepared as described in Example 4. The starting material was prepared as described in Example 2 using 2-aminoacetonitrile in place of 3-nitrobenzylamine in Step 2, and skipping Step 6. MS m/z: 486.2 (M+H$^+$). $^1$H NMR (400 MHz, CD$_3$OD): δ: 8.06 (1H, s), 7.76 (1H, d), 7.51 (1H, d), 7.32 (2H, m), 6.56 (2H, s), 6.47 (3H, m), 5.79 (1H, dd), 4.7 (2H, s), 4.72 (2H, s), 3.77 (6H, s).

Example 51: Synthesis of I-49

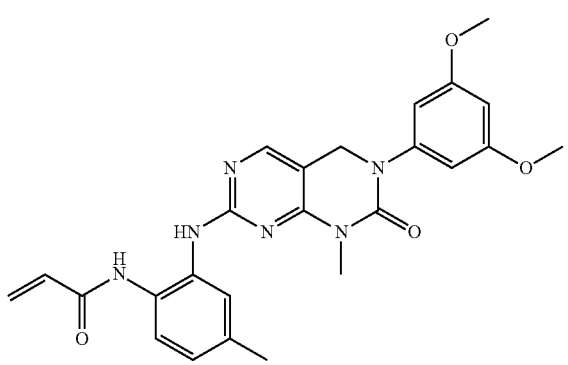 [SMILES: C=CC(=O)Nc1ccc(C)cc1Nc1ncc2c(n1)N(C)C(=O)N(c1cc(OC)cc(OC)c1)C2]

Compound I-49 was prepared as described in Example 7 using tert-butyl (2-amino-5-methylphenyl)carbamate in place of 1,2-benzenediamine in Step 1. A BOC deprotection step was performed prior to Step 2 (as described in Example 3, Step 5). MS m/z: 475.4 (M+H$^+$).

Example 52: Synthesis of I-50

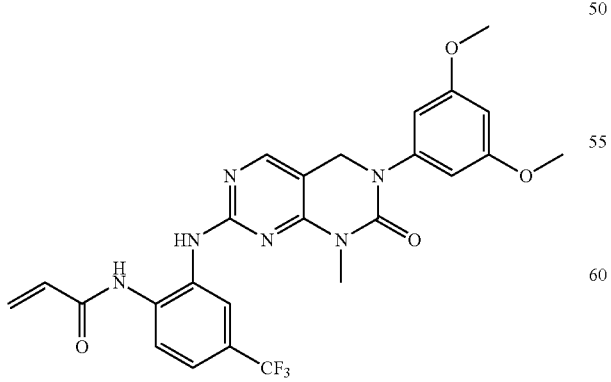

Compound I-50 was prepared as described in Example 7 using tert-butyl (2-amino-5-trifluoromethylphenyl)carbam-ate in place of 1,2-benzenediamine in Step 1. A BOC deprotection step was performed prior to Step 2 (as described in Example 3, Step 5). MS m/z: 529.4 (M+H$^+$).

Example 53: I-51

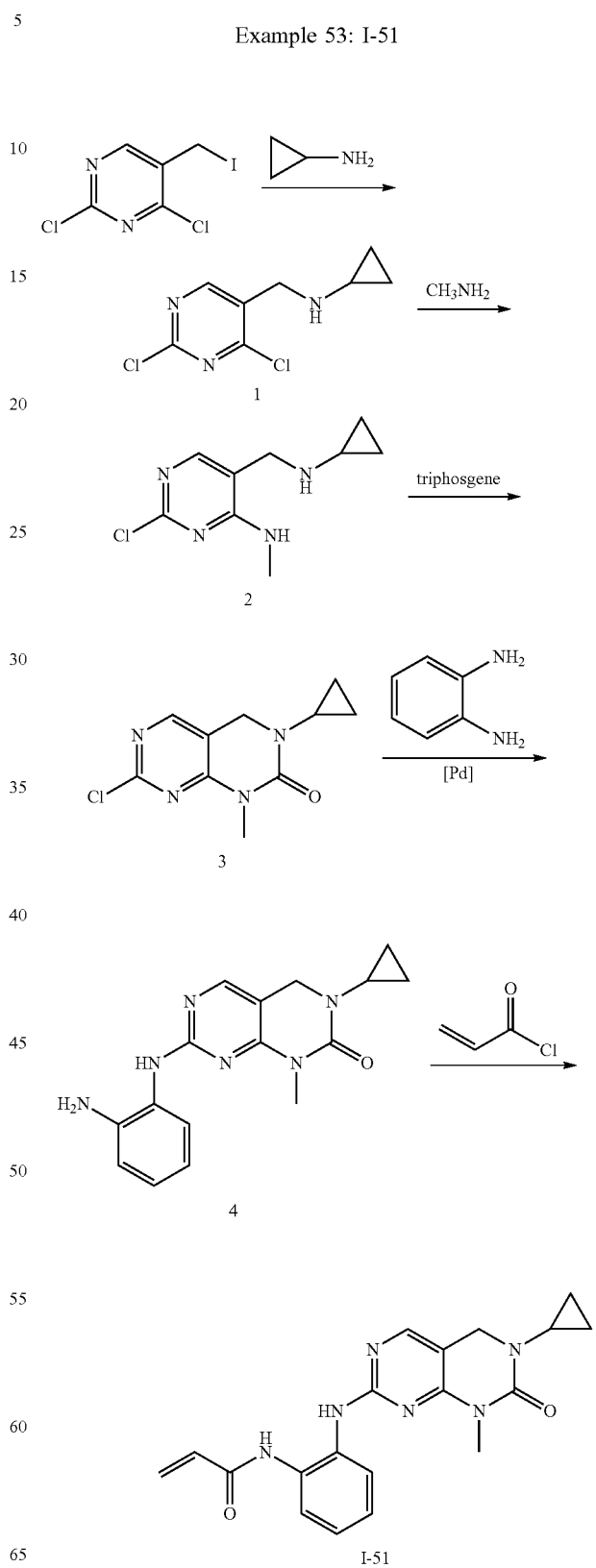

Step 1: Intermediate 1

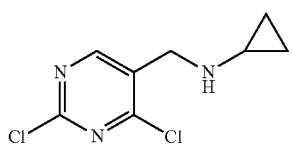 [SMILES: Clc1ncc(CNC2CC2)c(Cl)n1]

To a solution of 2,4-dichloro-5-(iodomethyl)pyrimidine (1.70 g, 5.88 mmol) in MeCN (5 mL) and toluene (15 mL) was add aqueous NaOH (1.5 mL 5.88 mmol), cyclopropanamine (580 mg, 5.88 mmol) in MeCN (6 mL)/toluene (6 mL). The mixture was allowed to stir at 0° C. for 4 h. The mixture was partitioned between EtOAc and $H_2O$. The organic layer was washed with brine, dried over $Na_2SO_4$ and concentrated. The residue was purified by column chromatography on silica gel (eluting with 30% EtOAc in hexanes) to afford 540 mg of the title compound. MS m/z: 218.2 $(M+1)^+$. $^1$H NMR (400 MHz, $CDCl_3$): δ 0.40-0.54 (m, 4H), 2.13-2.18 (m, 1H), 3.97 (s, 2H), 8.62 (s, 1H)

Step 2: Intermediate 2

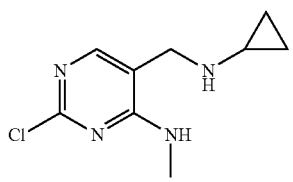

A solution of Intermediate 1 (540 mg, 2.55 mmol) in methanamine (ethanol solution, 10 mL) was allowed to stir at 0° C. for 1 h. The volatiles were evaporated under reduced pressure. The residue was partitioned between EtOAc and water and the organic layer was washed with brine, dried over $Na_2SO_4$ and concentrated. The residue was purified by column chromatography on silica gel (eluting with 5% MeOH in DCM) to afford 350 mg of the title compound. MS m/z: 213.3 $(M+1)^+$. $^1$H NMR (400 MHz, $CDCl_3$): δ 0.29-0.33 (m, 2H), 0.45-0.50 (m, 2H), 2.08-2.13 (m, 1H), 2.98 (d, 3H), 3.74 (s, 2H), 7.17 (br, 1H), 7.75 (s, 1H).

Step 3: Intermediate 3

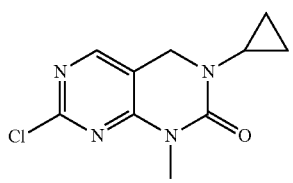 [SMILES: CN1C(=O)N(C2CC2)Cc2cnc(Cl)nc21]

A mixture of Intermediate 2 (100 mg, 0.47 mmol), triphosgene (83 mg, 0.28 mmol), TEA (95 mg, 0.94 mmol) in THF (3 mL) were allowed to stir at 80° C. for 16 h. The mixture was partitioned between EtOAc and $H_2O$. The organic layer was washed with brine, dried over $Na_2SO_4$ and concentrated. The residue was purified by column chromatography on silica gel (eluting with 2% MeOH in DCM) to afford 60 mg of the title compound. MS m/z: 239.3 $(M+1)^+$.

Step 4: Intermediate 4

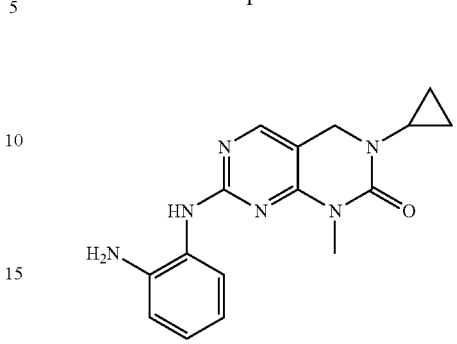

A mixture of Intermediate 3 (60 mg, 0.25 mmol), benzene-1,2-diamine (32.7 mg, 0.30 mmol), $Cs_2CO_3$ (164 mg, 0.50 mmol), $Pd_2(dba)_3$ (21.7 mg, 0.038 mmol) and Xantphos (43.7 mg, 0.076 mmol) in 1,4-dioxane (2 mL) was allowed to stir at 90° C. for 16 h under $N_2$ atmosphere. The volatiles were evaporated under reduced pressure. The residue was diluted with water and extracted with EtOAc (20 mL×3). The organic layer was washed with brine, dried over $Na_2SO_4$, and concentrated. The residue was purified by column chromatography on silica gel (eluting with 5% MeOH in DCM) to afford 39 mg of the title compound. MS m/z: 311.3 $(M+1)^+$

Step 5: I-51

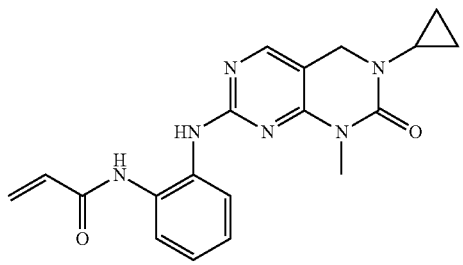 [SMILES: C=CC(=O)Nc1ccccc1Nc1ncc2c(n1)N(C)C(=O)N(C1CC1)C2]

To a solution of Intermediate 4 (39 mg, 0.13 mmol) and DIPEA (38.7 mg, 0.3 mmol) in THF (5 mL) at −78° C. was added acrylol chloride (13.6 g, 0.15 mmol). The reaction mixture was allowed to stir at −78° C. for 20 min. Water was added and the mixture was extracted with EtOAc (20 mL×3). The organic layer was washed with brine, dried over $Na_2SO_4$ and concentrated. The residue was purified by column chromatography on silica gel (eluting with 5% MeOH in DCM) to afford 9.3 mg of the title compound. MS m/z: 365.4 $(M+1)^+$. $^1$H NMR (400 MHz, $CDCl_3$): δ 0.63-0.71 (m, 2H), 0.88 (q, 2H), 2.62-2.69 (m, 1H), 3.30 (s, 3H), 4.25 (s, 2H), 5.71 (d, 1H), 6.21 (dd, 1H), 6.38 (d, 1H), 7.18-7.22 (m, 2H), 7.28 (br s, 1H), 7.50 (br, 1H), 7.89 (s, 1H), 8.38 (br s, 1H).

Example 54: Synthesis of I-52

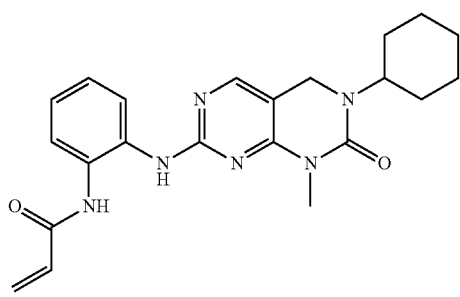 [SMILES: C=CC(=O)Nc1ccccc1Nc1ncc2c(n1)N(C)C(=O)N(C1CCCCC1)C2]

Compound I-52 was prepared as described in Example 53 using cyclohexanamine in place of cyclopropanamine in Step 1. MS m/z: 407.4 (M+H$^+$).

Example 55: Synthesis of I-53

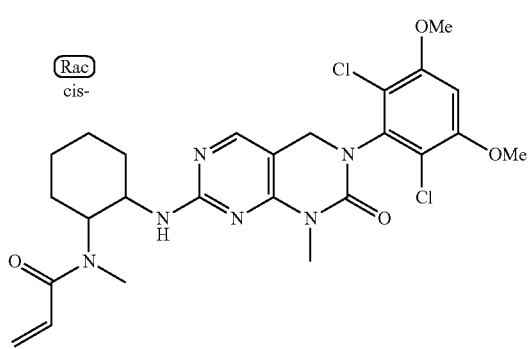 [SMILES: C=CC(=O)N(C)C1CCCCC1Nc1ncc2c(n1)N(C)C(=O)N(c1c(Cl)c(OC)cc(OC)c1Cl)C2]

Compound I-53 was prepared as described in Example 21 using tert-butyl (cis-2-aminocyclohexyl)(methyl)carbamate in place of cis-cyclohexane-1,2-diamine in Step 2. A BOC deprotection step was performed prior to Step 3 (as described in Example 3, Step 5). MS m/z: 549.5 (M+H$^+$).

Example 56: Synthesis of I-54

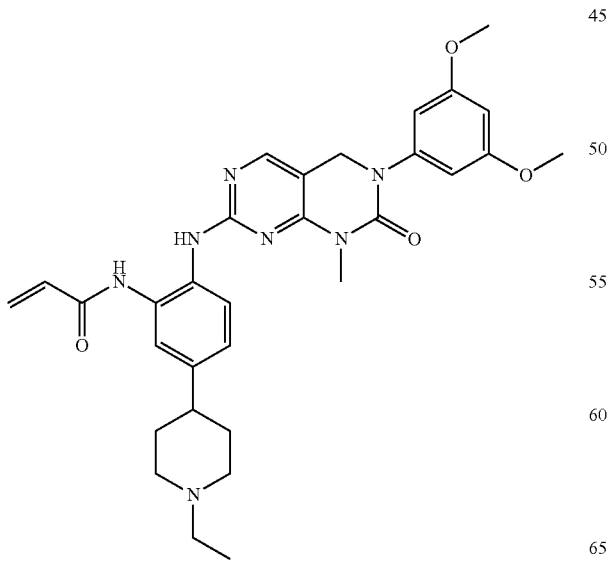

Compound I-54 was prepared as described in Example 17 using tert-butyl (2-amino-5-(1-ethylpiperidin-4-yl)phenyl)carbamate in place of Intermediate 3. MS m/z: 572.6 (M+H$^+$).

Example 57: Synthesis of I-55

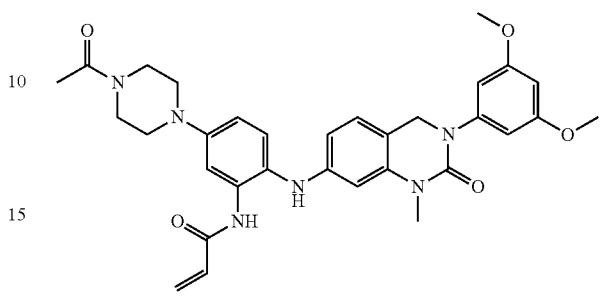

Compound I-55 was prepared as described in Example 17 using tert-butyl (5-(4-acetylpiperazin-1-yl)-2-aminophenyl)carbamate in place of Intermediate 3. MS m/z: 587.5 (M+H$^+$).

Example 58: Synthesis of I-56

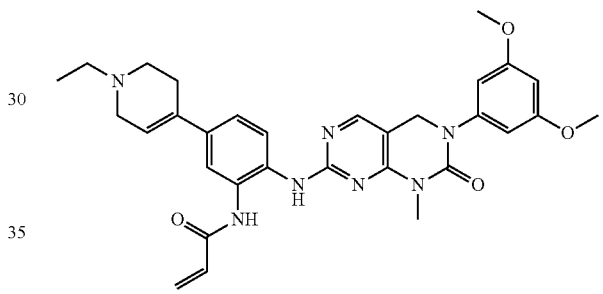

Compound I-56 was prepared as described in Example 17 using tert-butyl (2-amino-5-(1-ethyl-1,2,3,6-tetrahydropyridin-4-yl)phenyl)carbamate in place of Intermediate 3. MS m/z: 570.6 (M+H$^+$).

Example 59: Synthesis of I-57

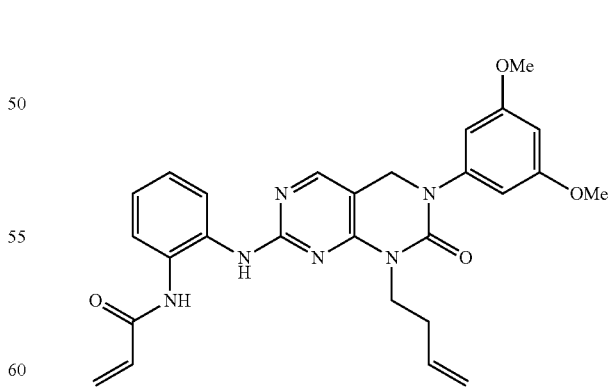

Compound I-57 was prepared as described in Example 25 using but-3-en-1-amine in place of cyclopropanamine in Step 1 and mCPBA instead of SO$_2$Cl$_2$ in Step 5 (mCPBA oxidation is described in Example 2, step 7). MS m/z: 501.1 (M+H$^+$).

Example 60: Synthesis of I-58

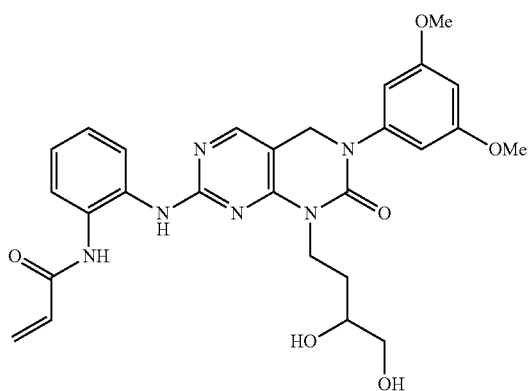 [SMILES: C=CC(=O)Nc1ccccc1Nc1ncc2c(n1)N(CCC(O)CO)C(=O)N(c1cc(OC)cc(OC)c1)C2]

Compound I-58 was prepared as described in Example 25 using 4-aminobutane-1,2-diol in place of cyclopropanamine in Step 1 and mCPBA instead of SO$_2$Cl$_2$ in Step 5 (mCPBA oxidation is described in Example 2, step 7). MS m/z: 535.1 (M+H$^+$).

Example 61: I-59

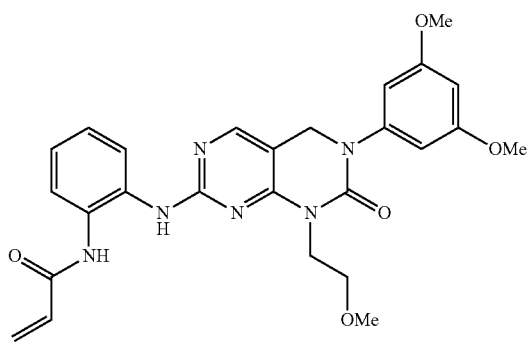 [SMILES: C=CC(=O)Nc1ccccc1Nc1ncc2c(n1)N(CCOC)C(=O)N(c1cc(OC)cc(OC)c1)C2]

The title compound was prepared as described in Example 7. The starting material was prepared as described in Example 1 using 2-methoxyethanamine in place of methylamine in Step 5 and skipping Step 6. MS m/z: 505.3 (M+H$^+$). $^1$H NMR (400 MHz, CD$_3$OD): δ: 7.97 (1H, s), 7.67 (1H, m), 7.56 (1H, m), 7.34 (2H, m), 6.53 (2H, s), 6.46 (2H, m), 6.39 (1H, m), 5.80 (1H, dd), 4.70 (2H, s), 4.20 (2H, t), 3.77 (6H, s), 3.57 (2H, t), 3.25 (3H, s).

Example 62: Synthesis of I-60

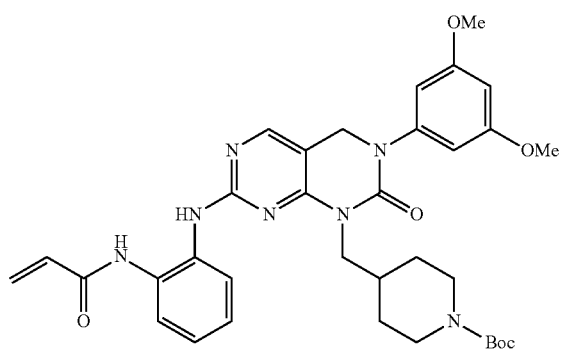 [SMILES: C=CC(=O)Nc1ccccc1Nc1ncc2c(n1)N(CC1CCN(C(=O)OC(C)(C)C)CC1)C(=O)N(c1cc(OC)cc(OC)c1)C2]

Compound I-60 was prepared as described in Example 25 using tert-butyl 4-(aminomethyl)piperidine-1-carboxylate in place of cyclopropanamine in Step 1 and mCPBA instead of SO$_2$Cl$_2$ in Step 5 (mCPBA oxidation is described in Example 2, step 7). MS m/z: 644.7 (M+H$^+$).

Example 63: I-61, (Racemic)

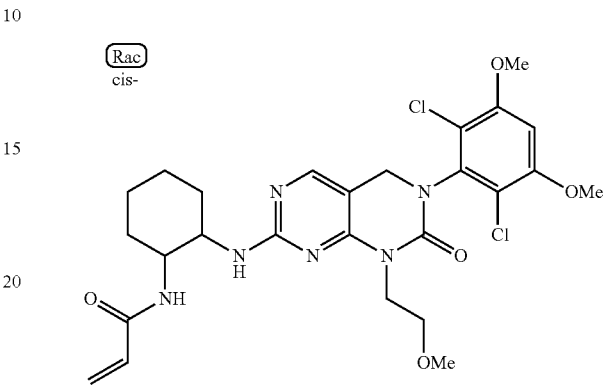

The title compound was prepared as outlined in Example 116. The starting material was prepared as described in Example 1 using 2-methoxyethanamine in place of methylamine in Step 5. MS m/z: 579.2 (M+H$^+$). $^1$H NMR (400 MHz, CD$_3$OD): δ: 7.97 (1H, s), 6.91 (1H, s), 6.34 (1H, m), 6.17 (1H, dd), 5.63 (1H, d), 4.59 (2H, m), 4.48 (1H, br s), 4.37 (1H, br s), 4.29 (2H, m), 3.97 (6H, s), 3.48 (2H, s), 3.35 (3H, s), 1.76 (6H, m).

Example 64: Synthesis of I-62

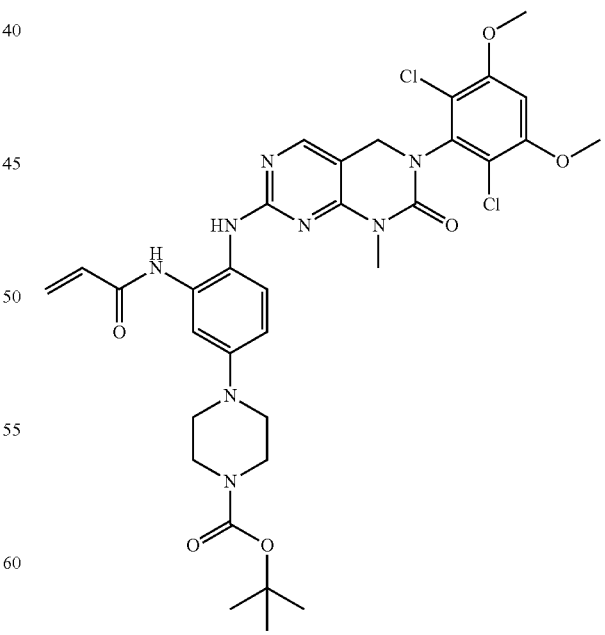

Compound I-62 was prepared as described in Example 17 using tert-butyl piperazine-1-carboxylate in place of N-ethylpiperizine in Step 2. MS m/z: 713.5 (M+H$^+$).

Example 65: Synthesis of I-63 (Racemic)

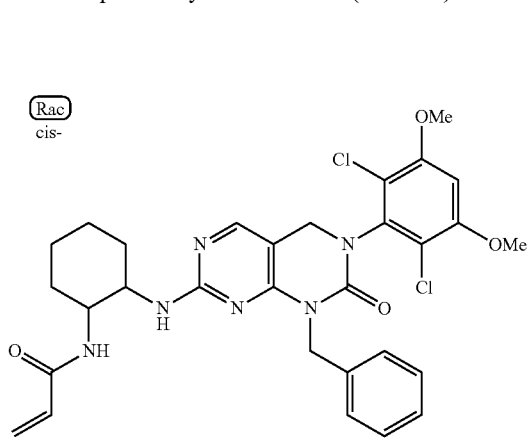

Compound I-63 was prepared as described in Example 21. Intermediate 1 was prepared as described in Example 2 using benzylamine in place of 3-nitrobenzylamine in Step 2. MS m/z: 611.4 (M+H$^+$).

Example 66: Synthesis of I-64

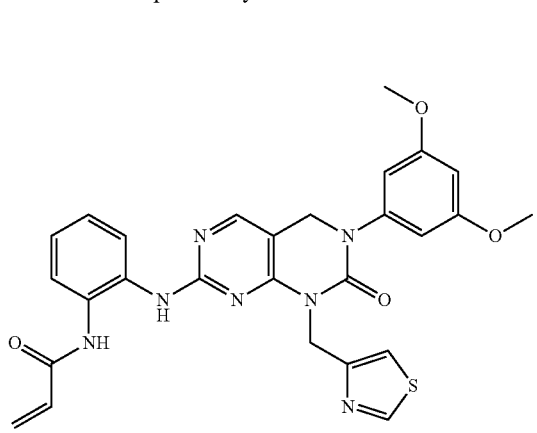

Compound I-64 was prepared as described in Example 7. The starting material was prepared as described in Example 1 using thiazol-4-ylmethanamine in place of methylamine in Step 5. MS m/z: 544.4 (M+H$^+$).

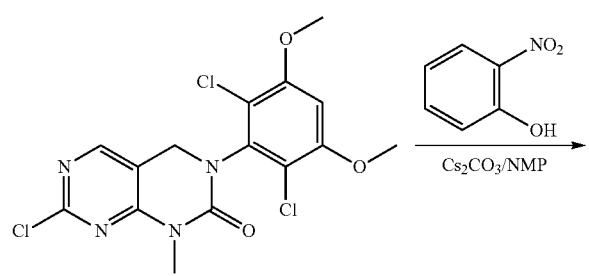

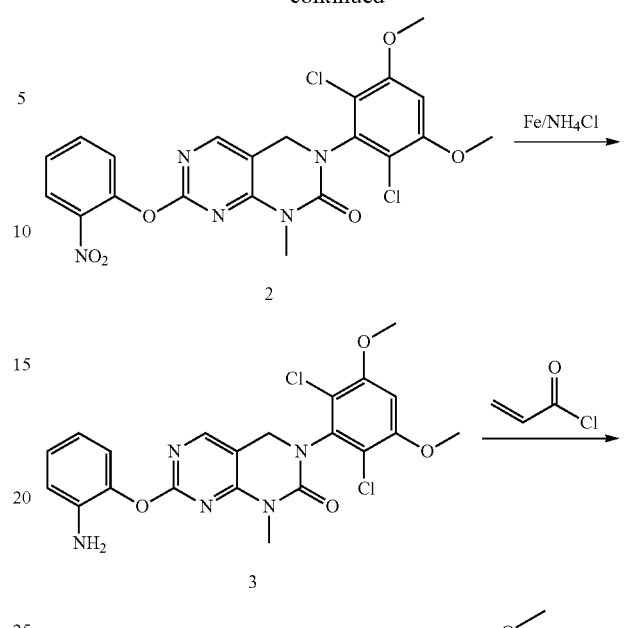

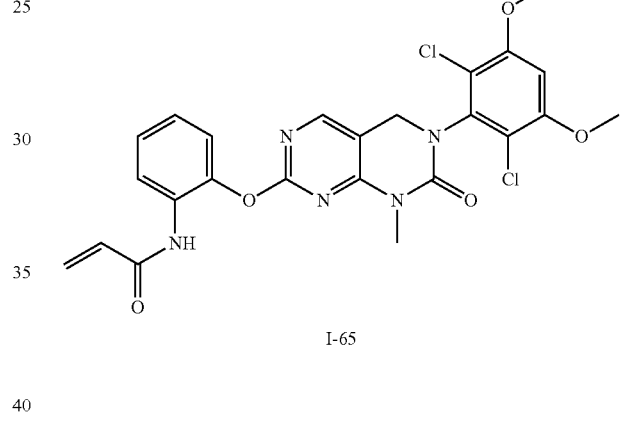

I-65

Step 1: Intermediate 2

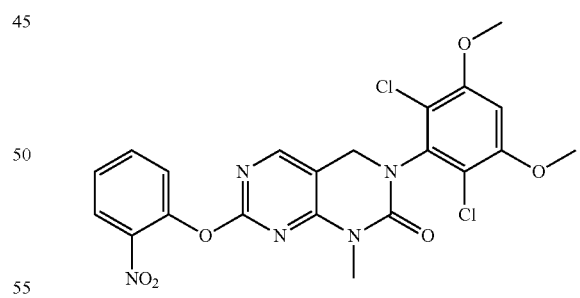

A mixture of Intermediate 6 from Example 1 (100 mg, 0.25 mmol), 2-nitrophenol (51.7 mg, 0.37 mmol), Cs$_2$CO$_3$ (162 mg, 0.50 mmol) in NMP (5 mL) was heated at 100° C. for 16 h. The mixture was cooled to ambient temperature. Water was added and the resultant mixture was extracted with EtOAc (35 mL×3). The combined organic layers were washed with water, dried (Na$_2$SO$_4$), filtered and concentrated in vacuo. The crude product was purified by column chromatography on silica gel (4% EtOAc/DCM) to afford 52.5 mg of the title compound.

Step 2: Intermediate 3

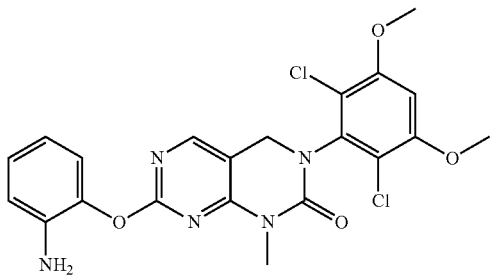 [SMILES: COc1cc(OC)c(Cl)c(N2Cc3cnc(Oc4ccccc4[N+](=O)[O-])nc3N(C)C2=O)c1Cl]

A mixture of Intermediate 2 (52.5 mg, 0.10 mmol), Fe (34.5 mg, 0.62 mmol), NH₄Cl (33.3 mg, 0.62 mmol) in ethanol (4 mL) and H₂O (2 mL) was heated to reflux for 2 h. The mixture was allowed cool to ambient temperature and filtered. The filtrate was concentrated in vacuo, water was added and the resultant mixture was extracted with EtOAc (35 mL×3). The combined organic layers were washed with saturated NaHCO₃, dried (Na₂SO₄), filtered and concentrated in vacuo. The crude product was purified by column chromatography on silica gel (3% MeOH/DCM) to afford 7.1 mg of the title compound. MS m/z: 476.3 (M+1)⁺

Step 3: I-65

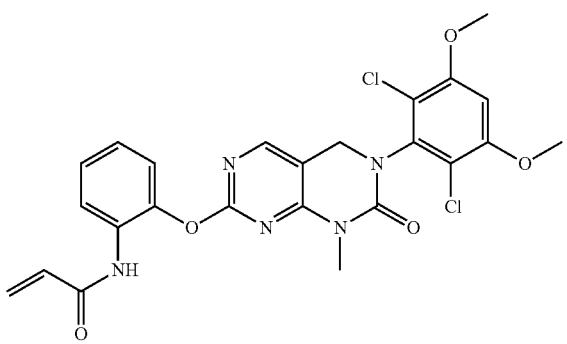 [SMILES: C=CC(=O)Nc1ccccc1Oc1ncc2c(n1)N(C)C(=O)N(c1c(Cl)c(OC)cc(OC)c1Cl)C2]

To a cooled (0° C.) solution of Intermediate 3 (7.10 mg, 0.02 mmol) and DIPEA (3.9 mg, 0.03 mmol) in THF (4 mL) was added acryloyl chloride (1.6 mg, 0.02 mmol). The reaction was stirred at 0° C. for 10 min after which it was quenched with saturated NaHCO₃ and extracted with EtOAc (20 mL×3). The combined organic layers were washed with saturated NaHCO₃, dried (Na₂SO₄), filtered and concentrated in vacuo. The residue was purified by column chromatography on silica gel (4% EtOAc in DCM) to afford 3.0 mg of the title compound. MS m/z: 530.4 (M+1)⁺. ¹H NMR (400 MHz, CDCl₃): δ 3.45 (s, 3H), 3.94 (s, 6H), 4.57 (s, 2H), 6.08 (d, 1H), 6.41 (dd, 1H), 6.61 (s, 1H), 6.67 (d, 1H), 7.05-7.11 (m, 1H), 7.20 (d, 1H), 7.27-7.30 (m, 1H), 7.97 (s, 1H), 8.38 (d, 1H).

Example 68: I-66

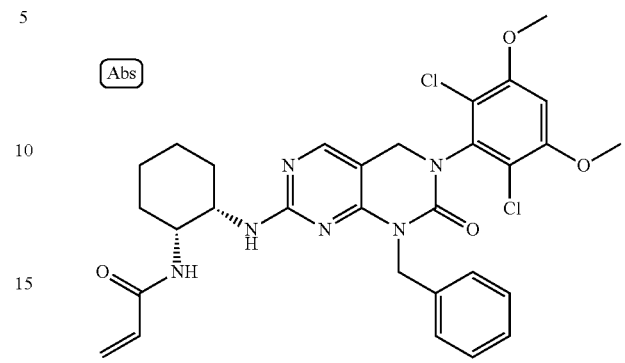

The title compound (40 mg) was prepared as described in Example 84 using tert-butyl (1R,2S)-2-aminocyclohexyl) carbamate in place of tert-butyl (1S,2R)-2-aminocyclohexyl)carbamate in Step 3. MS m/z: 611.1 (M+H⁺). ¹H NMR (400 MHz, DMSO-d6): δ: 7.96 (1H, d), 7.71 (1H, d), 7.28 (4H, m), 7.2 (1H, m), 7.0 (1H, s), 6.3 (1H, dd), 6.05 (1H, dd), 5.55 (1H, dd), 5.12 (1H, br s), 4.5 (2H, s), 3.96 (6H, s), 1.2-1.8 (8H, m).

Example 69: I-67

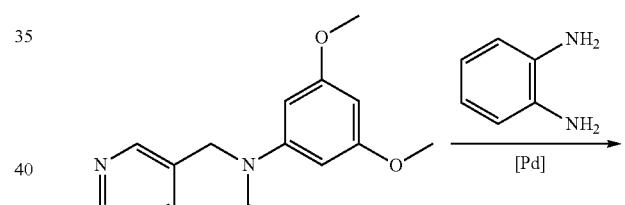

5

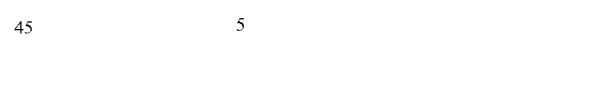

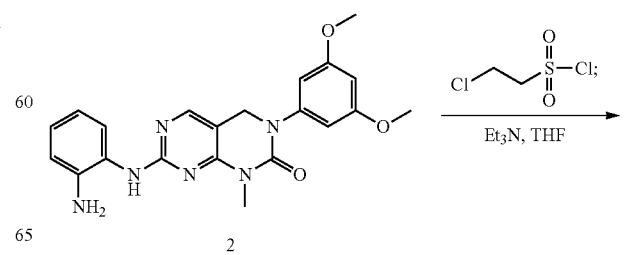

2

-continued

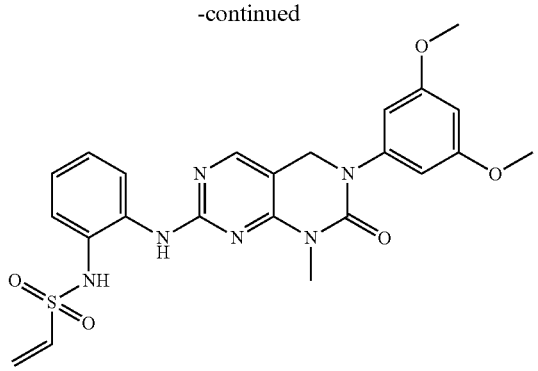

I-67

Step 1: Intermediate 2

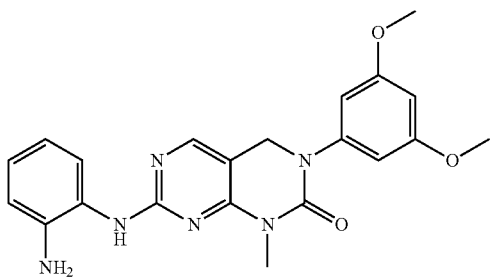 [SMILES: COc1cc(OC)cc(N2Cc3cnc(Nc4ccccc4N)nc3N(C)C2=O)c1]

A mixture of Intermediate 5 from Example 1 (150 mg, 0.45 mmol), benzene-1,2-diamine (48.5 mg, 0.45 mmol), Cs$_2$CO$_3$ (292 mg, 0.90 mmol), Pd$_2$(dba)$_3$ (41.0 mg, 0.045 mmol) and xantphos (51.8 mg, 0.09 mmol) in 1,4-dioxane (6 mL) was allowed to stir at 90° C. for 5 h under nitrogen atmosphere. The mixture was allowed to cool to ambient temperature. Water was added and the resultant mixture was extracted with EtOAc (30 mL×3). The combined organic layers were washed with brine, dried (Na$_2$SO$_4$), filtered and concentrated in vacuo. The crude product was purified by column chromatography on silica gel (3% MeOH/DCM) to afford 88.5 mg of the title compound. MS m/z: 407.4 (M+1)$^+$.

Step 2: I-67

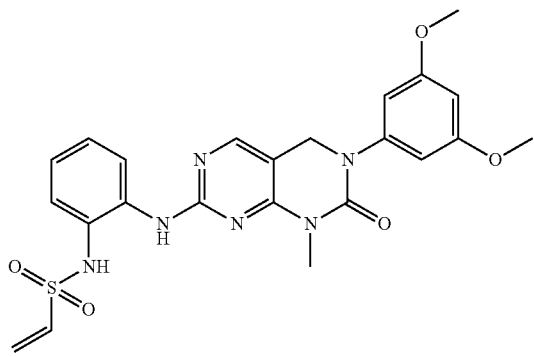 [SMILES: C=CS(=O)(=O)Nc1ccccc1Nc1ncc2c(n1)N(C)C(=O)N(c1cc(OC)cc(OC)c1)C2]

To a cooled (0° C.) solution of Intermediate 2 (88.2 mg, 0.22 mmol) and Et$_3$N (87.8 mg, 0.87 mmol) in THF (6 mL) was added 2-chloroethanesulfonyl chloride (35.4 mg, 0.22 mmol). The reaction was heated at 40° C. for 6 h. Water was added and the resultant mixture was extracted with EtOAc (30 mL×3). The combined organic layers were dried (Na$_2$SO$_4$), filtered and concentrated in vacuo. The crude product was purified by column chromatography on silica gel (3% MeOH/DCM) to afford 8.8 mg of the title compound. MS m/z: 497.4 (M+1)$^+$. $^1$H NMR (400 MHz, CDCl$_3$): δ 3.40 (s, 3H), 3.79 (s, 6H), 4.64 (s, 2H), 5.86 (d, 1H), 6.14 (d, 1H), 6.39 (s, 1H), 6.48 (d, 2H), 6.55 (dd, 9.6 Hz, 1H), 7.17-7.27 (m, 3H), 7.46-7.52 (m, 2H), 7.95 (s, 1H), 8.12 (s, 1H).

Example 70: Synthesis of I-68 (Racemic)

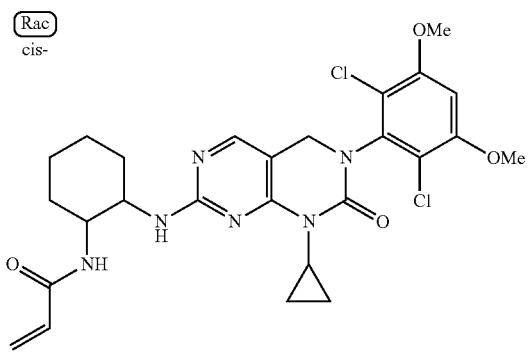 [SMILES: C=CC(=O)NC1CCCCC1Nc1ncc2c(n1)N(C1CC1)C(=O)N(c1c(Cl)c(OC)cc(OC)c1Cl)C2]

Compound I-68 was prepared as described in Example 21 using Intermediate 6 from Example 25 in place of Intermediate 2. MS m/z: 561.5 (M+H$^+$).

Example 71: Synthesis of I-69 (Racemic)

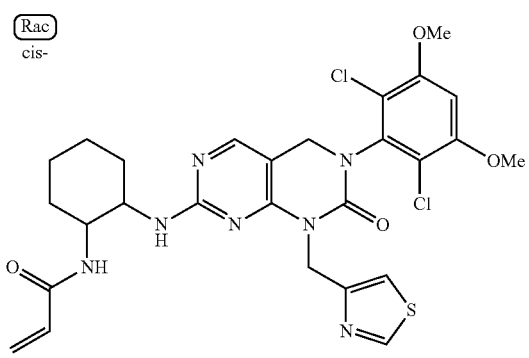 [SMILES: C=CC(=O)NC1CCCCC1Nc1ncc2c(n1)N(Cc1cscn1)C(=O)N(c1c(Cl)c(OC)cc(OC)c1Cl)C2]

Compound I-69 was prepared as described in Example 21 using Intermediate 1 from Example 116 in place of Intermediate 2. MS m/z: 618.4 (M+H$^+$).

Example 72: Synthesis of I-70 (Racemic)

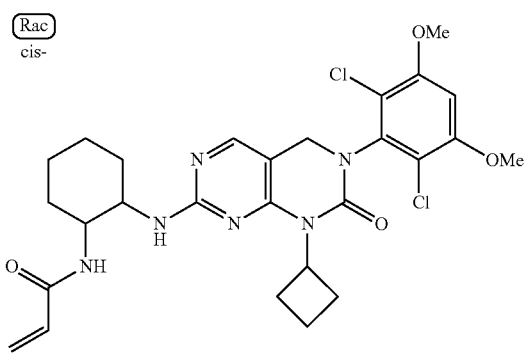 [SMILES: C=CC(=O)NC1CCCCC1Nc1ncc2c(n1)N(C1CCC1)C(=O)N(c1c(Cl)c(OC)cc(OC)c1Cl)C2]

Compound I-70 was prepared as described in Example 21. The starting material was prepared as described in Example 2 using cyclobutylamine in place of 3-nitrobenzylamine in Step 2. MS m/z: 575.3 (M+H⁺).

Example 73: Synthesis of I-71 (Racemic)

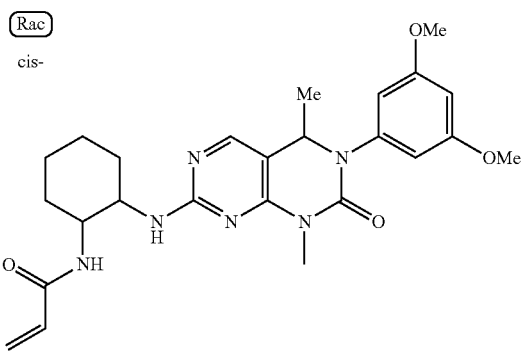 [SMILES: C=CC(=O)NC1CCCCC1Nc1ncc2c(n1)N(C)C(=O)N(c1cc(OC)cc(OC)c1)C2C]

Compound I-71 was prepared as described in Example 10 using 7-chloro-3-(3,5-dimethoxyphenyl)-1,4-dimethyl-3,4-dihydropyrimido[4,5-d]pyrimidin-2(1H)-one in place of Intermediate 8 in Step 1 (prepared as described in Example 2 using 1-(2,4-dichloropyrimidin-5-yl)ethanone in place of Intermediate 2, methylamine in place of 3-nitrobenzylamine in Step 2, and omitting step 6) and omitting steps 2-5. MS m/z: 481.5 (M+H⁺).

Example 74: Synthesis of I-72 (Racemic)

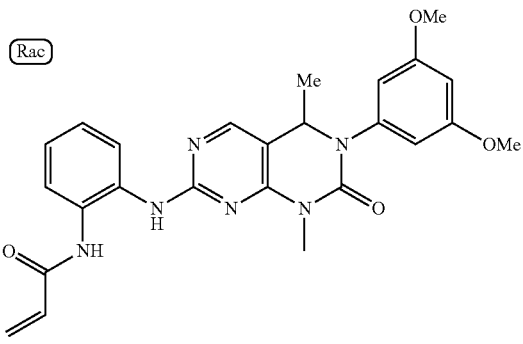 [SMILES: C=CC(=O)Nc1ccccc1Nc1ncc2c(n1)N(C)C(=O)N(c1cc(OC)cc(OC)c1)C2C]

Compound I-72 was prepared as described in Example 4 using 7-chloro-3-(3,5-dimethoxyphenyl)-1,4-dimethyl-3,4-dihydropyrimido[4,5-d]pyrimidin-2(1H)-one in place of Intermediate 1 in Step 1 (prepared as described in Example 2 using 1-(2,4-dichloropyrimidin-5-yl)ethanone in place of Intermediate 2, methylamine in place of 3-nitrobenzylamine in Step 2, and omitting step 6). MS m/z: 475.5 (M+H⁺).

Example 75: Synthesis of I-73 (Racemic)

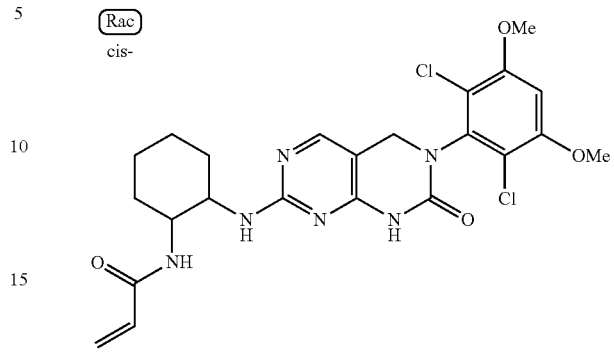

Compound I-73 was prepared as described in Example 21. The starting material was prepared as described in Example 2 using ammonia in place of 3-nitrobenzylamine in Step 2. MS m/z: 521.2 (M+H⁺).

Example 76: I-74

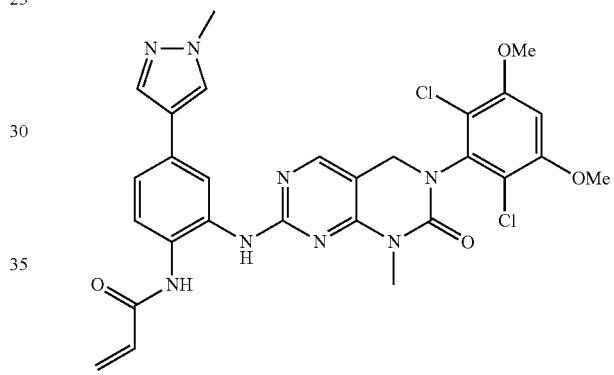

The title compound was prepared as described in Example 29 using Intermediate 6 from Example 1 in place of Intermediate 5. MS m/z: 609.0 (M+H⁺). ¹H NMR (400 MHz, CDCl₃): δ: 8.01 (1H, s), 7.95 (2H, m), 7.84 (1H, s), 7.52 (1H, dd), 7.44 (1H, dd), 6.88 (1H, s), 6.47 (1H, dd), 6.38 (1H, dd), 5.80 (1H, dd), 4.60 (2H, s), 3.95 (6H, s), 3.91 (3H, s), 3.35 (3H, s).

Example 77: Synthesis of I-75

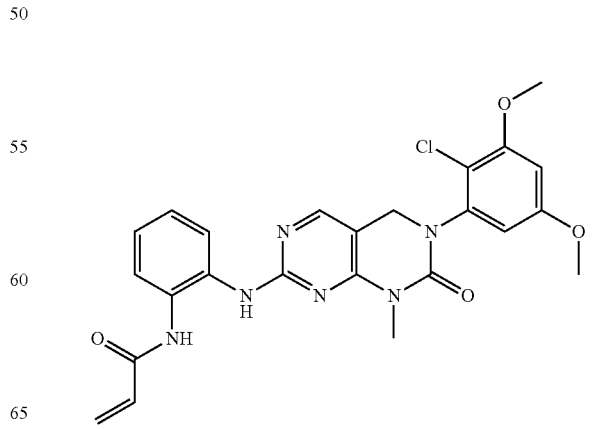

Compound I-75 was prepared as described in Example 102 using methylamine in place of cyclopropanamine in Step 5. MS m/z: 495.3 (M+H⁺).

Example 78: Synthesis of I-76 (Racemic)

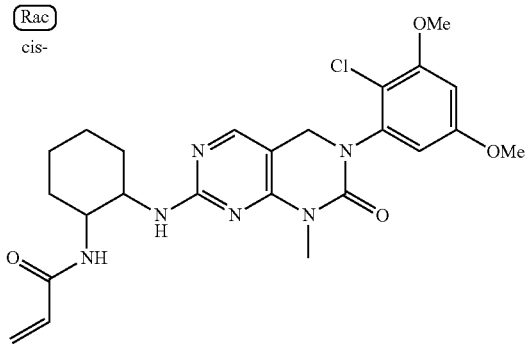 [SMILES: C=CC(=O)NC1CCCCC1Nc1ncc2c(n1)N(C)C(=O)N(c1cc(OC)cc(OC)c1Cl)C2]

Compound I-76 was prepared as described in Example 21. The starting material was prepared as described in Example 2 using methylamine in place of 3-nitrobenzylamine in Step 2, using 2-chloro-3,5-dimethoxyaniline in place of 3,5-dimethoxyaniline in Step 4, and skipping Step 6. MS m/z: 501.3 (M+H⁺).

Example 79; I-77

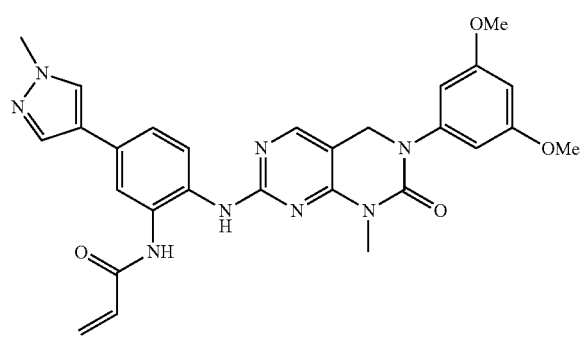 [SMILES: C=CC(=O)Nc1cc(-c2cnn(C)c2)ccc1Nc1ncc2c(n1)N(C)C(=O)N(c1cc(OC)cc(OC)c1)C2]

The title compound was prepared as described in Example 29 using 5-bromo-2-nitroaniline in place of Intermediate 1 in Step 1. MS m/z: 541.2 (M+H⁺). ¹H NMR (400 MHz, CDCl₃): δ: 8.00 (1H, s), 7.95 (1H, s), 7.84 (1H, s), 7.77 (1H, s), 7.64 (1H, d), 7.53 (1H, m), 6.54 (2H, s), 6.46 (1H, m), 6.41 (1H, m), 5.83 (1H, dd), 4.71 (2H, s), 3.93 (3H, s), 3.78 (6H, s), 3.36 (3H, s).

Example 80: I-78

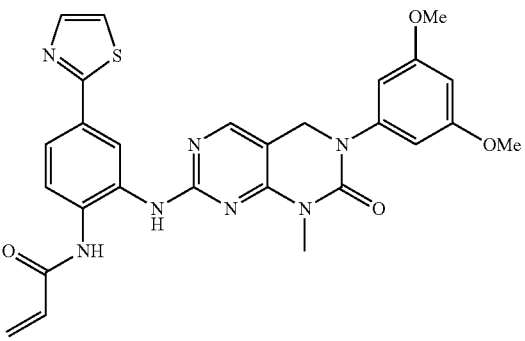 [SMILES: C=CC(=O)Nc1ccc(-c2nccs2)cc1Nc1ncc2c(n1)N(C)C(=O)N(c1cc(OC)cc(OC)c1)C2]

The title compound was prepared as outlined in Example 29 using 2-(4,4,5,5-tetramethyl-1,3,2-dioxaborolan-2-yl)thiazole in place of Intermediate 3 in Step 2. MS m/z: 544.2 (M+H⁺). ¹H NMR (400 MHz, DMSO-d6): δ: 9.94 (1H, s), 8.91 (1H, s), 8.52 (1H, s), 8.12 (1H, s), 7.89 (1H, d), 7.74 (1H, d), 7.68 (1H, dd), 6.54 (3H, m), 6.41 (1H, m), 6.27 (1H, dd), 5.79 (1H, dd), 4.69 (2H, s), 3.72 (6H, s), 3.26 (3H, s).

Example 81: Synthesis of I-79

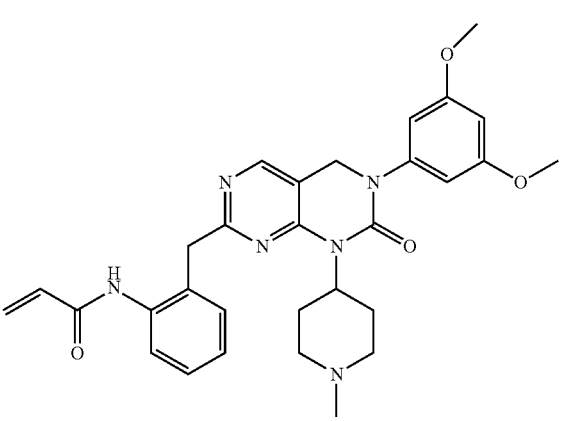 [SMILES: C=CC(=O)Nc1ccccc1Cc1ncc2c(n1)N(C1CCN(C)CC1)C(=O)N(c1cc(OC)cc(OC)c1)C2]

Compound I-79 was prepared as described in Example 7. The starting material was prepared as described in Example 1 using 1-methylpiperidin-4-amine in place of methylamine in Step 5. MS m/z: 468.3 (M+H⁺).

Example 82: Synthesis of I-80

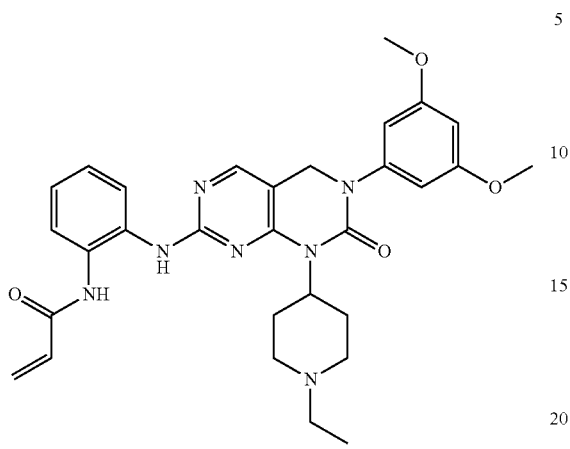

Compound I-80 was prepared as described in Example 7. The starting material was prepared as described in Example 1 using 1-ethylpiperidin-4-amine in place of methylamine in Step 5. MS m/z: 558.4 (M+H$^+$).

Example 83: Synthesis of I-81

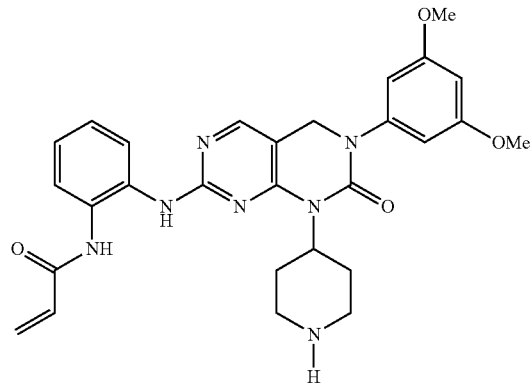 [SMILES: C=CC(=O)Nc1ccccc1Nc1ncc2c(n1)N(C1CCNCC1)C(=O)N(c1cc(OC)cc(OC)c1)C2]

Compound I-81 was prepared as described in Example 7. The starting material was prepared as described in Example 1 using tert-butyl 4-aminopiperidine-1-carboxylate in place of methylamine in Step 5. A final BOC deprotection was performed (as described in Example 3, Step 5). MS m/z: 530.3 (M+H$^+$).

Example 84: Synthesis of I-82

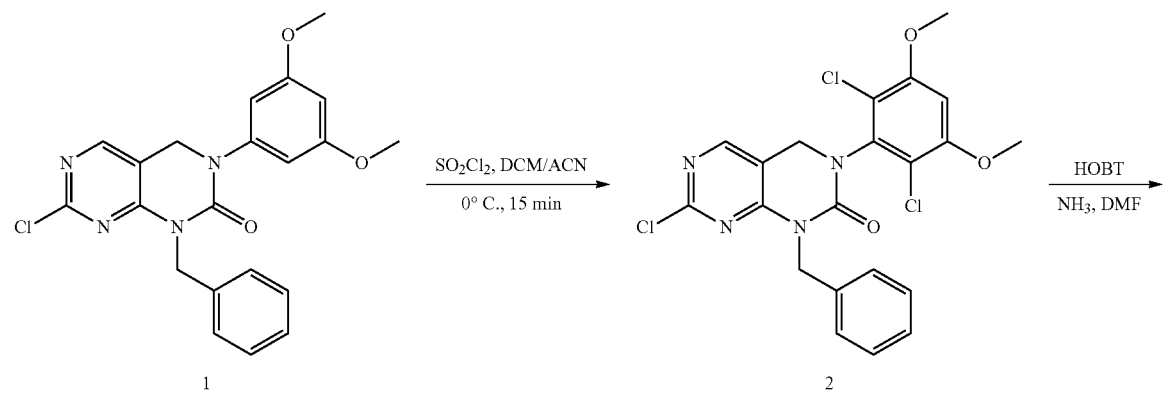

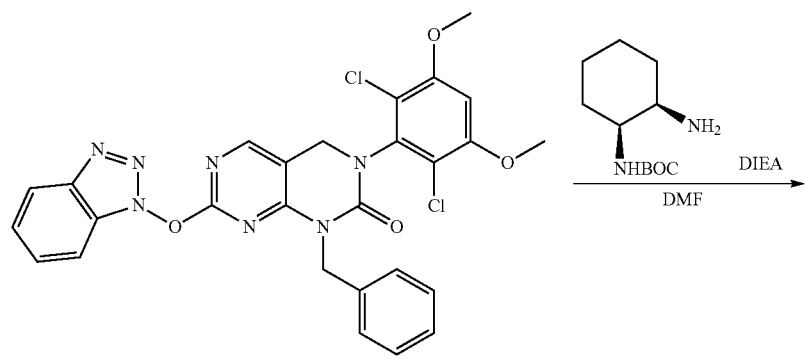

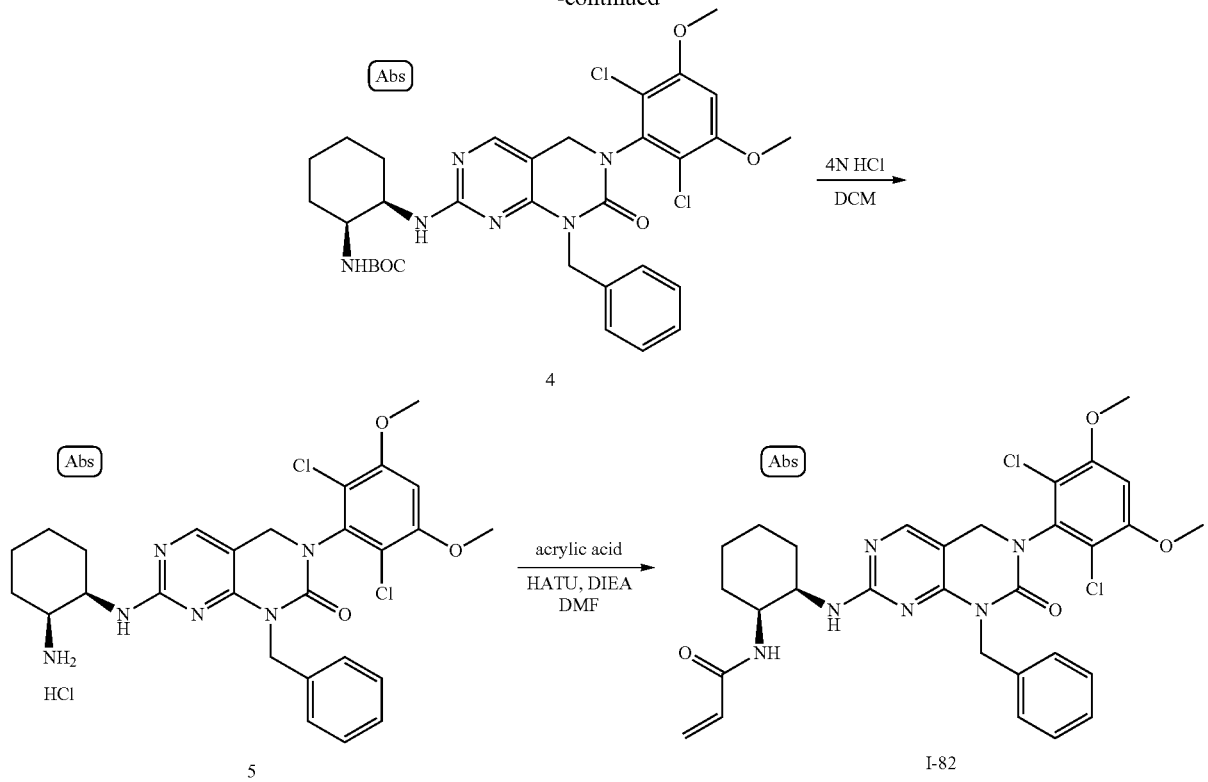

Step 1: Intermediate 2

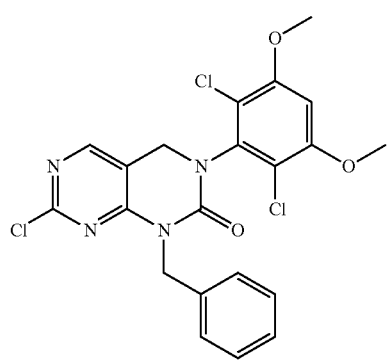 [SMILES: COc1cc(OC)c(Cl)c(N2Cc3cnc(Cl)nc3N(Cc3ccccc3)C2=O)c1Cl]

The title compound was prepared as described in Example 1 using benzylamine in place of methylamine in Step 5.

Step 2: Intermediate 3

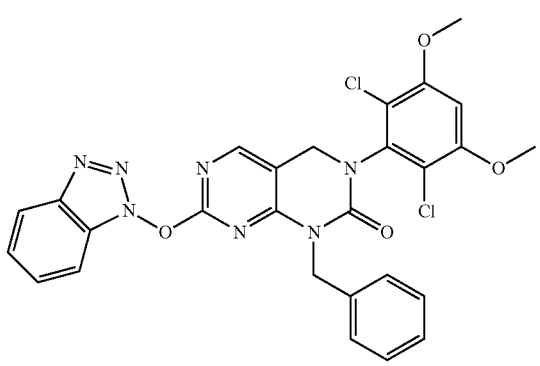 [SMILES: COc1cc(OC)c(Cl)c(N2Cc3cnc(On4nnc5ccccc54)nc3N(Cc3ccccc3)C2=O)c1Cl]

The title compound was prepared as described in the literature (*Chemistry & Biology* 2010, 17, 285-295). Intermediate 2 (150 mg, 0.31 mmol) and HOBT (78 mg, 0.51 mmoL) were dissolved in 4 mL of DMF and allowed to stir for 90 min. Ammonia (3.8 mL, 0.5 N in dioxane, 1.9 mmoL) was added and the reaction mixture was allowed to stir at ambient temperature overnight. Solvent was removed under reduced pressure and the reaction mixture partitioned with water, brine and chloroform. The organic phase was dried over sodium sulfate and the solvent removed under reduced pressure to provide 300 mg of the title compound which was used as is in the next reaction. MS m/z: 578.2 (M+H$^+$).

Step 3: Intermediate 4

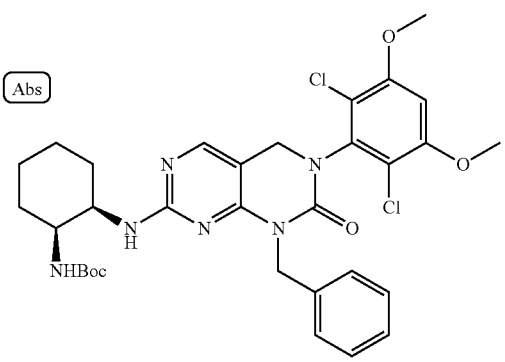 [SMILES: COc1cc(OC)c(Cl)c(N2Cc3cnc(N[C@@H]4CCCC[C@@H]4NC(=O)OC(C)(C)C)nc3N(Cc3ccccc3)C2=O)c1Cl]

To a solution of Intermediate 3 (300 mg, 0.52 mmoL), tert-butyl ((1S,2R)-2-aminocyclohexyl)carbamate (214 mg, 1 mmoL) and DIPEA (170 uL, 1.56 mmoL) in 4 mL of DMF

345 was heated to 70° C. for 4 h. The reaction mixture was allowed to cool and partitioned with water, brine and EtOAc. The organic phase was dried over sodium sulfate and the solvent under reduced pressure. The crude product was subjected to chromatography on silica gel (eluting with a gradient of 0-75% EtOAc in heptane), which gave 57 mg of the title compound. MS m/z: 657.2 (M+H$^+$).

Step 4: Intermediate 5

To a solution of the Intermediate 4 (57 mg, 0.087 mmol) in 5 mL of DCM was added 500 uL of HCl (4 N in dioxane) and the reaction was stirred at ambient temperature for 1 h. Solvent was removed under reduced pressure which gave 77 mg of the title compound. MS m/z: 557.2 (M+H$^+$).

Step 5: I-82

To a solution of Intermediate 5 (77 mg, 0.13 mmoL) and acrylic acid (9 ul, 0.13 mmoL) in 500 uL of DMF was added DIPEA (114 uL, 0.65 mmoL) and HATU (49 mg, 0.13 mmoL). The reaction was allowed to stir at ambient temperature for 15 mins then purified directly by flash chromatography (eluting with a gradient of 0-70% acetone in heptane), which gave 16 mg of the title compound. MS m/z: 611.1 (M+H$^+$). $^1$H NMR (400 MHz, DMSO-d6): δ: 7.96 (1H, d), 7.72 (1H, d), 7.28 (4H, m), 7.2 (1H, m), 7.0 (1H, s), 6.31 (1H, dd), 6.05 (1H, dd), 5.55 (1H, dd), 5.12 (2H, br s), 4.5 (2H, s), 3.96 (6H, s), 1.2-1.8 (8H, m).

346

Example 85: Synthesis of I-83

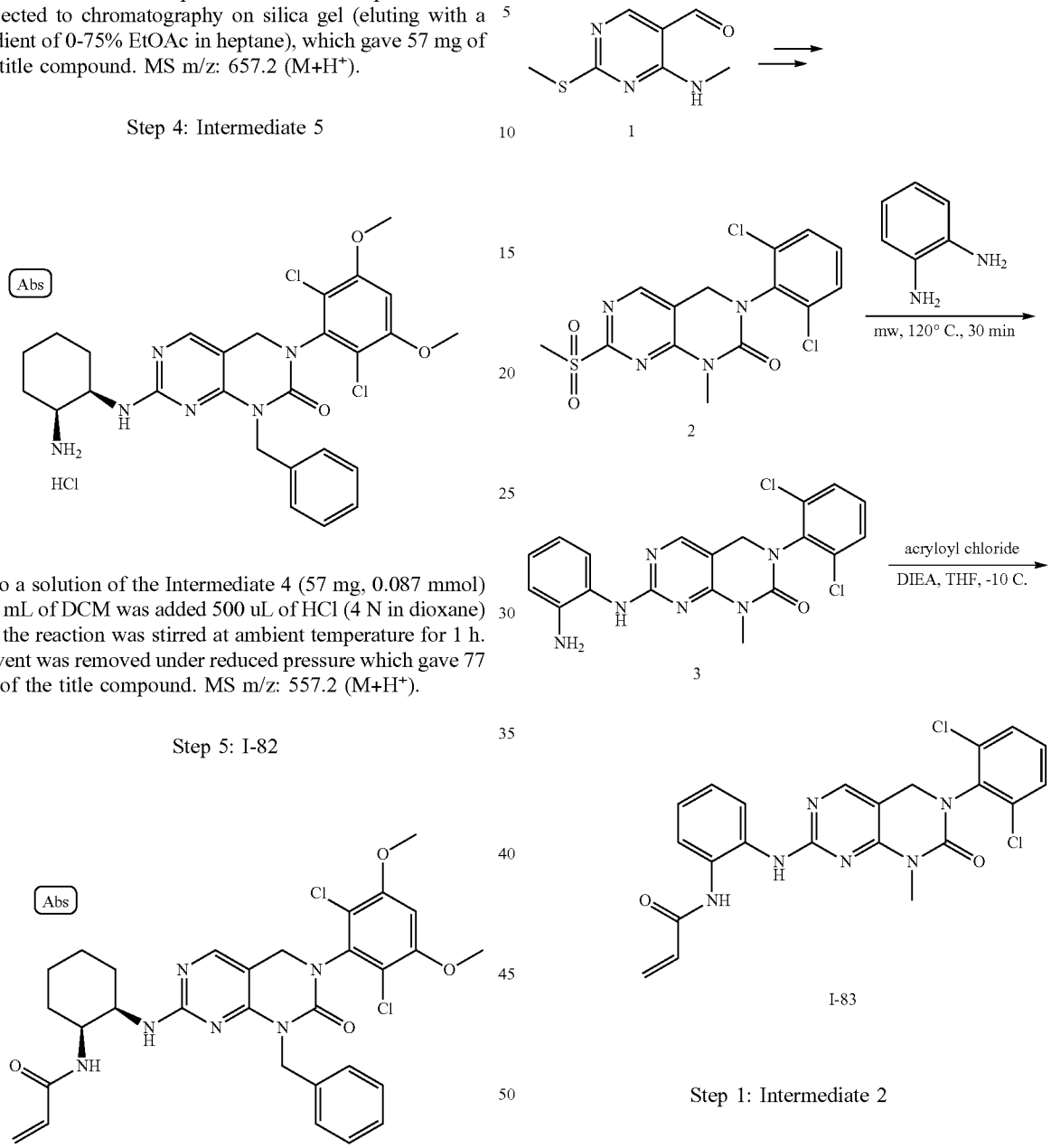

Step 1: Intermediate 2

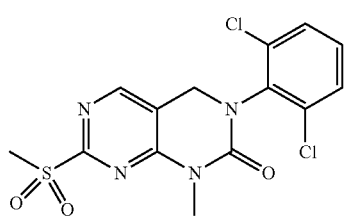 [SMILES: CN1C(=O)N(c2c(Cl)cccc2Cl)Cc2cnc(S(C)(=O)=O)nc21]

The title compound was prepared from Intermediate 1 according to literature procedures (WO 01/29042; PCT/EP00/10088).

Step 2: Intermediate 3

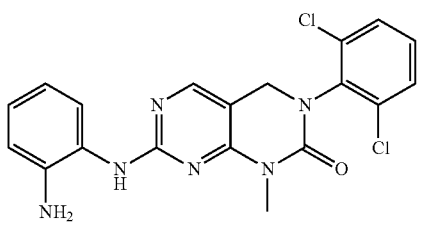 [SMILES: CN1C(=O)N(c2c(Cl)cccc2Cl)Cc2cnc(Nc3ccccc3N)nc21]

Intermediate 2 (53 mg, 0.14 mmol) and phenylenediamine (74 mg, 0.69 mmoL) were heated neat in a microwave at 120° C. for 30 min. The crude product was subjected to flash chromatography on silica gel (eluting with a gradient of 0-80% EtOAc in heptane) to provide 30 mg of the title compound. MS m/z: 415.1 (M+H⁺).

Step 3: I-83

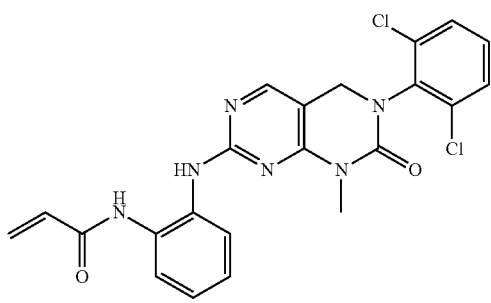 [SMILES: C=CC(=O)Nc1ccccc1Nc1ncc2c(n1)N(C)C(=O)N(c1c(Cl)cccc1Cl)C2]

To a cooled (−10° C.) solution of Intermediate 3 (30 mg, 0.072 mmoL) in 500 uL of THF was added acryloyl chloride (6.1 μL, 0.076 mmoL). The reaction was allowed to stir at −10° C. for 5 min, then treated with DIPEA (14 uL, 0.079 mmoL) and allowed to stir for an additional 5 min. The reaction mixture was partitioned between water, brine and the organic layer separated and purified using flash chromatography on silica gel (eluting with a gradient of 0-100% EtOAc in heptane), which gave 25 mg of the title compound. MS m/z: 469.1 (M+H⁺). ¹H NMR (400 MHz, DMSO-d6): δ: 8.68 (1H, s), 8.12 (1H, s), 7.8 (1H, d), 7.64 (2H, d), 7.58 (1H, d), 7.48 (1H, t), 7.2 (1H, t), 7.12 (1H, t), 6.5 (1H, dd), 6.3 (1H, dd), 5.79 (1H, dd), 4.57 (2H, s), 3.25 (3H, s).

Example 86: Synthesis of I-84

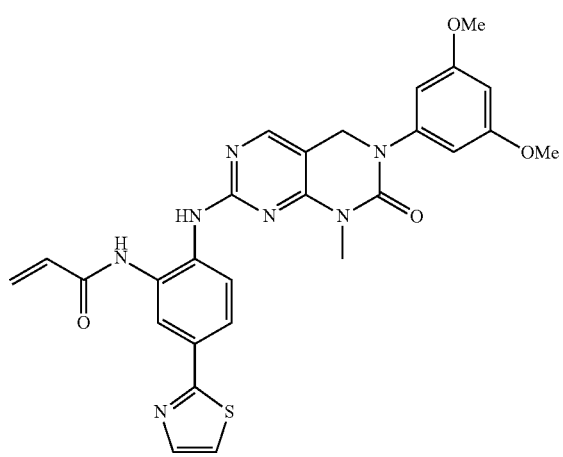 [SMILES: C=CC(=O)Nc1cc(-c2nccs2)ccc1Nc1ncc2c(n1)N(C)C(=O)N(c1cc(OC)cc(OC)c1)C2]

Compound I-84 was prepared as described in Example 31 using 2-(4,4,5,5-tetramethyl-1,3,2-dioxaborolan-2-yl)thiazole in place of Intermediate 3 in Step 2. MS m/z: 544.4 (M+H⁺).

Example 87: Synthesis of I-85

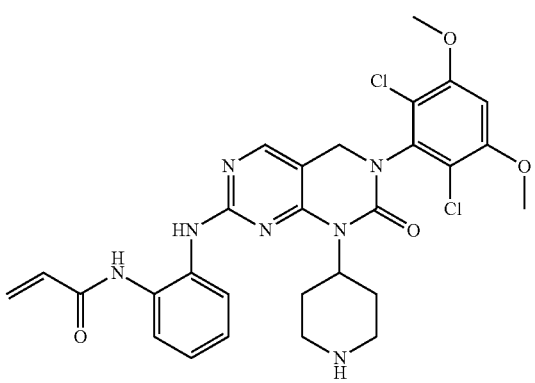 [SMILES: C=CC(=O)Nc1ccccc1Nc1ncc2c(n1)N(C1CCNCC1)C(=O)N(c1c(Cl)c(OC)cc(OC)c1Cl)C2]

Compound I-85 was prepared as described in Example 7. The starting material was prepared as described in Example 1 using tert-butyl 4-aminopiperidine-1-carboxylate in place of methylamine in Step 5. A final BOC deprotection was performed (as described in Example 3, Step 5). MS m/z: 598.2 (M+H⁺).

Example 88: Synthesis of I-86

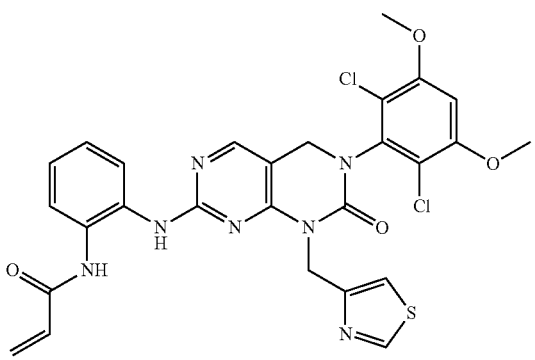 [SMILES: C=CC(=O)Nc1ccccc1Nc1ncc2c(n1)N(Cc1cscn1)C(=O)N(c1c(Cl)c(OC)cc(OC)c1Cl)C2]

Compound I-86 was prepared as described in Example 7. The starting material was prepared as described in Example 1 using thiazol-4-ylmethanamine in place of methylamine in Step 5. MS m/z: 612.3 (M+H⁺).

Example 89: Synthesis of I-87

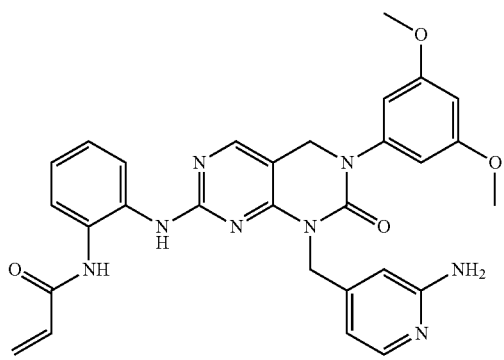

Compound I-87 was prepared as described in Example 7. The starting material was prepared as described in Example 1 using 4-(aminomethyl)pyridin-2-amine in place of methylamine in Step 5. MS m/z: 553.4 (M+H$^+$).

Example 90: Synthesis of I-88

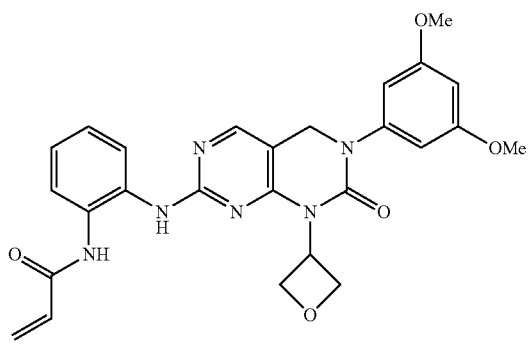 [SMILES: C=CC(=O)Nc1ccccc1Nc1ncc2c(n1)N(C1COC1)C(=O)N(c1cc(OC)cc(OC)c1)C2]

Compound I-88 was prepared as described in Example 7. The starting material was prepared as described in Example 1 using oxetan-3-amine in place of methylamine in Step 5. MS m/z: 503.4 (M+H$^+$).

Example 91: Synthesis of I-89 (Racemic)

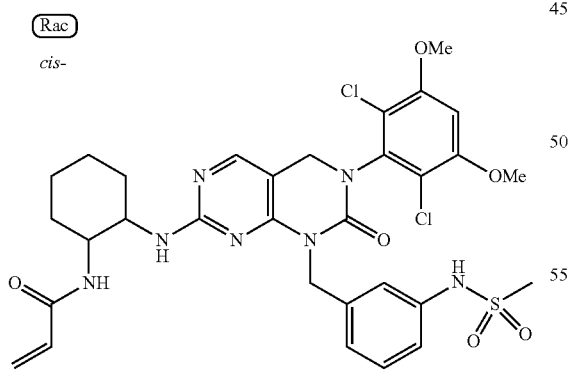

Compound I-89 was prepared as described in Example 21. N-(3-((7-chloro-3-(2,6-dichloro-3,5-dimethoxyphenyl)-2-oxo-3,4-dihydropyrimido[4,5-d]pyrimidin-1(2H)-yl) methyl)phenyl)methanesulfonamide was used in place of Intermediate 2 and was prepared as described in Example 1 using N-(3-(aminomethyl)phenyl)methanesulfonamide in place of methylamine in Step 5. MS m/z: 704.3 (M+H$^+$).

Example 92: Synthesis of I-90

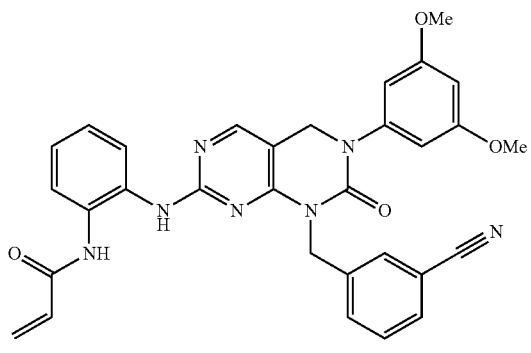 [SMILES: C=CC(=O)Nc1ccccc1Nc1ncc2c(n1)N(Cc1cccc(C#N)c1)C(=O)N(c1cc(OC)cc(OC)c1)C2]

Compound I-90 was prepared as described in Example 7. The starting material was prepared as described in Example 1 using 3-(aminomethyl)benzonitrile in place of methylamine in Step 5. MS m/z: 562.5 (M+H$^+$).

Example 93: I-91

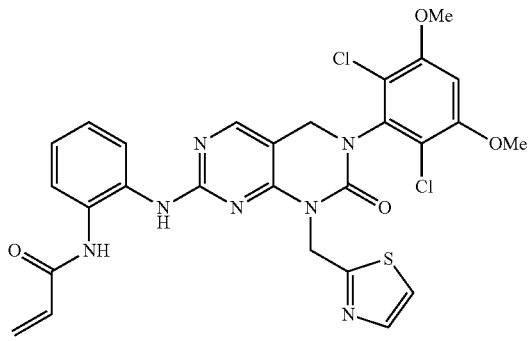 [SMILES: C=CC(=O)Nc1ccccc1Nc1ncc2c(n1)N(Cc1nccs1)C(=O)N(c1c(Cl)c(OC)cc(OC)c1Cl)C2]

The title compound was prepared as described in Example 5. The starting material was prepared as described in Example 1 using thiazol-2-ylmethanamine in place of methylamine in Step 5. MS m/z: 612.0 (M+H$^+$). $^1$H NMR (400 MHz, CDCl$_3$): δ: 8.07 (1H, s), 7.11 (1H, d), 7.51 (3H, m), 7.23 (2H, m), 6.90 (1H, s), 6.45 (1H, dd), 6.34 (1H, dd), 5.79 (1H, dd), 5.50 (2H, s), 4.67 (2H, s), 3.96 (6H, s).

Example 94: I-92

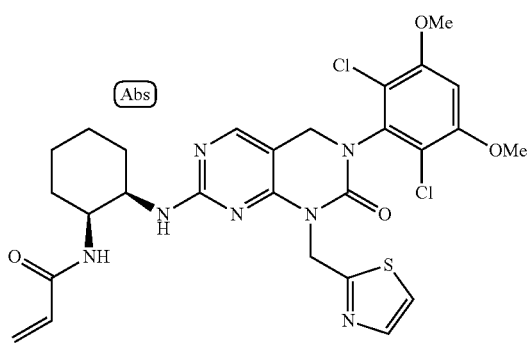 [SMILES: C=CC(=O)N[C@H]1CCCC[C@H]1Nc1ncc2c(n1)N(Cc1nccs1)C(=O)N(c1c(Cl)c(OC)cc(OC)c1Cl)C2]

The title compound was prepared as outlined in Example 116. The starting material was prepared as described in Example 1 using thiazol-2-ylmethanamine in place of methylamine in Step 5. MS m/z: 618.2 (M+H$^+$). $^1$H NMR (400

MHz, CD₃OD): δ: 8.00 (1H, s), 7.70 (1H, d), 7.52 (1H, d), 6.92 (1H, s), 6.32 (1H, dd), 6.16 (1H, d), 5.62 (1H, dd), 5.56 (2H, br), 4.65 (2H, s), 3.97 (6H, s), 1.69 (6H, br), 1.51 (2H, br).

Example 95: Synthesis of I-93

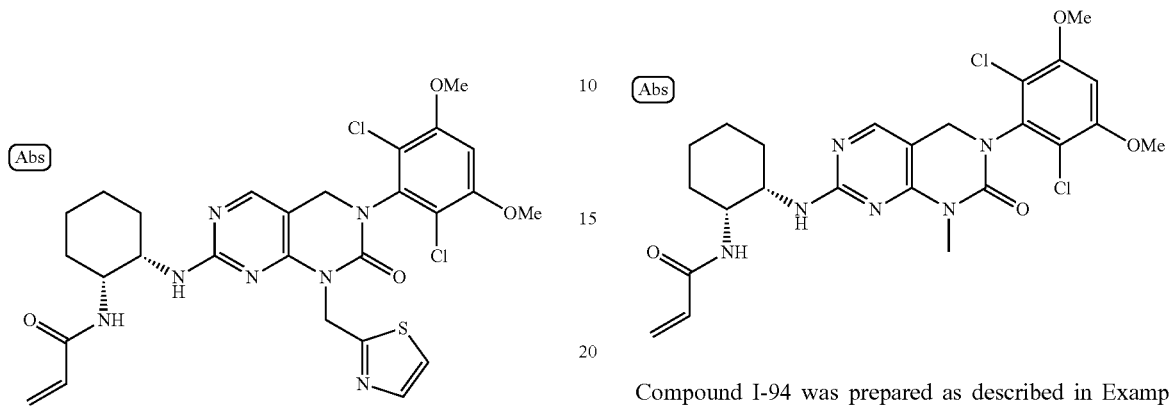

Compound I-93 was prepared as described in Example 116 using ((1R,2S)-2-aminocyclohexyl)carbamate in place of ((1S,2R)-2-aminocyclohexyl)carbamate in Step 2. The starting material was prepared as described in Example 1 using thiazol-2-ylmethanamine in place of methylamine in Step 5. MS m/z: 618.1 (M+H⁺).

Example 96: Synthesis of I-94

Compound I-94 was prepared as described in Example 116 using ((1R,2S)-2-aminocyclohexyl)carbamate in place of ((1S,2R)-2-aminocyclohexyl)carbamate in Step 2. The starting material was Intermediate 6 from Example 1. MS m/z: 535.1 (M+H⁺).

Example 97: Synthesis of I-95

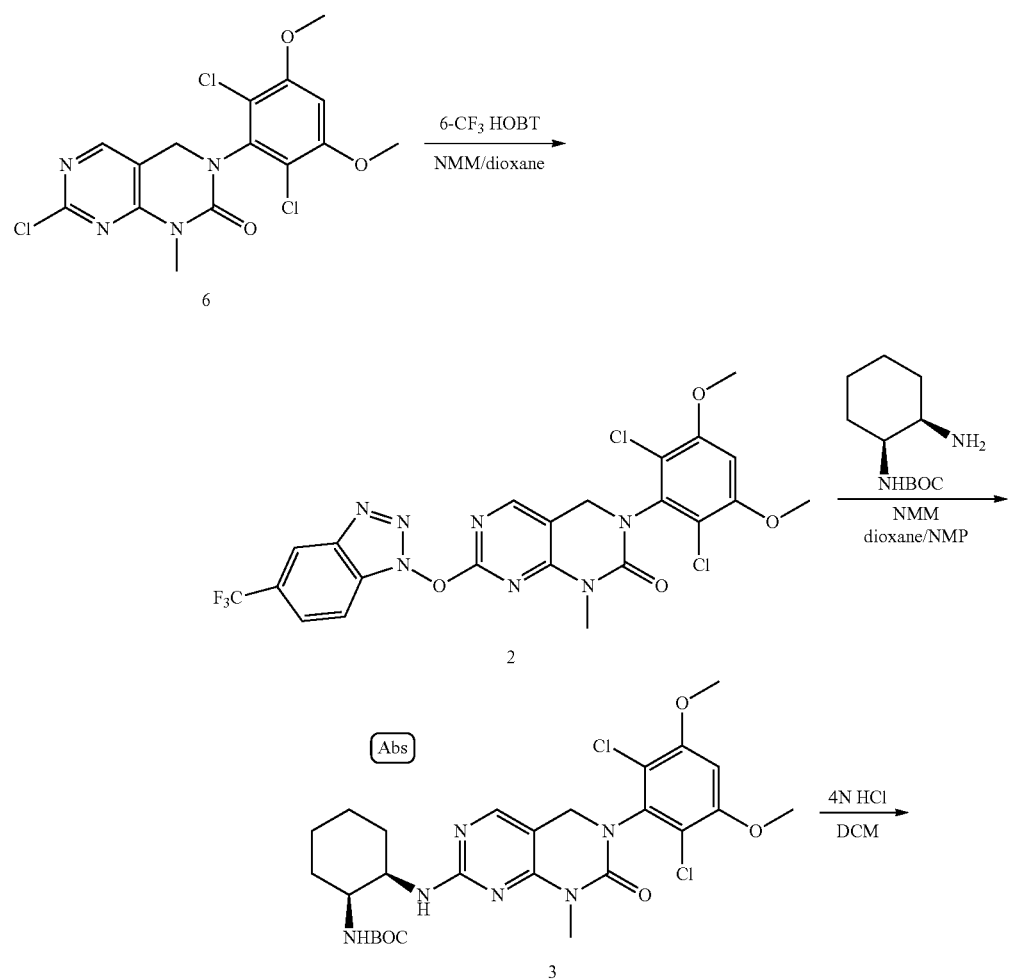

-continued

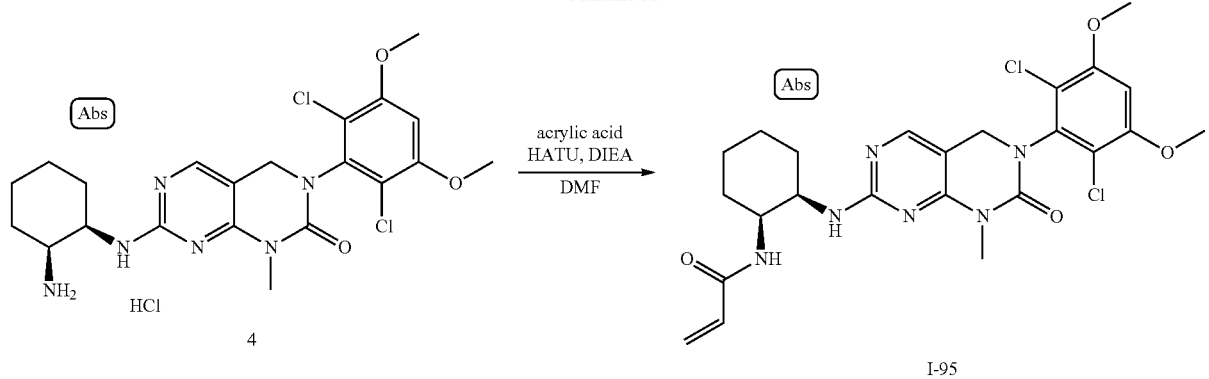

Step 1: Intermediate 2

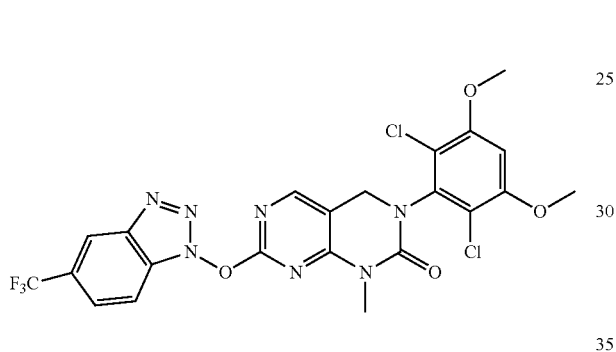

The title compound (645 mg, MS m/z: 570.0 (M+H+)) was prepared from Intermediate 6 (Example 1), as described in Example 84 using 6-CF$_3$-HOBT in place of HOBT in Step 2.

Step 2: Intermediate 3

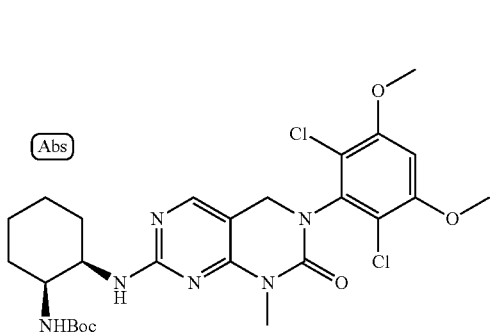 [SMILES: COc1cc(OC)c(Cl)c(N2Cc3cnc(N[C@@H]4CCCC[C@@H]4NC(=O)OC(C)(C)C)nc3N(C)C2=O)c1Cl]

The title compound (440 mg, MS m/z: 581.2 (M+H+) was prepared from Intermediate 2, as described in Example 84, Step 3.

Step 3: Intermediate 4

To a solution of the Intermediate 3 (440 mg, 0.76 mmoL) in 10 mL of DCM was added 10 mL of HCl (4 N in dioxane) and the reaction was allowed to stir at ambient temperature for 2 h. Solvent was removed under reduced pressure and the resulting solid used directly in the subsequent reaction.

Step 4: I-95

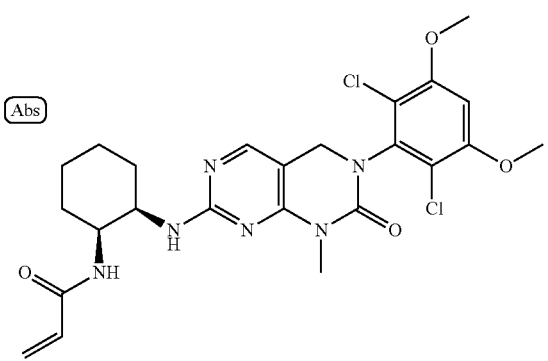 [SMILES: C=CC(=O)N[C@H]1CCCC[C@H]1Nc1ncc2c(n1)N(C)C(=O)N(c1c(Cl)c(OC)cc(OC)c1Cl)C2]

The title compound (190 mg) was prepared as described in Example 84, Step 5. MS m/z: 535.1 (M+H)+. $^1$H NMR (400 MHz, DMSO-d6): δ: 7.96 (1H, s), 7.77 (1H, d), 6.98 (1H, s), 6.7 (1H, br s), 6.32 (1H, br s), 6.04 (1H, d), 5.55 (1H, dd), 4.44 (2H, s), 4.14 (2H, m), 3.97 (6H, s), 3.22 (3H, s), 1.37-1.76 (8H, m).

Example 98: Synthesis of I-96

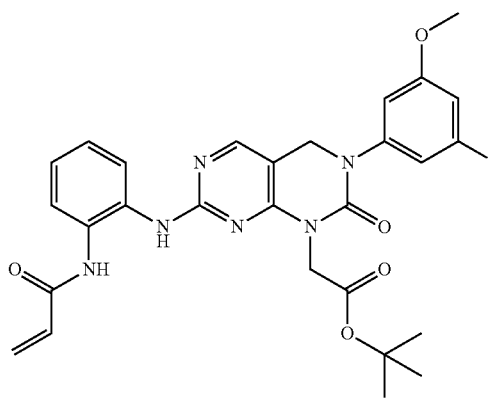

Compound I-96 was prepared as described in Example 7. The starting material was prepared as described in Example 1 using tert-butyl 2-aminoacetate in place of methylamine in Step 5. MS m/z: 561.5 (M+H$^+$).

Example 99: Synthesis of I-97

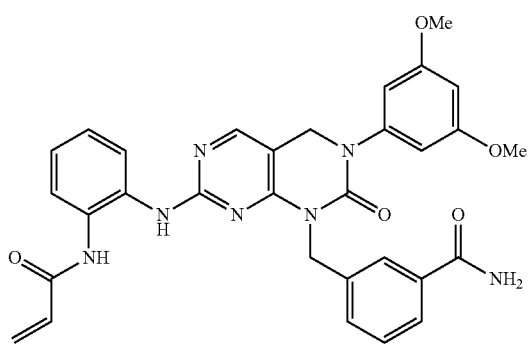 [SMILES: C=CC(=O)Nc1ccccc1Nc1ncc2c(n1)N(Cc1cccc(C(N)=O)c1)C(=O)N(c1cc(OC)cc(OC)c1)C2]

Compound I-97 was prepared as described in Example 7. The starting material was prepared as described in Example 1 using 3-(aminomethyl)benzamide in place of methylamine in Step 5. MS m/z: 580.4 (M+H$^+$).

Example 100: Synthesis of I-98

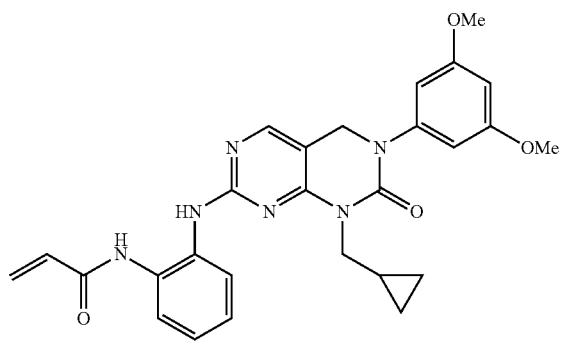 [SMILES: C=CC(=O)Nc1ccccc1Nc1ncc2c(n1)N(CC1CC1)C(=O)N(c1cc(OC)cc(OC)c1)C2]

Compound I-98 was prepared as described in Example 7. The starting material was prepared as described in Example 1 using cyclopropylmethanamine in place of methylamine in Step 5. MS m/z: 501.5 (M+H$^+$).

Example 101: Synthesis of I-99

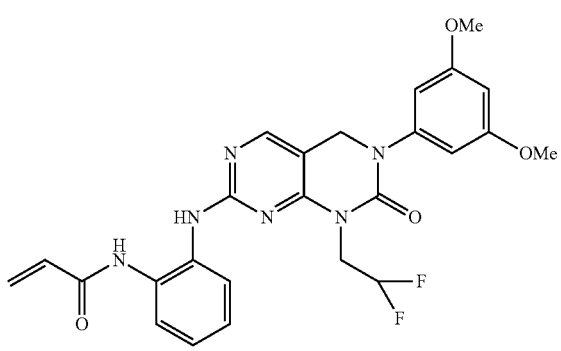 [SMILES: C=CC(=O)Nc1ccccc1Nc1ncc2c(n1)N(CC(F)F)C(=O)N(c1cc(OC)cc(OC)c1)C2]

Compound I-99 was prepared as described in Example 7. The starting material was prepared as described in Example 1 using 2,2-difluoropropan-1-amine in place of methylamine in Step 5. MS m/z: 511.6 (M+H$^+$).

Example 102: I-100

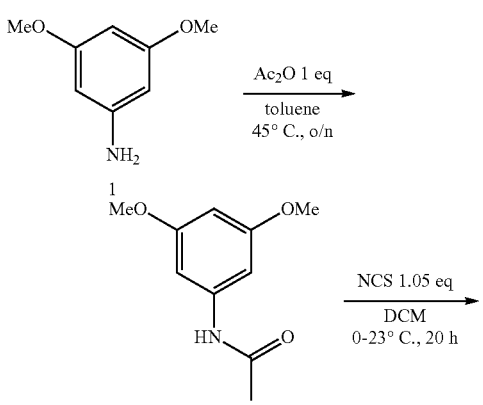

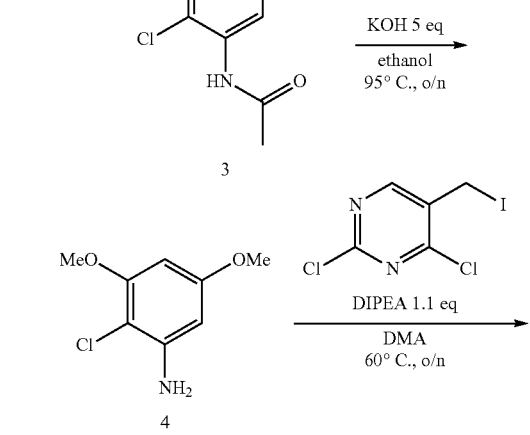

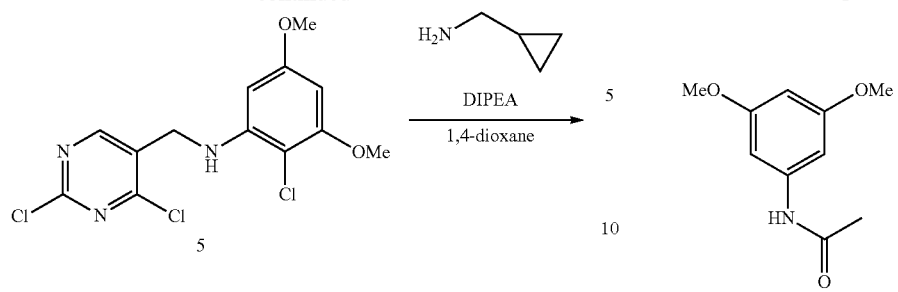

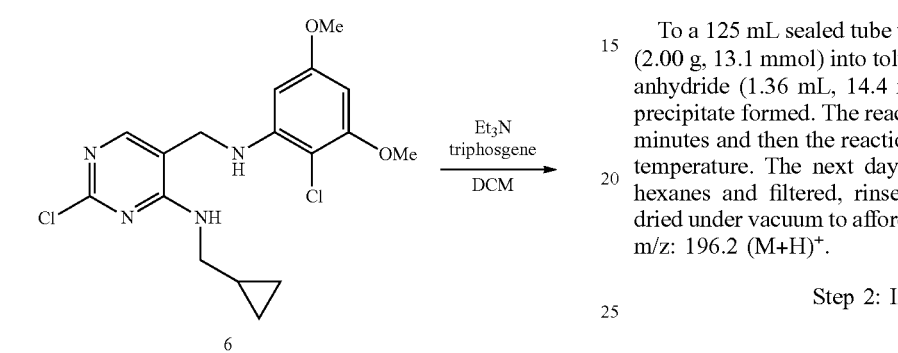

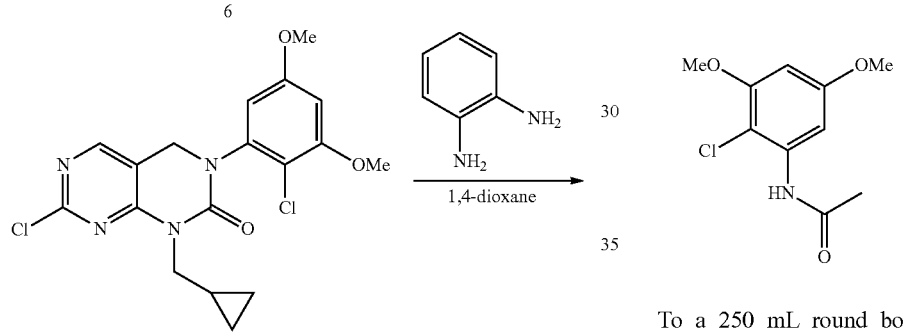

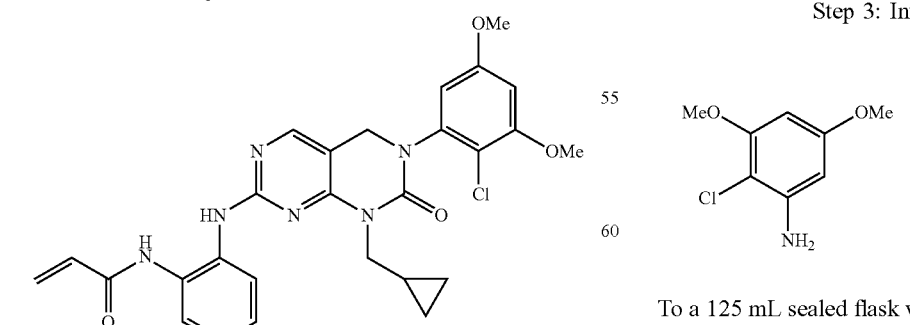

Step 1: Intermediate 2

To a 125 mL sealed tube was added 3,5-dimethoxyaniline (2.00 g, 13.1 mmol) into toluene (50 mL, 469 mmol). Acetic anhydride (1.36 mL, 14.4 mmol) was added slowly and a precipitate formed. The reaction was heated to 45° C. for 30 minutes and then the reaction was stirred overnight at room temperature. The next day, the reaction was diluted with hexanes and filtered, rinsed with additional hexanes and dried under vacuum to afford 2.5 g of the title compound MS m/z: 196.2 (M+H)$^+$.

Step 2: Intermediate 3

To a 250 mL round bottom flask was added N-(3,5-dimethoxyphenyl)acetamide (3.20 g, 16.4 mmol) in DCM (75 mL). The reaction mixture was cooled to 0° C. N-chlorosuccinimide (2.30 g, 17.2 mmol) in 25 mL of DCM was slowly added and the mixture was allowed to stir at ambient temperature for 16 h. The reaction was concentrated and taken up in a 1-1 mixture of hexanes-EtOAc. The resultant precipitate was filtered the filtrate was concentrated, taken up in 1:1 hexanes-EtOAc and the solid filtered to yield a second crop of solid. The precipitates collected were combined and purified on silica gel (eluting with 25% EtOAc in hexane to afford 1.50 g of the title compound. MS m/z: 230.2 (M+H)$^+$.

Step 3: Intermediate 4

To a 125 mL sealed flask was added Intermediate 3 (1.90 g, 8.27 mmol) in EtOH (50 mL, 856 mmol) followed by potassium hydroxide (2.32 g, 41.4 mmol) in 10 mL of water. The reaction was allowed to stir at 95° C. for 16 h after which it was cooled and concentrated. The resultant oil was partitioned between water and EtOAc, the organic layer was dried over MgSO4, filtered and concentrated to provide 1.00 g of the title compound MS m/z: 188.1 (M+H)+.

Step 4: Synthesis of Intermediate 5

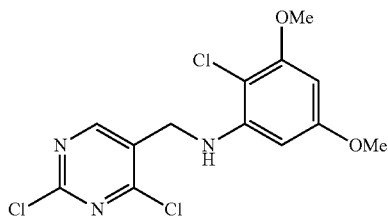 [SMILES: COc1cc(NCc2cnc(Cl)nc2Cl)c(Cl)c(OC)c1]

Into a sealed vessel was added Intermediate 4 (1.50 g, 8.00 mmol) in DMA (5 mL, 53.3 mmol), followed by DIPEA (820 µl, 8.80 mmol). The reaction mixture was allowed to stir for 10 min. at ambient temperature, and 2,4-dichloro-5-(iodomethyl)pyrimidine from Example 1 (2.31 g, 8.00 mmol) was added. The reaction mixture was allowed to stir at 60° C. for 7.5 h, then 16 h at ambient temperature. The reaction mixture was concentrated and azeotroped several times with toluene. EtOAc was added and the organic layer washed with brine (3×). The organic layers were dried with sodium sulfate, concentrated and purified by flash column chromatography (eluting with 5-25% EtOAc in heptane) to give 1.75 g of the title compound MS m/z: 348.2 (M+H)+.

Step 5: Synthesis of Intermediate 6

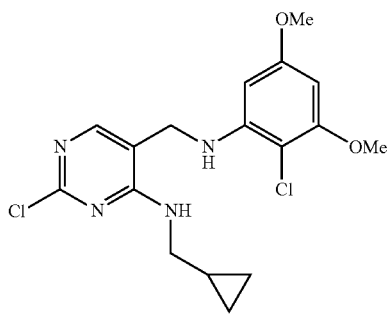 [SMILES: COc1cc(NCc2cnc(Cl)nc2NCC2CC2)c(Cl)c(OC)c1]

Intermediate 5 (1.50 g, 4.30 mmol) was dissolved in 1,4-dioxane (20 mL). cyclopropylmethanamine (612 mg, 8.61 mmol) and DIPEA (1.54 mL, 8.61 mmol) were added. The solution was allowed to stir at 35° C. for 3 h. Water (20 mL) was added and the organic layer was separated, dried over magnesium sulfate, filtered, and concentrated under reduced pressure. The residue was chromatographed through silica gel (eluted with DCM) to afford 1.17 g of the title compound MS m/z: 383.4 (M+H)+.

Step 6: Intermediate 7

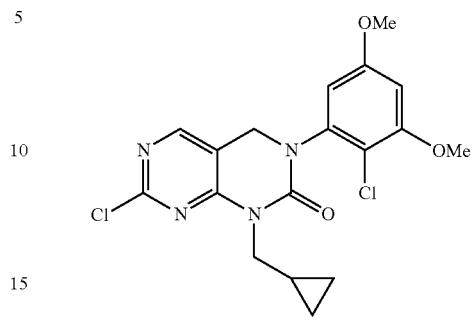

Intermediate 6 (1.16 g, 3.03 mmol) was dissolved in DCM (15 mL). Triphosgene (873 mg, 3.33 mmol) was added in one portion. The yellow solution turned partially cloudy then back to a solution. The mixture was stirred at ambient temperature for 30 min. Triethylamine (2.11 mL, 15.13 mmol) was added and the resulting suspension was stirred at ambient temperature for 18 h. Formation of a chloroformate intermediate was observed ([M+H]+=445 m/z). The suspension was transferred into a pressure vessel and stirred at 50° C. for an additional 48 h. The mixture was allowed to cool and the organic phase was washed with water (20 mL) and saturated aqueous sodium bicarbonate (20 mL). The organic layer was dried over magnesium sulfate, filtered, and concentrated under reduced pressure. The residue was chromatographed through silica gel (0-5% EtOAC in DCM) to afford 1.04 g of the title compound MS m/z: 409.4 (M+H)+.

Step 7: Intermediate 8

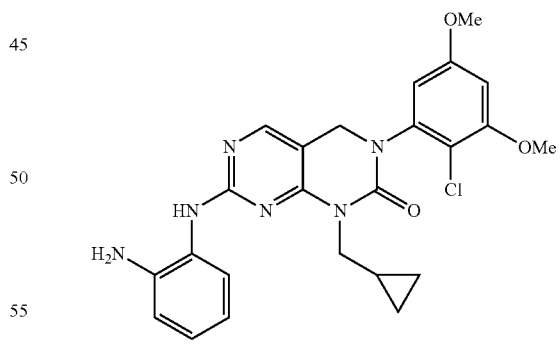

Intermediate 7 was dissolved in 1,4-dioxane (3 mL), and benzene-1,2-diamine (52.85 mg, 489 µmol) and TFA (244 µmol) were added. The solution was stirred at 95° C. for 20 h. The solution was diluted with EtOAc and washed with saturated aqueous sodium bicarbonate (5 mL) and brine (5 mL) then dried over magnesium sulfate, filtered, and concentrated under reduced pressure. The residue was chromatographed through silica gel 5% MeOH in DCM to afford 100 mg of the title compound MS m/z: 481.5 (M+H)+

Step 8: I-100

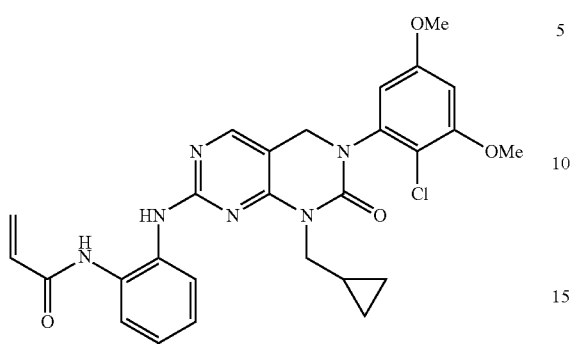

Intermediate 8 (98.0 mg, 204 μmol) was dissolved in DCM (2 mL). Et₃N (56.8 μl, 408 μmol) was added followed by acryloyl chloride (19.9 μl, 245 μmol). The solution was stirred at ambient temperature for 30 min then MeOH was added and the reaction mixture was concentrated under reduced pressure. The residue was chromatographed via reverse phase chromatography (pre-eluted with MeOH then 1 N NH₃ in methanol. Subsequent chromatography through silica gel (20-30% EtOAc in DCM provided 21.0 mg of the title compound MS m/z: 535.6 (M+H)⁺. ¹H NMR (400 MHz, DMSO-d6) δ 9.84 (s, 1H), 8.56 (s, 1H), 8.08 (d, 1H), 7.74 (dd, 1H), 7.57 (d, 1H), 7.19 (td, 1H), 7.12 (td, 1H), 6.76 (dd, 2H), 6.52 (dd, 1H), 6.28 (dd, 1H), 5.78 (dd, 1H), 4.78-4.67 (m, 1H), 4.47 (d, 1H), 4.14-3.93 (m, 1H), 3.87 (s, 3H), 3.79 (m, 5H), 1.17 (m, 1H), 1.01-0.69 (m, 1H), 0.48-0.10 (m, 4H).

Example 103: I-101

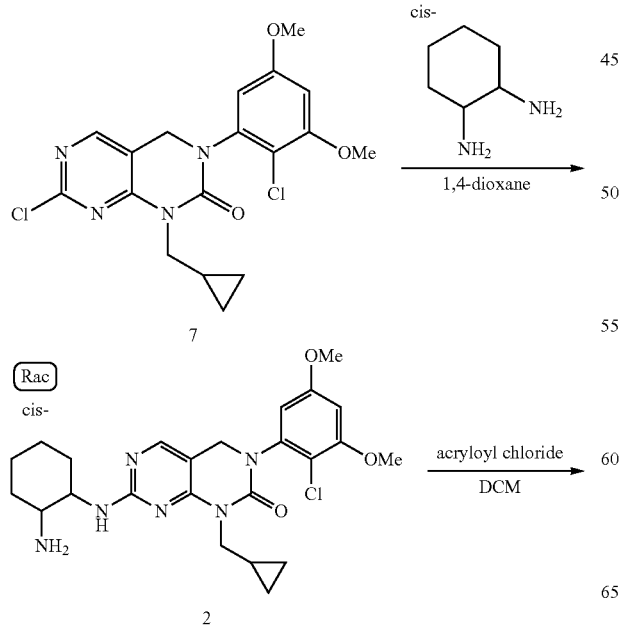

Step 1: Intermediate 2

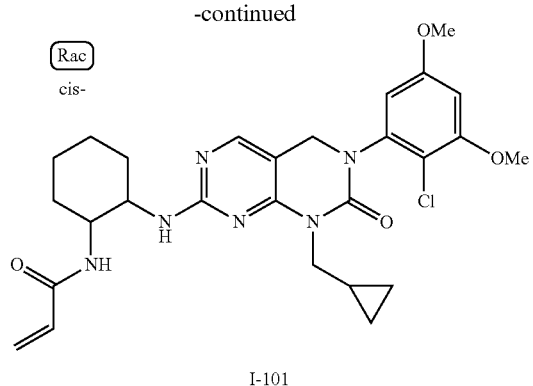

Intermediate 7 from Example 102 (100 mg, 244 μmol) was combined with cis cyclohexane-1,2-diamine (69.75 mg, 610.85 μmol) and dissolved in 1,4-dioxane (3 mL). The solution was stirred at 95° C. for 20 h. The solution was allowed cool to ambient temperature and was concentrated under reduced pressure. The residue was chromatographed through silica gel (3% 1 N NH₃ in MeOH in DCM to afford 90 mg of the title compound. MS m/z: 487.5 (M+H)⁺.

Step 2: I-101

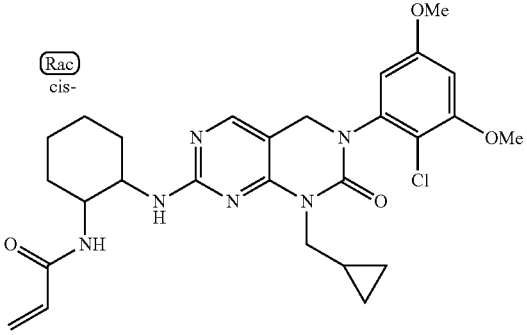 [SMILES: C=CC(=O)NC1CCCCC1Nc1ncc2c(n1)N(CC1CC1)C(=O)N(c1cc(OC)cc(OC)c1Cl)C2]

Intermediate 2 (90 mg, 185 μmol) was dissolved in DCM (2 mL). Triethylamine (51.5 μl, 370 μmol) was added, followed by acryloyl chloride (18.0 μl, 222 μmol). The solution was allowed to stir at ambient temperature for 30 min after which it was quenched with MeOH and concentrated under reduced pressure. The residue was chromatographed via reverse phase HPLC and then on silica gel to afford the title compound. MS m/z: 541.6 (M+H)+. 1H NMR (400 MHz, DMSO-d6) δ 7.95 (s, 1H), 7.74 (d, 1H), 6.78 (t, 1H), ), 6.73 (d, 1H), 6.60 (br s, 1H), 6.34 (dd, 2H), 6.04 (dd, 1H), 5.56 (dd, 1H), 4.64 (d, 1H), 4.41 (d, 1H), 4.22 (br s, 1H), 4.05 (br s, 1H), 3.90-3.80 (3, 7H), 1.84-1.03 (m, 10H), 0.92-0.73 (m, 1H), 0.61-0.3 (m, 4H).

Example 104: Synthesis of I-102

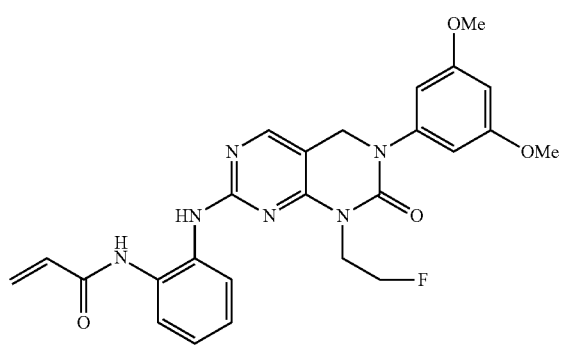 [SMILES: C=CC(=O)Nc1ccccc1Nc1ncc2c(n1)N(CCF)C(=O)N(c1cc(OC)cc(OC)c1)C2]

Compound I-102 was prepared as described in Example 7. The starting material was prepared as described in Example 1 using 2-fluoropropan-1-amine in place of methylamine in Step 5. MS m/z: 493.6 (M+H+).

Example 105: Synthesis of I-103

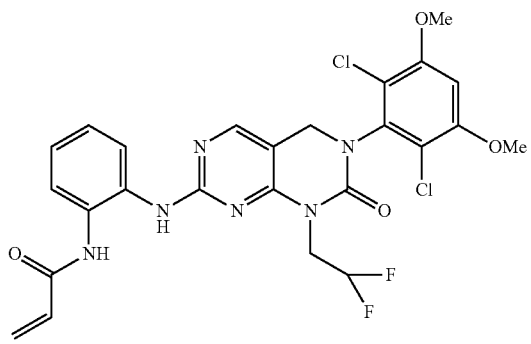 [SMILES: C=CC(=O)Nc1ccccc1Nc1ncc2c(n1)N(CC(F)F)C(=O)N(c1c(Cl)c(OC)cc(OC)c1Cl)C2]

Compound I-103 was prepared as described in Example 7. The starting material was prepared as described in Example 1 using 2,2-difluoropropan-1-amine in place of methylamine in Step 5. MS m/z: 579.5 (M+H+).

Example 106: Synthesis of I-104

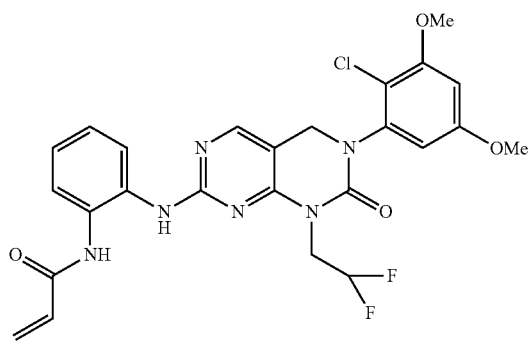 [SMILES: C=CC(=O)Nc1ccccc1Nc1ncc2c(n1)N(CC(F)F)C(=O)N(c1cc(OC)cc(OC)c1Cl)C2]

Compound I-104 was prepared as described in Example 7. The starting material was prepared as described in Example 1 using 2,2-difluoropropan-1-amine in place of methylamine in Step 5 and 2-chloro-3,5-dimethoxyaniline in place of 3,5-dimethoxyaniline in Step 4. MS m/z: 545.5 (M+H+).

Example 107: Synthesis of I-105 (Racemic)

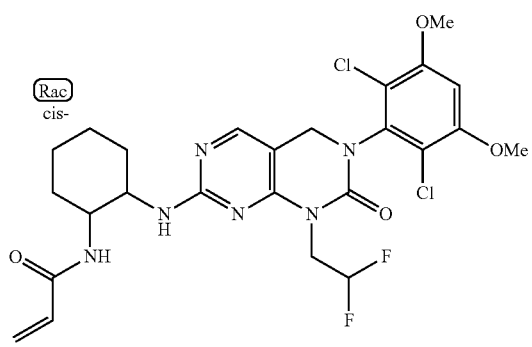 [SMILES: C=CC(=O)NC1CCCCC1Nc1ncc2c(n1)N(CC(F)F)C(=O)N(c1c(Cl)c(OC)cc(OC)c1Cl)C2]

Compound I-105 was prepared as described in Example 21. 7-chloro-3-(2,6-dichloro-3,5-dimethoxyphenyl)-1-(2,2-difluoroethyl)-3,4-dihydropyrimido[4,5-d]pyrimidin-2(1H)-one was used in place of Intermediate 2 and was prepared as described in Example 1 using 2,2-difluoropropan-1-amine in place of methylamine in Step 5. MS m/z: 585.5 (M+H+).

Example 108: Synthesis of I-106 (Racemic)

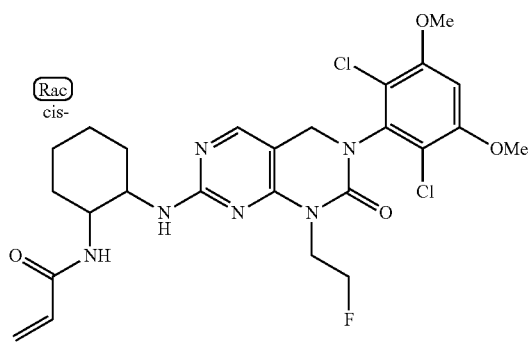 [SMILES: C=CC(=O)NC1CCCCC1Nc1ncc2c(n1)N(CCF)C(=O)N(c1c(Cl)c(OC)cc(OC)c1Cl)C2]

Compound I-106 was prepared as described in Example 21. 7-chloro-3-(2,6-dichloro-3,5-dimethoxyphenyl)-1-(2-fluoroethyl)-3,4-dihydropyrimido[4,5-d]pyrimidin-2(1H)-one was used in place of Intermediate 2 and was prepared as described in Example 1 using 2-fluoropropan-1-amine in place of methylamine in Step 5. MS m/z: 567.5 (M+H⁺).

Example 109: Synthesis of I-107 (Racemic)

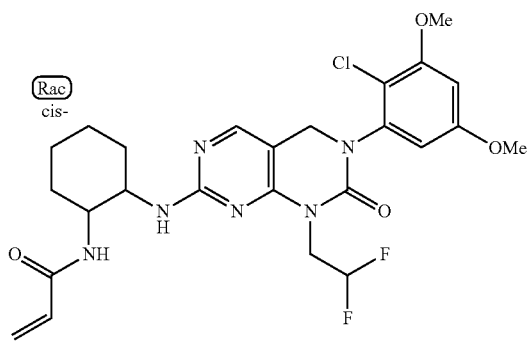 [SMILES: C=CC(=O)NC1CCCCC1Nc1ncc2c(n1)N(CC(F)F)C(=O)N(c1cc(OC)cc(OC)c1Cl)C2]

Compound I-107 was prepared as described in Example 21. 7-chloro-3-(2-chloro-3,5-dimethoxyphenyl)-1-(2,2-difluoroethyl)-3,4-dihydropyrimido[4,5-d]pyrimidin-2(1H)-one was used in place of Intermediate 2 and was prepared as described in Example 1 using 2,2-difluoropropan-1-amine in place of methylamine in Step 5 and 2-chloro-3,5-dimethoxyaniline in place of 3,5-dimethoxyaniline in Step 4. MS m/z: 551.6 (M+H⁺).

Example 110: Synthesis of I-108

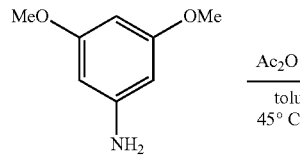

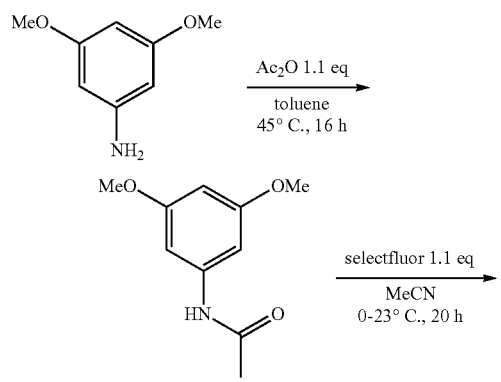

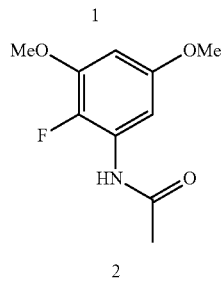

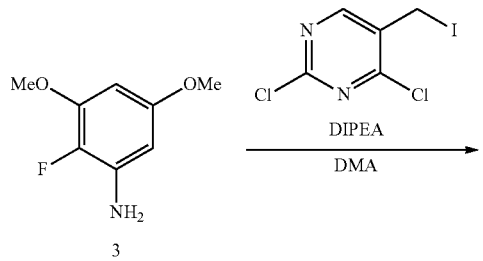

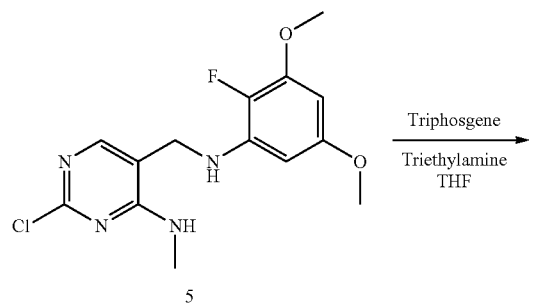

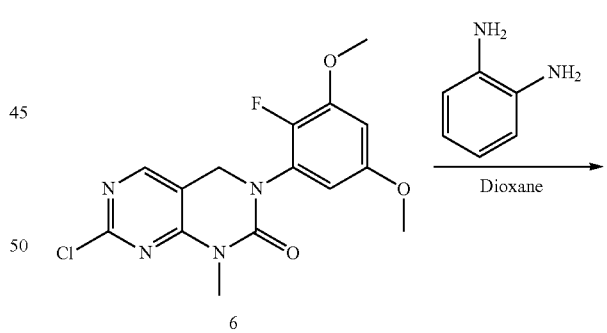

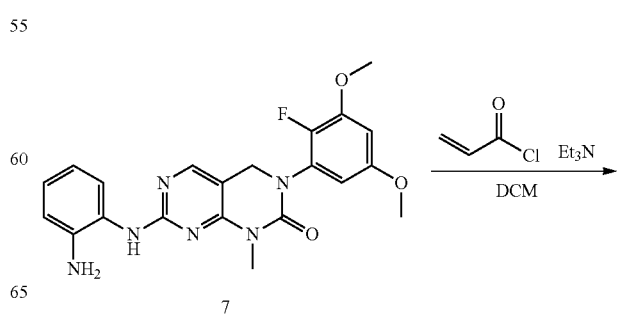

367
-continued

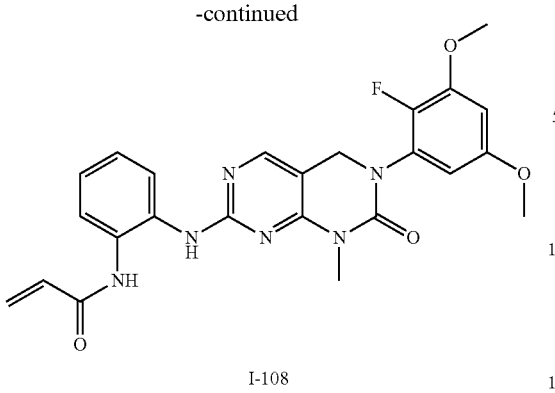

I-108

Step 1: Intermediate 1

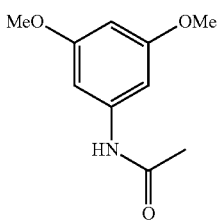

To a 125 mL sealed tube was added 3,5-dimethoxyaniline (2.00 g, 13.1 mmol) in toluene (50 mL). Acetic anhydride (1.36 mL, 14.4 mmol) was added and a precipitate began to form. The reaction was heated to 45° C. for 30 min and then cooled to ambient temperature and allowed to stir 16 h. The reaction mixture was diluted with hexanes and filtered. The solid was rinsed with additional hexanes and the filtrate dried under vacuum to afford 2.50 g of the title compound. MS m/z: 196.2 (M+H)$^+$.

Step 2: Intermediate 2

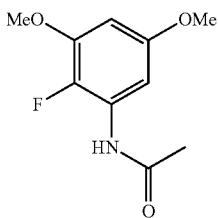

To a 125 mL round bottom flask, selectfluor (5.99 g, 16.9 mmol) and MeCN (40 mL) were added and cooled to 0° C. Intermediate 1 (3.00 g, 15.4 mmol) in 10 mL of MeCN was added at 0° C. and the reaction was allowed to stir and warm to ambient temperature for 16 h. The reaction was concentrated, EtOAc and H$_2$O were added, and the organic layer separated, dried over MgSO$_4$, filtered, and the filtrate concentrated. The resultant residue was purified on silica gel (eluting with DCM-EtOAc). A second purification (eluting with 4% MeOH in DCM) provided 800 mg of the title compound. LC. MS m/z: 214.2 (M+H)$^+$

368

Step 3: Intermediate 3

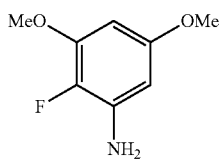

To a 125 mL round bottom was added Intermediate 2 (700 mg, 3.28 mmol) in EtOH (9.6 mL) and potassium hydroxide (918 mg, 16.4 mmol) in 4 mL H$_2$O and the reaction was sealed and heated for 20 h at 90° C. The reaction mixture was concentrated, H$_2$O and EtOAc were added, and the organic layer separated, dried over MgSO4, filtered and concentrated. The resultant solid was purified on silica gel (eluting with 40% EtOAc in hexane) to afford 450 mg of the title compound. LC. MS m/z: 172.1 (M+H)$^+$.

Step 4: Intermediate 4

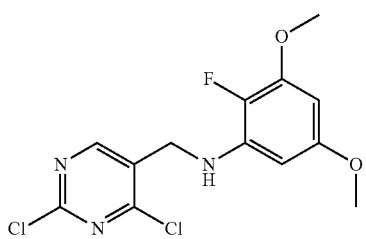 [SMILES: COc1cc(NCc2cnc(Cl)nc2Cl)c(F)c(OC)c1]

To a sealed vessel was added Intermediate 3 (2.38 g, 13.9 mmol), DMA (20 mL) and DIPEA (27.8 mmol, 2.59 mL). The reaction mixture was allowed to stir at ambient temperature for 15 min after which 2,4-dichloro-5-(iodomethyl) pyrimidine (4.02 g, 13.9 mmol) was added. The reaction mixture was heated at 50° C. for 16 h after which it was allowed cool to ambient temperature then partitioned between saturated aqueous NH$_4$Cl (40 mL) and EtOAc (40 mL). The organic phase was collected and the aqueous phase extracted one more time with EtOAc (40 mL). The organice phases were combined, dried over MgSO$_4$ and concentrated. Purification by flash chromatography on silica gel (eluting with 30% EtOAc in hexanes) provided 4.07 g of the title compound. MS m/z: 332.2 (M+H)$^+$.

Step 5: Intermediate 5

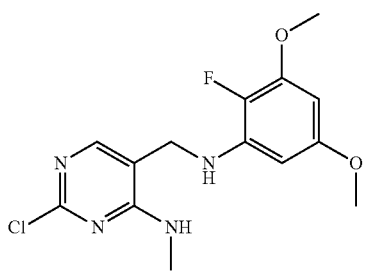 [SMILES: CNc1nc(Cl)ncc1CNc1cc(OC)cc(OC)c1F]

To a solution of Intermediate 4 (1.00 g, 3.00 mmol) in dioxane (10 mL), was added DIPEA (0.70 mL, 7.53 mmol) and 2 M methylamine in THF (4.52 mL, 9.03 mmol). The reaction mixture was heated to 50° C. for 16 h. Additional methylamine was added (9.03 mmol, 4.52 mL) and the reaction mixture was allowed to stir at 50° C. for an additional 16 h. The reaction mixture was concentrated and purified by flash chromatography on silica gel (eluting with 50% EtOAC in heptanes) to provide 570 mg of the title compound. MS m/z: 327.3 (M+H)$^+$.

Step 6: Intermediate 6

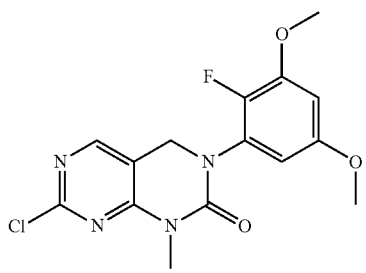 [SMILES: COc1cc(OC)c(F)c(N2Cc3cnc(Cl)nc3N(C)C2=O)c1]

To a solution of Intermediate 5 (570 mg, 1.74 mmol) in THF (10 mL) at ambient temperature was added triphosgene (1.92 mmol, 569 mg). The mixture was allowed to stir at ambient temperature for 30 minutes after which Et$_3$N (0.74 mL, 5.23 mmol) was added and the reaction mixture was allowed to stir at ambient temperature for 5 h. H$_2$O was added slowly to the reaction mixture (5 mL) followed by saturated aqueous NaH$_2$CO$_3$ (20 mL) until a pH of 10 was achieved.

The reaction mixture was extracted with EtOAc (2×20 mL), the combined organic phases were washed with brine and dried over MgSO4 and solvent was removed under reduced pressure. The resultant residue was titrated with Et$_2$O, and the solid filtered to provide 490 mg of the title compound. The filtrate was concentrated to provide an additional 100 mg of the title compound which was purified by flash chromatography on silica gel (eluting with 10% EtOAc in DCM to provide an additional 20 mg of the title compound. MS m/z: 353.3 (M+H)$^+$.

Step 7: Intermediate 7

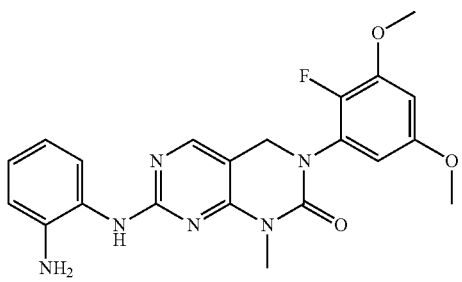 [SMILES: COc1cc(OC)c(F)c(N2Cc3cnc(Nc4ccccc4N)nc3N(C)C2=O)c1]

To a solution of Intermediate 6 (250 mg, 0.71 mmol) in 1,4-dioxane (5 mL) at ambient temperature was added 1,2-phenyl diamine (230 mg, 2.3 mmol) followed 2 drops of TFA. The reaction mixture was heated 95° C. for 16 h after which it was allowed cool to ambient temperature and partitioned between saturated aqueous NH$_4$Cl (10 mL) and EtOAc (20 mL). The organic phase was washed with brine, dried over MgSO$_4$, concentrated under reduced pressure and the resultant residue purified by flash chromatography on silica gel (eluting with 20% EtOAc in DCM) to provide 163 mg of title compound. MS m/z: 425.5 (M+H)$^+$.

Step 8: I-108

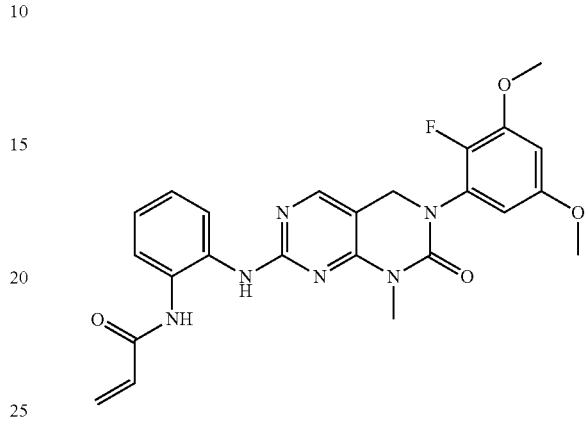

To a solution of Intermediate 7 (163 mg, 0.38 mmol) in DCM (5 mL) was added Et$_3$N (0.05 mL, 0.38 mmol). The mixture was cooled to 0° C. and acryloyl chloride (34.8 mg, 0.38 mmol) was added dropwise. The reaction mixture was allowed to stir at 0° C. for 5 minutes then allowed warm to ambient temperature for 30 min. The reaction mixture was partitioned between saturated aqueous NH$_4$Cl (10 mL) and EtOAc (20 mL). The organic phase was dried over MgSO4, concentrated, and the residue purified by flash chromatography on silica gel (eluting with 60% EtOAc in DMC) to provide 32 mg of the title compound. MS m/z: 479.5 (M+H)$^+$. $^1$H NMR (400 MHz, CDCl3): δ 3.4 (s, 3H), 3.80 (s, 3H), 3.90 (s, 3H), 4.6 (s, 2H), 5.75 (d, 1H), 6.2 (m, 1H), 6.4 (m, 2H), 6.55 (d, 1H), 7.25 (m, 3H), 7.5 (s, 1H), 7.8 (s, 1H), 7.9 (s, 1H), 8.4 (s, 1H).

Example 111: Synthesis of I-109

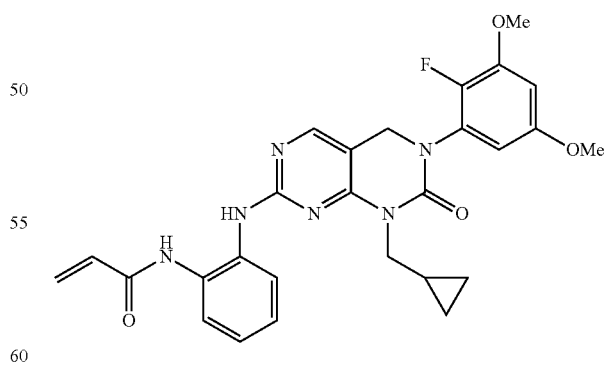

Compound I-109 was prepared as described in Example 7. The starting material was prepared as described in Example 1 using cyclopropylmethanamine in place of methylamine in Step 5 and 2-fluoro-3,5-dimethoxyaniline in place of 3,5-dimethoxyaniline in Step 4. MS m/z: 519.6 (M+H$^+$).

Example 112: Synthesis of I-110

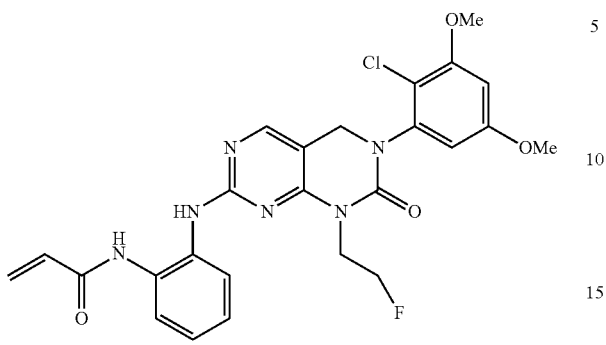

Compound I-110 was prepared as described in Example 7. The starting material was prepared as described in Example 1 using 2-fluoropropan-1-amine in place of methylamine in Step 5 and 2-chloro-3,5-dimethoxyaniline in place of 3,5-dimethoxyaniline in Step 4. MS m/z: 527.5 (M+H$^+$).

Example 113: Synthesis of I-111 (Racemic)

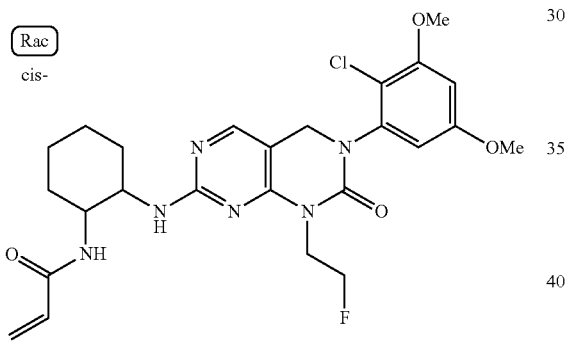

Compound I-111 was prepared as described in Example 21. 7-chloro-3-(2-chloro-3,5-dimethoxyphenyl)-1-(2-fluoroethyl)-3,4-dihydropyrimido[4,5-d]pyrimidin-2(1H)-one was used in place of Intermediate 2 and was prepared as described in Example 1 using 2-fluoropropan-1-amine in place of methylamine in Step 5 and 2-chloro-3,5-dimethoxyaniline in place of 3,5-dimethoxyaniline in Step 4. MS m/z: 533.5 (M+H$^+$).

Example 114: Synthesis of I-112 (Racemic)

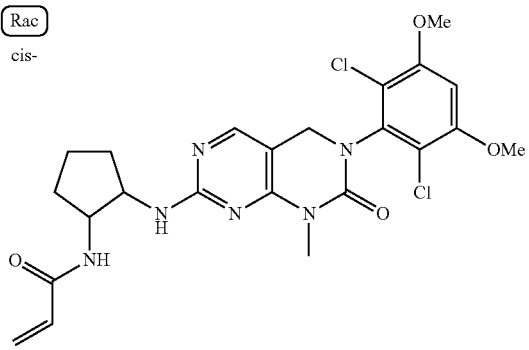 [SMILES: C=CC(=O)NC1CCCC1Nc1ncc2c(n1)N(C)C(=O)N(c1c(Cl)c(OC)cc(OC)c1Cl)C2]

Compound I-112 was prepared as described in Example 21 using cis-cyclopentane-1,2-diamine in place of cis-cyclohexane-1,2-diamine in Step 2. MS m/z: 521.3 (M+H$^+$).

Example 115: Synthesis of I-113 (Racemic)

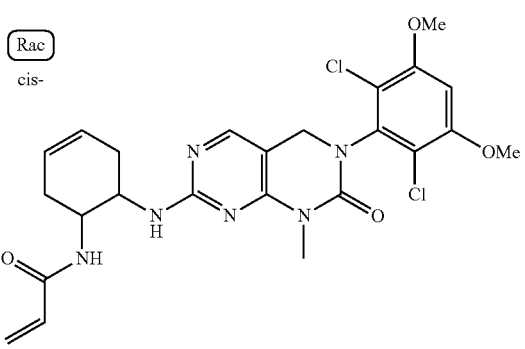 [SMILES: C=CC(=O)NC1CC=CCC1Nc1ncc2c(n1)N(C)C(=O)N(c1c(Cl)c(OC)cc(OC)c1Cl)C2]

Compound I-113 was prepared as described in Example 21 using cis-cyclohex-4-ene-1,2-diamine in place of cis-cyclohexane-1,2-diamine in Step 2. MS m/z: 533.4 (M+H$^+$).

Example 116: Synthesis of I-114

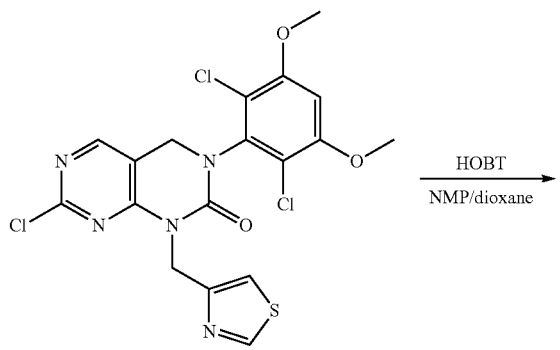

-continued

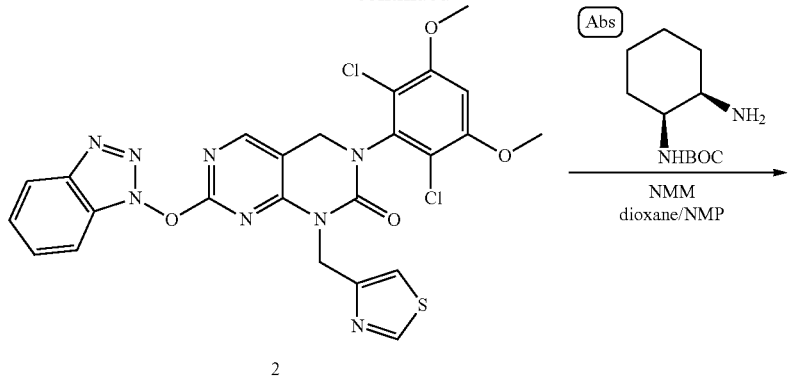

2

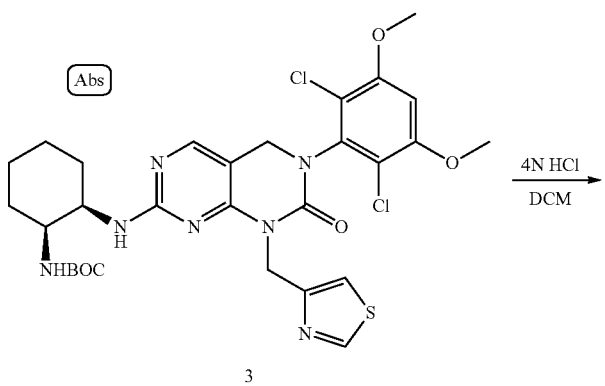

3

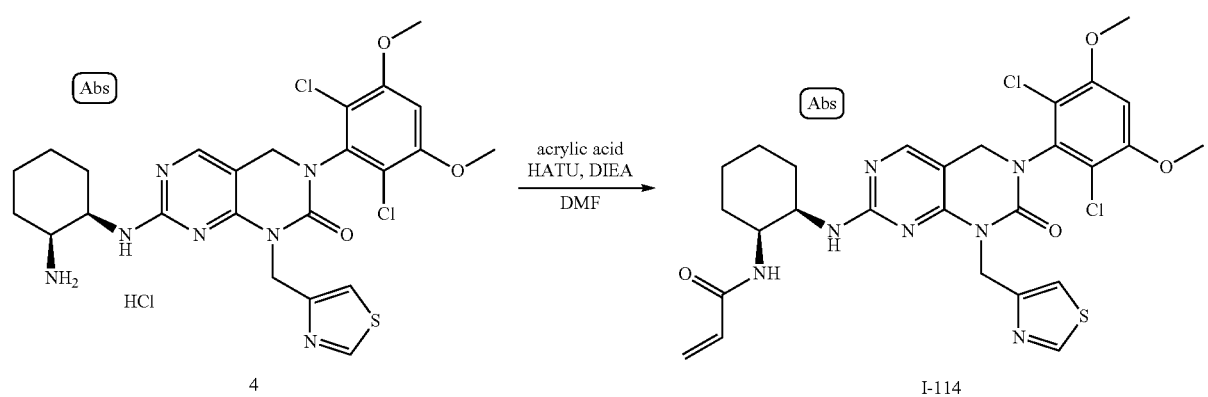

4                                                    I-114

Step 1: Intermediate 2

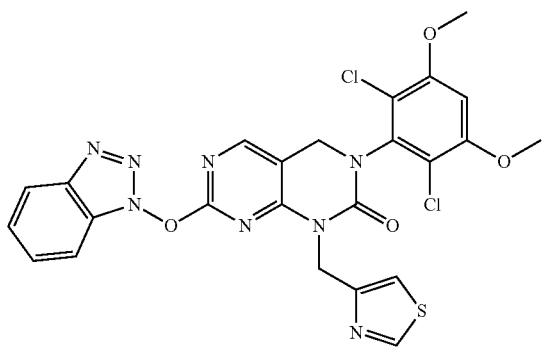 [SMILES: COc1cc(OC)c(Cl)c(N2Cc3cnc(On4nnc5ccccc54)nc3N(Cc3cscn3)C2=O)c1Cl]

The title compound was prepared from Intermediate 1 according to a modified literature procedure (WO 2009; PCT/US2009/002401.) Intermediate 1 was prepared as outlined in Example 1 using thiazol-4-ylmethanamine in place of methylamine in Step 5. Intermediate 1 (540 mg, 1.11 mmoL), HOBT (340 mg, 2.23 mmoL) and NMP (735 uL, 6.68 mmoL) were charged in 12 mL of dioxane; heated to 100° C. for 2 h. Solvent was removed under reduced pressure and water was added to cause precipitation, the resulting solid was removed by filtration and the filtrate concentrated to provide 672 mg of the title compound which was used directly in the next reaction. MS m/z: 585.0 (M+H$^+$).

Step 2: Intermediate 3

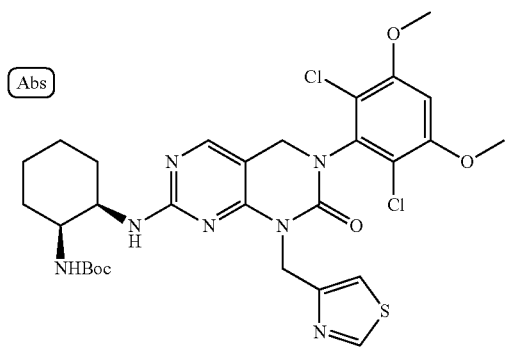 [SMILES: COc1cc(OC)c(Cl)c(N2Cc3cnc(N[C@@H]4CCCC[C@@H]4NC(=O)OC(C)(C)C)nc3N(Cc3cscn3)C2=O)c1Cl]

A solution of Intermediate 2 (672 mg, 1.15 mmoL), tert-butyl ((1S,2R)-2-aminocyclohexyl)carbamate (492 mg, 2.3 mmoL), and NMP (400 uL, 3.67 mmoL) in 12 mL of DMF/1.2 mL of NMP was heated to 100° C. for 16 h. Solvent was removed under reduced pressure and the crude product was subjected to chromatography on silica gel (eluting with a gradient of 0-100% EtOAc in heptane), which gave 650 mg of the title compound. MS m/z: 664.1 (M+H$^+$).

Step 3: Intermediate 4

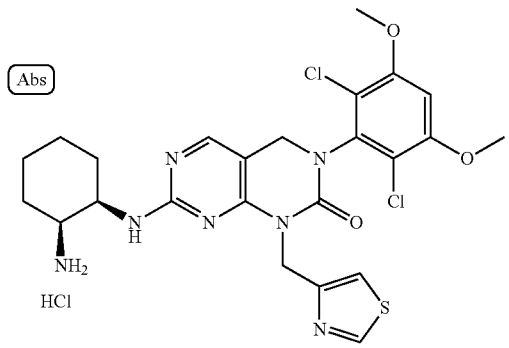 [SMILES: COc1cc(OC)c(Cl)c(N2Cc3cnc(N[C@@H]4CCCC[C@@H]4N)nc3N(Cc3cscn3)C2=O)c1Cl ; Cl]

To a solution of the Intermediate 3 (650 mg, 0.98 mmoL) in 10 mL of DCM was added 10 mL of HCl (4 N in dioxane) and the reaction was stirred at ambient temperature for 2 h. The solvent was removed under reduced pressure to provide the title compound. MS m/z: 564.0 (M+H$^+$).

Step 4: I-114

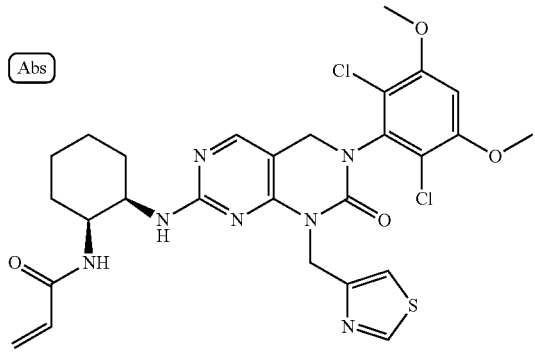 [SMILES: C=CC(=O)N[C@H]1CCCC[C@H]1Nc1ncc2c(n1)N(Cc1cscn1)C(=O)N(c1c(Cl)c(OC)cc(OC)c1Cl)C2]

A solution of Intermediate 4 (552 mg, 0.98 mmoL) in 3 mL of DMF was cooled in ice-water/methanol bath and acrylic acid (62 ul, 0.98 mmoL) was added. To the mixture was added DIPEA (1 mL, 5.9 mmoL) and then HATU (345 mg, 0.98 mmoL). The reaction was allowed to stir at ambient temperature for 15 min and purified directly by flash chromatography (eluting with a gradient of 0-100% acetone in heptane), which gave 515 mg of the title compound. MS m/z: 618.0 (M+H$^+$).

Example 117: Synthesis of I-115

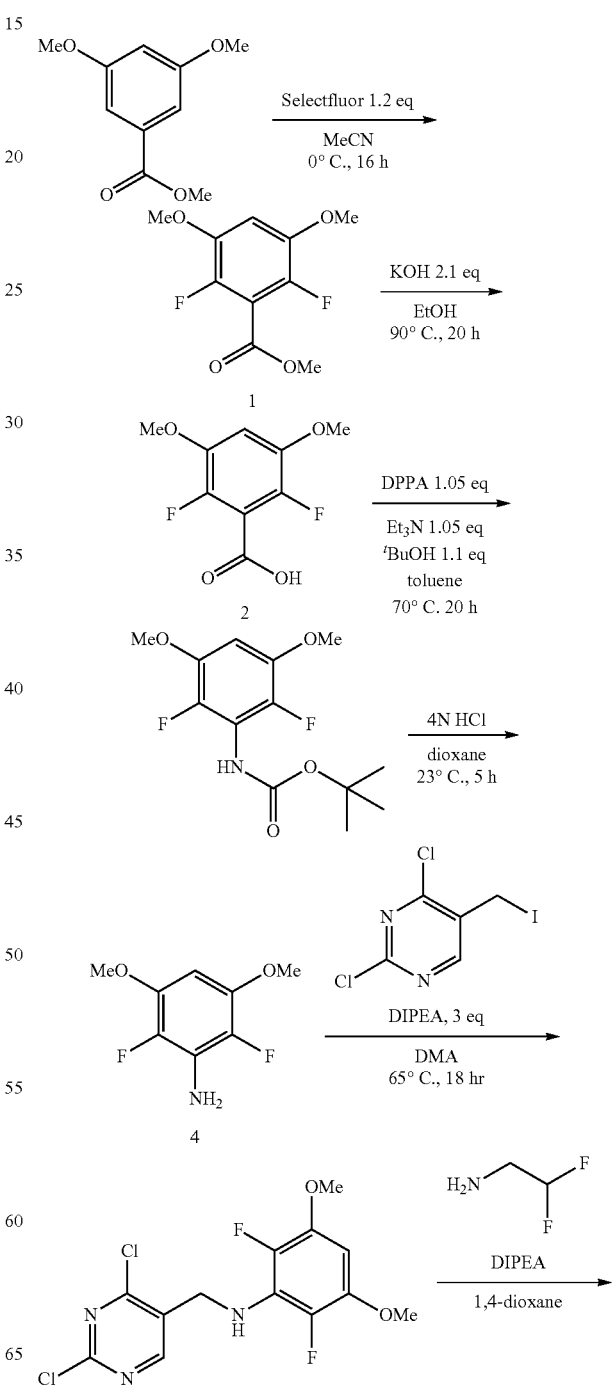

-continued

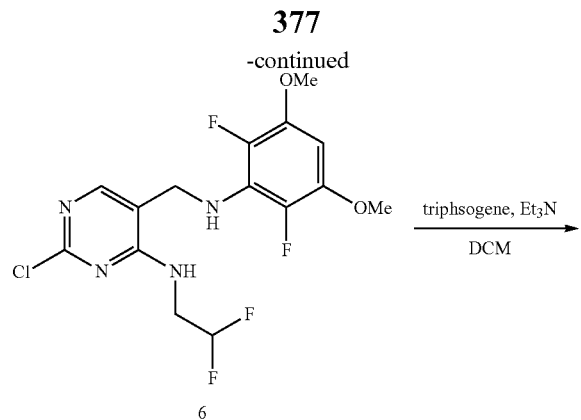

6

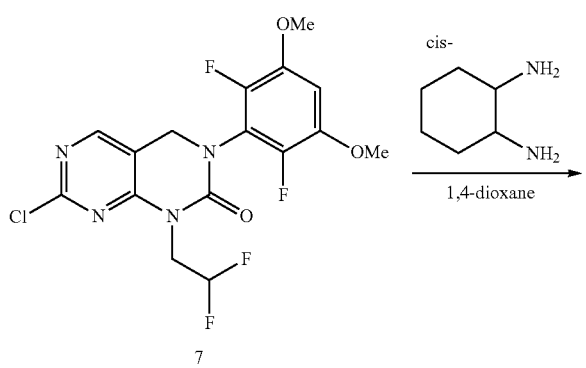

7

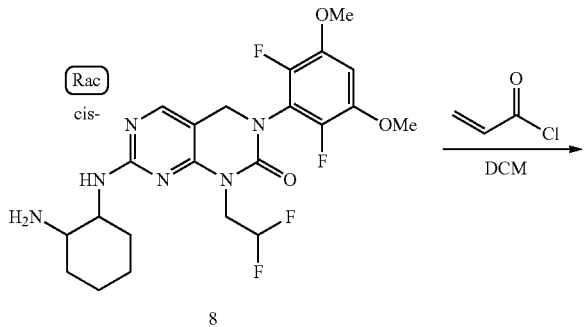

8

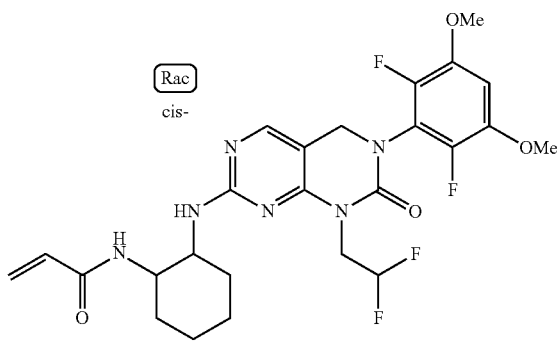

I-115

Step 1: Intermediate 1

To a 1000 mL round bottom flask was added selectfluor (13.5 g, 38.2 mmol) and MeCN (400 mL) The suspension was cooled to 0° C. and methyl 3,5-dimethoxybenzoate (5.00 g, 25.5 mmol) in minimal MeCN was added slowly over 10 minutes. The reaction mixture was allowed to stir and warm to room temperature over 2 days after which a saturated aqueous solution of sodium carbonate was added and the reaction mixture was allowed to stir for 15 minutes and MeCN was removed under reduced pressure. Water and EtOAc were added and the organic layer was washed with an aqueous saturated solution of NaCl (3×). The organic layer was dried over MgSO$_4$, filtered, and dried concentrated and purified through flash chromatography on silica gel: (eluting with 30 to 50% hexanes in DCM) to afford 1.0 g of the title compound MS m/z: 233.3 (M+H$^+$).

Step 2: Synthesis Intermediate 2

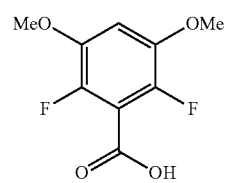

To a 125 mL sealed tube was added methyl Intermediate 1 (1.00 g, 4.31 mmol) and KOH (507 mg, 9.04 mmol) in EtOH (25 mL). The reaction mixture was heated to 90° C. for 20 h and then cooled and concentrated. Water was added and the resultant solution was treated with 1 N HCl until a pH<3 was achieved. A white precipitate formed which was filtered and rinsed with water. The solid was dissolved in EtOAc, dried over MgSO4, and the organic filtrate was concentrated to afford 600 mg of the title compound MS m/z: 219.2 (M+H$^+$).

Step 3: Intermediate 3

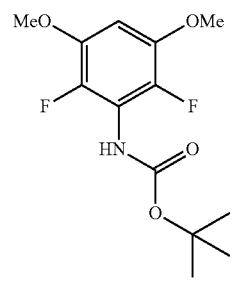 [SMILES: COc1cc(OC)c(F)c(NC(=O)OC(C)(C)C)c1F]

To a 125 mL round bottom tube was added Intermediate 2 (0.62 g, 2.84 mmol), diphenyl phosphorazidate (647 μl, 2.98 mmol), Et₃N (416 μl, 2.98 mmol) and 2-methylpropan-2-ol (299 μl, 3.13 mmol) in toluene (5 mL) and the reaction mixture was sealed and heated to 70° C. for 2 h. The reaction mixture was allowed cool and toluene was removed under reduced pressure. EtOAc was added and the organic phase washed with sequentially with saturated aqueous Na₂CO₃ (2×) and saturated aqueous NaCl (2×). The organic phase was dried over MgSO₄, concentrated, and the resultant residue was purified on silica gel (eluting with 100% DCM) to give 500 mg of the title compound. ¹H NMR (500 MHz, DMSO-d6): δ 8.81 (s, 1H), 6.89 (t, 1H), 3.32 (s, 6H), 1.42 (s, 9H).

Step 4: Intermediate 4

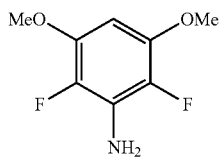 [SMILES: COc1cc(OC)c(F)c(N)c1F]

To a 125 mL round bottom flask was added Intermediate 3 (500 mg, 1.73 mmol), 4 N HCl in dioxane (8.64 mL, 34.6 mmol) and the reaction mixture was allowed to stir at ambient temperature for 5 h after which it was concentrated to give the HCl salt of title compound. ¹H NMR (500 MHz, DMSO-d6): δ 6.17 (s, 2H), 3.77 (s, 6H).

Step 5: Intermediate 5

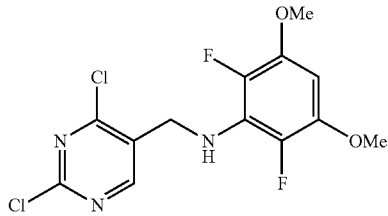 [SMILES: COc1cc(OC)c(F)c(NCc2cnc(Cl)nc2Cl)c1F]

To a 125 mL tube was added Intermediate 4 (360 mg, 1.60 mmol) 2,4-dichloro-5-(iodomethyl)pyrimidine (461 mg, 1.60 mmol) and DIPEA (848 μl, 4.79 mmol) in DMA (4 mL). The tube was sealed and the reaction mixture heated to 65° C. with stirring for 4 h after which it was cooled, concentrated and co-evaporated with toluene several times. The resultant oil was dissolved in EtOAc, and solids were removed by filtration. The filtrate was concentrated, dissolved in DCM and purified through flash chromatography on silica gel (eluting with EtOAc/hexanes) to provide 350 mg of the title compound. MS m/z: 350.3 (M+H⁺).

Step 6: Intermediate 6

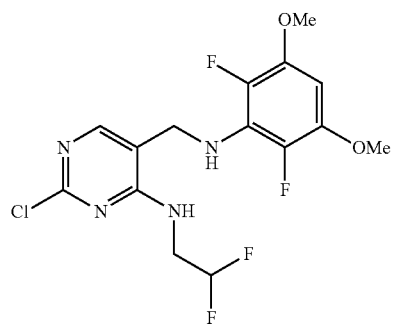 [SMILES: COc1cc(OC)c(F)c(NCc2cnc(Cl)nc2NCC(F)F)c1F]

Intermediate 5 (128 mg, 365.56 μmol) and 2,2-difluoroethanamine (59.3 mg, 731 μmol) were dissolved in 1,4-dioxane. DIPEA (131 μl, 731 μmol) was added and the solution was allowed to stir at 45° C. for 5 h then at 40° C. for 2 d. The solution was concentrated under reduced pressure and the resultant residue was purified through flash chromatography on silica gel (30% EtOAc in hexanes) to afford 105 mg of the title compound. MS m/z: 395.4 (M+H⁺).

Step 7: Intermediate 7

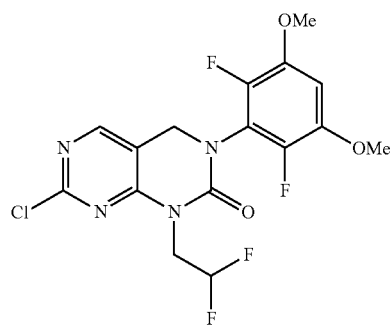 [SMILES: COc1cc(OC)c(F)c(N2Cc3cnc(Cl)nc3N(CC(F)F)C2=O)c1F]

Intermediate 6 (103 mg, 261 μmol) was dissolved in DCM (2 mL) and triphosgene (85.2 mg, 287 μmol) was added. The solution was allowed to stir at ambient temperature for 1 h. Et₃N (182 μl, 1.30 mmol) was added and the solution was allowed to stir an additional 1 h. LCMS showed disappearance of Intermediate 6 and formation of the carbamic chloride intermediate. The reaction mixture was heated at 50° C. for 72 h after which it was allowed cool to ambient temperature and water (2 mL) was added followed by saturated aqueous sodium bicarbonate (3 mL). The mixture was allowed to stir at ambient temperature for 30 min then was extracted with DCM and the organic layers dried over MgSO₄, filtered, and concentrated under reduced pressure. The resultant residue was purified through flash chromatography on silica gel (eluting with DCM) to afford 80 mg of the title compound. MS m/z: 421.4 (M+H⁺).

Step 8: Intermediate 8

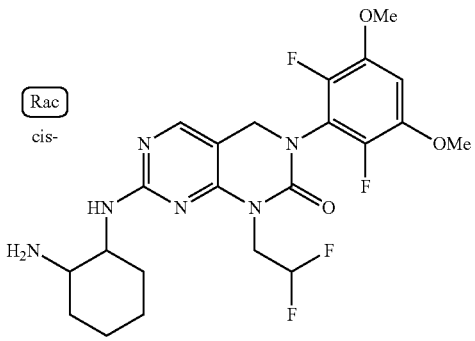 [SMILES: COc1cc(OC)c(F)c(N2Cc3cnc(NC4CCCCC4N)nc3N(CC(F)F)C2=O)c1F]

Intermediate 7 (32.0 mg, 76.1 µmol) was dissolved in 1,4-dioxane (0.5 mL) and cis-cyclohexane-1,2-diamine (21.7 mg, 190 µmol) was added. The solution was allowed to stir in a sealed tube at 90° C. for 18 h after which it was concentrated under reduced pressure and the resultant residue was purified through flash chromatography on silica gel (eluting with 10% MeOH in DCM) to afford 33 mg of the title compound. MS m/z: 499.6 (M+H$^+$).

Step 9: I-115

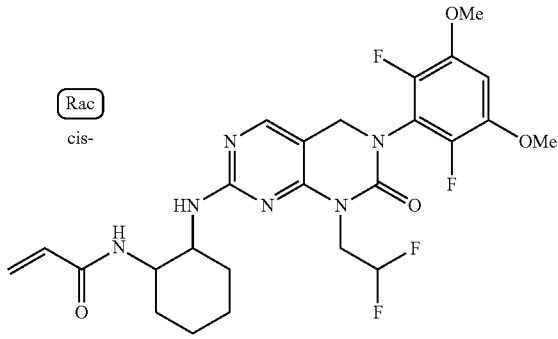 [SMILES: C=CC(=O)NC1CCCCC1Nc1ncc2c(n1)N(CC(F)F)C(=O)N(c1c(F)c(OC)cc(OC)c1F)C2]

Intermediate 8 (30 mg, 60.2 µmol) was dissolved in DCM. The solution was cooled to 0° C. and Et$_3$N (16.8 µl, 120 µmol) was added, followed by acryloyl chloride (4.87 µl, 60.2 µmol). The suspension was stirred at 0° C. for 45 min. Methanol was added and the resulting solution was concentrated under reduced pressure. The residue was chromatographed through silica gel (eluting with 60% EtOAc in DCM) to afford 20 mg of the title compound. MS m/z: 553.6 (M+H$^+$). $^1$H NMR (400 MHz, DMSO-d6) δ 8.01 (s, 1H), 7.76 (m, 1H), 7.07 (t, 1H), 7.00-6.60 (m, 1H), 6.48-6.11 (m, 2H), 6.03 (dd, 1H), 5.54 (dd, 1H), 4.57 (s, 2H), 4.37 (m, 2H), 4.18 (m, 2H), 4.09 (s, 6H), 1.86-1.24 (m, 8H).

Example 118: Synthesis of I-116

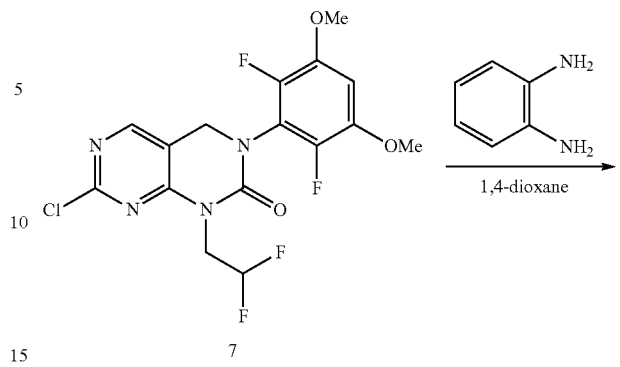

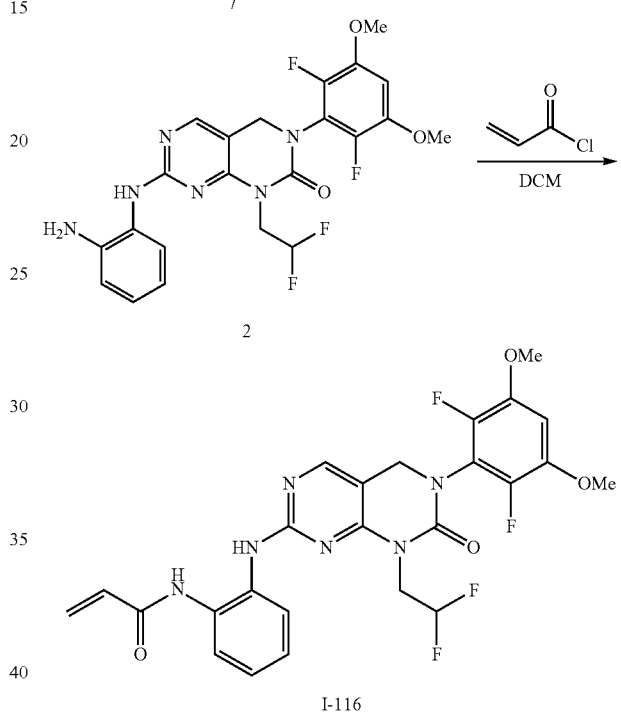

I-116

Step 1: Intermediate 2

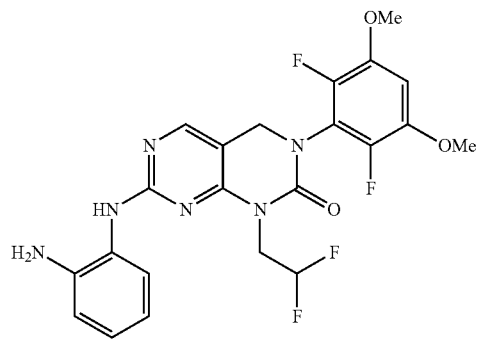 [SMILES: COc1cc(OC)c(F)c(N2Cc3cnc(Nc4ccccc4N)nc3N(CC(F)F)C2=O)c1F]

Intermediate 7 from Example 117 was dissolved in 1,4-dioxane (0.5 mL) and benzene-1,2-diamine (16.5 mg, 152 µmol) and 2 drops of TFA were added. The vessel was sealed and the solution was stirred at 90° C. for 18 h after which the reaction mixture was concentrated under reduced pressure and the resultant residue was purified through chromatography on silica gel (60% EtOAc in DCM) to afford 21.0 mg of the title compound. MS m/z: 493.5 (M+H$^+$).

Step 2: I-116

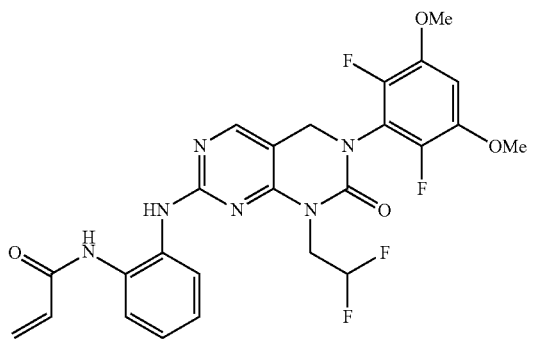 [SMILES: C=CC(=O)Nc1ccccc1Nc1ncc2c(n1)N(CC(F)F)C(=O)N(c1c(F)c(OC)cc(OC)c1F)C2]

Intermediate 2 (20.0 mg, 40.6 μmol) was dissolved in DCM and the solution cooled to 0° C. Et₃N (11.3 μl, 81.2 μmol) was added followed by acryloyl chloride (3.21 μl, 40.6 μmol). The suspension was allowed to stir at 0° C. for 1.5 h after which methanol was added and the mixture was concentrated under reduced pressure. The resultant residue was chromatographed through silica gel (30% EtOAc in DCM/to afford 11.0 mg of the title compound MS m/z: 547.6 (M+H⁺). ¹H NMR (400 MHz, DMSO-d6) δ 9.82 (s, 1H), 8.75 (s, 1H), 8.14 (s, 1H), 7.72 (dd, 1H), 7.65-7.53 (m, 1H), 7.25-7.01 (m, 3H), 6.51 (dd, 1H), 6.40-6.04 (m, 2H), 5.78 (dd, 1H), 4.65 (s, 2H), 4.32 (m, 2H), 3.90 (s, 6H).

Example 119; Synthesis of I-117

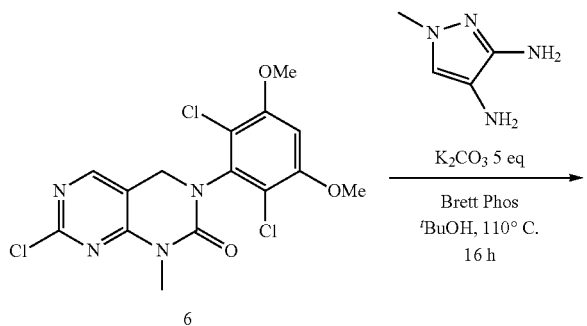

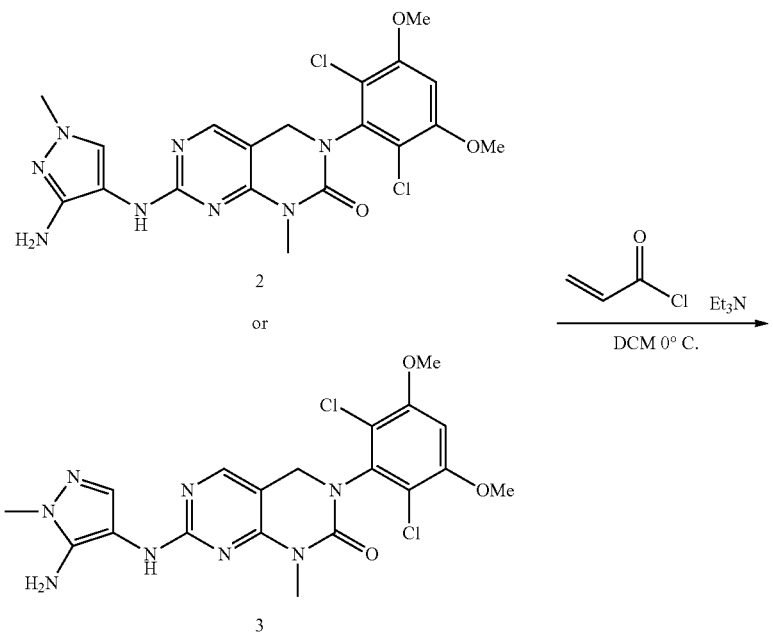

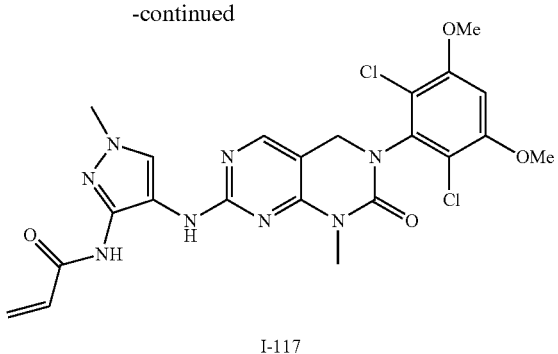

I-117

Step 1: Intermediate 2

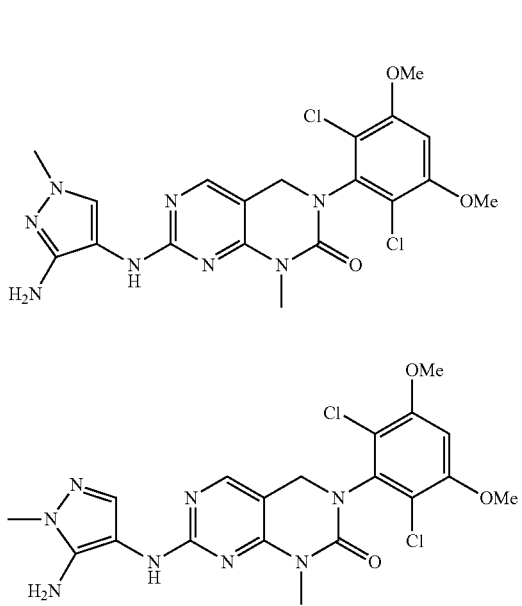

To a 10 mL tube was added Intermediate 6 from Example 1 (140 mg, 347 μmol), potassium carbonate (240 mg, 1.73 mmol), Brett Phos (16.2 mg, 17.3 μmol), 1-methyl-1H-pyrazole-3,4-diamine dihydrochloride (64.2 mg, 347 μmol) in tert-butanol (6 ml, 62.7 mmol) and the reaction mixture was sealed and purged with nitrogen. The mixture was heated to 110° C. for 8 h after which it was allowed to cool to ambient temperature and water was added. The resultant precipitate was collected via filtration. And the filtrate was extracted with DCM. The organic layer was dried over MgSO4, filtered, and concentrated. The combined solids were purified through flash chromatography on silica gel (MeOH/DCM) to provide 48.0 mg of the title compound. MS m/z: 479.4 (M+H)+. 1HNMR was consistent with a single isomer although 2D NMR correlations did not confirm which isomer formed. Material was assigned regiochemical assignment of Intermediate 2 based on presumed decreased electophilicity of the N-methylpyrazole amine and material was carried on to the next step.

Step 2: I-117

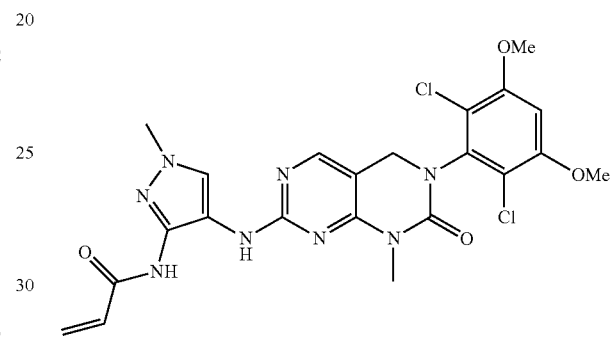

Intermediate 2 (48.0 mg, 100 μmol) was dissolved in DCM (1 ml). The suspension was cooled to 0° C. Et₃N (27.9 μl, 200 μmol) was added followed by acryloyl chloride (7.92 μl, 100 μmol). The resultant suspension was allowed to stir at 0° C. for 90 min. Methanol was added and the mixture was concentrated under reduced pressure. The resultant residue was purified through flash chromatography on silica gel (30% DCM in EtOAc) to afford 30.0 mg of the tittle compound. MS m/z: 533.5 (M+H)+. 1H NMR (400 MHz, DMSO-d6) δ 10.74 (s, 1H), 8.95 (s, 1H), 8.10 (d, 2H), 7.01 (s, 1H), 6.53 (m, 1H), 6.36 (m, 1H), 5.82 (dd, 1H), 4.53 (s, 2H), 3.98 (s, 6H), 3.81 (s, 3H).

Example 120: I-119

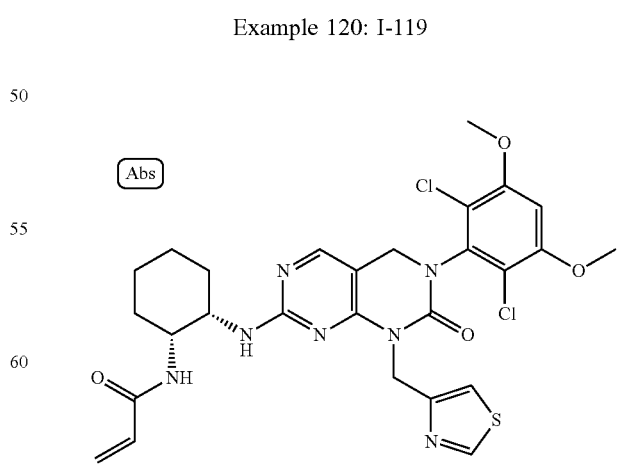

The title compound was prepared as outlined in the Example 116 using tert-butyl ((1R,2S)-2-aminocyclohexyl)

carbamate in place of tert-butyl ((1S,2R)-2-aminocyclohexyl)carbamate in Step 2. MS m/z: 618.0 (M+H⁺). ¹H NMR (400 MHz, DMSO-d6): δ: 9.01 (1H, d), 8.0 (1H, s), 7.69 (1H, d), 6.99 (1H, s), 6.3 (1H, dd), 6.05 (1H, dd), 5.55 (1H, dd), 5.26 (2H, bs), 4.52 (2H, s), 3.96 (6H, s), 3.3 (4H, m), 2.16 (4H, m), 1.9 (4H, m).

Example 121: Synthesis of I-120

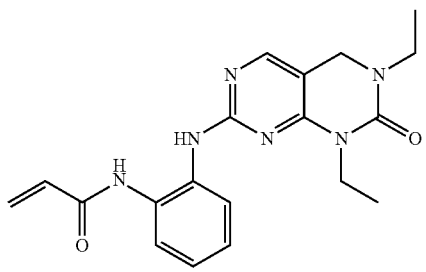 [SMILES: C=CC(=O)Nc1ccccc1Nc1ncc2c(n1)N(CC)C(=O)N(CC)C2]

Compound I-120 was prepared as described in Example 53 using ethylamine in place of cyclopropanamine in Step 1 and in place of methylamine in Step 2. MS m/z: 367.3 (M+H⁺).

Example 122: Synthesis of I-121

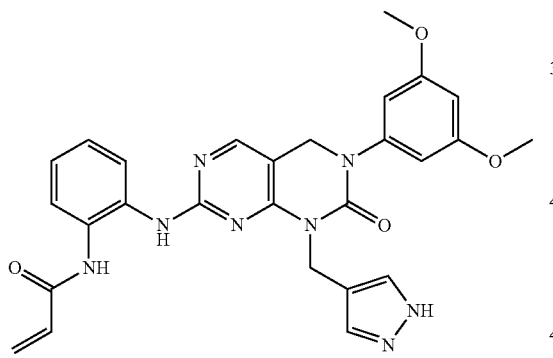

Compound I-121 was prepared as described in Example 7. The starting material was prepared as described in Example 1 using (1H-pyrazol-4-yl)methanamine in place of methylamine in Step 5. MS m/z: 527.5 (M+H⁺).

Example 123; Synthesis of I-122

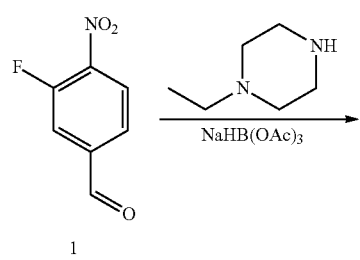

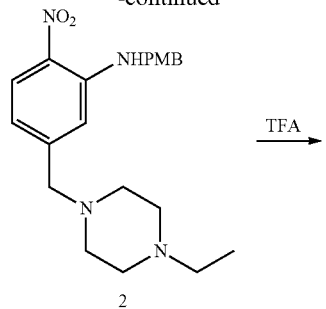

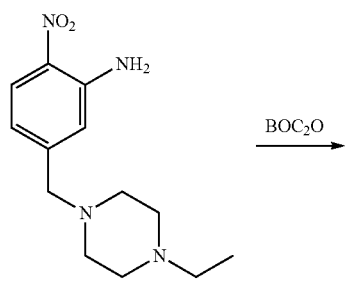

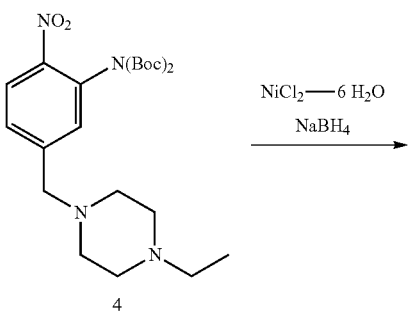

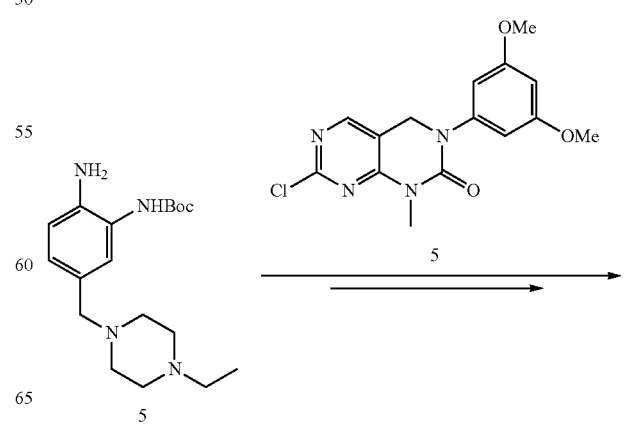

-continued

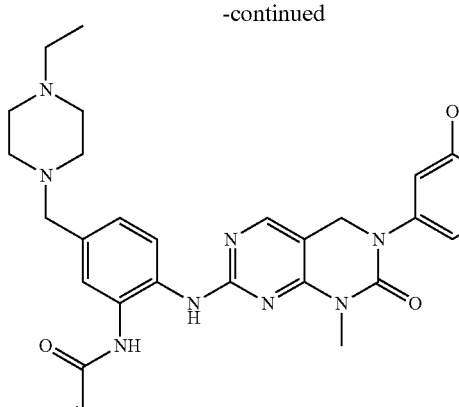

I-122

Step 1, Intermediate 2

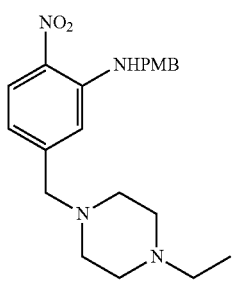

Intermediate 1 (57.0 mg, 0.034 mmol) and PMB-NH₂ (0.13 mL, 1.01 mmol) in DMF (2.0 mL) were heated at 110° C. for 4 h. DMF was removed in vacuo, and the resultant residue was dissolved in DCM (5 mL), followed with addition of AcOH (0.1 mL) and N-ethylpiperazine (0.10 mL, 7.90 mmol). After 1 h, NaHB(OAc)₃ (100 mg, 0.47 mmol) was added and the reaction was allowed to stir for 16 h. EtOAc was added and the organic phase washed with saturated aqueous NaHCO₃ and brine, dried (Na₂SO₄), filtered and concentrated in vacuo. Flash chromatography on silica gel, provided 80 mg of the title compound. MS m/z: 385.2 (M+H⁺).

Step 2: Intermediate 3

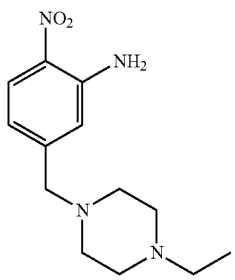 [SMILES: CCN1CCN(Cc2ccc([N+](=O)[O-])c(N)c2)CC1]

Intermediate 2 (80.0 mg, 0.21 mmol) was treated with 20% (v/v) TFA in DCM at ambient temperature and the reaction mixture was allowed to stir for 30 min. The reaction mixture was concentrated in vacuo and the resultant residue was treated with silica supported carbonate, filtered, and concentrated to afford quantitative yield of the title compound which was used without further purification. MS m/z: 265.2 (M+H⁺).

Step 3, Intermediate 4

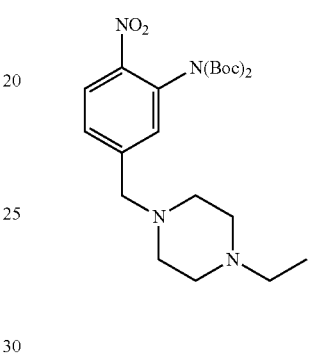

To a solution of Intermediate 3 (56.0 mg, 0.21 mmol) in DMF (4.0 mL) was added (Boc)₂O (100 mg, 0.46 mmol) and DMAP (10.0 mg, 0.08 mmol). The reaction was stirred at ambient temperature overnight. DMF was removed under reduced pressure and the product was isolated by silica gel chromatography (98.0 mg). MS m/z: 465.3 (M+H⁺).

Step 4, Intermediate 5

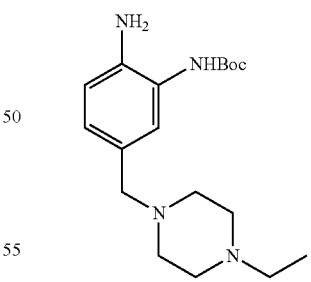

To a solution of Intermediate 4 (98.0 mg, 0.21 mmol) in MeOH (5 mL) at 0° C. was added NiCl₂-6H₂O and NaBH₄. After 30 min, the reaction was quenched through addition of water, filtered through celite, and concentrated to afford 62.0 mg of the title compound which was used without further purification. MS m/z: 335.3 (M+H⁺).

Step 5: I-122

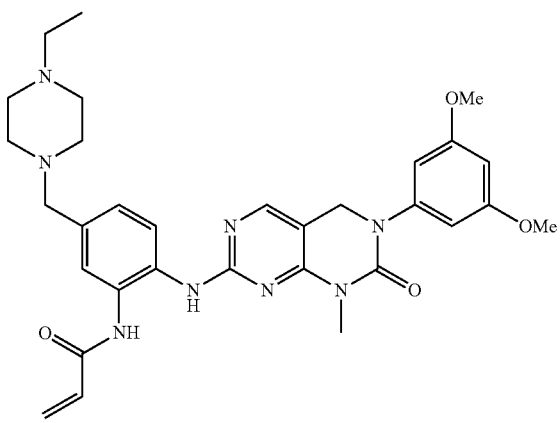 [SMILES: C=CC(=O)Nc1cc(CN2CCN(CC)CC2)ccc1Nc1ncc2c(n1)N(C)C(=O)N(c1cc(OC)cc(OC)c1)C2]

The title compound was prepared as described in Example 5 using Intermediate 5 from Example 1. MS m/z: 587.3 (M+H$^+$). $^1$H NMR (400 MHz, CD$_3$OD): δ: 8.00 (1H, s), 7.79 (1H, d), 7.64 (1H, s), 7.55 (1H, d), 7.29 (1H, dd), 6.53 (2H, s), 6.45 (2H, m), 5.81 (1H, dd), 4.71 (2H, s), 3.78 (6H, s), 3.77 (2H, s), 3.35 (3H, s), 3.35 (4H, d) 3.30 (4H, d) 3.19 (2H, q), 1.32 (3H, t).

Example 124: Synthesis of I-123

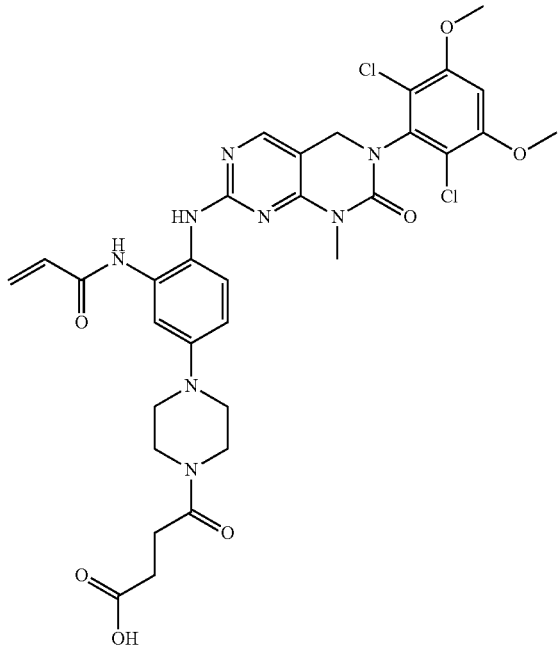 [SMILES: C=CC(=O)Nc1cc(N2CCN(C(=O)CCC(=O)O)CC2)ccc1Nc1ncc2c(n1)N(C)C(=O)N(c1c(Cl)c(OC)cc(OC)c1Cl)C2]

Compound I-123 was prepared as described in Example 128 using succinic acid in place of N-biotinyl-NH-(PEG)2-COOH in Step 2. MS m/z: 713.5 (M+H$^+$).

Example 125: Synthesis of I-124

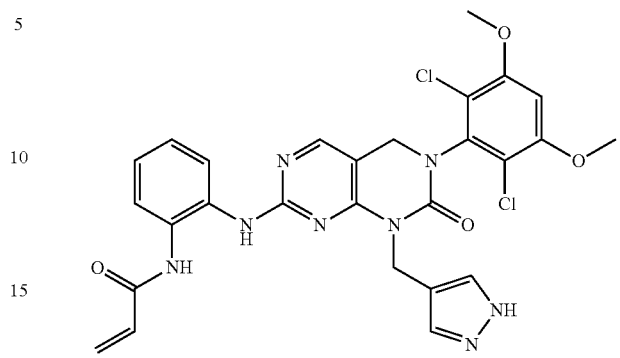

Compound I-124 was prepared as described in Example 7. The starting material was prepared as described in Example 1 using tert-butyl 4-(aminomethyl)-1H-pyrazole-1-carboxylate in place of methylamine in Step 5. A final BOC deprotection step was performed (as described in Example 3, Step 5). MS m/z: 595.4 (M+H$^+$).

Example 126: Synthesis of I-125

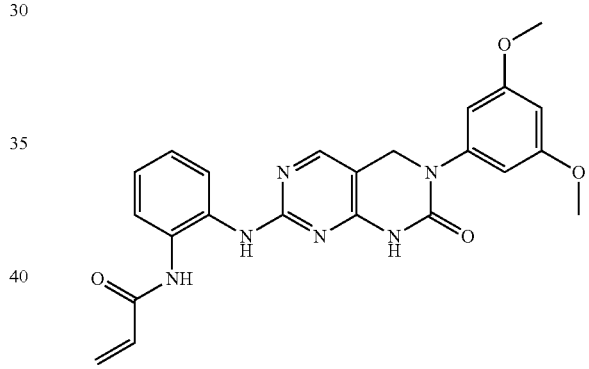

Compound I-125 was prepared as described in Example 7. The starting material was prepared as described in Example 1 using ammonia in place of methylamine in Step 5. MS m/z: 447.4 (M+H$^+$).

Example 127: Synthesis of I-126

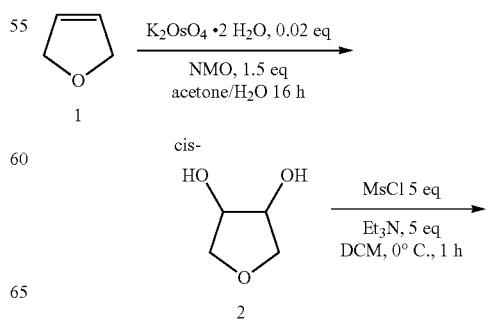

-continued

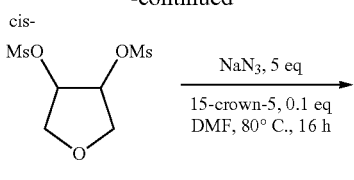

3

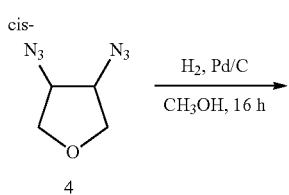

4

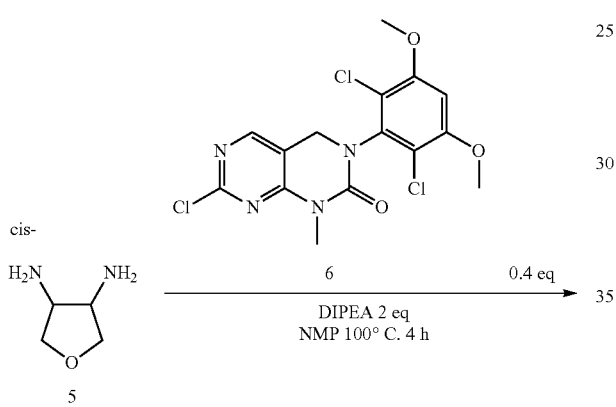

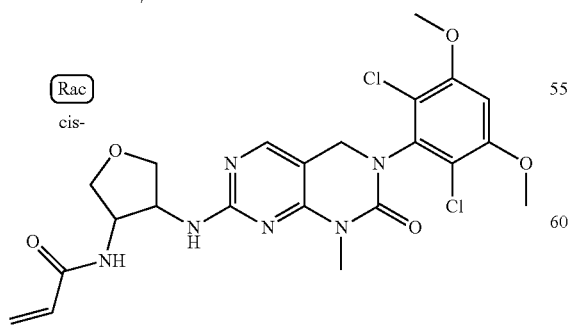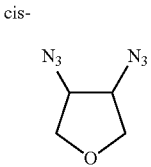

I-126

Step 1: Intermediate 2

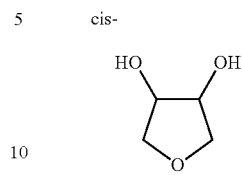

To a solution of Intermediate 1 (2.00 g, 28.53 mmol) in 50 mL of acetone/H₂O (4:1) was added NMO (10 g, 50% aqueous solution, 42.7 mmol) and K₂OsO₄.2H₂O (210 mg, 0.57 mmol). The reaction mixture was allowed to stir at ambient temperature for 16 h. Na₂SO₃ (8.0 g) was added and the resultant mixture was allowed to stir for 10 min. The reaction mixture was evaporated to dryness and the residue taken up in EtOAc. The resultant suspension was filtered and the filtrate was evaporated to dryness to afford 2.50 g of the title compound.

Step 2: Intermediate 3

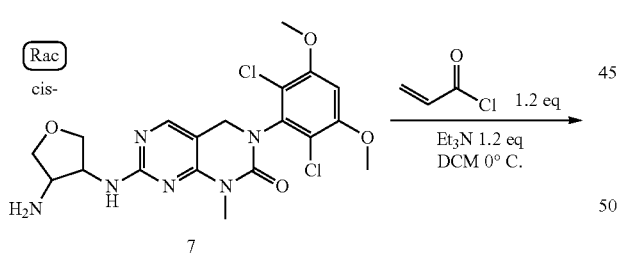

To an ice cooled solution of Intermediate 2 (2.50 g, 24.0 mmol) and Et₃N (12.2 g, 121 mmol) in DCM (50 mL) was added methanesulfonyl chloride (13.8 g, 121 mmol). The mixture was allowed stirred at 0° C. for 30 min. Saturated aqueous Na₂CO₃ solution was added and the reaction mixture was partitioned between DCM and water. The organic layer was separated, washed with brine, dried over anhydrous Na₂SO₄, and evaporated. The crude solid was re-crystallized with ethanol to afford 4.83 g of the title compound. ¹H NMR (400 MHz, CDCl₃): δ 3.15 (s, 6H), 3.98-4.02 (m, 2H), 4.14-4.19 (m, 2H), 5.18-5.21 (m, 2H).

Step 3: Intermediate 4

To a solution of Intermediate 3 (4.83 g, 18.6 mmol) in DMF (50 mL) was added 15-crown-5 (0.40 g, 1.82 mmol) and NaN₃ (6.03 g, 92.8 mmol). The mixture was heated to 100° C. under N₂ overnight. The reaction solution was diluted with EtOAc, washed with water and brine, dried over anhydrous Na₂SO₄ and evaporated to dryness to afford the 2.60 g of the title compound.

Step 4: Intermediate 5

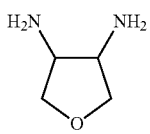

To a solution of Intermediate 4 (2.60 g, 16.9 mmol) in MeOH (15 mL) was added Pd/C (10%, w/w, 0.78 g) and the reaction mixture was allowed to stir at ambient temperature for 16 h. The reaction mixture was filtered and the filtrate was concentrated to afford 1.45 g of the title compound which was used without further purification.

Step 5: Intermediate 6

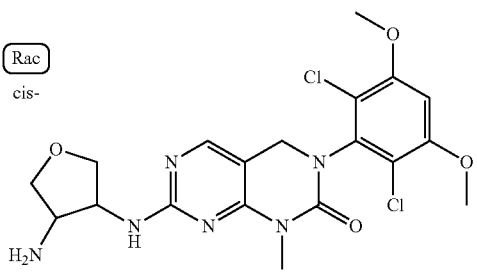 [SMILES: COc1cc(OC)c(Cl)c(N2Cc3cnc(NC4COCC4N)nc3N(C)C2=O)c1Cl]

To a solution of Intermediate 5 (0.90 g, 8.81 mmol) and Intermediate 6 from Example 1 (1.42 g, 0.40 eq) in NMP (10 mL) was added DIPEA (2.30 g, 17.8 mmol). The reaction mixture was heated at 100° C. for 16 h under nitrogen. The reaction mixture was cooled to ambient temperature, water was added and the aqueous layer was extracted with EtOAc (40 mL×3). The combined organic layers were dried (anhydrous $Na_2SO_4$), filtered and concentrated. Purification by column chromatography on silica gel (5% MeOH in DCM) afforded 162 mg of the title compound. MS m/z: 469.4 $(M+H)^+$.

Step 9: I-126

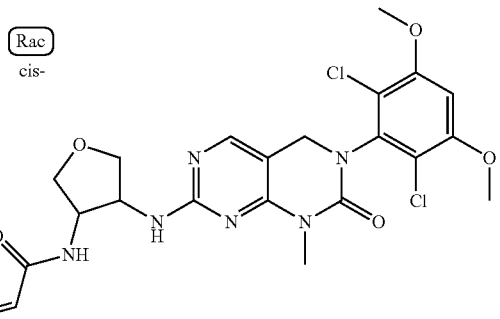

To an ice-cooled solution of Intermediate 6 (162 mg, 0.35 mmol) and $Et_3N$ (37.5 mg, 0.41 mmol) in DCM (10 mL) was added acryloyl chloride (41.9 mg, 0.41 mmol). The mixture was stirred at 0° C. for 10 min. The reaction mixture was quenched with saturated aqueous $NaHCO_3$ and the resultant mixture was extracted with EtOAc. The organic phase was dried, concentrated, and the residue was purified by column chromatography on silica gel (3% MeOH in DCM) to afford 112 mg of the title compound. MS m/z: 523.4 $(M+H)^+$. $^1H$ NMR (400 MHz, $CDCl_3$) δ: 3.39 (s, 3H), 3.71-3.81 (m, 2H), 3.94 (s, 6H), 4.17-4.21 (m, 2H), 4.52 (s, 2H), 4.73-4.79 (m, 2H), 5.62-5.65 (m, 2H), 6.02-6.07 (m, 1H), 6.26 (d, 1H), 6.32 (br, 1H), 6.60 (s, 1H), 7.84 (s, 1H).

Example 128: Synthesis of I-127

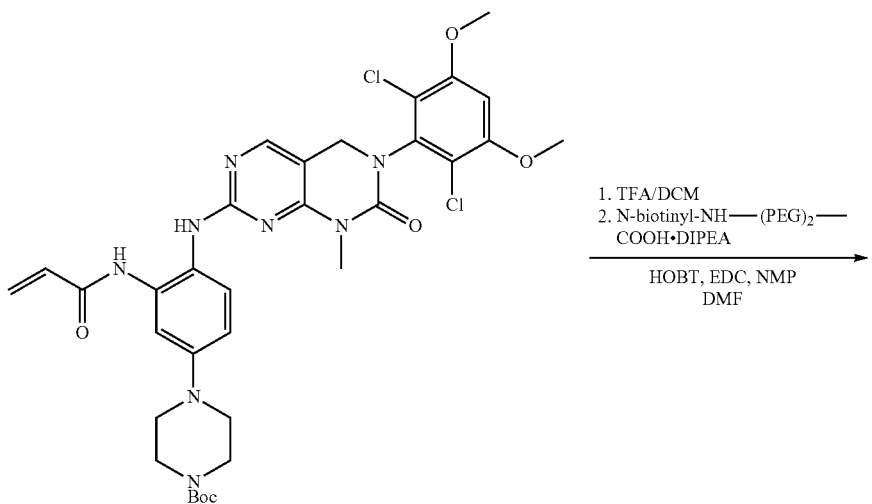

I-62

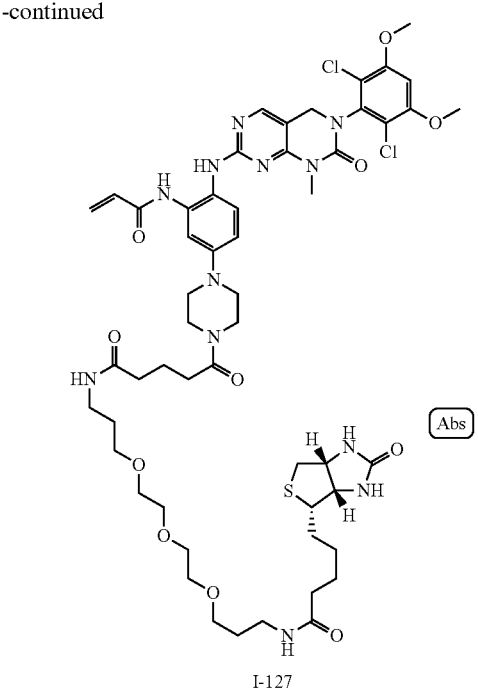

I-127

To a solution of I-62 (30.0 mg, 0.042 mmol) in 2 mL of DCM was added 200 uL of TFA and the reaction mixture was allowed to stir for 1 h at ambient temperature. Solvent was removed under reduced pressure and the resulting solid was dissolved in 300 ul of DMF. To this solution was added the N-biotinyl-NH-(PEG)$_2$-COOH.DIPEA (35 mg, 0.049 mmol), HOBT (7 mg, 0.046 mmol), EDC (9 mg, 0.046 mmol) and NMM (30 uL, 0.28 mmol), and the mixture was allowed to stir at ambient temperature for 16 h. The crude product was purified by reverse phase preparative HPLC (eluting with a gradient of 10-90% MeCN in H$_2$O with 0.1% aqueous TFA), which gave 22 mg of the title compound. MS m/z: 1155.3 (M+H$^+$). $^1$H NMR (400 MHz, DMSO-d6): δ: 9.73 (1H, s), 8.05 (1H, s), 7.77 (2H, m), 7.47 (1H, d), 7.3 (1H, s), 7.0 (1H, s), 6.86 (1H, dd), 6.5 (1H, dd), 6.45 (1H, br s), 6.25 (1H, dd), 5.77 (1H, dd), 4.51 (2H, s), 4.3 (1H, m), 4.1-3.0 (31H, m), 2.8 (1H, dd), 2.34 (3H, m), 2.08 (5H, tt), 1.73 (3H, m), 1.6 (6H, m), 1.5-1.2 (8H, m).

Example 129: Synthesis of I-128

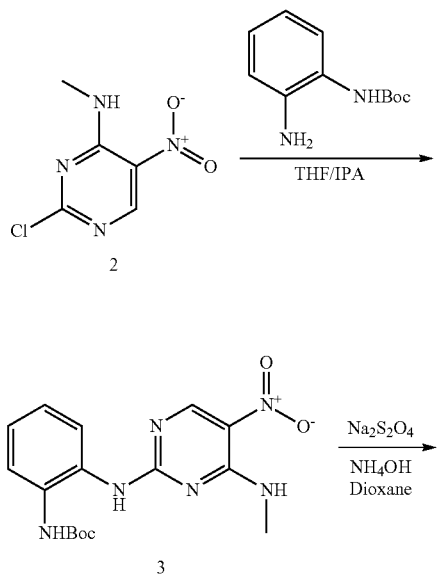

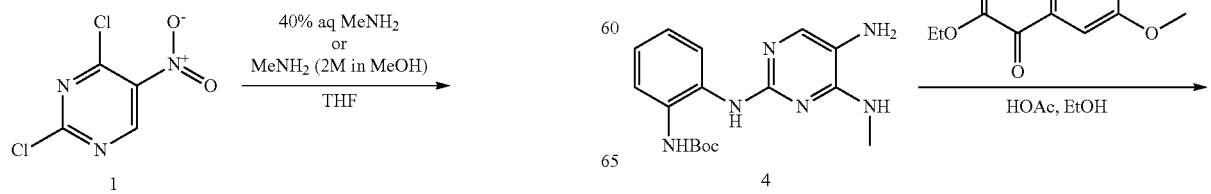

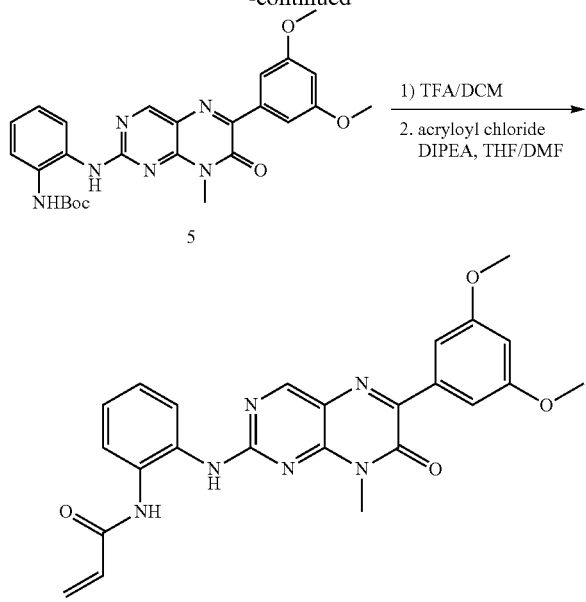

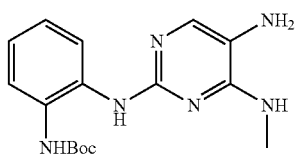

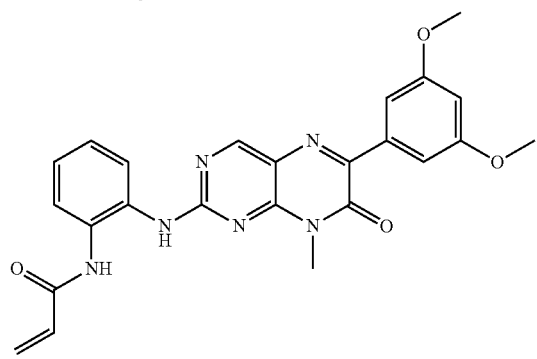

I-128

Step 1: Intermediate 2

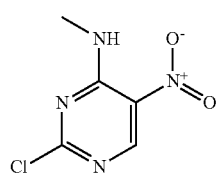

The title compound was prepared from Intermediate 1 according to literature procedures (WO 01/19825; PCT/US00/17037; WO 2008/051820; PCT/US2007/081899).

Step 2: Intermediate 3

A solution of Intermediate 2 (200 mg, 1.04 mmol) and mono-BOC phenylene diamine (450 mg, 2.07 mmol) in 9 mL of 1:2 THF/IPA was heated to 100° C. for 1 h. The solvent was removed under reduced pressure and the reaction mixture was partitioned between water and EtOAc. The organic layer was dried with Na$_2$SO$_4$, filtered and concentrated under reduced pressure. The crude product was subjected to chromatography on silica gel (eluting with a gradient of 0-50% EtOAc in heptane), which gave 150 mg of the title compound. MS m/z: 361.1 (M+H$^+$)

Step 3: Intermediate 4

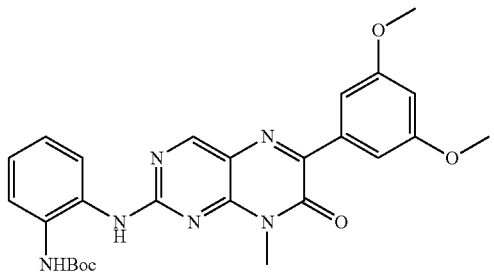 [SMILES: COc1cc(OC)cc(-c2nc3cnc(Nc4ccccc4NC(=O)OC(C)(C)C)nc3n(C)c2=O)c1]

To a solution of Intermediate 3 (250 mg, 0.69 mmol) in 6 mL of dioxane was added a solution of sodium hydrosulfite (1.5 g, 8.68 mmol in 12 mL of water) and 500 ul of concentrated ammonium hydroxide. A solid formed which was sonicated until a solution was achieved. The solution was concentrated and partitioned with brine and EtOAc; the organic layer was dried with Na$_2$SO$_4$, filtered and the solvent was removed under reduced pressure to provide 260 mg of the title compound. MS m/z: 331.1 (M+H$^+$)

Step 4: Intermediate 5

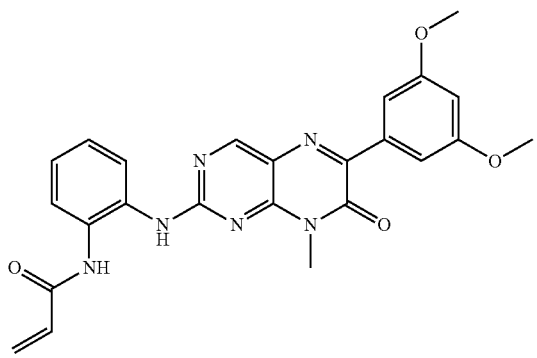 [SMILES: C=CC(=O)Nc1ccccc1Nc1ncc2nc(-c3cc(OC)cc(OC)c3)c(=O)n(C)c2n1]

A solution of Intermediate 4 (260 mg, 0.79 mmol) and ethyl 2-(3,5-dimethoxyphenyl)-2-oxoacetate (220 mg, 0.94 mmol) in 10 mL of EtOH containing 400 ul of acetic acid; was refluxed for 16 h. A solid formed which was filtered to provide 150 mg of the title compound. MS m/z: 505.2 (M+H$^+$)

Step 6: I-128

To a solution of intermediate 5 (150 mg, 0.3 mmol) in 10 mL of DCM was added 2 mL of TFA and the reaction mixture was allowed to stir for 2 h at ambient temperature. Solvent was removed under reduced pressure and partitioned with cold (0° C.) saturated NaHCO$_3$ and EtOAc. The solid formed was filtered to provide 122 mg. of free amine intermediate. MS m/z: 405.2 (M+H⁺). The solid was then suspended in 5 mL of THF and 500 uL of DMF and the solution was cooled in an ice-water/methanol bath. Acryloyl chloride (20 μL, 0.23 mmol) was added and the reaction mixture was allowed to stir at −10° C. for 5 min after which it was treated with DIPEA (50 uL, 0.276 mmol) and allowed to stir at ambient temperature for 30 min. The solvent was reduced in volume and the crude product was subjected to chromatography on silica gel (eluting with a gradient of 0-75% EtOAc in heptane). The title compound was purified further by reverse phase preparative HPLC (eluting with a gradient of 10-90% acetonitrile in H₂O with 0.1% aqueous TFA), which gave 10 mg of the title compound. MS m/z: 459.0 (M+H⁺). ¹H NMR (400 MHz, DMSO-d6): δ: 9.87 (1H, s), 9.43 (1H, s), 8.87 (1H, s), 7.81 (1H, d), 7.649 (1H, d), 7.408 (2H, d), 7.25 (2H, m), 6.64 (1H, dd), 6.5 (1H, dd), 6.3 (1H, dd), 5.78 (1H, dd), 3.8 (6H, s), 3.50 (3H, s).

Example 130: Synthesis of I-129 (Racemic)

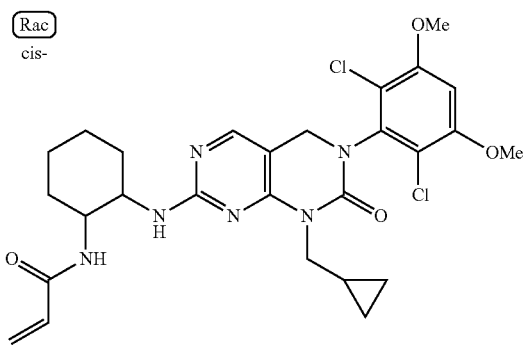 [SMILES: C=CC(=O)NC1CCCCC1Nc1ncc2c(n1)N(CC1CC1)C(=O)N(c1c(Cl)c(OC)cc(OC)c1Cl)C2]

Compound I-129 was prepared as described in Example 21. 7-chloro-1-(cyclopropylmethyl)-3-(2,6-dichloro-3,5-dimethoxyphenyl)-3,4-dihydropyrimido[4,5-d]pyrimidin-2 (1H)-one was used in place of Intermediate 2 and was prepared as described in Example 1 using cyclopropylmethanamine in place of methylamine in Step 5. MS m/z: 575.5 (M+H⁺).

Example 131: Synthesis of I-130

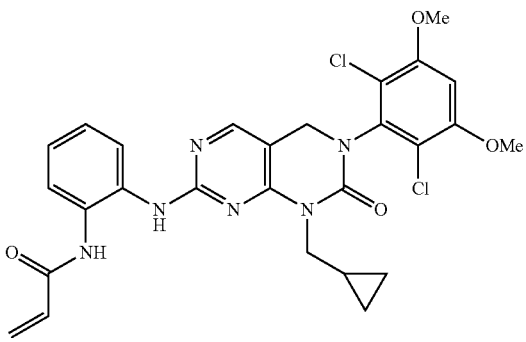 [SMILES: C=CC(=O)Nc1ccccc1Nc1ncc2c(n1)N(CC1CC1)C(=O)N(c1c(Cl)c(OC)cc(OC)c1Cl)C2]

Compound I-130 was prepared as described in Example 7. The starting material was prepared as described in Example 1 using cyclopropylmethanamine in place of methylamine in Step 5. MS m/z: 569.5 (M+H⁺).

Example 132: Synthesis of I-131

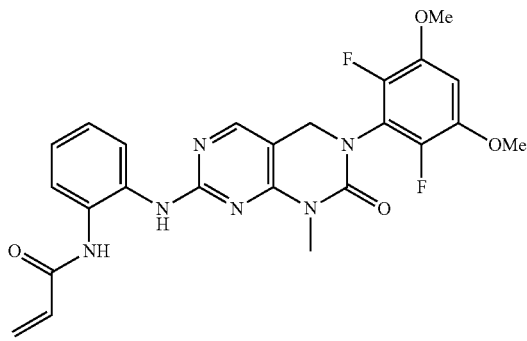 [SMILES: C=CC(=O)Nc1ccccc1Nc1ncc2c(n1)N(C)C(=O)N(c1c(F)c(OC)cc(OC)c1F)C2]

Compound I-131 was prepared as described in Example 7. The starting material was prepared as described in Example 1 using 2,6-difluoro-3,5-dimethoxyaniline in place of 3,5-dimethoxyaniline in Step 4. MS m/z: 497.5 (M+H⁺).

Example 133: Synthesis of I-132

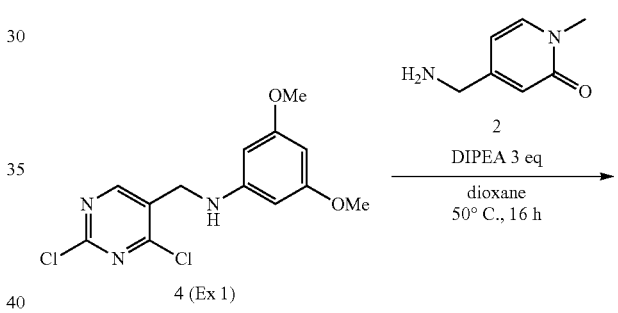

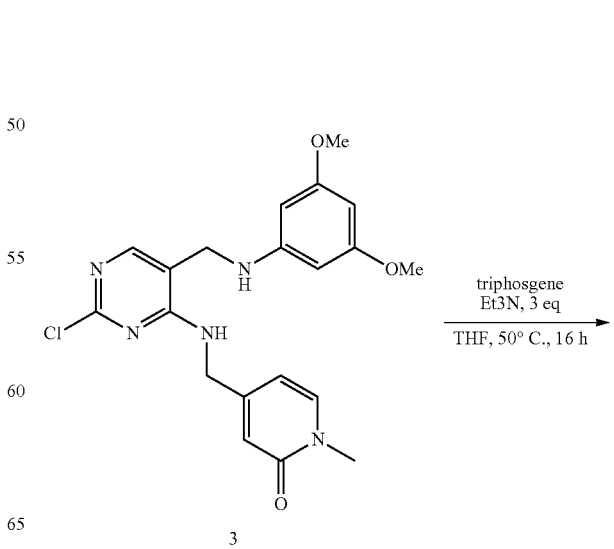

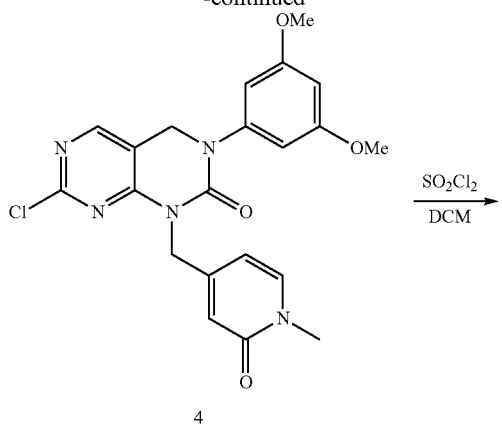

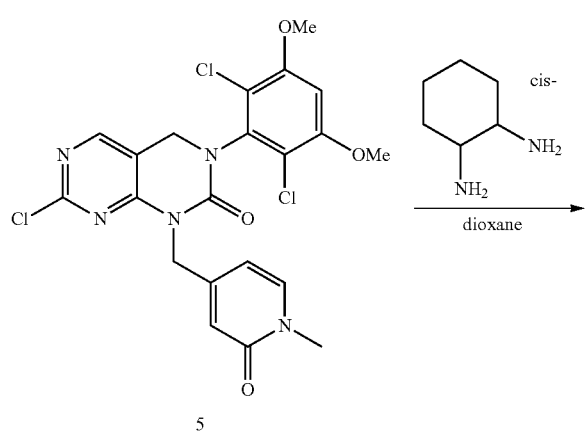

Step 1: Intermediate 3

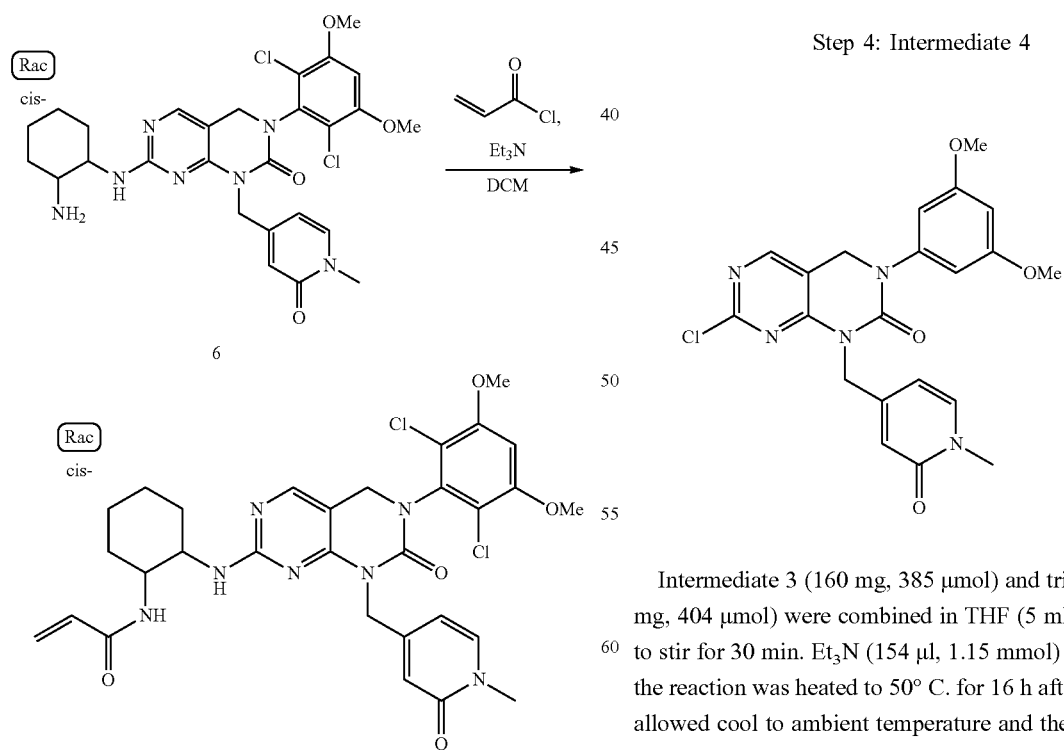

Intermediate 4 from Example 1 (380 mg, 1.21 mmol), Intermediate 2 (prepared as described in U.S. Pat. No. 7,713,994) (251 mg, 1.81 mmol) and DIPEA (642 μl, 3.63 mmol) were combined in 1,4-dioxane (5 mL). The reaction vessel was sealed and heated to 50° C. for 16 h after which it was concentrated and the resultant residue taken up in DCM. Solids were filtered and the filtrate purified through flash chromatography on silica gel (eluting with 1-5% MeOH in EtOAc) to provide 160 mg of the title compound with 20% regioisomer impurity which was carried on without further purification. MS m/z: 416.4 (M+H⁺).

Step 4: Intermediate 4

Intermediate 3 (160 mg, 385 μmol) and triphosgene (120 mg, 404 μmol) were combined in THF (5 mL) and allowed to stir for 30 min. Et₃N (154 μl, 1.15 mmol) was added and the reaction was heated to 50° C. for 16 h after which it was allowed cool to ambient temperature and the resultant residue was purified through flash chromatography on silica gel (eluting with MeOH/DCM) to afford 60 mg of the title compound MS m/z: 442.4 (M+H⁺).

Step 5: Intermediate 5

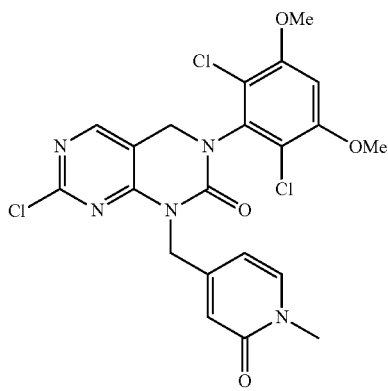 [SMILES: COc1cc(OC)c(Cl)c(N2Cc3cnc(Cl)nc3N(Cc3ccn(C)c(=O)c3)C2=O)c1Cl]

Intermediate 4 (56 mg, 127 µmol) was dissolved in MeCN (0.3 mL) and DCM (0.3 mL). The solution was cooled to 0° C. and sulfuryl dichloride (20.6 µl, 254 µmol) was added. The mixture was allowed to stir at 0° C. for 2 h. Water was added followed by saturated aqueous sodium bicarbonate and the mixture was allowed to stir for an additional 20 min at ambient temperature. The reaction mixture was extracted with DCM and the combined organic layers were dried over MgSO$_4$, and concentrated under reduced pressure and purified by flash chromatograph on silica gel (eluting with 30% EtOAc in DCM) to provide 16 mg of the title compound MS m/z: 510 (M+H$^+$).

Step 6: Intermediate 6

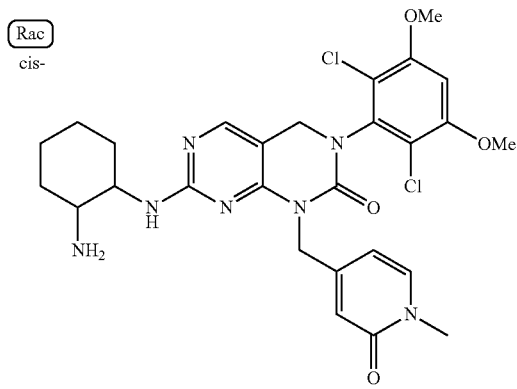 [SMILES: COc1cc(OC)c(Cl)c(N2Cc3cnc(NC4CCCCC4N)nc3N(Cc3ccn(C)c(=O)c3)C2=O)c1Cl]

Intermediate 5 (16.0 mg, 31.3 µmol) was suspended in 1,4-dioxane (0.5 mL) and (cis)-cyclohexane-1,2-diamine (7.15 mg, 62.3 µmol) and Et$_3$N (13.1 µl, 94.0 µmol) were added. The resultant suspension was allowed to stir at 95° C. for 6 h after which the reaction mixture was concentrated under reduced pressure and the resultant residue was purified by flash chromatography on silica gel (eluting with 15% MeOH in DCM) to afford 15.0 mg of the title compound.

Step 7: I-132

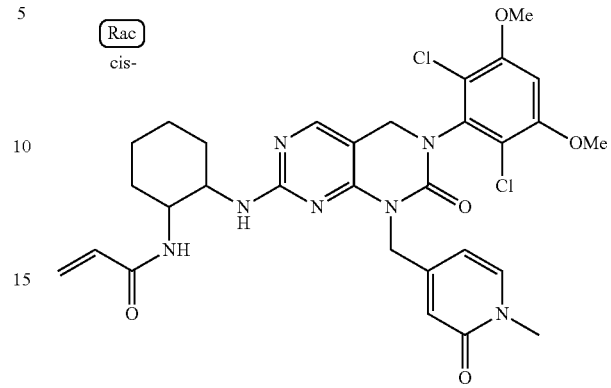

Intermediate 6 (15.0 mg, 25.5 µmol) was suspended in DCM (0.25 mL) and Et$_3$N (7.11 µl, 51.0 µmol) was added. The mixture was cooled to 0° C. and acryloyl chloride (1.60 µl, 25.5 µmol) was added. The mixture was allowed to stir at 0° C. for 30 min then MeOH (3 mL) was added. The solution was concentrated under reduced pressure and the resultant residue was purified through flash chromatography on silica gel (10% MeOH in DCM) to provide 5 mg of the title compound. MS m/z: 642.6 (M+H$^+$). $^1$H NMR (400 MHz, DMSO-d6) δ 8.01 (m, 1H), 7.68 (d, 1H), 7.61 (d, 1H), 7.00 (s, 1H), 6.74 (m, 1H), 6.40-6.23 (m, 1H), 6.17-5.98 (m, 3H), 5.54 (dt, 1H), 4.91 (s, 2H), 4.53 (s, 2H), 3.96 (s, 5H), 4.01 (m, 1H), 3.36 (s, 6H), 1.87-1.11 (m, 8H).

Example 134: Synthesis of I-133

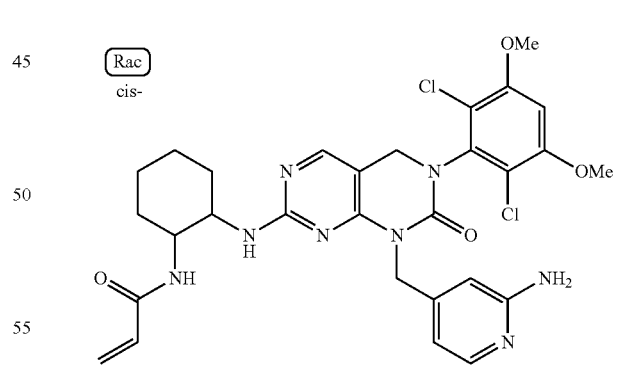

Compound I-133 was prepared as described in Example 21. 1-((2-aminopyridin-4-yl)methyl)-7-chloro-3-(2,6-dichloro-3,5-dimethoxyphenyl)-3,4-dihydropyrimido[4,5-d]pyrimidin-2(1H)-one was used in place of Intermediate 2 and was prepared as described in Example 1 using 4-(aminomethyl)pyridin-2-amine in place of methylamine in Step 5. MS m/z: 627.5 (M+H$^+$).

Example 135: Synthesis of I-134

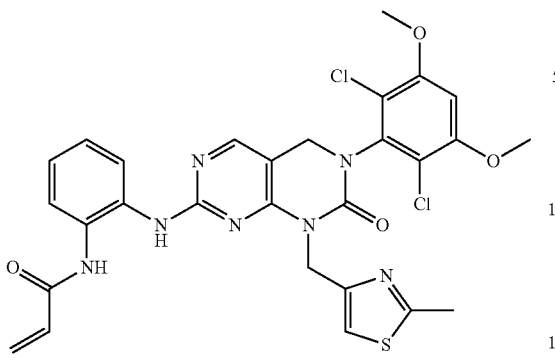

Compound I-134 was prepared as described in Example 7. The starting material was prepared as described in Example 1 using (2-methylthiazol-4-yl)methanamine in place of methylamine in Step 5. MS m/z: 626.4 (M+H$^+$).

Example 136: Synthesis of I-135

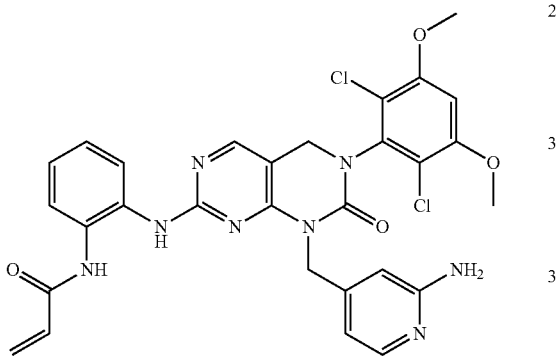

Compound I-135 was prepared as described in Example 7. The starting material was prepared as described in Example 1 using 4-(aminomethyl)pyridin-2-amine in place of methylamine in Step 5. MS m/z: 621.4 (M+H$^+$).

Example 137: Synthesis of I-136

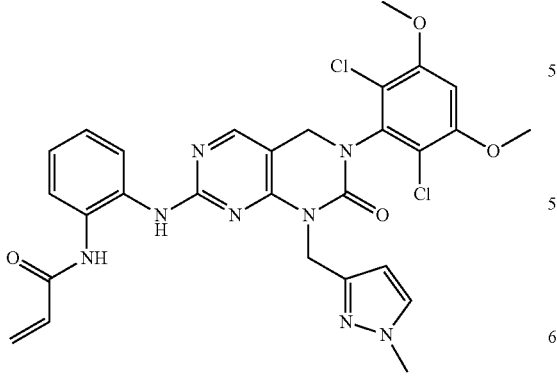

Compound I-136 was prepared as described in Example 7. The starting material was prepared as described in Example 1 using (1-methyl-1H-pyrazol-3-yl)methanamine in place of methylamine in Step 5. MS m/z: 609.4 (M+H$^+$).

Example 138: Synthesis of I-137

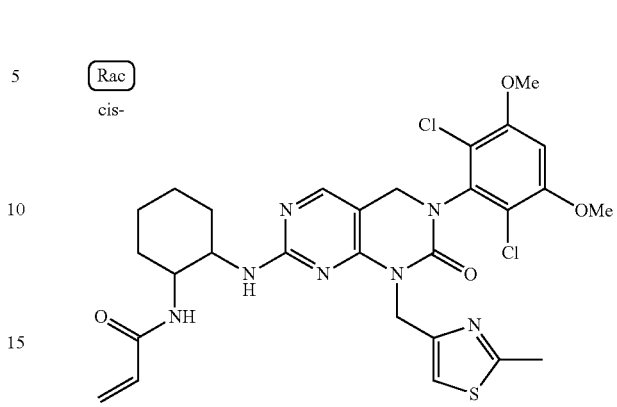

Compound I-137 was prepared as described in Example 21. 7-chloro-3-(2,6-dichloro-3,5-dimethoxyphenyl)-1-((2-methylthiazol-4-yl)methyl)-3,4-dihydropyrimido[4,5-d]pyrimidin-2(1H)-one was used in place of Intermediate 2 and was prepared as described in Example 1 using (2-methylthiazol-4-yl)methanamine in place of methylamine in Step 5. MS m/z: 632.5 (M+H$^+$).

Example 139: Synthesis of I-138 (Racemic)

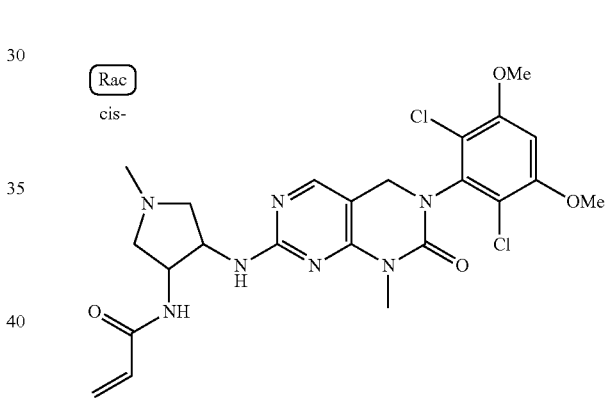

Compound I-138 was prepared as described in Example 21 using cis-1-methylpyrrolidine-3,4-diamine in place of cis-cyclohexane-1,2-diamine in Step 2. MS m/z: 536.4 (M+H$^+$).

Example 140: Synthesis of I-139 (Racemic)

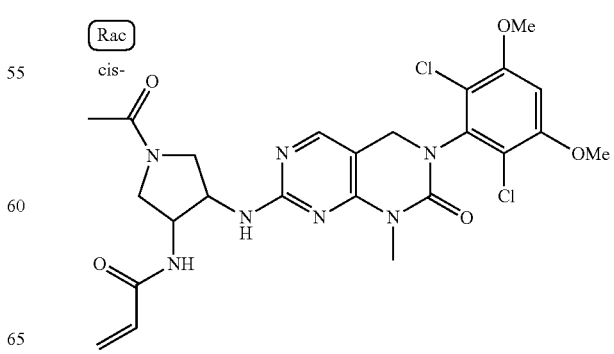

409

Compound I-139 was prepared as described in Example 21 using cis-1-(3,4-diaminopyrrolidin-1-yl)ethanone in place of cis-cyclohexane-1,2-diamine in Step 2. MS m/z: 564.5 (M+H$^+$).

Example 141: Synthesis of I-140

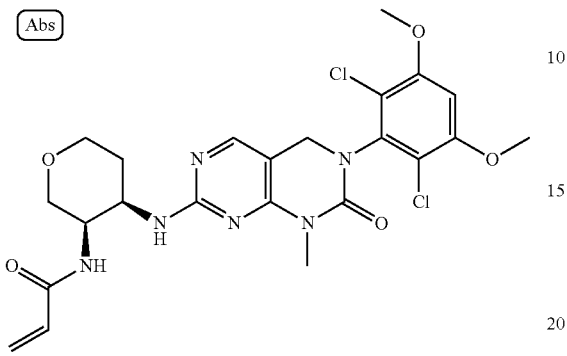

The title compound (2 mg) was prepared as described in Example 84 using tert-butyl ((3R,4R)-4-aminotetrahydro-2H-pyran-3-yl)carbamate in place of ((1S, 2R)-2-aminocyclohexyl)carbamate in Step 3, and starting with a derivative of Intermediate 6 from Example 1 (prepared using benzylamine in place of methylamine in Step 5). MS m/z: 537.2 (M+H$^+$).

Example 142: Synthesis of I-141

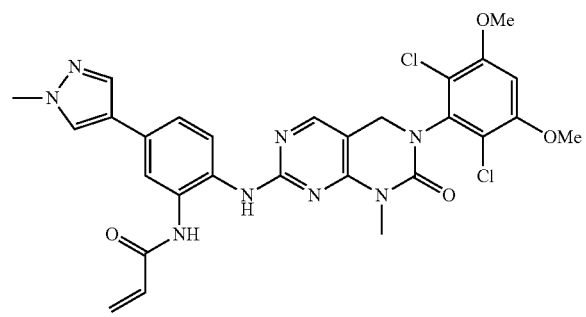 [SMILES: C=CC(=O)Nc1cc(-c2cnn(C)c2)ccc1Nc1ncc2c(n1)N(C)C(=O)N(c1c(Cl)c(OC)cc(OC)c1Cl)C2]

Compound I-141 was prepared as described in Example 29 using 1-methyl-4-(4,4,5,5-tetramethyl-1,3,2-dioxaborolan-2-yl)-1H-pyrazole in place of Intermediate 3 in Step 2 and Common Intermediate 6 from Example 1 in Step 4. MS m/z: 609.4 (M+H$^+$).

Example 143: Synthesis of I-142

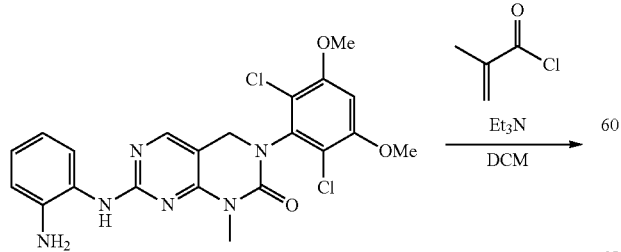

410

-continued

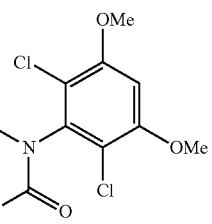

Step 1: I-142

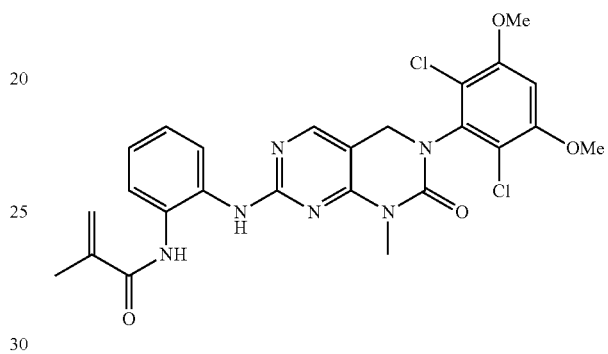

Intermediate 2 from Example 4 (43.0 mg, 90.5 µmol) was suspended in DCM (1 mL) and Et$_3$N (37.8 µl, 272 µmol) was added. The suspension was cooled to 0° C. and methacryloyl chloride (9.81 µl, 99.5 µmol) was added. The reaction mixture was allowed to stir at 0° C. for 45 min, methanol was added at 0° C., and the reaction mixture was concentrated under reduced pressure. The resultant residue was purified through flash chromatography on silica gel (5% EtOAc in DCM) to afford 3.4 mg of the title compound. MS m/z: 543.5 (M+H$^+$). $^1$H NMR (400 MHz, DMSO-d6) δ 9.49 (s, 1H), 8.71 (s, 1H), 8.11 (d, 1H), 7.74 (dd, 1H), 7.50 (dd, 1H), 7.17 (ddd, 2H), 7.00 (s, 1H), 5.80 (m, 1H), 5.52 (t, 1H), 4.52 (s, 2H), 3.96 (s, 6H), 3.22 (s, 3H), 1.94 (s, 3H).

Example 144: I-143

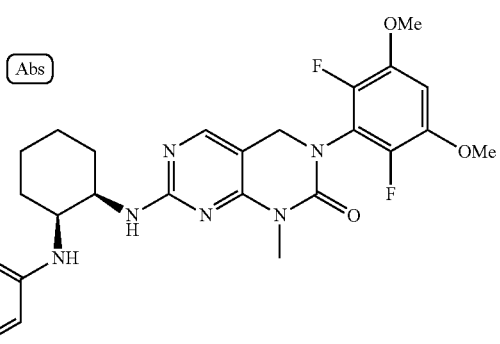

The title compound was prepared as described in Example 84 starting from Step 2. Intermediate 2 was prepared as described in Example 117, Intermediate 7 substituting methylamine for 2,2-difluoroethanamine in Step 6. MS m/z:

503.1 (M+H⁺). ¹H NMR (400 MHz, CD₃OD): δ: 7.94 (1H, s), 6.96 (1H, t), 6.29 (1H, br), 6.19 (1H, dd), 5.64 (1H, dd), 4.65 (2H, s), 4.44 (2H, br), 3.92 (6H, s), 3.42 (3H, s), 1.78 (6H, br), 1.56 (2H, br).

Example 145: Synthesis of I-144

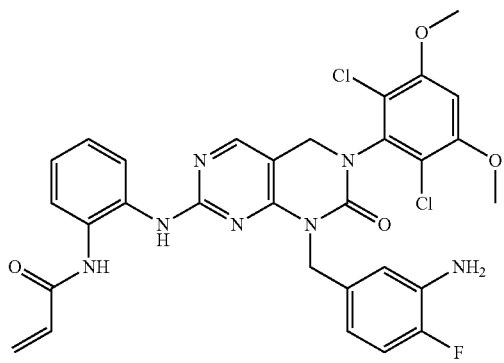 [SMILES: C=CC(=O)Nc1ccccc1Nc1ncc2c(n1)N(Cc1ccc(F)c(N)c1)C(=O)N(c1c(Cl)c(OC)cc(OC)c1Cl)C2]

Compound I-144 was prepared as described in Example 7. The starting material was prepared as described in Example 1 using tert-butyl (5-(aminomethyl)-2-fluorophenyl)carbamate in place of methylamine in Step 5. A final BOC deprotection step was performed (as described in Example 3, Step 5). MS m/z: 638.5 (M+H⁺).

Example 146: Synthesis of I-145

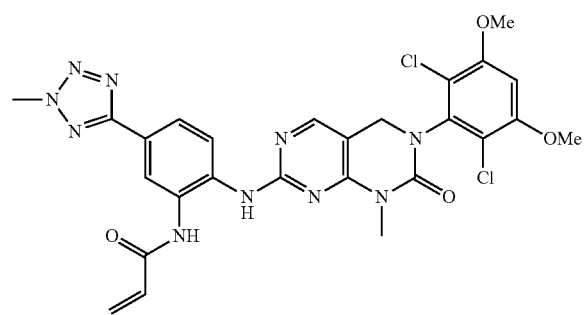 [SMILES: C=CC(=O)Nc1cc(-c2nnn(C)n2)ccc1Nc1ncc2c(n1)N(C)C(=O)N(c1c(Cl)c(OC)cc(OC)c1Cl)C2]

Compound I-145 was prepared as described in Example 17 using 4-(2-methyl-2H-tetrazol-5-yl)-2-nitroaniline (Bioorganic & Medicinal Chemistry Letters, 18(18), 4997-5001; 2008) in place of Intermediate 1, and skipping Step 2. MS m/z: 611.4 (M+H⁺).

Example 147: Synthesis of I-146

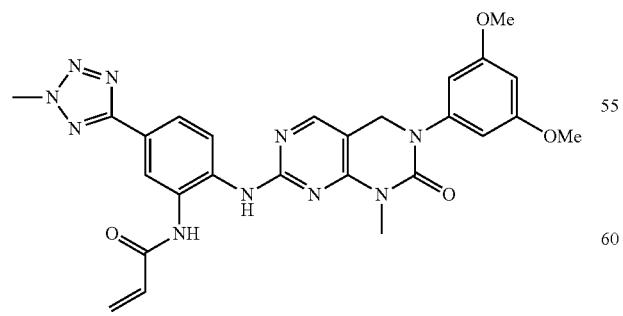

Compound I-146 was prepared as described in Example 17 using 4-(2-methyl-2H-tetrazol-5-yl)-2-nitroaniline (Bioorganic & Medicinal Chemistry Letters, 18(18)), in place of Intermediate 1, using Intermediate 5 from Example 1, and skipping Step 2. MS m/z: 543.5 (M+H⁺).

Example 148: Synthesis of I-147

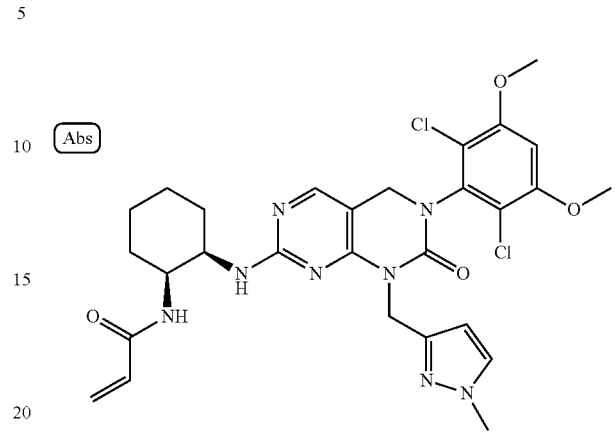

Compound I-147 was prepared as described in Example 116. The starting material was prepared as described in Example 1 using (1-methyl-1H-pyrazol-3-yl)methanamine in place of methylamine in Step 5. MS m/z: 615.5 (M+H⁺).

Example 149: Synthesis of I-148

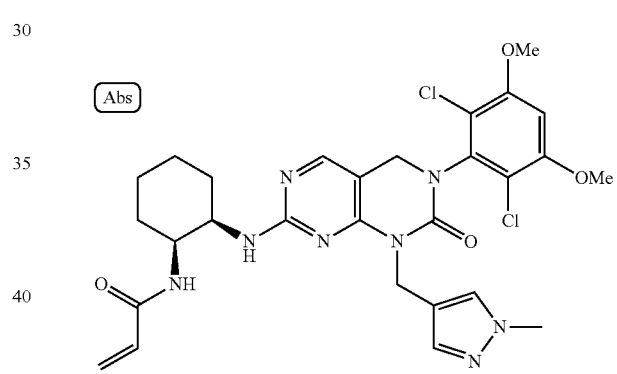

Compound I-148 was prepared as described in Example 116. The starting material was prepared as described in Example 1 using (1-methyl-1H-pyrazol-4-yl)methanamine in place of methylamine in Step 5. MS m/z: 605.6 (M+H⁺).

Example 150: Synthesis of I-149

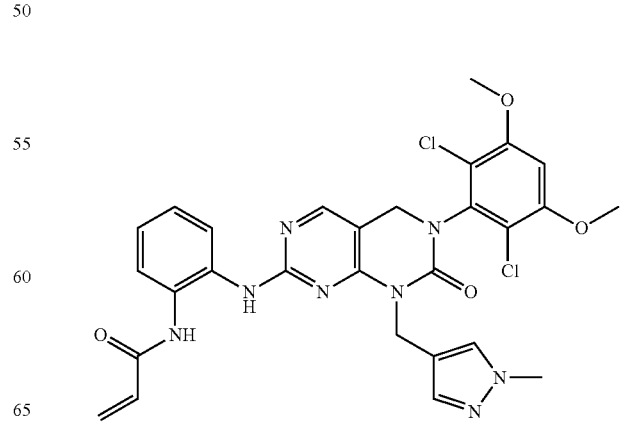

Compound I-149 was prepared as described in Example 7. The starting material was prepared as described in Example 1 using (1-methyl-1H-pyrazol-4-yl)methanamine in place of methylamine in Step 5. MS m/z: 522.6 (M+H⁺).

Example 151: Synthesis of I-150

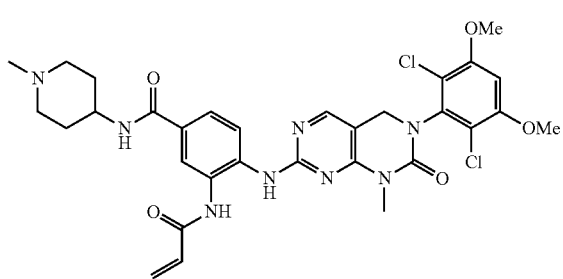 [SMILES: C=CC(=O)Nc1cc(C(=O)NC2CCN(C)CC2)ccc1Nc1ncc2c(n1)N(C)C(=O)N(c1c(Cl)c(OC)cc(OC)c1Cl)C2]

Compound I-150 was prepared as described in Example 7. tert-butyl (2-amino-5-(((1-methylpiperidin-4-yl)carbamoyl)phenyl)carbamate was used in place of benzene-1,2-diamine in Step 1. Intermediate 6 from Example 1 was used in place of Intermediate 5. MS m/z: 669.5 (M+H⁺).

Example 152: Synthesis of I-151

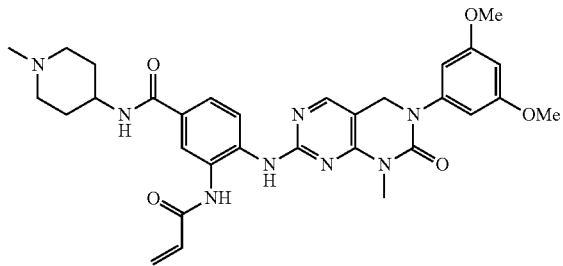 [SMILES: C=CC(=O)Nc1cc(C(=O)NC2CCN(C)CC2)ccc1Nc1ncc2c(n1)N(C)C(=O)N(c1cc(OC)cc(OC)c1)C2]

Compound I-151 was prepared as described in Example 7. tert-butyl (2-amino-5-(((1-methylpiperidin-3-yl)carbamoyl)phenyl)carbamate was used in place of benzene-1,2-diamine in Step 1. MS m/z: 601.5 (M+H⁺).

Example 153: Synthesis of I-152

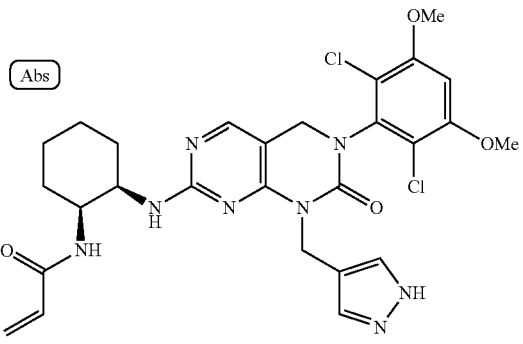 [SMILES: C=CC(=O)N[C@H]1CCCC[C@H]1Nc1ncc2c(n1)N(Cc1cn[nH]c1)C(=O)N(c1c(Cl)c(OC)cc(OC)c1Cl)C2]

Compound I-152 was prepared as described in Example 116. The starting material was prepared as described in Example 1 using tert-butyl 4-(aminomethyl)-1H-pyrazole-1-carboxylate in place of methylamine in Step 5. A final BOC deprotection step was performed as described in Example 3, Step 5. MS m/z: 601.4 (M+H⁺).

Example 154: Synthesis of I-153

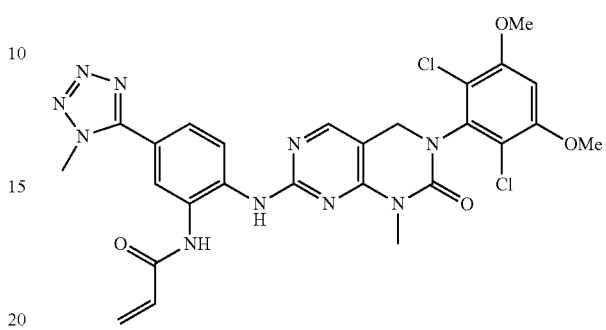

Compound I-154 was prepared as described in Example 17 using 4-(1-methyl-1H-tetrazol-5-yl)-2-nitroaniline (prepared as described in PCT Int. Appl., 2007066201, 14 Jun. 2007) in place of Intermediate 1, and skipping Step 2. MS m/z: 611.4 (M+H⁺).

Example 155: Synthesis of I-154 (Racemic)

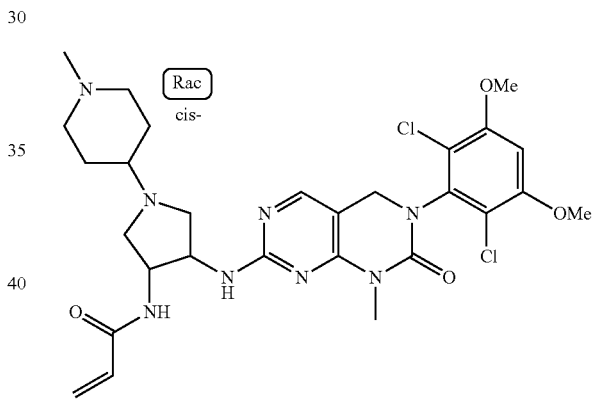

Compound I-155 was prepared as described in Example 7. Cis-1-(1-methylpiperidin-4-yl)pyrrolidine-3,4-diamine was used in place of benzene-1,2-diamine in Step 1. Intermediate 6 from Example 1 was used in place of Intermediate 5. MS m/z: 547.1 (M+H⁺).

Example 156: I-155

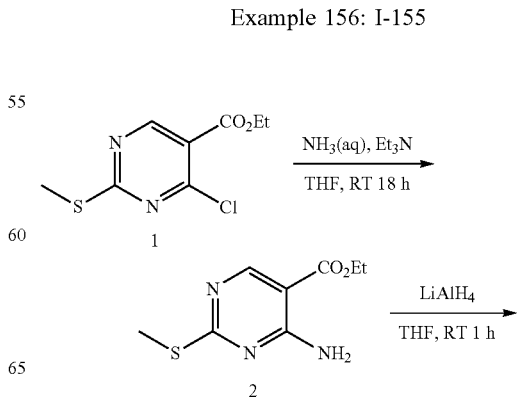

415
-continued

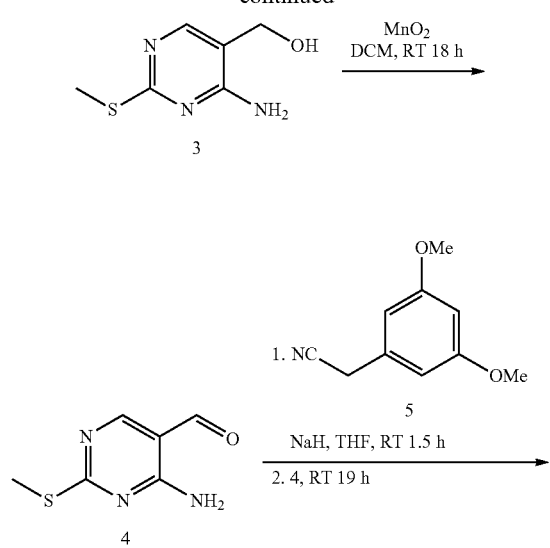

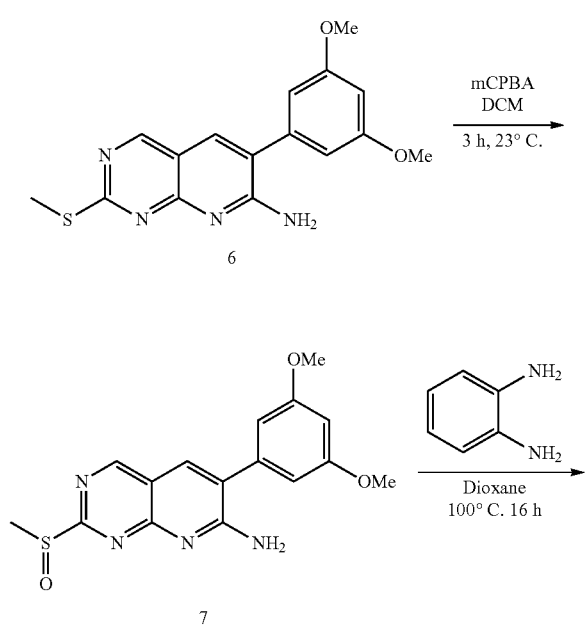

I-155

Intermediate 7

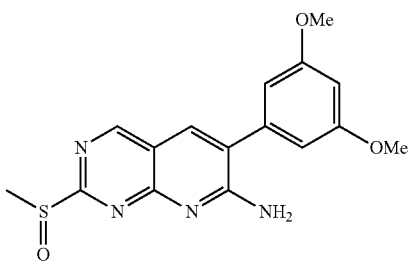 [SMILES: COc1cc(OC)cc(-c2cc3cnc(S(C)=O)nc3nc2N)c1]

The title compound was prepared according the literature (*J. Med. Chem.* 2005, 48, 4628-4653) and as outlined in the scheme above.

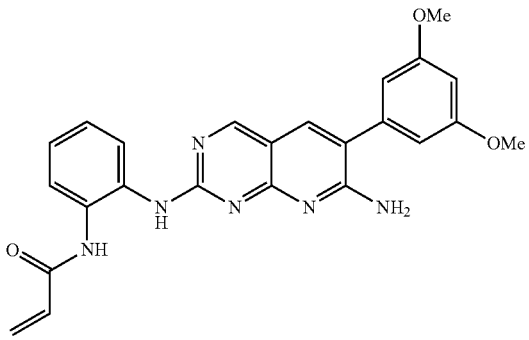

I-155

The title compound was prepared form Intermediate 7 as outlined in Example 7 Step 2. MS m/z: 443.1 (M+H⁺). ¹H NMR (400 MHz, DMSO-d6): δ 0.9.92 (1H, br s), 9.51 (1H, br s), 8.99 (1H, s), 8.15 (2H, br s), 7.76-7.67 (2H, m), 7.26-7.26 (2H, m), 6.64-6.62 (4H, m), 6.62 (1H, dd), 6.28 (1H, dd), 5.78 (1H, dd).

Example 157: Synthesis of I-156

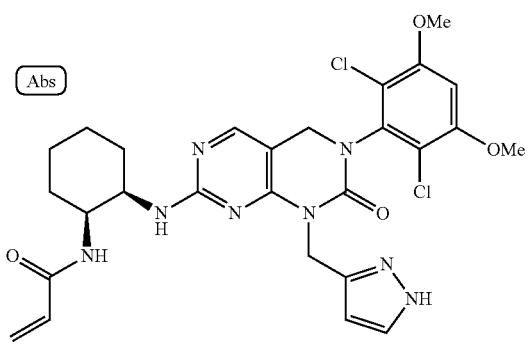 [SMILES: C=CC(=O)N[C@H]1CCCC[C@H]1Nc1ncc2c(n1)N(Cc1cc[nH]n1)C(=O)N(c1c(Cl)c(OC)cc(OC)c1Cl)C2]

Compound I-156 was prepared as described in Example 116. The starting material was prepared as described in Example 1 using tert-butyl 3-(aminomethyl)-1H-pyrazole-1-carboxylate in place of methylamine in Step 5. A final BOC deprotection step was performed as described in Example 3, Step 5. MS m/z: 601.4 (M+H⁺).

Example 158: Synthesis of I-157

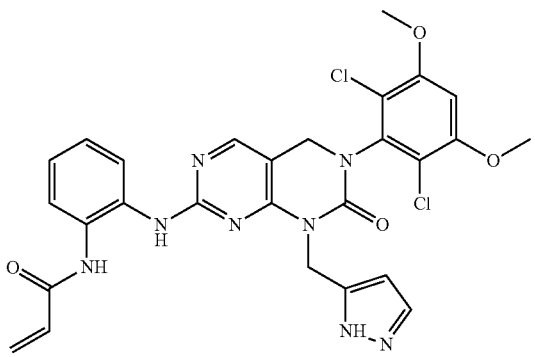 [SMILES: C=CC(=O)Nc1ccccc1Nc1ncc2c(n1)N(Cc1ccn[nH]1)C(=O)N(c1c(Cl)c(OC)cc(OC)c1Cl)C2]

Compound I-157 was prepared as described in Example 7. The starting material was prepared as described in Example 1 using tert-butyl 5-(aminomethyl)-1H-pyrazole-1-carboxylate in place of methylamine in Step 5. A final BOC deprotection step was performed as described in Example 3, Step 5. MS m/z: 595.4 (M+H$^+$).

Example 159: Synthesis of I-158

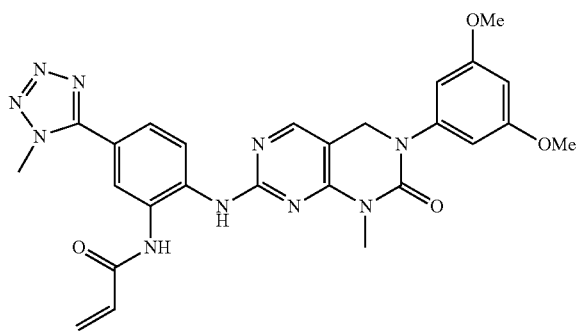 [SMILES: C=CC(=O)Nc1cc(-c2nnnn2C)ccc1Nc1ncc2c(n1)N(C)C(=O)N(c1cc(OC)cc(OC)c1)C2]

Compound I-158 was prepared as described in Example 17 using 4-(1-methyl-1H-tetrazol-5-yl)-2-nitroaniline (prepared as described in PCT Int. Appl., 2007066201, 14 Jun. 2007) in place of Intermediate 1, Intermediate 5 from Example 1 in place of Intermediate 6, and skipping Step 2. MS m/z: 543.5 (M+H$^+$).

Example 160: Synthesis of I-159 (Racemic)

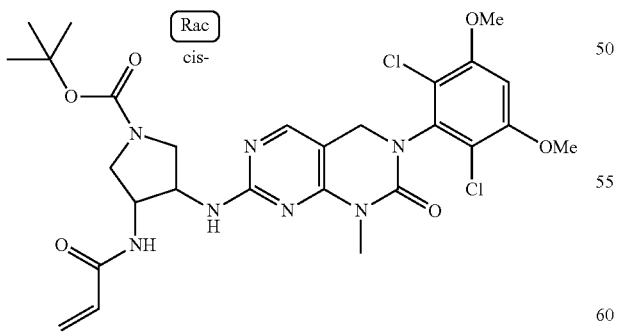

Compound I-159 was prepared as described in Example 7. cis-tert-butyl 3,4-diaminopyrrolidine-1-carboxylate was used in place of benzene-1,2-diamine in Step 1. Intermediate 6 from Example 1 was used in place of Intermediate 5. MS m/z: 622.5 (M+H$^+$).

Example 161: Synthesis of I-160 (Racemic)

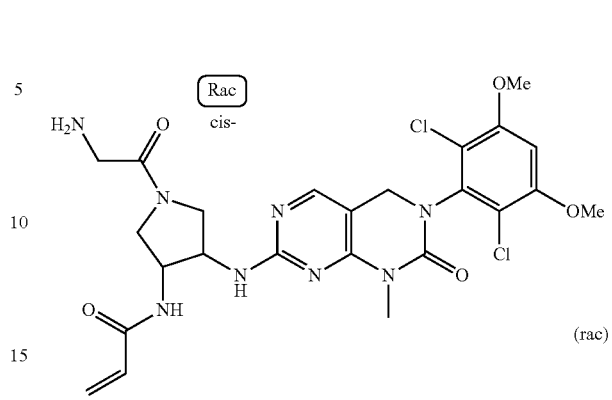

Compound I-160 was prepared as described in Example 7. tert-butyl (2-((cis)-3,4-diaminopyrrolidin-1-yl)-2-oxoethyl)carbamate was used in place of benzene-1,2-diamine in Step 1. Intermediate 6 from Example 1 was used in place of Intermediate 5. A final BOC deprotection step was performed as described in Example 3, Step 5. MS m/z: 579.5 (M+H$^+$).

Example 162: Synthesis of I-161 (Racemic)

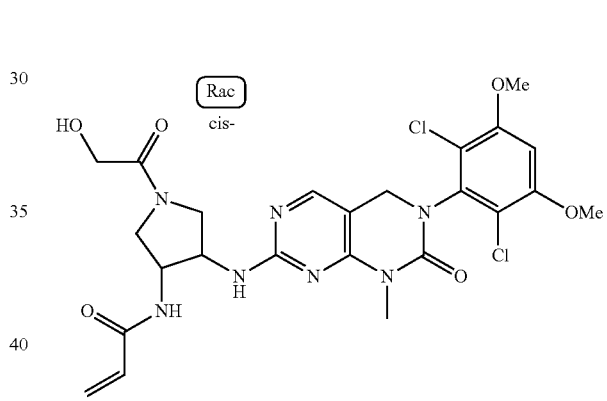

Compound I-161 was prepared as described in Example 7. 1-((cis)-3,4-diaminopyrrolidin-1-yl)-2-hydroxyethanone was used in place of benzene-1,2-diamine in Step 1. Intermediate 6 from Example 1 was used in place of Intermediate 5. MS m/z: 580.4 (M+H$^+$).

Example 163: Synthesis of I-162

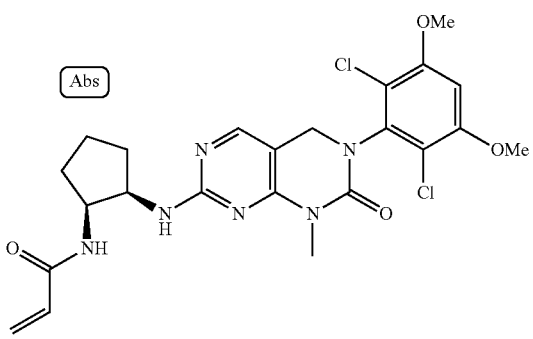 [SMILES: C=CC(=O)N[C@H]1CCC[C@H]1Nc1ncc2c(n1)N(C)C(=O)N(c1c(Cl)c(OC)cc(OC)c1Cl)C2]

Compound I-162 was prepared as described in Example 116 using tert-butyl ((1S,2R)-2-aminocyclopentyl)carbamate in place of tert-butyl ((1S, 2R)-2-aminocyclohexyl)carbamate in Step 2, and starting with Intermediate 6 from Example 1. MS m/z: 521.1 (M+H⁺).

Example 164: Synthesis of I-163

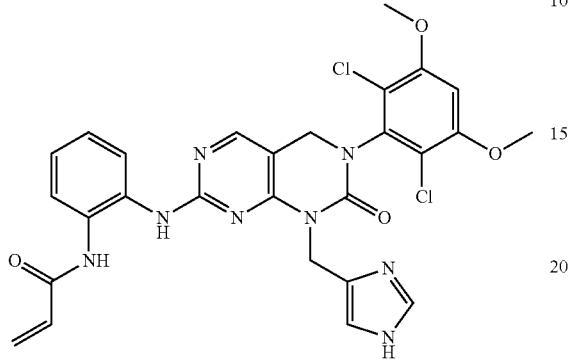

Compound I-163 was prepared as described in Example 7. The starting material was prepared as described in Example 1 using tert-butyl 5-(aminomethyl)-1H-imidazole-1-carboxylate in place of methylamine in Step 5. A final BOC deprotection step was performed as described in Example 3, Step 5. MS m/z: 595.4 (M+H⁺).

Example 165: Synthesis of I-164

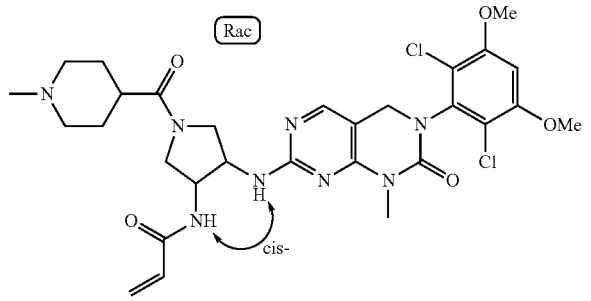 [SMILES: C=CC(=O)NC1CN(C(=O)C2CCN(C)CC2)CC1Nc1ncc2c(n1)N(C)C(=O)N(c1c(Cl)c(OC)cc(OC)c1Cl)C2]

Compound I-164 was prepared as described in Example 7. ((cis)-3,4-diaminopyrrolidin-1-yl)(1-methylpiperidin-4-yl)methanone was used in place of benzene-1,2-diamine in Step 1. Intermediate 6 from Example 1 was used in place of Intermediate 5. MS m/z: 647.5 (M+H⁺).

Example 166: Synthesis of I-165

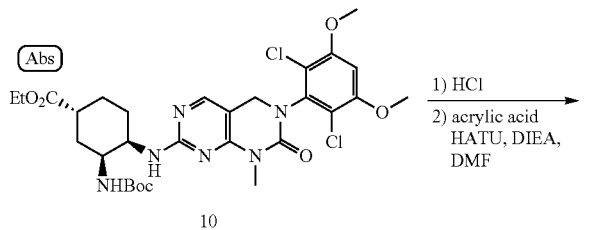

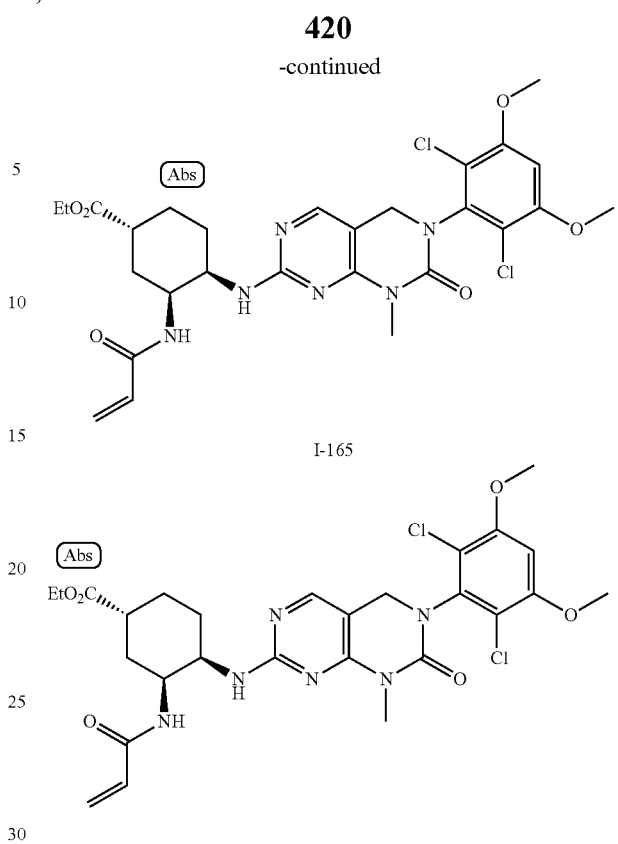

I-165

To a solution of Intermediate 10 from Example 178 (86.0 mg, 0.13 mmoL) in 2 mL DCM was added 200 uL of HCl (4 N in dioxane) and the reaction was stirred at rt for 30 min. The solvent was removed under reduced pressure to obtain the amine hydrochloride salt. MS m/z: 553.2 (M+H⁺). To a solution of salt and acrylic acid (10 uL, 0.13 mmoL) in 500 uL of DMF was cooled in ice-water/methanol bath. To the mixture was added DIEA (130 uL, 0.74 mmol) and then HATU (55 mg, 0.13 mmol). The reaction was stirred at rt for 15 mins and directly purified by flash chromatography (eluting with a gradient of 0-70% acetone in heptane), which gave 36 mg of the title compound. MS m/z: 607.1 (M+H⁺).

Example 167: Synthesis of I-166 (Racemic)

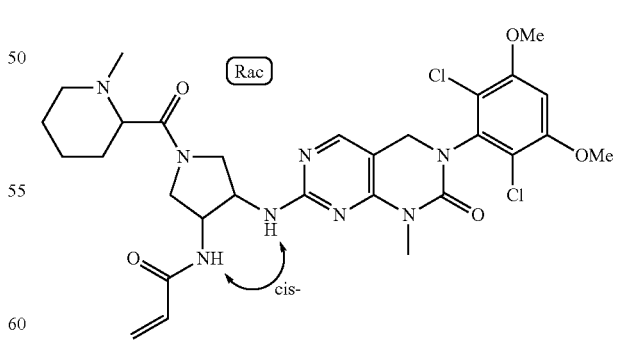

Compound I-166 was prepared as described in Example 7. ((cis)-3,4-diaminopyrrolidin-1-yl)(1-methylpiperidin-2-yl)methanone was used in place of benzene-1,2-diamine in Step 1. Intermediate 6 from Example 1 was used in place of Intermediate 5. MS m/z: 647.5 (M+H⁺).

Example 168: Synthesis of I-167 (Racemic)

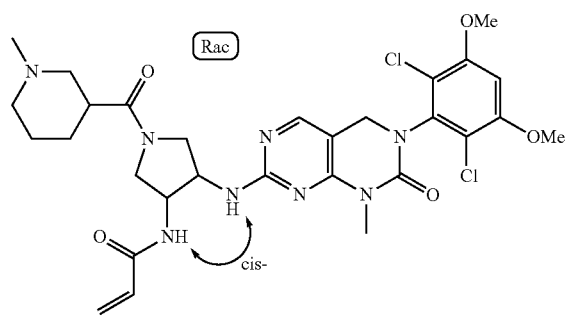 [SMILES: C=CC(=O)NC1CN(C(=O)C2CCCN(C)C2)CC1Nc1ncc2c(n1)N(C)C(=O)N(c1c(Cl)c(OC)cc(OC)c1Cl)C2]

Compound I-167 was prepared as described in Example 7. ((cis)-3,4-diaminopyrrolidin-1-yl)(1-methylpiperidin-3-yl)methanone was used in place of benzene-1,2-diamine in Step 1. Intermediate 6 from Example 1 was used in place of Intermediate 5. MS m/z: 647.5 (M+H$^+$).

Example 169: Synthesis of I-168

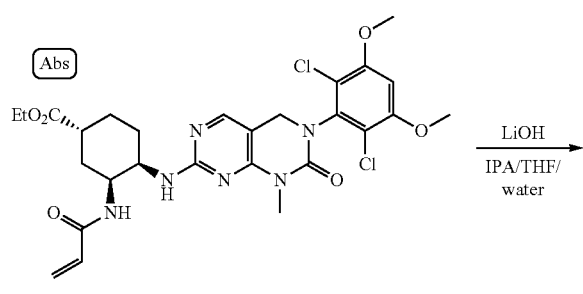

I-165

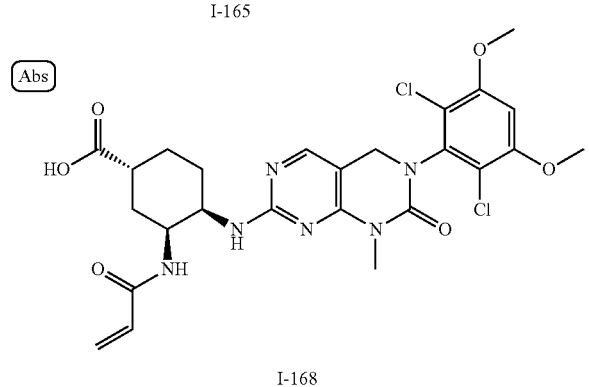

I-168

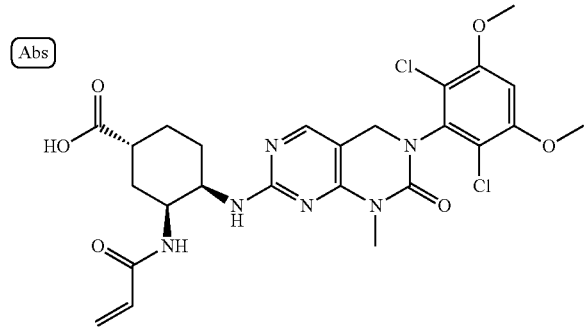

To a solution of I-165, from Example 166, (34.0 mg, 0.06 mmoL) in 500 ul each of IPA, THF, and water, was added LiOH mono-hydrate (7.50 mg, 0.18 mmoL), and the reaction mixture was allowed to stir at ambient temperature for 2 h. The solvent was removed under reduced pressure and the resultant residue treated with 2 drops of 3 N HCl to cause precipitation. The precipitate was filtered and dried to provide 14.0 mg of the title compound. MS m/z: 579.2 (M+H$^+$).

Example 170: Synthesis of I-169

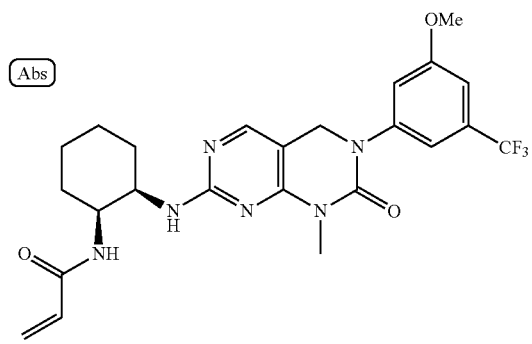 [SMILES: C=CC(=O)N[C@H]1CCCC[C@H]1Nc1ncc2c(n1)N(C)C(=O)N(c1cc(OC)cc(C(F)(F)F)c1)C2]

Compound I-169 was prepared as described in Example 116. The starting material was prepared as described in Example 1 using 3-methoxy-5-(trifluoromethyl)aniline in place of 3,5-dimethoxyaniline in Step 4 and skipping Step 7. MS m/z: 505.5 (M+H$^+$).

Example 171: Synthesis of I-170 (Racemic)

Compound I-170 was prepared as described in Example 7. (cis)-1-(pyridin-2-yl)pyrrolidine-3,4-diamine was used in place of benzene-1,2-diamine in Step 1. Intermediate 6 from Example 1 was used in place of Intermediate 5. MS m/z: 559.4 (M+H$^+$).

Example 172: Synthesis of I-171

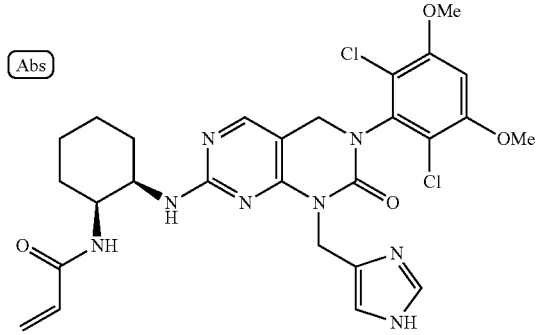 [SMILES: C=CC(=O)N[C@H]1CCCC[C@H]1Nc1ncc2c(n1)N(Cc1c[nH]cn1)C(=O)N(c1c(Cl)c(OC)cc(OC)c1Cl)C2]

Compound I-171 was prepared as described in Example 116. The starting material was prepared as described in Example 1 using tert-butyl 5-(aminomethyl)-1H-imidazole-1-carboxylate in place of methylamine in Step 5. A final BOC deprotection step was performed as described in Example 3, Step 5. MS m/z: 601.4 (M+H⁺).

Example 173: Synthesis of I-172 (Racemic)

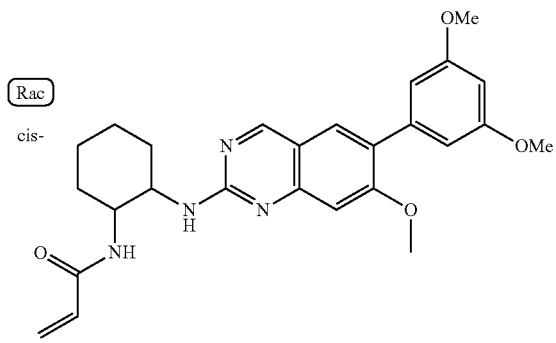 [SMILES: C=CC(=O)NC1CCCCC1Nc1ncc2cc(-c3cc(OC)cc(OC)c3)c(OC)cc2n1]

Compound I-172 was prepared as described in Example 174 skipping Step 4. MS m/z: 463.2 (M+H⁺).

Example 174: Synthesis of I-173

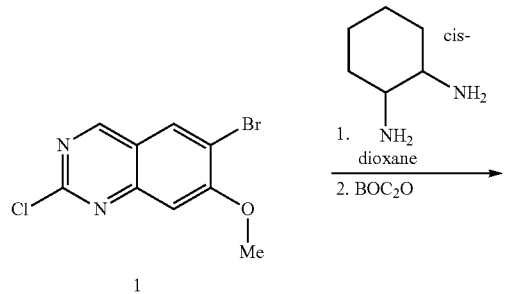

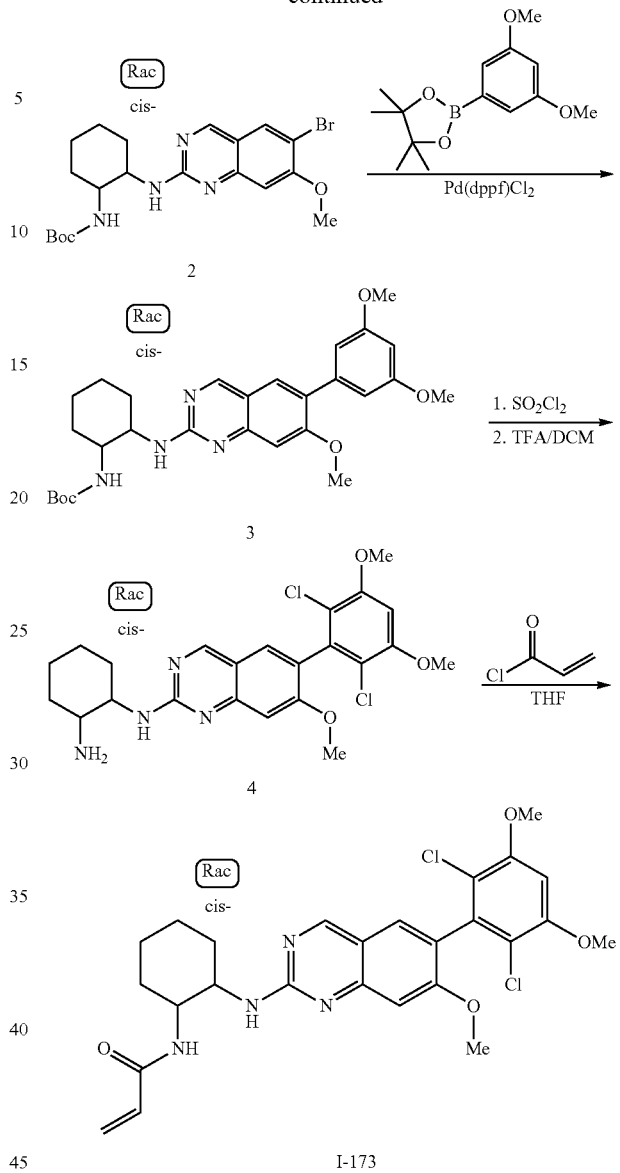

Steps 1-2: Intermediate 2

A mixture of Intermediate 1 (WO 2009153313) (102 mg, 0.37 mmol) and cis-1,2-diaminocylcohexane (0.20 mL, 1.67 mmol) in dioxane (2.0 mL) was heated at 110° C. for 16 h. The reaction mixture was allowed to cool to ambient temperature, concentrated to dryness, dissolved in DCM (20 mL), and treated with (Boc)₂O (1.20 g) at ambient temperature, then allowed to stir overnight. The crude reaction was then concentrated and subjected to flash chromatography on silica gel (0-100% EtOAc/hexanes) to afford 50 mg for the title compound. MS: 452.2 [M+H]⁺

Step 3: Intermediate 3

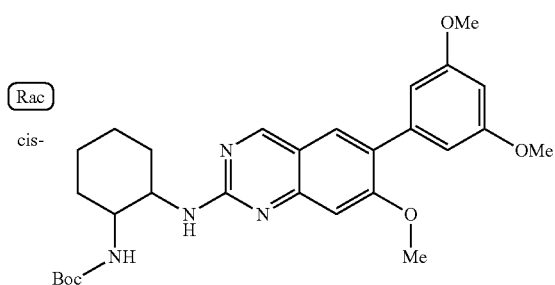 [SMILES: COc1cc(OC)cc(-c2cc3cnc(NC4CCCCC4NC(=O)OC(C)(C)C)nc3cc2OC)c1]

Intermediate 2 (50.0 mg, 0.110 mmol) and 2-(3,5-dimethoxyphenyl)-4,4,5,5-tetramethyl-1,3,2-dioxaborolane (60.0 mg, 0.22 mmol), and Pd(dppf)Cl₂ (10.0 mg, 0.014 mmol) were combined in dioxane (3 mL) and 2.0 M aqueous Na₂CO₃ (0.7 mL). The mixture was heated at 120° C. for 30 min in a microwave reactor. The reaction mixture was diluted with EtOAc, washed with saturated aqueous NaHCO₃, brine, dried over Na₂SO₄, filtered and concentrated in vacuo. The resultant residue was purified by flash chromatography on silica gel to provide 48 mg of the title compound. MS m/z: 509.4 (M+H⁺).

Steps 4-5: Intermediate 4

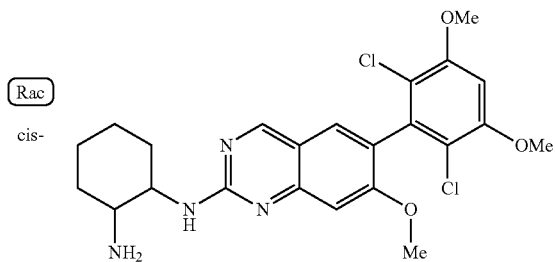 [SMILES: COc1cc2nc(NC3CCCCC3N)ncc2cc1-c1c(Cl)c(OC)cc(OC)c1Cl]

Intermediate 3 (40.0 mg, 0.079 mmol) was dissolved in DCM (2 mL) and MeCN (2 mL). At 0° C., SO₂Cl₂ (13 µL, 0.16 mmol) was added and the reaction was kept at 0° C. for 2.5 hr. After removing solvents, the crude mixture was treated with 20% TFA/DCM (4.0 mL) at room temperature for 30 min. After evaporating all volatiles, the residue was taken up in DCM and treated with silica supported carbonate to free the basic amine. After filtration and concentration, quantitative amount of product was obtained and the crude was used as-is in the next step. MS m/z: 477.4 (M+H⁺).

Step 6: I-173

Intermediate 4 (40 mg, 0.088 mmol) was dissolved in THF (3.0 mL) and cooled to −10° C. Acryloyl chloride (7.2 µL, 0.088 mmol) was added and the reaction mixture was allowed to stir at −10° C. for 10 min. The reaction mixture was concentrated and the resultant residue dissolved in DMSO and purified by prep-HPLC. MS m/z: 531.2 (M+H⁺). ¹H NMR (400 MHz, CD3OD): 9.25 (1H, s), 8.15 (1H, s), 7.77 (1H, s), 6.91 (1H, s), 6.36 (1H, dd), 6.16 (1H, dd), 5.62 (1H, dd), 4.56 (2H, m), 3.97 (6H, s), 3.95 (3H, s), 1.86 (6H, m), 1.60 (2H, m).

Example 175: Synthesis of I-174 (Racemic)

Compound I-174 was prepared as described in Example 7. tert-butyl ((trans)-4-amino-6-oxopiperidin-3-yl)carbamate was used in place of benzene-1,2-diamine in Step 1. Intermediate 6 from Example 1 was used in place of Intermediate 5. A final BOC deprotection step was performed as described in Example 3, Step 5. MS m/z: 550.4 (M+H⁺).

Example 176: Synthesis of I-175

The title compound was prepared as outlined in Example 102 where the chloro pyrimidine cyclic urea intermediate (equivalent of Intermediate 7 in Example 102) was prepared as described in Example 102 using 2-chloro-6-fluoro-3,5-dimethoxyaniline in place of Intermediate 4, methylamine in place of cyclopropylmethanamine in Step 5, and tert-butyl ((1S,2R)-2-aminocyclohexyl)carbamate in place of 1,2-benzenediamine in Step 7. MS m/z: 519.4 (M+H)+. 1H NMR (400 MHz, Chloroform-d) δ 7.81 (s, 1H), 6.63 (d, 1H), 6.23 (ddd, 1H), 6.03 (ddd, 1H), 5.59 (ddd, 1H), 4.52 (d, 2H), 4.41 (s, 1H), 4.17 (d, 1H), 3.92 (d, 6H), 3.38 (s, 3H), 2.00-1.00 (m, 9H).

Example 177: Synthesis of I-176

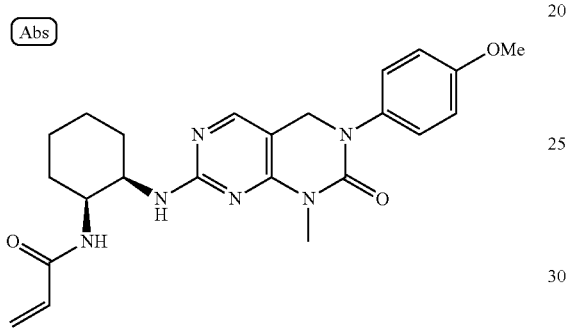

Compound I-176 was prepared as described in Example 116. The starting material was prepared as described in Example 1 using 4-methoxyaniline in place of 3,5-dimethoxyaniline in Step 4 and skipping Step 7. MS m/z: 437.4 (M+H+).

Example 178: Synthesis of I-177

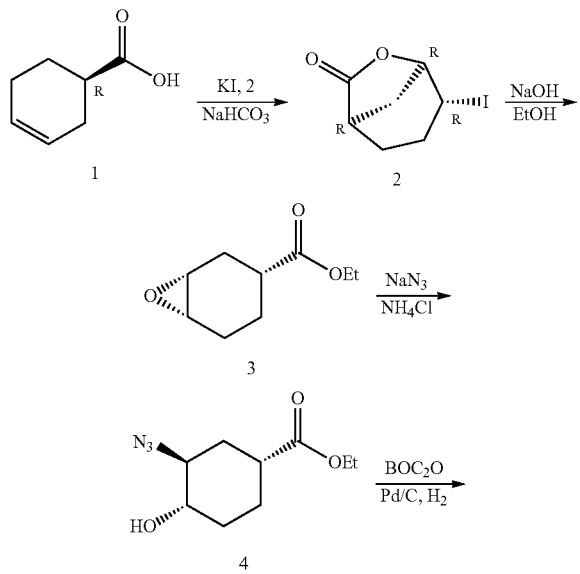

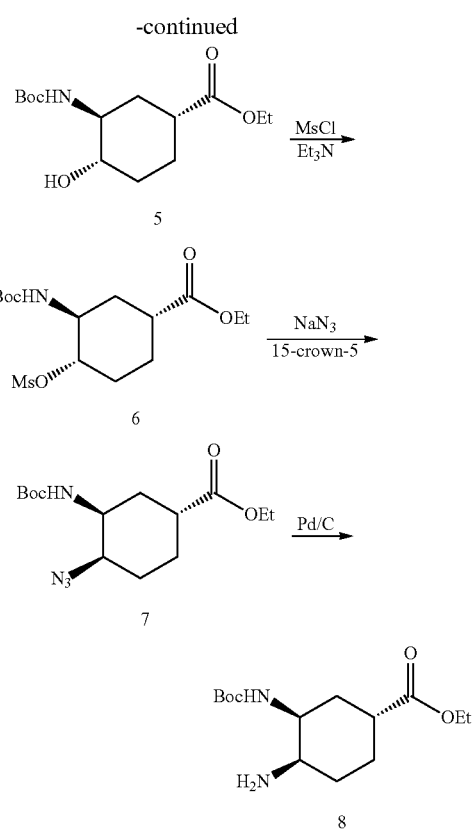

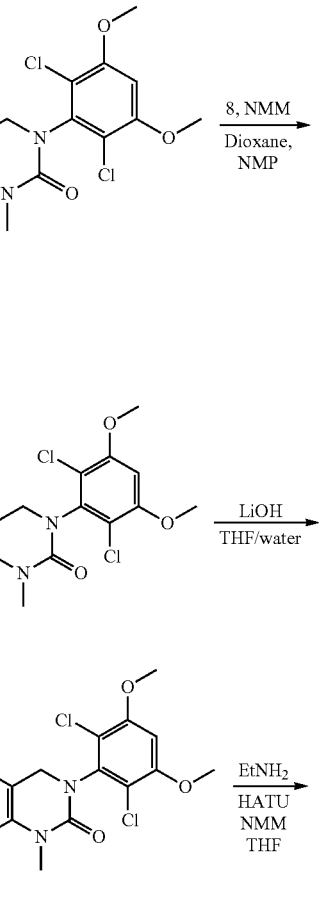

429
-continued

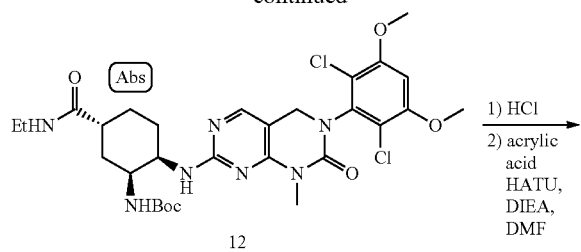

12

1) HCl
2) acrylic acid HATU, DIEA, DMF

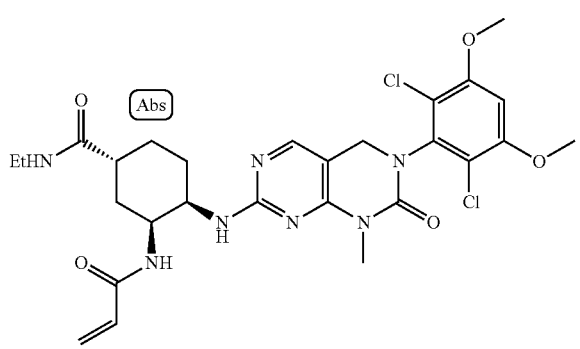

I-177

Step 1: Intermediate 10

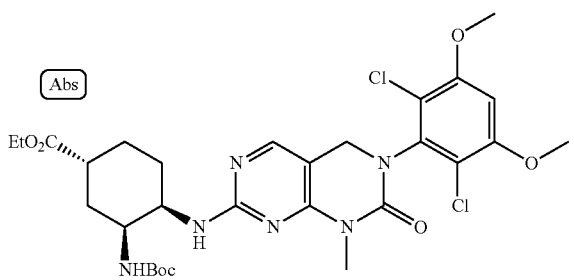 [SMILES: CCOC(=O)[C@@H]1CC[C@@H](Nc2ncc3c(n2)N(C)C(=O)N(c2c(Cl)c(OC)cc(OC)c2Cl)C3)[C@@H](NC(=O)OC(C)(C)C)C1]

The title compound was prepared according to the literature and as outlined in the scheme above. A solution of Intermediate 8 (US 2005/0020645 A1; *Bioorganic & Medicinal Chemistry*, 2009, 17, 1193-1206) (45.0 mg, 0.16 mmoL), Intermediate 9, prepared in a manner as described in Example 116, using Intermediate 6 from Example 1, (45 mg, 0.08 mmoL), NMM (26 uL, 0.24 mmoL) in 1 mL of dioxane, and 100 uL of NMP, was heated to 100° C. for 16 h. The solvent was removed under reduced pressure and the resultant residue was purified by flash chromatography on silica gel (eluting with a gradient of 0-100% EtOAc in heptane), which gave 40 mg of the title compound. MS m/z: 653.2 (M+H$^+$).

430

Step 2: Intermediate 11

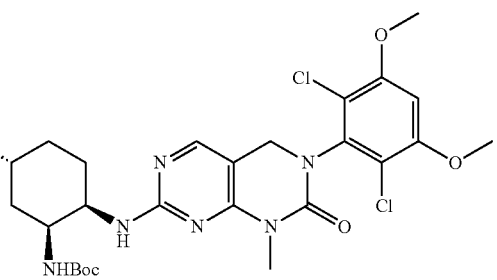

To a solution of the Intermediate 10 (100 mg, 0.15 mmoL) in 1 mL of THF and 500 uL of water was added LiOH mono-hydrate (20.0 mg, 0.46 mmoL), and the reaction was stirred at 60° C. for 2 h. The solvent was removed under reduced pressure and the resultant residue treated with 5 drops of 3 N HCl to cause precipitation. The precipitate was filtered and dried which gave 50 mg of the title compound. MS m/z: 625.1 (M+H$^+$).

Step 3: Intermediate 12

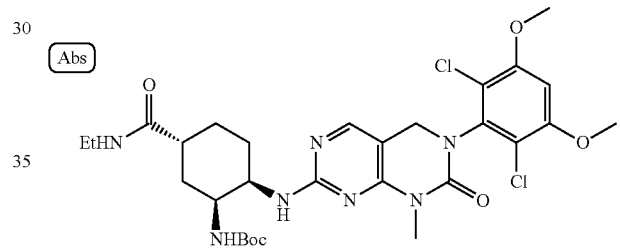

To a solution of the Intermediate 11 (50 mg, 0.08 mmoL) in 500 uL of THF was added HATU (30.0 mg, 0.08 mmoL), NMM (26 uL, 0.24 mmoL) and excess ethylamine (2 M in THF, 5 mL). The reaction mixture was allowed to stir at ambient temperature for 5 days. The solvent was removed under reduced pressure and the resultant residue purified by flash chromatography on silica gel (eluting with a gradient of 0-100% acetone in heptane) which gave 25.0 mg of the title compound. MS m/z: 652.2 (M+H$^+$).

Steps 4 & 5: I-177

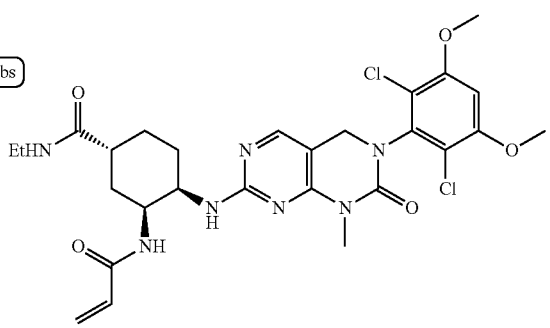

To a solution of the Intermediate 12 (25 mg, 0.04 mmoL) in 5 mL of DCM was added 1 mL of HCl (4 N in dioxane) and the reaction was allowed to stir at ambient temperature for 30 min. The solvent was removed under reduced pressure to obtain the amine hydrochloride salt of Intermediate 12, MS m/z: 552.2 (M+H$^+$), which was taken up in 500 uL of DMF and acrylic acid (2.4 ul, 0.04 mmoL) was added. The reaction mixture was cooled in ice-water/methanol bath and DIPEA was added (40 uL, 0.21 mmoL) followed by HATU (14.0 mg, 0.04 mmol). The reaction mixture was allowed to stir at ambient temperature for 15 min then purified by preparative HPLC (eluting with a gradient of 10-90% water containing 0.1% TFA and MeCN), which gave 7.0 mg of the title compound. MS m/z: 606.2 (M+H$^+$).

Example 180: Synthesis of I-179

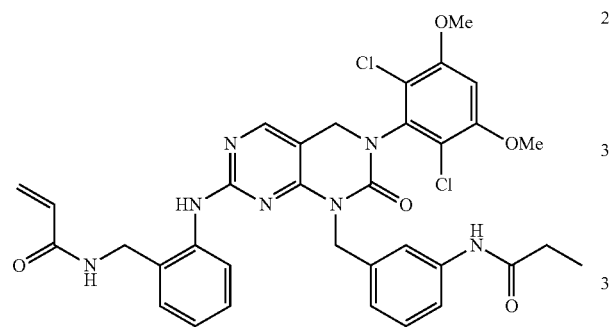

The title compound was prepared as described in Example 3. Tert-butyl 3-aminobenzylcarbamate was used in place of benzene-1,2-diamine in Step 1, and the Boc protection of Step 2 was skipped. MS m/z: 690.2 (M+H$^+$).

Example 181: Synthesis of I-180

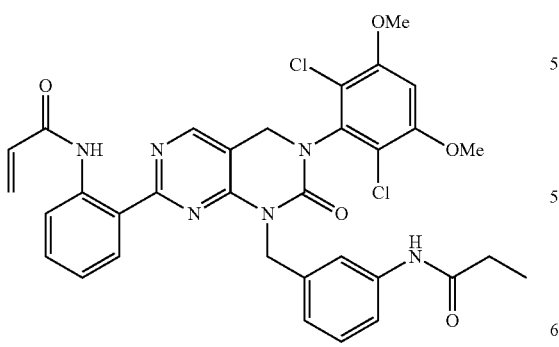

The title compound was prepared as described in Example 3. Tert-butyl 3-aminobenzylcarbamate was used in place of benzene-1,2-diamine in Step 1. A BOC deprotection step was performed prior to Step 2 (as described in Example 3, Step 5). MS m/z: 690.1 (M+H$^+$).

Example 182: Synthesis of I-181

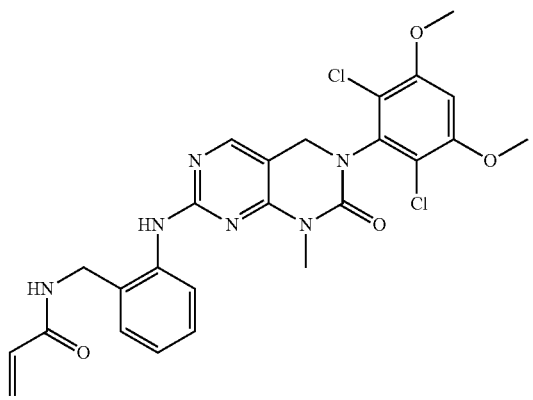 [SMILES: C=CC(=O)NCc1ccccc1Nc1ncc2c(n1)N(C)C(=O)N(c1c(Cl)c(OC)cc(OC)c1Cl)C2]

The title compound was prepared as described in Example 7. Tert-butyl 3-aminobenzylcarbamate was used in place of benzene-1,2-diamine in Step 1. Intermediate 6 from Example 1 was used in place of Intermediate 5. A BOC deprotection step was performed prior to Step 2 (Boc deprotection is described in Example 3, Step 5). MS m/z: 543.3 (M+H$^+$).

Example 183: Synthesis of I-182 (Racemic)

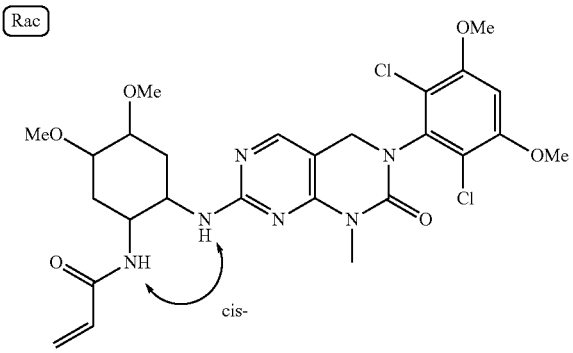 [SMILES: C=CC(=O)NC1CC(OC)C(OC)CC1Nc1ncc2c(n1)N(C)C(=O)N(c1c(Cl)c(OC)cc(OC)c1Cl)C2]

The title compound was prepared as described in Example 7. 4,5-dimethoxycyclohexane-cis-1,2-diamine was used in place of benzene-1,2-diamine in Step 1. Intermediate 6 from Example 1 was used in place of Intermediate 5. MS m/z: 595.5 (M+H$^+$).

Example 184: Synthesis of I-183 (Racemic)

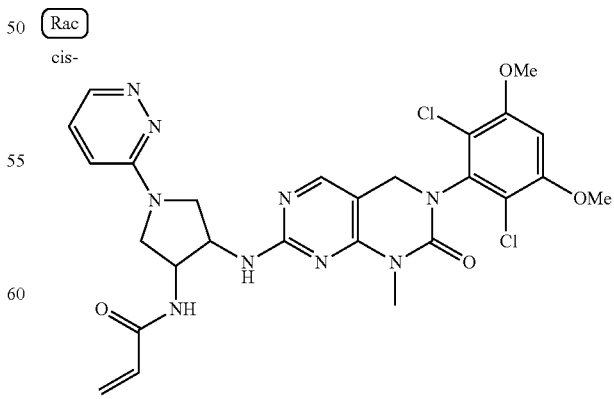

The title compound was prepared as described in Example 7. Cis-1-(pyridazin-3-yl)pyrrolidine-3,4-diamine was used Example 185: Synthesis of I-184 (Racemic)

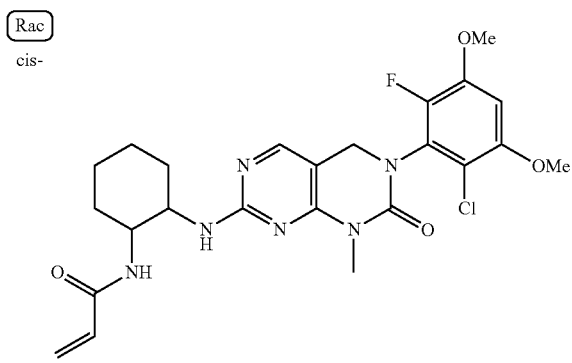 [SMILES: C=CC(=O)NC1CCCCC1Nc1ncc2c(n1)N(C)C(=O)N(c1c(F)c(OC)cc(OC)c1Cl)C2]

The title compound was prepared as described in Example 116. The starting material was prepared as described in Example 1 using 2-chloro-6-fluoro-3,5-dimethoxyaniline in place of 3,5-dimethoxyaniline in Step 4 and skipping Step 7. MS m/z: 519.4 (M+H⁺).

Example 186: Chiral Separation of I-185 and I-186

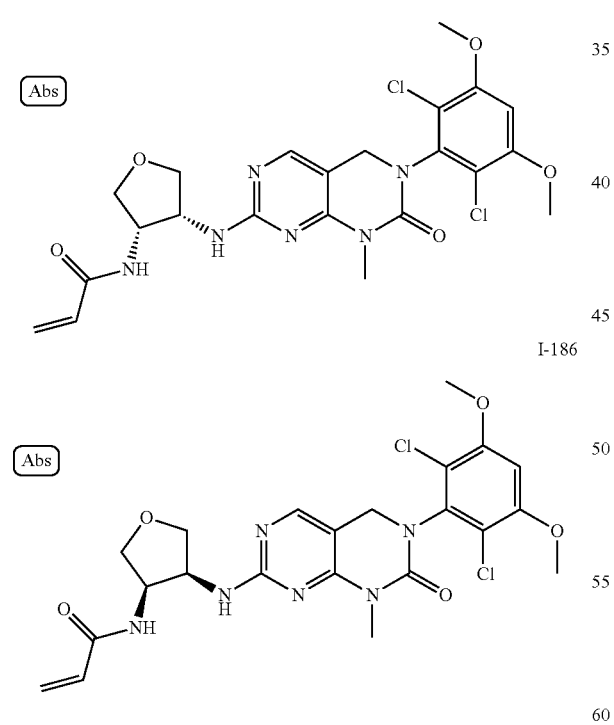

Chiral separation of I-126, (Chiralpak IA, 250 mm×4.6 mm ID, 5 micron, 0.4 mL/min, 30% heptane in EtOH) provided two enantiomers with Rt=23 and 31 min which were assigned absolute configurations of I-186 and I-185, respectively (>98% ee). Absolute configurations were assigned by analogy to I-94 and I-95 based on enzymatic and cellular potency.

I-185: MS m/z: 523.5 (M+H⁺), [α]$_D$=−20 (C=1.00 mg/mL, CH$_2$Cl$_2$, 23° C.), ¹H NMR (400 MHz, CDCl$_3$) δ: 3.39 (s, 3H), 3.71-3.81 (m, 2H), 3.94 (s, 6H), 4.17-4.21 (m, 2H), 4.52 (s, 2H), 4.73-4.79 (m, 2H), 5.62-5.65 (m, 2H), 6.02-6.07 (m, 1H), 6.26 (d, 1H), 6.32 (br, 1H), 6.60 (s, 1H), 7.84 (s, 1H).

I-186: MS m/z: 523.5 (M+H⁺), [α]$_D$=+38 (C=1.00 mg/mL, CH$_2$Cl$_2$, 23° C.), ¹H NMR (400 MHz, CDCl$_3$) δ: 3.39 (s, 3H), 3.71-3.81 (m, 2H), 3.94 (s, 6H), 4.17-4.21 (m, 2H), 4.52 (s, 2H), 4.73-4.79 (m, 2H), 5.62-5.65 (m, 2H), 6.02-6.07 (m, 1H), 6.26 (d, 1H), 6.32 (br, 1H), 6.60 (s, 1H), 7.84 (s, 1H).

The absolute configuration of I-186 was confirmed through enantioselective synthesis according to the below scheme. N-((3R,4S)-4-aminotetrahydrofuran-3-yl)acrylamide was prepared according to literature (*JACS*, 1995, 117, 5897-5898) and as described in Example 226, and used in place of cis-tetrahydrofuran-3,4-diamine in Example 127.

Steroechemical Proof and Enantioselective Synthesis of I-186

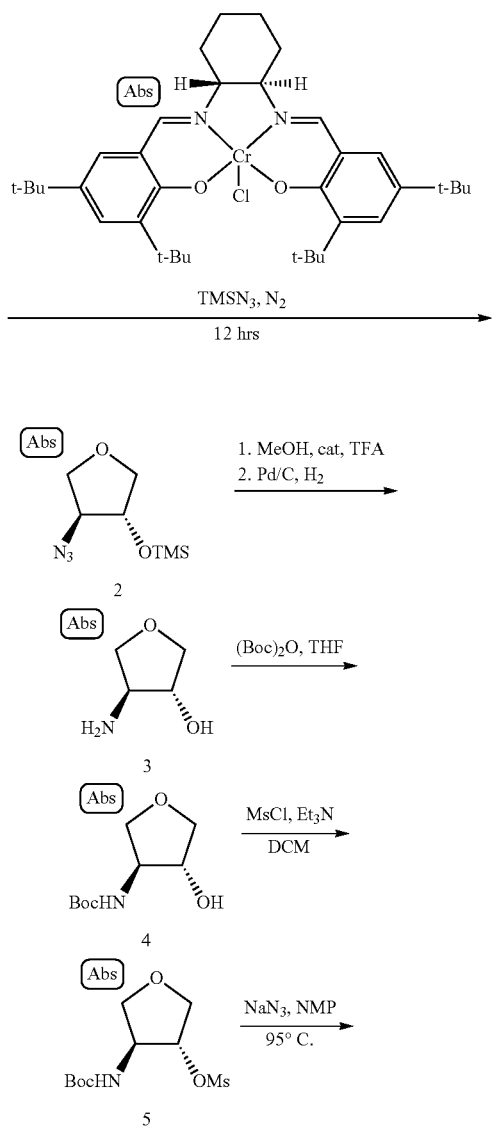

-continued

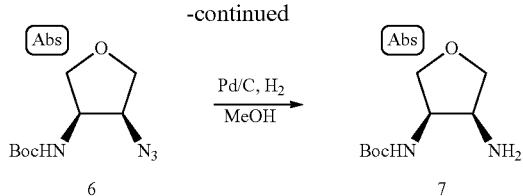

Intermediate 7 (scheme above) was synthesized according to the procedure described in Example 226. Intermediate 7 was used to make I-186, by coupling with Intermediate 6 from Example 127 followed by Boc deprotection and acrylamide formation using the procedure described in Example 127. I-186: MS m/z: 523.5 (M+H$^+$), $^1$H NMR (400 MHz, CDCl$_3$) δ: 3.39 (s, 3H), 3.71-3.81 (m, 2H), 3.94 (s, 6H), 4.17-4.21 (m, 2H), 4.52 (s, 2H), 4.73-4.79 (m, 2H), 5.65 (dd, 1H), 6.02-6.07 (m, 1H), 6.26 (d, 1H), 6.32 (br, 1H), 6.60 (s, 1H), 7.84 (s, 1H).

Example 187: Synthesis

Using the techniques described herein, the following compounds can be prepared. For compounds prepared as racemic or diastereomeric mixtures, the single isomers can be prepared in optically pure form by either employing chiral starting materials or performing chiral chromatography.

Compound I-187

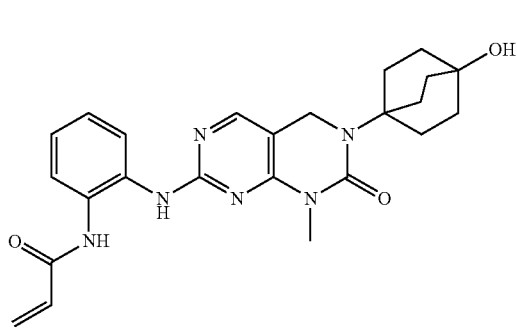 [SMILES: C=CC(=O)Nc1ccccc1Nc1ncc2c(n1)N(C)C(=O)N(C13CCC(O)(CC1)CC3)C2]

The title compound is prepared as described in Example 7. The starting material is prepared as described in Example 1 using 4-aminobicyclo[2.2.2]octan-1-ol in place of 3,5-dimethoxyaniline in Step 4 and skipping Step 7.

Compound I-188

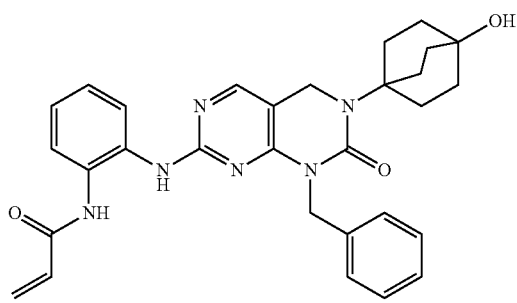 [SMILES: C=CC(=O)Nc1ccccc1Nc1ncc2c(n1)N(Cc1ccccc1)C(=O)N(C13CCC(O)(CC1)CC3)C2]

The title compound is prepared as described in Example 7. The starting material is prepared as described in Example 1 using 4-aminobicyclo[2.2.2]octan-1-ol in place of 3,5-dimethoxyaniline in Step 4, benzylamine in place of methylamine in Step 5, and skipping Step 7.

Compound I-189

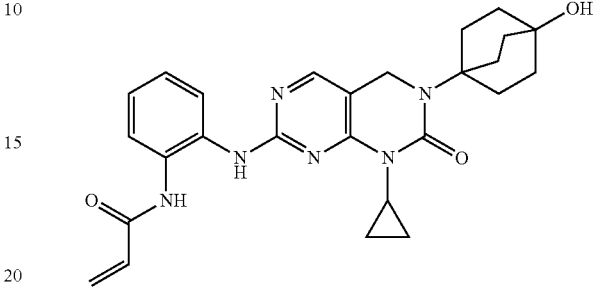

The title compound is prepared as described in Example 7. The starting material is prepared as described in Example 1 using 4-aminobicyclo[2.2.2]octan-1-ol in place of 3,5-dimethoxyaniline in Step 4, cyclopropanamine in place of methylamine in Step 5, and skipping Step 7.

Compound I-190

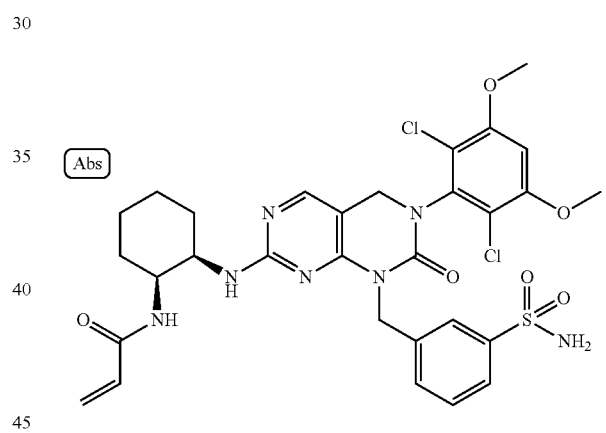

The title compound is prepared as described in Example 116. The starting material is prepared as described in Example 1 using 3-(aminomethyl)benzenesulfonamide in place of methylamine in Step 5.

Compound I-191

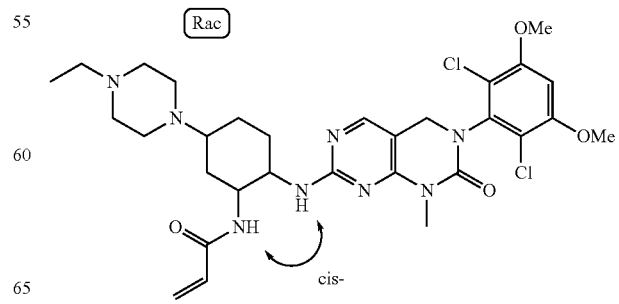

437

The title compound is prepared as described in Example 7 using tert-butyl tert-butyl (2-amino-5-(4-ethylpiperazin-1-yl)cyclohexyl)carbamate in place of benzene-1,2-diamine in Step 1, Intermediate 6 from Example 1 in place of Intermediate 5, and adding a final BOC deprotection step as described in Example 3, Step 5.

Compound I-193

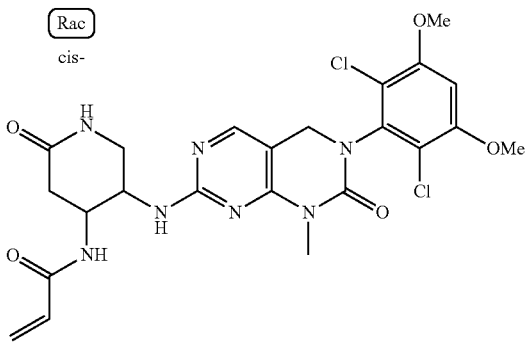 [SMILES: C=CC(=O)NC1CC(=O)NCC1Nc1ncc2c(n1)N(C)C(=O)N(c1c(Cl)c(OC)cc(OC)c1Cl)C2]

The title compound is prepared as described in Example 7 using tert-butyl ((cis)-5-amino-2-oxopiperidin-4-yl)carbamate in place of benzene-1,2-diamine in Step 1, Intermediate 6 from Example 1 in place of Intermediate 5, and adding a final BOC deprotection step as described in Example 3, Step 5.

Compound I-194

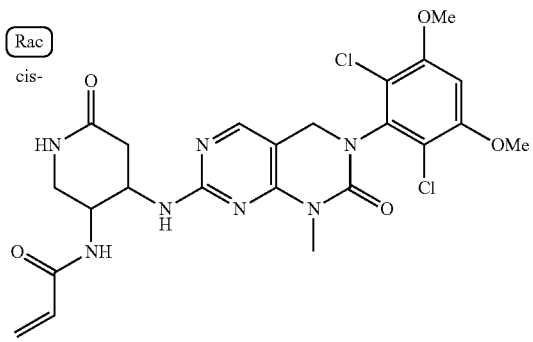 [SMILES: C=CC(=O)NC1CNC(=O)CC1Nc1ncc2c(n1)N(C)C(=O)N(c1c(Cl)c(OC)cc(OC)c1Cl)C2]

The title compound is prepared as described in Example 7 using tert-butyl ((cis)-4-amino-6-oxopiperidin-3-yl)carbamate in place of benzene-1,2-diamine in Step 1, Intermediate 6 from Example 1 in place of Intermediate 5, and adding a final BOC deprotection step as described in Example 3, Step 5.

438

Compound I-195

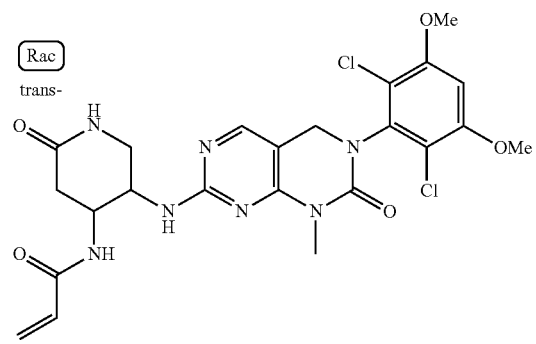 [SMILES: C=CC(=O)NC1CC(=O)NCC1Nc1ncc2c(n1)N(C)C(=O)N(c1c(Cl)c(OC)cc(OC)c1Cl)C2]

The title compound is prepared as described in Example 7 using tert-butyl ((trans)-5-amino-2-oxopiperidin-4-yl)carbamate in place of benzene-1,2-diamine in Step 1, Intermediate 6 from Example 1 in place of Intermediate 5, and adding a final BOC deprotection step as described in Example 3, Step 5.

Example 188: Synthesis of I-196

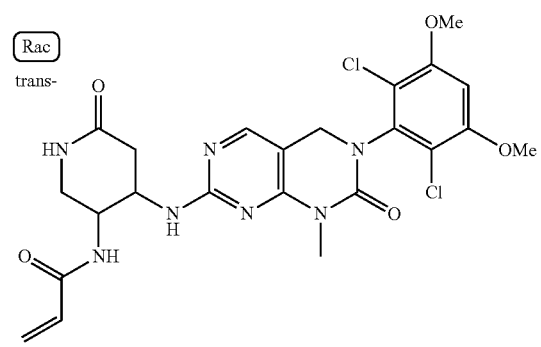 [SMILES: C=CC(=O)NC1CNC(=O)CC1Nc1ncc2c(n1)N(C)C(=O)N(c1c(Cl)c(OC)cc(OC)c1Cl)C2]

The title compound was prepared as described in Example 7 using tert-butyl ((trans)-4-amino-6-oxopiperidin-3-yl)carbamate in place of benzene-1,2-diamine in Step 1, Intermediate 6 from Example 1 in place of Intermediate 5, and adding a final BOC deprotection step as described in Example 3, Step 5. MS m/z: 550.4 (M+H$^+$).

Example 189: Synthesis

Using the techniques described herein, the following compounds can be prepared. For compounds prepared as racemic or diastereomeric mixtures, the single isomers can be prepared in optically pure form by either employing chiral starting materials or performing chiral chromatography.

Compound I-197

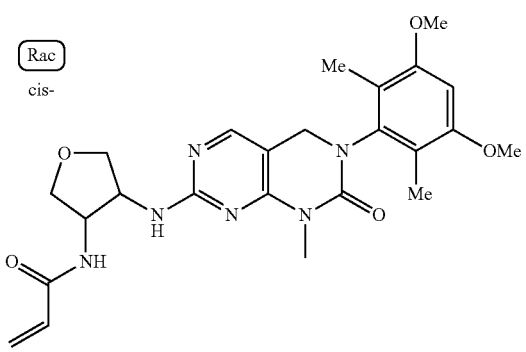 [SMILES: C=CC(=O)NC1COCC1Nc1ncc2c(n1)N(C)C(=O)N(c1c(C)c(OC)cc(OC)c1C)C2]

The title compound is prepared as described in Example 127. The chloro cyclic urea derivative is prepared as described in Example 1 using 3,5-dimethoxy-2,6-dimethyl-aniline in place of 3,5-dimethoxyaniline in Step 4, and skipping Step 7.

Compound I-198

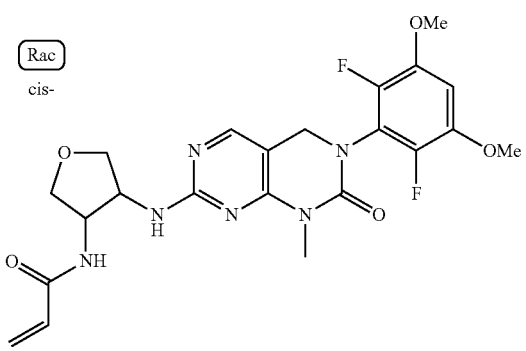 [SMILES: C=CC(=O)NC1COCC1Nc1ncc2c(n1)N(C)C(=O)N(c1c(F)c(OC)cc(OC)c1F)C2]

The title compound was prepared as described in Example 127. The chloro cyclic urea derivative was prepared as described in Example 1 using 2,6-difluoro-3,5-dimethoxyaniline in place of 3,5-dimethoxyaniline in Step 4 and skipping Step 7. MS m/z: 491.5 (M+H⁺).

Compound I-199

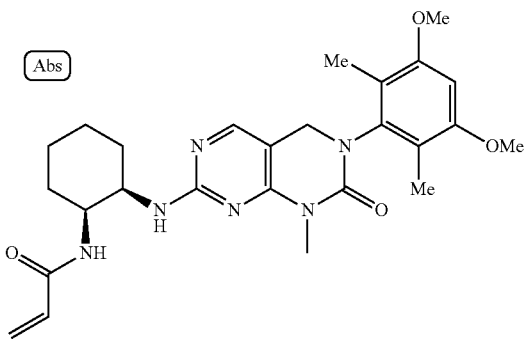 [SMILES: C=CC(=O)N[C@H]1CCCC[C@H]1Nc1ncc2c(n1)N(C)C(=O)N(c1c(C)c(OC)cc(OC)c1C)C2]

The title compound is prepared as described in Example 116. The starting material is prepared as described in Example 1 using 2,6-dimethyl-3,5-dimethoxyaniline in place of 3,5-dimethoxyaniline in Step 4 and skipping Step 7.

Compound I-200

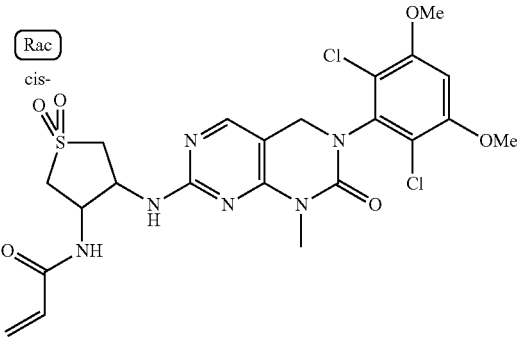 [SMILES: C=CC(=O)NC1CS(=O)(=O)CC1Nc1ncc2c(n1)N(C)C(=O)N(c1c(Cl)c(OC)cc(OC)c1Cl)C2]

The title compound was prepared as described in Example 127 using 2,5-dihydrothiophene in place of Intermediate 2 and oxidation of sulfur was performed as described in the literature (*JOC*, 2010, 75, 4629-4631). MS m/z: 571.4 (M+H⁺).

Compound I-201

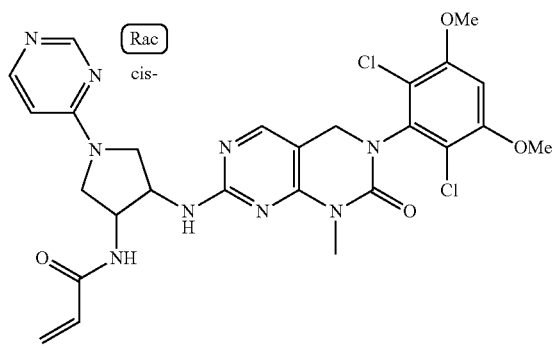 [SMILES: C=CC(=O)NC1CN(c2ccncn2)CC1Nc1ncc2c(n1)N(C)C(=O)N(c1c(Cl)c(OC)cc(OC)c1Cl)C2]

The title compound was prepared as described in Example 7 using (cis)-1-(pyrimidin-4-yl)pyrrolidine-3,4-diamine in place of benzene-1,2-diamine in Step 1, and Intermediate 6 from Example 1 in place of Intermediate 5. MS m/z: 600.5 (M+H⁺).

Example 190: Synthesis of I-202

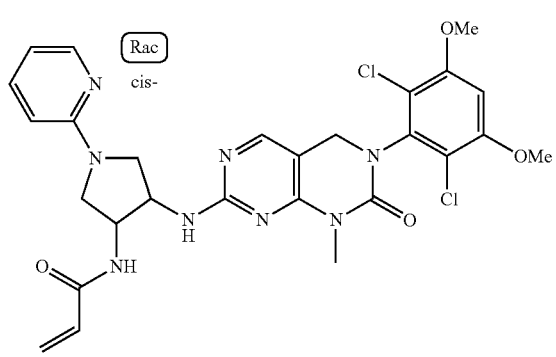 [SMILES: C=CC(=O)NC1CN(c2ccccn2)CC1Nc1ncc2c(n1)N(C)C(=O)N(c1c(Cl)c(OC)cc(OC)c1Cl)C2]

The title compound was prepared as described in Example 7 using (cis)-1-(pyridin-2-yl)pyrrolidine-3,4-diamine in place of benzene-1,2-diamine in Step 1, and Intermediate 6 from Example 1 in place of Intermediate 5. MS m/z: 599.4 (M+H⁺).

Example 191: Synthesis

Using the techniques described herein, the following compounds can be prepared. For compounds prepared as racemic or diastereomeric mixtures, the single isomers can be prepared in optically pure form by either employing chiral starting materials or performing chiral chromatography.

Compound I-203

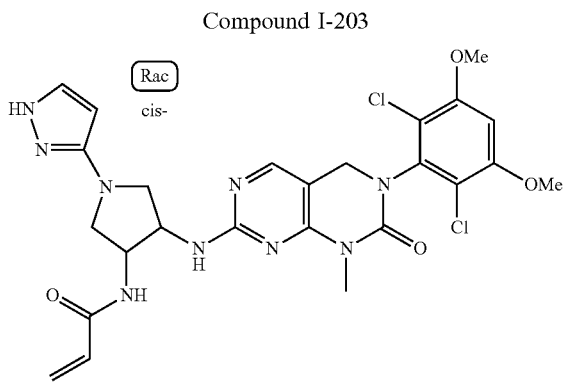

The title compound is prepared as described in Example 7 using (cis)-1-(1H-pyrazol-3-yl)pyrrolidine-3,4-diamine in place of benzene-1,2-diamine in Step 1 and Intermediate 6 from Example 1 in place of Intermediate 5.

Example 192: Synthesis of I-204

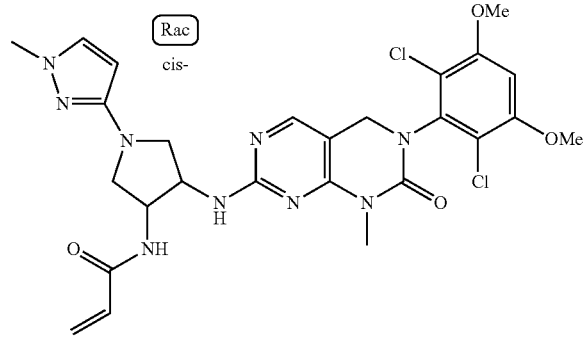 [SMILES: C=CC(=O)NC1CN(c2ccn(C)n2)CC1Nc1ncc2c(n1)N(C)C(=O)N(c1c(Cl)c(OC)cc(OC)c1Cl)C2]

The title compound was prepared as described in Example 7 using (cis)-1-(1-methyl-1H-pyrazol-3-yl)pyrrolidine-3,4-diamine in place of benzene-1,2-diamine in Step 1 and Intermediate 6 from Example 1 in place of Intermediate 5. MS m/z: 602.5 (M+H$^+$).

Example 193: Synthesis of I-205

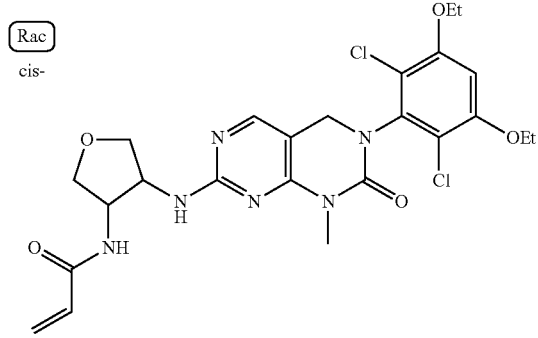 [SMILES: C=CC(=O)NC1COCC1Nc1ncc2c(n1)N(C)C(=O)N(c1c(Cl)c(OCC)cc(OCC)c1Cl)C2]

The title compound was prepared as described in Example 127. The chloro cyclic urea derivative was prepared as described in Example 1 using 3,5-diethoxyaniline in place of 3,5-dimethoxyaniline in Step 4. MS m/z: 551.5 (M+H$^+$).

Example 194: Synthesis of I-206

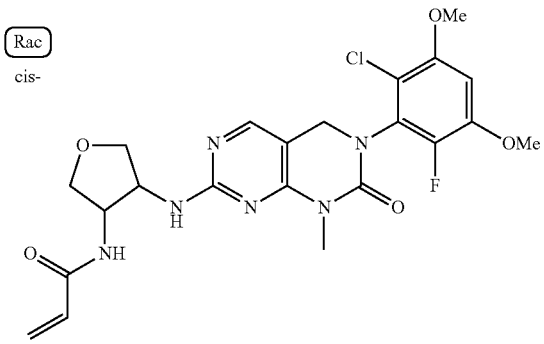 [SMILES: C=CC(=O)NC1COCC1Nc1ncc2c(n1)N(C)C(=O)N(c1c(F)c(OC)cc(OC)c1Cl)C2]

The title compound was prepared as described in Example 127. The chloro cyclic urea derivative was prepared as described in Example 1 using 2-chloro-6-fluoro-3,5-dimethoxyaniline in place of 3,5-dimethoxyaniline in Step 4 and skipping Step 7. MS m/z: 507.4 (M+H$^+$).

Example 195: Synthesis of I-207

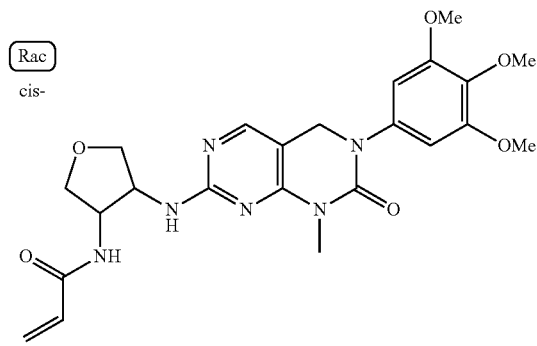 [SMILES: C=CC(=O)NC1COCC1Nc1ncc2c(n1)N(C)C(=O)N(c1cc(OC)c(OC)c(OC)c1)C2]

The title compound was prepared as described in Example 127. The chloro cyclic urea derivative was prepared as described in Example 1 using 3,4,5-trimethoxyaniline in place of 3,5-dimethoxyaniline in Step 4 and skipping Step 7. MS m/z: 485.5 (M+H$^+$).

Example 196: Synthesis of I-208

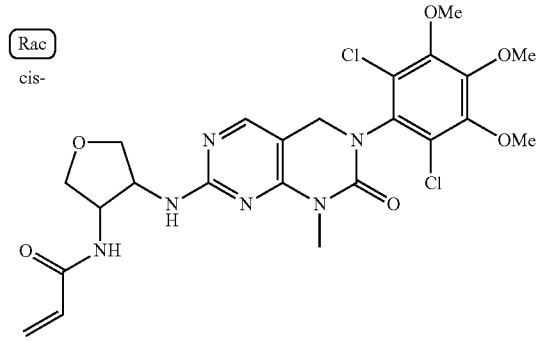 [SMILES: C=CC(=O)NC1COCC1Nc1ncc2c(n1)N(C)C(=O)N(c1c(Cl)c(OC)c(OC)c(OC)c1Cl)C2]

The title compound was prepared as described in Example 127. The chloro cyclic urea derivative was prepared as described in Example 1 using 3,4,5-trimethoxyaniline in place of 3,5-dimethoxyaniline in Step 4. MS m/z: 553.4 (M+H$^+$).

Example 197: Synthesis of I-209

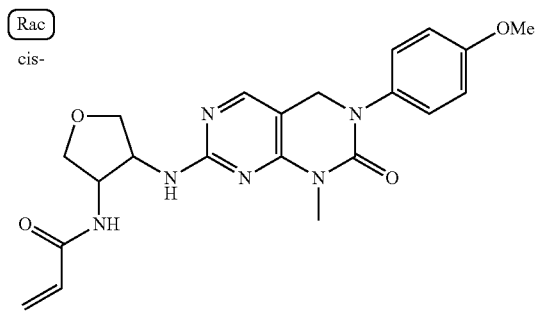 [SMILES: C=CC(=O)NC1COCC1Nc1ncc2c(n1)N(C)C(=O)N(c1ccc(OC)cc1)C2]

The title compound was prepared as described in Example 127. The chloro cyclic urea derivative was prepared as described in Example 1 using 4-methoxyaniline in place of 3,5-dimethoxyaniline in Step 4 and skipping Step 7. MS m/z: 425.4 (M+H$^+$).

Example 198: Synthesis of I-210

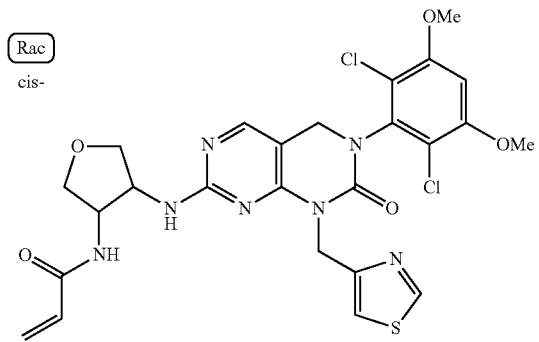 [SMILES: C=CC(=O)NC1COCC1Nc1ncc2c(n1)N(Cc1cscn1)C(=O)N(c1c(Cl)c(OC)cc(OC)c1Cl)C2]

The title compound was prepared as described in Example 127. The chloro cyclic urea derivative was prepared as described in Example 1 using thiazol-4-ylmethanamine in place of methylamine in Step 5. MS m/z: 606.4 (M+H$^+$).

Example 199: Synthesis of I-212

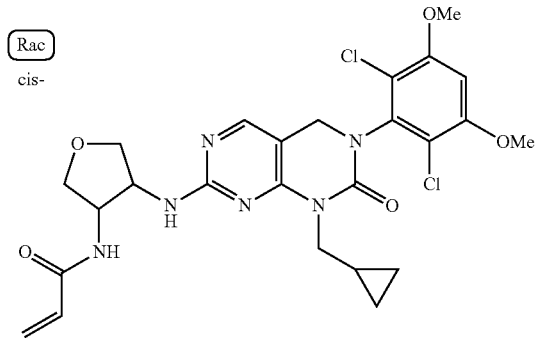 [SMILES: C=CC(=O)NC1COCC1Nc1ncc2c(n1)N(CC1CC1)C(=O)N(c1c(Cl)c(OC)cc(OC)c1Cl)C2]

The title compound was prepared as described in Example 127. The chloro cyclic urea derivative was prepared as described in Example 1 using cyclopropylmethanamine in place of methylamine in Step 5. MS m/z: 563.4 (M+H$^+$).

Example 200: Synthesis of I-213

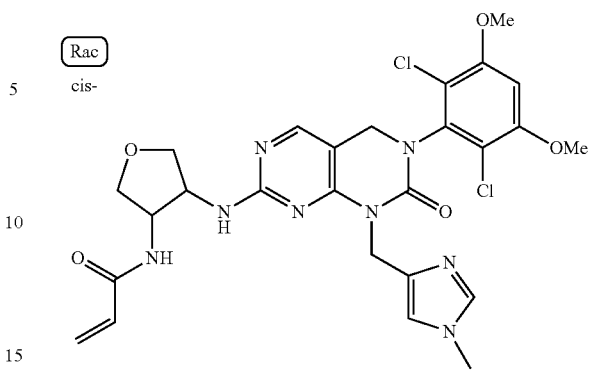

The title compound was prepared as described in Example 127. The chloro cyclic urea derivative was prepared as described in Example 1 using (1-methyl-1H-pyrazol-4-yl)methanamine in place of methylamine in Step 5. MS m/z: 603.5 (M+H$^+$).

Example 201: Synthesis of I-214

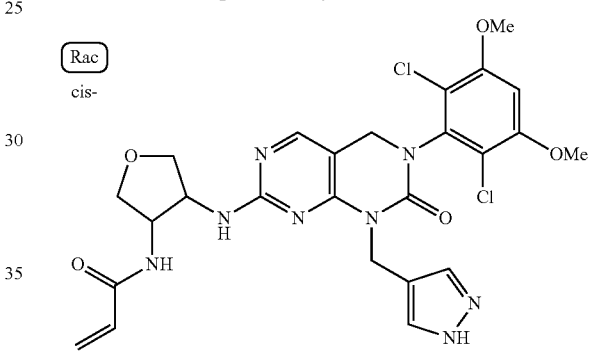

The title compound was prepared as described in Example 127. The chloro cyclic urea derivative is prepared as described in Example 1 using (1H-pyrazol-4-yl)methanamine in place of methylamine in Step 5. MS m/z: 589.5 (M+H$^+$).

Example 202: Synthesis of I-215

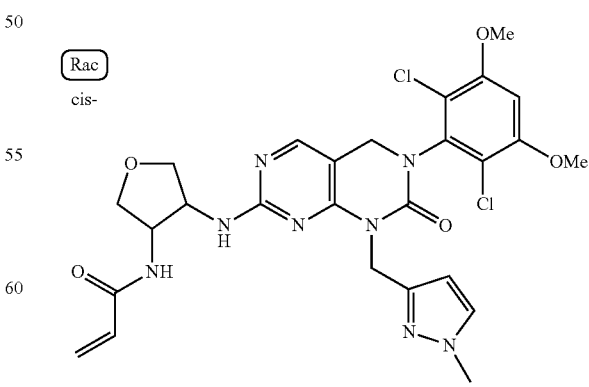

The title compound was prepared as described in Example 127. The chloro cyclic urea derivative is prepared as described in Example 1 using (1-methyl-1H-pyrazol-3-yl)methanamine in place of methylamine in Step 5. MS m/z: 603.5 (M+H⁺).

Example 203: Synthesis of I-216

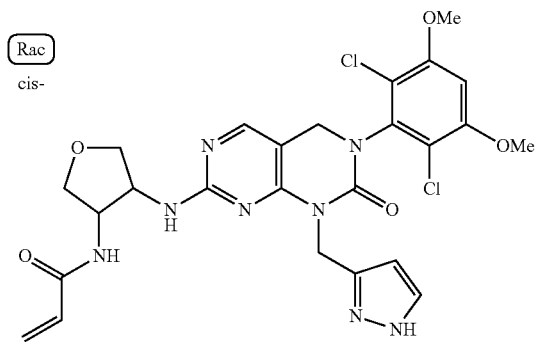 [SMILES: C=CC(=O)NC1COCC1Nc1ncc2c(n1)N(Cc1cc[nH]n1)C(=O)N(c1c(Cl)c(OC)cc(OC)c1Cl)C2]

The title compound was prepared as described in Example 127. The chloro cyclic urea derivative is prepared as described in Example 1 using (1H-pyrazol-3-yl)methanamine in place of methylamine in Step 5. MS m/z: 589.5 (M+H⁺).

Example 204: Synthesis of I-217

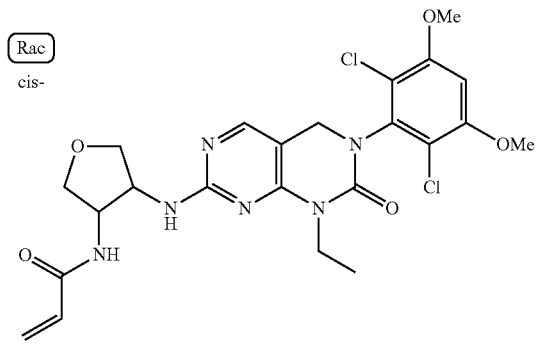 [SMILES: C=CC(=O)NC1COCC1Nc1ncc2c(n1)N(CC)C(=O)N(c1c(Cl)c(OC)cc(OC)c1Cl)C2]

The title compound was prepared as described in Example 127. The chloro cyclic urea derivative is prepared as described in Example 1 using ethylamine in place of methylamine in Step 5. MS m/z: 537.4 (M+H⁺).

Example 205: Synthesis of I-218

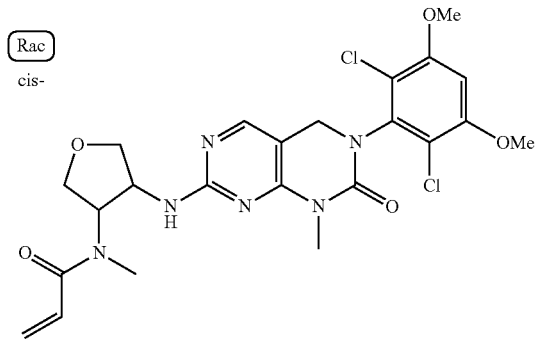 [SMILES: C=CC(=O)N(C)C1COCC1Nc1ncc2c(n1)N(C)C(=O)N(c1c(Cl)c(OC)cc(OC)c1Cl)C2]

The title compound was prepared as described in Example 127 with a methylation step (as described in Example 31, Step 1) prior to Step 5. MS m/z: 537.5 (M+H⁺).

Example 206: Synthesis of I-219

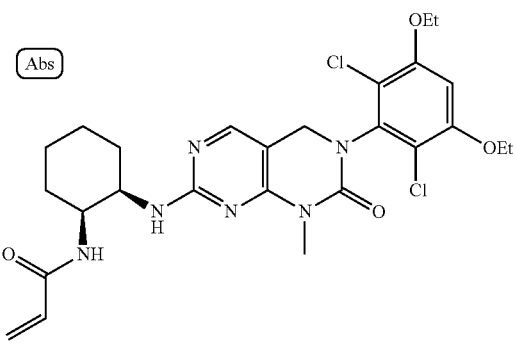 [SMILES: C=CC(=O)N[C@H]1CCCC[C@H]1Nc1ncc2c(n1)N(C)C(=O)N(c1c(Cl)c(OCC)cc(OCC)c1Cl)C2]

The title compound was prepared as described in Example 116. The starting material was prepared as described in Example 1 using 3,5-diethoxyaniline in place of 3,5-dimethoxyaniline in Step 4. MS m/z: 563.5 (M+H⁺).

Example 207: Synthesis of I-220

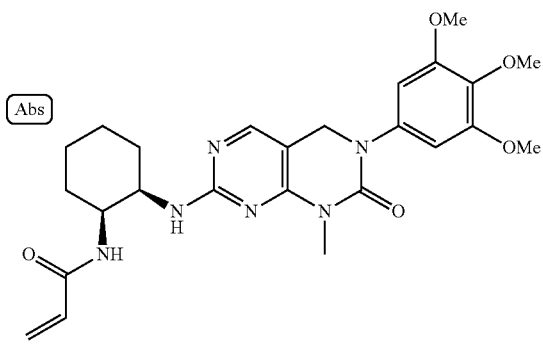 [SMILES: C=CC(=O)N[C@H]1CCCC[C@H]1Nc1ncc2c(n1)N(C)C(=O)N(c1cc(OC)c(OC)c(OC)c1)C2]

The title compound was prepared as described in Example 116. The starting material was prepared as described in Example 1 using 3,4,5 trimethoxyaniline in place of 3,5-dimethoxyaniline in Step 4 and skipping Step 7. MS m/z: 497.5 (M+H⁺).

Example 208: Synthesis

Using the techniques described herein, the following compounds can be prepared. For compounds prepared as racemic or diastereomeric mixtures, the single isomers can be prepared in optically pure form by either employing chiral starting materials or performing chiral chromatography.

Compound I-221

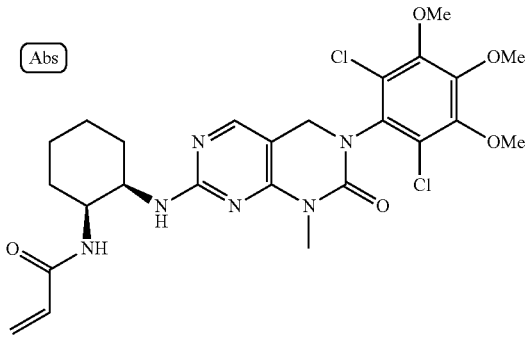 [SMILES: C=CC(=O)N[C@H]1CCCC[C@H]1Nc1ncc2c(n1)N(C)C(=O)N(c1c(Cl)c(OC)c(OC)c(OC)c1Cl)C2]

The title compound was prepared as described in Example 116. The starting material was prepared as described in Example 1 using 3,4,5 trimethoxyaniline in place of 3,5-dimethoxyaniline in Step 4. MS m/z: 565.5 (M+H$^+$).

Example 209: Synthesis of I-222

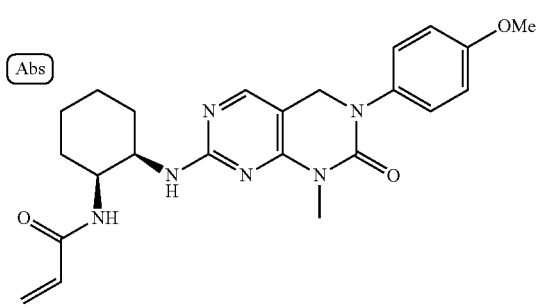 [SMILES: C=CC(=O)N[C@H]1CCCC[C@H]1Nc1ncc2c(n1)N(C)C(=O)N(c1ccc(OC)cc1)C2]

The title compound was prepared as described in Example 116. The starting material was prepared as described in Example 1 using 4-methoxyaniline in place of 3,5-dimethoxyaniline in Step 4, and skipping Step 7. MS m/z: 437.5 (M+H$^+$).

Example 210: Synthesis of I-223

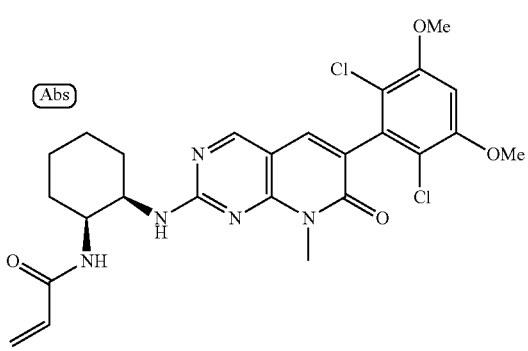 [SMILES: C=CC(=O)N[C@H]1CCCC[C@H]1Nc1ncc2cc(-c3c(Cl)c(OC)cc(OC)c3Cl)c(=O)n(C)c2n1]

The title compound was prepared as described in Example 224 using tert-butyl ((1S,2R)-2-aminocyclohexyl)carbamate in place of cis-tetrahydrofuran-3,4-diamine in Step 1. MS m/z: 532.5 (M+H$^+$). $^1$HNMR (400 MHz, CDCl3): 1.50-1.78 (m, 8H), 3.68 (s, 3H), 3.95 (s, 6H), 4.30 (br, 1H), 4.53 (br, 1H), 5.61 (d, 1H), 5.99-6.05 (m, 1H), 6.26 (d, 1H), 6.63 (s, 1H), 7.41 (s, 1H), 8.44 (s, 1H).

Example 211: Synthesis

Using the techniques described herein, the following compounds can be prepared. For compounds prepared as racemic or diastereomeric mixtures, the single isomers can be prepared in optically pure form by either employing chiral starting materials or performing chiral chromatography.

Compound I-224

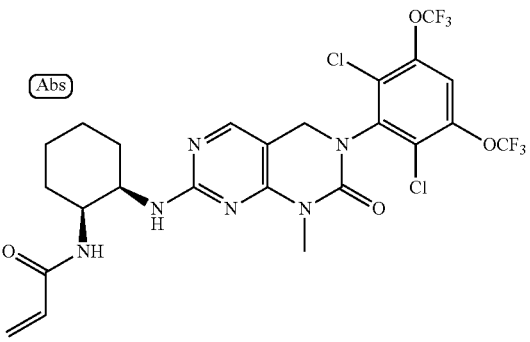 [SMILES: C=CC(=O)N[C@H]1CCCC[C@H]1Nc1ncc2c(n1)N(C)C(=O)N(c1c(Cl)c(OC(F)(F)F)cc(OC(F)(F)F)c1Cl)C2]

The title compound is prepared as described in Example 116. The starting material is prepared as described in Example 1 using 3,5-bis(trifluoromethoxy)aniline in place of 3,5-dimethoxyaniline in Step 4.

Compound I-225

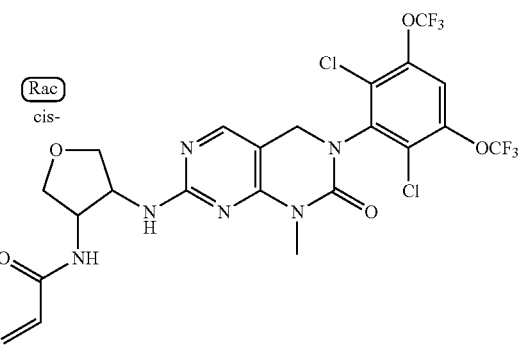 [SMILES: C=CC(=O)NC1COCC1Nc1ncc2c(n1)N(C)C(=O)N(c1c(Cl)c(OC(F)(F)F)cc(OC(F)(F)F)c1Cl)C2]

The title compound is prepared as described in Example 127. The chloro cyclic urea derivative is prepared as described in Example 1 using 3,5-bis(trifluoromethoxy) aniline in place of 3,5-dimethoxyaniline in Step 4.

Compound I-226

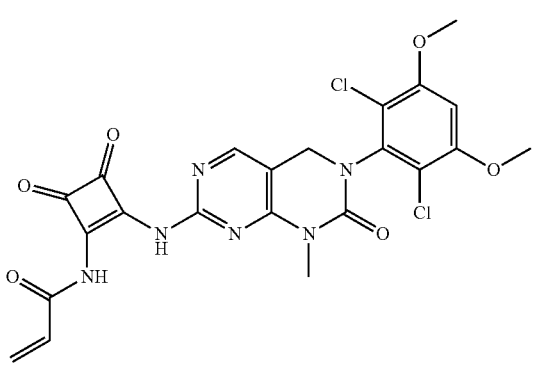 [SMILES: C=CC(=O)Nc1c(Nc2ncc3c(n2)N(C)C(=O)N(c2c(Cl)c(OC)cc(OC)c2Cl)C3)c(=O)c1=O]

The title compound is prepared as described in Example 7 using 3,4-diaminocyclobut-3-ene-1,2-dione in place of benzene-1,2-diamine in Step 1 and Intermediate 6 from Example 1 in place of Intermediate 5.

Compound I-227

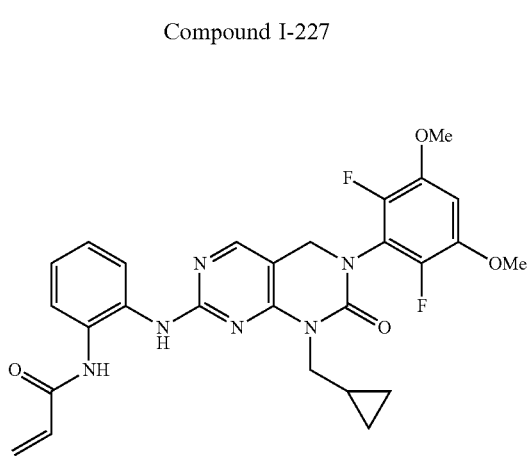

The title compound is prepared as described in Example 7. The starting material is prepared as described in Example 1 using 2-bromo-6-fluoro-3,5-dimethoxyaniline in place of 3,5-dimethoxyaniline in Step 4, cyclopropylmethanamine in place of methylamine in Step 5, and skipping Step 7.

Example 212: Synthesis of I-228

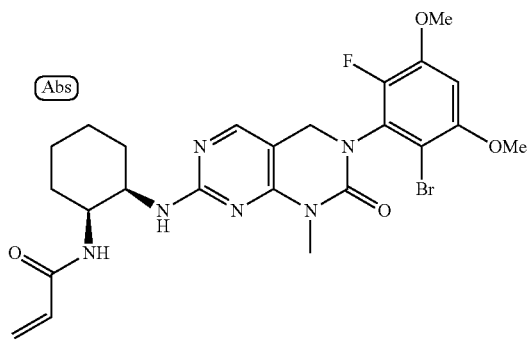 [SMILES: C=CC(=O)N[C@H]1CCCC[C@H]1Nc1ncc2c(n1)N(C)C(=O)N(c1c(F)c(OC)cc(OC)c1Br)C2]

The title compound was prepared as described in Example 116. The starting material was prepared as described in Example 1 using 2-bromo-6-fluoro-3,5-dimethoxyaniline in place of 3,5-dimethoxyaniline in Step 4 and skipping Step 7. MS m/z: 563.4 (M+H$^+$).

Example 213: Synthesis

Using the techniques described herein, the following compounds can be prepared. For compounds prepared as racemic or diastereomeric mixtures, the single isomers can be prepared in optically pure form by either employing chiral starting materials or performing chiral chromatography.

Compound I-229

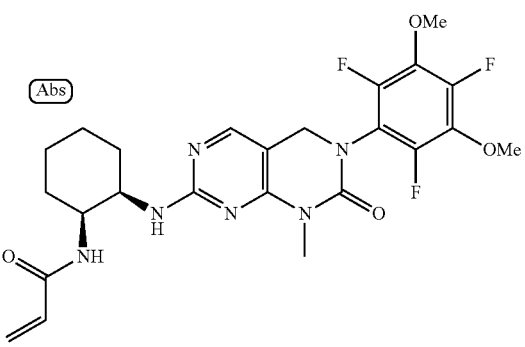 [SMILES: C=CC(=O)N[C@H]1CCCC[C@H]1Nc1ncc2c(n1)N(C)C(=O)N(c1c(F)c(OC)c(F)c(OC)c1F)C2]

The title compound is prepared as described in Example 116. The starting material is prepared as described in Example 1 using 2,4,6-trifluoro-3,5-dimethoxyaniline in place of 3,5-dimethoxyaniline in Step 4 and skipping Step 7.

Compound 363 I-230

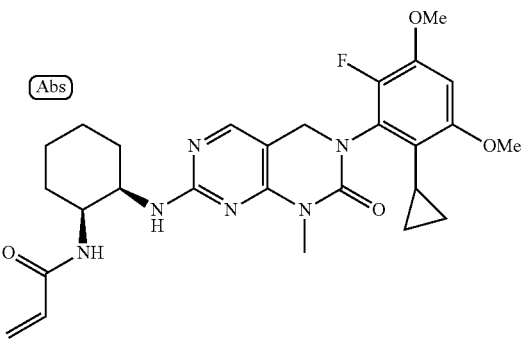 [SMILES: C=CC(=O)N[C@H]1CCCC[C@H]1Nc1ncc2c(n1)N(C)C(=O)N(c1c(F)c(OC)cc(OC)c1C1CC1)C2]

The title compound is prepared as described in Example 116. The starting material is prepared as described in Example 1 using 2-cyclopropyl-6-fluoro-3,5-dimethoxyaniline in place of 3,5-dimethoxyaniline in Step 4 and skipping Step 7.

Compound I-231

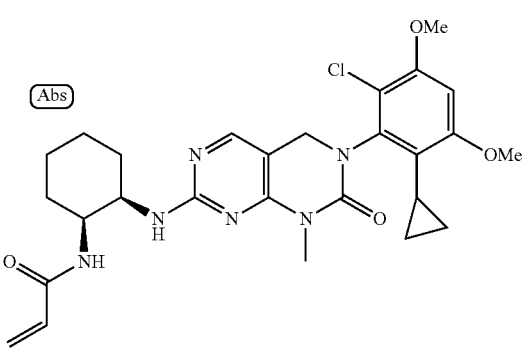 [SMILES: C=CC(=O)N[C@H]1CCCC[C@H]1Nc1ncc2c(n1)N(C)C(=O)N(c1c(Cl)c(OC)cc(OC)c1C1CC1)C2]

The title compound is prepared as described in Example 116. The starting material is prepared as described in Example 1 using 2-cyclopropyl-6-chloro-3,5-dimethoxyaniline in place of 3,5-dimethoxyaniline in Step 4 and skipping Step 7.

Example 214: Synthesis of I-118

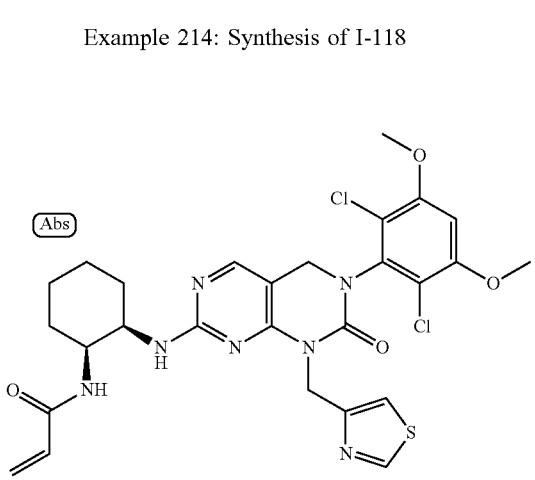

Compound I-118 was prepared as described in Example 116 using propionic acid in place of acrylic acid in Step 4. MS m/z: 602.2 (M+H$^+$).

Example 215: Synthesis of I-232

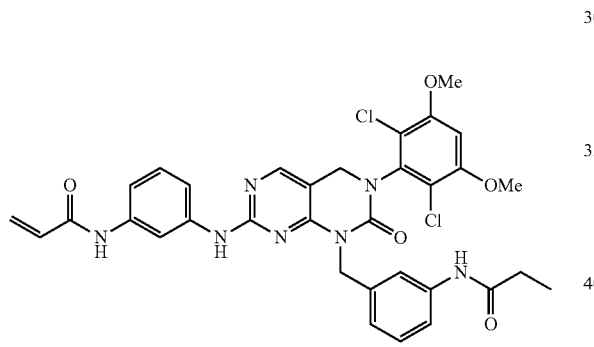

Compound I-232 was prepared as described in Example 3. Tert-butyl (3-aminophenyl)carbamate was used in place of benzene-1,2-diamine in Step 1. MS m/z: 676.4 (M+H$^+$).

Example 216: Synthesis of I-233

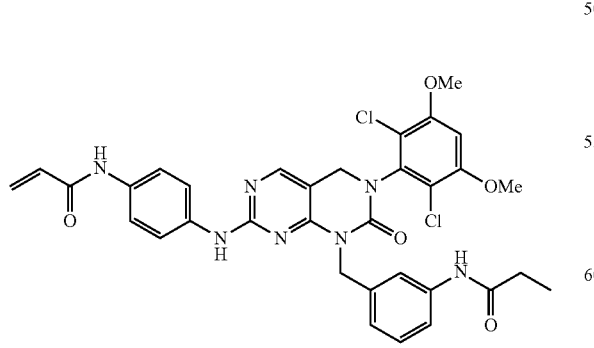

Compound I-233 was prepared as described in Example 3. Tert-butyl (4-aminophenyl)carbamate was used in place of benzene-1,2-diamine in Step 1. MS m/z: 676.3 (M+H$^+$).

Example 217: Synthesis of I-234

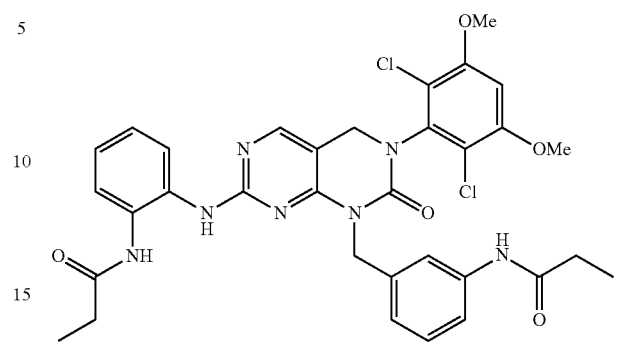

Compound I-234 was prepared as described in Example 3. Propionyl chloride was used in place of acryloyl chloride in Step 6. MS m/z: 678.2 (M+H$^+$).

Example 218: Synthesis of I-235

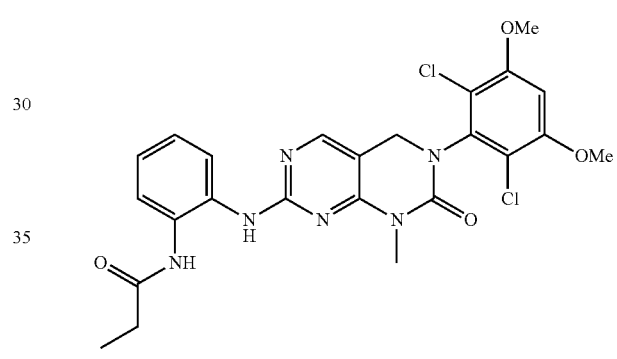

Compound I-235 was prepared as described in Example 7. Intermediate 6 from Example 1 was used in place of Intermediate 5. Propionyl chloride was used in place of acryloyl chloride in Step 2. MS m/z: 531.0 (M+H$^+$).

Example 219: Synthesis of I-236

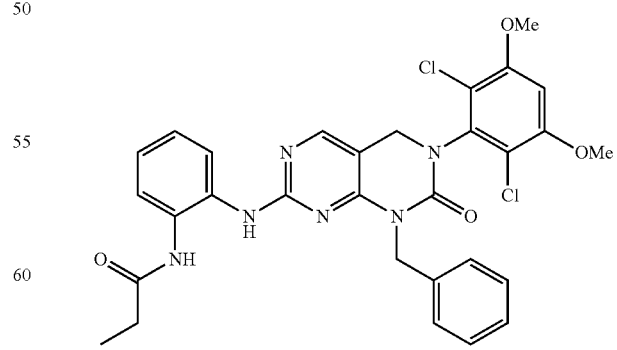

Compound I-236 was prepared as described in Example 5. Propionyl chloride was used in place of acryloyl chloride in Step 2. MS m/z: 607.1 (M+H$^+$).

Example 220: Synthesis of I-237

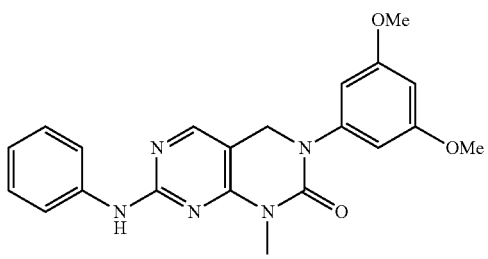 [SMILES: COc1cc(OC)cc(N2Cc3cnc(Nc4ccccc4)nc3N(C)C2=O)c1]

Compound I-237 was prepared as described in Example 7. Aniline was used in place of in place of benzene-1,2-diamine in Step 1. MS m/z: 392.3 (M+H$^+$).

Example 221: Synthesis of I-238

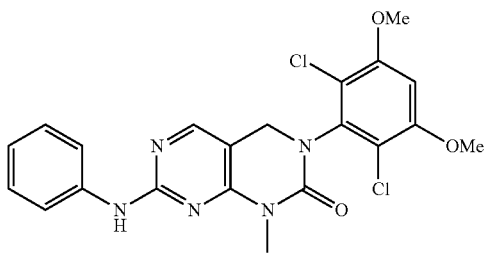 [SMILES: COc1cc(OC)c(Cl)c(N2Cc3cnc(Nc4ccccc4)nc3N(C)C2=O)c1Cl]

Compound I-238 was prepared as described in Example 7. Aniline was used in place of benzene-1,2-diamine in Step 1. Intermediate 6 from Example 1 was used in place of Intermediate 5. MS m/z: 460.1 (M+H$^+$).

Example 222: Synthesis of I-239

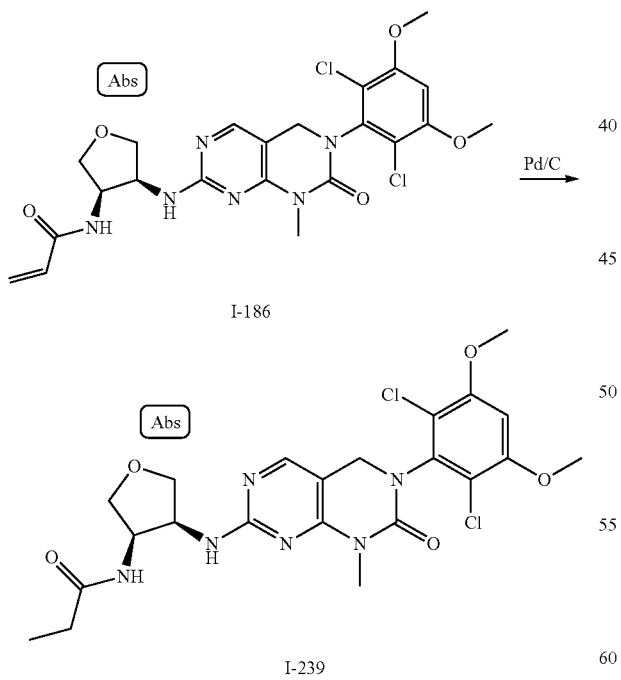

I-186

I-239

To a solution of the intermediate I-186 (3.80 mg, 0.007 mmoL) in 500 uL of THF was added catalytic 10% Pd/C. 1 atm of H$_2$ was introduced via balloon and the reaction mixture was allowed to stir at ambient temperature for 1 h. The reaction mixture was filtered, through a pad of celite and the solvent was removed under reduced pressure to afford 3.7 mg of the title compound. MS m/z: 525.2 (M+H$^+$).

Example 223: Synthesis of Common Intermediate 8

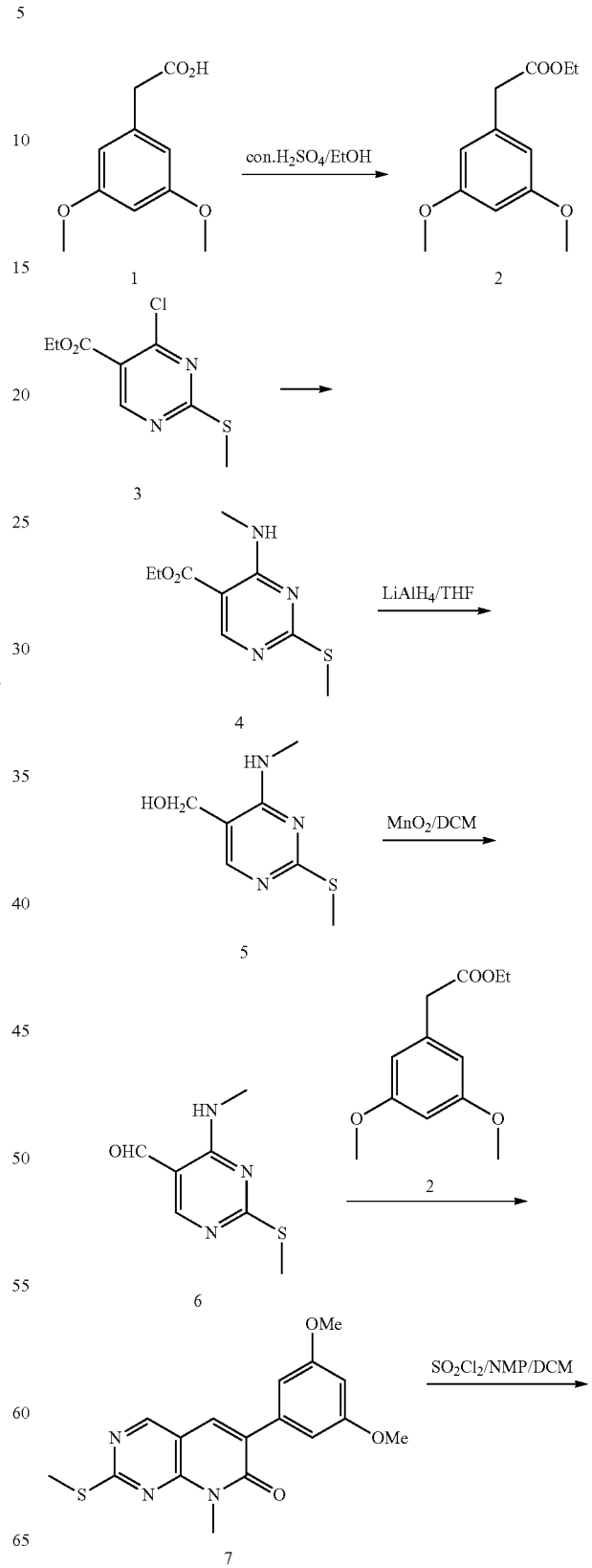

-continued

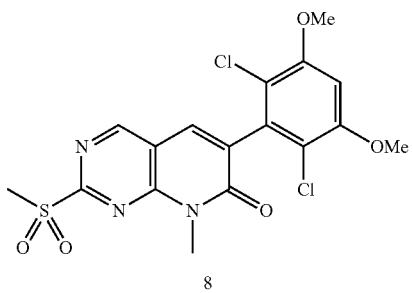 [SMILES: COc1cc(OC)c(Cl)c(-c2cc3cnc(S(C)(=O)=O)nc3n(C)c2=O)c1Cl]

8

Step 1: Intermediate 2

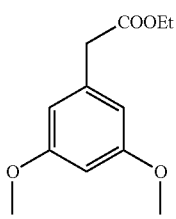 [SMILES: CCOC(=O)Cc1cc(OC)cc(OC)c1]

To a mixture of Intermediate 1 (1.35 g, 6.88 mmol) in EtOH was added conc. H₂SO₄ (4 drops). The reaction mixture was heated at 85° C. for 16 h after which it was cooled to ambient temperature and concentrated. The resultant residue was diluted with water (20 mL) and extracted with DCM (25 mL×3). The combined organic layers were washed with brine (50 mL), dried over Na₂SO₄ and concentrated to afford the title compound (2.85 g, 100%) as a yellow solid.

Step 2: Intermediate 4

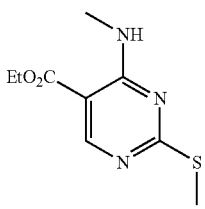

Methylamine in EtOH (33%, 17.5 mL, 140 mmol) was slowly added to a solution of Intermediate 3 (10.0 g, 43.1 mmol) in 120 mL of dichloromethane at 0° C. The solution was stirred for 30 min. Water (150 ml) was added, and the resultant mixture was separated, the organic layer was dried over MgSO₄, filtered, and concentrated to afford the title compound (9.77 g, 100%) as white solid.

Step 3: Intermediate 5

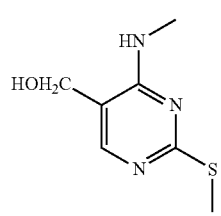

To a mixture of LAH (2.45 g, 64.6 mmol) in anhydrous THF (30 mL) at 0° C. a solution of Intermediate 4 (9.77 g, 43.0 mmol) in anhydrous THF (45 mL) was added dropwise. The reaction mixture was allowed to stir for 15 min at ambient temperature. Water (18 mL) was added dropwise with caution. The mixture was stirred for 30 min. Aqueous NaOH solution (15%, 8.5 mL) was added dropwise, followed by addition of water (26 mL). The resulting suspension was allowed to stir for 17 h at ambient temperature after which the reaction mixture was filtered and sequentially washed with THF (100 mL×2). The combined filtrate and washings were concentrated and the resultant residue was suspended in ethyl acetate/hexane (v/v: 2:1, 200 mL). Solids were collected by filtration to afford the title compound as yellow solid (4.23 g, 53%).

Step 4: Intermediate 6

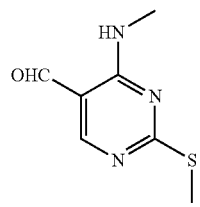

Compound 5 (4.23 g, 23.2 mmol) was taken into dichloromethane (1 L) and treated with manganese dioxide (18.0 g, 207 mmol) with stirring. The resultant suspension was stirred for 24 h, then filtered through Celite, washed with dichloromethane (100 mL), and the combined organic layers were concentrated to afford the title compound (3.00 g, 75%).

Step 5: Intermediate 7

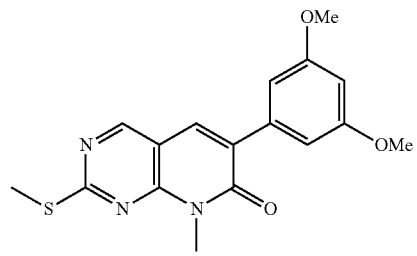 [SMILES: COc1cc(OC)cc(-c2cc3cnc(SC)nc3n(C)c2=O)c1]

A mixture of Intermediate 2 (1.29 g, 5.75 mmol), Intermediate 6 (1.00 g, 5.46 mmol) and K₂CO₃ (1.50 g, 10.9 mmol) in DMF (100 mL) was heated to 110° C. for 4 h. The mixture was allowed to cool to ambient temperature, poured into water, filtered, and the solids were dried to afford the title compound (1.20 g, 63%) as white solid.

Step 6: Intermediate 8

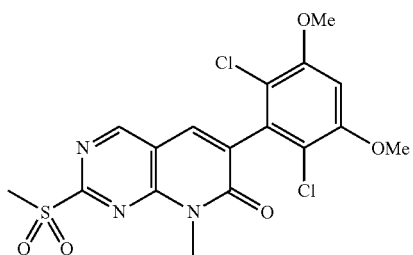 [SMILES: COc1cc(OC)c(Cl)c(-c2cc3cnc(S(C)(=O)=O)nc3n(C)c2=O)c1Cl]

To a solution of Intermediate 7 (1.33 g, 3.88 mmol) in DCM (15 mL) and NMP (5 mL), was added $SO_2Cl_2$ (2.10 g, 15.6 mmol) dropwise at 0° C. The resultant mixture was allowed to stir at 0° C. for 30 min after which it was concentrated, diluted with water, extracted with EtOAc (25 mL×4) and the combined organic layers were dried over $Na_2SO_4$. The organic layers were concentrated to afford the title compound (1.50 g, 87%) as a white solid. The resultant solid was recrystallized with ethyl acetate or purified by silica gel column chromatography to afford the title compound as white solid (1.20 g, 70%).

Example 224: Synthesis of I-211

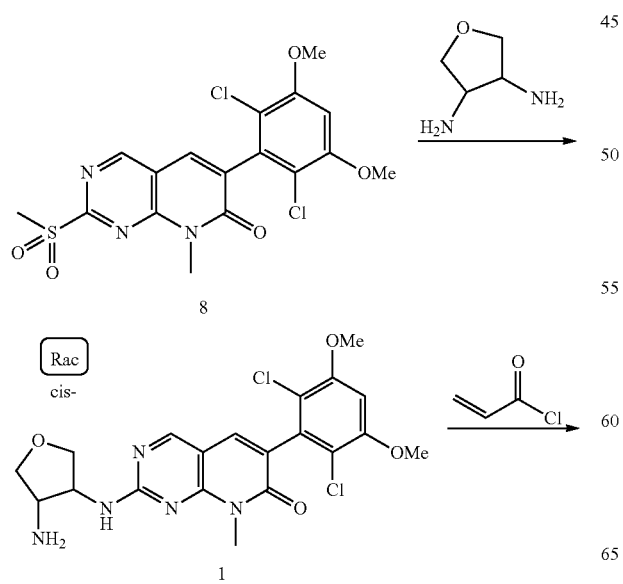

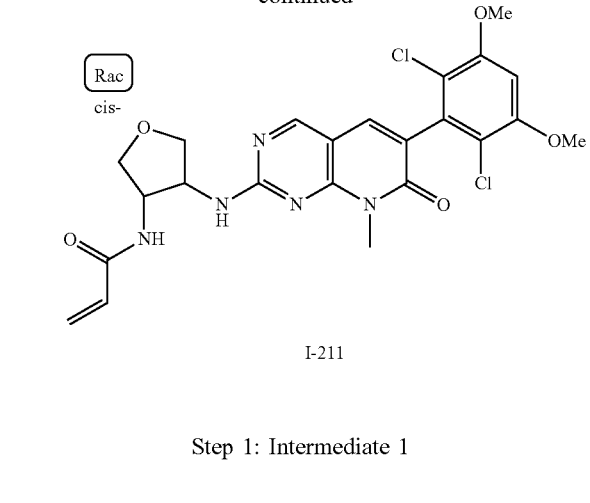

I-211

Step 1: Intermediate 1

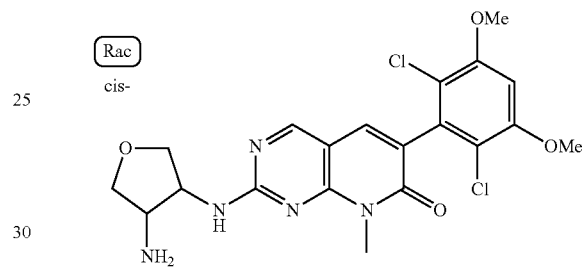

A mixture of Common Intermediate 8 from Example 223 (300 mg, 0.68 mmol), cis-tetrahydrofuran-3,4-diamine (204 mg, 2.0 mmol), and DIPEA (387 mg, 3.0 mmol) in NMP (5 mL) was heated to 80° C. for 3 h. The mixture was allowed to cool to ambient temperature and partitioned between EtOAc and water. The organic phase was separated, washed with water, brine, dried over anhydrous $Na_2SO_4$ and the resultant residue was purified through column chromatography on silica to afford the title compound (137 mg, 44%). MS m/z: 466.3 (M+H$^+$).

Step 2: I-211

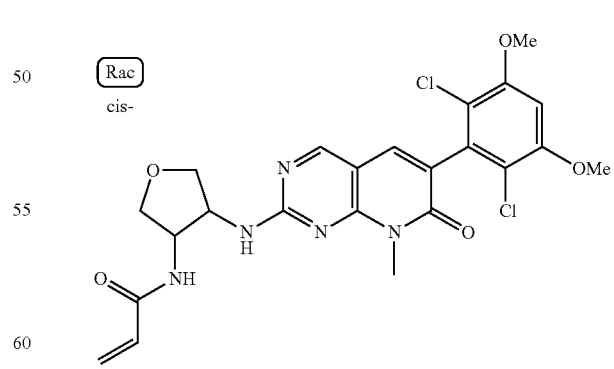

To a solution of Intermediate 1 (3.50 g, 7.5 mmol), DIPEA (1.94 g, 15 mmol) in anhydrous DCM (100 mL) at 0° C. was added a solution of acryloyl chloride (680 mg, 7.50 mmol) in anhydrous DCM (5 mL) dropwise. The reaction mixture was allowed to stir for 10 min after which was partitioned between DCM and H₂O. The organic phase was separated, washed with brine, dried over Na₂SO₄ and the crude product was purified through silica gel column chromatography to afford the title compound (2.90 g, 74%). MS m/z: 520.4 (M+H⁺). ¹HNMR (400 Hz, CDCl₃): 3.68-3.85 (m, 5H), 3.95 (s, 6H), 4.16-4.24 (m, 2H), 4.87 (br, 2H), 5.62 (d, 1H), 6.02-6.08 (m, 1H), 6.24-6.39 (m, 3H), 6.63 (s, 1H), 7.43 (s, 1H), 8.47 (s, 1H).

Example 225: Chiral Separation of I-211 to Afford I-240 and I-241

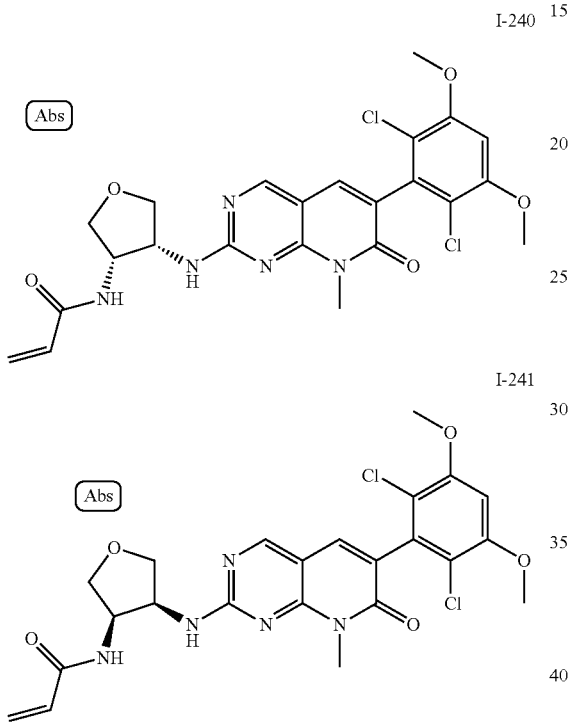

Chiral SFC separation of I-211 (ChiralCel OD-3, 150×4.6 mm, 5 micron, 2.4 mL/min, 40% MeOH with 0.05% DEA in CO₂) provided two enantiomers with Rt=3.46 and 4.89 min which were assigned absolute configurations of I-240 and I-241 respectively (>98% ee). Absolute configurations were assigned by analogy to I-94 and I-95, based on enzymatic and cellular potency.

I-241: MS m/z: 520.4 (M+H⁺), [α]$_D$=+75 (C=4.00 mg/mL, CH₂Cl₂, 23° C.), ¹HNMR (400 Hz, CDCl₃): 3.68-3.85 (m, 5H), 3.95 (s, 6H), 4.16-4.24 (m, 2H), 4.87 (br, 2H), 5.62 (d, 1H), 6.02-6.08 (m, 1H), 6.24-6.39 (m, 3H), 6.63 (s, 1H), 7.43 (s, 1H), 8.47 (s, 1H).

I-240: MS m/z: 520.4 (M+H⁺), [α]$_D$=−65 (C=4.00 mg/mL, CH₂Cl₂, 23° C.), ¹HNMR (400 Hz, CDCl₃): 3.68-3.85 (m, 5H), 3.95 (s, 6H), 4.16-4.24 (m, 2H), 4.87 (br, 2H), 5.62 (d, 1H), 6.02-6.08 (m, 1H), 6.24-6.39 (m, 3H), 6.63 (s, 1H), 7.43 (s, 1H), 8.47 (s, 1H).

The absolute configuration of I-241 was confirmed through enantioselective synthesis according to the below scheme. N-((3R,4S)-4-aminotetrahydrofuran-3-yl)acrylamide was prepared according to literature (*JACS*, 1995, 117, 5897-5898) and as described in Example 226, and used in place of cis-tetrahydrofuran-3,4-diamine in Example 224.

Example 226: Steroechemical Proof and Enantioselective Synthesis of I-241

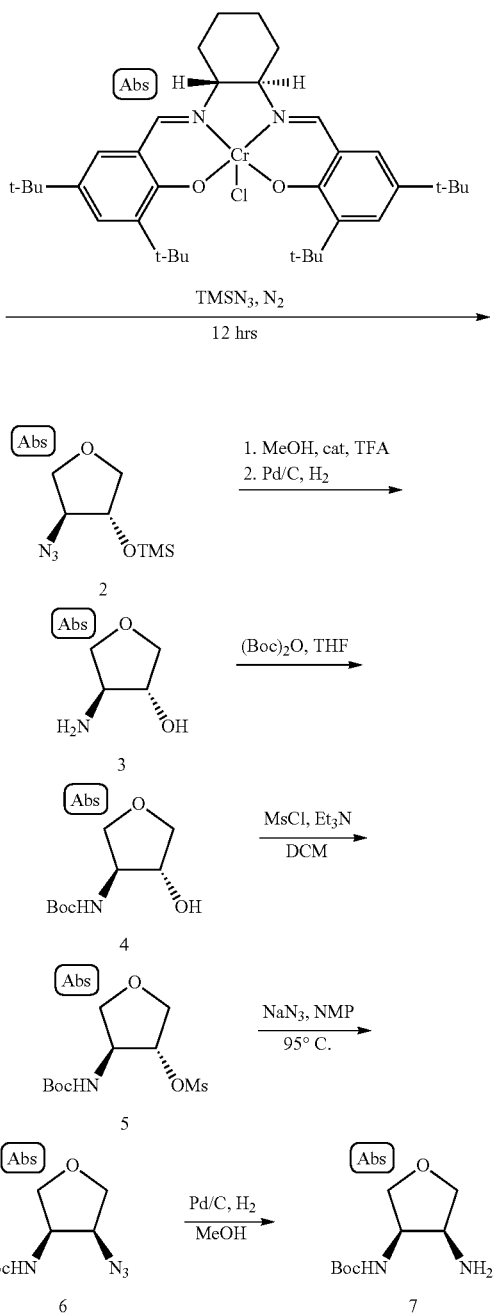

Step 1: Intermediate 2, ((3R,4S)-4-azidotetrahydrofuran-3-yloxy)trimethylsilane

A flask equipped with a stir bar was charged with (R,R)-Salen catalyst (600 mg, 0.02 equiv, Sigma Aldrich, catalog 531944, CAS #164931-83-3), and flushed with N₂. Cyclopentene oxide (4.30 g, 50.0 mmol) and TMSN₃ (6.00 g, 1.05 equiv) were added sequentially at ambient temperature. The reaction mixture was allowed to stir 12 h, at which time excess TMSN₃ was removed under reduced pressure, and the residue was purified by silica gel column chromatography (eluting with 30% EtOAc/hexane) to afford the title compound as a yellow oil (7.80 g, 78%, 91% ee, JACS, 1995, 117, 5897-5898). ¹HNMR (CDCl₃, 400 MHz): δ 0.00 (s, 9H), 3.46-3.49 (m, 1H), 3.64-3.69 (m, 2H), 3.83 (dd, 1H), 3.89 (dd, 1H), 4.08-4.11 (m, 1H).

Step 2: Intermediate 3, (3R,4S)-4-aminotetrahydrofuran-3-ol

To a solution of ((3R,4S)-4-azidotetrahydrofuran-3-yloxy)trimethylsilane (7.80 g, 38.8 mmol) in MeOH (100 mL), was added TFA (10.0 mg, 0.002 equiv), and the mixture was allowed to stir at room temperature for 30 min. The resulting solution was treated with Pd/C (1.90 g, 25 wt %) and allowed to stir at ambient temperature under H₂ atmosphere for 40 h. The reaction solution was filtered through Celite and the filter cake was washed with MeOH. The combined organics were concentrated under reduced pressure to afford the title compound (3.10 g). ¹HNMR (CDCl₃, 400 MHz): δ 3.38-3.40 (m, 2H), 3.54 (m, 2H), 3.68-3.72 (m, 2H), 3.75 (dd, 1H), 3.83 (dd, 1H), 4.00-4.03 (m, 1H).

Step 3: Intermediate 4, tert-butyl (3S,4R)-4-hydroxytetrahydrofuran-3-yl carbamate To a solution of (3R,4S)-4-aminotetrahydrofuran-3-ol (1.00 g, 9.71 mmol) in THF (30 mL) was added (Boc)₂O (2.70 g, 1.30 equiv). The mixture was allowed to stir at ambient temperature overnight. The reaction solution was concentrated under reduced pressure. The residue was partitioned between EtOAc and water, the organic layer was washed with water and brine, dried over anhydrous Na₂SO₄ and concentrated under reduced pressure. The crude product was purified by column chromatography (eluting with 5% EtOAc/hexane) to afford the title compound as a white solid (1.20 g, 61%). ¹HNMR (CDCl₃, 400 MHz): δ 1.45 (s, 9H), 3.11 (s, 1H), 3.60-3.63 (m, 1H), 3.68-3.71 (1H), 3.95 (s, br, 1H), 4.04-4.11 (m, 2H), 4.28-4.30 (m, 1H), 4.74 (s, br, 1H).

Step 4: Intermediate 5, (3R,4S)-4-(tert-butoxycarbonylamino)tetrahydrofuran-3-ylmethanesulfonate To the solution of tert-butyl (3S,4R)-4-hydroxytetrahydrofuran-3-yl carbamate (1.20 g, 5.91 mmol) and TEA (0.89 g, 1.50 eq) in DCM (40 mL), was added methanesulfonyl chloride (0.88 g, 1.30 eq), in portions at 0° C. under a nitrogen atmosphere. The mixture was slowly warmed to room temperature and was stirred for 1 h. The resultant solution was washed with water, 1 N HCl, and saturated aqueous sodium bicarbonate, dried over anhydrous Na₂SO₄ and concentrated under reduced pressure to afford the title compound (1.60 g, 96%). ¹HNMR (CDCl₃, 400 MHz): δ 1.45 (s, 9H), 3.21 (s, 3H), 3.70-3.73 (m, 1H), 3.97-3.99 (m, 1H), 4.05-4.07 (m, 1H), 4.17-4.19 (m, 2H), 4.76 (s, 1H), 5.05 (d, 1H).

Step 5, Intermediate 6, tert-butyl (3R,4S)-4-azidotetrahydrofuran-3-yl carbamate To a solution of (3R,4S)-4-(tert-butoxycarbonylamino)tetrahydrofuran-3-yl methanesulfonate (1.60 g, 5.70 mmol) in NMP (10 mL), was added NaN₃ (0.92 g, 2.50 eq). The mixture was stirred at 95° C. for 5 h. The resultant solution was quenched with water and extracted with ethyl acetate. The organic phase was washed with brine, dried over sodium sulfate, filtered, and concentrated under reduced pressure to afford the title compound (620 mg, 48%). ¹HNMR (CDCl₃, 400 MHz): δ 1.47 (s, 9H), 3.45 (t, 1H), 3.87-3.89 (m, 1H), 4.02-4.07 (m, 2H), 4.21 (s, br, 1H), 4.36-4.44 (m, 1H), 4.85 (s, br, 1H).

Step 6: Intermediate 7, tert-butyl (3R,4S)-4-aminotetrahydrofuran-3-yl carbamate To a solution of tert-butyl (3R,4S)-4-azidotetrahydrofuran-3-ylcarbamate (620 mg, 2.72 mmol) in methanol (15 ml), was added Pd/C (10%, 170 mg). The mixture was hydrogenated (3 atm) at ambient temperature under hydrogen overnight, after which the reaction mixture was filtered and the filtrate concentrated to afford the title compound (350 mg, 63%, 91% ee). ¹HNMR (CDCl₃, 400 MHz): δ 1.26 (s, br, 1H), 1.46 (s, 9H), 1.68 (s, br, 1H), 3.47-3.49 (m, 1H), 3.57-3.59 (m, 2H), 3.98-4.06 (m, 2H), 4.10 (d, 1H), 5.24 (s, br, 1H).

Intermediate 7 was used to make I-241, by coupling with Intermediate 8 from Example 224 followed by Boc deprotection and acrylamide formation using the procedure described in Example 224. I-241: MS m/z: 520.4 (M+H⁺), ¹HNMR (400 MHz, CDCl₃): 3.68-3.85 (m, 5H), 3.95 (s, 6H), 4.16-4.24 (m, 2H), 4.87 (br, 2H), 5.62 (d, 1H), 6.02-6.08 (m, 1H), 6.24-6.39 (m, 3H), 6.63 (s, 1H), 7.43 (s, 1H), 8.47 (s, 1H).

Example 227: Synthesis of I-242

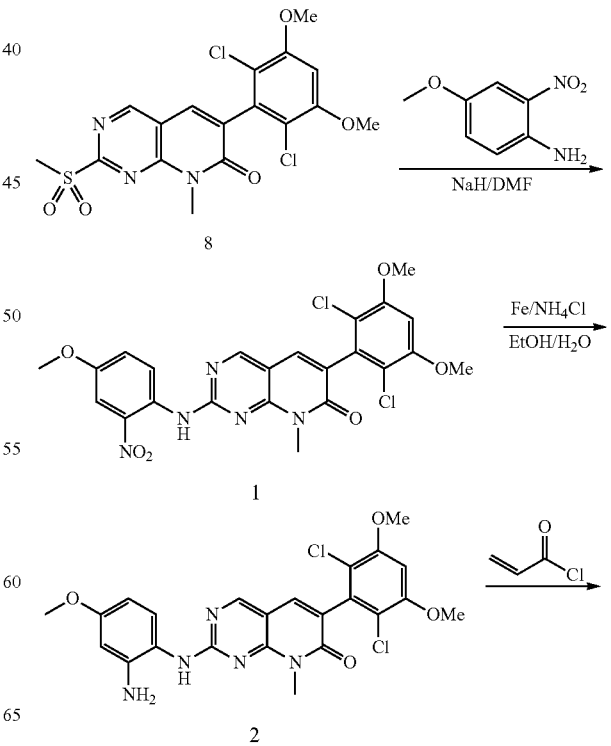

-continued

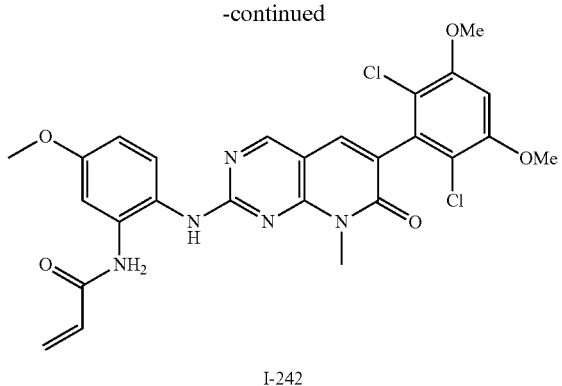

I-242

Step 1: Intermediate 1

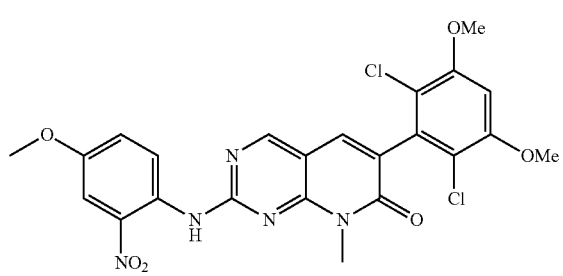 [SMILES: COc1ccc(Nc2ncc3cc(-c4c(Cl)c(OC)cc(OC)c4Cl)c(=O)n(C)c3n2)c([N+](=O)[O-])c1]

To a solution of 4-methoxy-2-nitroaniline (170 mg, 1.02 mmol) in anhydrous NMP (5 mL) was added NaH (60%, 42.0 mg, 1.02 mmol). The reaction mixture was stirred for 10 min at room temperature after which it was heated at 100° C. for 0.5 h, followed by addition of Common Intermediate 8 from Example 223 (300 mg, 0.68 mmol). The reaction mixture was allowed to stir at 100° C. overnight after which it was cooled to room temperature and partitioned between EtOAc and water. The organic phase was separated and washed with water, brine, dried over anhydrous $Na_2SO_4$ and the crude product was purified through silica gel column chromatography to afford the title compound (200 mg, 55%). MS m/z: 532.4 (M+H$^+$).

Step 2: Intermediate 2

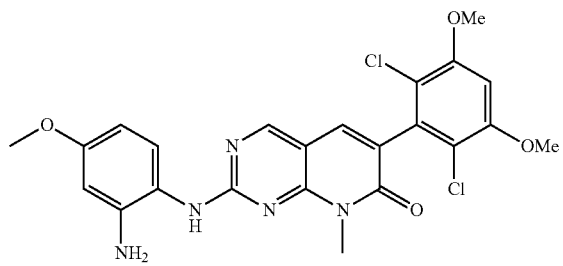

A mixture of Intermediate 1 (200 mg, 0.38 mmol), Fe (130 mg, 2.26 mmol), and $NH_4Cl$ (130 mg, 2.43 mmol), in EtOH (10 mL) with $H_2O$ (6 mL), was heated to reflux for 1 h. The resultant solid was removed by filtration and the filtrate was extracted with DCM. The organic phase was washed with brine, dried over $Na_2SO_4$ and the crude product purified through silica gel column chromatography to afford the title compound (180 mg, 95%). MS m/z: 502.4 (M+H$^+$).

Step 3: I-242

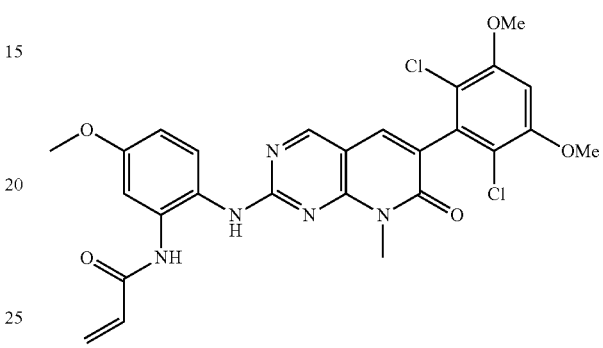

To a solution of Intermediate 2 (180 mg, 0.36 mmol) and DIPEA (70 mg, 0.54 mmol) in anhydrous DCM (5 ml) at 0° C., was added a solution of acryloyl chloride (40 mg, 0.43 mmol) in anhydrous DCM (1 mL) dropwise. After 10 min., the reaction mixture was partitioned between DCM/$H_2O$ and the organic phase was separated, washed with brine, and dried over $Na_2SO_4$. The resultant solid was purified through column chromatography on silica gel to afford the title compound (60.0 mg, 30%). MS m/z: 556.4 (M+H$^+$). $^1$HNMR (400 Hz, DMSO-d6): δ 3.48 (s, 3H), 3.78 (s, 3H), 3.96 (q, 6H), 5.74 (d, 1H), 6.27 (dd, 1H), 6.53 (q, 1H), 6.82 (dd, 1H), 6.99 (s, 1H), 7.40 (br, 1H), 7.58 (br, 1H), 7.76 (s, 1H), 8.73 (s, 1H), 9.15 (s, 1H), 9.68 (br, 1H).

Example 228: Synthesis of I-243

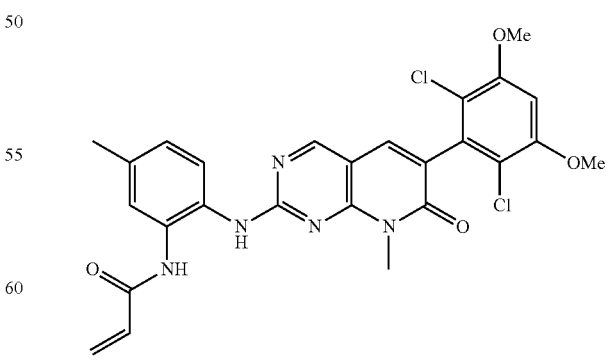

The title compound was prepared as described in Example 227 using 4-methyl-2-nitroaniline in place of 4-methoxy-2-nitroaniline in Step 1. MS m/z: 540.5 (M+H$^+$).

Example 229: Synthesis of I-244

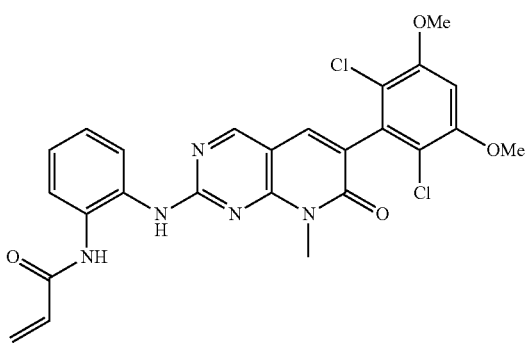

The title compound was prepared as described in Example 227 using 2-nitroaniline in place of 4-methoxy-2-nitroaniline in Step 1. MS m/z: 526.4 (M+H$^+$).

Example 230: Synthesis of I-245

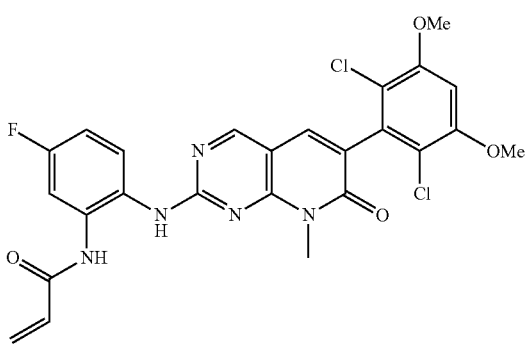 [SMILES: C=CC(=O)Nc1cc(C)ccc1Nc1ncc2cc(-c3c(Cl)c(OC)cc(OC)c3Cl)c(=O)n(C)c2n1]

The title compound was prepared as described in Example 227 using 4-fluoro-2-nitroaniline in place of 4-methoxy-2-nitroaniline in Step 1. MS m/z: 544.4 (M+H$^+$).

Example 231: Synthesis of I-246

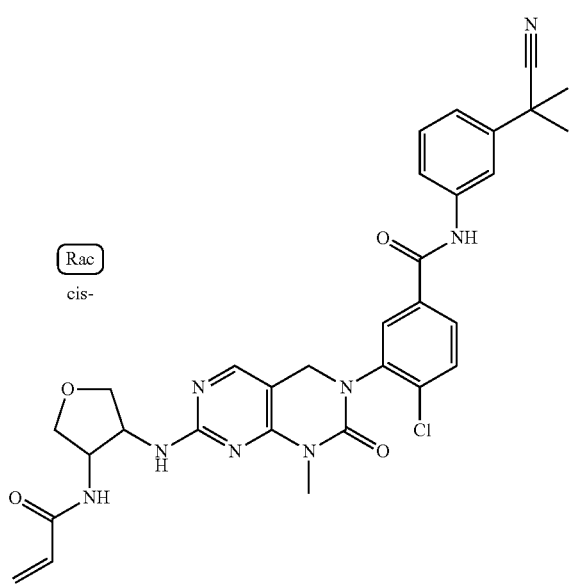 [SMILES: C=CC(=O)NC1COCC1Nc1ncc2c(n1)N(C)C(=O)N(c1cc(C(=O)Nc3cccc(C(C)(C)C#N)c3)ccc1Cl)C2]

The title compound was prepared as described in Example 127 using 4-chloro-3-(7-chloro-1-methyl-2-oxo-1,2-dihydropyrimido[4,5-d]pyrimidin-3 (4H)-yl)-N-(3-(2-cyanopropan-2-yl)phenyl)benzamide in place of Intermediate 6 in Step 5 (which was prepared as described in Example 1 using 3-amino-4-chloro-N-(3-(2-cyanopropan-2-yl)phenyl)benzamide in place of 3,5-dimethoxyaniline in Step 4. MS m/z: 615.6 (M+H$^+$).

Example 232: Synthesis of I-247

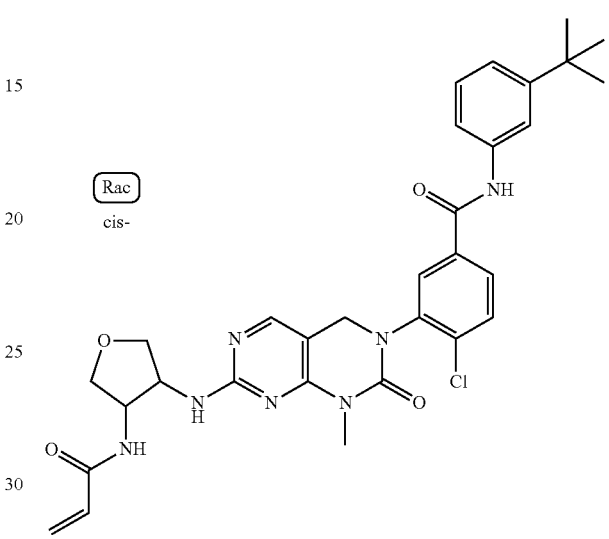

The title compound was prepared as described in Example 127 using N-(3-(tert-butyl)phenyl)-4-chloro-3-(7-chloro-1-methyl-2-oxo-1,2-dihydropyrimido[4,5-d]pyrimidin-3(4H)-yl)benzamide in place of Intermediate 6 in Step 5 (which was prepared as described in Example 1 using 3-amino-N-(3-(tert-butyl)phenyl)-4-chlorobenzamide in place of 3,5-dimethoxyaniline in Step 4. MS m/z: 604.6 (M+H$^+$).

Example 233: Common Intermediate 2

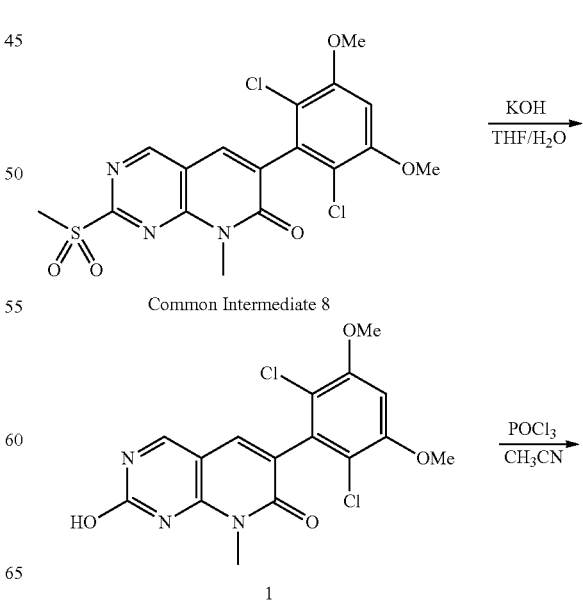

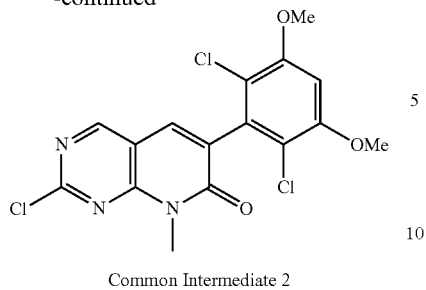

Common Intermediate 2

Step 1: Intermediate 1

KOH (1.30 g, 23.6 mmol) was added in portions to a mixture of Common Intermediate 8 from Example 223 (3.50 g, 7.88 mmol) in THF/H$_2$O (50/50 mL) at 0° C. The resulting mixture was allowed to stir at room temperature for 4 h after which it was concentrated and the pH was adjusted to 2. The resulting precipitate was collected by filtration, and dried to afford the title compound (2.50 g, 83%) as white solid. LCMS: 382.3 [M+1]. $^1$H NMR (400 MHz, DMSO-d$_6$): δ 3.46 (s, 3H), 3.96 (s, 6H), 6.99 (s, 1H), 7.63 (s, 1H), 8.57 (s, 1H), 12.43 (s, 1H).

Step 2: Common Intermediate 2

POCl$_3$ (10.0 mL) was added to a mixture of Intermediate 1 (2.50 g, 6.56 mmol) in CH$_3$CN (80 mL). The mixture was allowed to stir at 90° C. for 6 h after which it was concentrated and taken up in water. The precipitate was filtered and dried (Na$_2$SO$_4$) to afford the title compound (2.50 g, 95%) as white solid. LCMS: 400.3 [M+1]$^+$. $^1$H NMR (400 MHz, DMSO-d$_6$): δ 3.65 (s, 3H), 3.98 (s, 6H), 7.04 (s, 1H), 8.09 (s, 1H), 9.08 (s, 1H).

Example 234: I-248

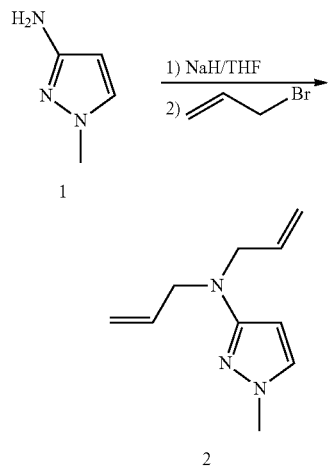

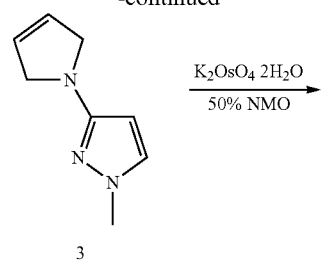

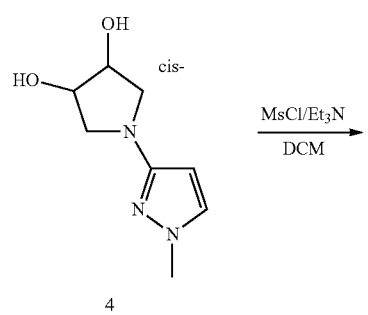

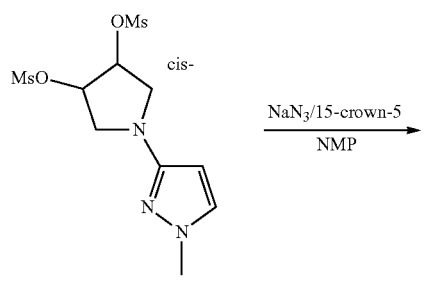

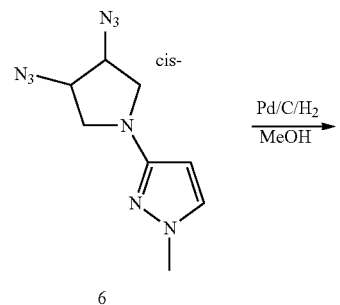

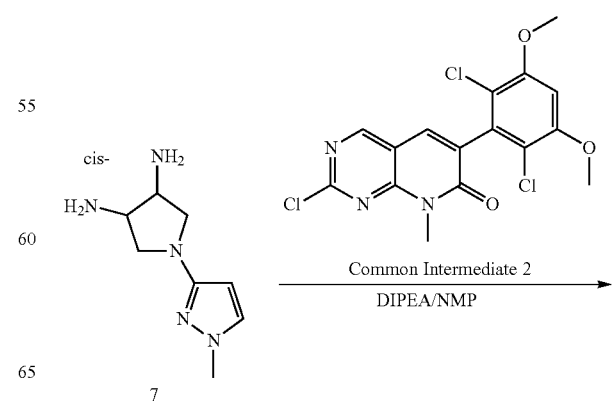

-continued

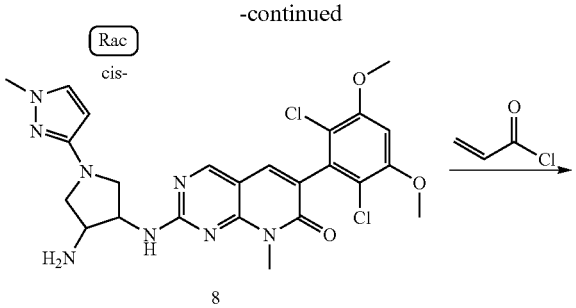

8

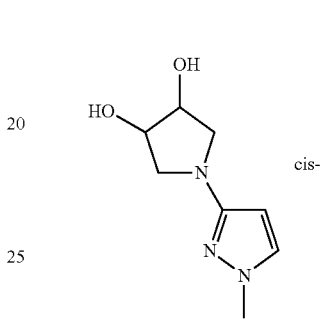

I-248

Step 1: Intermediate 2

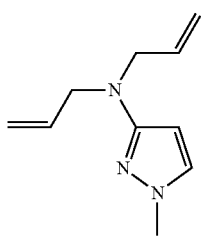

To a solution of 1-methyl-1H-pyrazol-3-amine (2.0 g, 20.6 mmol), 3-bromoprop-1-ene (5.25 g, 43.4 mmol) in dry THF (50 mL) was added NaH (60%, 1.73 g, 43.3 mmol) in portions at room temperature. The mixture was allowed to stir at 60° C. for 16 h. The mixture was cooled to room temperature and carefully quenched through dropwise addition of water with cooling. The reaction mixture was concentrated and extracted with EtOAc (50 mL×2). The combined organic layers were washed with brine (50 mL), dried over anhydrous Na₂SO₄ and concentrated. The crude product was purified by silica gel chromatography eluting with 50% EtOAc in hexanes to afford the title compound (2.07 g, 54%) as yellow oil.

Step 2: Intermediate 3

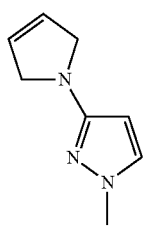

To a solution of Intermediate 2 (1.00 g, 5.65 mmol) in toluene (50 mL) was added Grubbs $2^{nd}$ generation catalyst (50 mg, 43.3 mmol). The mixture was allowed to stir at 95° C. for 16 h under nitrogen atmosphere after which it was cooled to room temperature and concentrated. The resultant residue was purified by silica gel chromatography eluting with 50% EtOAc in hexanes to afford the title compound (130 mg, 15%) as yellow oil. LCMS: 150.2 [M+1]⁺. ¹H NMR (400 MHz, CDCl₃): δ 3.61-3.64 (m, 2H), 3.75 (s, 3H), 3.77-3.82 (m, 2H), 5.26-5.29 (m, 2H), 5.46 (d, 1H), 7.15 (d, 1H).

Step 3: Intermediate 4

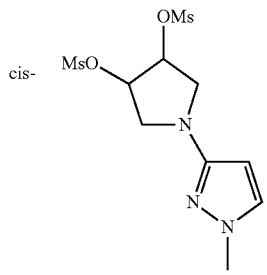 [SMILES: Cn1ccc(N2CC(OS(C)(=O)=O)C(OS(C)(=O)=O)C2)n1]

To a solution of Intermediate 3 (130 mg, 0.87 mmol) and K₂OsO₄ 2H₂O (38.0 mg, 0.10 mmol) in THF (50 mL) was added 50% NMO (306 mg, 1.31 mmol). The mixture was stirred at room temperature for 4 h. Na₂SO₃ (200 mg) was added and the reaction mixture was allowed to stir for an additional 30 min. The mixture was concentrated and the resultant residue was purified by silica gel chromatography eluting with 5% MeOH in DCM to afford the title compound (90 mg, 60%) as colorless oil. LCMS: 184.2 [M+1]⁺. ¹H NMR (400 MHz, CDCl₃): δ 3.27-3.30 (m, 2H), 3.70 (s, 3H), 3.47-3.51 (m, 2H), 4.28 (m, 2H), 5.41 (d, 1H), 7.09 (d, 1H).

Step 4: Intermediate 5

To a solution of Intermediate 4 (456 mg, 2.49 mmol) and Et₃N (754 mg, 7.47 mmol) in DCM (20 mL) was added MsCl (115 mg, 7.43 mmol) dropwise at 0° C. The mixture was stirred at 0° C. for 30 min. The mixture was quenched with H₂O (25 mL) and extracted with DCM (50 mL×2). The combined organic layers were washed with brine (50 mL), dried over anhydrous Na₂SO₄ and concentrated to afford the title compound (103 g) as light yellow solid which was used without further purification. LCMS: 340.2 [M+1]⁺.

Step 5: Intermediate 6

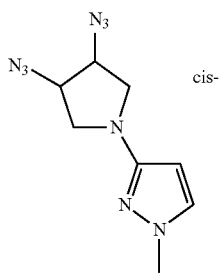 [SMILES: Cn1ccc(N2CC(N=[N+]=[N-])C(N=[N+]=[N-])C2)n1]

Intermediate 5 (103 mg, 3.03 mmol), NaN$_3$ (601 mg, 9.25 mmol), and 15-crown-5 (102 mg, 0.46 mmol) were combined in NMP (4 mL) and the resultant mixture was allowed to stir at 85° C. overnight. The mixture was cooled to room temperature and partitioned between EtOAc and water. The organic phase was washed with water, brine, dried over anhydrous Na$_2$SO$_4$, and concentrated to afford the title compound (905 mg) as light yellow oil which was used without further purification. LCMS: 234.2 [M+1]$^+$. $^1$H NMR (400 MHz, CDCl$_3$): δ 3.38-3.42 (m, 2H), 3.58-3.62 (m, 2H), 3.70 (s, 3H), 4.13-4.17 (m, 2H), 5.41 (d, 1H), 7.10 (d, 1H).

Step 6: Intermediate 7

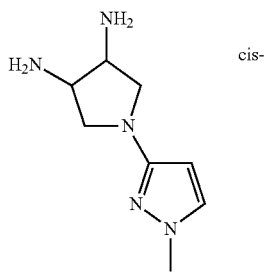

To a solution of Intermediate 6 (905 mg, 3.88 mmol) in MeOH (50 mL) was added 10% Pd/C (200 mg). The resultant suspension was degassed under vacuum and purged with H$_2$. The mixture was allowed to stir at room temperature for 16 h under hydrogen atmosphere. The suspension was filtered through a pad of Celite and washed with MeOH. The combined filtrates were concentrated to dryness to afford the title compound (682 mg, 97%) as light yellow oil. MS: 182.2[M+1

Step 7: Intermediate 8

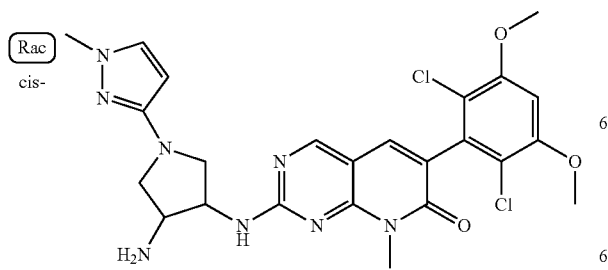

A mixture of Intermediate 7 (100 mg, 0.55 mmol), Common Intermediate 2 from Example 233 (148 mg, 0.37 mmol), and DIPEA (142 mg, 1.10 mmol) in NMP (10 mL) was degassed and purged with N$_2$. The resulting reaction mixture was heated at 100° C. for 1 h. The reaction mixture was cooled to room temperature and poured into ice-water. The resulting solid was filtered, washed with water and dried to afford the crude product, which was purified by silica gel chromatography eluting with 5% MeOH in DCM to afford the title compound (170 mg, 84%) as yellow solid. LCMS: 545.6 [M+1]$^+$. $^1$H NMR (400 MHz, CDCl$_3$): δ 3.27-3.35 (m, 2H), 3.63-3.67 (m, 1H), 3.73 (br, 3H), 3.75 (s, 3H), 3.77-3.81 (m, 2H), 3.95 (s, 6H), 4.67-4.68 (m, 1H), 5.49 (d, 1H), 6.63 (s, 1H), 7.14 (d, 1H), 7.42 (s, 1H), 8.47 (s, 1H).

Step 8: I-248

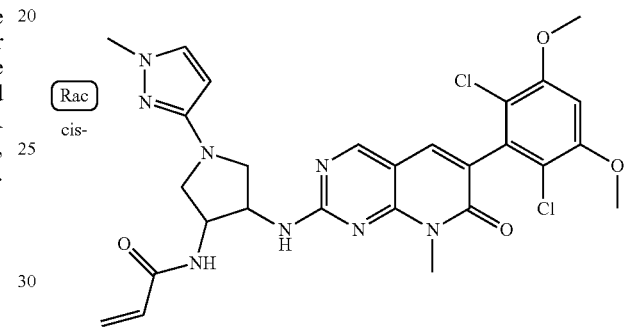

To a solution of Intermediate 8 (190 mg, 0.35 mmol), and DIPEA (90.0 mg, 0.70 mmol) in DCM (10 mL) was added acryloyl chloride (31.6 mg, 0.35 mmol) dropwise at 0° C. The mixture was stirred at 0° C. for 30 min. The mixture was quenched with water and extracted with DCM (50 mL×3). The combined organic layer was washed with brine (50 mL), dried over anhydrous Na$_2$SO$_4$ and concentrated. The residue was purified by silica gel chromatography eluting with 5% MeOH in DCM to afford the title compound (90.0 mg, 43%) as off-white solid. MS: 599.5 [M+1]$^+$. $^1$H NMR (400 MHz, CDCl$_3$): δ 3.38-3.46 (m, 2H), 3.71-3.76 (m, 7H), 3.81-3.85 (m, 1H), 3.95 (s, 6H), 4.91-4.93 (m, 2H), 5.51 (d, 1H), 5.63 (d, 1H), 6.03-6.10 (m, 1H), 6.28 (d, 1H), 6.35 (br, 1H), 6.63 (s, 1H), 7.17 (d, 1H), 7.40 (s, 1H), 8.45 (s, 1H).

Example 235: I-252

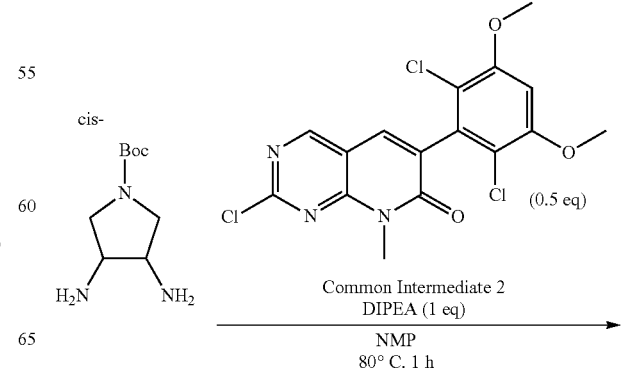

-continued

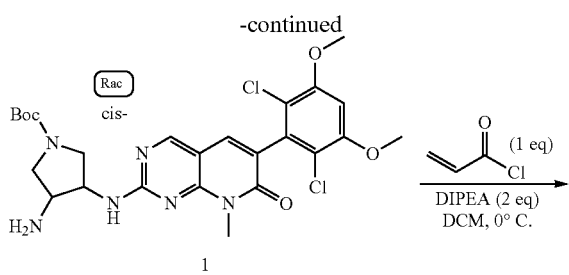

1

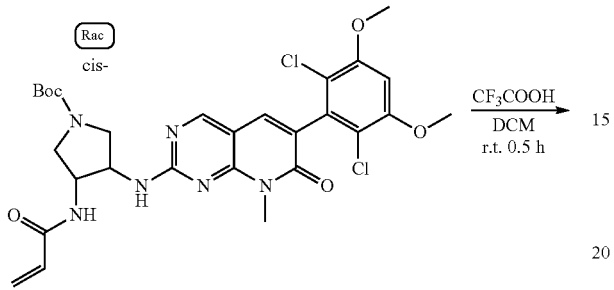

2

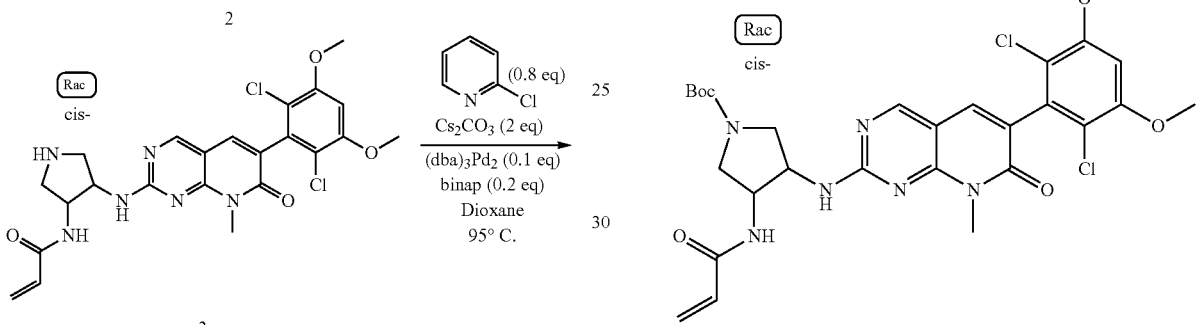

I-252

Step 1: Intermediate 1

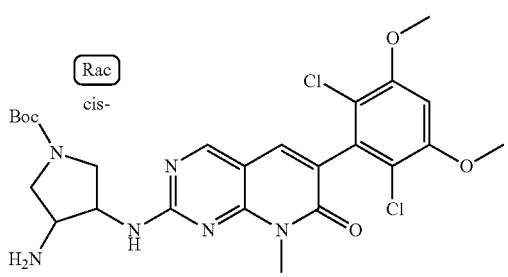 [SMILES: COc1cc(OC)c(Cl)c(-c2cc3cnc(NC4CN(C(=O)OC(C)(C)C)CC4N)nc3n(C)c2=O)c1Cl]

A mixture of Common Intermediate 2 from Example 233 (200 mg, 0.45 mmol), cis-tert-butyl 3,4-diaminopyrrolidine-1-carboxylate (180 mg, 0.90 mmol) and DIPEA (116. mg, 0.90 mmol) in NMP (4 mL) was heated at 80° C. under $N_2$ for 1 h. The mixture was cooled to room temperature and partitioned between EtOAc and water. The organic phase was separated, washed with water, brine, dried over anhydrous $Na_2SO_4$ and evaporated to afford the title compound (270 mg, 91%) as yellow solid.

Step 2: Intermediate 2

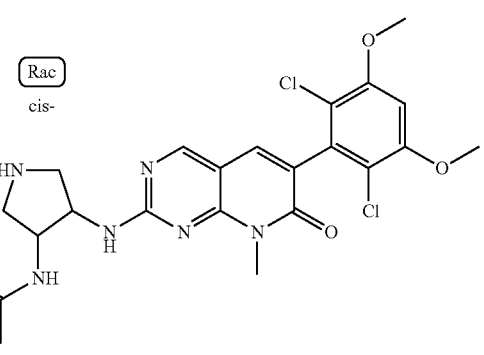

Acryloylation was carried out according the above scheme and as previously described to afford the title compound.

Step 3: Intermediate 3

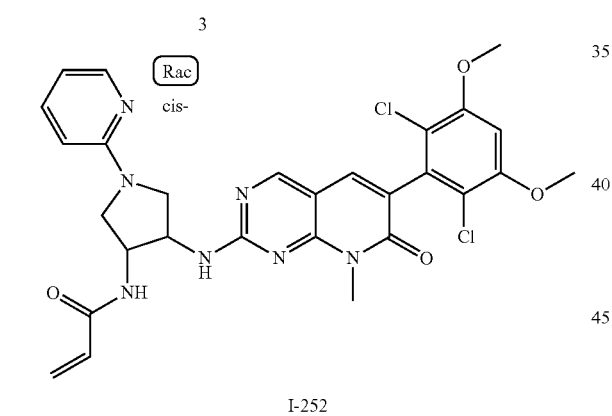

Boc deprotection was carried out according the above scheme and as previously described to afford the title compound.

Step 3: Intermediate 4

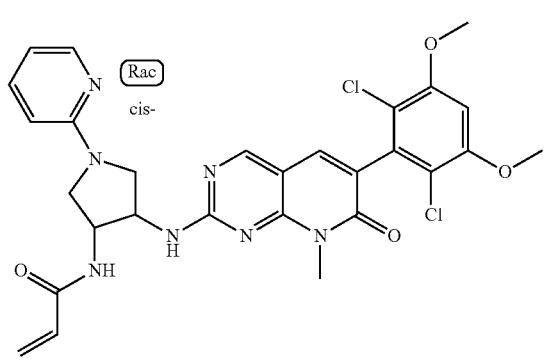

To a solution of Intermediate 3 (207 mg, 0.40 mmol) in 1,4-dioxane (8 mL) was added 2-chloropyridine (37.0 mg, 0.36 mmol), BINAP (46.0 mg, 0.08 mmol), Pd$_2$(dba)$_3$ (37.0 mg, 0.04 mmol) and Cs$_2$CO$_3$ (260 mg, 0.80 mg), and the mixture was stirred at 95° C. under N$_2$ overnight. The mixture was cooled to room temperature and partitioned between DCM and water. The organic phase was separated, washed with sat. NaHCO$_3$, dried over anhydrous Na$_2$SO$_4$, and subjected to column chromatography on silica gel (eluted with 5% MeOH in DCM) to afford the title compound (35.0 mg, 15%). LCMS: 596.1 [M+1]$^+$. $^1$H NMR (400 MHz, CDCl$_3$) δ 3.53 (dd, 1H), 3.61 (dd, 1H), 3.71 (s, 3H), 3.95 (s, 6H), 3.96-4.07 (m, 2H), 4.95 (s, 2H), 5.66 (d, 1H), 6.06 (dd, 1H), 6.30 (d, 1H), 6.41 (d, 1H), 6.61-6.67 (m, 2H), 7.41 (s, 1H), 7.48 (t, 1H), 8.18 (d, 1H), 8.46 (s, 1H).

Example 236: I-253

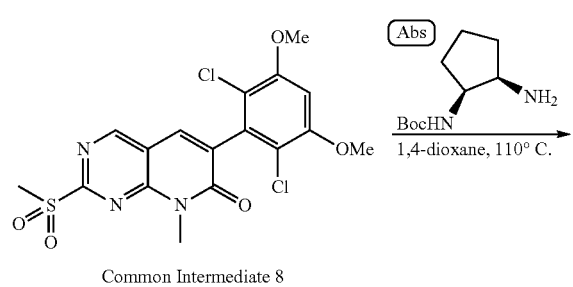

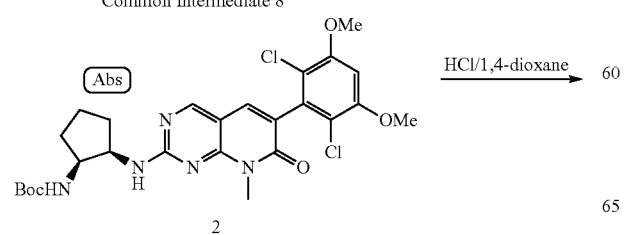

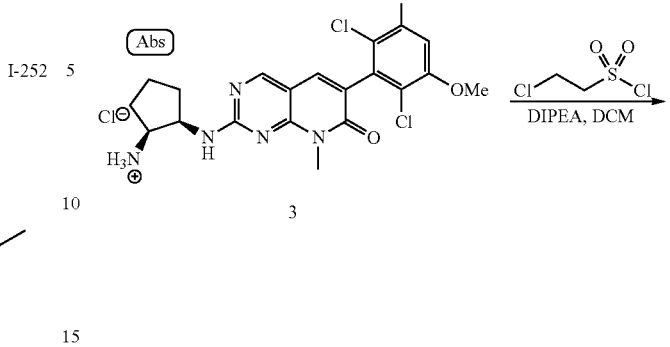

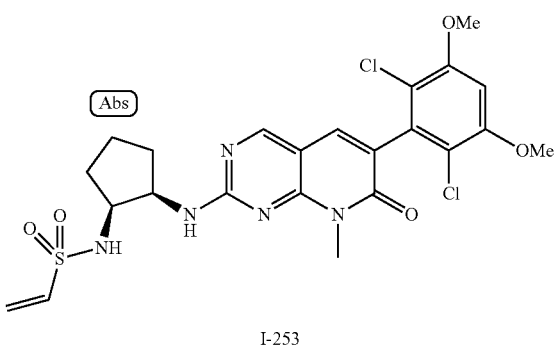

Step 1: Intermediate 2

Common Intermediate 8 from Example 223 (96.0 mg, 0.22 mmol) and tert-butyl ((1S,2R)-2-aminocyclopentyl) carbamate (200 mg, 1.00 nmol) were heated in 1,4-dioxane (2.0 mL) at 110° C. for 20 h. The reaction mixture was concentrated and purified by silica gel chromatography (0-100% EtOAc/Hexanes) to afford the title compound (120 mg, 97%). LCMS m/z: 564.2 [M+H]$^+$.

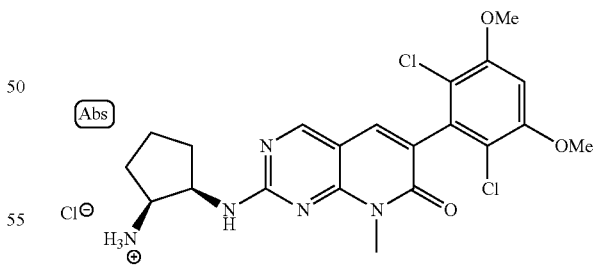

Step 2: Intermediate 3

Intermediate 2 (120 mg) was taken up in 4.0 M HCl/dioxane at room temperature and allowed to stir for 2 h after which the reaction mixture was evaporated to dryness and the resultant residue was used in the next step without further purification.

477

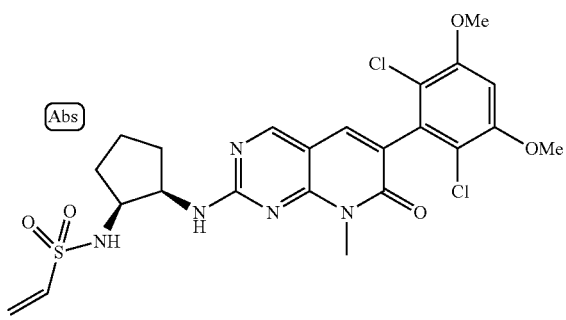 [SMILES: C=CS(=O)(=O)N[C@H]1CCC[C@H]1Nc1ncc2cc(-c3c(Cl)c(OC)cc(OC)c3Cl)c(=O)n(C)c2n1]

Step 3: I-253

To a solution of Intermediate 3 (23.0 mg, 0.046 mmol) in DCM (2.0 mL) was added DIPEA (100 uL) and 3-chloro-propane-1-sulfonyl chloride (8 uL, 0.066 mmol). The reaction mixture was stirred at room temperature for 4 h then concentrated and purified by prep-HPLC to afford the title compound, LCMS: 554.2 [M+H]+.

Example 237: I-255

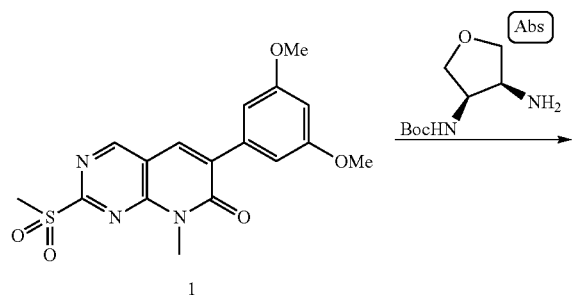

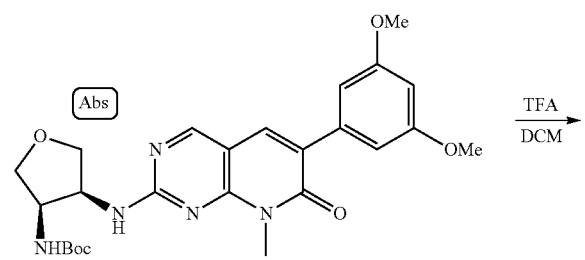

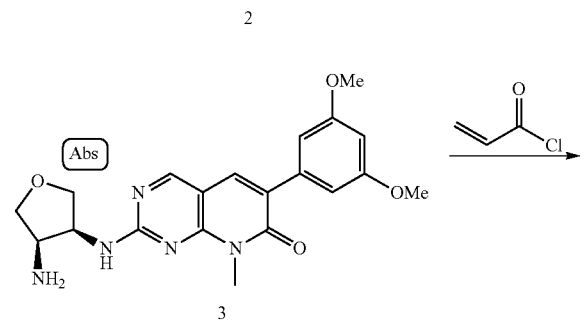

478

-continued

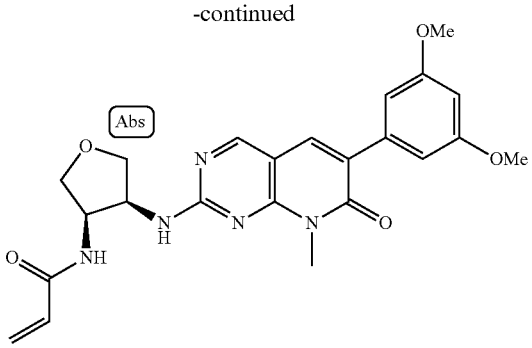

I-255

Step 1: Intermediate 2

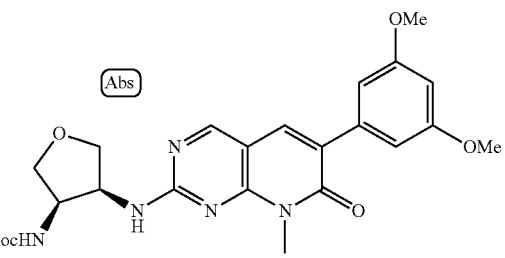

Intermediate 1 was prepared as described in Example 223 using 3 equiv of $SO_2Cl_2$ in step 6. Intermediate 1 (139 mg, 0.37 mmol), tert-butyl (3R,4S)-4-aminotetrahydrofuran-3-ylcarbamate which was prepared as described in Example 226 (112 mg, 0.55 mmol) and DIPEA (95.0 mg, 0.74 mmol) were taken up in NMP (6 mL) and heated to 80° C. for 1 h. The mixture was cooled to room temperature and partitioned between EtOAc and water. The organic phase was separated, washed with water, brine, dried over anhydrous $Na_2SO_4$, and concentrated. The resultant residue was purified through silica gel chromatography (10% MeOH in DCM) to afford the title compound (90.0 mg, 49%). LCMS: 498.6 [M+1]+. $^1$H NMR (400 MHz, $CDCl_3$): 1.38 (s, 9H), 2.00-2.04 (m, 1H), 2.36-2.40 (m, 1H), 3.73 (s, 3H), 3.95 (s, 6H), 3.83 (s, 6H), 4.23-4.27 (m, 1H), 4.51 (br, 1H), 4.76-4.81 (m, 1H), 4.90 (d, 1H), 6.48 (t, 1H), 6.82 (d, 2H), 7.63 (s, 1H), 8.49 (s, 1H).

Step 2: Intermediate 3

To a solution of Intermediate 2 (70.0 mg, 0.14 mmol) in DCM (2 mL) was added TFA (4 mL). The reaction mixture was stirred at room temperature for 1 h. The reaction mixture was concentrated to afford the title compound as yellow solid. LCMS: 398.4 [M+1]+

Step 3: I-255

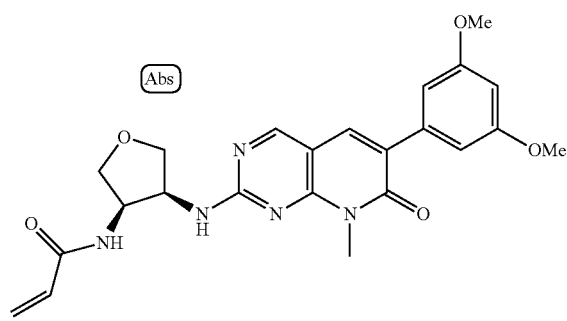 [SMILES: C=CC(=O)N[C@H]1COC[C@H]1Nc1ncc2cc(-c3cc(OC)cc(OC)c3)c(=O)n(C)c2n1]

To a solution of Intermediate 2, and DIPEA (39.0 mg, 0.30 mmol) in dry DCM (6 mL) was added a solution of acryloyl chloride (14.0 mg, 0.15 mmol) in dry DCM (1 mL) dropwise at −78° C. The reaction was allowed to stir for 10 minutes after which it was partitioned between DCM and H$_2$O. The organic phase was separated, washed with brine, and dried over Na$_2$SO$_4$. The resultant residue was purified through silica gel chromatography to afford the title compound (50.0 mg, 74%). LCMS: 452.4 [M+1]+. $^1$H NMR (400 MHz, CDCl$_3$): 3.72 (s, 3H), 3.75-3.79 (m, 8H), 4.18-4.21 (m, 1H), 4.25-4.29 (m, 1H), 4.83-4.88 (m, 2H), 5.63 (dd, 1H), 5.86 (br, 1H), 5.98-6.05 (m, 2H), 6.26 (dd, 1H), 6.49 (t, 1H), 6.81 (d, 2H), 7.62 (s, 1H), 8.49 (s, 1H).

Example 238: I-256

Step 1: Intermediate 2

To a solution of Intermediate 1 (120 mg, 0.207 mmol) in DCM (5 mL) was added m-CPBA (89.0 mg, 0.517 mmol) at 25° C. The mixture was allowed to stir at 25° C. for 5 h after which it was concentrated and the resultant residue purified by silica gel chromatography (5% MeOH in DCM) to give the title compound (40.0 mg, 31%) as a white solid. LCMS: 614.5 [M+1]+.

Step 2: Intermediate 3

To a solution of Intermediate 2 (40.0 mg, 0.065 mmol) in DCM (4 mL) was added TFA (4 mL) at 25° C. and the

Step 3: I-256

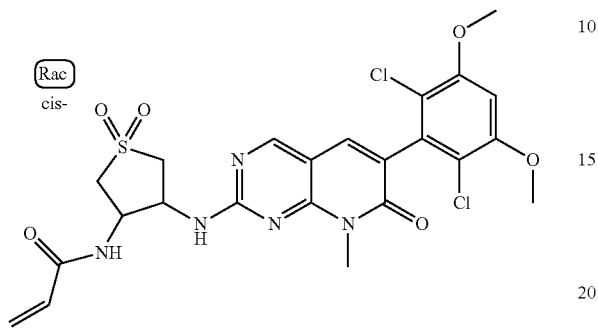

To a solution of Intermediate 3 (33.5 mg, 0.065 mmol) in THF (20 mL) at −20° C. was added acryloyl chloride (6.48 mg, 0.072 mmol). The mixture was allowed to stir at −20° C. for 30 minutes after which it was quenched with water and extracted with EtOAc. The combined organic layers were washed with brine (50 mL), dried over anhydrous $Na_2SO_4$ and concentrated. The resultant residue was purified through silica gel chromatography (5% MeOH in DCM) to give the title compound (13.5 mg, 36%) as white solid. LCMS: 568.5 [M+1]. $^1$H NMR (400 MHz, DMSO-$d_6$): δ 3.42-3.59 (m, 1H), 3.65 (s, 3H), 3.67-3.77 (m, 3H), 3.96 (s, 6H), 5.00-5.09 (m, 3H), 5.60-5.62 (m, 1H), 6.09-6.23 (m, 3H), 6.97 (s, 1H), 7.75 (s, 1H), 8.72 (s, 1H).

Example 239: I-257

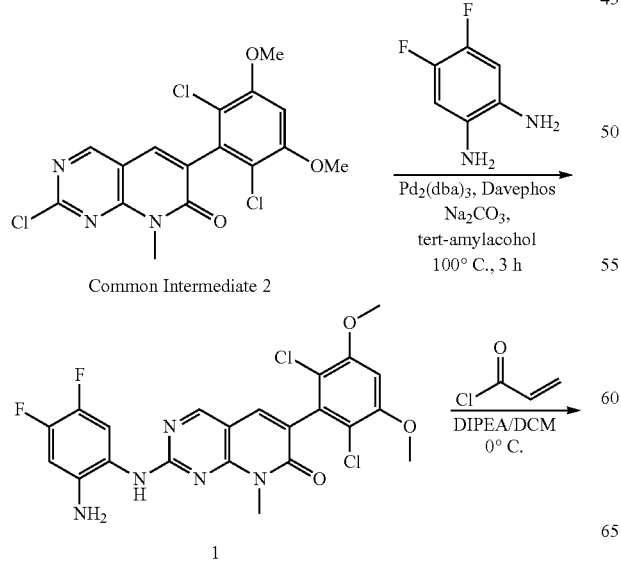

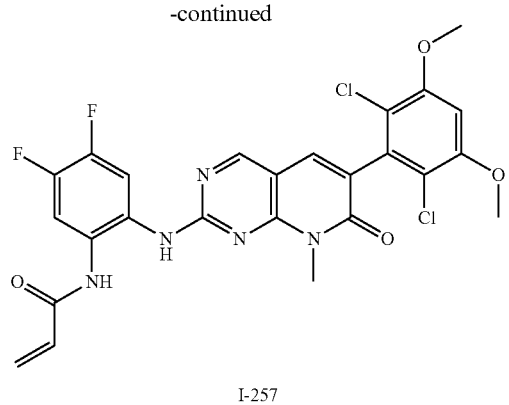

I-257

Step 1: Intermediate 1

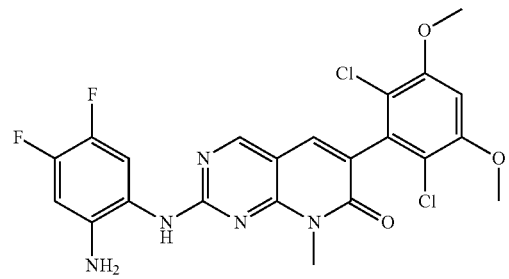 [SMILES: COc1cc(OC)c(Cl)c(-c2cc3cnc(Nc4cc(F)c(F)cc4N)nc3n(C)c2=O)c1Cl]

A mixture of Common Intermediate 2 from Example 233 (100 mg, 0.28 mmol), 4,5-difluorobenzene-1,2-diamine (48.0 mg, 0.34 mmol), $Pd_2(dba)_3$ (50.0 mg, 0.05 mmol), Davephos (43.0 mg, 0.11 mmol) and $Na_2CO_3$ (206 mg, 1.95 mmol) in tert-amyl alcohol (4 mL) was heated at 100° C. for 3 h under a nitrogen atmosphere. The reaction mixture was cooled to room temperature and diluted with water (25 mL). The resultant mixture was extracted with DCM. The combined organic layers were washed with brine (20 mL), dried over anhydrous $Na_2SO_4$ and concentrated. The resultant residue was purified by silica gel column chromatography (eluted with 1-2% MeOH in DCM) to afford the title compound (25 mg, 18%). LCMS: 508.4 [M+H]$^+$. $^1$H NMR (400 MHz, CDCl$_3$): δ 10.88 (s, 1H), 9.28 (d, 1H), 8.74 (s, 1H), 8.60 (s, 1H), 7.92 (d, 1H), 7.58 (s, 1H), 6.66 (s, 1H), 3.96 (s, 6H), 3.84 (s, 3H).

Step 2: I-257

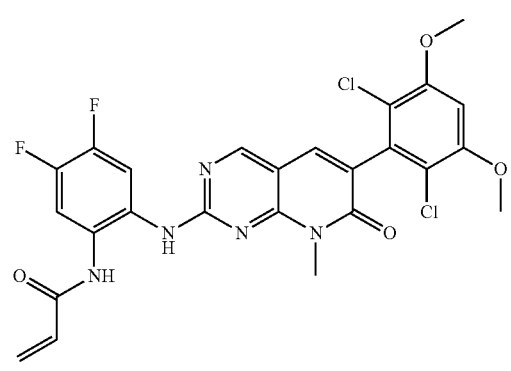 [SMILES: C=CC(=O)Nc1cc(F)c(F)cc1Nc1ncc2cc(-c3c(Cl)c(OC)cc(OC)c3Cl)c(=O)n(C)c2n1]

Acryloyl chloride (5.30 mg, 0.06 mmol) was added to a mixture of Intermediate 1 (30.0 mg, 0.05 mmol), DIPEA (14.2 mg, 0.05 mmol) in DCM (10 mL) at 0° C. and the resultant mixture was allowed to stir at 0° C. for 10 min. The reaction was quenched with water and the aqueous mixture extracted with EtOAc. The combined organic layers were washed with brine, dried (Na$_2$SO$_4$), filtered and concentrated. The resultant residue was purified by silica gel column chromatography (eluted with 2-5% MeOH in DCM) to afford the title compound as white solid (12.1 mg, 42%). LCMS: 562.5 [M+H]$^+$. $^1$H NMR (400 MHz, CDCl$_3$): δ 8.53 (s, 1H), 7.94 (s, 1H), 7.83 (t, 1H), 7.68-7.62 (m, 1H), 7.48 (s, 1H), 6.64 (s, 1H), 6.48 (d, 1H), 6.27 (q, 1H), 5.81 (d, 1H), 3.95 (s, 6H), 3.69 (s, 3H).

Example 240: I-258

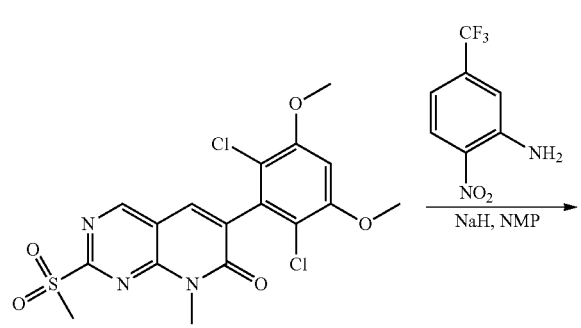

Common Intermediate 8

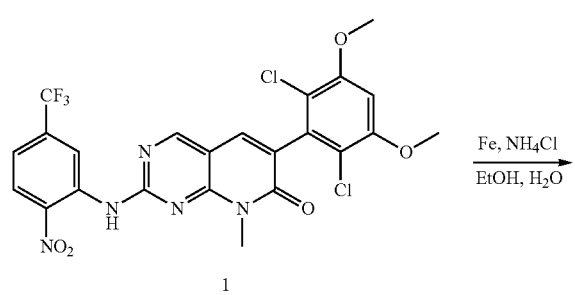

1

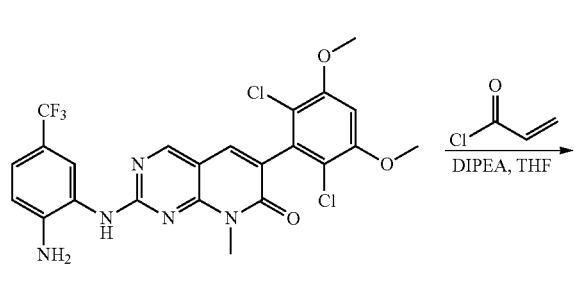

2

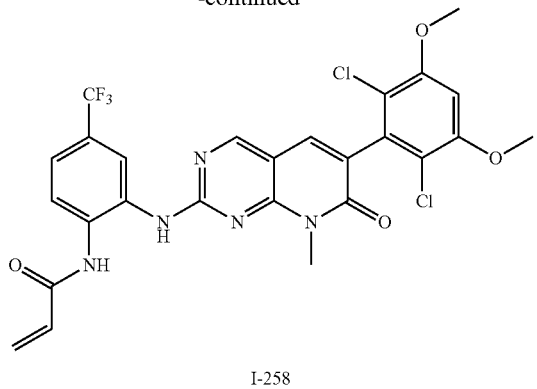

I-258

Step 1: Intermediate 1

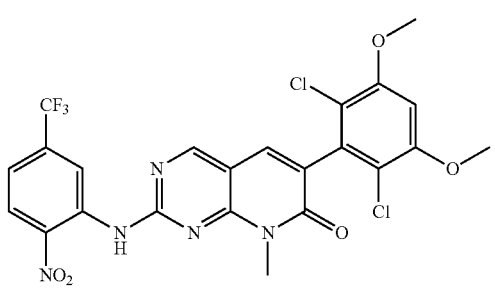 [SMILES: COc1cc(OC)c(Cl)c(-c2cc3cnc(Nc4cc(C(F)(F)F)ccc4[N+](=O)[O-])nc3n(C)c2=O)c1Cl]

To a solution of 2-nitro-5-(trifluoromethyl)aniline (100 mg, 0.23 mmol) in NMP (10 mL) was added dropwise NaH (5.40 mg, 0.23 mmol) at 25° C. The mixture was stirred at 25° C. for 0.5 h. Common Intermediate 8 from Example 223 (100 mg, 0.23 mmol) was added and the resultant mixture stirred at 100° C. for 1 h. The reaction was quenched with water, extracted with EtOAc and the combined organic layers washed with brine, dried (Na$_2$SO$_4$), filtered and concentrated in vacuo to afford the title compound (100 mg, 78%) as yellow solid.

Step 2: Intermediate 2

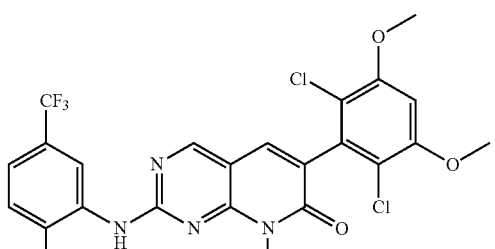

A mixture of Intermediate 1 (100 mg, 0.17 mmol), Fe (59.0 mg, 1.05 mmol), and NH$_4$Cl (57.0 mg, 1.05 mmol) in EtOH (10 mL)/water (10 mL) was refluxed for 1 h. The solid was removed by filtration and the filtrate concentrated. The resultant residue was exacted with EtOAc and the combined organic layers washed with brine, dried over anhydrous Na₂SO₄ and concentrated. The residue was purified by column chromatography on silica gel (eluted with 2-5% MeOH in DCM) to afford the title compound (10.0 mg, 11%) as yellow solid. LCMS: 540.5 [M+H]⁺.

Step 3: I-258

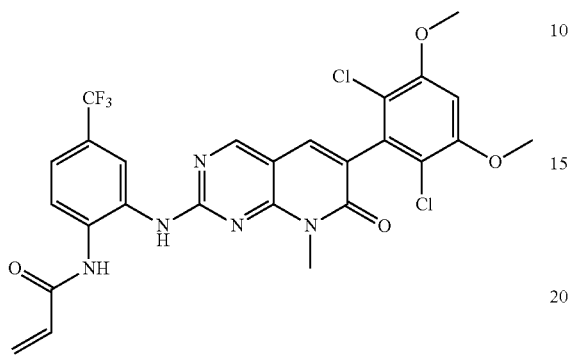

A mixture of Intermediate 2 (10.0 mg, 0.02 mmol), DIPEA (4.70 mg, 0.04 mmoL) in THF (10 mL) was stirred at 25° C. Acryloyl chloride (2.00 mg, 0.02 mmol) was added at 0° C. and the resulting mixture allowed to stir at 0° C. for 10 min. The reaction was quenched with water and extracted with EtOAc. The combined organic layers were washed with brine, dried (Na₂SO₄), filtered and concentrated in vacuo. The residue was purified by column chromatography on silica gel (eluted with 2-5% MeOH in DCM) to afford the title compound as yellow solid (4.60 mg, 42%). LCMS: 594.5 [M+H]⁺. ¹H NMR (400 MHz, CD₃OD): δ 8.65 (s, 1H), 8.29 (s, 1H), 7.72 (d, 1H), 7.62 (s, 1H), 7.40 (d, 1H), 6.78 (s, 1H), 6.45-6.31 (m, 2H), 5.73 (d, 1H), 3.86 (s, 6H), 3.56 (s, 3H).

Example 241: I-259

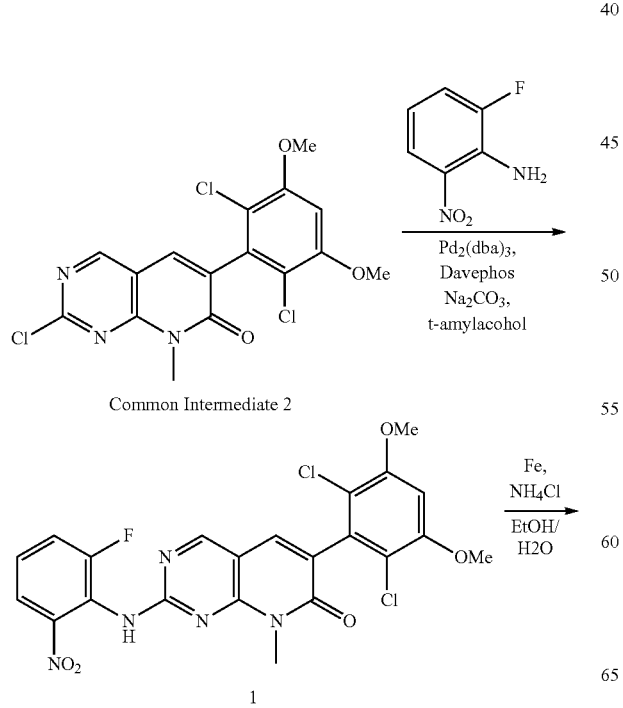

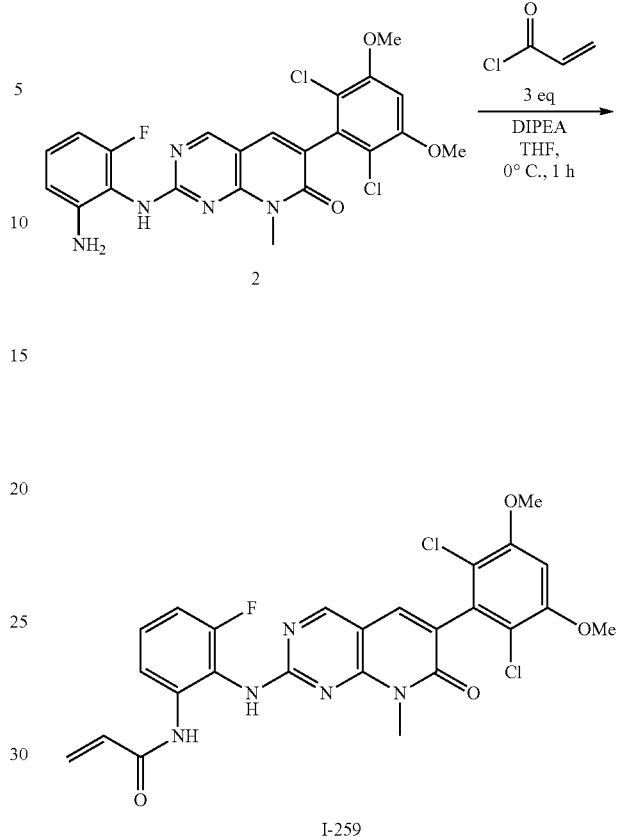

Step 1: Intermediate 1

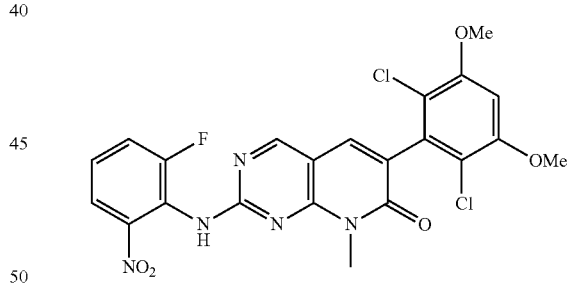

A mixture of Common Intermediate 2 from Example 233 (50.0 mg, 0.13 mmol), 2-fluoro-6-nitroaniline (23.5 mg, 0.15 mmol), Pd₂(dba)₃ (24.0 mg, 0.026 mmol), Davephos (20.0 mg, 0.052 mmol), and Na₂CO₃ (96.0 mg, 0.91 mmol) in tert-amyl alcohol (2 mL) was heated at 100° C. for 4 h under N₂ atmosphere. The reaction mixture was cooled to room temperature and partitioned between DCM and water. The organic layer was separated, washed with brine, dried over anhydrous Na₂SO₄ and concentrated. The resultant residue was purified by prep-TLC to afford the title compound (20.0 mg, 31%). LCMS: 520.4 [M+1]⁺.

487
Step 2: Intermediate 2

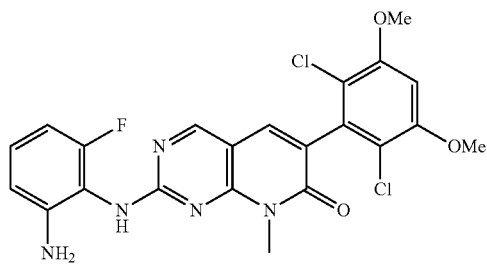 [SMILES: COc1cc(OC)c(Cl)c(-c2cc3cnc(Nc4c(N)cccc4F)nc3n(C)c2=O)c1Cl]

488
Step 3: I-259

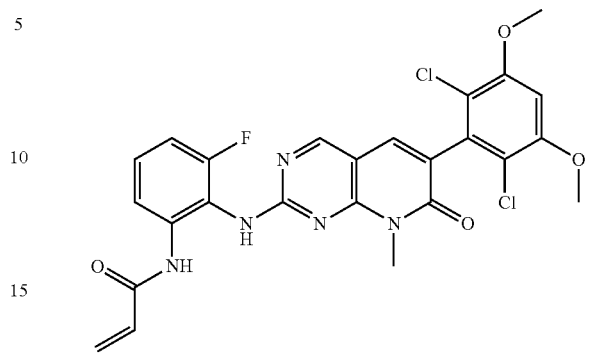

A mixture of Intermediate 1 (20.0 mg, 0.038 mmol), Fe (13.0 mg, 1.40 mmol) and NH$_4$Cl (80.0 mg, 1.40 mmol) in EtOH/H$_2$O (10/10 ml) was heated to 80° C. and stirred for 4 hours. The suspension was filtered and the filtrate concentrated. The resultant residue was purified by prep-TLC to give the product (10.0 mg, 53%) as a yellow solid. LCMS: 490.4 [M+1]$^+$.

Acryloylation of Intermediate 2 was carried out as described in previous examples to afford the title compound. LCMS: 544.5 [M+1]$^+$. $^1$H NMR (400 MHz, CD$_3$OD): δ 3.45 (s, 3H), 3.86 (s, 6H), 5.64-5.67 (m, 1H), 6.24-6.29 (m, 1H), 6.33-6.40 (m, 1H), 6.78 (s, 1H), 6.98-7.03 (m, 1H), 7.22-7.27 (m, 1H), 7.55 (d, 1H), 7.60 (s, 1H), 8.58 (s, 1H).

Example 242: I-265

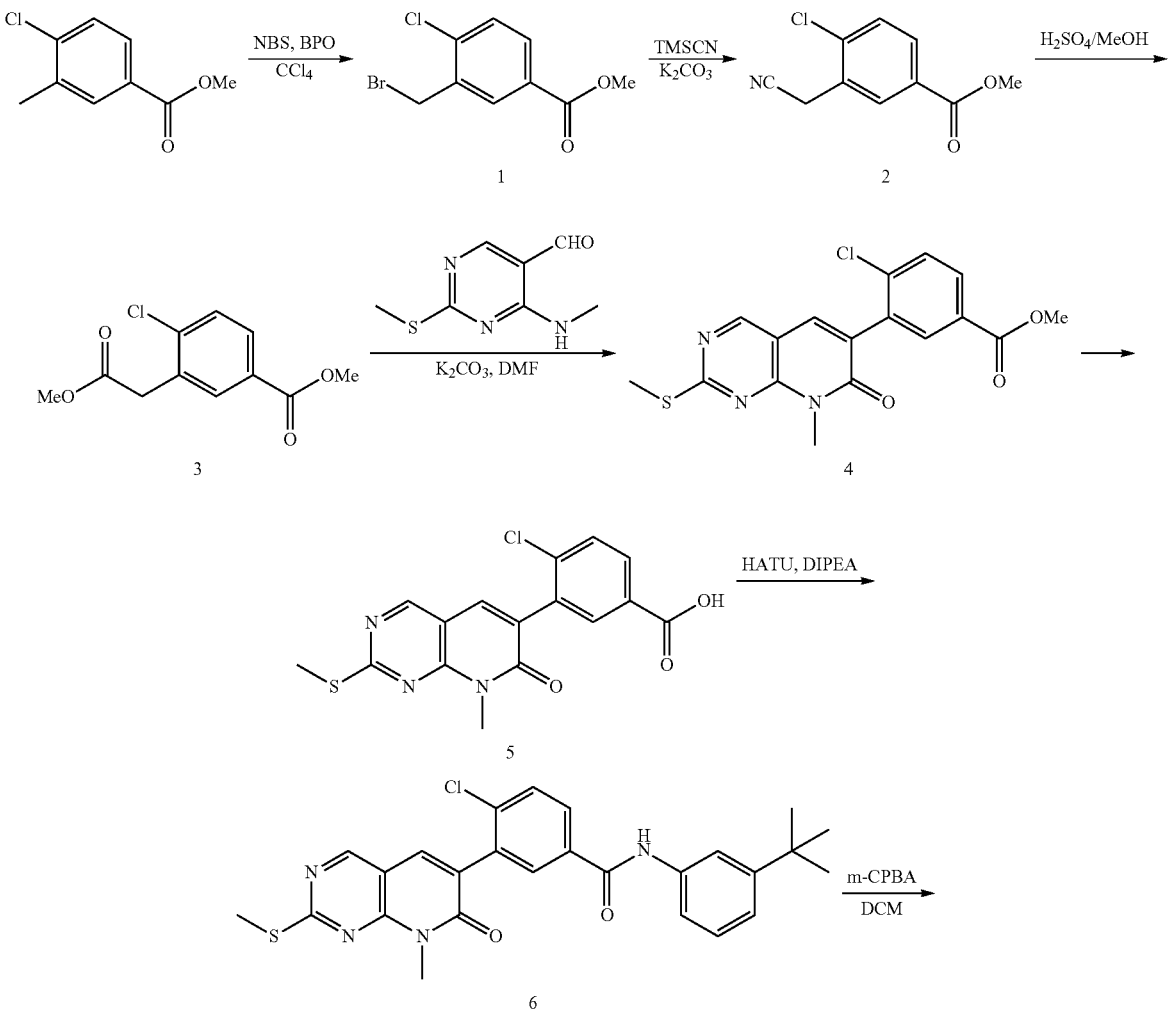

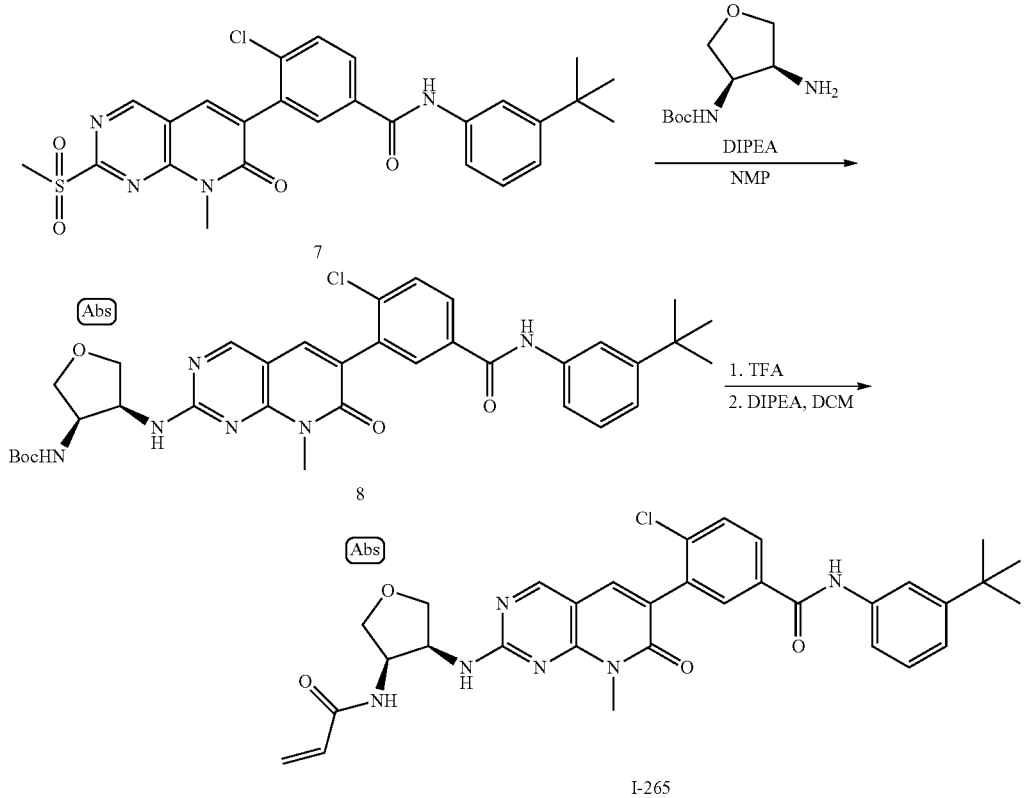

Step 1: Intermediate 1

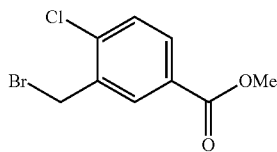 [SMILES: COC(=O)c1ccc(Cl)c(CBr)c1]

A mixture of methyl 4-chloro-3-methylbenzoate (4.00 g, 24.0 mmol), n-bromosuccinimide (NBS, 4.30 g, 24.0 mmol) and benzoyl peroxide (BPO, 0.58 g, 2.40 mmol) in CCl$_4$ (50 mL) was refluxed for 4 h. The mixture was cooled to room temperature, filtered and the filtrate was concentrated. The resultant residue was purified by column chromatography on silica gel (eluted with 2-5% EtOAc in hexane) to afford the title compound (2.70 g, 43%) as white solid. $^1$H NMR (400 MHz, CDCl$_3$): δ 8.12 (d, 1H), 7.92 (dd, Hz, 1H), 7.47 (d, 1H), 4.61 (s, 2H), 3.93 (s, 3H).

Step 2: Intermediate 2

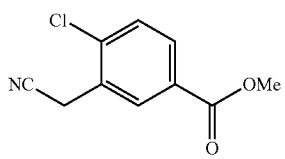 [SMILES: COC(=O)c1ccc(Cl)c(CC#N)c1]

A mixture of Intermediate 1 (1.00 g, 3.80 mmol), TMSCN (0.56 g, 5.69 mmol) and K$_2$CO$_3$ (786 mg, 5.69 mmol) in CH$_3$CN (50 mL) was refluxed for 16 h. The mixture was cooled to room temperature, filtered and the filtrate was concentrated. The resultant residue was purified by column chromatography on silica gel (eluted with 5-10% EtOAc in hexane) to afford the title compound (590 mg, 75%) as white solid. $^1$H NMR (400 MHz, CDCl$_3$): δ 8.18 (d, 1H), 7.99 (dd, 1H), 7.52 (d, 1H), 3.94 (s, 3H), 3.88 (s, 2H).

Step 3: Intermediate 3

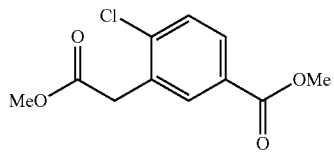 [SMILES: COC(=O)Cc1cc(C(=O)OC)ccc1Cl]

To a solution of Intermediate 2 (920 mg, 4.41 mmol) in MeOH (10 mL) was added H$_2$SO$_4$ (4 mL) at 25° C. The mixture was allowed to stir at 60° C. for 16 h. The mixture was basified with saturated aqueous Na$_2$CO$_3$ to pH 8 and extracted with DCM. The combined organic layers were dried over anhydrous Na$_2$SO$_4$ and concentrated to afford the title compound as off-white solid (910 mg, 86%). $^1$H NMR (400 MHz, CDCl$_3$): δ 7.97 (d, 1H), 7.46 (d, 1H), 7.90 (dd, 1H), 3.91 (s, 3H), 3.83 (s, 2H), 3.72 (s, 3H).

Step 4: Intermediate 4

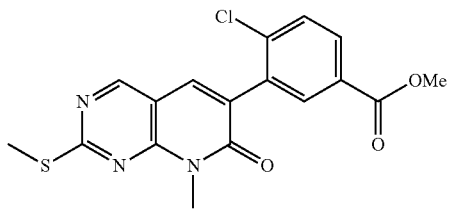 [SMILES: COC(=O)c1ccc(Cl)c(-c2cc3cnc(SC)nc3n(C)c2=O)c1]

To a solution of Intermediate 3 (270 mg, 1.11 mmol) and 4-(methylamino)-2-(methylthio)pyrimidine-5-carbaldehyde (204 mg, 1.11 mmol) in DMF (10 mL) was added $K_2CO_3$ (307 mg, 2.22 mmol) at 25° C. The mixture was stirred at 110° C. for 4 h after which water was added and the precipitate collected through filtration to afford the title compound (320 mg, 77%). LCMS: 376.3 [M+H]$^+$.

Step 5: Intermediate 5

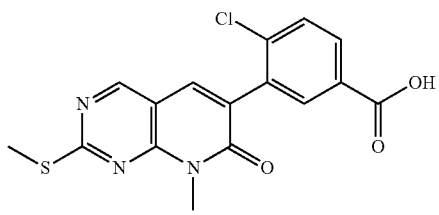 [SMILES: CSc1ncc2cc(-c3cc(C(=O)O)ccc3Cl)c(=O)n(C)c2n1]

To a solution of Intermediate 4 (320 mg, 0.85 mmol) in THF (10 mL) was added 5 M NaOH (5 mL). The mixture was allowed to stir at room temperature for 4 h after which it was basified with 1M HCl to pH=6 and the solid collected by filtration to provide the title compound (150 mg, 49%).

Step 6: Intermediate 6

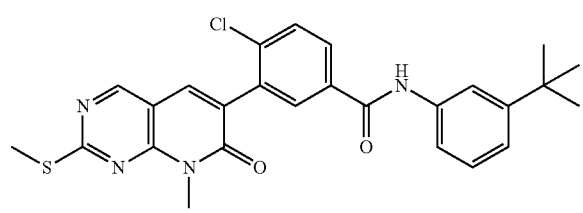 [SMILES: CSc1ncc2cc(-c3cc(C(=O)Nc4cccc(C(C)(C)C)c4)ccc3Cl)c(=O)n(C)c2n1]

To a solution of Intermediate 5 (180 mg, 0.50 mmol), HATU (87.0 mg, 0.23 mmol) and 3-tert-butylaniline (67.4 mg, 0.45 mmol) in DMF (20 mL), DIPEA (117 mg, 0.90 mmol) was added dropwise at room temperature. The mixture was allowed to stir at 40° C. for 4 h after which it was partitioned between EtOAc and $H_2O$. The organic phase was washed with brine, dried over $Na_2SO_4$, concentrated, and the resultant residue purified by column chromatography on silica gel (eluted with 5-10% EtOAc in hexanes) to afford the title compound (100 mg, 41%) as yellow powder. LCMS: 493.5 [M+1]$^+$.

Step 7: Intermediate 7

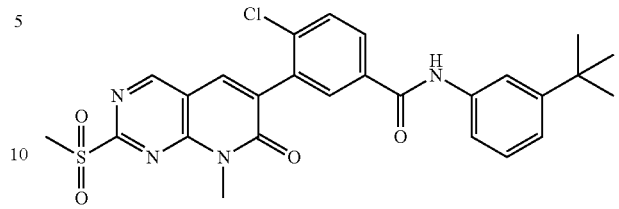

To a solution of Intermediate 6 (100 mg, 0.20 mmol) in DCM (10 mL) was added m-CPBA (87 mg, 0.51 mmol) at 0° C. The mixture was stirred at rt for 16 h. The mixture was partitioned between EtOAc and $H_2O$. The organic phase was washed with brine, dried over $Na_2SO_4$, concentrated, the crude product was purified by column chromatography on silica gel (eluted with 2-5% MeOH in DCM) to afford the title compound (80 mg, 75%) as yellow powder.

Step 8: Intermediate 8

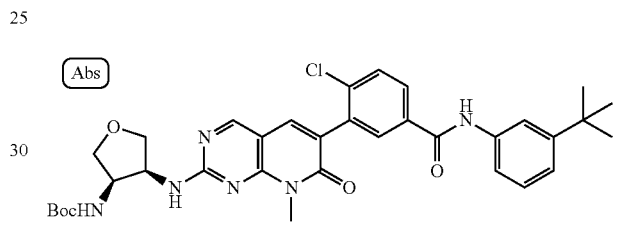

A solution of Intermediate 7 (80.0 mg, 0.15 mmol), tert-butyl (3R,4S)-4-aminotetrahydrofuran-3-ylcarbamate prepared as described in Example 226 (61.0 mg, 0.30 mmol) and DIPEA (39.0 mg, 0.30 mmol) in NMP was degassed and purged with $N_2$. The mixture was allowed to stir at 80° C. for 1 h after which it was partitioned between EtOAc and $H_2O$. The organic layer was washed with brine, dried over $Na_2SO_4$, concentrated, and the resultant residue purified by column chromatography on silica gel (eluted with 2-5% MeOH in DCM) to afford the title compound (30.0 mg, 31%). LCMS: 647.7 [M+1]$^+$.

Step 9: I-265

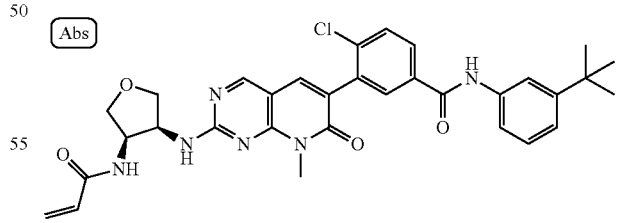

A solution of Intermediate 8 (30.0 mg, 0.05 mmol) in DCM (2 mL) and TFA (2 mL) was stirred at 25° C. for 1 h. The mixture was concentrated and the pH adjusted to >7 with DIPEA. To the mixture was added acryloyl chloride (4.20 mg, 0.05 mmol) at 0° C. The reaction mixture was allowed to stir for an additional 10 min after which it was quenched with saturated aqueous $NaHCO_3$ (25 mL) and extracted with DCM. The combined organic layers were washed with brine, dried over anhydrous Na₂SO₄ and concentrated. The resultant residue was purified by column chromatography on silica gel (eluted with 5-10% MeOH in DCM) to afford the title compound (7.50 mg, 25%) as yellow solid. LCMS: 601.6 [M+H]⁺. ¹H NMR (400 MHz, CDCl₃): δ 9.81 (s, 1H), 8.27 (s, 1H), 8.01 (s, 1H), 7.85 (d, 2H), 7.61-7.55 (m, 3H), 7.50 (d, 1H), 7.30 (t, 1H), 7.20 (d, 1H), 6.62 (s, 1H), 6.26 (d, 1H), 6.14 (q, 1H), 5.67 (d, 1H), 5.04-4.96 (m, 1H), 4.91-4.88 (m, 1H), 4.24-4.17 (m, 2H), 3.96-3.93 (m, 1H), 3.88-3.83 (m, 1H), 3.72 (s, 3H), 1.32 (s, 9H).

Example 243: I-269

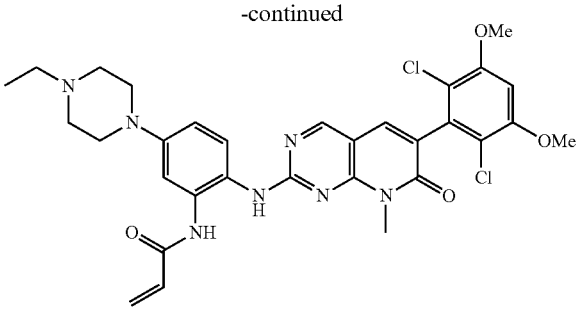

I-269

Step 1: Intermediate 1

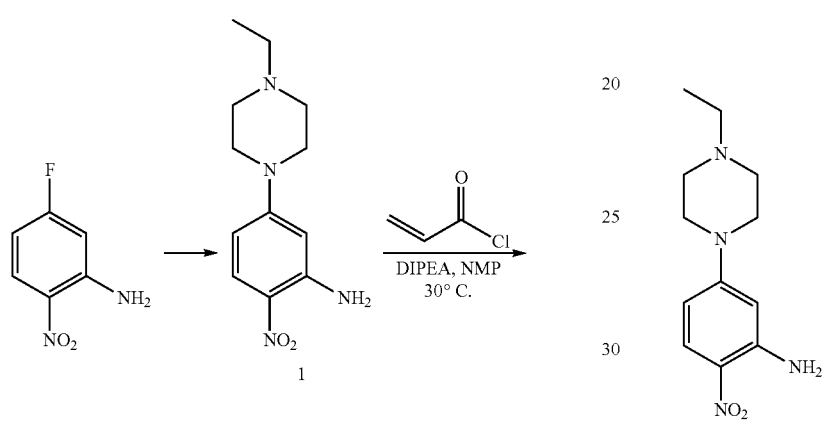

A mixture of 5-fluoro-2-nitroaniline (2.00 g, 12.8 mmol), 1-ethylpiperazine (1.60 g, 14.1 mmol) and K₂CO₃ (2.65 g, 119.2 mmol) in DMSO (50 mL) was stirred at 100° C. for 12 h. The reaction mixture was partitioned between EtOAc and H₂O, the organic layer washed with brine, dried (Na₂SO₄), filtered and concentrated in vacuo. The resulting residue was purified through silica gel (DCM:MeOH=30:1) to afford the title compound as yellow solid (1.40 g, 44%).

Step 2: Intermediate 2

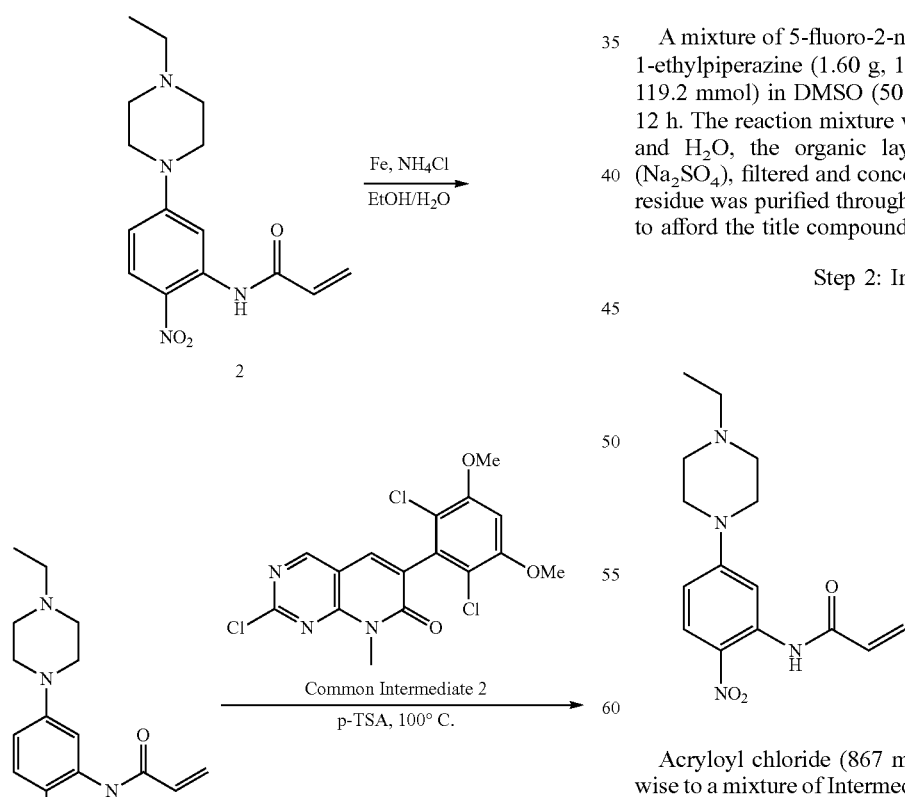

Acryloyl chloride (867 mg, 9.6 mmol) was added dropwise to a mixture of Intermediate 1 (400 mg, 1.60 mmol) and DIPEA (2.06 g, 16.0 mmol) in NMP (10 mL). The reaction mixture was stirred at 30° C. for 12 h. The reaction mixture was partitioned between EtOAc and H₂O, the combined organic layer was washed with brine, dried (Na₂SO₄), filtered and concentrated in vacuo to afford Intermediate 2 as yellow oil (400 mg, crude). LCMS: 305.4 [M+1]. 1H NMR (400 MHz, DMSO-d$_6$): δ 1.03 (t, 3H), 2.36 (q, 2H), 3.47-3.49 (m, 4H), 3.41-3.44 (m, 4H), 5.84-5.87 (m, 1H), 6.27-6.31 (m, 1H), 6.50-6.56 (m, 1H), 6.84 (dd, 1H), 7.75 (d, 1H), 8.01 (d, 1H), 10.65 (s, 1H).

Step 3: Intermediate 3

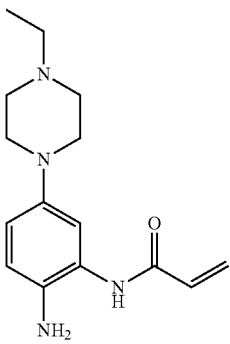 [SMILES: C=CC(=O)Nc1cc(N2CCN(CC)CC2)ccc1[N+](=O)[O-]]

Intermediate 2 from the previous step, Fe (1.16 g, 20.7 mmol) and NH$_4$Cl (1.12 g, 20.7 mmol) were taken up in EtOH/H$_2$O (20 mL/10 mL) and allowed to stir at 75° C. for 2 h after which the reaction mixture was cooled, filtered, and the precipitate washed with MeOH. The filtrate was concentrated in vacuo then partitioned between EtOAc and aq. NaHCO$_3$. The organic layer was washed with brine, dried (Na$_2$SO$_4$), filtered and concentrated. The resultant residue was purified by silica gel chromatography (DCM:MeOH:NH$_4$OH=400:8:4) to afford the title compound as yellow solid (200 mg, 22%). LCMS: 275.4 [M+1]$^+$.

Step 4: I-269

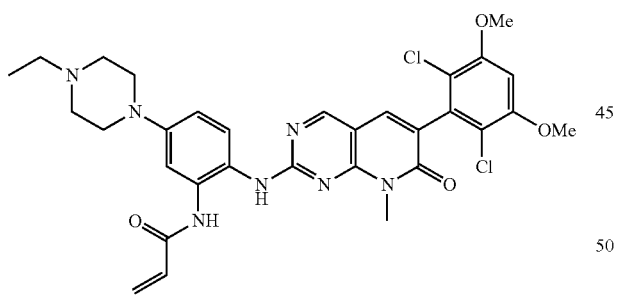

A mixture of Intermediate 3 (200 mg, 0.73 mmol), Common Intermediate 2 from Example 233 (290 mg, 0.73 mmol) and p-toluenesulfonic acid (62.0 mg, 0.36 mmol) in 1,4-dioxane (10 mL) was stirred at 100° C. for 12 h under N$_2$. The reaction mixture was partitioned between EtOAc and aq. NaHCO$_3$ and the organic layer washed with brine, dried (Na$_2$SO$_4$), filtered and concentrated in vacuo. The resultant residue was purified by reverse phase prep-HPLC to afford the title compound as yellow solid (29.2 mg, 6%). LCMS: 638.6 [M+1]$^+$. $^1$H NMR (400 MHz, CDCl$_3$): δ 1.43 (t, 3H), 3.12-3.15 (m, 2H), 3.24-3.33 (m, 4H), 3.63 (s, 3H), 3.70-3.73 (m, 2H), 3.91-3.98 (m, 8H), 5.79 (dd, 1H), 6.37-6.52 (m, 2H), 6.91 (s, 1H), 7.02 (dd, 1H), 7.43 (s, 1H), 7.68-7.70 (m, 2H), 8.70 (s, 1H).

Example 244: I-274

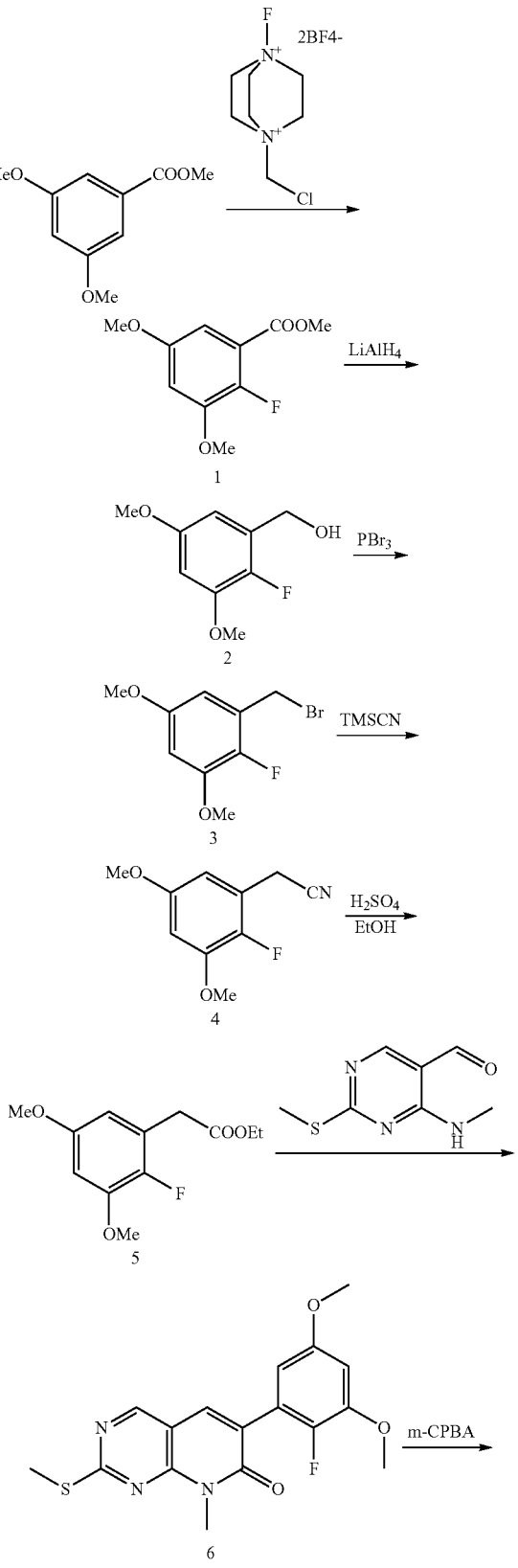

-continued

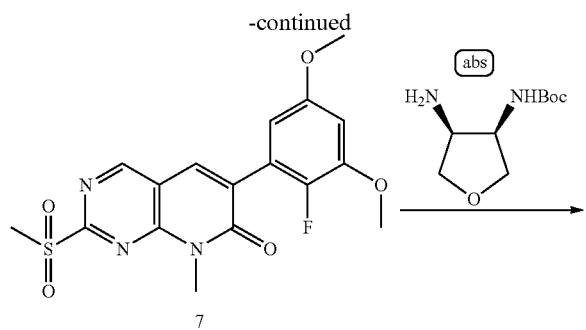

Step 1: Intermediate 1

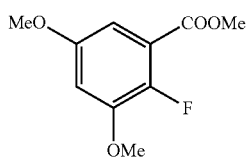 [SMILES: COC(=O)c1cc(OC)cc(OC)c1F]

To a solution of methyl 3,5-dimethoxybenzoate (2.00 g, 10.2 mmol) in CH$_3$CN (20 mL), 1-(chloromethyl)-4-fluoro-1,4-diazoniabicyclo[2.2.2]octane ditetrafluoroborate (Selectfluor™, 5.40 g, 15.2 mmol) was added. The reaction was stirred at room temperature overnight after which it was diluted with water and extracted with ethyl acetate. The organic layers were washed with water and brine, dried over sodium sulfate and concentrated in vacuo. The resultant residue was purified by column chromatography (hexane/ethyl acetate: 10/1) to afford the title compound as white solid (800 mg, 38%). $^1$H NMR (400 MHz, CDCl$_3$): δ 3.81 (s, 3H), 3.87 (s, 3H), 3.93 (s, 3H), 6.70 (dd, 1H), 6.91 (dd, 1H).

Step 2: Intermediate 2

To an ice-cooled solution of Intermediate 1 (800 mg, 3.70 mmol) in THF (10 mL) was added LiAlH$_4$ (0.30 g, 7.90 mmol) in portions. The reaction was stirred at room temperature for 30 min., then water was added slowly to the mixture and the resulting solid removed by filtration. The filtrate was concentrated in vacuo to afford the title compound as oil (610 mg, 87.9%) which was used directly in the next step. $^1$H NMR (400 MHz, CDCl$_3$): δ 3.79 (s, 3H), 3.86 (s, 3H), 3.88 (s, 1H), 4.74 (d, 2H), 6.45-6.49 (m, 1H), 6.49-6.55 (m, 1H).

Step 3: Intermediate 3

To a solution of Intermediate 2 (610 mg, 3.30 mmol) in DCM (10 mL), PBr$_3$ (1.06 g, 3.90 mmol) was added at 0° C. The reaction was stirred at room temperature for 4 h. Saturated aqueous NaHCO$_3$ was added to the reaction mixture and it was diluted with water and extracted with ethyl acetate. The organic layers were washed with water and brine, dried over sodium sulfate and concentrated in vacuo. The resultant residue was purified by column chromatography (hexane/ethyl acetate: 10/1) to afford the title compound as white solid (640 mg, 79%).

Step 4: Intermediate 4

To a solution of Intermediate 3 (640 mg, 2.60 mmol) in DCM (15 mL), TMSCN (510 mg, 5.1 mmol) and K$_2$CO$_3$ (709 mg, 5.10 mmol) were added. The reaction was stirred at 60° C. overnight, after which the reaction mixture was diluted with water and extracted with ethyl acetate. The organic layers were washed with water and brine, dried over sodium sulfate and concentrated in vacuo. The crude product was purified by column chromatography (hexane/ethyl acetate: 10/1) to afford the title compound as white solid (454 mg, 90%).

Step 5: Intermediate 5

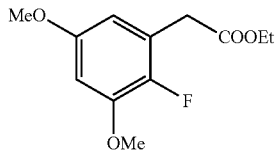

To a solution of Intermediate 4 (454 mg, 2.30 mmol) in EtOH (4 mL), concentrated H₂SO₄ (1 mL) was added. The reaction was stirred at 90° C. for 4 hours. The reaction mixture was diluted with water and extracted with ethyl acetate. The organic layers were washed with water and brine, dried over sodium sulfate and concentrated in vacuo to afford the title compound (400 mg, 59%) which was used in the next step without further purification.

Step 6: Intermediate 6

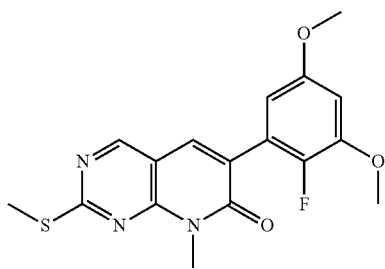

To a solution of Intermediate 5 (400 mg, 1.65 mmol) in DMF (10 mL), 4-(methylamino)-2-(methylthio)pyrimidine-5-carbaldehyde (302.6 mg. 1.65 mmol) and K₂CO₃ (456 mg, 3.3 mmol) were added. The reaction was stirred at 110° C. for 4 h. The reaction mixture was diluted with water and the precipitate collected by filtration to afford the title compound (500 mg, 84%) as white solid. LCMS: 362.4 [M+1]⁺.

Step 7: Intermediate 7

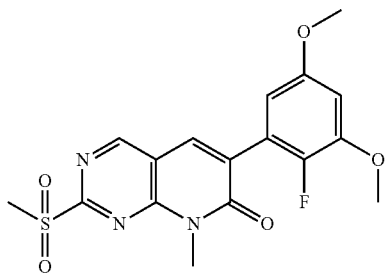

To a solution of Intermediate 6 (500 mg, 1.38 mmol) in DCM (10 mL), m-CPBA (594 mg. 3.45 mmol) was added. The reaction was stirred at room temperature overnight after which it was filtered and concentrated. The resultant residue was purified by silica gel column chromatography (DCM/MeOH: 40/1) to afford the title compound as light yellow solid (210 mg, 30%). LCMS: 394.3 [M+1]⁺.

Step 8: Intermediate 8

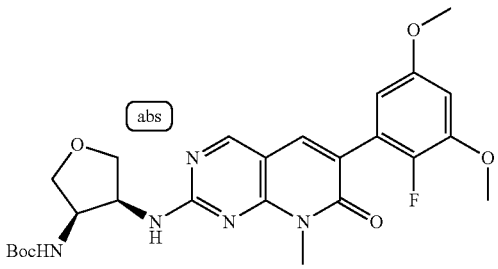 [SMILES: COc1cc(OC)c(F)c(-c2cc3cnc(N[C@@H]4COC[C@@H]4NC(=O)OC(C)(C)C)nc3n(C)c2=O)c1]

To a solution of Intermediate 7 (50.0 mg, 0.13 mmol) in NMP (5 mL), tert-butyl (3R,4S)-4-aminotetrahydrofuran-3-ylcarbamate (38.5 mg. 0.19 mmol) and DIPEA (33.0 mg, 0.26 mmol) were added. The reaction was stirred at 100° C. for 1 hour after which it was cooled to room temperature, diluted with water, and extracted with ethyl acetate. The organic layers were washed with water and brine, dried over sodium sulfate and concentrated in vacuo. The crude product was purified by silica gel column chromatography (DCM/MeOH: 20/1) to afford the title compound as a white solid (60.0 mg, 92%). LCMS: 516.6 [M+1]⁺.

Step 9: Intermediate 9

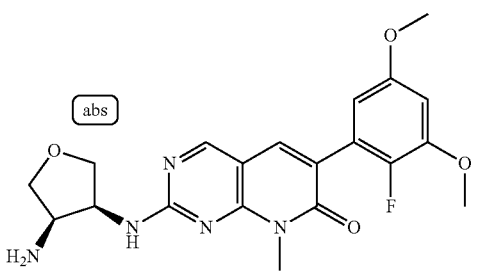 [SMILES: COc1cc(OC)c(F)c(-c2cc3cnc(N[C@@H]4COC[C@@H]4N)nc3n(C)c2=O)c1]

To a solution of Intermediate 8 (60.0 mg, 0.11 mmol) in DCM (3 mL) was added TFA (3 mL). The reaction mixture was allowed to stir for 30 min at ambient temperature after which the solvent was evaporated in vacuo to afford the title compound (52.0 mg) which was used in the next step without further purification.

Step 10: I-274

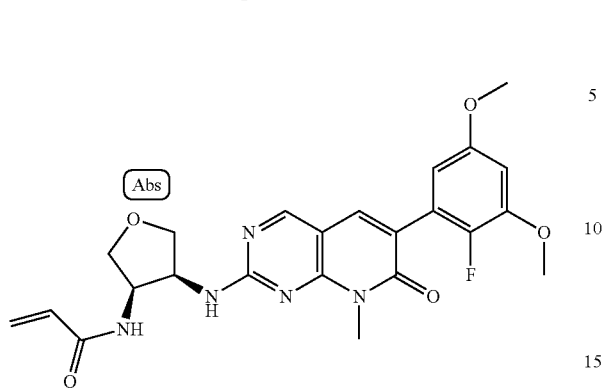

To a solution of Intermediate 9 (52.0 mg, 0.11 mmol) in DCM (5 mL), DIPEA (28.4 mL, 0.22 mmol) and acryloyl chloride (9.00 mg, 0.10 mmol) were added at 0° C. The reaction was warmed to room temperature with stirring for 30 min. The reaction mixture was diluted with water and extracted with DCM. The organic layers were washed with water and brine, dried over sodium sulfate and concentrated in vacuo. The resultant residue was purified by silica gel column chromatography (DCM/MeOH: 20/1) to afford the title compound as a white solid (7.10 mg, 12%). LCMS: 470.5 [M+1]$^+$. $^1$H NMR (400 MHz, CDCl$_3$): δ 3.71 (s, 3H), 3.75-3.78 (m, 1H), 3.80 (s, 3H), 3.81-3.85 (m, 1H), 3.89 (s, 3H), 4.17-4.22 (m, 1H), 4.24-4.31 (m, 1H), 4.81-4.90 (m, 2H), 5.65 (dd, 1H), 5.80-5.89 (m, 1H), 6.04 (d, 2H), 6.26 (dd, 1H), 6.56 (dd, 2H), 7.62 (s, 1H), 8.47 (s, 1H).

Example 245: I-276

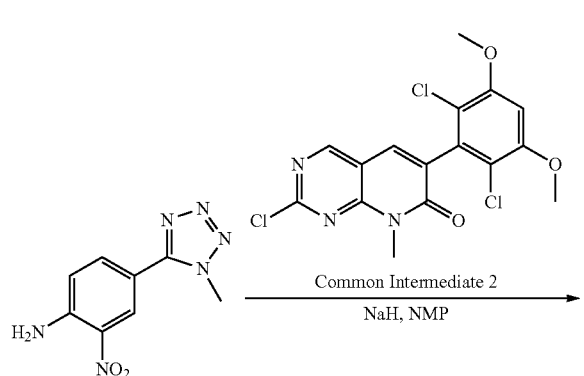

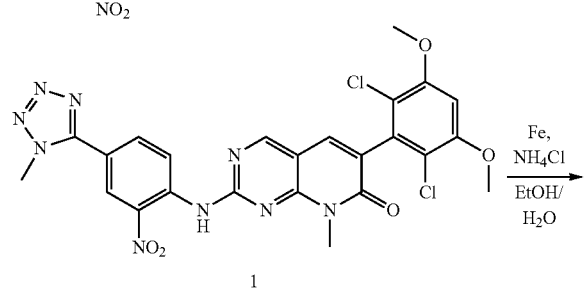

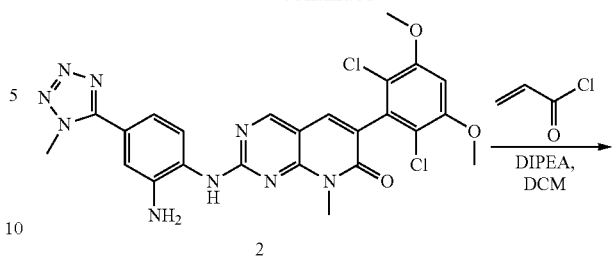

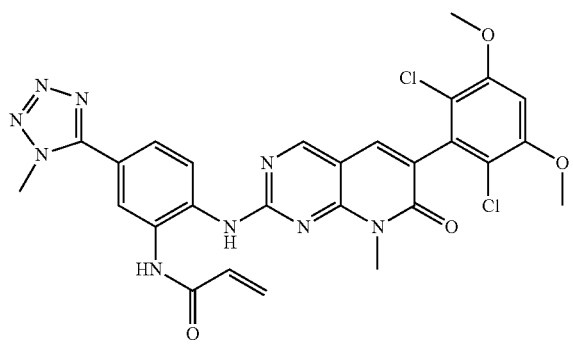 [SMILES: C=CC(=O)Nc1cc(-c2nnnn2C)ccc1Nc1ncc2cc(-c3c(Cl)c(OC)cc(OC)c3Cl)c(=O)n(C)c2n1]

I-276

Step 1: Intermediate 1

To a solution of 4-(1-methyl-1H-tetrazol-5-yl)-2-nitroaniline (30.0 mg, 0.14 mmol) in NMP (5 mL) was added NaH (11.3 mg, 0.47 mmol) at 25° C. The mixture was stirred at 25° C. for 0.5 h. Common Intermediate 2 from Example 233 (50.0 mg, 0.11 mmol) was added and the resultant mixture was stirred at 100° C. for 1 h. The reaction was quenched with water and extracted with EtOAc. The combined organic layers were washed with brine, dried (Na$_2$SO$_4$), filtered and concentrated in vacuo to afford the title compound (47.0 mg, 73%) as yellow solid. LCMS: 584.4 [M+H]$^+$.

503

Step 2: Intermediate 2

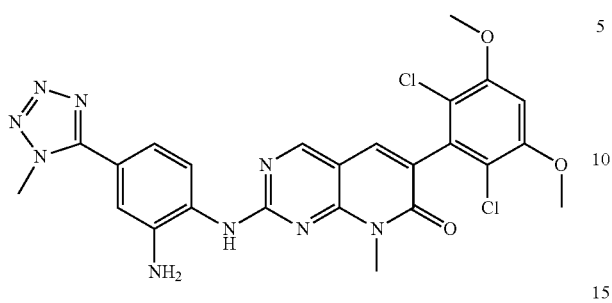

Intermediate 1 (47.0 mg, 0.08 mmol), Fe (27.0 mg, 0.48 mol), and NH$_4$Cl (26.0 mg, 0.48 mol) were taken up in EtOH (10 mL)/water (10 mL) and refluxed for 1 h. The solids were removed by filtration and the filtrate concentrated. The resulting residue was taken up in EtOAc washed with brine, dried over anhydrous Na$_2$SO$_4$, concentrated and purified by silica gel chromatography (eluted with 2-5% MeOH in DCM) to afford the title compound (30.0 mg, 68%) as yellow solid.

Step 3: I-276

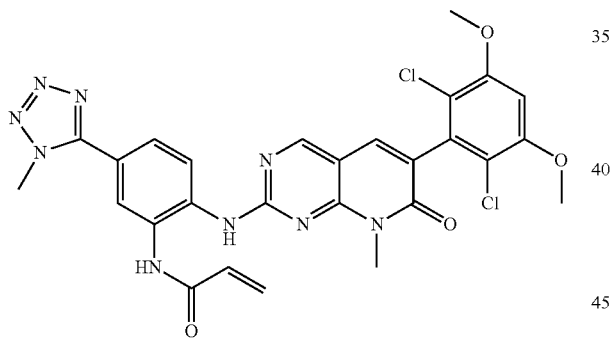

A solution of Intermediate 2 (30.0 mg, 0.05 mmol) and DIPEA (14.0 mg, 0.10 mmoL) in DCM (10 mL) was stirred at 25° C. Acryloyl chloride (5.00 mg, 0.05 mmol) was added at 0° C. and the resultant mixture was allowed to stir at 0° C. for 10 min. The reaction was quenched with water and extracted with EtOAc. The organic layer was washed with brine, dried (Na$_2$SO$_4$), filtered and concentrated in vacuo. The resultant residue was purified by column chromatography on silica gel (eluted with 2-5% MeOH in DCM) to afford the title compound as yellow solid (3.60 mg, 12%). LCMS: 608.6 [M+H]$^+$. $^1$H NMR (400 MHz, DMSO-d$_6$): δ 10.01 (s, 1H), 9.63 (s, 1H), 8.85 (s, 1H), 8.22 (s, 1H), 8.15 (d, 1H), 7.84 (s, 1H), 7.75 (d, 1H), 7.00 (s, 1H), 6.60-6.52 (m, 1H), 6.32 (d, 1H), 5.81 (d, 1H), 4.23 (s, 3H), 3.96 (s, 6H), 3.56 (s, 3H).

504

Example 246, I-278

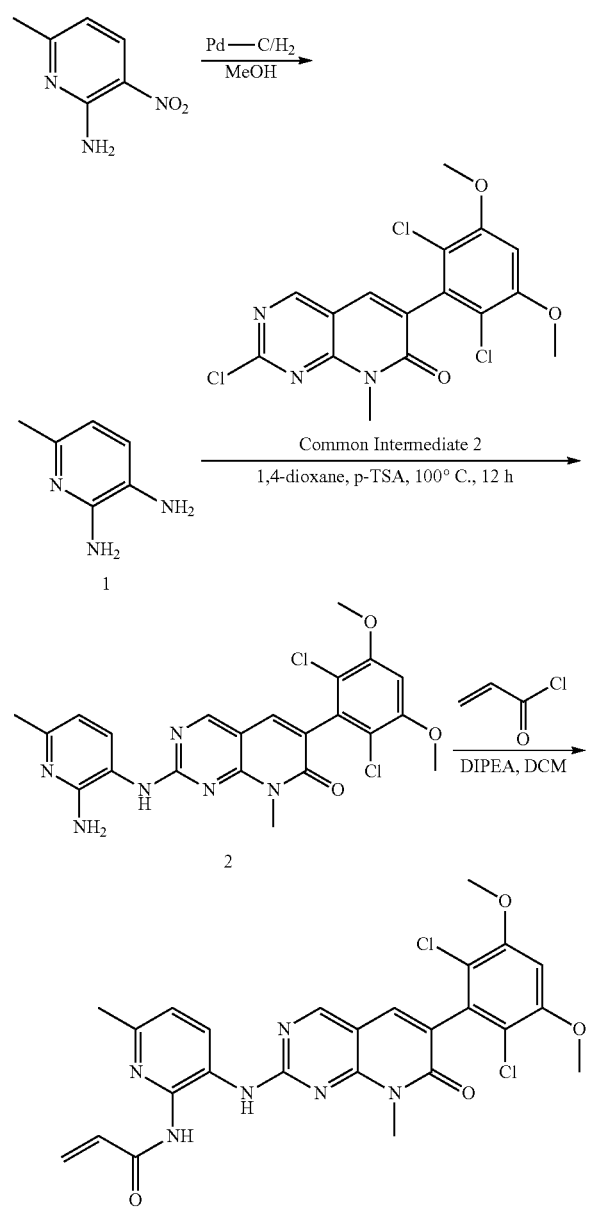

Step 1: Intermediate 1

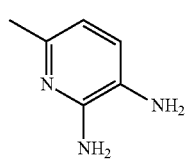

A mixture of 6-methyl-3-nitropyridin-2-amine (500 mg, 3.26 mmol) and Pt/C (250 mg) in MeOH (12 mL) was stirred at room temperature for 4 h under hydrogen atmosphere.

505

The reaction mixture was filtered, and the filtrate was concentrated to afford yellow solid (300 mg, 75% yield). LCMS: 124.3 [M+1]$^+$.

Step 2: Intermediate 2

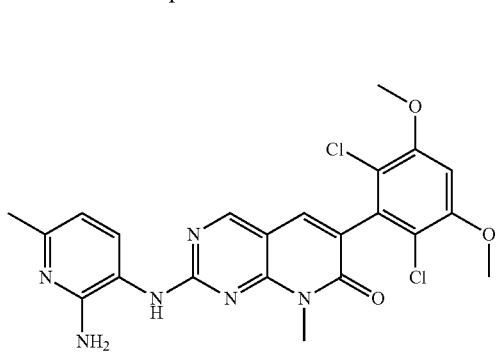

A mixture of Intermediate 1 (56.0 mg, 0.45 mmol), Common Intermediate 2 from Example 233 (150 mg, 0.38 mmol) and p-TSA (10.0 mg, 0.06 mmol) in 1,4-dioxane (12 mL) was heated at 100° C. overnight. After cooling to room temperature, the mixture was concentrated and the resulting residue dissolved in DCM, washed with sat. aq. NaHCO$_3$ and brine, concentrated and purified through silica gel column chromatography (10% MeOH in DCM) to afford the title compound as yellow solid (32.0 mg, 17% yield). LCMS: 487.4 [M+1]$^+$.

Step 3: I-278

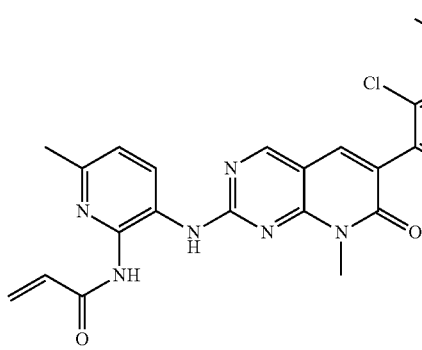

To a cooled (0° C.) solution of Intermediate 2 (32.0 mg, 0.07 mmol) and DIPEA (17.0 mg, 0.131 mmol) in DCM (6 mL) was added acryloyl chloride (6.00 mg, 0.07 mmol). The reaction was allowed to stir at 0° C. for 10 min after which it was quenched through addition of water and extracted with DCM. The combined organic layers were washed with brine, dried (Na$_2$SO$_4$), filtered and concentrated in vacuo. The resultant residue was purified by silica gel column chromatography (1% MeOH in DCM) to afford the title compound as white solid (20.0 mg, 56%). LCMS: 541.5 [M+1]$^+$. $^1$H NMR (400 MHz, CDCl$_3$): δ 2.55 (s, 3H), 3.71 (s, 3H), 3.97 (s, 6H), 5.92 (d, 1H), 6.49-6.54 (m, 1H), 6.59-6.67 (m, 2H), 7.19 (br, 1H), 7.46 (s, 1H), 8.50 (br, 1H), 8.57 (s, 1H), 9.50 (br, 1H).

506

Example 247: I-279

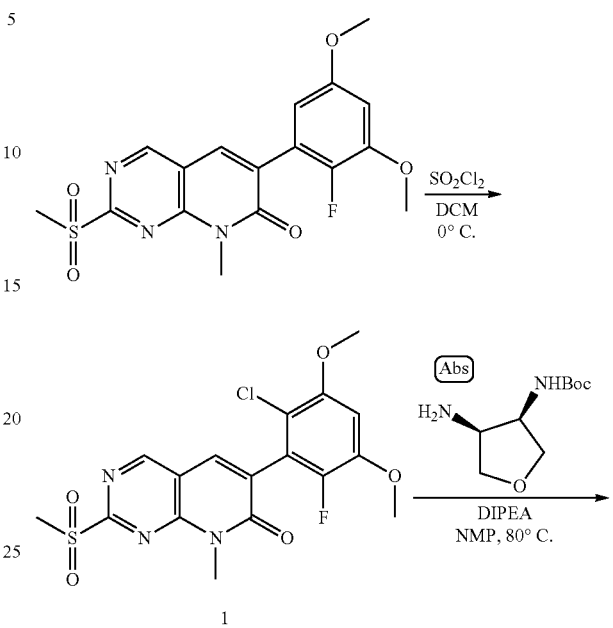

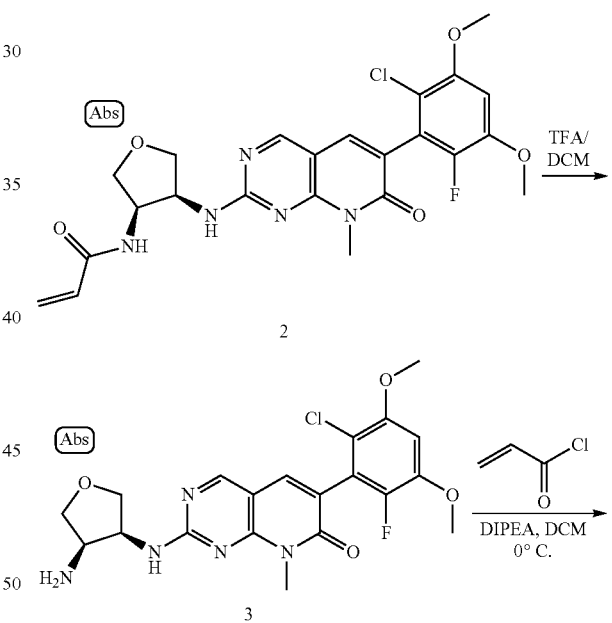

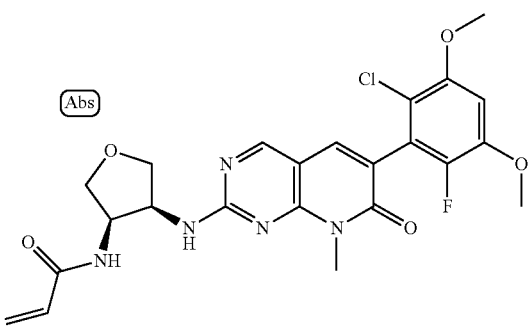

I-279

Step 1: Intermediate 1

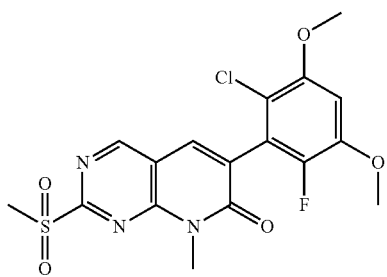

To an ice-cooled solution of 6-(2-fluoro-3,5-dimethoxyphenyl)-8-methyl-2-(methylsulfonyl)pyrido[2,3-d]pyrimidin-7(8H)-one prepared as described in Example 244 (160 mg, 0.40 mmol) in DCM (10 mL) was added $SO_2Cl_2$ (55.0 mg, 0.38 mmol), and the reaction was stirred at 0° C. for 30 min. Sat. $NaHCO_3$ was added, and the organic layer was separated, washed with brine, dried and concentrated in vacuo to afford the title compound (162 mg, 94%).

Step 2: Intermediate 2

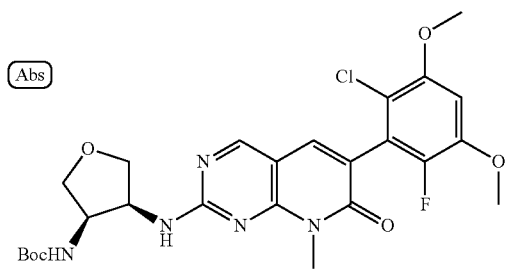 [SMILES: COc1cc(OC)c(Cl)c(-c2cc3cnc(N[C@@H]4COC[C@@H]4NC(=O)OC(C)(C)C)nc3n(C)c2=O)c1F]

The mixture of Intermediate 1 (180 mg, 0.42 mmol), tert-butyl (3R, 4S)-4-am inotetrahydrofuran-3-ylcarbamate prepared as described in Example 226 (97.0 mg, 0.48 mmol), DIPEA (10. mg, 0.80 mmol) in NMP (5 mL) was heated at 85° C. under $N_2$ for 3 h. The mixture was cooled to room temperature and partitioned between EtOAc and water. The organic phase was separated, washed with water, brine, dried over anhydrous $Na_2SO_4$ and the resultant residue subjected to column chromatography on silica gel (eluted with 5% MeOH in DCM) to afford the title compound (90.0 mg, 40%) as yellow solid. LCMS: 550.5 $[M+1]^+$.

Step 3: I-279

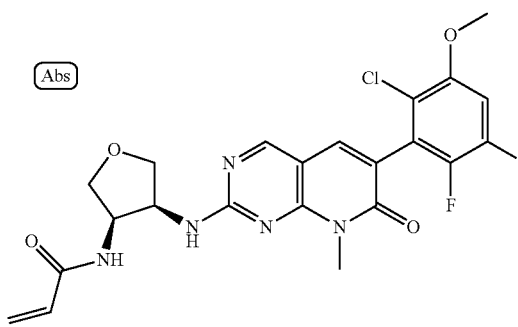

Acryloylation was carried out as previously described to afford the title compound (34%). Chiral HPLC indicated a 1:1 mixture of atropisomers which were separated by MG II preparative SFC chromatography using a ChiralCel OD-H column with a mobile phase of 60% $CO_2$ in Ethanol (0.1% $NH_3.H_2O$) and a flow rate of 50 mL/min. Pure fractions were isolated and upon storage at room temperature equilibrated to a mixture thus providing I-279 as a mixture of atropisomers. LCMS: 504.5 $[M+1]^+$. $^1$H NMR (400 MHz, $CDCl_3$): δ 3.71 (s, 3H), 3.76 (dd, 1H), 3.83 (dd, 1H), 3.92 (d, 6H), 4.19 (dd, 1H), 4.22-4.30 (m, 1H), 4.86 (s, 2H), 5.63 (d, 1H), 6.03 (dd, 1H), 6.26 (d, 2H), 6.66 (d, 1H), 7.52 (s, 1H), 8.47 (s, 1H).

Example 248: I-281

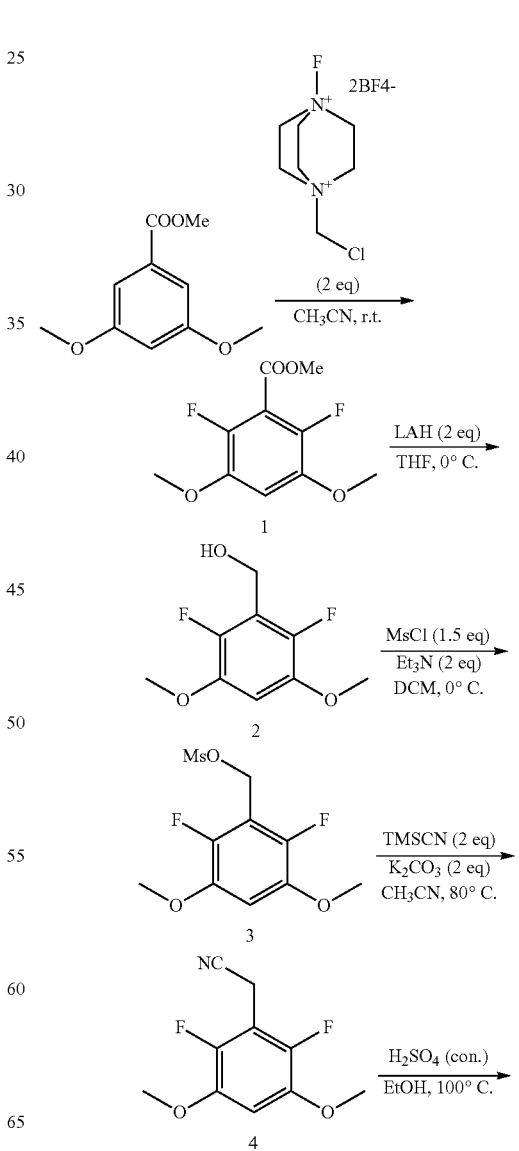

-continued

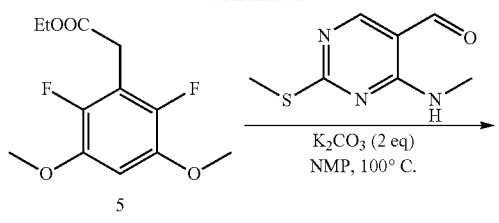
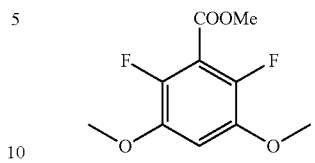

K₂CO₃ (2 eq)
NMP, 100° C.

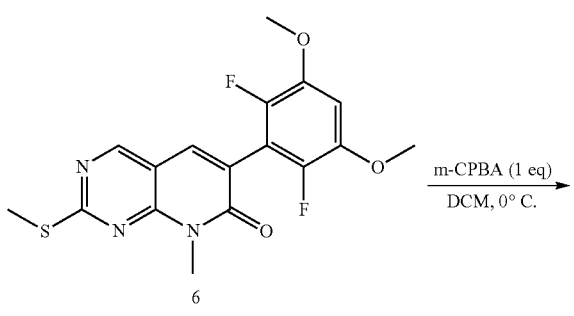

m-CPBA (1 eq)
DCM, 0° C.

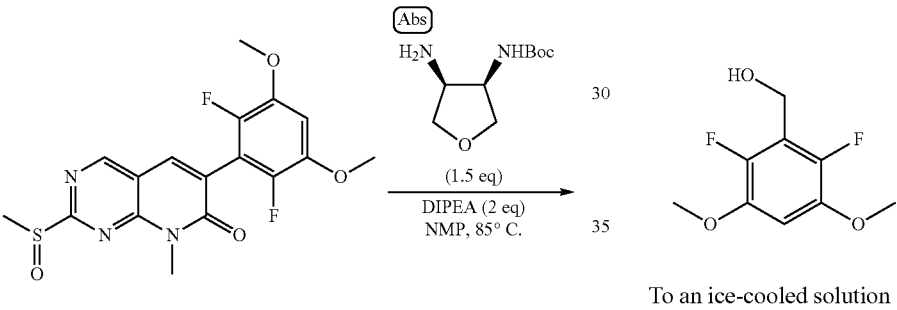

(1.5 eq)
DIPEA (2 eq)
NMP, 85° C.

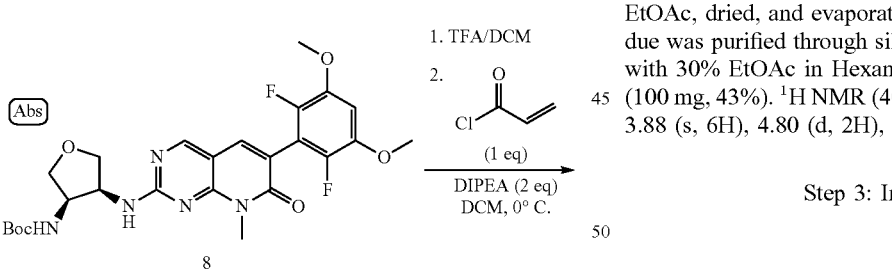

1. TFA/DCM
2.

(1 eq)
DIPEA (2 eq)
DCM, 0° C.

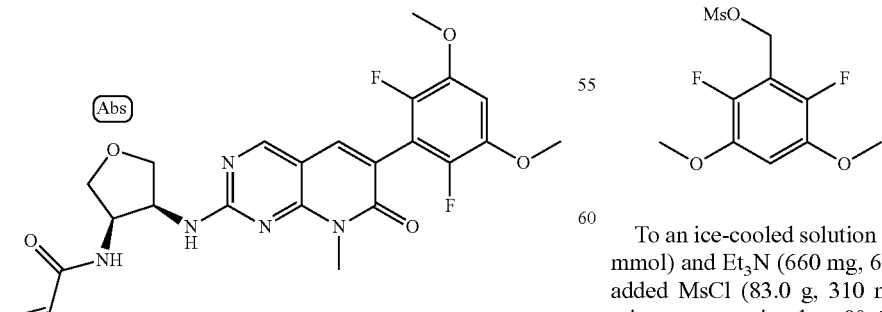

I-281

Step 1: Intermediate 1

[structure of methyl 2,6-difluoro-3,5-dimethoxybenzoate]

To a solution of methyl 3, 5-dimethoxybenzoate (500 mg, 2.55 mmol) in CH₃CN (25 mL) was added 1-(chloromethyl)-4-fluoro-1,4-diazoniabicyclo[2.2.2]octane ditetrafluoroborate (Selectfluor™, 1.80 g, 5.10 mmol) in small portions. The resultant mixture was stirred at room temperature overnight. The mixture was poured into water, extracted with EtOAc, dried and evaporated to dryness. The resultant residue was purified through silica gel chromatography (eluted with 20% EtOAc in hexane) to afford the title compound (240 mg, 49%). ¹H NMR (400 MHz, CDCl₃): δ 3.89 (s, 6H), 3.96 (s, 3H), 6.73 (t, 1H).

Step 2: Intermediate 2

[structure of hydroxymethyl difluorodimethoxybenzene]

To an ice-cooled solution of Intermediate 1 (240 mg, 1.03 mmol) in THF was added LAH (60.0 mg, 1.58 mmol), and the mixture was stirred at 0° C. for 30 min. EtOAc and water were added and the resulting mixture was extracted with EtOAc, dried, and evaporated in vacuo. The resultant residue was purified through silica gel chromatography (eluted with 30% EtOAc in Hexane) to afford the title compound (100 mg, 43%). ¹H NMR (400 MHz, CDCl₃): δ 1.93 (t, 1H), 3.88 (s, 6H), 4.80 (d, 2H), 6.62 (t, 1H).

Step 3: Intermediate 3

[structure of mesylate]

To an ice-cooled solution of Intermediate 2 (670 mg, 3.28 mmol) and Et₃N (660 mg, 6.0 mmol) in DCM (20 mL) was added MsCl (83.0 g, 310 mmol) slowly at 0° C. and the mixture was stirred at 0° C. for 0.5 h. The mixture was quenched with ice water, extracted with DCM, dried over anhydrous Na₂SO₄ and evaporate to dryness to afford the title compound (920 mg, 99%).

Step 4: Intermediate 4

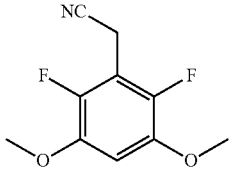

To a solution of Intermediate 3 (0.92 g, 3.28 mmol) and TMSCN (650 mg, 6.57 mmol) in CH$_3$CN (15 mL) was added K$_2$CO$_3$ (0.97 g, 6.57 mmol). The mixture was allowed to stir at 80° C. under N$_2$ over night. The mixture was quenched with saturated aqueous NaHCO$_3$, extracted with ethyl acetate, dried over anhydrous Na$_2$SO$_4$ and evaporate to dryness to afford the title compound as a brown oil which upon standing solidified (0.60 g, 85%). $^1$H NMR (400 MHz, CDCl$_3$): δ 3.74 (s, 2H), 3.89 (s, 6H), 6.65 (t, 1H).

Step 5: Intermediate 5

To a solution of Intermediate 4 (600 mg, 2.82 mmol) in EtOH (8 mL) was added H$_2$SO$_4$ (4 mL) slowly and the mixture was heated to reflux for 16 h. The mixture was quenched with saturated aqueous Na$_2$CO$_3$, the pH adjusted to >7. The aqueous layer was extracted with ethyl acetate, dried over anhydrous Na$_2$SO$_4$ and evaporate to dryness to afford the title compound (600 mg, 82%). $^1$H NMR (400 MHz, CDCl$_3$): δ 1.26 (t, 3H), 3.71 (t, 2H), 3.89 (s, 6H), 4.18 (q, 2H), 6.59 (t, 1H).

Step 6: Intermediate 6

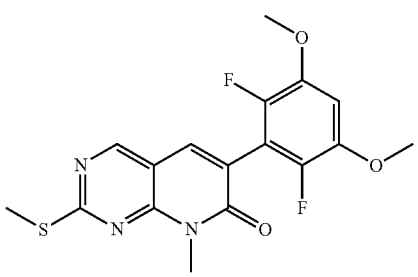

To a solution of 4-(methylamino)-2-(methylthio)pyrimidine-5-carbaldehyde (349 mg, 1.92 mmol) in DMF (10 mL) was added Intermediate 5 (500 mg, 1.92 mmol) and K$_2$CO$_3$ (530 mg, 3.84 mmol), and the mixture was stirred at 100° C. for 20 h. The reaction mixture was cooled to room temperature and poured into water. The resultant solid was filtered, washed with water, and recrystallized from ethanol to afford the title compound as yellow solid (250 mg, 34%). LCMS: 380.2 [M+1]$^+$.

Step 7: Intermediate 7

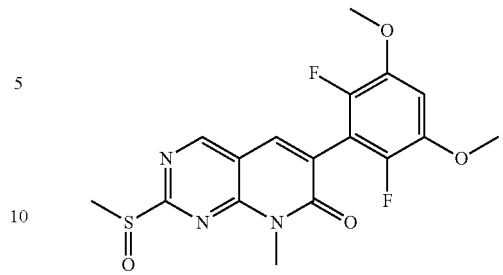

To a solution of Intermediate 6 (210 mg, 0.55 mmol) in DCM (20 mL) was added m-CPBA (146 mg, 0.85 mmol) in one portion, and the mixture was stirred at room temperature for 30 min. The mixture was diluted with DCM, washed with sat. Na$_2$SO$_3$ and sat. NaHCO$_3$. The organic layer was separated, dried over anhydrous Na$_2$SO$_4$ and concentrated in vacuo to afford the title compound (210 mg, 97%) as light yellow solid. LCMS: 396.2 [M+1]$^+$.

Step 8: Intermediate 8

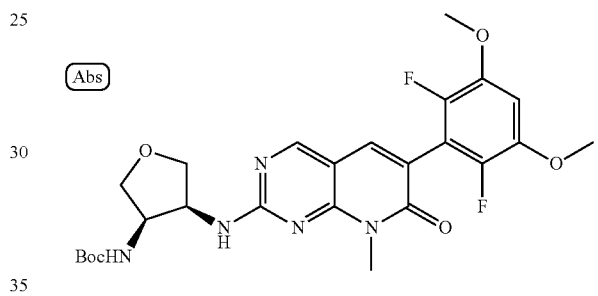

A mixture of Intermediate 7 (100 mg, 0.25 mmol), tert-butyl ((3R,4S)-4-aminotetrahydrofuran-3-yl)carbamate prepared as described in Example 226 (77.0 mg, 0.38 mmol), DIPEA (10.0 mg, 0.80 mmol) in NMP (3 mL) was heated at 85° C. under N$_2$ for 1.5 h. The reaction mixture was cooled to room temperature and partitioned between EtOAc and water. The organic phase was separated, washed with water, brine, and dried over anhydrous Na$_2$SO$_4$. The resultant residue was subjected to column chromatography on silica gel (eluted with 5% MeOH in DCM) to afford the titled product (106 mg, 79%) as yellow solid. LCMS: 534.5 [M+1]$^+$.

Step 9: I-281

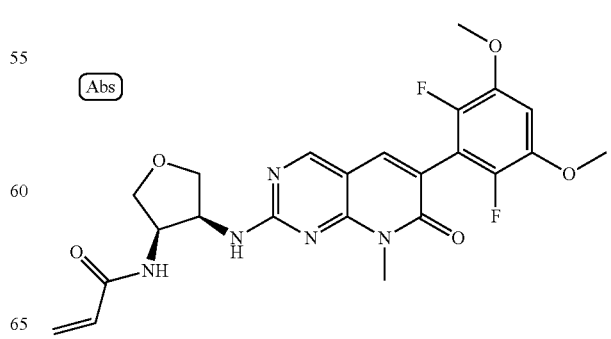

Acryloylation was carried out according to the above scheme and as previously described to afford the title compound (54.0 mg, 69%). LCMS: 488.5 [M+1]$^+$.
$^1$H NMR (400 MHz, CDCl$_3$): δ 3.71 (s, 3H), 3.75-3.80 (m, 1H), 3.83 (dd, 1H), 3.89 (s, 6H), 4.16-4.22 (m, 1H), 4.24-4.31 (m, 1H), 4.82-4.90 (m, 2H), 5.64 (d, 1H), 6.02 (dd, 2H), 6.27 (d, 1H), 6.69 (t, 1H), 7.59 (s, 1H), 8.47 (s, 1H).
Example 249: I-286
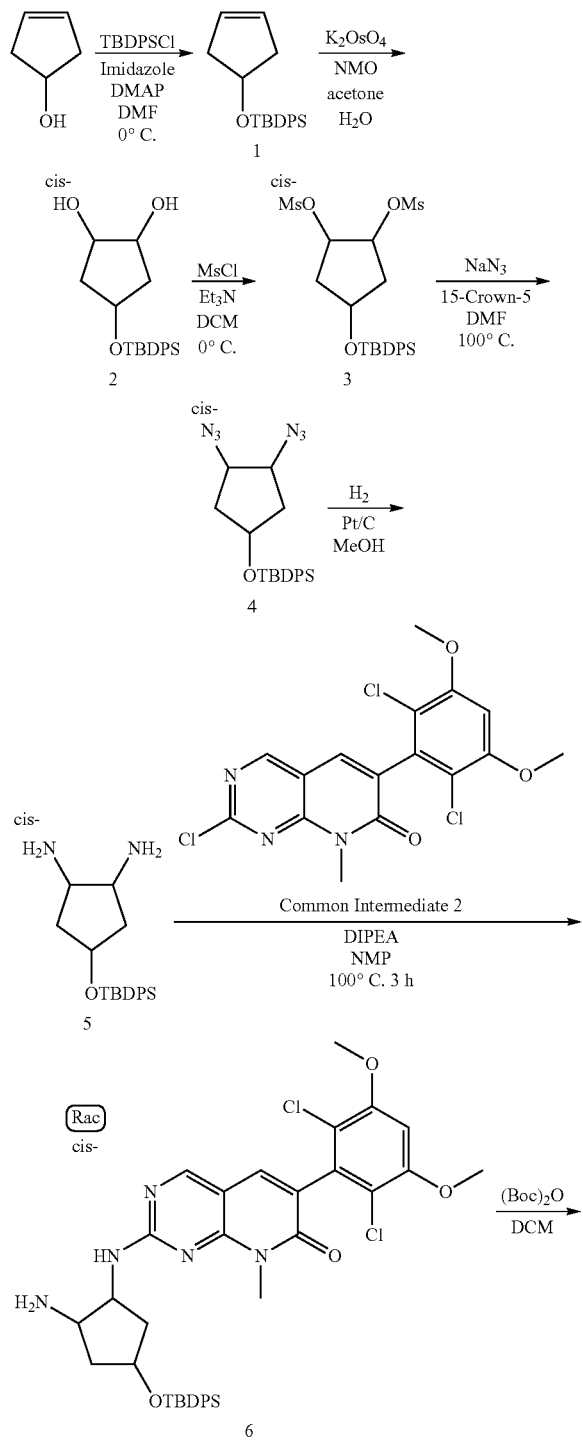
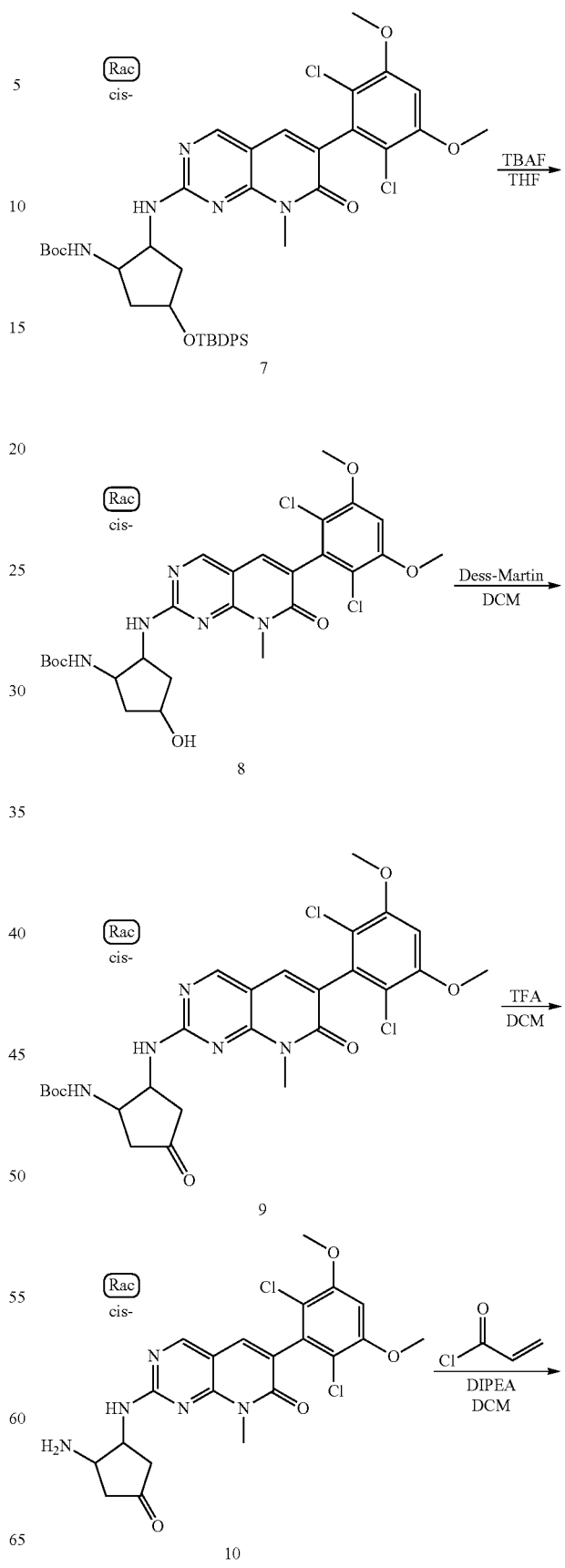

515
-continued

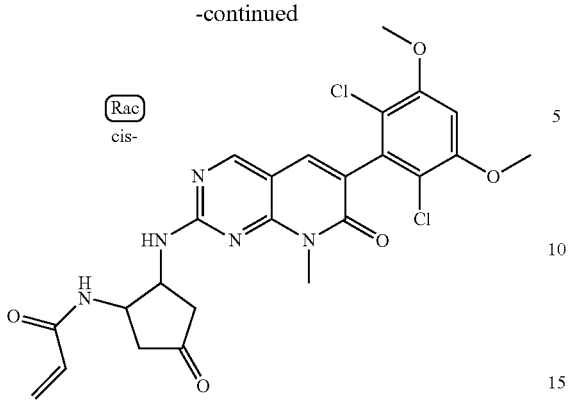

I-286

Step 1: Intermediate 1

A solution of the compound cyclopent-3-enol (1.5 g, 17.9 mmol) in 10 mL of DMF was cooled to 0° C. and to the mixture was added TBDPSCl (7.35 g, 26.8 mmol), imidazole (3.6 g, 53.6 mmol) and DMAP (0.2 g, 1.8 mmol) under $N_2$. The mixture was stirred at 28° C. under $N_2$ overnight after which it was quenched through addition of saturated aqueous $NaHCO_3$, extracted with EtOAc, dried and evaporated to dryness. (5.0 g, 87%). $^1H$ NMR (400 MHz, $CDCl_3$): δ1.08 (s, 9H), 2.32-2.51 (m, 4H), 4.54-4.59 (m, 1H) 5.62 (s, 2H), 7.35-7.46 (m, 6H), 7.68 (dd, 4H).

Step 2: Intermediate 5

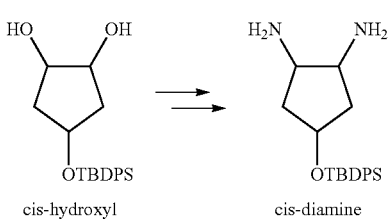

cis-hydroxyl    cis-diamine

Intermediate 1 was converted to Intermediate 5 according to the above a Scheme using protocols described in Example 226.

516
Step 6: Intermediate 6

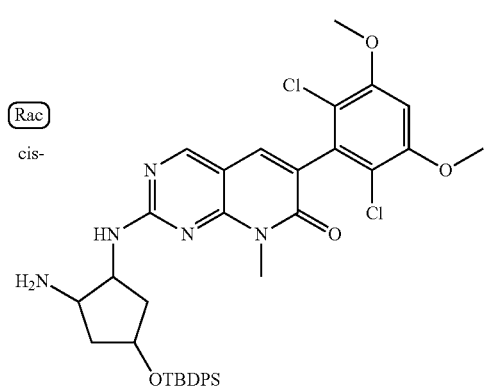

A mixture of Intermediate 5 (233 mg, 0.57 mmol), Common Intermediate 2 from Example 233 (200 mg, 0.57 mmol), and DIPEA (125 mg, 1.00 mmol) in NMP (6 mL) was heated to 80° C. for 1 h. The mixture was cooled to room temperature and partitioned between EtOAc and water. The organic phase was separated, washed with water, brine, dried over anhydrous $Na_2SO_4$ and the resultant residue purified through column chromatography to afford the title compound (60.0 mg, 15%). LCMS: 818.7 [M+1]$^+$.

Step 7: Intermediate 7

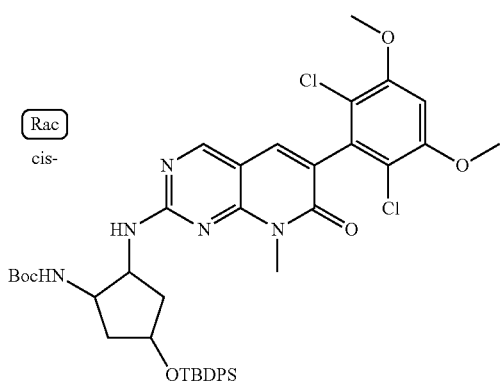

To a solution of Intermediate 6 (500 mg, 0.69 mmol) in 20 mL of DCM was added (Boc)$_2$O (304 mg, 1.38 mmol) and the mixture was stirred at 30° C. for 2 h. The mixture was quenched with $NaHSO_4$ (10%), sat. NaCl (sat. aq) and sat. $NaHCO_3$ (sat. aq), extracted with DCM, dried and concentrated to afford the title compound (400 mg, 71%). LCMS: 818.6 [M+H]$^+$.

Step 8: Intermediate 8

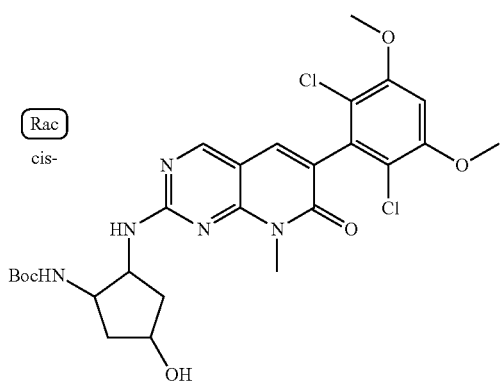 [SMILES: COc1cc(OC)c(Cl)c(-c2cc3cnc(NC4CC(O)CC4NC(=O)OC(C)(C)C)nc3n(C)c2=O)c1Cl]

To a solution of Intermediate 7 (300 mg, 0.37 mmol) in 8 mL THF was added TBAF (311 mg, 0.73 mmol) and the mixture was stirred at room temperature for 2 h. The mixture was quenched with water, extracted with EtOAc, dried and evaporated to dryness to afford the title compound. (160 mg, 74%). LCMS: 580.5 [M+H]+.

Step 9: Intermediate 9

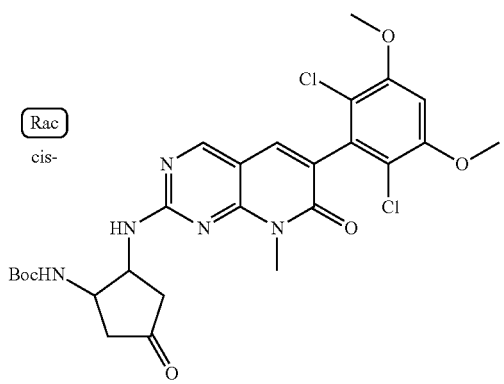

To a solution of the Intermediate 8 (160 mg, 0.27 mmol) in 6 mL DCM was added Dess-Martin Periodinane (234 mg, 0.54 mmol) and the mixture was stirred at room temperature for 2 h. The mixture was quenched with sat. NaHCO₃ (sat. aq), extracted with DCM, dried and evaporated to dryness. The resultant residue was purified by column chromatography (DCM:MeOH=20:1) to afford the title compound. (120 mg, 76%). LCMS: 578.5 [M+H]+.

Step 10: Intermediate 10

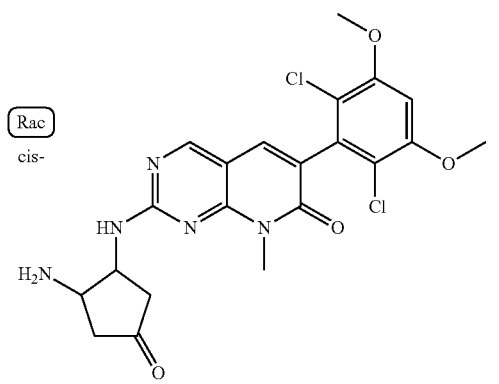 [SMILES: COc1cc(OC)c(Cl)c(-c2cc3cnc(NC4CC(=O)CC4N)nc3n(C)c2=O)c1Cl]

To a solution of Intermediate 9 (50.0 mg, 0.087 mmol) in DCM (2 mL) was added TFA (2 mL), and the mixture was stirred at room temperature for 30 min. Solvent was removed in vacuo to afford the product as TFA salt.

Step 11: I-286

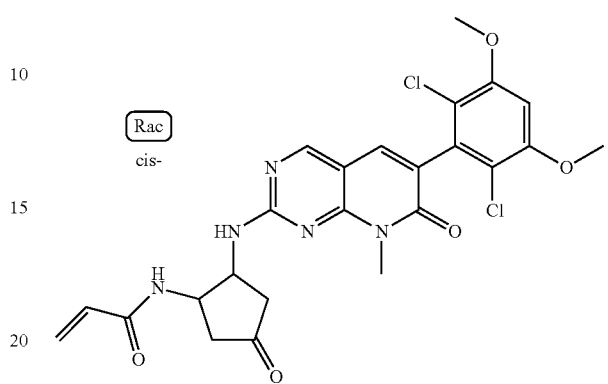

Acryloylation of Intermediate 10 was carried out according to the above scheme and as previously described to afford the title compound. LCMS: 532.5 [M+H]+. ¹H NMR (400 MHz, CDCl₃): δ 2.47-2.61 (m, 2H), 2.80 (s, 2H), 3.63 (d, 3H), 3.95 (d, 6H), 4.81-4.99 (m, 2H), 5.63 (s, 1H), 6.09 (dd, 1H), 6.28 (dd, 1H), 6.63 (s, 1H), 7.44 (s, 1H), 8.48 (s, 1H).

Example 250: I-288

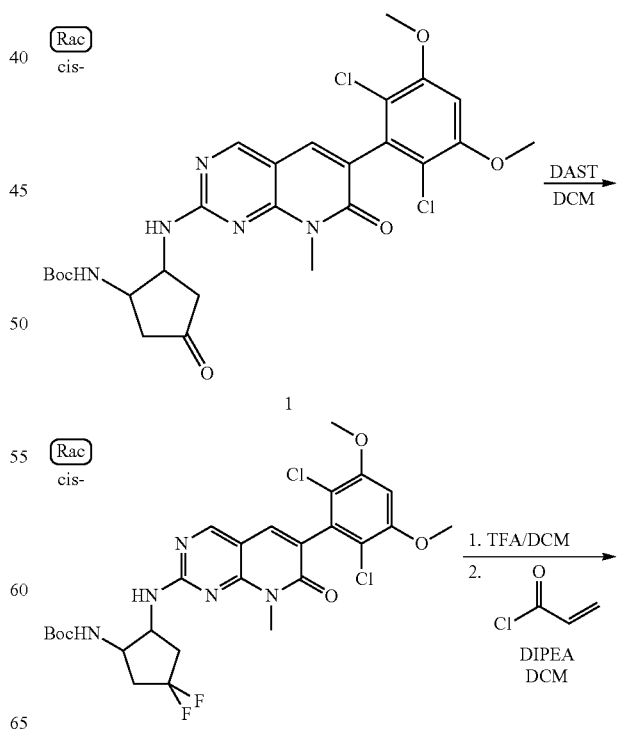

-continued

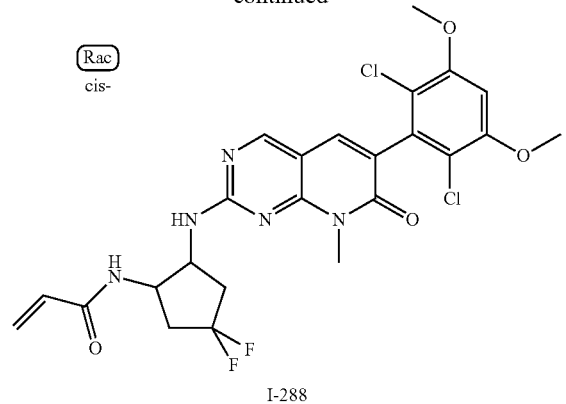

I-288

Step 1: Intermediate 2

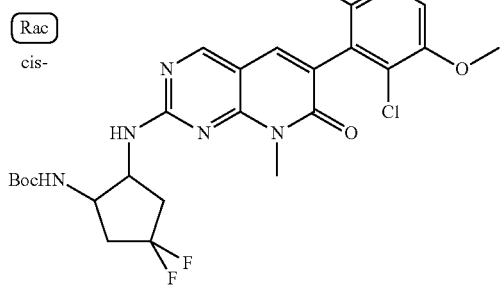

A solution of Intermediate 1 from Example 249 (60.0 mg, 0.10 mmol) in 10 mL of DCM was cooled to 0° C. and diethylaminosulfurtrifluoride (DAST) was added (8 mL) dropwise. The mixture was stirred at 0° C. for 0.5 h. The mixture was quenched with sat. NaHCO₃, extracted with DCM, dried, and concentrated. The resultant residue was purified by column chromatography (DCM:MeOH=30:1) to afford the title compound (40 mg, 67%) LCMS: 600.5 [M+H]⁺.

Step 2: I-288

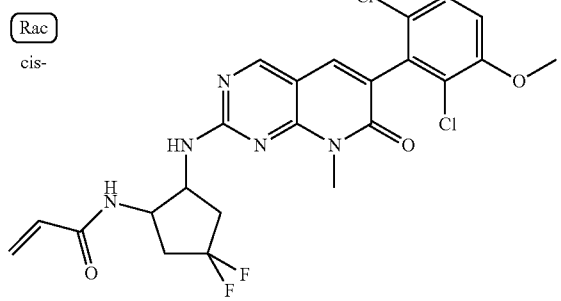

I-288 was prepared from Intermediate 2 as previously described. LCMS: 554.5 (M+H)⁺. ¹H NMR (400 MHz, CDCl₃): δ 2.28-2.41 (m, 2H), 2.65-2.79 (m, 2H), 3.68 (s, 3H), 3.95 (s, 6H), 4.74-4.90 (m, 2H), 5.64 (dd, 1H), 6.02 (dd, 2H), 6.26 (dd, 1H), 6.63 (s, 1H), 7.43 (s, 1H), 8.47 (s, 1H).

Example 251: I-290

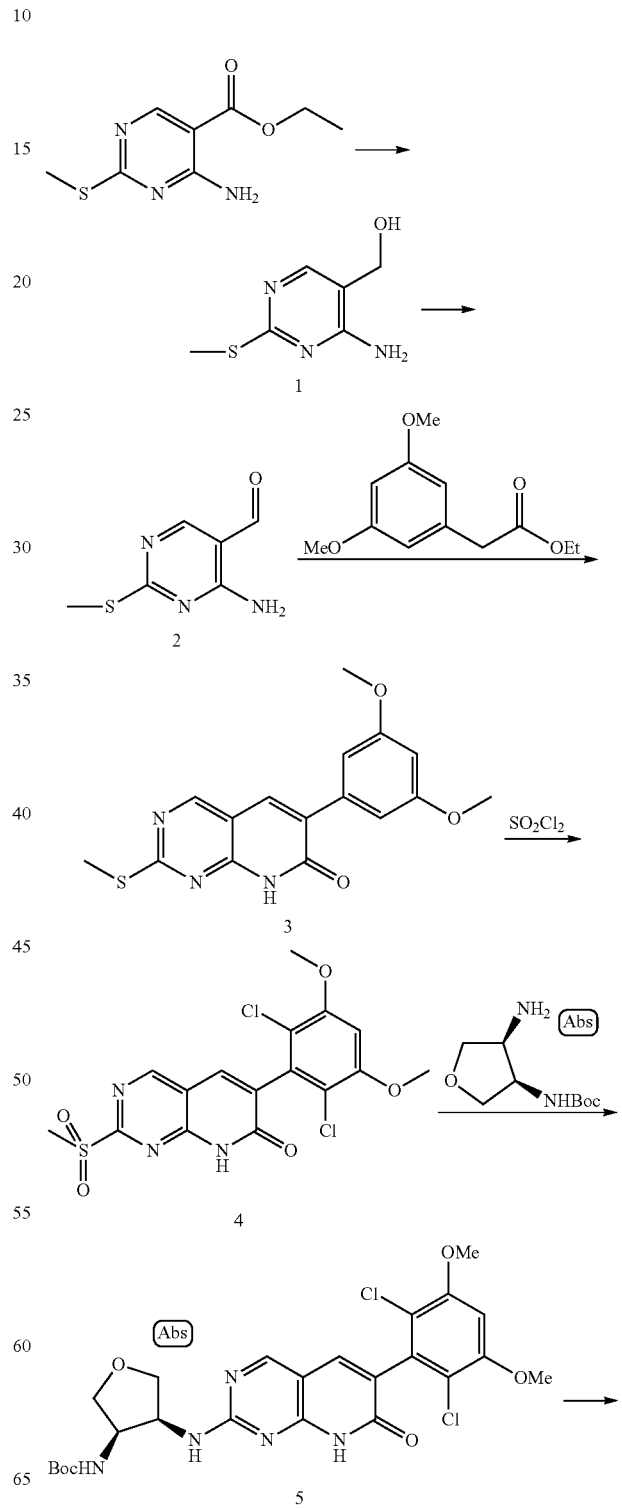

-continued

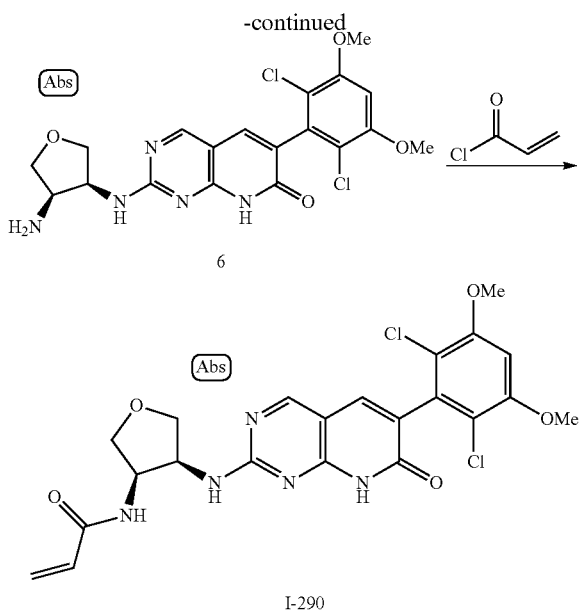

I-290

Step 1: Intermediate 1

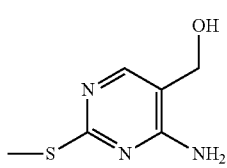

To a solution of (9.0 g, 42 mmol) in anhydrous THF (50 mL) was added LiAlH₄ (3.2 g, 84 mmol) in portions at 0° C. after which the mixture was stirred at room temperature for 1 h. Na₂SO₄-10H₂O was added to the mixture followed by filtration. The filtrate was concentrated to afford the title compound as a yellow solid (7.55 g). LCMS: 172.3 [M+1]⁺. ¹H NMR (400 MHz, CDCl₃): δ 1.38 (dd, 3H), 2.52 (s, 3H), 4.34 (q, 2H), 5.62-5.49 (m, 1H), 8.70 (s, 1H).

Step 2: Intermediate 2

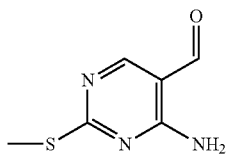

A mixture of Intermediate 1 (7.5 g, 44 mmol) and MnO₂ (55 g, 630 mmol) in DCM (60 mL) was allowed to stir at room temperature overnight. The mixture was filtered, and the filtrate was concentrated. The resultant residue was purified by column chromatography (DCM:MeOH=20:1) to afford the title compound as light yellow solid (3.85 g, 52%). LCMS: 170.2 [M+1]⁺. ¹H NMR (400 MHz, CDCl₃): δ 2.55 (s, 3H), 8.42 (s, 1H), 9.78 (s, 1H).

Step 3: Intermediate 3

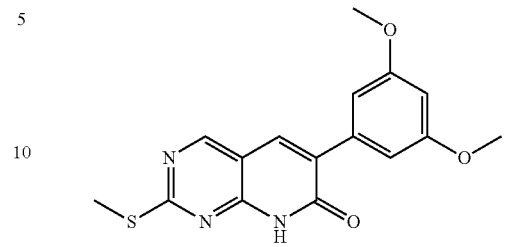

A mixture of Intermediate 2 (500 mg, 3.0 mmol), ethyl 2-(3,5-dimethoxyphenyl) acetate (1.0 g, 4.5 mmol), and K₂CO₃ (1.3 g, 9.4 mmol) in DMF (20 mL) was heated to 110° C. overnight. The mixture was diluted with water and the resulting suspension was filtered. The precipitate was washed with water and dried to afford the title compound (830 mg) as a white solid. LCMS: 330.3 [M+1]⁺. ¹H NMR (400 MHz, DMSO-d₆): δ 2.59 (s, 3H), 3.79 (s, 6H), 6.55 (t, 1H), 6.89 (d, 2H), 8.14 (s, 1H), 8.89 (s, 1H), 12.55 (s, 1H).

Step 4: Intermediate 4

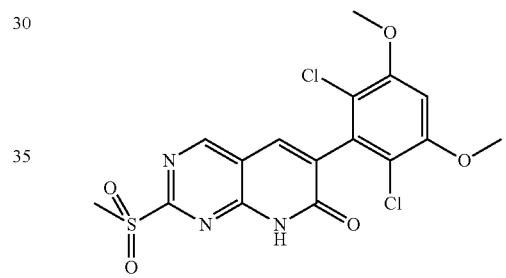

To a solution of Intermediate 3 (500 mg, 1.5 mmol) in NMP (10 mL) was added SO₂Cl₂ (620 mg, 4.6 mmol) dropwise at −10° C. and the resulting mixture was allowed to stir for 1 h. The mixture was diluted with water, the precipitate collected by filtration and dried to afford the title compound as off-white solid (770 mg, 100%). LCMS: 430.3[M+1]⁺. ¹H NMR (400 MHz, CDCl₃): δ 3.45-3.35 (m, 3H), 3.95 (t, 6H), 6.68 (s, 1H), 7.75 (s, 1H), 9.04 (s, 1H), 9.48 (s, 1H).

Step 5: Intermediate 5

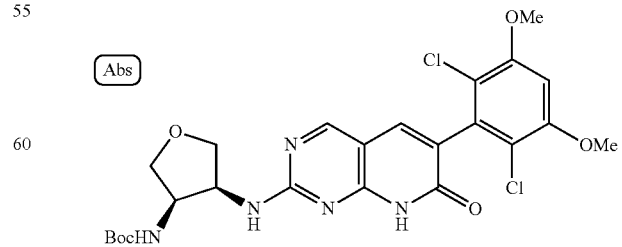

Intermediate 4 (200 mg, 0.47 mmol), DIPEA (91 mg, 0.71 mmol) and tert-butyl (3R,4S)-4-aminotetrahydrofuran-3-ylcarbamate from Example 226 (110 mg, 0.55 mmol) were taken up in NMP (10 mL) and stirred at 85° C. for 3 h under N₂ atmosphere. The mixture was cooled to room temperature, diluted with water, and extracted with ethyl acetate. The organic layers were washed with brine, dried over anhydrous Na₂SO₄ and concentrated. The resultant residue was purified by column chromatography (5% MeOH/DCM) to afford the title compound as white solid (214 mg, 85%). LCMS: 552.5 [M+1]⁺.

Step 6: Intermediate 6

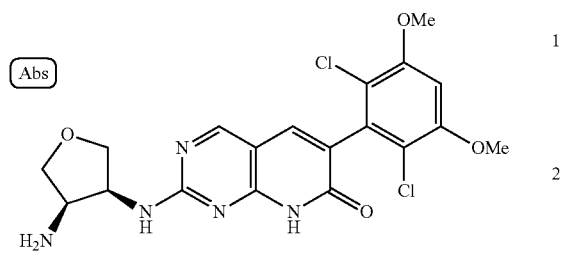

TFA (4 ml) was added to the solution of Intermediate 5 (214 mg) in DCM (8 mL), and the mixture was stirred at room temperature for 0.5 h. TFA was removed in vacuo, the residue was diluted with DCM (20 mL), washed with sat. sodium bicarbonate, dried, and concentrated to afford the title compound as a light yellow solid (170 mg). LCMS: 452.4 [M+1]⁺.

Step 7: I-290

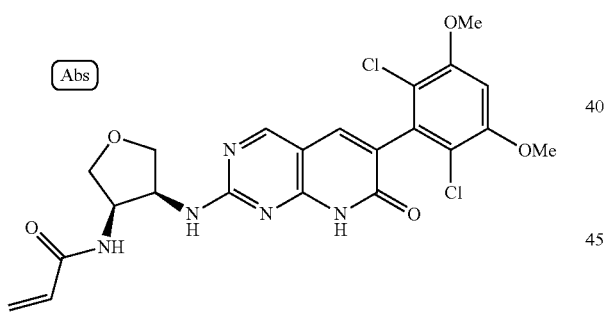

Acryloylation of Intermediate 6 was carried out as previously described to afford the title compound (50 mg, 55%) as white solid. LCMS: 506.4[M+1]⁺. ¹H NMR (400 MHz, DMSO-d₆): δ 3.72-3.92 (m, 2H), 3.98 (d, 8H), 4.83-4.96 (m, 2H), 5.46-5.54 (m, 1H), 5.71-5.81 (m, 1H), 6.07-6.16 (m, 1H), 6.65 (s, 1H), 7.06-7.11 (m, 1H), 7.60 (s, 1H), 8.64 (s, 1H), 8.85-8.77 (m, 1H).

Example 252: I-292, I-293

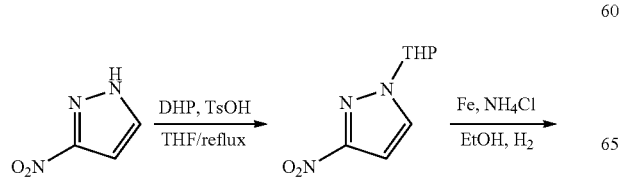

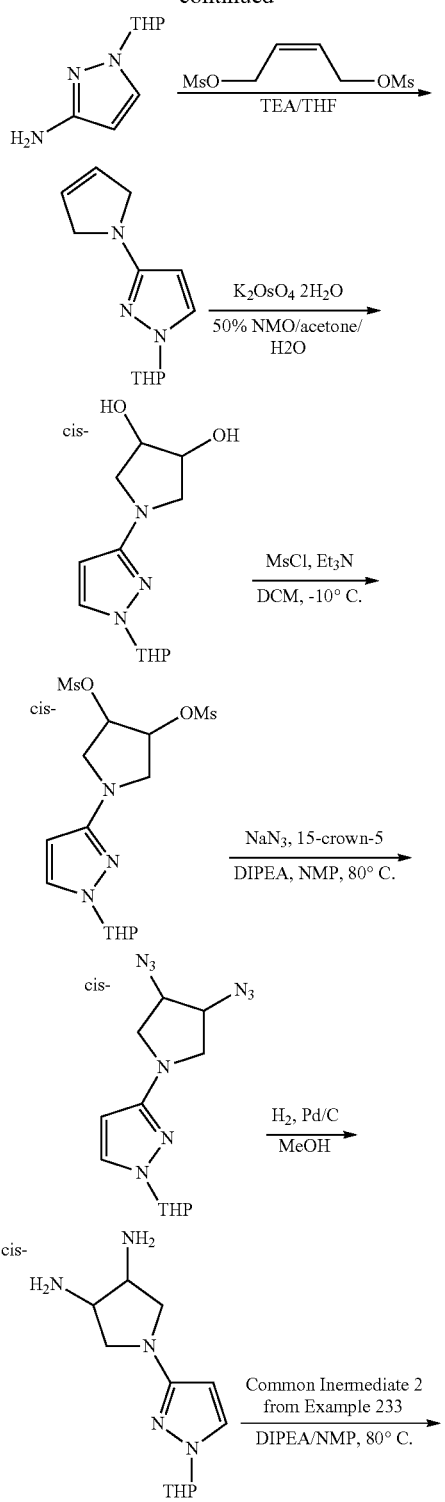

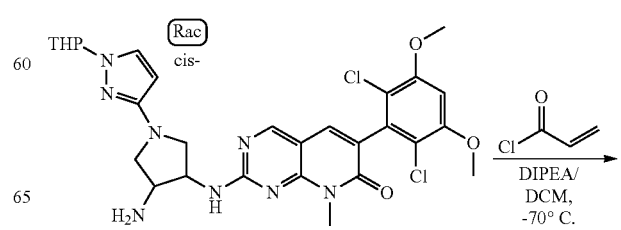

525
-continued

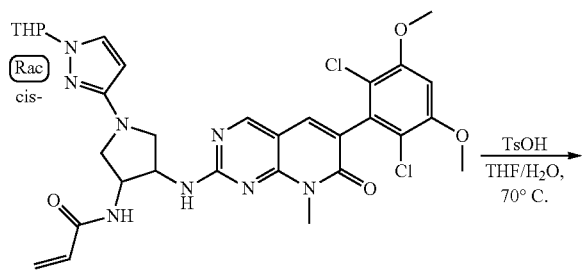

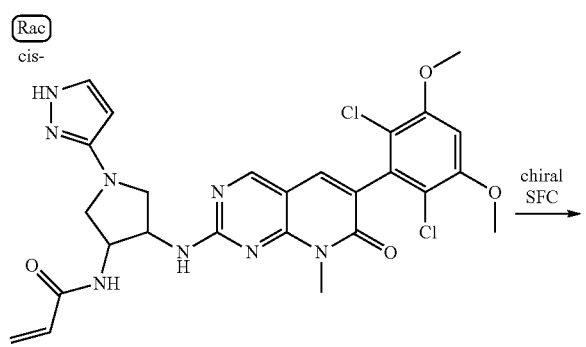

10

526
Steps 1-10: Intermediate 10

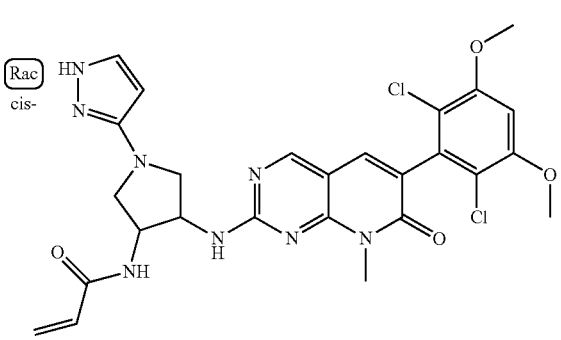 [SMILES: C=CC(=O)NC1CN(c2cc[nH]n2)CC1Nc1ncc2cc(-c3c(Cl)c(OC)cc(OC)c3Cl)c(=O)n(C)c2n1]

Intermediate 10 was prepared according to the above scheme and as described for I-248. LCMS: 585.2 [M+1]$^+$. $^1$H NMR (400 MHz, DMSO-d$_6$): δ 3.28-3.31 (m, 1H), 3.39-3.43 (m, 1H), 3.53-3.56 (m, 1H), 3.59 (s, 3H), 3.66-3.70 (m, 1H), 3.96 (s, 6H), 4.70-4.84 (m, 2H), 5.49-5.59 (m, 2H), 5.98-6.08 (m, 1H), 6.18-6.25 (m, 1H), 6.98 (s, 1H), 7.44 (s, 1H), 7.71 (s, 1H), 7.85 (d, 1H), 8.26 (d, 1H), 8.65 (s, 1H), 11.73 (br, 1H).

Step 11: I-292, I-293

I-292

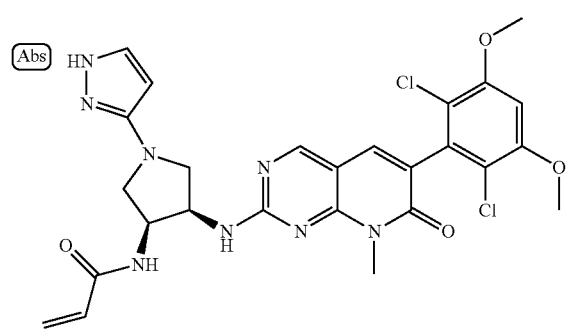

I-292

I-293

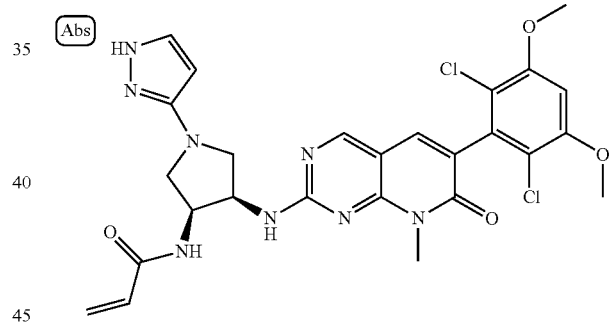

I-293

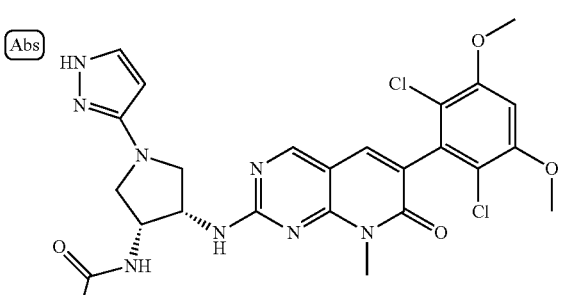

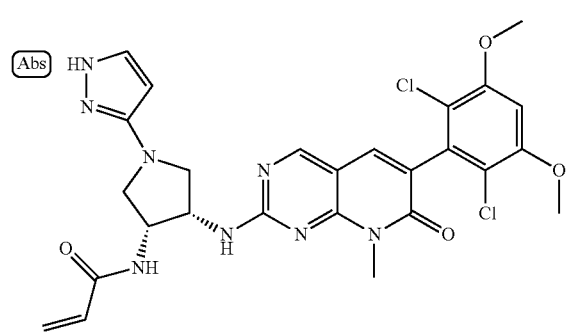

I-293

Intermediate 10 was purified by preparative SFC chromatography to provide the title compounds in >98% er (ChiralCel OJ-H column, 250×30 mmI.D, mobile phase 60% CO$_2$ in MEOH, 0.1% NH$_3$.H$_2$O, flow rate=50 ml/min, 38° C.). Absolute configurations were assigned by analogy to I-94/I-95 and I-240/I-241 based on enzymatic and cellular potency.

Example 253: I-294

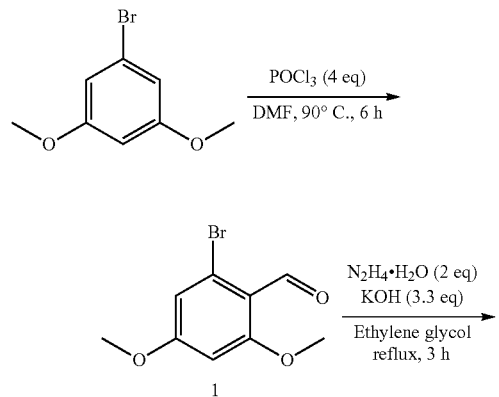

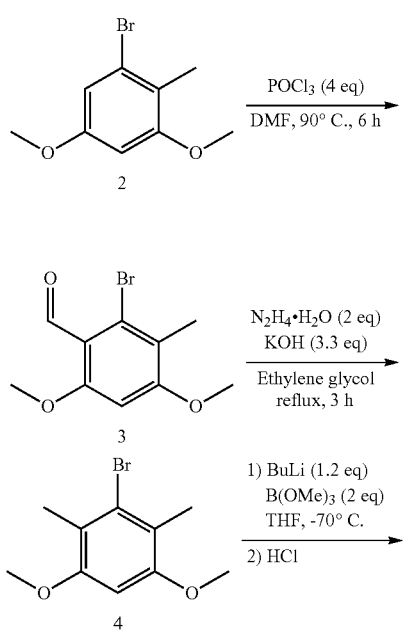

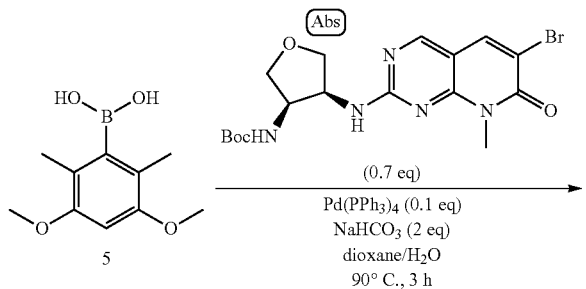

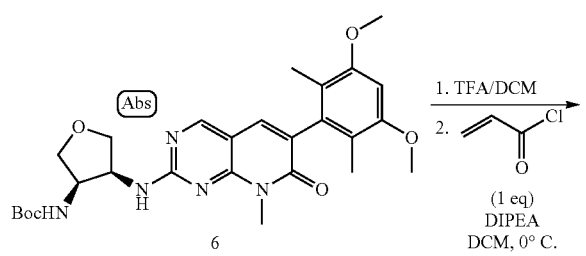

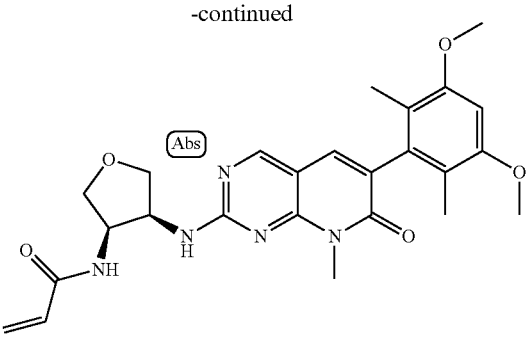

I-294

Step 1: Intermediate 1

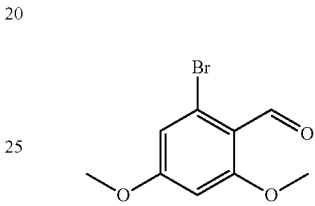

Under a nitrogen atmosphere, in a 250 ml 3-necked flask 1-bromo-3,5-dimethoxybenzene (3.5 g) was dissolved in DMF and cooled to −20° C. POCl$_3$ (4.8 g) was added dropwise through an addition funnel while the reaction temperature was maintained below 5° C. The reaction mixture was then warmed to 90° C. and allowed to stir overnight. The mixture was poured into ice water, extracted with EtOAc, washed with NaHCO$_3$, dried over anhydrous Na$_2$SO$_4$ and concentrated in vacuo. The resultant residue (5.0 g, 0.02 mol) was used directly in the next step. $^1$H NMR (400 MHz, CDCl$_3$): δ 3.88 (d, 6H), 6.44 (d, 1H), 6.79 (d, 1H), 10.32 (s, 1H).

Step 2: Intermediate 2

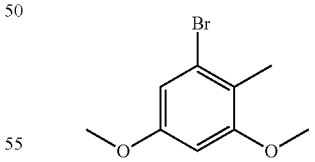

To a solution of Intermediate 2 (5.0 g, 0.021 mol) in ethylene glycol (10 mL) was added KOH (3.5 g, 6.3 mmol) and N$_2$H$_4$.H$_2$O (2.1 g, 42 mmol). The reaction was heated at reflux for 3 h, then was allowed to cool to room temperature, diluted with water and extracted with EtOAc. The organic layer was washed with NaHCO$_3$, dried over anhydrous Na$_2$SO$_4$ and concentrated in vacuo. The resultant residue was used directly in the next step. $^1$H NMR (400 MHz, CDCl$_3$): δ 2.22 (s, 3H), 378 (d, 6H), 6.38 (d, 1H), 6.70 (d, 1H).

Step 3: Intermediate 3

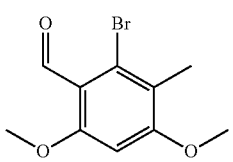

The procedure for synthesis of Intermediate 3 was the same as for Intermediate 1. $^1$H NMR (400 MHz, CDCl$_3$): δ 2.28 (s, 3H), 3.92 (d, 6H), 6.43 (s, 1H), 10.38 (s, 1H).

Step 4: Intermediate 4

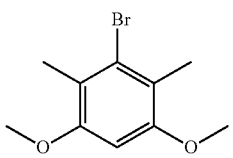

The procedure for synthesis of Intermediate 4 was the same as for Intermediate 2. $^1$H NMR (400 MHz, CDCl$_3$): δ 2.27 (s, 6H), 3.82 (d, 6H), 6.43 (s, 1H).

Step 5: Intermediate 5

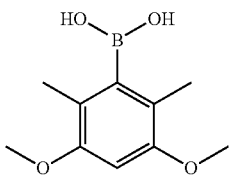

To a solution of Intermediate 4 (1.0 g, 4.1 mmol) in THF (5 mL) was added dropwise at −78° C. a solution of n-butyllithium (2 mL, 2.5 M in hexane, 4.9 mmol) in THF (10 mL). After 30 min, trimethylborate (0.9 g, 8.2 mol) was added and the mixture was allowed to warm to room temperature overnight. The mixture was poured onto 10% HCl and extracted with EtOAc. The organic layer was washed with saturated brine, dried (Na$_2$SO$_4$), and concentrated to afford the title compound as a brown oil. $^1$H NMR (400 MHz, CDCl$_3$): δ 0.07 (s, 1H), 2.27 (s, 6H), 3.82 (s, 6H), 6.43 (s, 1H).

Step 6: Intermediate 6

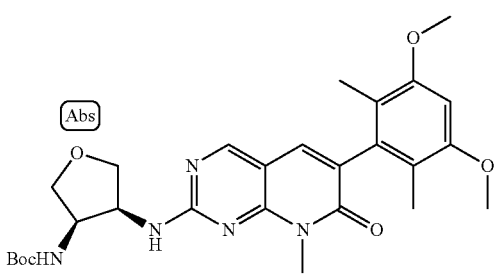

To a solution of ((3R,4S)-4-((6-bromo-8-methyl-7-oxo-7,8-dihydropyrido[2,3-d]pyrimidin-2-yl)amino)tetrahydrofuran-3-yl) carbamate (150 mg, 0.34 mmol) in toluene/H$_2$O (5 mL/0.5 mL) was added Intermediate 5 (200 mg, 0.68 mmol), Pd(PPh$_3$)$_4$ (39 mg, 0.03 mmol), and Na$_2$CO$_3$ (73 mg, 0.7 mmol). The resulting mixture was stirred at 95° C. overnight. The mixture was diluted with EtOAc, washed with water and brine, dried over anhydrous Na$_2$SO$_4$ and concentrated. The resultant residue was purified through silica gel chromatography (eluted with 50% EtOAc in hexanes to afford the title compound (80 mg, 45%). LCMS: 526.3 [M+1]$^+$.

Step 7: I-294

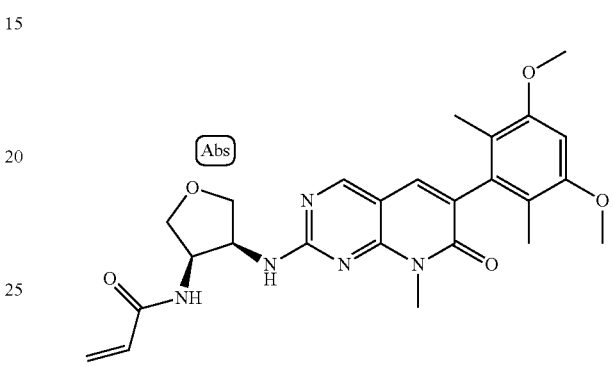

To a solution of Intermediate 6 (80 mg, 0.15 mmol) in DCM (5 mL) was added TFA (5 mL), and the mixture stirred at room temperature for 30 min. The volatiles were evaporated to afford the title compound as a TFA salt which was dissolved in DCM (10 mL). DIPEA was added until the pH>7, the mixture was cooled to 0° C., and a solution of acryloyl chloride (14 mg, 0.15 mmol) in DCM (1 mL) was added dropwise. The reaction mixture was stirred for 10 min. after which it was partitioned between DCM and water, the organic phase was separated, washed with brine, dried over Na$_2$SO$_4$ and the resultant residue was purified through silica gel column chromatography to afford the title compound (24 mg, 34%). LCMS: 480.3 [M+1]$^+$. $^1$H NMR (400 MHz, CDCl$_3$): δ 1.90 (d, 6H), 3.73 (s, 3H), 3.87 (d, 7H), 3.96 (dd, 1H), 4.18-4.24 (m, 2H), 4.92 (s, 1H), 5.02 (d, 1H), 5.66 (d, 1H), 6.15 (d, 1H), 6.26 (d, 1H), 6.52 (s, 1H), 6.79-6.81 (dd, 1H), 7.27 (s, 1H), 8.20 (s, 1H).

Example 254: I-296

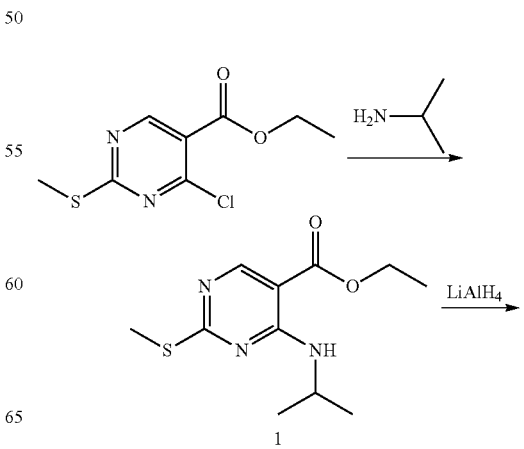

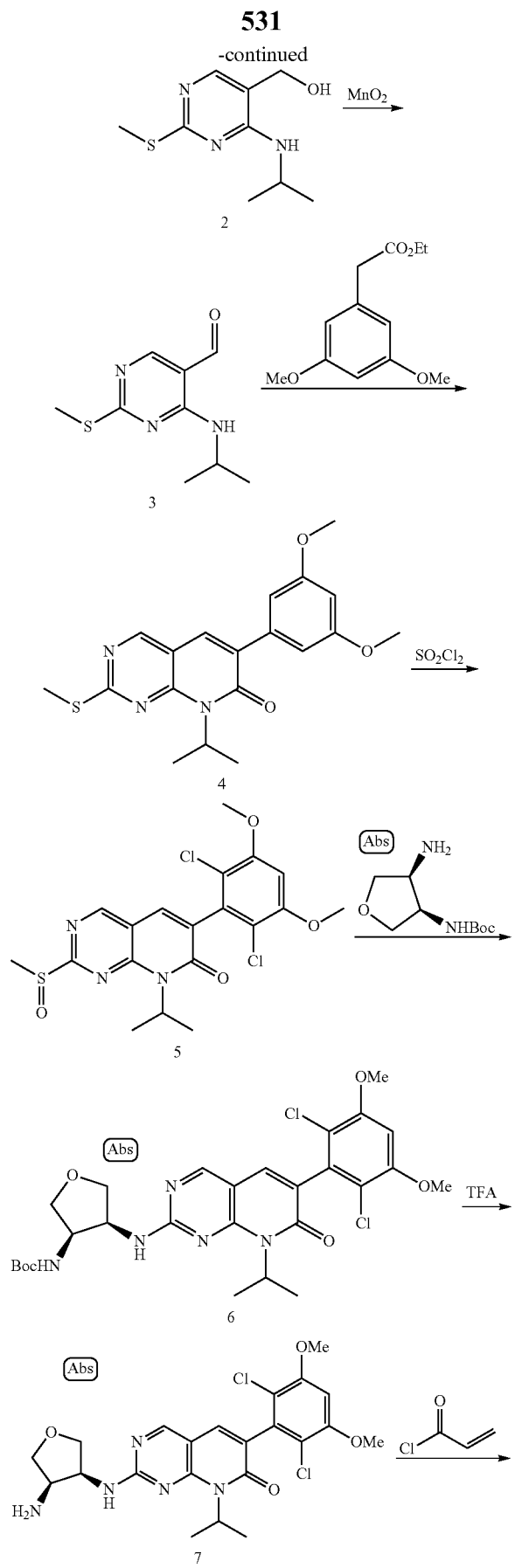

Step 1: Intermediate 1

A mixture of ethyl 4-chloro-2-(methylthio)pyrimidine-5-carboxylate (5.0 g, 21 mmol) and propan-2-amine (2.5 g, 43 mmol) in NMP (15 mL) was stirred at 60° C. overnight. The mixture was diluted with water and the resulting suspension filtered, dried, concentrated, and purified by column chromatography (12.5% ethyl acetate in hexane) to afford the title compound as off-white solid (4.9 g, 98%). LCMS: 256.3 [M+1]$^+$.

Step 2: Intermediate 2

To a solution of Intermediate 1 (4.9 g, 19 mmol) in anhydrous THF (50 mL) was added LiAlH$_4$ (1.4 g, 39 mmol) in portions at 0° C. The mixture was stirred at room temperature for 1 h then Na$_2$SO$_4$-10H$_2$O was added dropwise. The reaction mixture was filtered and the filtrate concentrated to afford the title compound as off-white solid (4.23 g, 100%). LCMS: 214.3 [M+1]$^+$.

Step 3: Intermediate 3

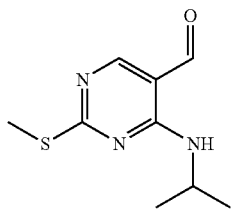

A mixture of Intermediate 2 (4.2 g, 19 mml) and MnO$_2$ (18 g, 210 mmol) in DCM (50 mL) was stirred at room temperature overnight. The mixture was filtered, and the filtrate concentrated and purified by silica gel chromatography (DCM:MeOH=20:1) to afford the title compound as brown solid (3.0 g, 75%). LCMS: 212.2 [M+1]$^+$.

Step 4: Intermediate 4

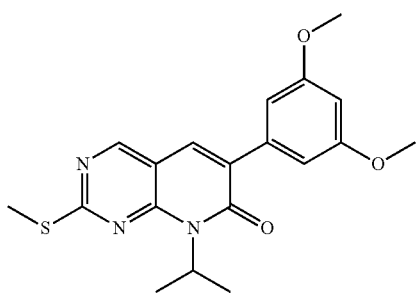

A mixture of ethyl 2-(3,5-dimethoxyphenyl)acetate (59 mg, 2.6 mmol), KF/Al$_2$O$_3$ (1.7 g, 12 mmol) and Intermediate 3 (500 mg, 2.4 mmol) in NMP (20 ml) was stirred at room temperature for 0.5 h. The mixture was added to brine, extracted with EtOAc, dried over (Na$_2$SO$_4$), and concentrated in vacuo to afford the title compound as oil. LCMS: 312.4 [M+1]$^+$.

Step 5: Intermediate 5

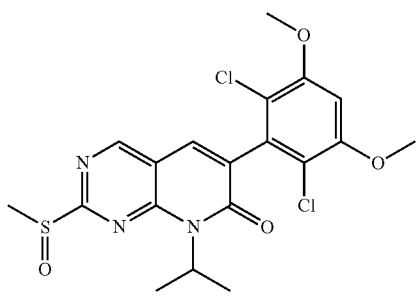

To a solution of Intermediate 4 (880 mg, 2.4 mmol) in DCM (30 mL) was added SO$_2$Cl$_2$ (640 mg, 4.7 mmol) dropwise at −10° C. The resulting mixture was stirred for 1 h after which it was quenched with saturated NaHCO$_3$ and extracted with DCM. The combined organic layers were washed with saturated NaHCO$_3$, dried, and concentrated in vacuo to afford the title compound as off-white solid (860 mg, 79%). LCMS: 456.1 [M+1]$^+$.

Step 6: Intermediate 6

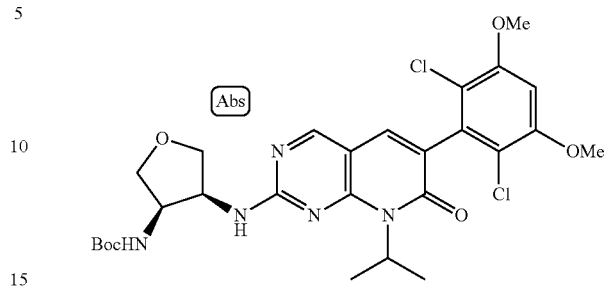

Intermediate 5 (200 mg, 0.44 mmol), DIPEA (85 mg, 0.66 mmol) and tert-butyl (3R,4S)-4-aminotetrahydrofuran-3-yl-carbamate from Example 226 (107 mg, 0.53 mmol) were combined in NMP (10 mL) and stirred at 85° C. for 2 h under N$_2$ atmosphere. The mixture was cooled to room temperature, diluted with water, extracted with ethyl acetate and the organic layers were washed with brine, dried over anhydrous Na$_2$SO$_4$, and concentrated. The resultant residue was purified by column chromatography (1% MeOH/DCM) to afford the title compound as white solid (190 mg, 73%). LCMS: 594.2 [M+1]$^+$.

Step 7: Intermediate 7

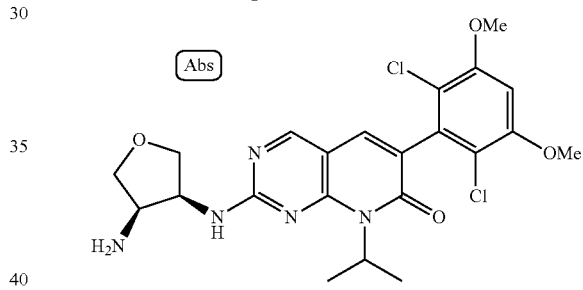

Boc deprotection of Intermediate 6 was carried out as previously described to afford the title compound (170 mg). $^1$H NMR (400 MHz, CDCl$_3$): δ 2.05 (s, 3H), 3.62-3.66 (m, 1H), 3.68-3.77 (m, 2H), 3.94 (s, 6H), 4.12 (q, 3H), 4.23-4.31 (m, 1H), 4.46-4.55 (m, 1H), 5.80 (s, 1H), 6.61 (s, 1H), 7.37 (s, 1H), 8.44 (s, 1H).

Step 8: I-296

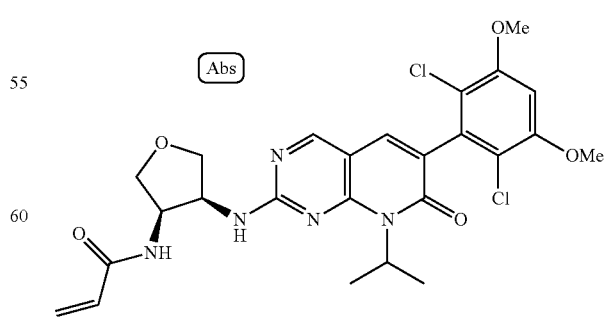

Acryloylation of Intermediate 7 was carried out as previously described to afford the title compound (40 mg, 46%)

as white solid. LCMS: 548.3 [M+1]⁺. ¹H NMR (400 MHz, CDCl₃): δ 1.61 (d, 6H), 3.86 (s, 3H), 3.94 (s, 6H), 4.23 (dd, 2H), 4.78-4.93 (m, 2H), 5.66 (dd, 1H), 5.74 (d, 1H), 6.12 (d, 1H), 6.29 (dd, 2H), 6.62 (s, 1H), 7.37 (s, 1H), 8.42 (s, 1H).
Example 255: I-307
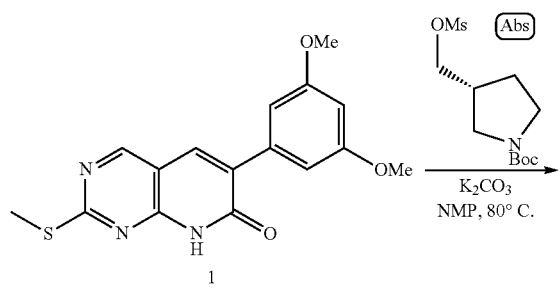
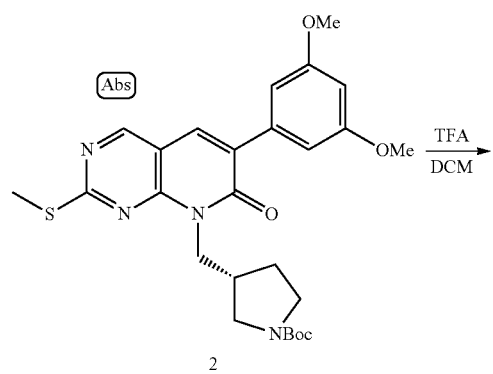
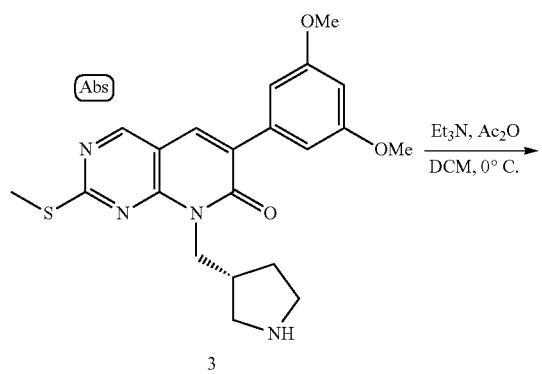
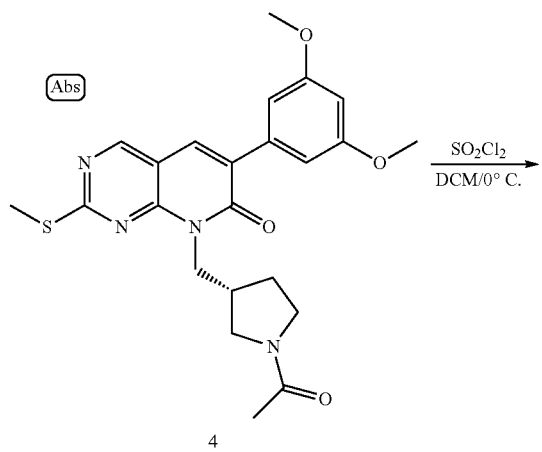
-continued
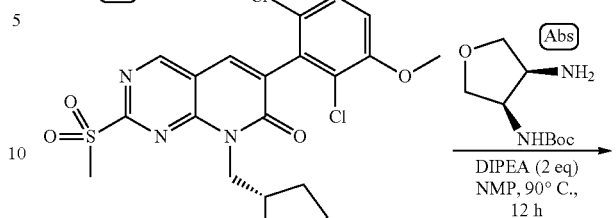
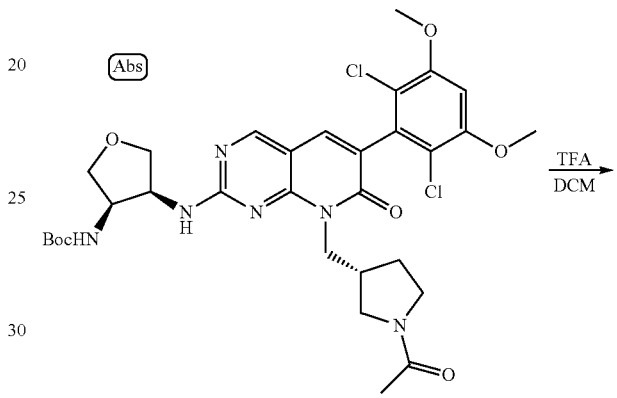
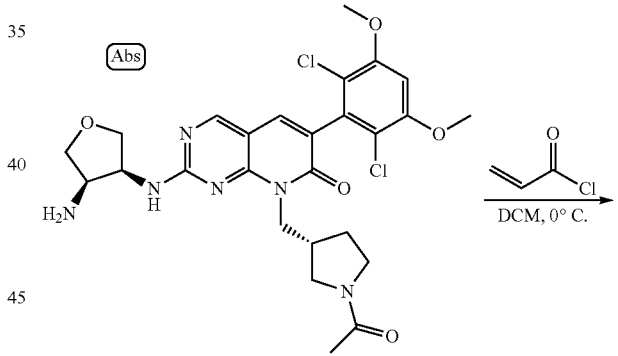
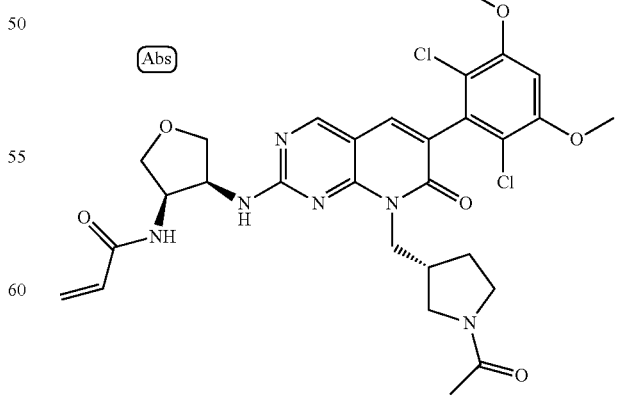

Step 1: Intermediate 2

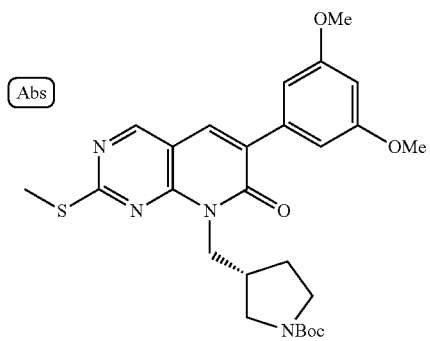 [SMILES: COc1cc(OC)cc(-c2cc3cnc(SC)nc3n(C[C@@H]3CCN(C(=O)OC(C)(C)C)C3)c2=O)c1]

A mixture of Intermediate 1 from Example 251 (654 mg, 1.99 mmol), (R)-tert-butyl 3-(((methylsulfonyl)oxy)methyl)pyrrolidine-1-carboxylate (832 mg, 2.98 mmol), and $K_2CO_3$ (550 mg, 3.98 mmol) in NMP (20 mL) was heated to 80° C. for 3 h. The mixture was cooled to room temperature and partitioned between EtOAc and water. The organic phase was separated, washed with water, brine, and dried over anhydrous $Na_2SO_4$. The resultant residue was purified through silica gel column chromatography (DCM:MeOH=120:1) to afford title product (1.0 g, 99%) as white solid. LCMS: 513.3 [M+1]$^+$.

Step 2: Intermediate 3

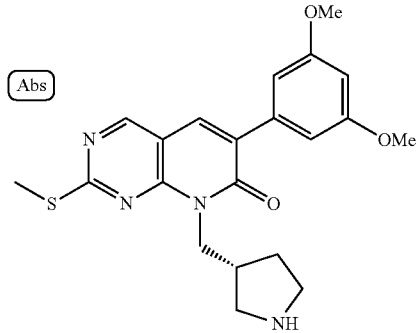 [SMILES: COc1cc(OC)cc(-c2cc3cnc(SC)nc3n(C[C@@H]3CCNC3)c2=O)c1]

A mixture of Intermediate 2 (1.00 g, 1.95 mmol) and TFA (8 mL) in DCM (16 mL) was stirred at room temperature for 1 h. The pH of the solution was adjusted to 9, diluted with DCM, washed with water, brine, dried over anhydrous $Na_2SO_4$ and concentrated. The resultant residue was purified through silica gel column chromatography (DCM:MeOH:$NH_4OH$=300:10:4) to afford the title compound (600 mg, 75%) as yellow solid. LCMS: 413.3 [M+1]$^+$.

Step 3: Intermediate 4

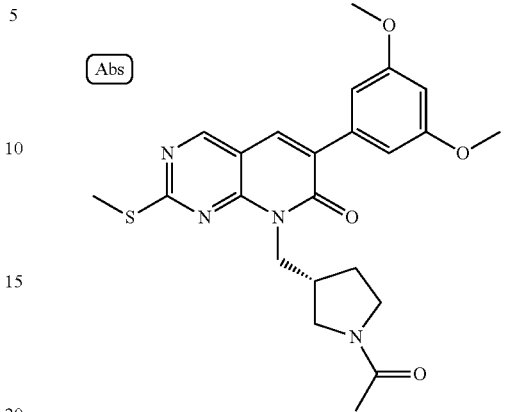

$Ac_2O$ (178 mg, 1.75 mmol) was added dropwise to a mixture of Intermediate 3 (600 mg, 1.46 mmol) and $Et_3N$ (220 mg, 2.18 mmol) in DCM (20 mL) at 0° C. The mixture was allowed to stir 0.5 h after which it was washed with 1N'HCl, aqueous $NaHCO_3$ and brine. The organic layer was dried over anhydrous $Na_2SO_4$ and concentrated to afford title compound (600 mg, 91%) as yellow oil. LCMS: 455.3 [M+1]$^+$.

Step 4: Intermediate 5

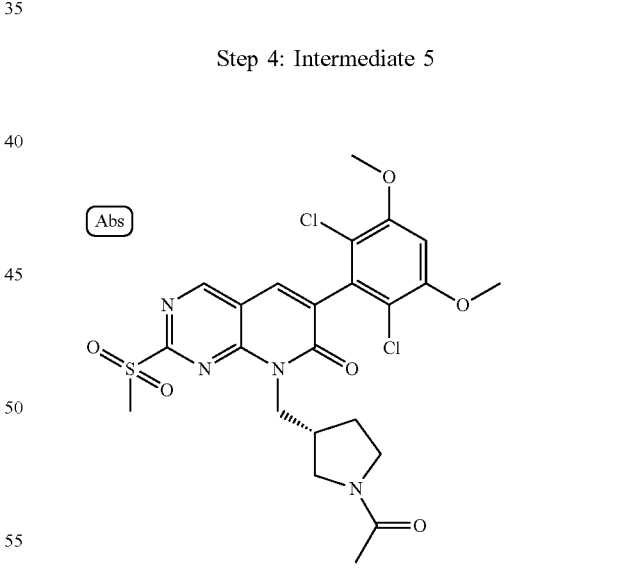

To a solution of Intermediate 4 (200 mg, 0.44 mmol) in DCM (20 mL) was added $SO_2Cl_2$ (148 mg, 1.1 mmol) dropwise at 0° C., then the mixture was stirred at 0° C. for 30 min, quenched with aqueous $NaHCO_3$, washed with brine, dried over anhydrous $Na_2SO_4$ and concentrated to afford title product (270 mg) as yellow oil which was used directly in the next step. LCMS: 677.3 [M+1]$^+$.

Step 5: Intermediate 6

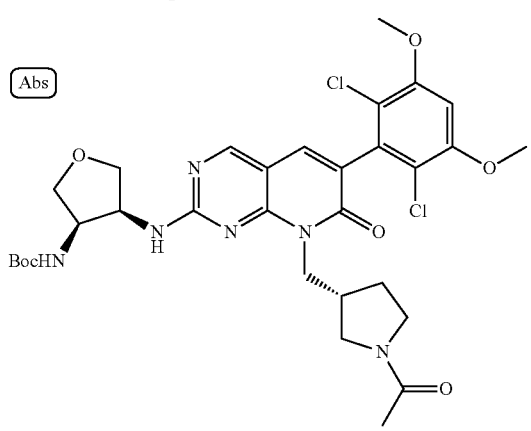

To a mixture of Intermediate 5 (270 mg, 0.48 mmol), tert-butyl ((3R,4S)-4-aminotetrahydrofuran-3-yl)carbamate (127 mg, 0.63 mmol), DIPEA (186 mg, 1.44 mmol) in NMP (10 mL) was heated to 80° C. for 3 h. The mixture was cooled to room temperature and partitioned between EtOAc and water. The organic phase was separated, washed with water, brine, and dried over anhydrous $Na_2SO_4$. The resultant residue was purified through column chromatography (DCM:MeOH=40:1) to afford title product (200 mg, 61%) as white solid.

Step 6: Intermediate 7

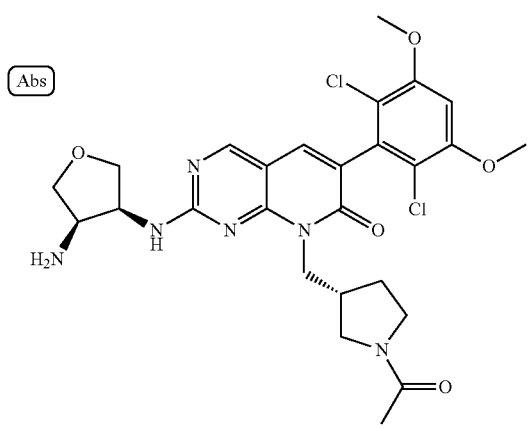 [SMILES: COc1cc(OC)c(Cl)c(-c2cc3cnc(N[C@@H]4COC[C@@H]4N)nc3n(C[C@@H]3CCN(C(C)=O)C3)c2=O)c1Cl]

A mixture of Intermediate 6 (100 mg, 0.15 mmol) and TFA (2 mL) in DCM (4 mL) was stirred at room temperature for 0.5 h. The reaction solution was concentrated and the resultant residue used directly in the next step (assume 100% yield). LCMS: 577.2 $[M+1]^+$.

Step 7: I-307

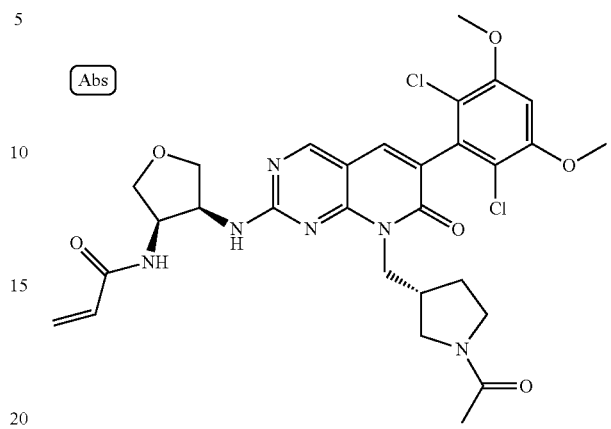

To a solution of Intermediate 7 and DIPEA (194 mg, 1.5 mmol) in dry DCM (20 mL) was added a solution of acryloyl chloride (13 mg, 0.15 mmol) in dry DCM (2 mL) dropwise in an ice-brine bath. The reaction mixture was allowed to stir for 10 min. after which it was partitioned between DCM and $H_2O$. The organic phase was separated, washed with brine, dried over $Na_2SO_4$ and the crude product was purified through prep-HPLC to afford the title compound (20 mg) as white solid. LCMS $[M+1]+$: 631.2. $^1H$ NMR (400 MHz, $CD_3OD$): δ 1.86-2.06 (m, 5H), 2.94-3.00 (m, 1H), 3.32-3.33 (m, 2H), 3.39-3.98 (m, 10H), 4.13-4.24 (m, 2H), 4.47-4.64 (m, 2H), 4.80-4.85 (m, 1H), 4.94-4.97 (m, 1H), 5.54-5.60 (m, 1H), 6.08-6.16 (m, 2H), 6.90 (s, 1H), 7.66 (s, 1H), 8.63 (s, 1H).

Example 256: Additional Compounds

Compounds presented below in Tables 7 and 8 were synthesized and characterized as described in the prior examples.

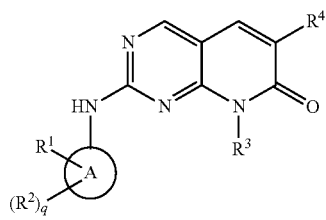

TABLE 7

| ID | R³ | R⁴ | ¹H NMR |
|---|---|---|---|
| I-249 | | Me | OMe, Cl, OMe, Cl (dimethoxy-dichlorophenyl) | LCMS: 536.5 $[M + H]^+$, $^1H$ NMR (400 MHz, $CDCl_3$): δ 2.75-2.76 (m, 2H), 3.33-3.43 (m, 2H), 3.69 (s, 3H), 3.95 (s, 6H), 4.87-4.91 (m, 2H), 5.67-5.69 (m, 1H), 6.07 (dd, 1H), 6.34 (d, 1H), 6.63 (s, 1H), 7.43 (s, 1H), 8.47 (s, 1H). |

TABLE 7-continued

| ID | R³ | R⁴ | ¹H NMR |
|---|---|---|---|
| I-250 | [structure: Abs, tetrahydrofuran with NH linker and vinylsulfonamide] | Me | [structure: 2,6-dichloro-3,5-dimethoxyphenyl] | LCMS: 556.0 [M + H]⁺, ¹HNMR (400 MHz, CD₃OD): δ 3.58-3.81 (m, 5H), 3.95 (s, 6H), 4.10-4.31 (m, 2H), 4.75-4.94 (m, 2H), 5.72 (d, 1H), 6.03 (m, 1H), 6.52 (m, 1H), 6.87 (s, 1H), 7.66 (s, 1H), 8.65 (s, 1H). |
| I-251 | [structure: Abs, tetrahydrofuran with NH linker and propiolamide] | Me | [structure: 2,6-dichloro-3,5-dimethoxyphenyl] | LCMS: 518.0 [M + H]⁺, ¹HNMR (400 MHz, CD₃OD): δ 2.80 (s, 3H), 3.60-3.74 (m, 5H), 3.95 (s, 6H), 4.08 (m, 1H), 4.13 (br, 1H), 6.87 (s, 1H), 7.63 (s, 1H), 8.62 (s, 1H). |
| I-254 | [structure: Abs, tetrahydrofuran with NH linker and acrylamide] | Me | [structure: 2-chloro-3,5-dimethoxyphenyl] | LCMS: 486.5 [M + H]⁺. ¹HNMR (400 MHz, CDCl₃): δ 3.71 (s, 3H), 3.74-3.86 (m, 5H), 3.90 (s, 3H), 4.18 (dd, 1H), 4.26 (dd, 1H), 4.80-4.93 (m, 2H), 5.62 (d, 1H), 6.04 (dd, 2H), 6.21-6.41 (m, 2H), 6.48 (d, 1H), 6.55 (d, 1H), 7.51 (s, 1H), 8.47 (s, 1H). |
| I-260 | [structure: 4-fluoro-2-(acrylamido)phenyl with NH linker] | Me | [structure: 2,6-dichloro-3,5-dimethoxyphenyl] | LCMS: 544.5 [M + H]⁺. ¹H NMR (400 MHz, DMSO-d₆): δ 3.56 (s, 3H), 3.96 (s, 6H), 5.77-5.80 (m, 1H), 6.26-6.30 (m, 1H), 6.47-6.51(m, 1H), 7.00-7.05 (m, 2H), 7.59-7.61 (m, 1H), 7.83-7.88 (m, 2H), 8.83 (s, 1H), 9.38 (s, 1H), 9.87 (s, 1H). |
| I-261 | [structure: 4-methyl-2-(acrylamido)phenyl with NH linker] | Me | [structure: 2,6-dichloro-3,5-dimethoxyphenyl] | LCMS: 540.5 [M + H]⁺. ¹H NMR (400 MHz, DMSO-d₆): δ 2.32 (s, 3H), 3.52 (s, 3H), 3.96 (s, 6H), 5.73-5.76 (m, 1H), 6.24-6.29 (m, 1H), 6.46-6.53(m, 1H), 7.00-7.02 (m, 2H), 7.48 (d, 1H), 7.70 (s, 1H), 7.78 (s, 1H), 8.78 (s, 1H), 9.24 (s, 1H), 9.78(s, 1H). |

US 10,065,966 B2

TABLE 7-continued

| ID | R³ | R⁴ | ¹H NMR |
|---|---|---|---|
| I-262 | 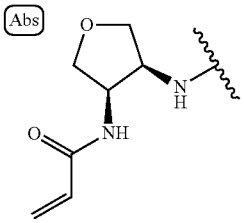 [SMILES: *N[C@@H]1COC[C@@H]1NC(=O)C=C] | 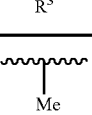 Me | 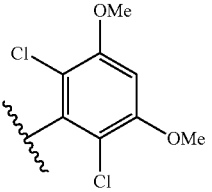 [SMILES: *c1c(Cl)c(OC)cc(OC)c1Cl] | LCMS: 518.5 [M + H]⁺. ¹HNMR (400 MHz, CD₃OD): δ 1.71-1.84 (m, 3H), 1.95-2.22 (m, 3H), 3.72 (s, 3H), 3.97 (s, 6H), 4.57-4.68 (m, 2H), 5.49-5.51 (m, 1H), 6.08 (s, 2H), 6.89 (s, 1H), 7.61 (s, 1H), 8.58 (s, 1H). |
| I-263 | 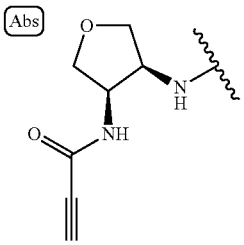 [SMILES: *N[C@@H]1COC[C@@H]1NC(=O)C#C] | 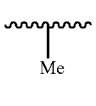 Me | 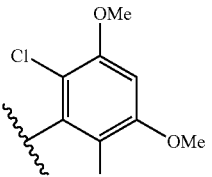 | LCMS: 516.0 [M + H]⁺. ¹HNMR (400 MHz, CD₃OD): δ 1.60-1.82 (m, 3H), 1.86-1.98 (m, 1H), 2.01-2.19 (m, 2H), 3.30 (s, 3H), 3.60-3.79 (m, 1H), 3.94 (s, 6H), 4.53 (m, 1H), 4.61 (m, 1H), 6.86 (s, 1H), 7.64 (s, 1H), 8.63 (s, 1H). |
| I-264 | 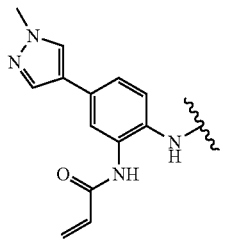 [SMILES: *Nc1ccc(-c2cnn(C)c2)cc1NC(=O)C=C] |  Me | 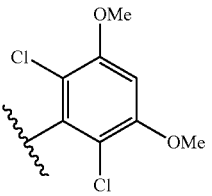 [SMILES: *c1c(Cl)c(OC)cc(OC)c1Cl] | LCMS: 606.5 [M + H]⁺. ¹H NMR (400 MHz, DMSO-d₆): δ 3.53(s, 3H), 3.88 (s, 3H), 3.96 (s, 6H), 5.77-5.80 (m, 1H), 6.30 (d, 1H), 6.50-6.57 (m, 1H), 6.99 (s, 1H), 7.45 (d, 1H), 7.79-7.84 (m, 4H), 8.13 (s, 1H), 8.78 (s, 1H), 9.26 (s, 1H), 9.87 (s, 1H). |
| I-266 | 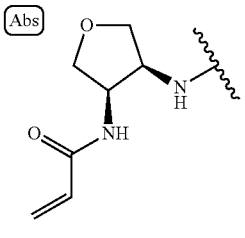 [SMILES: *N[C@@H]1COC[C@@H]1NC(=O)C=C] |  Me | 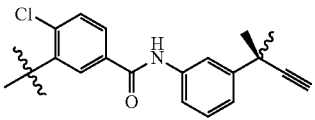 | LCMS: 612.6 [M + H]⁺. ¹H NMR (400 MHz, MeOD): δ 8.65 (s, 1H), 7.99-7.92 (m, 3H), 7.84 (s, 1H), 7.73-7.69 (m, 1H), 7.65 (d, 1H), 7.42 (t, 1H), 7.32 (d, 1H), 6.20-6.08 (m, 2H), 5.60-5.53 (m, 1H), 4.96-4.91 (m, 2H), 4.28-4.19 (m, 1H), 4.14 (dd, 1H), 3.88 (m, 1H), 3.81-3.76 (m, 4H), 1.75 (s, 6H). |
| I-267 | 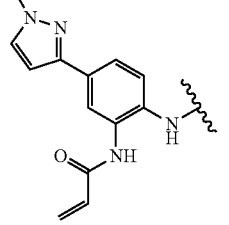 |  Me | 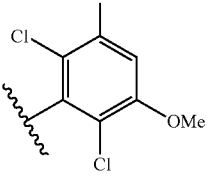 | LCMS: 606.5 [M + H]⁺. ¹H NMR (400 MHz, DMSO-d₆): δ 3.32(s, 3H), 3.53 (s, 3H), 3.96 (s, 6H), 6.28 (d, 1H), 6.51-6.58 (m, 1H), 6.67 (s, 1H), 7.00 (s, 1H), 7.65 (d, 1H), 7.74(s, 1H), 7.80 (s, 1H), 7.89 (d, 1H), 8.07 (s, 1H), 8.79 (s, 1H), 9.34(s, 1H), 9.95 (s, 1H). |
| I-268 | 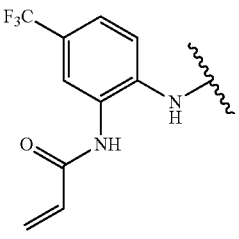 [SMILES: *Nc1ccc(C(F)(F)F)cc1NC(=O)C=C] |  Me | 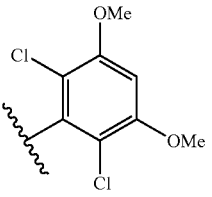 [SMILES: *c1c(Cl)c(OC)cc(OC)c1Cl] | LCMS: 594.5 [M + H]⁺. ¹H NMR (400 MHz, DMSO-d₆): δ 8.78 (s, 1H), 8.22 (d, 1H), 7.98 (s, 1H), 7.75 (s, 1H), 7.61 (d, 1H), 6.91 (s, 1H), 6.57-6.43 (m, 2H), 5.85 (d, 1H), 3.98 (s, 6H), 3.30 (s, 3H). |

TABLE 7-continued

| ID | R³ | R⁴ | ¹H NMR |
|---|---|---|---|
| I-270 | 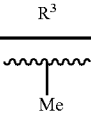 | 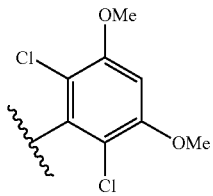 [SMILES: *c1c(Cl)c(OC)cc(OC)c1Cl]Me |  | LCMS: 608.5 [M + H]⁺. ¹H NMR (400 MHz, DMSO-d₆): δ 3.54 (s, 3H), 3.96 (s, 6H), 4.44 (s, 3H), 5.79 (d, 1H), 6.31 (d, 1H), 6.52-6.57 (m, 1H), 7.00 (s, 1H), 7.82 (s, 1H), 7.91 (d, 1H), 8.07 (d, 1H), 8.46 (s, 1H), 8.83 (s, 1H), 9.56 (s, 1H), 9.95 (s, 1H). |
| I-271 | 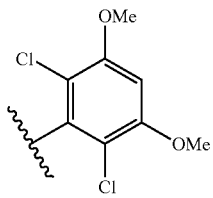 [SMILES: *c1c(Cl)c(OC)cc(OC)c1Cl] | Me |  | LCMS: 544.5 [M + H]⁺. ¹H NMR (400 MHz, CDCl₃): δ 8.68 (s, 1H), 8.56 (s, 1H), 7.91 (s, 1H), 7.47 (s, 2H), 7.36-7.30 (m, 1H), 6.98 (t, 1H), 6.63 (s, 1H), 6.56 (d, 1H), 6.41-6.35 (m, 1H), 5.99 (d, 1H), 3.95 (s, 6H), 3.72 (s, 3H). |
| I-272 | 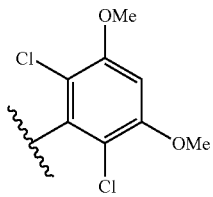 [SMILES: *c1c(Cl)c(OC)cc(OC)c1Cl] | Me |  | LCMS: 566.6 [M + H]⁺. ¹H NMR (400 MHz, CDCl₃): δ 0.68-0.77 (m, 2H), 0.94-1.02 (m, 2H), 1.86-1.98 (m, 1H), 3.67 (s, 3H), 3.94 (s, 6H), 5.76 (d, 1H), 6.23 (dd, 1H), 6.44 (d, 1H), 6.62 (s, 1H), 6.97 (d, 1H), 7.46 (d, 2H), 7.62-7.50 (m, 1H), 7.8 (s, 1H), 8.0 (d, 1H), 8.53 (s, 1H). |
| I-273 | 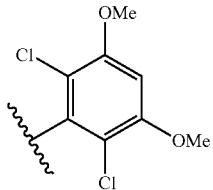 [SMILES: *c1c(Cl)c(OC)cc(OC)c1Cl] | Me |  | LCMS: 561.5 [M + H]⁺. ¹HNMR (400 Hz, CDCl₃): δ 2.10 (s, 3H), 3.46-3.63 (m, 2H), 3.70 (s, 3H), 3.83-3.91 (m, 1H), 3.95 (s, 6H), 4.01-4.12 (m, 1H), 4.76-4.91 (m, 2H), 5.64-5.72 (m, 1H), 6.02-6.13 (m, 1H), 6.25-6.37 (m, 1H), 6.63 (s, 1H), 7.44 (d, 1H), 8.46 (s, 1H). |
| I-275 | 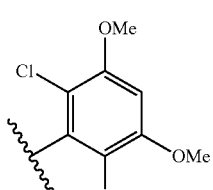 | Me |  | LCMS: 527.5 [M + H]⁺. ¹H NMR (400 MHz, CDCl₃): δ 3.79 (s, 3H), 3.94 (s, 6H), 5.88 (d, 1H), 6.39-6.46 (m, 1H), 6.56-6.61(m, 2H), 7.51 (s, 1H), 8.31-8.38 (m, 2H), 8.47 (d, 1H), 8.54 (s, 1H), 8.64 (s, 1H), 8.83 (br, 1H). |
| I-277 | 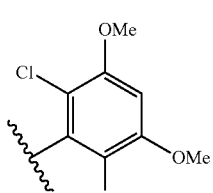 | Me |  | LCMS: 557.5 [M + H]⁺. ¹H NMR (400 MHz, CDCl₃): δ 3.66 (s, 3H), 3.91 (s, 3H), 3.94 (s, 6H), 5.91 (d, 1H), 6.35-6.42 (m, 1H), 6.57-6.62 (m, 2H), 6.77 (d, 1H), 7.43 (s, 1H), 7.75 (s, 1H), 8.21 (br, 1H), 8.52 (s, 1H). |

TABLE 7-continued

| ID | R³ | R⁴ | ¹H NMR |
|---|---|---|---|
| I-280 | (Abs) 1-methylpyrazol-5-yl substituted pyrrolidine with acrylamide | Me | 2,6-dichloro-3,5-dimethoxyphenyl | LCMS: 599.5 [M + H]⁺. ¹H NMR (400 MHz, CDCl₃): δ 3.38-3.46 (m, 2H), 3.71-3.76 (m, 7H), 3.81-3.85 (m, 1H), 3.95 (s, 6H), 4.91-4.93 (m, 2H), 5.51 (d, 1H), 5.63 (d, 1H), 6.03-6.10 (m, 1H), 6.28 (d, 1H), 6.35 (br, 1H), 6.63 (s, 1H), 7.17 (d, 1H), 7.40 (s, 1H), 8.45 (s, 1H). |
| I-282 | 2,3-difluoro-6-acrylamidophenyl-NH- | Me | 2,6-dichloro-3,5-dimethoxyphenyl | LCMS: 562.4 [M + H]⁺. ¹H NMR (400 MHz, MeOD): δ 8.78 (s, 1H), 8.22 (d, 1H), 7.98 (s, 1H), 7.75 (s, 1H), 7.61 (d, 1H), 6.91 (s, 1H), 6.57-6.43(m, 2H), 5.85 (d, 1H), 3.70 (s, 6H), 3.98 (s, 3H). |
| I-284 | R+S mixture cis-diamine hydroxycyclopentyl acrylamide | Me | 2,6-dichloro-3,5-dimethoxyphenyl | LCMS: 534.4 [M + H]⁺. ¹H NMR (400 MHz, CDCl₃): δ 1.76-1.86 (m, 2H), 2.40-2.52 (m, 2H), 3.70 (s, 3H), 3.94 (s, 6H), 4.54-4.59 (m, 1H), 4.65-4.74 (m, 2H), 5.59 (d, 1H), 6.19 (d, 1H), 5.95-6.04 (m, 1H), 6.33-6.50 (m, 2H), 6.63 (s, 1H), 7.40 (s, 1H), 8.44 (s, 1H). |
| I-285 | 3,4-difluoro-2-acrylamidophenyl-NH- | Me | 2,6-dichloro-3,5-dimethoxyphenyl | LCMS: 562.3 [M + H]⁺. ¹H NMR (400 MHz, DMSO-d₆): δ 9.71 (s, 1H), 9.40 (s, 1H), 8.77 (s, 1H), 7.80 (s, 1H), 7.76-7.70 (m, 1H), 7.44-7.36 (m, 1H), 6.99 (s, 1H), 6.57-6.48 (m, 1H), 6.28 (d, 1H), 5.75 (dd, 1H), 3.53-3.36 (m, 1H), 3.96 (s, 6H). |
| I-297 | (Abs) tetrahydrofuran-diamine acrylamide | H | 2,6-dichloro-3,5-dimethoxyphenyl | LCMS: 472.2 [M + H]⁺. ¹H NMR (400 MHz, CDCl₃): δ 3.76-3.80 (m, 1H), 3.83 (s, 3H), 3.92 (s, 3H), 3.94-3.95 (m, 1H), 4.07-4.14 (m, 2H), 4.81-4.82 (m, 1H), 4.91-4.96 (m, 1H), 5.41 (d, 1H), 5.67 (dd, 1H), 6.06 (d, 1H), 6.50 (d, 1H), 6.59 (d, 1H), 7.13 (br, 1H), 7.68 (s, 1H), 8.62 (s, 1H), 8.88 (br, 1H), 13.68 (br, 1H). |
| I-298 | (Abs) tetrahydrofuran-diamine acrylamide | tetrahydrofuran-3-ylmethyl | 2,6-dichloro-3,5-dimethoxyphenyl | LCMS: 590.2 [M + H]⁺. ¹HNMR (400 MHz, CDCl₃): 1.74-1.80 (m, 1H), 1.91-2.04 (m, 1H), 2.82-2.87 (m, 1H), 3.63-3.67 (m, 1H), 3.73-3.85 (m, 4H), 3.89-3.99 (m, 7H), 4.12-4.28 (m, 2H), 4.41 (d, 2H), 4.78-4.83 (m, 2H), 5.63 (ddd, 1H), 6.00-6.10 (m, 1H), 6.23-6.29 (m, 1H), 6.62 (s, 1H), 7.44 (s, 1H), 8.49 (s, 1H). |

TABLE 7-continued

| ID | R³ | R⁴ | ¹H NMR |
|---|---|---|---|
| I-299 | [Abs] tetrahydrofuran with acrylamide NH and NH linker | 1-acetylpyrrolidin-3-ylmethyl | 2,6-dichloro-3,5-dimethoxyphenyl | LCMS: 631.3 [M + H]⁺. ¹H NMR (400 MHz, CD₃OD): δ 1.91 (d, 6H), 2.70-2.93 (m, 1H), 3.23-3.94(m, 13H), 4.02 (dd, 2H), 4.21-4.36 (m, 1H), 4.44-4.64 (m, 1H), 5.42 (d, 1H), 5.98 (s, 2H), 6.77 (d, 1H), 7.54 (d, 1H), 8.51 (s, 1H). |
| I-300 | [Abs] tetrahydrofuran with acrylamide NH and NH linker | tetrahydropyran-4-yl | 2,6-dichloro-3,5-dimethoxyphenyl | LCMS: 590.1 [M + H]⁺. ¹HNMR (400 MHz, DMSO-d₆): δ 1.33-1.54 (m, 2H), 2.51-2.88 (m, 2H), 3.42-3.82 (m, 4H), 3.95-4.23 (m, 10H), 4.61-4.65 (m, 1H), 4.78-4.80 (m, 1H), 5.53-5.57 (m, 2H), 5.95-5.99 (m, 1H), 6.16-6.20 (m, 1H), 6.98 (s, 1H), 7.66 (s, 1H), 7.75 (d, 1H), 8.07 (d, 1H), 8.64 (s, 1H). |
| I-301 | [Abs] tetrahydrofuran with acrylamide NH and NH linker | 1-acetylpyrrolidin-3-ylmethyl | 2-chloro-3,5-dimethoxyphenyl | LCMS: 597.3 [M + H]⁺. ¹H NMR (400 MHz, CD₃OD): δ 2.06 (t, 5H), 2.81-3.06 (m, 1H), 3.42 (dd, 3H), 3.63-3.80 (m, 2H), 3.83 (s, 3H), 3.90 (t, 4H), 4.10-4.18 (m, 1H), 4.18-4.28 (m, 1H), 4.30-4.47 (m, 1H), 4.58-4.75 (m, 1H), 4.90 (s, 2H), 5.57 (s, 1H), 6.11 (s, 2H), 6.52-6.58 (m, 1H), 6.70 (t, 1H), 7.71 (d, 1H), 8.61 (s, 1H). |
| I-302 | [Rac] cis tetrahydrofuran with acrylamide NH and NH linker | 2,3-dihydroxypropyl | 2,6-dichloro-3,5-dimethoxyphenyl | LCMS: 580.5 [M + H]⁺. ¹HNMR (400 Hz, CDCl₃): δ 3.47-3.72 (m, 3H) 3.72-3.90 (m, 3H), 3.95 (s, 6H), 4.12 (d, 4H), 4.50-4.75 (m, 2H), 4.84-4.99 (m, 2H), 5.63 (d, 1H), 5.95-6.08 (m, 1H), 6.26 (d, 2H), 6.63 (s, 1H), 7.50 (d, 1H), 8.53 (s, 1H). |
| I-306 | [Abs] tetrahydrofuran with acrylamide NH and NH linker | Me | 2-chloro-3-ethoxy-5-methoxyphenyl | LCMS: 500.3 [M + H]⁺. ¹H NMR (400 MHz, CDCl₃): δ 1.41 (t, 3H), 3.71 (s, 3H), 3.78 (d, 1H), 3.87-3.81 (m, 1H), 3.90 (s, 3H), 4.02 (q, 2H), 4.31-4.14 (m, 2H), 4.94-4.79 (m, 2H), 5.64 (d, 1H), 6.04 (d, 1H), 6.23-6.13 (m, 1H), 6.27 (d, 1H), 6.47 (d, 1H), 6.56 (d, 1H), 7.51 (s, 1H), 8.46 (s, 1H). |
| I-308 | [Abs] tetrahydrofuran with acrylamide NH and NH linker | 1-acetylpyrrolidin-3-ylmethyl | 2-chloro-3,5-dimethoxyphenyl | LCMS: 597.3 [M + H]⁺. ¹H NMR (400 MHz, CD₃OD): δ 1.88-2.07 (m, 5H), 2.94-2.96 (m, 1H), 3.32-3.33 (m, 2H), 3.42-3.91 (m, 10H), 4.13-4.24 (m, 2H), 4.46-4.63(m, 2H), 4.85-4.89 (m, 2H), 5.57-5.60 (m, 1H), 6.09-6.13 (m, 2H), 6.54-6.55 (m, 1H), 6.70-6.71 (m, 1H), 7.72 (s, 1H), 8.62 (s, 1H). |

TABLE 7-continued

| ID | R³ | R⁴ | ¹H NMR |
|---|---|---|---|
| I-309 | 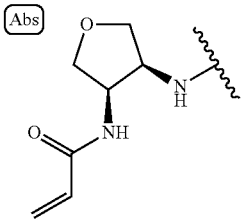 [SMILES: *N[C@@H]1COC[C@@H]1NC(=O)C=C] | 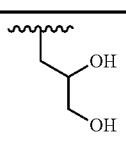 | 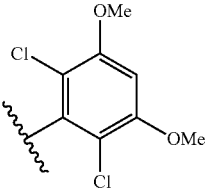 [SMILES: *c1c(Cl)c(OC)cc(OC)c1Cl] | LCMS: 580.5 [M + H]⁺. ¹HNMR (400 Hz, CDCl₃): δ 3.47-3.72 (m, 3H) 3.72-3.90 (m, 3H), 3.95 (s, 6H), 4.12 (d, 4H), 4.50-4.75 (m, 2H), 4.84-4.99 (m, 2H), 5.63 (d, 1H), 5.95-6.08 (m, 1H), 6.26 (d, 2H), 6.63 (s, 1H), 7.50 (d, Hz, 1H), 8.53 (s, 1H). |

TABLE 8

| ID | R³ | R⁴ | ¹H NMR |
|---|---|---|---|
| I-295 | 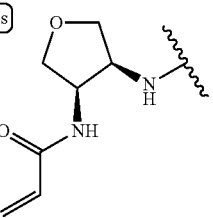 | 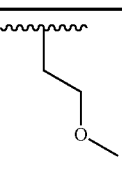 | 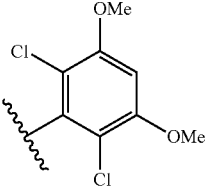 [SMILES: *c1c(Cl)c(OC)cc(OC)c1Cl] | LCMS: 564.4 [M + H]⁺. ¹H NMR (400 MHz, CDCl₃) δ 3.34 (s, 3H), 3.63-4.07 (m, 10H), 4.07-4.29 (m, 2H), 4.37-4.94 (m, 4H), 5.49-5.70 (m, 1H), 6.01 (dd, 1H), 6.15-6.32 (m, 1H), 6.63 (d, 3H), 7.44 (s, 1H), 8.49 (s, 1H). |
| I-291 | 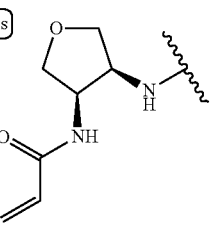 | Me |  | LCMS: 534.4 [M + H]⁺. ¹H NMR (400 MHz, CDCl₃) δ 1.47 (td, 3H), 3.38-3.88 (m, 5H), 3.91 (d, 3H), 4.01-4.42 (m, 4H), 4.77-4.93 (m, 2H), 5.56 (dd, 1H), 5.96-6.07 (m, 1H), 6.22 (dd, 1H), 6.61 (s, 2H), 6.75 (s, 1H), 7.44 (s, 1H), 8.50 (s, 1H). |
| I-287 | 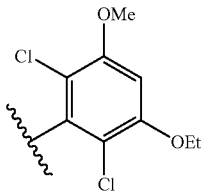 [SMILES: *c1c(Cl)c(OC)cc(OCC)c1Cl] | Me | 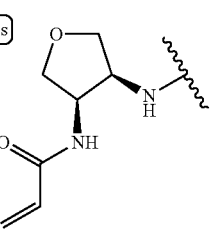 | LCMS: 554.4 [M + H]⁺. ¹H NMR (400 MHz, CDCl₃), δ ppm: 8.49 (s, 1H), 7.46 (s, 1H), 6.92 (s, 1H), 6.55 (t, 1H), 6.29 (s, 1H), 6.25 (s, 1H), 5.95-6.1 (m, 2H), 5.65 (d, 1H), 4.82-4.93 (m, 2H), 4.23-4.31 (m, 1H), 4.16-4.22 (m, 1H), 3.93 (s, 3H), 3.74-3.86 (m, 2H), 3.71 (s, 3H). |
| I-283 |  | Me | 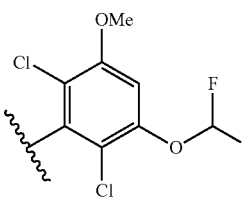 | LCMS: 464.8 [M + H]⁺. ¹H NMR (400 MHz, CDCl₃) δ 3.63-3.91 (m, 4H), 3.95 (s, 3H), 4.06-4.39 (m, 2H), 4.68-4.98 (m, 2H), 5.65 (dd, 1H), 6.03 (dd, 2H), 6.27 (dd, 1H), 7.21 (dd, 1H), 7.45 (dd, 1H), 7.64 (d, 1H), 8.50 (s, 1H). |
| I-289 | 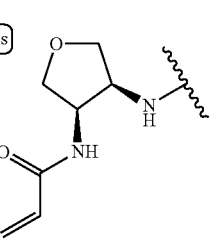 | Me |  | LCMS: 562.0 [M + H]⁺. ¹H NMR (400 MHz, CDCl₃), δ ppm: 8.24 (br s, 1H), 7.97 (s, 1H), 7.84 (m, 1H), 7.52 (m, 1H), 7.23 (m, 1H), 7.14 (br s, 1H),691 (s, 1H), 6.55 (t, 1H), 6.26-6.41 (m, 1H), 6.18-6.24 (m, 1H), 5.76 (d, 1H), 4.57 (s, 2H), 3.93 (s, 3H), 3.39 (s, 3H). |

TABLE 8-continued

| ID | R³ | R⁴ | ¹H NMR |
|---|---|---|---|
| I-303 [Abs] (tetrahydrofuran-acrylamide structure) | (propyl-OH) | 2,6-dichloro-3,5-dimethoxyphenyl | LCMS: 550.3 [M + H]⁺. ¹H NMR (400 MHz, CDCl₃) δ 3.60 (s, 1H), 3.67-3.88 (m, 2H), 3.94 (m, 8H), 4.06-4.28 (m, 2H), 4.49-4.76 (m, 2H), 5.60 (m, 1H), 5.82-6.11 (m, 1H), 6.11-6.44 (m, 3H), 6.62 (s, 1H), 7.47 (s, 1H), 8.49 (s, 1H). |
| I-305 [Abs] (tetrahydrofuran-acrylamide structure) | (diol branched chain) | 2,6-difluoro-3,5-dimethoxyphenyl | LCMS: 608.3 [M + H]⁺. ¹H NMR (400 MHz, CDCl₃), δ ppm: 8.53 (s, 1H), 7.65 (s, 1H), 6.68 (t, 1H,), 6.33 (m, 2H), 6.21-6.25 (dd, 1H), 5.9-6.1 (m, 1H), 5.60-5.65 (dd, 1H), 4.97 (br s, 2H), 4.55-4.70 (m, 1H), 4.55-4.65 (m, 1H), 4.46-4.56 (m, 1H), 4.1-4.25 (m, 2H), 3.85-3.96 (m, 2H), 3.89 (s, 6H), 3.8-3.9 (m, 4H), 3.52-3.62 (m, 1H). |
| I-304 [Abs] (tetrahydrofuran-acrylamide structure) | (propyl-F) | 2,6-dichloro-3,5-dimethoxyphenyl | LCMS: 552.2 [M + H]⁺. ¹H NMR (500 MHz, CDCl₃) δ 9.82 (br s, 1H), 8.34 (s, 1H), 7.47 (s, 1H), 6.75 (d, 1H), 6.67 (s, 1H), 6.28 (dd, 1H), 6.16-6.11 (m, 1H), 5.67 (dd, 1H), 5.02-4.99 (m, 1H), 4.89-4.81 (m, 3H), 4.74-4.70 (m, 2H), 4.24-4.20 (m, 2H), 3.07 (s, 7H), 3.89-3.86 (m, 1H) ppm. |
| I-310 [Abs] (tetrahydrofuran-acrylamide structure) | (alkyl chain) | 2,6-dichloro-3,5-dimethoxyphenyl | LCMS: 608.3 [M + H]⁺. ¹HNMR (400 MHz, CDCl3): 0.87 (m, 3H), 3.03-3.57 (m, 4H), 3.72-3.87 (m, 3H), 3.95 (s, 6H), 4.07-4.54 (m, 5H), 4.90 (m, 2H), 5.50-5.71 (m, 1H), 5.84-6.43 (m, 4H), 6.63 (s, 1H), 7.51 (s, 1H), 8.56 (s, 1H). |
| I-311 [Rac] cis (N-acetyl pyrrolidine-acrylamide structure) | (CH₂CH₂OMe) | 2,6-dichloro-3,5-dimethoxyphenyl | LCMS: 604.8 [M + H]⁺. ¹H NMR (500 MHz, CDCl₃) δ 8.48 (d, 1H), 7.44 (d, 1H), 7.01 (br s, 1H), 6.62 (s, 1H), 6.37-6.27 (m, 1H), 6.19-6.08 (m, 1H), 5.70-5.63 (m, 1H), 4.85-4.55 (m, 4H), 4.20-4.03 (m, 1H), 3.94 (s, 6H), 3.84-3.48 (m, 5H), 3.35 (d, 3H), 2.10 (s, 3H) ppm. |
| I-312 [Abs] (tetrahydrofuran-acrylamide structure) | Me | 2,6-dichloro-3-methoxy-5-hydroxyphenyl | LCMS: 506.3 [M + H]⁺. ¹H NMR (400 MHz, DMSO-d₆) δ 10.47 (s, 1H), 8.69-8.65 (m, 1H), 8.09-8.07 (m, 1H), 7.89-7.49 (m, 2H), 6.79 (s, 1H), 6.40-5.84 (m, 2H), 5.67-5.34 (m, 1H), 4.79-4.64 (m, 2H), 4.25-3.95 (m, 2H), 3.84 (s, 3H), 3.82-3.76 (m, 1H), 3.67-3.64 (m, 1H), 3.58-3.56 (m, 3H). |

Example 257: Protein Mass Modification Assays

An FGFR4 intact protein (from either SignalChem (method a in Table 9) or Invitrogen (method b in Table 9), and a compound of the invention (10-fold excess of Compound to protein) were incubated for 60 min. After incubation, 5 μL aliquots of the samples were diluted with 15 μL of 0.2% TFA prior to desalting using a micro C4 ZipTip protocol, which was added directly onto the MALDI target using sinapinic acid as the desorption matrix (10 mg/mL in 0.1% TFA:Acetonitrile 50:50, v/v). The centroid mass of FGFR4 in the control sample was compared with the centroid mass of FGFR4 incubated with the compound of the invention. A shift in the centroid mass of the treated FGFR4 compared to the untreated FGFR4 was divided by the molecular weight of the compound of the invention. This calculation provided the percentage of modified protein after one hour incubation. This assay confirms whether or not the FGFR4 target is covalently bound to a test compound (i.e., whether the protein's mass is modified).

For example, to assess mass modification of FGFR4 with I-1, intact FGFR4 (Invitrogen, Cat. No.: P3054) was incubated alone and with I-1 (10-fold excess of I-1 to protein). After 60 minutes, the protein samples were diluted and prepared as described above. The centroid mass of the protein (m/z: 42761.7; shown in FIG. 1, panel A) was compared with the centroid mass of the treated protein (m/z: 43350.2; shown FIG. 1, panel B). The centroid mass shift of 589 Da (87%), indicated complete modification of FGFR4 by I-1. Other compounds also were tested in this fashion. The results of these experiments are depicted in Table 9.

Tables 9, 10, and 11 show the activities of selected compounds of this invention in various FGFR assays. Compound numbers in Tables 9, 10 and 11 correspond to the Compound numbers above.

Compounds having an activity designated as "A" provided an $EC_{50}/IC_{50}/GI_{50} \leq 100$ nM; compounds having an activity designated as "B" provided an $EC_{50}/IC_{50}/GI_{50}$ of 101-500 nM; compounds having an activity designated as "C" provided an $EC_{50}/IC_{50}/GI_{50}$ of 501-999 nM; compounds having an activity designated as "D" provided an $EC_{50}/IC_{50}/GI_{50}$ of $\geq 1000$ nM.

Compounds having an activity designated as "E" provided a mass modification of $\geq 70\%$; compounds having an activity designated as "F" provided a mass modification of 31-69%; compounds having an activity designated as "G" provided a mass modification $\leq 30\%$.

TABLE 9

Summary of Mass Modification Data for Test Compounds

| CMPD | MS FGFR4 | Method |
|---|---|---|
| I-1 | E | a |
| I-2 | E | a |
| I-3 | F | a |
| I-5 | E | a |
| I-7 | F | a |
| I-8 | F | a |
| I-9 | F | a |
| I-10 | G | a |
| I-11 | F | a |
| I-12 | E | a |
| I-13 | E | a |
| I-14 | E | a |
| I-15 | E | a |
| I-17 | E | a |
| I-19 | E | a |
| I-20 | F | a |
| I-21 | F | a |
| I-23 | E | a |
| I-24 | E | a |
| I-25 | E | a |
| I-26 | E | a |
| I-28 | F | a |
| I-30 | F | a |
| I-31 | E | a |
| I-32 | F | a |
| I-33 | F | a |
| I-34 | E | a |
| I-35 | E | a |
| I-36 | F | a |
| I-38 | E | a |
| I-42 | F | a |
| I-43 | E | b |
| I-44 | E | b |
| I-45 | F | b |
| I-46 | G | a |
| I-47 | E | a |
| I-48 | E | a |
| I-49 | E | a |
| I-50 | E | a |
| I-52 | F | a |
| I-54 | F | a |
| I-55 | F | a |
| I-57 | F | a |
| I-58 | F | a |
| I-64 | E | b |
| I-66 | G | b |
| I-69 | E | b |
| I-82 | F | b |
| I-83 | E | b |
| I-117 | E | b |
| I-155 | E | a |
| I-179 | E | a |
| I-180 | F | a |
| I-181 | E | a |
| I-232 | G | a |
| I-233 | G | a |
| I-236 | G | a |
| I-237 | G | a |
| I-238 | G | a |
| I-241 | E | a |

Example 257: Omnia Assay Protocol for Potency Assessment Against FGFR 4 Enzyme

A 10× stock solution of FGFR4-WT (PR4380C or P3054), (from Invitrogen, Carlsbad, Calif.) corresponding to method a in Table 10, was prepared as described below. Alternatively, a 10× stock solution of FGFR4-WT (F01-11G), (SignalChem, Richmond, BC) corresponding to method b in Table 10, was prepared as described below. A solution of 1.4×ATP (AS001A) and 5×Tyr-Sox conjugated peptide substrate (KNZ3101) were prepared in 1× kinase reaction buffer consisting of 20 mM Tris, pH 7.5, 5 mM $MgCl_2$, 1 mM EGTA, 5 mM β-glycerophosphate, 5% glycerol (10× stock, KB002A) and 0.2 mM DTT (DS001A). 5 µL of FGFR4 was pipetted into a Corning (#3574) 384-well, white, non-binding surface microtiter plate (Corning, N.Y.), containing a 0.5 µL volume of 100% DMSO. The serially diluted compounds were prepared on a Tecan EVO100. A second addition of 10 µl of Tyr-Sox FGFR4 substrate was added to each well and the kinase reactions were started with the addition of 35 L of 1.4×ATP. The reactions were monitored every 71 seconds for 240 minutes at $\lambda_{ex}360/\lambda_{em}485$ in a Synergy plate reader from BioTek (Winooski, Vt.). At the conclusion of each assay, progress curves from each well were examined for linear reaction kinetics and fit statistics ($R^2$, 95% confidence interval, absolute sum of squares). Initial velocity (0 minutes to ~60 minutes) from each reaction was determined from the slope of a plot of relative fluorescence units vs time (seconds) and then plotted against inhibitor concentration to estimate $IC_{50}$ from log [Inhibitor] vs Response (Variable Slope model in GraphPad Prism from GraphPad Software (San Diego, Calif.)). Methods:

a) [FGFR4-WT]=10 nM, [ATP]=300 uM, [Y10-Sox]=10 uM (ATP $K_{Mapp}$~300 uM),
b) [FGFR4-WT]=2.5 nM, [ATP]=250 uM, [Y10-Sox]=10 uM (ATP $K_{Mapp}$~250 uM),
tools.invitrogen.com/content/sfs/manuals/omnia_kinase_assay_man.pdf The results of these experiments, reported as $IC_{50}$, show the ability of the compounds of the invention to inhibit FGFR enzyme activity and are depicted in Table 10.

TABLE 10

Summary of Enzymatic Data for Test Compounds

| Cmpd | FGFR4 $IC_{50}$ (nM) | Method |
| --- | --- | --- |
| I-1 | A | a |
| I-2 | A | b |
| I-3 | A | b |
| I-5 | A | a |
| I-6 | C | b |
| I-7 | C | b |
| I-8 | A | b |
| I-9 | A | b |
| I-10 | D | b |
| I-11 | C | b |
| I-12 | B | b |
| I-13 | B | b |
| I-14 | A | b |
| I-15 | A | b |
| I-17 | A | a |
| I-18 | D | b |
| I-19 | B | a |
| I-20 | A | b |
| I-21 | A | a |
| I-22 | C | a |
| I-23 | A | b |
| I-24 | A | b |
| I-25 | B | b |
| I-26 | A | b |
| I-27 | A | a |
| I-28 | A | a |
| I-29 | B | a |
| I-30 | A | a |
| I-31 | A | a |
| I-32 | A | a |
| I-34 | A | a |
| I-35 | A | a |
| I-36 | A | a |
| I-37 | B | a |
| I-38 | C | a |
| I-39 | D | a |
| I-40 | A | a |
| I-41 | A | a |
| I-42 | A | a |
| I-43 | A | a |
| I-44 | A | a |
| I-45 | D | a |
| I-46 | D | a |
| I-47 | A | a |
| I-48 | A | a |
| I-49 | A | a |
| I-50 | A | a |
| I-51 | D | a |
| I-52 | C | a |
| I-53 | A | a |
| I-54 | A | a |
| I-55 | A | a |
| I-56 | A | a |
| I-57 | A | a |
| I-58 | A | a |
| I-59 | A | a |
| I-60 | A | a |
| I-61 | A | a |
| I-62 | A | a |
| I-63 | A | a |
| I-64 | A | a |
| I-65 | A | a |
| I-66 | D | a |
| I-67 | A | a |
| I-68 | B | a |
| I-69 | A | a |
| I-70 | A | a |
| I-73 | B | a |
| I-74 | A | a |
| I-75 | A | a |
| I-76 | C | a |
| I-77 | A | a |
| I-78 | A | a |
| I-79 | B | a |
| I-80 | B | a |
| I-81 | B | a |
| I-82 | A | a |
| I-83 | B | a |
| I-84 | C | a |
| I-85 | A | a |
| I-86 | A | a |
| I-87 | A | a |
| I-88 | A | a |
| I-89 | A | a |
| I-90 | A | a |
| I-91 | A | a |
| I-92 | A | a |
| I-93 | D | a |
| I-94 | D | a |
| I-95 | A | a |
| I-96 | D | a |
| I-97 | A | a |
| I-98 | A | a |
| I-99 | A | a |
| I-100 | A | a |
| I-101 | B | a |
| I-102 | A | a |
| I-103 | A | a |
| I-104 | A | a |
| I-105 | B | a |
| I-106 | B | a |
| I-107 | D | a |
| I-108 | A | a |
| I-109 | A | a |
| I-110 | A | a |
| I-111 | C | a |
| I-112 | A | a |
| I-113 | A | a |
| I-114 | A | a |
| I-115 | B | a |
| I-116 | A | a |
| I-117 | A | a |
| I-118 | D | a |
| I-119 | D | a |
| I-120 | D | a |
| I-121 | A | a |
| I-122 | B | a |
| I-123 | A | a |
| I-124 | A | a |
| I-125 | B | a |
| I-126 | A | a |
| I-127 | A | a |
| I-128 | B | a |
| I-129 | A | a |
| I-130 | A | a |
| I-131 | A | a |
| I-132 | A | a |
| I-133 | A | a |
| I-134 | A | a |
| I-135 | A | a |
| I-136 | A | a |
| I-137 | A | a |
| I-138 | B | a |
| I-139 | A | a |
| I-140 | B | a |
| I-141 | A | a |

TABLE 10-continued

Summary of Enzymatic Data for Test Compounds

| Cmpd | FGFR4 IC$_{50}$ (nM) | Method |
|---|---|---|
| I-142 | A | a |
| I-143 | A | a |
| I-144 | A | a |
| I-145 | A | a |
| I-146 | A | a |
| I-147 | A | a |
| I-148 | A | a |
| I-149 | A | a |
| I-150 | A | a |
| I-151 | A | a |
| I-152 | A | a |
| I-153 | A | a |
| I-154 | B | a |
| I-155 | A | a |
| I-181 | A | b |
| I-185 | D | a |
| I-186 | A | a |
| I-196 | A | a |
| I-198 | A | a |
| I-200 | A | a |
| I-201 | A | a |
| I-202 | A | a |
| I-204 | A | a |
| I-205 | B | a |
| I-206 | A | a |
| I-207 | D | a |
| I-208 | C | a |
| I-209 | D | a |
| I-210 | A | a |
| I-211 | A | a |
| I-212 | A | a |
| I-213 | A | a |
| I-214 | A | a |
| I-215 | A | a |
| I-216 | A | a |
| I-217 | A | a |
| I-218 | D | a |
| I-219 | B | a |
| I-220 | D | a |
| I-221 | D | a |
| I-222 | D | a |
| I-223 | A | a |
| I-228 | B | a |
| I-232 | A | b |
| I-233 | A | b |
| I-234 | B | b |
| I-235 | B | b |
| I-236 | B | b |
| I-237 | B | a |
| I-238 | A | a |
| I-241 | A | a |
| I-240 | D | a |
| I-242 | A | a |
| I-243 | A | a |
| I-244 | A | a |
| I-245 | A | a |
| I-246 | B | a |
| I-247 | B | a |
| I-248 | A | a |
| I-249 | A | a |
| I-250 | A | a |
| I-251 | A | a |
| I-252 | A | a |
| I-253 | A | a |
| I-254 | A | a |
| I-255 | C | a |
| I-256 | A | a |
| I-257 | A | a |
| I-258 | A | a |
| I-259 | A | a |
| I-260 | A | a |
| I-261 | A | a |
| I-262 | A | a |
| I-263 | A | a |
| I-264 | A | a |
| I-265 | A | a |
| I-266 | A | a |
| I-267 | A | a |
| I-268 | A | a |
| I-269 | A | a |
| I-270 | A | a |
| I-271 | A | a |
| I-272 | A | a |
| I-273 | A | a |
| I-274 | A | a |
| I-275 | A | a |
| I-276 | A | a |
| I-277 | A | a |
| I-278 | A | a |
| I-279 | A | a |
| I-280 | A | a |
| I-281 | A | a |
| I-282 | A | a |
| I-283 | C | a |
| I-284 | A | a |
| I-285 | A | a |
| I-286 | A | a |
| I-287 | A | a |
| I-288 | A | a |
| I-289 | A | a |
| I-290 | A | a |
| I-291 | A | a |
| I-292 | A | a |
| I-293 | B | a |
| I-294 | A | a |
| I-295 | A | a |
| I-296 | A | a |
| I-297 | A | a |
| I-298 | A | a |
| I-299 | A | a |
| I-300 | A | a |
| I-301 | A | a |
| I-302 | A | a |
| I-303 | A | a |
| I-304 | A | a |
| I-305 | A | a |
| I-306 | A | a |
| I-307 | A | a |
| I-308 | A | a |
| I-309 | A | a |

Example 258: FGFR4 Signaling

Preparation of Cells: MDA-MB-453 (breast carcinoma) and Huh7 (hepatocellular carcinoma) cells were used. Huh7 cells were grown in DMEM (Invitrogen, Carlsbad, Calif.) supplemented with 10% FBS (Invitrogen) and 1% Penicillin-Streptomycin (P/S, Lonza, Walkersville, Md.). MDA-MB-453 cells were grown in complete RPMI 1640 (Invitrogen), supplemented with 10% FBS and 1% P/S. All cells were maintained and propagated as monolayer cultures at 37° C. in a humidified 5% CO$_2$ incubator.

For the MSD and ELISA assays, total FGFR4 antibodies were obtained from R&D Systems (Minneapolis, Minn.) and used at 1:500. For the immunoblotting (Western blotting) assay, total FGFR4 antibody was obtained from Santa Cruz (Santa Cruz, Calif.) and used at 1:1000. Phospho-FGFR antibodies were obtained from Cell Signaling (Danvers, Mass.) or R&D Systems and used at 1:1000. The phopho-FGFR antibody from Cell Signaling was used for immunoblotting, whereas the phopho-FGFR antibody from R&D was used for MSD and ELISA assays. Secondary antibodies were used at 1:10,000. The goat anti-mouse IgG IRDye 800CW antibody was obtained from LiCor Biosciences (Lincoln, Nebr.) and the goat anti-rabbit IgG Alexa Fluor 680 was obtained from Invitrogen. The anti-rabbit Sulfo-tag and anti-streptavidin Sulfo-tag antibodies was obtained from Meso Scale Discovery (Gaithersburg, Md.), and were used at 1:1000 and 1:5000, respectively.

Immunoblotting (Western Blotting, WB)—Method a (Only for MDA-MB-453)

For MDA-MB-453 cells signaling, cells were grown in 96-well poly-D-lysine plates (BD Bioscience, San Jose, Calif.) to 90% confluence, and were then incubated in low-serum (0.1% FBS) media for 16-18 hr. The cells were then treated with 5, 1.25, 0.31, 0.078, 0.020 or 0.005 µM of test compound in low-serum (0.1% FBS) media for 1 hr. After treatment, the cells were washed with cold PBS (Invitrogen) and were immediately lysed by freeze/thawing 3× in 32 µL of cold Cell Extraction Buffer (Invitrogen) which was supplemented with Complete Protease inhibitors (Roche, Indianapolis, Ind.) and PhosphoSTOP (Roche) phosphatase inhibitors.

The MDA-MB-453 protein concentrations were determined by a BCA Assay (Pierce, Rockford, Ill.). A sample of 50-100 µg of each lysate was separated by a 4-12% gradient (SDS-PAGE (Invitrogen)), transferred to a nitrocellulose membrane (Biorad, Hercules, Calif.), and probed with specific antibodies. Phospho-protein signals were quantitated using Odyssey Infrared Imaging (Li-Cor Biosciences).

To assess phospho-FGFR signaling, the blots were probed with anti-Phospho-FGFR (Y653/Y654) and total anti-FGFR antibodies. The phospho-FGFR signal was normalized to total FGFR expression for each sample. The results are indicated as % DMSO control. The normalized data was fitted using a sigmoidal curve analysis program (Graph Pad Prism version 5) with variable Hill slope to determine the $EC_{50}$ values. The results are provided in Table 11, under the column titled "Signaling $EC_{50}$ (nM)".

Meso Scale Assay (MSD)—Method B (for Both MDA-MB-453 and Huh7)

MDA-MB-453 and Huh7 cells were grown in 96-well poly-D-lysine plates (BD Bioscience, San Jose, Calif.) to 90% confluence. The cells were then incubated in low-serum (0.1% FBS) media for 16-18 hr. and then treated with 5, 1.67, 0.56, 0.185, 0.068, 0.021 or 0.007 µM of test compound in low-serum (0.1% FBS) media for 1 hr. After treatment, the cells were washed with cold PBS (Invitrogen), and were immediately lysed by freeze/thawing 3× in 32 µL of cold Cell Extraction Buffer (Invitrogen), which was supplemented with Complete Protease inhibitors (Roche) and PhosphoSTOP (Roche) phosphatase inhibitors.

MSD plates (Meso Scale Discovery) were coated with total FGFR-4 antibodies overnight at 4° C. A lysate (25 µL) was added to the MSD plate overnight at 4° C. The MSD signals were obtained by incubating with a phospho-FGFR antibody (R&D Systems) and an anti-rabbit sulfo-tag antibody (Meso Scale), for 2 hr at room temperature. The results are indicated as % DMSO control. The data was fitted using a sigmoidal curve analysis program (Graph Pad Prism version 5) with variable Hill slope to determine the $EC_{50}$ values. The results are provided in Table 11, under the column titled "Signaling $EC_{50}$ (nM)".

ELISA—Method C (Only for MDA-MB-453)

MDA-MB-453 cells were grown in 96-well poly-D-lysine plates (BD Bioscience, San Jose, Calif.) to 90% confluence. The cells were then incubated in low-serum (0.1% FBS) media for 16-18 hr. The MDA-MB-453 cells were then treated with 5, 1.67, 0.56, 0.185, 0.068, 0.021 or 0.007 µM of test compound in low-serum (0.1% FBS) media for 1 hr. After treatment, the MDA-MB-453 cells were washed with cold PBS (Invitrogen) and were immediately lysed by freeze/thawing 3× in 32 µL of cold Cell Extraction Buffer (Invitrogen), which was supplemented with Complete Protease inhibitors (Roche) and PhosphoSTOP (Roche) phosphatase inhibitors.

Nunc-immuno plates (96-well; Sigma, St. Louis, Mo.) were coated with total FGFR-4 antibodies overnight at 4° C. A lysate (25 µL) was added to the plate for 2 hr at room temperature. A phospho-FGFR detection antibody (100 µL) was added per well for 2 hr at room temperature, followed by a goat anti-rabbit HRP antibody (100 µL) for 45 min. The results are indicated as % DMSO control. The data was fitted using a sigmoidal curve analysis program (Graph Pad Prism version 5) with variable Hill slope to determine the $EC_{50}$ values.

The results of these experiments show the ability of the compounds of the invention to inhibit phosphor-signaling of FGFR4 in cells. The results are depicted in Table 11 under the column titled "Signaling $EC_{50}$ (nM)". MDA-MB-453 cell results fall under the heading "pFGFR4 (MDA)" and Huh7 results fall under the heading "pFGFR4 (Huh)"

Example 259: Cell Proliferation

MDA-MB-453 and Huh7 cells were plated in the appropriate Growth Media supplemented with 5% FBS and 1% P/S in a 96 well tissue culture plates (Corning), as indicated in Table 11. For both MDA-MB-453 and Huh7 cells the starting density was 5000 cells per well. The cells were allowed to settle down for 4 hr and were then treated with 5, 1.25, 0.31, 0.078, 0.020 or 0.005 µM of test compound for: 96 hr for MDA-MB-453 and 120 hr for Huh7 cells. Cell viability was determined by CellTiter Glo (Promega, Madison, Wis.) and the results were converted to cell numbers using a standard curve. The growth inhibition ($GI_{50}$) values were determined by Graph Pad Prism.

The results of these experiments show the ability of compounds to inhibit cell growth in FGFR dependant cell lines and are depicted in Table 11, in the columns titled "Cell Proliferation $GI_{50}$ (nM)". MDA-MB-453 cell results fall under the heading "MDA" and Huh7 cell results fall under the heading "Huh."

Example 260: Target Occupancy Assay

In order to assess free FGFR4 protein a biotinylated covalent probe was utilized. As described in Example 235, Method B, MDA-MB-453 cells were treated with test compound, washed, and lysed. Each lysate (25 µL) was added to a 96-well plate and 2 µM of a biotinylated covalent probe (I-127) was added. The reaction was incubated for 2 hr at room temperature. The samples and probe mixture were transferred to a FGFR4-coated MSD plate for 2 hr at room temperature. MSD signals were obtained with an anti-streptavidin Sulfo-tag (Meso Scale) antibody for 1 hr at room temperature. The results are indicated as % DMSO control. The data was fitted using a sigmoidal curve analysis program (Graph Pad Prism version 5) with variable Hill slope to determine the $EC_{50}$ values.

The results of these experiments show the ability of the compounds of the invention to covalently modify FGFR4 in MDA-MB-453 cells by assessing the amount of free FGFR4 protein. If a compound completely (100%) covalently modies FGFR4 no free FGFR4 should be available for covalent modification by the biotinylated probe and subsequent binding to streptavidin and detection. Results are depicted in Table 11, in the column titled "FGFR4 Occupancy $EC_{50}$ (nM)".

TABLE 11

Summary of Cellular Data for Test Compounds

| Compound | Signaling $EC_{50}$ (nM) pFGFR4 (MDA) | Signaling $EC_{50}$ (nM) pFGFR4 (Huh) | Cell Proliferation $GI_{50}$ (nM) MDA | Cell Proliferation $GI_{50}$ (nM) HUH | FGFR4 Occupancy $EC_{50}$ (nM) | Method for Signaling $EC_{50}$ Determination MDA |
|---|---|---|---|---|---|---|
| I-1 | A | A | A | B | A | B |
| I-2 | A |   | A | B |   | A |
| I-3 | A |   | A | A | A | C |
| I-5 | B | B | C | D | B | B |
| I-6 | B | B | A |   | B | B |
| I-7 | C |   |   |   |   | B |
| I-8 | A | B | A | B | B | B |
| I-9 | A | B | A | C | A | B |
| I-10 | D |   |   |   |   | B |
| I-11 | D |   |   |   |   | B |
| I-12 | A |   | B |   | B | B |
| I-13 | B | B | B | D | B | B |
| I-14 | B |   |   |   |   | B |
| I-15 | A |   | A |   | B | B |
| I-17 | A |   | B |   | B | B |
| I-18 | D |   |   |   |   | B |
| I-19 | B | B | B | C | C | B |
| I-20 | A |   | A |   | B | B |
| I-21 | A | A | B | C | B | B |
| I-22 | D |   |   |   |   | B |
| I-23 | A |   | A |   |   | B |
| I-24 | A |   | A |   |   | B |
| I-25 | A | B | A | C | B | B |
| I-26 | A | A | A | A | A | B |
| I-28 | A |   |   |   |   | B |
| I-30 | B |   |   |   |   | B |
| I-31 | B |   | B |   |   | B |
| I-32 | A |   | C |   |   | B |
| I-33 | B | D |   | D |   | B |
| I-34 | A |   | C |   |   | B |
| I-35 | B |   | B | C | B | B |
| I-36 | B | B |   | D |   | B |
| I-38 | D |   |   |   |   | B |
| I-40 | D |   |   |   |   | B |
| I-41 | B | B |   | D |   | B |
| I-42 | B | A |   | D |   | B |
| I-43 | C | D |   | B |   | B |
| I-44 | A | A | B | D | B | B |
| I-45 | D |   |   |   |   | B |
| I-46 | D |   |   |   |   | B |
| I-47 | B | C |   | D |   | B |
| I-48 | B | B | C | D |   | B |
| I-49 | C |   |   |   |   | B |
| I-50 | B | B |   | D |   | B |
| I-52 | D |   |   |   |   | B |
| I-54 | B |   |   |   |   | B |
| I-55 | A |   | B | B | B | B |
| I-56 | A |   |   |   |   | B |
| I-57 | A |   |   |   |   | B |
| I-58 | B |   |   |   |   | B |
| I-59 | B | B | C | D | B | B |
| I-60 | B |   |   |   |   | B |
| I-61 | B | B | B | C | B | B |
| I-62 | A |   |   |   |   | B |
| I-63 | B | A | B | B | B | B |
| I-64 | B | B | B | D |   | B |
| I-65 | B |   |   |   |   | B |
| I-66 | D |   |   |   |   | B |
| I-67 | A |   | C |   |   | B |
| I-68 | B | C | D | D |   | B |
| I-69 | A | B | B | C |   | B |
| I-70 | B |   |   |   |   | B |
| I-73 | B |   |   |   |   | B |
| I-74 | A |   |   |   |   | B |
| I-75 | A |   | B |   |   | B |
| I-76 | C | D |   | D |   | B |
| I-77 | A |   | B |   |   | B |
| I-78 | B |   | B |   |   | B |
| I-79 | B | C |   |   |   | B |
| I-80 | B | D |   | D |   | B |
| I-81 | C | D |   | D |   | B |
| I-82 | A |   | A |   |   | B |
| I-83 | B | B | C | D |   | B |
| I-84 | B |   |   |   |   | B |
| I-85 | A |   | A | B |   | B |
| I-86 | A |   | A |   |   | B |
| I-87 | A | A | A | B |   | B |
| I-88 | B | B | C | D |   | B |
| I-89 | B |   |   |   |   | B |
| I-90 | B |   | B |   |   | B |
| I-91 | A |   | A |   |   | B |
| I-92 | B |   | B |   |   | B |
| I-93 | D |   |   |   |   | B |
| I-94 | D |   |   |   |   | B |
| I-95 | B | B | B | C | B | B |
| I-96 | D |   |   |   |   | B |
| I-97 | B | B | B | D |   | B |
| I-98 | A | A | B | D |   | B |
| I-99 | B | B | B | D |   | B |
| I-100 | A | A | B | C |   | B |
| I-101 | B |   |   |   |   | B |
| I-102 | B | A |   | D |   | B |
| I-103 | A |   | A | B |   | B |
| I-104 | A | A | A | B |   | B |
| I-105 | B | B |   | C |   | B |
| I-106 | B | B |   | D |   | B |
| I-107 | C | D |   | D |   | B |
| I-108 | A |   | B |   |   | B |
| I-109 | A |   | A |   |   | B |
| I-110 | A | A | B | C |   | B |
| I-111 | C | D |   | D |   | B |
| I-112 | B |   |   |   |   | B |
| I-113 | B | B |   | C |   | B |
| I-114 | B | B | B | B | B | B |
| I-115 | B | B |   | D |   | B |
| I-116 | A | A | A | B |   | B |
| I-117 | A | A |   | B |   | B |
| I-118 | D |   |   |   |   | B |
| I-119 | D |   |   |   |   | B |
| I-120 | D |   |   |   |   | B |
| I-121 | A | A | B | C |   | B |
| I-122 | B |   |   |   |   | B |
| I-123 | A |   |   |   |   | B |
| I-124 | A |   | A | B |   | B |
| I-125 | C | D |   | D |   | B |
| I-126 | A | A | A | B | A | B |
| I-127 | B | B |   | D |   | B |
| I-128 | D |   |   |   |   | B |
| I-129 | B |   |   |   |   | B |
| I-130 | A |   |   |   |   | B |
| I-131 | A | A | A | B |   | B |
| I-132 | B | B |   | D |   | B |
| I-133 | A | A | A | B |   | B |
| I-134 | A |   | A |   | A | B |
| I-135 | A |   | A |   |   | B |
| I-136 | A |   | A |   |   | B |
| I-137 | B | B |   | C |   | B |
| I-138 | B | B |   | D |   | B |
| I-139 | B | B |   | C |   | B |
| I-140 | B | B |   | C |   | B |
| I-141 | A |   |   |   |   | B |

TABLE 11-continued

Summary of Cellular Data for Test Compounds

| compound | Signaling EC$_{50}$ (nM) pFGFR4 (MDA) | Signaling EC$_{50}$ (nM) pFGFR4 (Huh) | Cell Proliferation GI$_{50}$ (nM) MDA | Cell Proliferation GI$_{50}$ (nM) HUH | FGFR4 Occupancy EC$_{50}$ (nM) | Method for Signaling EC$_{50}$ Determination MDA |
|---|---|---|---|---|---|---|
| I-142 | B | | | | | B |
| I-143 | B | B | | | | B |
| I-144 | A | | | | | B |
| I-145 | A | | | | | B |
| I-146 | B | B | | D | | B |
| I-147 | A | | | | | B |
| I-148 | A | | | | | B |
| I-149 | A | | | A | | B |
| I-150 | A | | | | | B |
| I-151 | C | D | | D | | B |
| I-152 | A | | | | | B |
| I-153 | A | A | | B | | B |
| I-154 | B | D | | D | | B |
| I-155 | B | D | | | | B |
| I-179 | A | | B | B | | A |
| I-180 | A | | | | | C |
| I-181 | A | | | | | B |
| I-185 | B | D | | D | | B |
| I-186 | A | A | | A | | B |
| I-198 | | A | | B | | |
| I-200 | | B | | | | |
| I-201 | | B | | C | | |
| I-204 | | A | | | | |
| I-205 | | B | | | | |
| I-206 | | A | | A | | |
| I-207 | | D | | | | |
| I-208 | | D | | | | |
| I-209 | | D | | | | |
| I-210 | | A | | B | | |
| I-211 | | A | | A | | |
| I-212 | | A | | A | | |
| I-213 | | A | | A | | |
| I-214 | | B | | B | | |
| I-215 | | A | | B | | |
| I-216 | | B | | B | | |
| I-217 | | A | | A | | |
| I-218 | | D | | | | |
| I-219 | | C | | | | |
| I-220 | | D | | | | |
| I-221 | | D | | | | |
| I-223 | | A | | B | | |
| I-228 | | B | | B | | |
| I-232 | A | | | | | A |
| I-233 | A | | | | | A |
| I-234 | B | | D | | D | A |
| I-235 | C | | | | | B |
| I-236 | B | | | D | | B |
| I-237 | B | | | | | B |
| I-238 | A | A | | A | | B |
| I-241 | A | A | A | A | A | B |
| I-240 | | D | | D | | |
| I-242 | | A | A | | | |
| I-243 | | A | | | | |
| I-244 | | A | | | | |
| I-245 | | A | | | | |
| I-246 | | B | | | | |
| I-247 | | A | | | | |
| I-248 | | A | A | | | |
| I-249 | | A | | | | |
| I-250 | | A | | | | |
| I-251 | | A | | | | |
| I-252 | | A | | | | |
| I-253 | | A | | | | |
| I-254 | | A | | B | | |
| I-255 | | C | | | | |
| I-256 | | A | | | | |
| I-257 | | A | | B | | |
| I-258 | | A | | | | |
| I-259 | | A | | B | | |
| I-260 | | A | | | | |
| I-261 | | A | | | | |
| I-262 | | A | B | B | | |
| I-263 | | A | | | | |
| I-264 | | A | | | | |
| I-265 | | A | | | | |
| I-266 | | B | | | | |
| I-267 | | A | | | | |
| I-268 | | A | | | | |
| I-269 | | A | A | B | | |
| I-270 | | A | A | B | | |
| I-271 | | A | | | | |
| I-272 | | A | A | B | | |
| I-273 | | A | | C | | |
| I-274 | | A | | | | |
| I-275 | | A | A | B | | |
| I-276 | | A | A | B | | |
| I-277 | | A | B | D | | |
| I-278 | | A | | | | |
| I-279 | | A | A | A | | |
| I-280 | | A | A | A | | |
| I-281 | | A | B | A | | |
| I-282 | | B | | | | |
| I-283 | | B | | | | |
| I-284 | | B | | | | |
| I-285 | | A | A | A | | |
| I-286 | | A | | | | |
| I-287 | | A | | | | |
| I-288 | | A | | | | |
| I-289 | | A | A | C | | |
| I-290 | | A | | A | | |
| I-291 | | A | | A | | |
| I-292 | | A | | A | | |
| I-293 | | B | | | | |
| I-294 | | A | | B | | |
| I-295 | | A | | A | | |
| I-296 | | A | | | | |
| I-297 | | B | | | | |
| I-298 | | A | | A | | |
| I-299 | | A | | B | | |
| I-300 | | A | | | | |
| I-301 | | A | | A | | |
| I-302 | | A | | B | | |
| I-303 | | A | | B | | |
| I-304 | | A | | | | |
| I-305 | | A | | | | |
| I-306 | | A | | | | |
| I-307 | | A | | B | | |
| I-308 | | A | | B | | |
| I-309 | | A | | B | | |

Example 261: Washout Experiment

MDA-MB-453 cells were plated in the appropriate Growth Media supplemented with 10% FBS and 1% P/S, to 90% confluence in either 12- or -96 well tissue culture plates. The cells were allowed to settle down for 4 hrs and were then maintained in low-serum (0.1% FBS) media overnight.

The following morning, the media was removed and the cells were treated with 1000-2000 nM of test compound in low-serum media for 1 hr. The cells were washed free of test compound (3×) with PBS (Invitrogen). One set of cells was immediately lysed as indicated above as the 0 hr time point. The remaining cells were incubated with the appropriate complete growth media (10-20% FBS) for 1, 2, 4, 8, 16 (in certain circumstances) and 24 hr. DMSO (0.5%) controls were collected at all time points.

Figure 2:
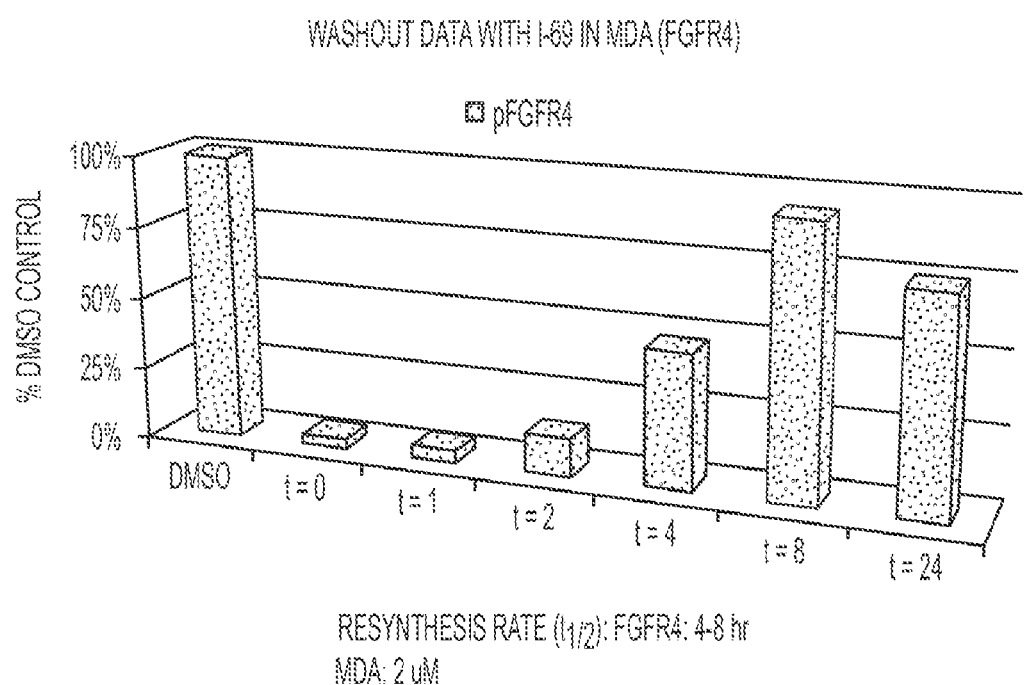
FIG. 2: Data showing that compound I-69 has prolonged duration of action (PDA) against pFGFR4 signalling in MDA-MB-453 cells consistent with the resynthesis rate of FGFR4.
Figure 3:
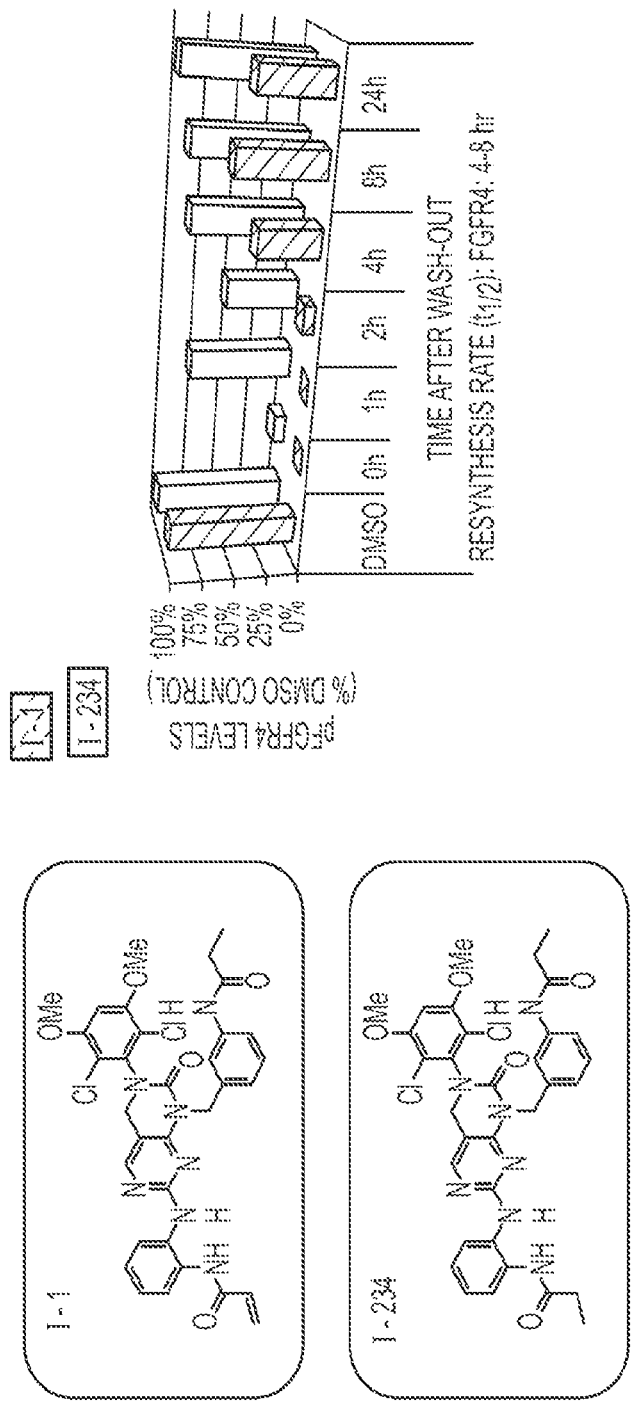
FIG. 3: Data showing that compound I-1 has PDA against pFGFR4 signalling in MDA-MB-453 cells consistent with the resynthesis rate of FGFR4, whereas its noncovalent, reversible analog, I-234 does not have PDA.

Representative data is shown in FIGS. 2 and 3. The data in FIG. 2 show that a representative compound, I-69, provides prolonged inhibition of autophosphorylation of FGFR4 assessed by detection of phosphorylated FGFR4 (pFGFR4) after cells are washed. The graph in FIG. 2 shows that inhibition of pFGFR4 is consistent with the resynthesis rate of FGFR4 in the cells examined (T1/2~4-8 h). The data in FIG. 3 compares the duration of action of a covalently modifying (irreversible) compound, I-1, and its corresponding noncovalently modifying (reversible) analog, I-234. I-1 which covalently modifies FGFR4 has prolonged duration of action consistent with the resynthesis rate of FGFR4 in the cells whereas I-234 does not show prolonged duration of action post washout.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

---

We claim:

1. A method for inhibiting fibroblast growth factor receptor 4, or a mutant thereof, activity in a patient or in a biological sample comprising the step of administering to said patient or contacting said biological sample with a compound of formula I-h:

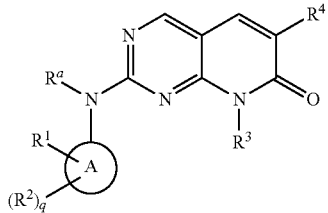

I-h or a pharmaceutically acceptable salt thereof, wherein:

Ring A is

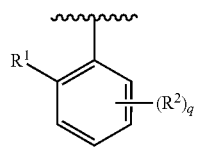

or an optionally substituted group selected from a 3-8 membered saturated or partially unsaturated carbocyclic ring, a 5-6 membered monocyclic heteroaryl ring having 1-4 heteroatoms independently selected from nitrogen, oxygen, or sulfur, a 4-7 membered saturated or partially unsaturated heterocyclic ring having 1-4 heteroatoms independently selected from nitrogen, oxygen, or sulfur, or a 7-10 membered bicyclic saturated, partially unsaturated or aryl ring;

each R is independently hydrogen or an optionally substituted group selected from $C_{1-6}$ aliphatic, phenyl, a 3-8 membered saturated or partially unsaturated carbocyclic ring, a 4-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; or two R groups on the same nitrogen are taken together with the nitrogen atom to which they are attached to form a 4-7 membered heterocyclic ring having 0-2 additional heteroatoms independently selected from nitrogen, oxygen, or sulfur, or a 4-7 membered heteroaryl ring having 0-4 additional heteroatoms independently selected from nitrogen, oxygen, or sulfur;

$R^1$ is a warhead group -L-Y; wherein $R^1$ is attached to an atom adjacent to the atom where —$NR^a$— is attached, wherein:

$R^1$ is selected from

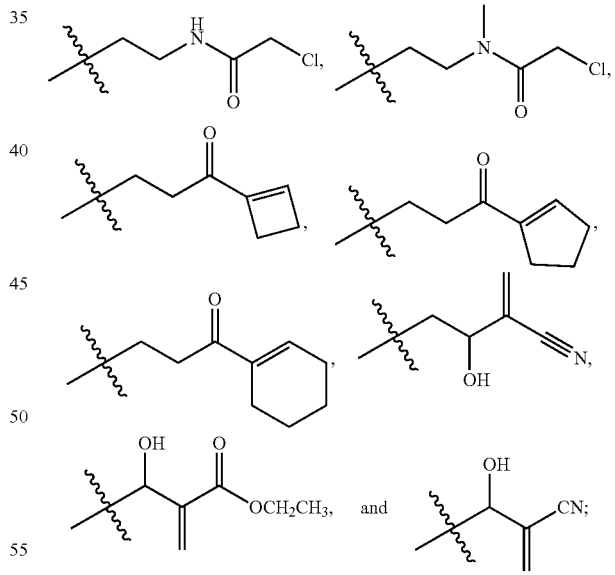

or

L is a bivalent $C_{2-8}$ straight or branched, hydrocarbon chain wherein L has at least one double bond and one or two methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O)—; or L is a bivalent $C_{2-8}$ straight or branched, hydrocarbon chain wherein L has at least one alkylidenyl double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one additional methylene unit of L is optionally replaced by cyclopropylene, —O—, —N(R)—, or —C(O)—; or L is a bivalent C$_{2-8}$ straight or branched, hydrocarbon chain wherein one methylene unit of L is replaced by cyclopropylene and one additional methylene unit of L is replaced by —NRC(O)—, —C(O)NR—, —N(R)SO$_2$—, —SO$_2$N(R)—, —S—, —S(O)—, —SO$_2$—, —OC(O)—, or —C(O)O—; or L is a bivalent C$_{2-8}$ straight or branched, hydrocarbon chain wherein L has at least one triple bond and one or two methylene units of L are optionally and independently replaced by —NRC(O)—, —C(O)NR—, —N(R)SO$_2$—, —SO$_2$N(R)—, —S—, —S(O)—, —SO$_2$—, —OC(O)—, or —C(O)O—; and Y is hydrogen, C$_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 R$^e$ groups; or L is a covalent bond, —CH$_2$—, —NH—, —C(O)—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, or —SO$_2$NH—, and Y is selected from:

(i) C$_{1-6}$ alkyl substituted with oxo, halogen, NO$_2$, or CN; or (ii) C$_{2-6}$ alkenyl substituted with oxo, halogen, NO$_2$, or CN; or (iii) C$_{2-6}$ alkynyl optionally substituted with oxo, halogen, NO$_2$, or CN; or (iv) a saturated 3-4 membered heterocyclic ring having 1 heteroatom selected from oxygen or nitrogen wherein said ring is substituted with 1-2 R$^e$ groups; or (v) a saturated 5-6 membered heterocyclic ring having 1-2 heteroatom selected from oxygen or nitrogen wherein said ring is substituted with 1-4 R$^e$ groups; or

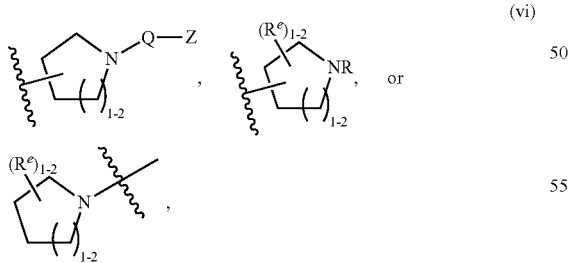

or (vii) a saturated 3-6 membered carbocyclic ring, wherein said ring is substituted with 1-4 R$^e$ groups; or (viii) a partially unsaturated 3-6 membered monocyclic ring having 0-3 heteroatoms independently selected from nitrogen, oxygen, or sulfur, wherein said ring is substituted with 1-4 R$^e$ groups; or (ix) a partially unsaturated 3-6 membered carbocyclic ring, wherein said ring is substituted with 1-4 R$^e$ groups; or

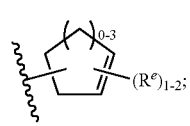

or (xi) a partially unsaturated 4-6 membered heterocyclic ring having 1-2 heteroatoms independently selected from nitrogen, oxygen, or sulfur, wherein said ring is substituted with 1-4 R$^e$ groups; or

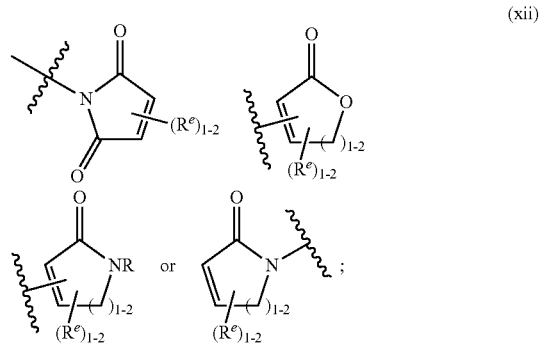

or (xiii) a 6-membered aromatic ring having 0-2 nitrogens wherein said ring is substituted with 1-4 R$^e$ groups; or

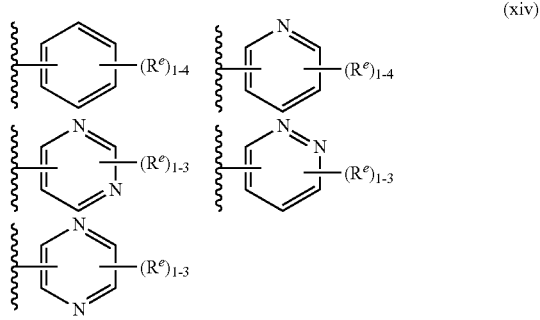

or (xv) a 5-membered heteroaryl ring having 1-3 heteroatoms independently selected from nitrogen, oxygen, or sulfur, wherein said ring is substituted with 1-3 R$^e$ groups; or

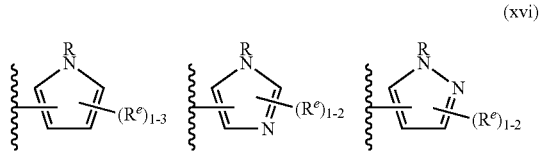

-continued

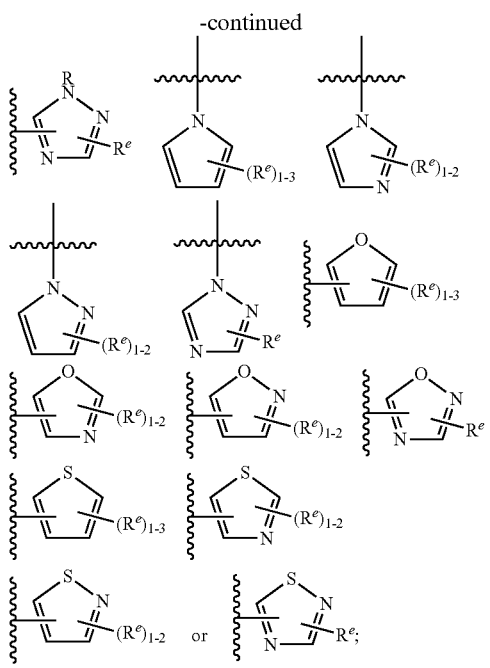

or
(xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups; or L is a covalent bond, —C(O)—, —N(R)C(O)—, or a bivalent $C_{1-8}$ saturated or unsaturated, straight or branched, hydrocarbon chain; and Y is selected from:
(i) $C_{1-6}$ alkyl substituted with oxo, halogen, $NO_2$, or CN;
(ii) $C_{2-6}$ alkenyl optionally substituted with oxo, halogen, $NO_2$, or CN; or
(iii) $C_{2-6}$ alkynyl optionally substituted with oxo, halogen, $NO_2$, or CN; or
(iv) a saturated 3-4 membered heterocyclic ring having 1 heteroatom selected from oxygen or nitrogen wherein said ring is substituted with 1-2 $R^e$ groups; or
(v) a saturated 5-6 membered heterocyclic ring having 1-2 heteroatom selected from oxygen or nitrogen wherein said ring is substituted with 1-4 $R^e$ groups; or (vi)

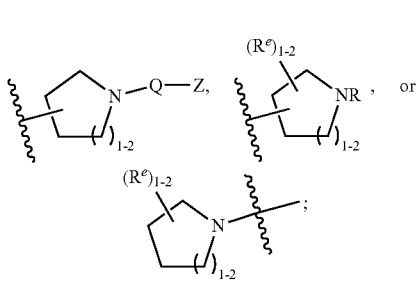

or
(vii) a saturated 3-6 membered carbocyclic ring, wherein said ring is substituted with 1-4 $R^e$ groups; or (viii) a partially unsaturated 3-6 membered monocyclic ring having 0-3 heteroatoms independently selected from nitrogen, oxygen, or sulfur, wherein said ring is substituted with 1-4 $R^e$ groups; or
(ix) a partially unsaturated 3-6 membered carbocyclic ring, wherein said ring is substituted with 1-4 $R^e$ groups; or

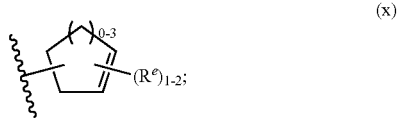

(x)

or
(xi) a partially unsaturated 4-6 membered heterocyclic ring having 1-2 heteroatoms independently selected from nitrogen, oxygen, or sulfur, wherein said ring is substituted with 1-4 $R^e$ groups; or (xii)

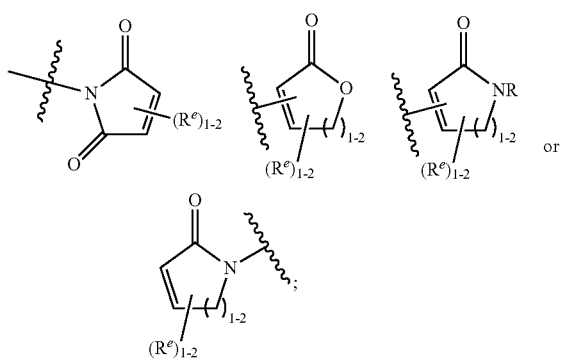

or
(xiii) a 6-membered aromatic ring having 0-2 nitrogens wherein said ring is substituted with 1-4 $R^e$ groups; or (xiv)

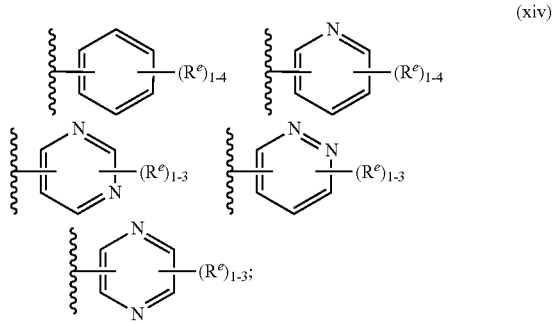

or
(xv) a 5-membered heteroaryl ring having 1-3 heteroatoms independently selected from nitrogen, oxygen, or sulfur, wherein said ring is substituted with 1-3 $R^e$ groups; or (xvi)

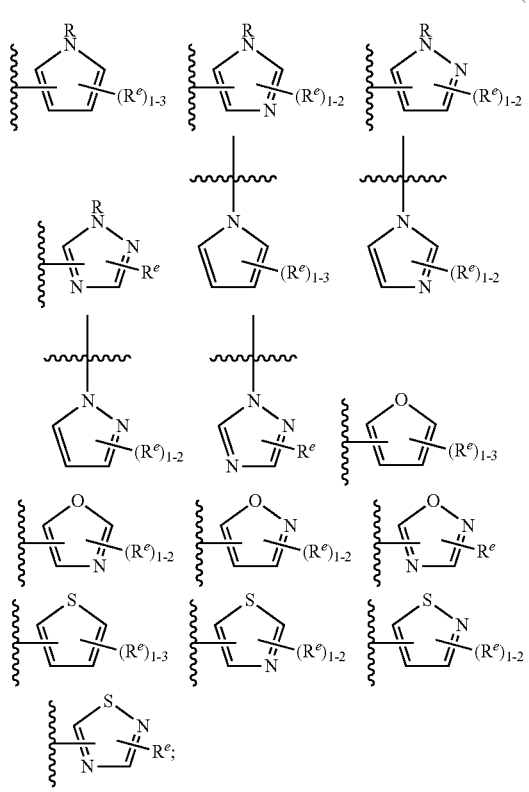

or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups;

each $R^e$ is independently selected from -Q-Z, oxo, $NO_2$, halogen, CN, $C_{1-6}$ aliphatic optionally substituted with oxo, halogen, $NO_2$, or CN, or a suitable leaving group selected from alkoxy, sulfonyloxy, optionally substituted alkylsulfonyloxy, optionally substituted alkenylsulfonyloxy, optionally substituted arylsulfonyloxy, acyl, and diazonium, wherein:

Q is a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, —$SO_2$-, —N(R)C(O)—, —C(O)N(R)—, —N(R)$SO_2$—, or —$SO_2$N(R)—; and each Z is independently hydrogen or $C_{1-6}$ aliphatic substituted with oxo, halogen, $NO_2$, or CN;

each $R^2$ is independently halogen, -haloalkyl, —OR, —SR, —CN, —$NO_2$, —$SO_2$R, —SOR, —C(O)R, —$CO_2$R, —C(O)N(R)$_2$, —NRC(O)R, —NRC(O)N(R)$_2$, —NR$SO_2$R, or —N(R)$_2$;

$R^3$ is hydrogen, $C_{2-6}$ alkenyl, —W-Cy, or $C_{1-6}$ alkyl, wherein the $C_{1-6}$ alkyl is optionally substituted with 1-3 groups independently selected from halogen, —CN, oxo, —OR', or —C(O)O($C_{1-6}$ alkyl);

W is absent or is a bivalent $C_{1-3}$ alkylene chain optionally substituted with one or more R" and wherein one methylene unit of W is optionally replaced with —O—, —S—, or —NR'—;

each R' is independently hydrogen or $C_{1-6}$ alkyl;

each R" is independently halogen or $C_{1-6}$ alkyl, wherein the $C_{1-6}$ alkyl is optionally substituted with 1-3 groups independently selected from halogen, —CN, oxo, or —OR';

Cy is phenyl, $C_{3-7}$ cycloalkyl, or a 3-7 membered monocyclic or 5-10 membered bicyclic saturated, partially unsaturated, or heteroaryl ring having 1-3 heteroatoms independently selected from nitrogen, oxygen, or sulfur, wherein Cy is optionally substituted with 1-3 R';

each $R^x$ is independently H, —CN, oxo, —$NH_2$, $C_{1-6}$ alkyl, halogen, —OR, —N(R')$_2$, —NHC(O)($C_{1-6}$ alkyl), —C(O)N(R')$_2$, —C(O)O($C_{1-6}$ alkyl), —NH$SO_2$ ($C_{1-6}$ alkyl), or —$SO_2$N(R')$_2$;

$R^4$ is

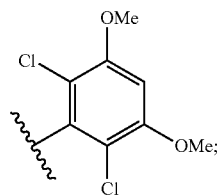 [SMILES: *c1c(Cl)c(OC)cc(OC)c1Cl]

$R^a$ is hydrogen or an optionally substituted $C_{1-6}$ aliphatic group; and q is 0, 1, 2, 3, 4, 5, or 6.

2. The method according to claim 1, wherein the patient suffers from a fibroblast growth factor receptor 4-mediated disorder selected from the group consisting of hepatocellular carcinoma and rhabdomyosarcoma.

3. The method according to claim 1, wherein Ring A is

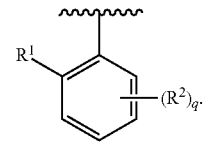

4. The method according to claim 1, wherein Ring A is an optionally substituted group selected from a 3-8 membered saturated or partially unsaturated carbocyclic ring, a 5-6 membered monocyclic heteroaryl ring having 1-4 heteroatoms independently selected from nitrogen, oxygen, or sulfur, a 4-7 membered saturated or partially unsaturated heterocyclic ring having 1-4 heteroatoms independently selected from nitrogen, oxygen, or sulfur, a 7-10 membered bicyclic saturated, partially unsaturated or aryl ring.

5. The method according to claim 1, wherein Ring A is cyclohexyl, cyclohexenyl, cyclopentyl, cyclobutyl, cyclopropyl, pyridinyl, pyrimidinyl, pyrazinyl, pyridazinyl, pyrrolyl, pyrazolyl, piperidinyl, piperidinonyl, pyrrolidinyl, tetrahydropyranyl, tetrahydrofuranyl, 1,1,-dioxidotetrahydrothiophenyl, or cyclobutenedionyl.

6. The method according to claim 1, wherein Ring A is

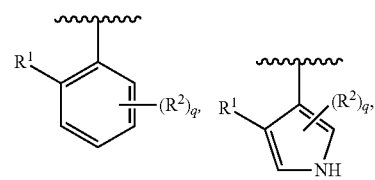

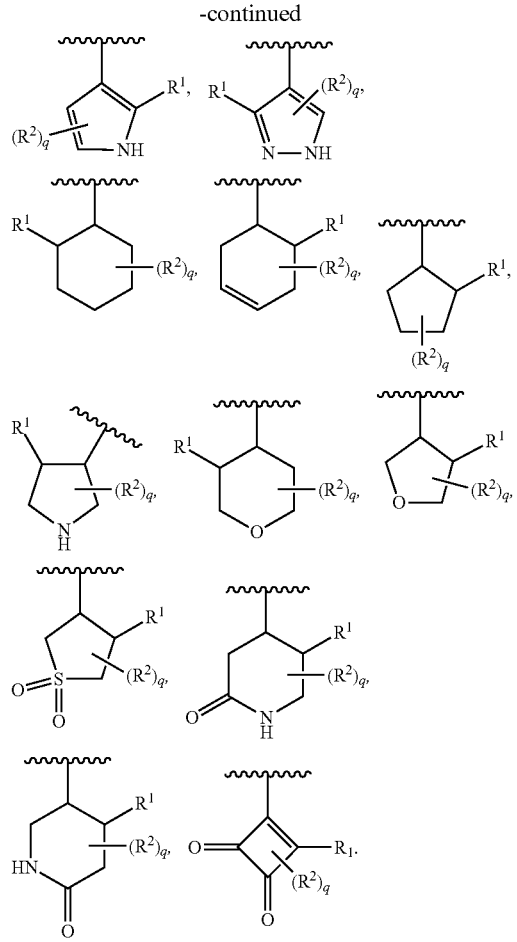
7. The method according to claim 1, wherein Ring A is selected from:
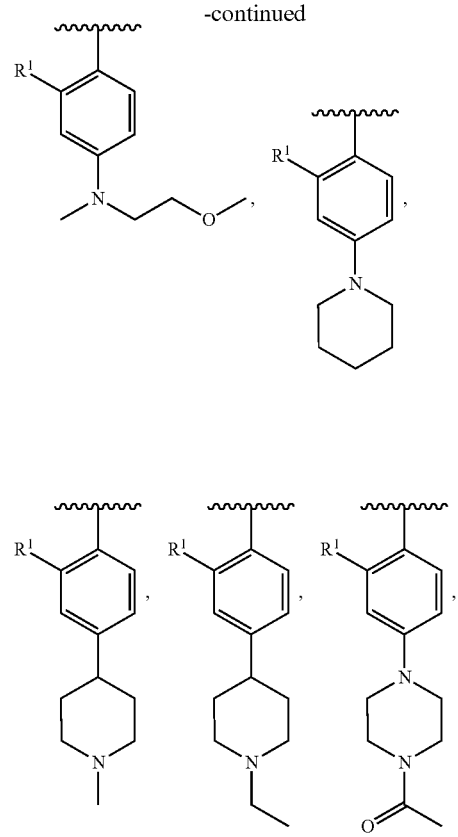

581
-continued
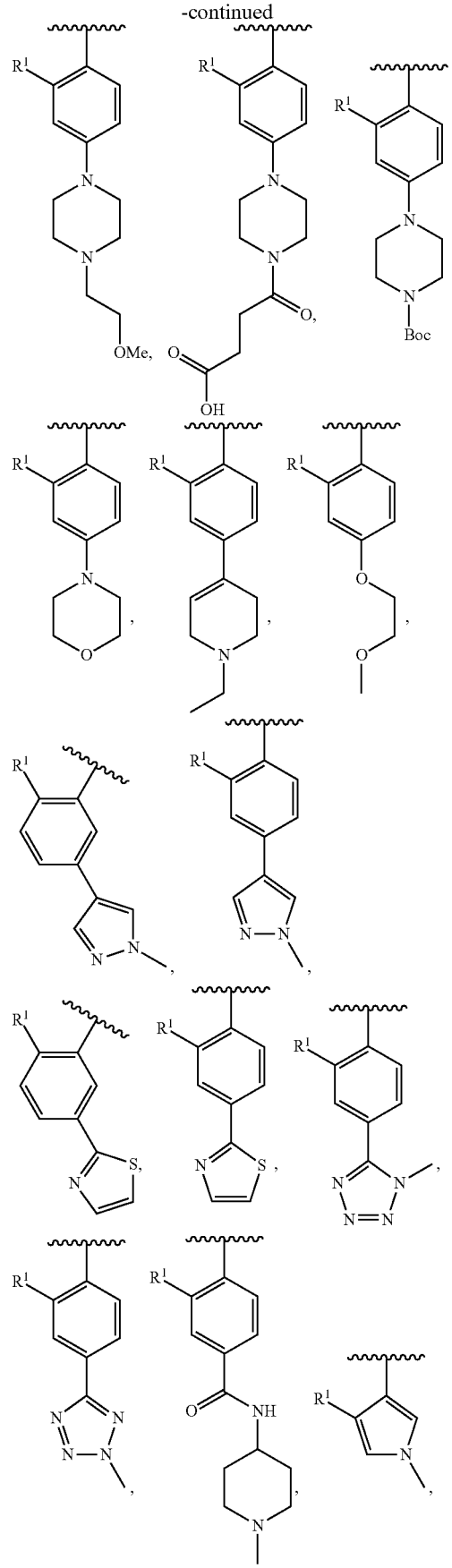
582
-continued
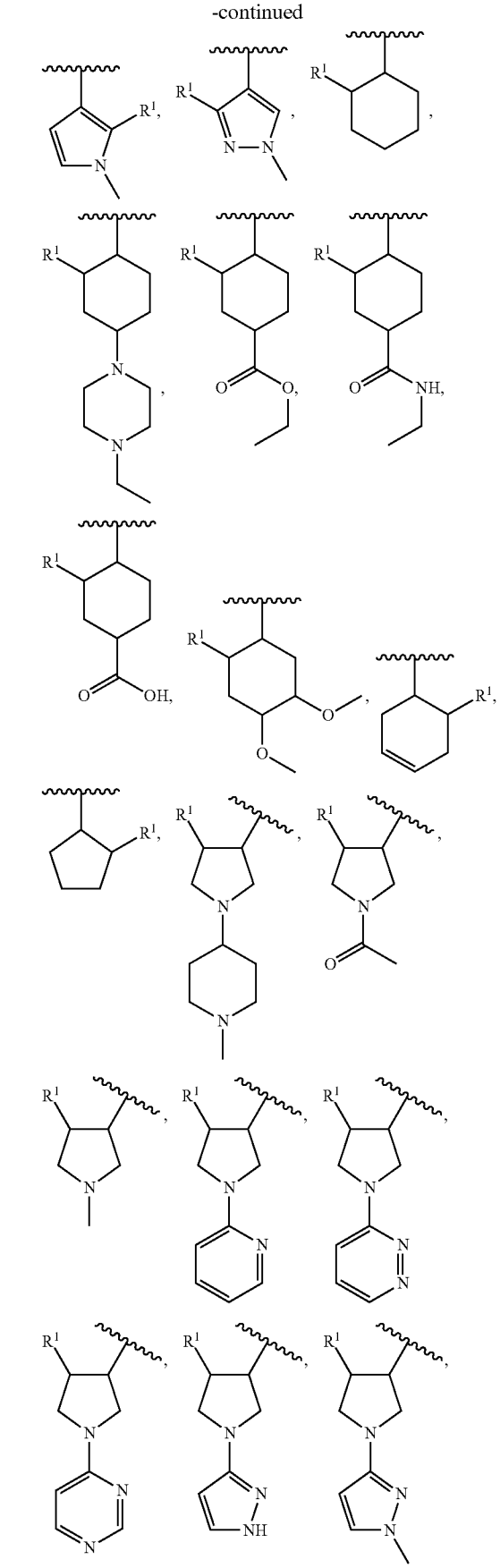

-continued

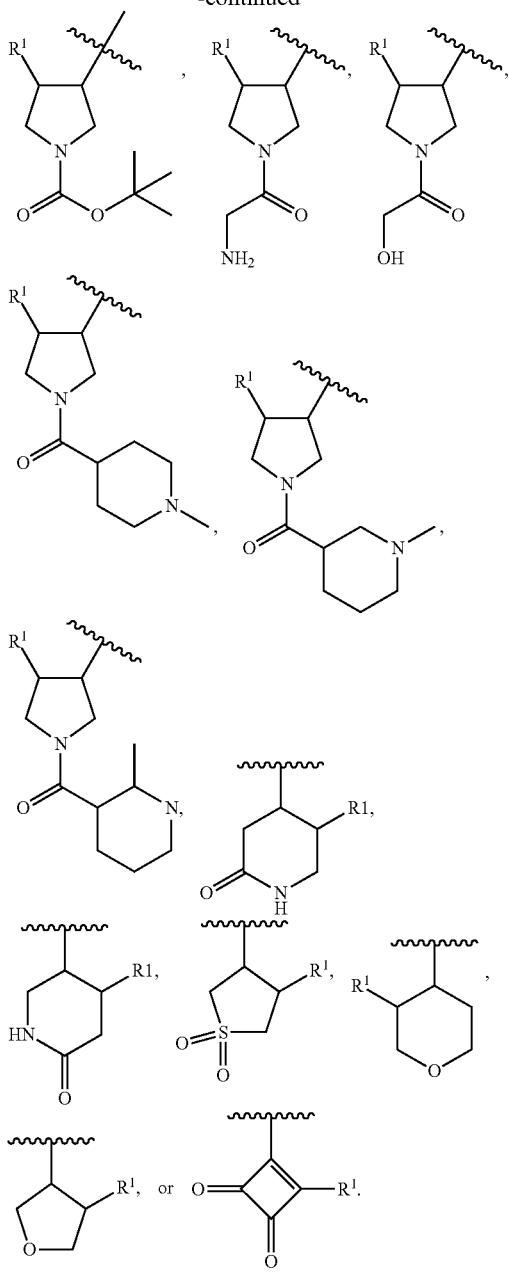

8. The method according to claim 1, wherein:
L is a bivalent C$_{2-8}$ straight or branched, hydrocarbon chain wherein L has at least one double bond and one or two methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O)—.

9. The method according to claim 8, wherein:
L is a bivalent C$_{2-8}$ straight or branched, hydrocarbon chain wherein L has at least one double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one additional methylene unit of L is optionally replaced by cyclopropylene, —O—, —N(R)—, or —C(O)—; and
Y is hydrogen or C$_{1-6}$ aliphatic optionally substituted with oxo, halogen, NO$_2$, or CN.

10. The method according to claim 9, wherein L is a bivalent C$_{2-8}$ straight or branched, hydrocarbon chain wherein L has at least one double bond and at least one methylene unit of L is replaced by —C(O)—, and one additional methylene unit of L is optionally replaced by cyclopropylene, —O—, —N(R)—, or —C(O)—.

11. The method according to claim 9, wherein L is a bivalent C$_{2-8}$ straight or branched, hydrocarbon chain wherein L has at least one double bond and at least one methylene unit of L is replaced by —OC(O)—.

12. The method according to claim 9, wherein L is —NRC(O)CH=CH—, —NRC(O)CH=CHCH$_2$N(CH$_3$)—, —NRC(O)CH=CHCH$_2$O—, —CH$_2$NRC(O)CH=CH—, —NRSO$_2$CH=CH—, —NRSO$_2$CH=CHCH$_2$—, or —NRC(O)C(=CH$_2$)CH$_2$—; wherein the R group of L is H or optionally substituted C$_{1-6}$ aliphatic; and Y is hydrogen or C$_{1-6}$ aliphatic optionally substituted with oxo, halogen, NO$_2$, or CN.

13. The method according to claim 12, wherein L is —NHC(O)CH=CH—, —NHC(O)CH=CHCH$_2$N(CH$_3$)—, —NHC(O)CH=CHCH$_2$O—, —CH$_2$NHC(O)CH=CH—, —NHSO$_2$CH=CH—, —NHSO$_2$CH=CHCH$_2$—, or —NHC(O)C(=CH$_2$)CH$_2$—.

14. The method according to claim 1, wherein L is a bivalent C$_{2-8}$ straight or branched, hydrocarbon chain wherein L has at least one alkylidenyl double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one additional methylene unit of L is optionally replaced by cyclopropylene, —O—, —N(R)—, or —C(O)—.

15. The method according to claim 1, wherein:
L is a bivalent C$_{2-8}$ straight or branched, hydrocarbon chain wherein L has at least one triple bond and one or two methylene units of L are optionally and independently replaced by —NRC(O)—, —C(O)NR—, —N(R)SO$_2$—, —SO$_2$N(R)—, —S—, —S(O)—, —SO$_2$—, —OC(O)—, or —C(O)O—.

16. The method according to claim 15, wherein Y is hydrogen or C$_{1-6}$ aliphatic optionally substituted with oxo, halogen, NO$_2$, or CN.

17. The method according to claim 16, wherein L is —NHC(O)C≡CCH$_2$CH$_2$—, —CH$_2$—C≡C—CH$_2$—, or CH$_2$OC(O)C≡C—.

18. The method according to claim 1, wherein:
L is a bivalent C$_{2-8}$ straight or branched, hydrocarbon chain wherein one methylene unit of L is replaced by cyclopropylene and one additional methylene unit of L is replaced by —NRC(O)—, —C(O)NR—, —N(R)SO$_2$—, —SO$_2$N(R)—, —S—, —S(O)—, —SO$_2$—, —OC(O)—, or —C(O)O—.

19. The method according to claim 1, wherein:
L is a covalent bond, —C(O)—, —N(R)C(O)—, or a bivalent C$_{1-8}$ aliphatic chain.

20. The method according to claim 1, wherein L is a covalent bond, —CH$_2$—, —NH—, —C(O)—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, or —SO$_2$NH—.

21. The method according to claim 20, wherein L is a covalent bond.

22. The method according to claim 1, wherein R$^1$ is selected from:

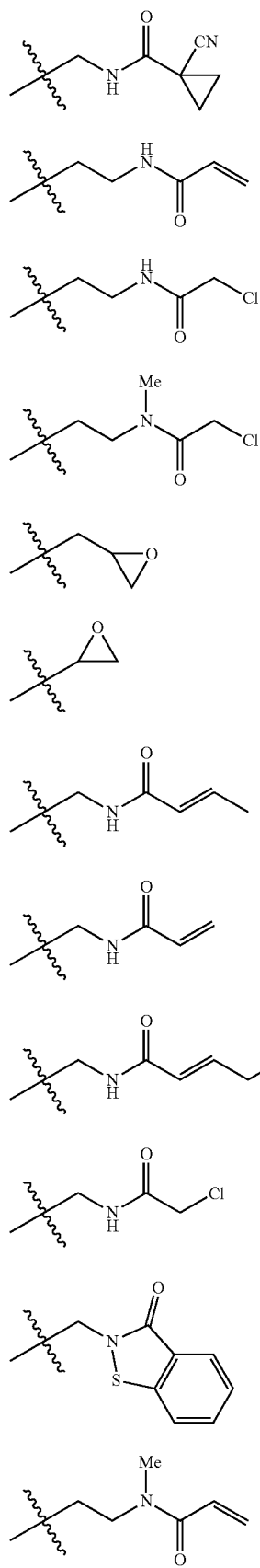
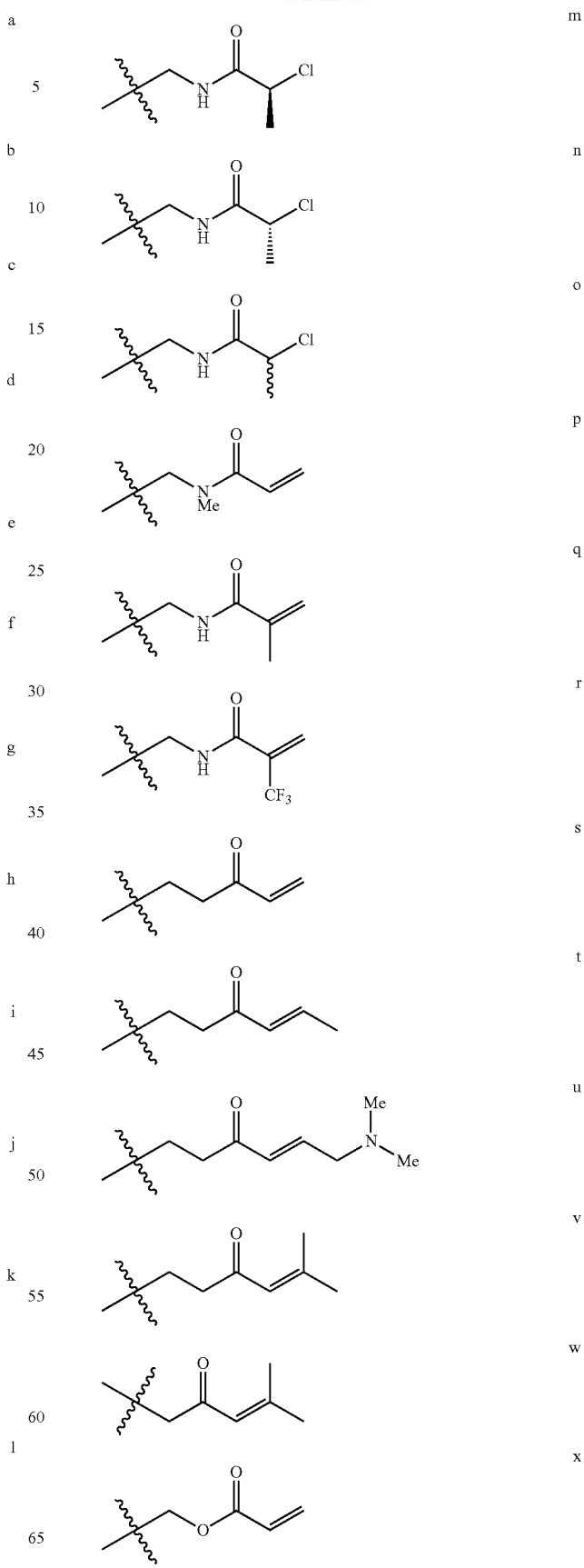

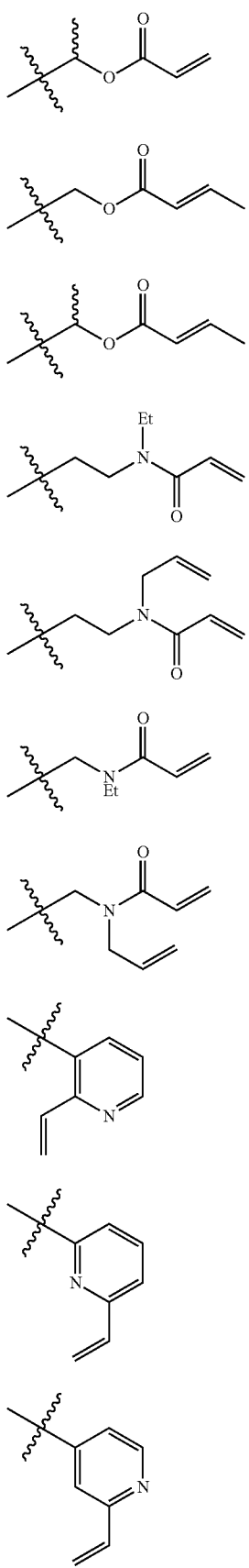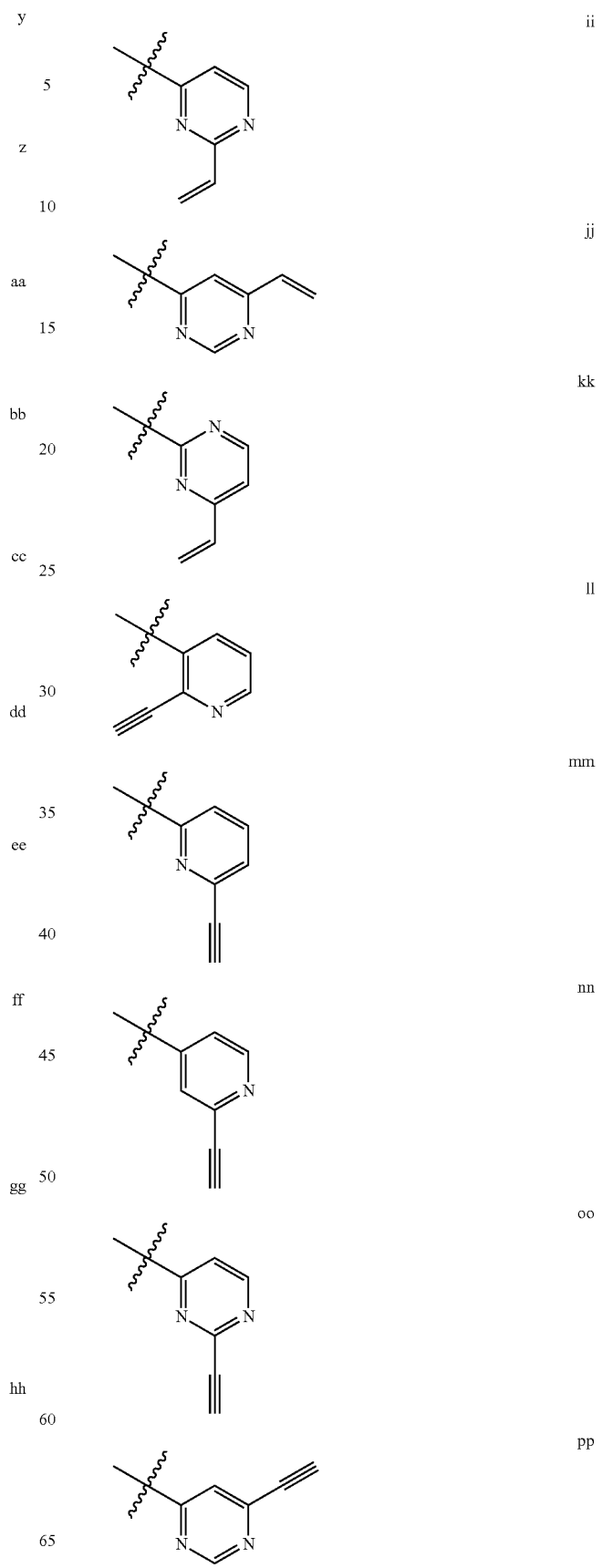

| | | |
|---|---|---|
| 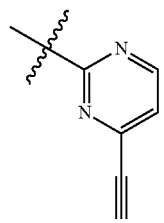 | qq | 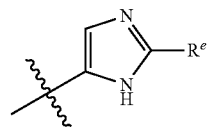 zz |
| 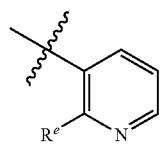 rr | 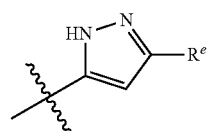 aaa | |
| 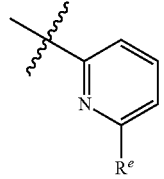 ss | 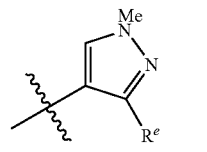 bbb | |
| 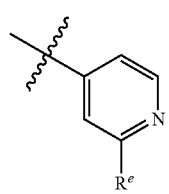 tt | 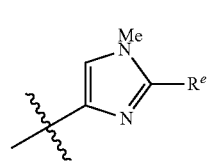 ccc | |
| 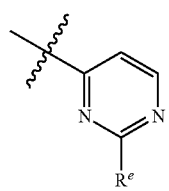 uu | 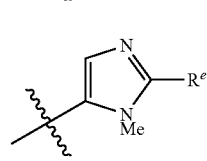 ddd | |
| 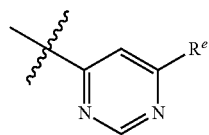 vv | 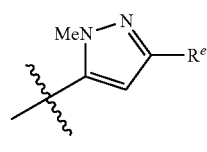 eee | |
| 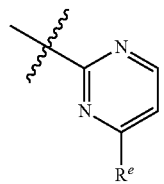 ww | 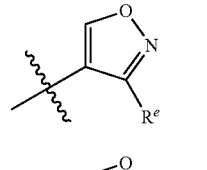 fff | |
| 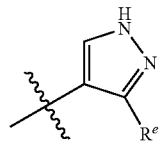 xx | 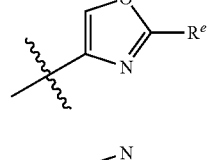 ggg | |
| 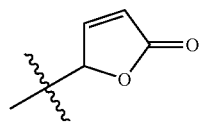 yy | 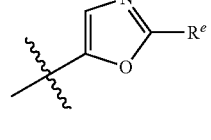 hhh | |
| | 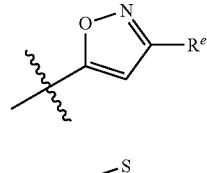 iii | |
| | 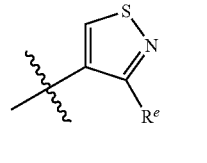 jjj | |

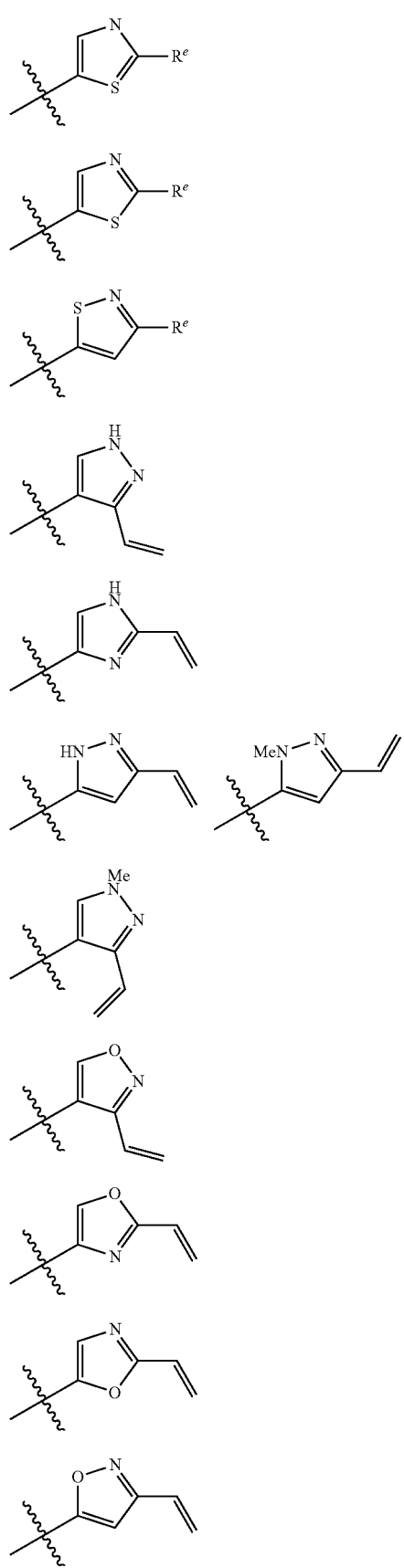
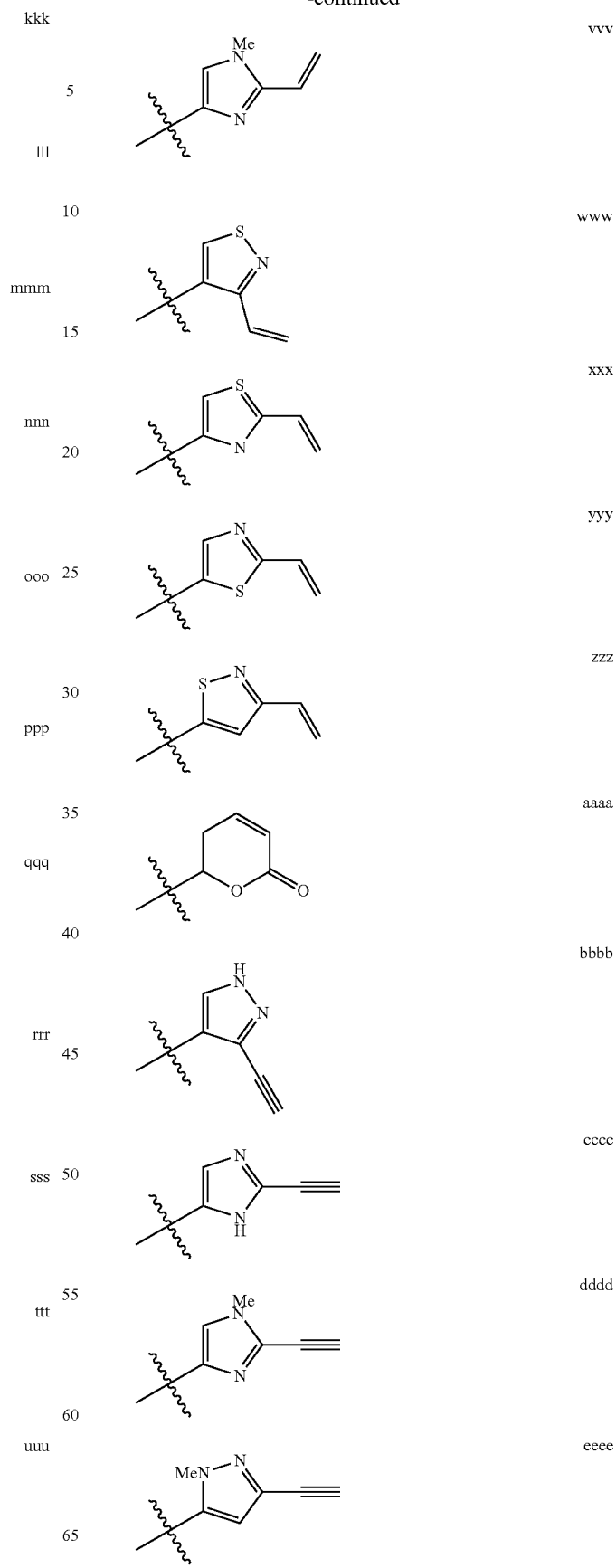

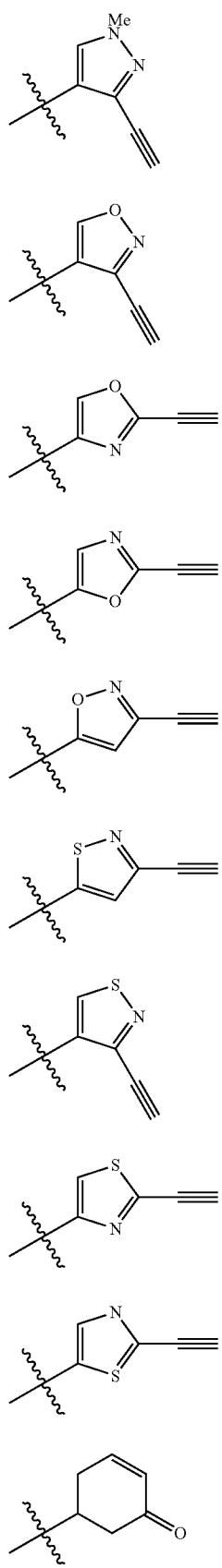
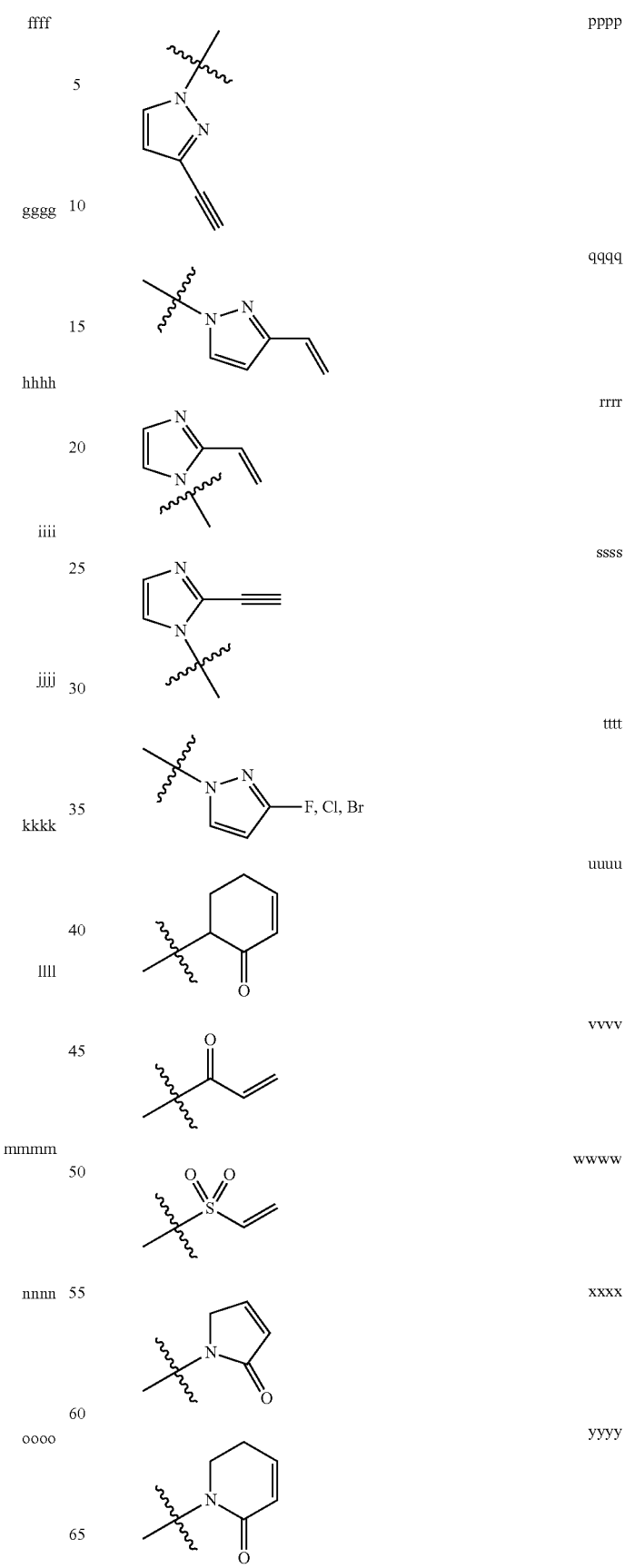

| | | | |
|---|---|---|---|
| zzzz | 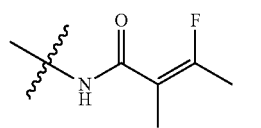 | kkkkk | 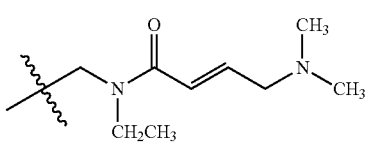 |
| aaaaa | 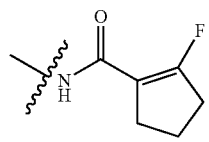 | lllll | 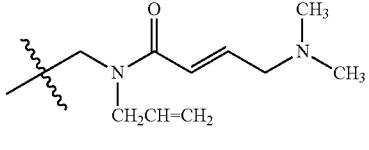 |
| bbbbb | 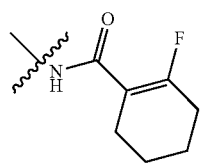 | mmmmm | 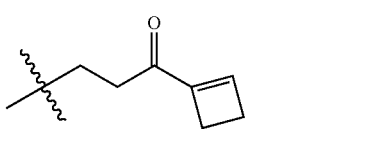 |
| ccccc | 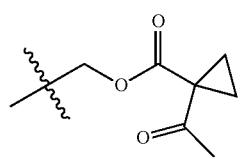 | nnnnn | 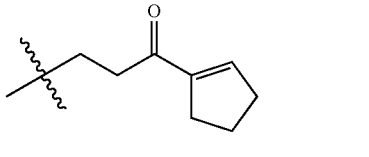 |
| ddddd | 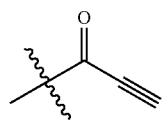 | ooooo | 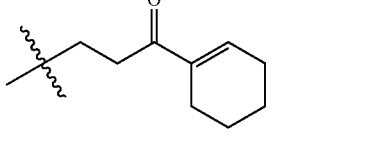 |
| eeeee | 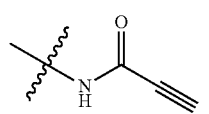 | ppppp | 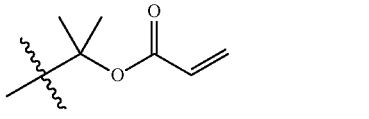 |
| fffff | 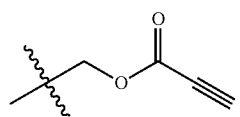 | qqqqq | 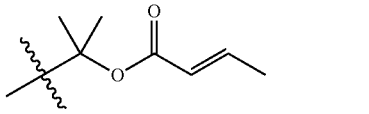 |
| ggggg | 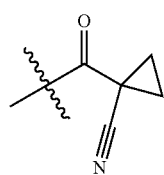 | rrrrr | 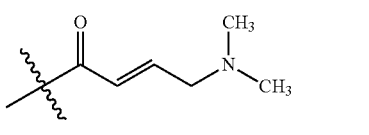 |
| hhhhh | 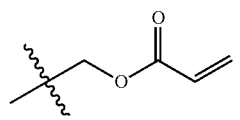 | sssss | 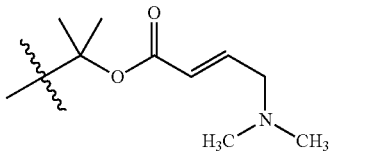 |
| iiiii | 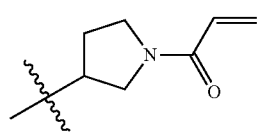 | ttttt | 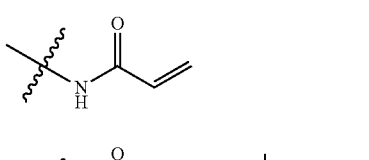 |
| jjjjj | 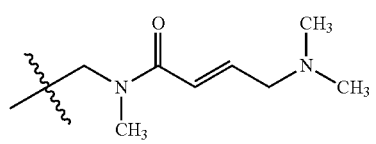 | uuuuu | 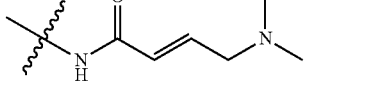 |

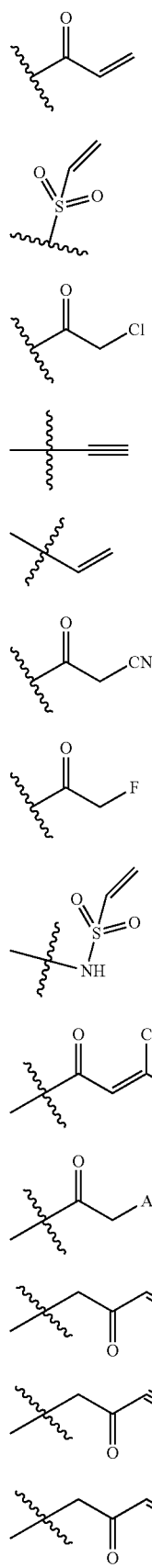
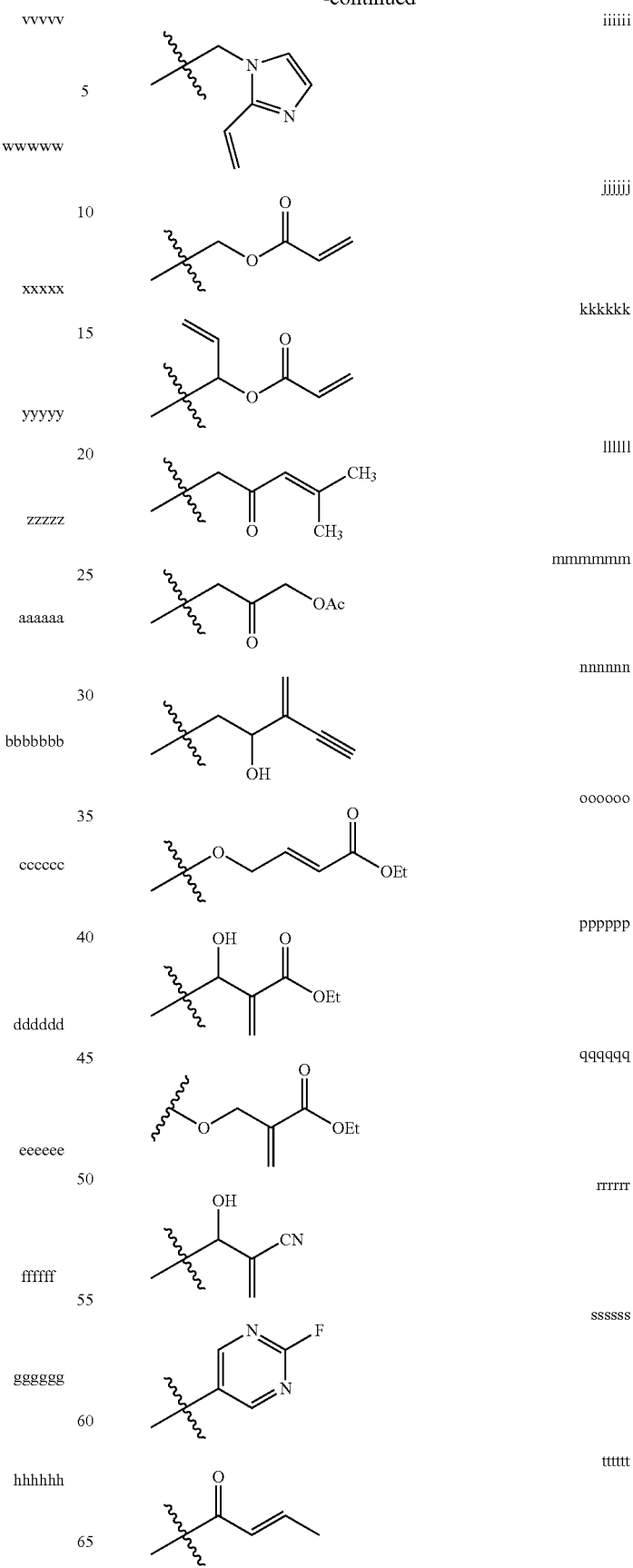

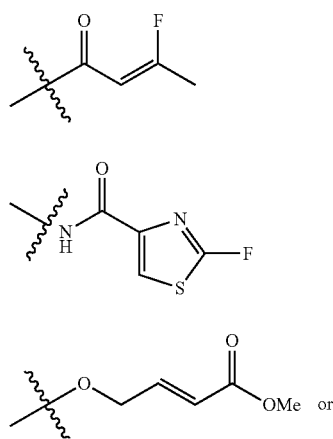
wherein each $R^e$ is independently a suitable leaving group, $NO_2$, CN, or oxo.
23. The method according to claim 1, wherein $R^1$ is selected from:
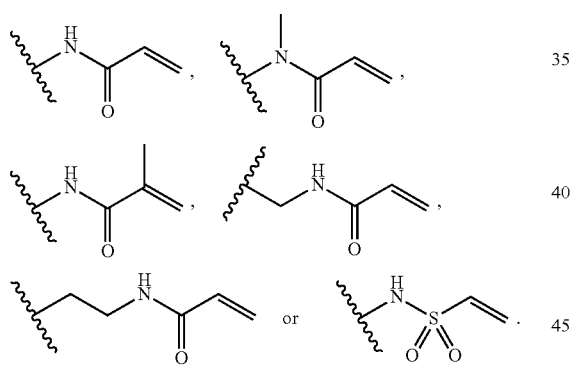
24. The method according to claim 6, wherein each $R^2$ is independently —Cl, —F, —$CF_3$, or —OMe; or is selected from
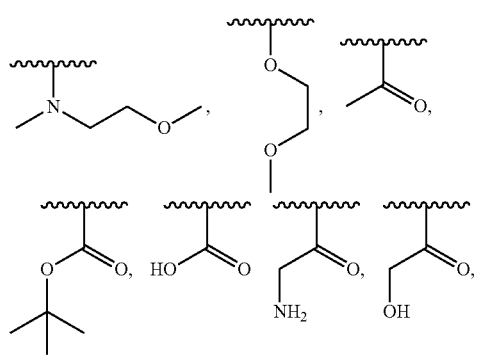
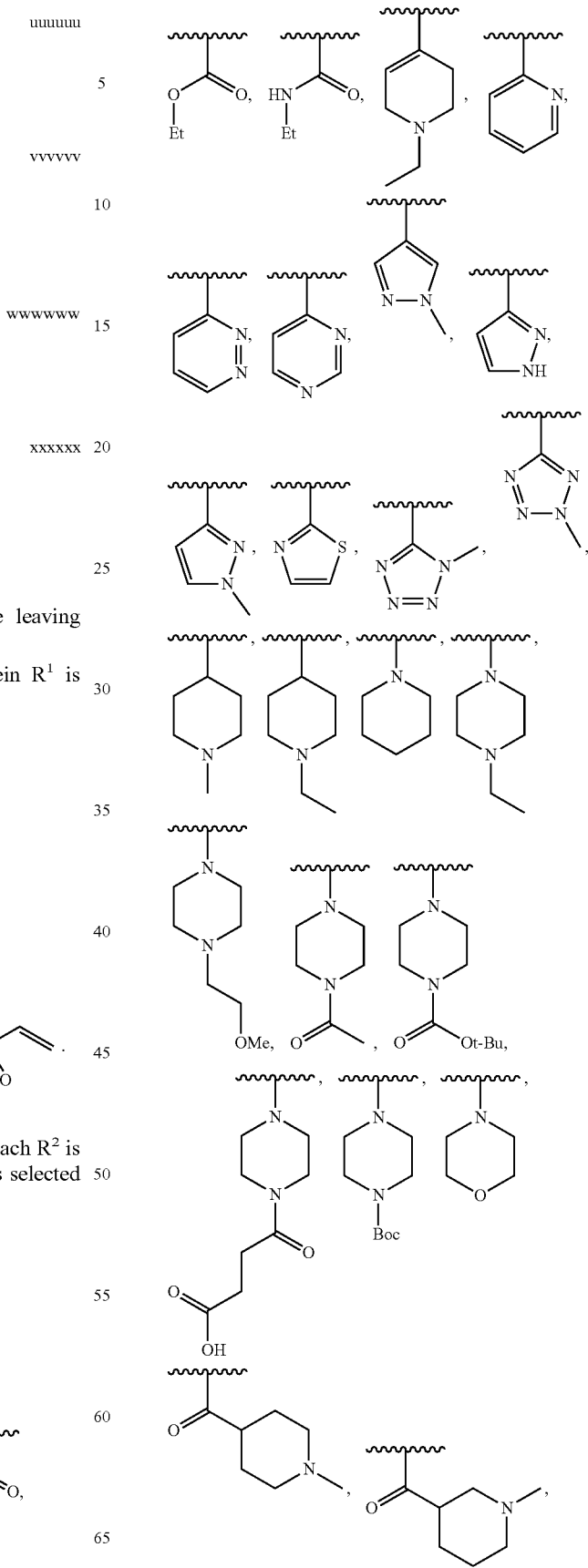

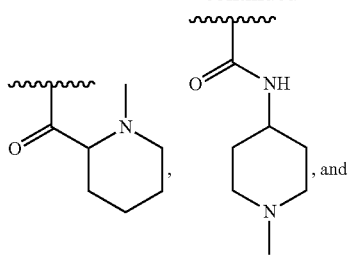
25. The method according to claim 1, wherein R³ is
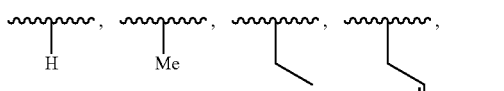
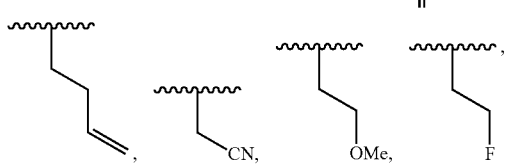
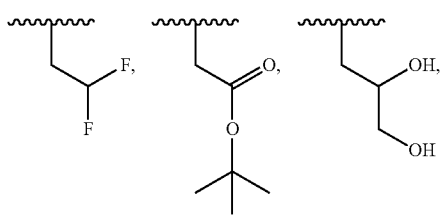
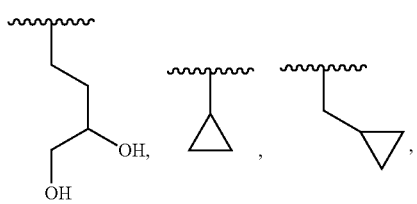
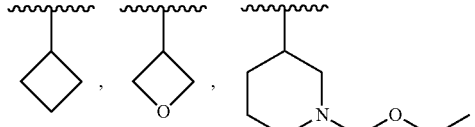
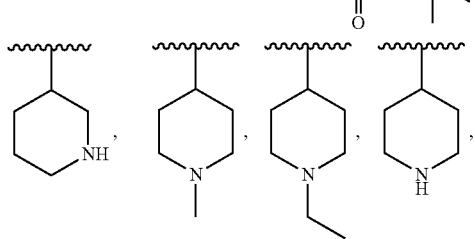
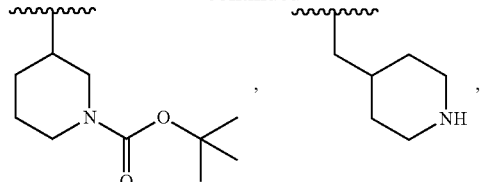
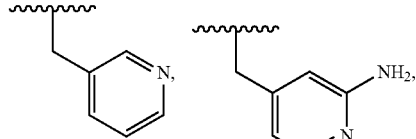
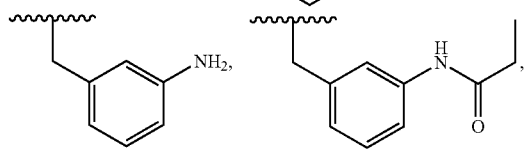
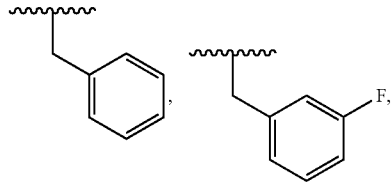
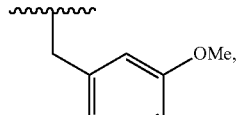
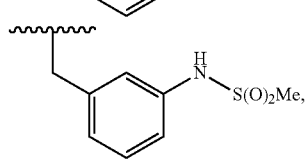
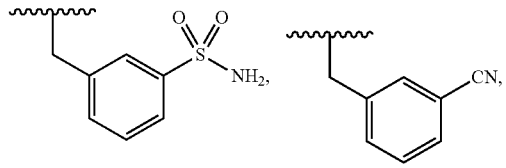
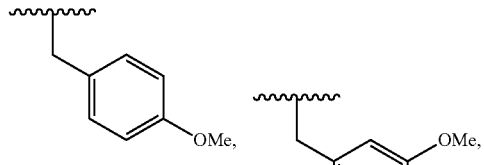
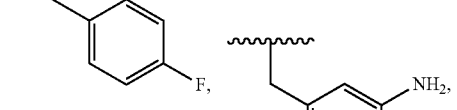
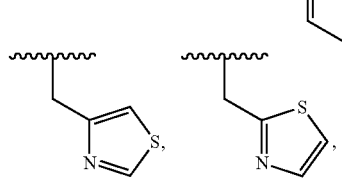

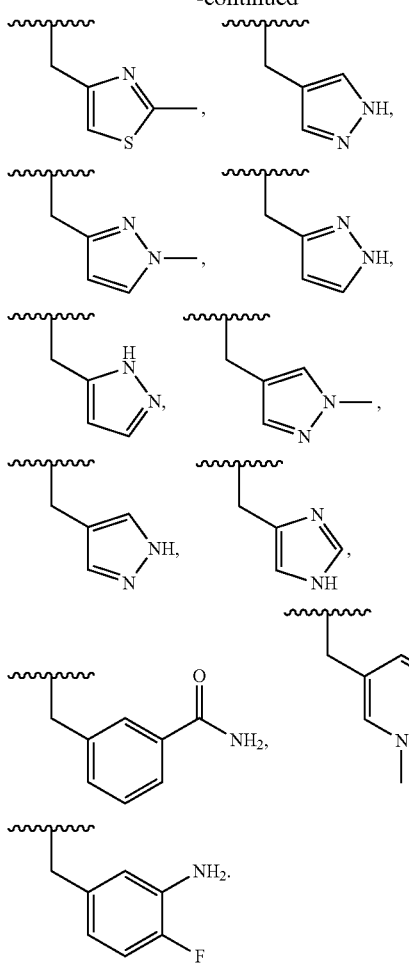
26. The method according to claim 1, wherein Y is selected from:
a
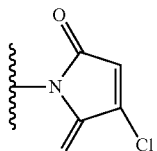
b
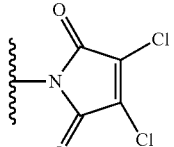
c
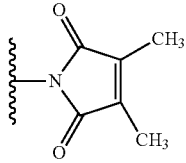
d
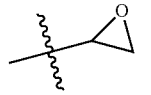
e
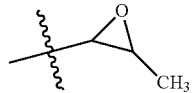
f
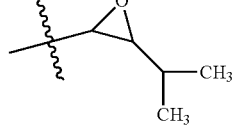
g, h, i
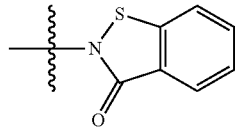
j
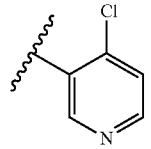
k
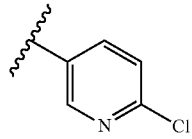
l
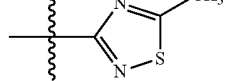
m, n
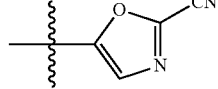

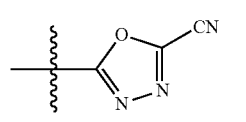
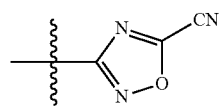
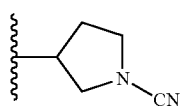
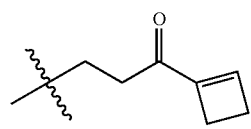
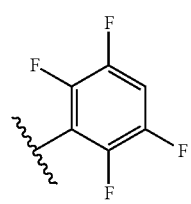
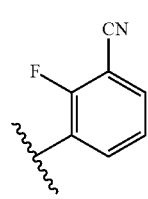
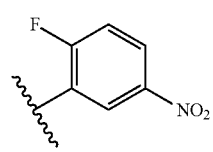
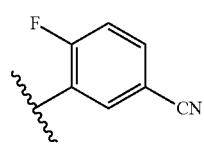
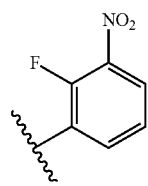
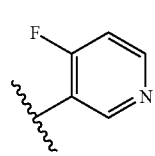
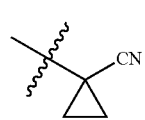
o
p
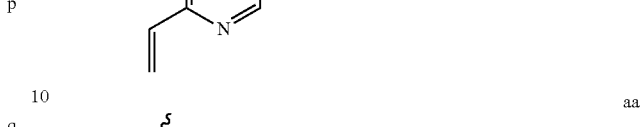
q
r
s
t
u
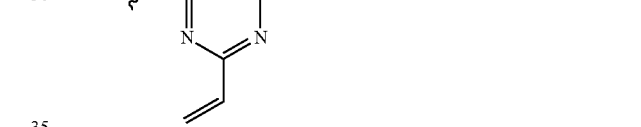
v
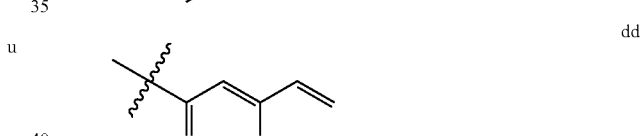
w
x
y
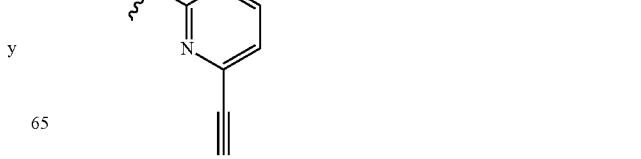
z
aa
bb
cc
dd
ee
ff
gg

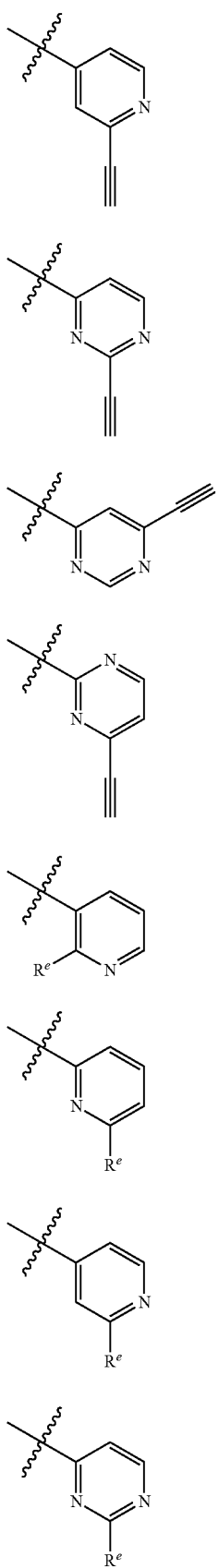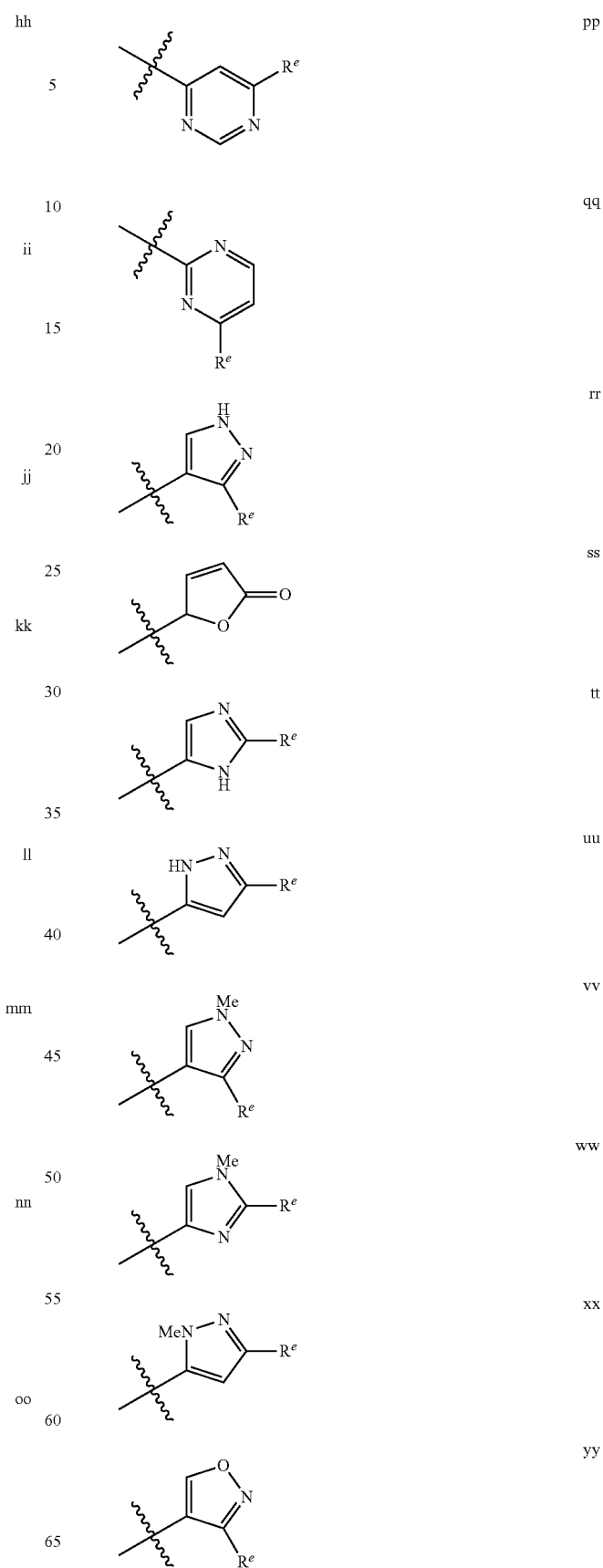

-continued
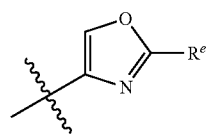 zz
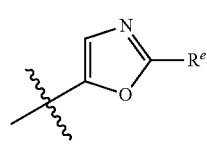 aaa
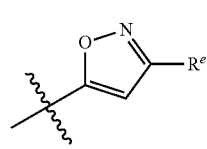 bbb
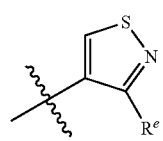 ccc
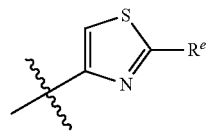 ddd
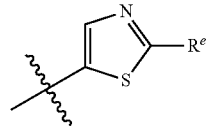 eee
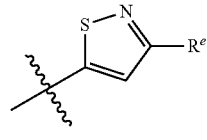 fff
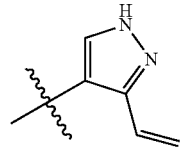 ggg
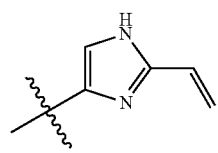 hhh
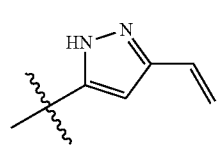 iii
-continued
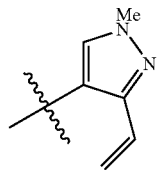 jjj
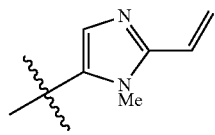 kkk
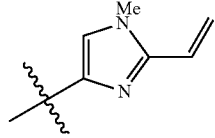 lll
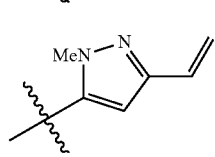 mmm
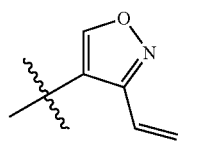 nnn
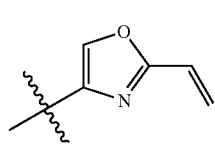 ooo
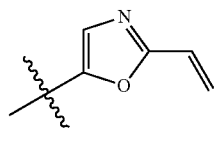 ppp
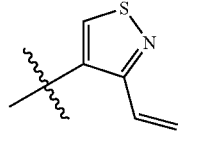 qqq
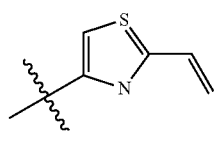 rrr
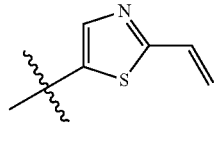 sss
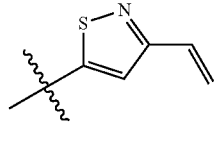 ttt

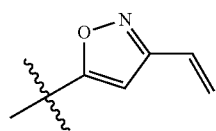
uuu
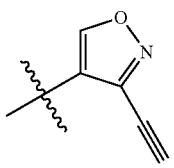
dddd
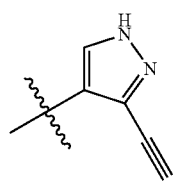
vvv
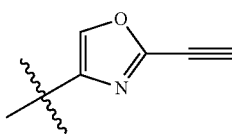
eeee
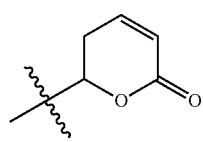
qqq
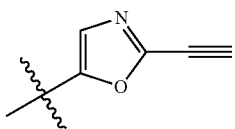
ffff
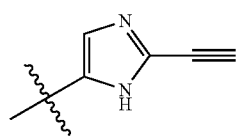
www
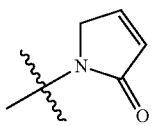
gggg
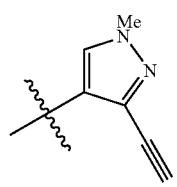
xxx
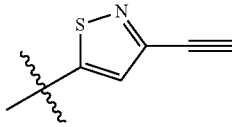
hhhh
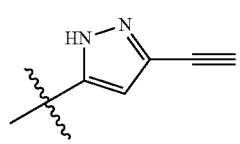
yyy
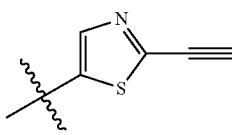
iiii
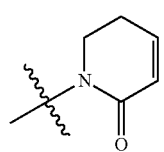
zzz
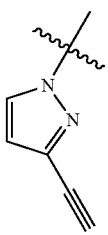
jjjj
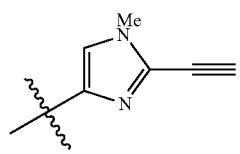
aaaa
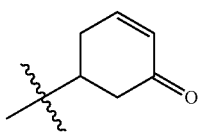
kkkk
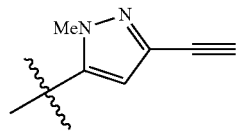
bbbb
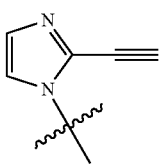
llll
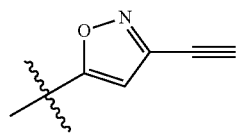
cccc
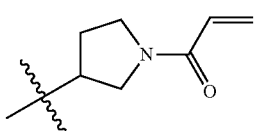
mmmm

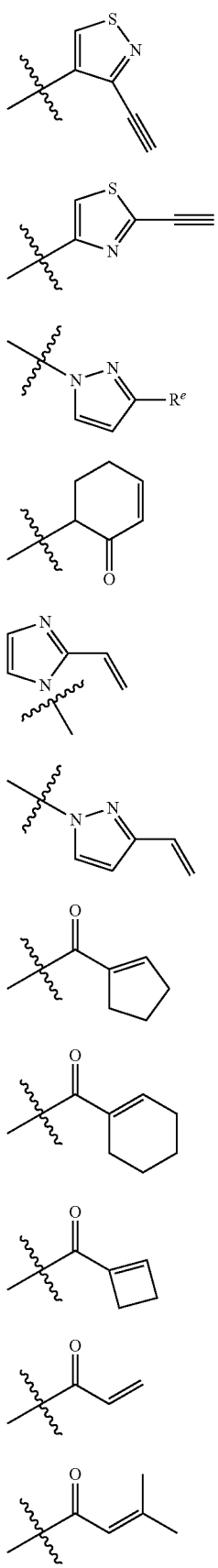
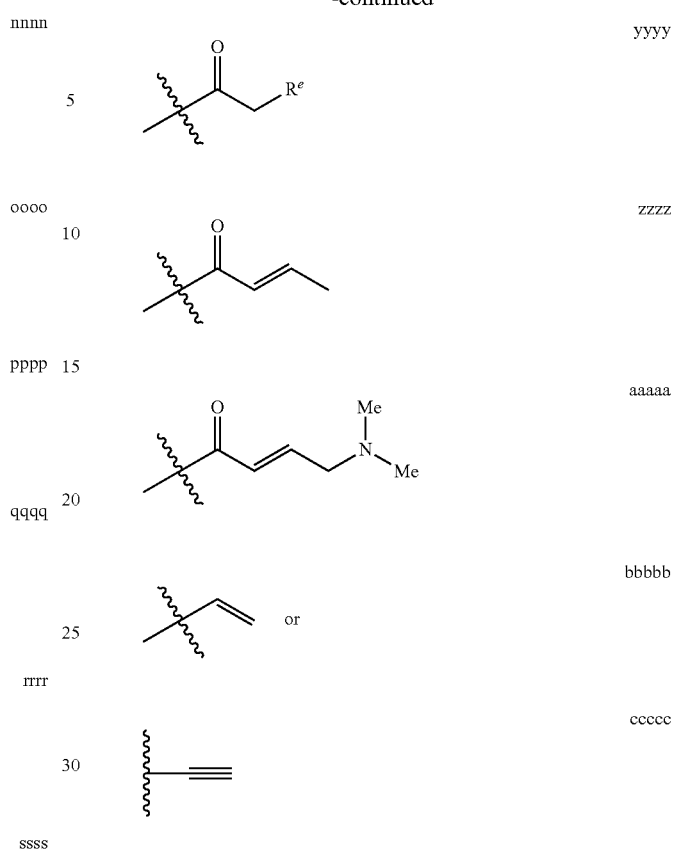
wherein each $R^e$ is independently selected from halogen.
27. The method according to claim 1, selected from:
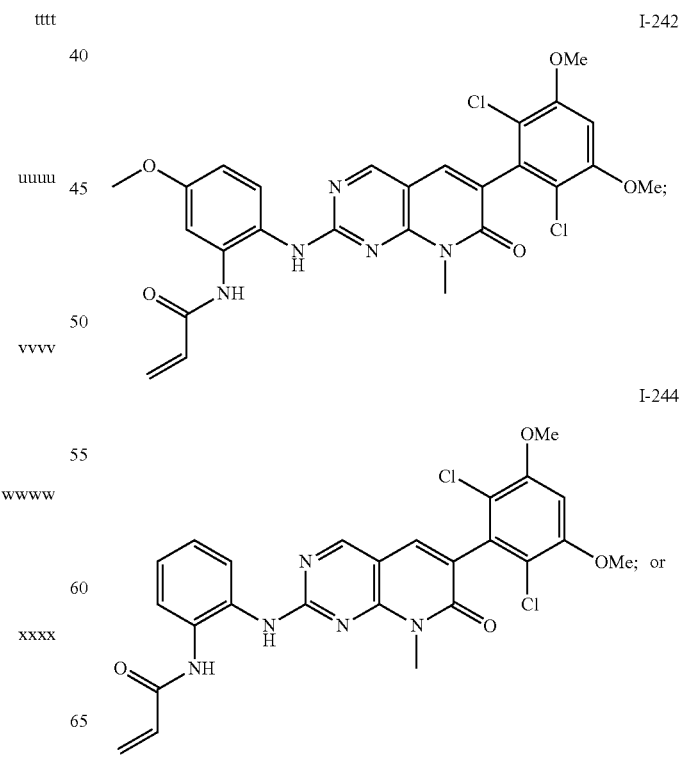

I-245
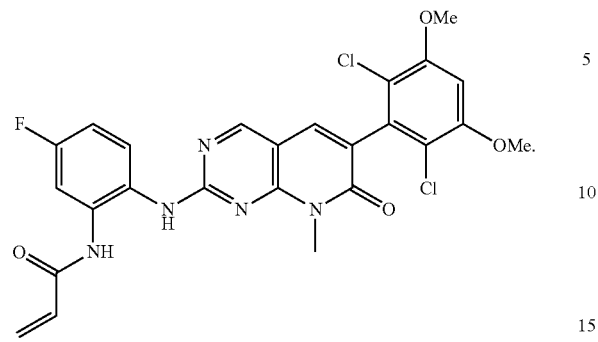
or a pharmaceutically acceptable salt thereof.
* * * * *

SEQUENCE LISTING

<160> NUMBER OF SEQ ID NOS: 1

<210> SEQ ID NO 1
<211> LENGTH: 802
<212> TYPE: PRT
<213> ORGANISM: Homo sapiens

<400> SEQUENCE: 1

```
Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
            20                  25                  30

Cys Leu Ala Pro Ser Leu Glu Gln Gln Glu Gln Glu Leu Thr Val Ala
        35                  40                  45

Leu Gly Gln Pro Val Arg Leu Cys Cys Gly Arg Ala Glu Arg Gly Gly
    50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
    210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270
```

Val Tyr Ser Asp Ala Gln Pro His Ile Gln Trp Leu Lys His Ile Val
            275                 280                 285

Ile Asn Gly Ser Ser Phe Gly Ala Asp Gly Phe Pro Tyr Val Gln Val
    290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350

Glu Glu Asp Pro Thr Trp Thr Ala Ala Ala Pro Glu Ala Arg Tyr Thr
        355                 360                 365

Asp Ile Ile Leu Tyr Ala Ser Gly Ser Leu Ala Leu Ala Val Leu Leu
    370                 375                 380

Leu Leu Ala Gly Leu Tyr Arg Gly Gln Ala Leu His Gly Arg His Pro
385                 390                 395                 400

Arg Pro Pro Ala Thr Val Gln Lys Leu Ser Arg Phe Pro Leu Ala Arg
                405                 410                 415

Gln Phe Ser Leu Glu Ser Gly Ser Ser Gly Lys Ser Ser Ser Ser Leu
            420                 425                 430

Val Arg Gly Val Arg Leu Ser Ser Ser Gly Pro Ala Leu Leu Ala Gly
        435                 440                 445

Leu Val Ser Leu Asp Leu Pro Leu Asp Pro Leu Trp Glu Phe Pro Arg
    450                 455                 460

Asp Arg Leu Val Leu Gly Lys Pro Leu Gly Glu Gly Cys Phe Gly Gln
465                 470                 475                 480

Val Val Arg Ala Glu Ala Phe Gly Met Asp Pro Ala Arg Pro Asp Gln
                485                 490                 495

Ala Ser Thr Val Ala Val Lys Met Leu Lys Asp Asn Ala Ser Asp Lys
            500                 505                 510

Asp Leu Ala Asp Leu Val Ser Glu Met Glu Val Met Lys Leu Ile Gly
        515                 520                 525

Arg His Lys Asn Ile Ile Asn Leu Leu Gly Val Cys Thr Gln Glu Gly
    530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
                565                 570                 575

Pro Arg Ser Ser Glu Gly Pro Leu Ser Phe Pro Val Leu Val Ser Cys
            580                 585                 590

Ala Tyr Gln Val Ala Arg Gly Met Gln Tyr Leu Glu Ser Arg Lys Cys
        595                 600                 605

Ile His Arg Asp Leu Ala Ala Arg Asn Val Leu Val Thr Glu Asp Asn
    610                 615                 620

Val Met Lys Ile Ala Asp Phe Gly Leu Ala Arg Gly Val His His Ile
625                 630                 635                 640

Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val
            660                 665                 670

Trp Ser Phe Gly Ile Leu Leu Trp Glu Ile Phe Thr Leu Gly Gly Ser
        675                 680                 685

Pro Tyr Pro Gly Ile Pro Val Glu Glu Leu Phe Ser Leu Leu Arg Glu

```
              690                 695                 700
Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
                725                 730                 735

Lys Gln Leu Val Glu Ala Leu Asp Lys Val Leu Leu Ala Val Ser Glu
                740                 745                 750

Glu Tyr Leu Asp Leu Arg Leu Thr Phe Gly Pro Tyr Ser Pro Ser Gly
                755                 760                 765

Gly Asp Ala Ser Ser Thr Cys Ser Ser Ser Asp Ser Val Phe Ser His
                770                 775                 780

Asp Pro Leu Pro Leu Gly Ser Ser Ser Phe Pro Phe Gly Ser Gly Val
785                 790                 795                 800

Gln Thr
```